(12) United States Patent
Jones et al.

(10) Patent No.: US 7,470,699 B2
(45) Date of Patent: Dec. 30, 2008

(54) TRISUBSTITUTED ARYL AND HETEROARYL DERIVATIVES AS MODULATORS OF METABOLISM AND THE PROPHYLAXIS AND TREATMENT OF DISORDERS RELATED THERETO

(75) Inventors: Robert M. Jones, San Diego, CA (US); Graeme Semple, San Diego, CA (US); Yifeng Xiong, San Diego, CA (US); Young-Jun Shin, San Diego, CA (US); Albert S. Ren, San Diego, CA (US); Imelda Calderon, San Diego, CA (US); Beatriz Fioravanti, Tucson, AZ (US); Jin Sun Karoline Choi, San Diego, CA (US); Juerg Lehmann, San Diego, CA (US); Marc A. Bruce, San Marcos, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 499 days.

(21) Appl. No.: 10/888,747

(22) Filed: Jul. 9, 2004

(65) Prior Publication Data

US 2005/0070562 A1    Mar. 31, 2005

Related U.S. Application Data

(60) Provisional application No. 60/487,370, filed on Jul. 14, 2003, provisional application No. 60/486,728, filed on Jul. 11, 2003.

(51) Int. Cl.
*C07D 401/12* (2006.01)
*A61K 31/506* (2006.01)

(52) U.S. Cl. ...................... 514/269; 544/319
(58) Field of Classification Search ............... 544/319; 514/269
See application file for complete search history.

(56) References Cited

U.S. PATENT DOCUMENTS

| | | | |
|---|---|---|---|
| 3,503,963 A | 3/1970 | Schweizer et al. | |
| 3,592,932 A | 7/1971 | Duerr et al. | |
| 3,608,087 A | 9/1971 | Patchett et al. | |
| 3,686,238 A | 8/1972 | Zaffaroni et al. | |
| 3,690,834 A | 9/1972 | Goldstein et al. | |
| 3,849,420 A | 11/1974 | Tong | |
| 3,852,434 A | 12/1974 | Kahan et al. | |
| 3,862,117 A | 1/1975 | Leverenz | |
| 3,887,329 A | 6/1975 | Hegar et al. | |
| 3,966,744 A | 6/1976 | Goldstein et al. | |
| 3,966,764 A | 6/1976 | Goldstein et al. | |
| 3,975,384 A | 8/1976 | Narr et al. | |
| 3,984,411 A | 10/1976 | Claverie et al. | |
| 4,101,541 A | 7/1978 | Petitpierre et al. | |
| 4,189,427 A | 2/1980 | Komorowski | |
| 4,242,507 A | 12/1980 | Itoh et al. | |
| 4,267,174 A | 5/1981 | Berger et al. | |
| 4,275,148 A | 6/1981 | Endo et al. | |
| 4,397,848 A | 8/1983 | Bosies et al. | |
| 4,517,183 A | 5/1985 | Bosies et al. | |
| 5,691,364 A | 11/1997 | Buckman et al. | |
| 5,849,759 A | 12/1998 | Arnaiz et al. | |
| 5,948,786 A | 9/1999 | Fujiwara et al. | |
| 5,962,479 A | 10/1999 | Chen | |
| 6,008,234 A | 12/1999 | Kochanny et al. | |
| 6,187,777 B1 | 2/2001 | Norman et al. | |
| 6,191,149 B1 * | 2/2001 | Chokai et al. | 514/351 |
| 6,218,431 B1 | 4/2001 | Schoen et al. | |
| 6,239,126 B1 | 5/2001 | Kelly et al. | |
| 6,414,002 B1 | 7/2002 | Cheng et al. | |
| 6,525,064 B1 | 2/2003 | Dellaria et al. | |
| 6,545,016 B1 | 4/2003 | Dellaria et al. | |
| 6,545,017 B1 | 4/2003 | Dellaria et al. | |
| 6,583,154 B1 | 6/2003 | Norman et al. | |
| 6,844,351 B1 | 1/2005 | Chen et al. | |
| 6,956,047 B1 | 10/2005 | Chen et al. | |
| 7,083,933 B1 | 8/2006 | Griffin | |
| 7,132,426 B2 * | 11/2006 | Jones et al. | 514/262.1 |

FOREIGN PATENT DOCUMENTS

| | | |
|---|---|---|
| AT | 327605 | 6/2006 |
| AU | 492126 | 11/1975 |
| BE | 829845 | 12/1975 |
| BE | 868796 | 1/1979 |
| CH | 560197 | 3/1975 |
| DE | 2048375 | 4/1971 |
| DE | 2223644 | 11/1972 |

(Continued)

OTHER PUBLICATIONS

Ulrich, Chapter 4: Crystallization, Kirk-Othmer Encyclopedia of Chemical Technology, Aug. 2002.*

(Continued)

*Primary Examiner*—Deepak Rao
(74) *Attorney, Agent, or Firm*—Fish & Richardson P.C.

(57) ABSTRACT

The present invention relates to certain trisubstituted aryl and heteroaryl derivatives of Formula (I) that are modulators of metabolism.

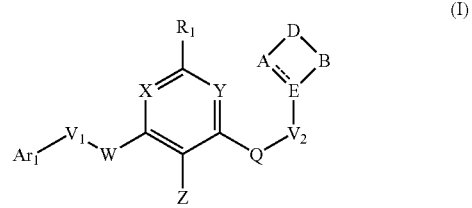

Accordingly, compounds of the present invention are useful in the prophylaxis or treatment of metabolic disorders and complications thereof, such as, diabetes and obesity.

57 Claims, 4 Drawing Sheets

FOREIGN PATENT DOCUMENTS

| | | |
|---|---|---|
| DE | 2356644 | 5/1974 |
| DE | 2341925 | 3/1975 |
| DE | 2460238 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 | 7/1987 |
| DE | 19602095 | 7/1997 |
| DE | 19737723 | 2/1999 |
| DE | 19962936 | 6/2001 |
| EP | 0 014 976 | 9/1980 |
| EP | 0 055 693 | 7/1982 |
| EP | 0 149 088 | 12/1984 |
| EP | 0 154 190 | 9/1985 |
| EP | 0 191 603 | 8/1986 |
| EP | 0 193 249 | 9/1986 |
| EP | 0 283 261 | 9/1988 |
| EP | 0 324 426 | 7/1989 |
| EP | 0 518 675 | 12/1992 |
| EP | 0 556 889 | 8/1993 |
| EP | 0 565 488 | 10/1993 |
| EP | 0 604 800 | 7/1994 |
| EP | 0 667 343 | 8/1995 |
| EP | 0 801 059 | 10/1997 |
| EP | 0 857 483 | 8/1998 |
| EP | 0 940 387 | 9/1999 |
| EP | 1 074 549 | 2/2001 |
| EP | 1287133 B1 | 3/2003 |
| EP | 1 040 831 | 5/2003 |
| EP | 1 340 749 | 9/2003 |
| EP | 1 475 094 | 11/2004 |
| FR | 1551400 | 12/1968 |
| GB | 935595 | 8/1963 |
| GB | 1311956 | 3/1973 |
| JP | 55-17382 | 2/1980 |
| JP | 61-057587 | 3/1986 |
| JP | 05-33359 | 12/1993 |
| JP | 07-53546 | 2/1995 |
| JP | 11-193277 | 7/1999 |
| JP | 2000-038350 | 2/2000 |
| JP | 2001-089452 | 4/2001 |
| JP | 2004-269468 | 9/2004 |
| JP | 2004-269469 | 9/2004 |
| NL | 6614961 | 4/1967 |
| NL | 6814810 | 4/1969 |
| SU | 938 559 | 11/1993 |
| WO | WO 94/13677 | 6/1994 |
| WO | WO 95/33750 | 12/1995 |
| WO | WO 96/28427 | 9/1996 |
| WO | WO 96/32383 | 10/1996 |
| WO | WO 96/33994 | 10/1996 |
| WO | WO 96/36613 | 11/1996 |
| WO | WO 97/08152 | 3/1997 |
| WO | WO 97/26252 | 7/1997 |
| WO | WO 97/29109 | 8/1997 |
| WO | WO97/40832 | 11/1997 |
| WO | WO 97/49706 | 12/1997 |
| WO | WO 98/04528 | 2/1998 |
| WO | WO 98/08846 | 3/1998 |
| WO | WO 98/08847 | 3/1998 |
| WO | WO 98/11094 | 3/1998 |
| WO | WO98/19998 | 5/1998 |
| WO | WO 98/47874 | 10/1998 |
| WO | WO 98/47903 | 10/1998 |
| WO | WO 99/09026 | 2/1999 |
| WO | WO 99/51599 | 10/1999 |
| WO | WO 00/11003 | 3/2000 |
| WO | WO 00/27825 | 5/2000 |
| WO | WO 00/31068 | 6/2000 |
| WO | WO00/34241 | 6/2000 |
| WO | WO 00/35875 | 6/2000 |
| WO | WO 00/35886 | 6/2000 |
| WO | WO 01/22938 | 4/2001 |
| WO | WO 01/23387 | 4/2001 |
| WO | WO 01/23388 | 4/2001 |
| WO | WO 01/25210 | 4/2001 |
| WO | WO 01/27107 | 4/2001 |
| WO | WO 01/47887 | 7/2001 |
| WO | WO 01/49677 | 7/2001 |
| WO | WO 01/53263 | 7/2001 |
| WO | WO 01/58900 | 8/2001 |
| WO | WO 01/62233 | 8/2001 |
| WO | WO 01/85699 | 11/2001 |
| WO | WO 02/02549 | 1/2002 |
| WO | WO 02/06237 | 1/2002 |
| WO | WO 02/06274 | 1/2002 |
| WO | WO 02/19975 | 3/2002 |
| WO | WO 02/32893 | 4/2002 |
| WO | WO 02/40451 | 5/2002 |
| WO | WO 02/40456 | 5/2002 |
| WO | WO 02/40458 | 5/2002 |
| WO | WO 02/40480 | 5/2002 |
| WO | WO 02/44362 | 6/2002 |
| WO | WO 02/59083 | 8/2002 |
| WO | WO 02/070485 | 9/2002 |
| WO | WO 02/072101 | 9/2002 |
| WO | WO 02/98864 | 12/2002 |
| WO | WO 02/98878 | 12/2002 |
| WO | WO 03/000666 | 1/2003 |
| WO | WO 03/002544 | 1/2003 |
| WO | WO03/04498 | 1/2003 |
| WO | WO 03/026661 | 4/2003 |
| WO | WO 03/032989 | 4/2003 |
| WO | WO 03/050117 | 6/2003 |
| WO | WO 03/057689 | 7/2003 |
| WO | WO 03/077656 | 9/2003 |
| WO | WO 03/087064 | 10/2003 |
| WO | WO 03/094845 | 11/2003 |
| WO | WO 2004/000819 | 12/2003 |
| WO | WO 2004/000843 | 12/2003 |
| WO | WO 2004/009596 | 1/2004 |
| WO | WO 2004/009597 | 1/2004 |
| WO | WO 2004/009602 | 1/2004 |
| WO | WO 2004/024943 | 3/2004 |
| WO | WO 2004/029204 | 4/2004 |
| WO | WO 2004/031189 | 4/2004 |
| WO | WO 2004/035588 | 4/2004 |
| WO | WO 2004/041164 | 5/2004 |
| WO | WO 2004/056825 | 7/2004 |
| WO | WO 2004/056829 | 7/2004 |
| WO | WO 2004/062665 | 7/2004 |
| WO | WO 2004/065380 | 8/2004 |
| WO | WO 2004/074218 | 9/2004 |
| WO | WO 2004/076413 | 9/2004 |
| WO | WO 2004/111000 | 12/2004 |
| WO | WO 2005/016894 | 2/2005 |
| WO | WO2005/020920 | 3/2005 |
| WO | WO2005/023762 | 3/2005 |
| WO | WO2005/025554 | 3/2005 |
| WO | WO2005/026148 | 3/2005 |
| WO | WO 2005/030129 | 4/2005 |
| WO | WO2005/030751 | 4/2005 |
| WO | WO2005/033099 | 4/2005 |
| WO | WO 2005/035525 | 4/2005 |
| WO | WO 2005/037215 | 4/2005 |
| WO | WO2005030127 | 4/2005 |
| WO | WO2005/040095 | 5/2005 |
| WO | WO2005/042488 | 5/2005 |
| WO | WO 2005/046603 | 5/2005 |
| WO | WO2005/047297 | 5/2005 |
| WO | WO 2005/049033 | 6/2005 |
| WO | WO 2005/058315 | 6/2005 |
| WO | WO2005/058849 | 6/2005 |

| WO | WO 2005/061489 | 7/2005 |
| WO | WO2005/063750 | 7/2005 |
| WO | WO2005/072530 | 8/2005 |
| WO | WO2005/075426 | 8/2005 |
| WO | WO 2005/090348 | 9/2005 |
| WO | WO 2005/100365 | 10/2005 |
| WO | WO 2005/117909 | 12/2005 |
| WO | WO2005/121121 | 12/2005 |
| WO | WO 2006/040966 | 4/2006 |
| WO | WO 2006/043490 | 4/2006 |
| WO | WO 2006/067531 | 6/2006 |
| WO | WO 2006/067532 | 6/2006 |
| WO | WO 2006/070208 | 7/2006 |

OTHER PUBLICATIONS

Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Jones et al., Caplus Abstract 142:176857 (2005).*
Peterson et al., Expanding the Scope of Crystal Form Evaluation in Pharmaceutical Science, J Pharm Pharmaceut Sci, 9(3), pp. 317-326, 2006.*
Abdalla et al., "Synthesis and reaction of 3-cyano 2-(1H)-pyridones," *Pakistan Journal of Scientific and Industrial Research* (1977) 20(3):139-149.
Abramovitch et al., "Solution and flash vacuum pyrolysis of some 2,6-disubstituted β-phenethylsulfonyl azides and of β-styrenesulfonyl azide," *J Org Chem* (1985) 50:2066-2073.
Appukkuttan et al., "Transition-Metal-Free Sonogashira-Type Coupling Reactions In Water," *European Journal Of Organic Chemistry* (2003) 24:4713-4716.
Arvanitis et al., "Non-peptide corticotropin-releasing hormone antagonists: syntheses and structure-activity relationships of 2-anilinopyrimidines and -triazines.," *J Med Chem.* (1999) 42(5):805-18.
Arvanitis et al., "Non-peptide corticotropin-releasing hormone antagonists: syntheses and structure-acitvity relationships of 2-anilinopyrimidines and -triazines.," *J Med Chem.* (1999) Supporting Material, pp. 1-10.
Arvanitis et al., "CRF Ligands via suzuki and negishi couplings of 3-pyridyl boronic acids or halides with 2-benzyloxy-4-chloro-3-nitropyridine," *Bioorganic & Medicinal Chemistry Letters* (2003) 13(2):289-291.
Arvanitis et al., "Imidazo[4,5-b]pyridines as corticotropin releasing factor receptor ligands," *Bioorganic & Medicinal Ch emistry Letters* (2003) 13(1):125-128.
Arvela et al., "Rapid, Easy Cyanation of Aryl Bromides and Chlorides Using Nickel Salts in Conjunction with Microwave Promotion," *J. Org. Chem.* (2003) 68:9122-9125.
Arvela et al., "Rapid cyanation of aryl iodides in water using microwave promotion," *Org. Biomol. Chem.* (2003) 1:1119-1121.
Baindur et al., "Solution-Phase Synthesis of a Library of 3,5,7-Trisubstituted 3H-[1,2,3]triazolo[4,5-Id]pyrimidines," *J. Comb. Chem.* (2003) 5:653-659.
Bakkestuen et al., "Regioselective N-9 arylation of purines employing arylboronic acids in the presence of Cu(II)," *Tetrahedron Letters* (2003) 44:3359-3362.
Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions," *Tetrahedron* (2002) 58:7607-7611.
Barta et al., "Synthesis and activity of selective MMP inhibitors with an aryl backbone," *Bioorg & Med Chem Ltrs* (2000) 10(24):2815-2817.
Baskin et al., "A mild, convenient synthesis of sulfinic acid salts and sulfonamides from alkyl and aryl halides," *Tetrahedron Letters* (2002) 43:8479-8483.
Baskin et al., "An Efficient Copper Catalyst for the Formation of Sulfones from Sulfinic Acid Salts and Aryl Iodides," *Org. Lett.* (2002) 4(25):4423-4425.
Baskin et al., "An Efficient Copper Catalyst for the Formation of Sulfones from Sulfinic Acid Salts and Aryl Iodides," *Org. Lett.* (2002) 4(25):4423-4425, Supporting Material #1.
Baskin et al., "An Efficient Copper Catalyst for the Formation of Sulfones from Sulfinic Acid Salts and Aryl Iodides," *Org. Lett.* (2002) 4(25):4423-4425, Supporting Material #2.
Bedford et al., "Nonquaternary cholinesterase reactivators. 3. 3(5)-Substituted 1,2,4-oxadiazol-5(3)-aldoximes and 1,2,4-oxadiazole-5(3)-thiocarbohydroximates as reactivators of organophosphonate-inhibited eel and human acetylcholinesterase in vitro," *J Med Chem* (1986) 29(11):2174-2183.
Beller et al., "Base-catalyzed amination of olefins: an example of an environmentally friendly synthesis of amines," *Chemosphere* (2001) 43(1):21-26.
Biagi et al., "4,5,6-trisubstituted 2-phenylpyrimidines and their affinity towards A1 adenosine receptors," *Farmaco* (1997) 52(1):61-65.
Betti, et al., "Novel 3-Aralkyl-7-(amino-substituted)-1,2,3-triazole[4,5-d]pyrimidines with High Affinity toward A1 Adenoside Receptors," *J. Med. Chem.* (1998) 41:668-673.
Boldt et al., "Synthesis of 2,4-diaminopyridines," *Angewandte Chemie International Edition* (1970) 9(5):377.
Bomika et al., Translation of "Certain reactions of nucleophilic substitution in the 2-chloro-3-cyanopyridine series," *Kyimiya Geterotsiklicheskikh Soedinenii* (1976) (8):1085-1088 (Translated pp. 896-899).
Boschelli et al., "1,3,4-Oxadiazole, 1,3,4-thiadiazole, and 1,2,4-triazole analogs of the fenamates: in vitro inhibition of cyclooxygenase and 5-lipoxygenase activities," *J Med Chem* (1993) 36:1802-1810.
Boswell et al., "Synthesis of some N-carboxylic acid derivatives of 3-phenoxypyrrolidines, 4-phenoxypiperidines, and 3-phenoxynortropanes with muscle relaxant and anticonvulsant activities," *J Med Chem* (1974) 17(9):1000-1008.
Brancati et al., "Body Weight Patterns From 20 to 49 Years of Age and Subsequent Risk for Diabetes Mellitus: The Johns Hopkins Precursors Study," *Arch Intern Med.* (1999) 159:957-963.
Bromidge et al., "Design of [R-(Z)]-(+)-alpha-(methoxyimino)-1-azabicyclo[2.2.2]octane-3-acetonitri le (SB 202026), a functionally selective azabicyclic muscarinic M1 agonist incorporating the N-methoxy imidoyl nitrile group as a novel ester bioisostere," *J Med Chem* (1997) 40(26):4265-4280.
Muci et al., "Practical Palladium Catalysts for C-N anc C-O Bond Formation," *Topics in Current Chemistry* (2002) 219:131-209.
Buehler et al., "Physiologically active compounds. VI. Cyclic amino thiolesters of substituted chloroacetic, benzilic and glycolic acids," *J Med Chem* (1965) 8:643-647.
Bulger et al., "An investigation into the alkylation of 1,2,4-triazole," *Tetrahedron Letters* (2000) 41:1297-1301.
Chan et al., "Isoquinoline-6-Carboxamides as Potent and Selective Anti-Human Cytomegalovirus (HCMV)Inhibitors," *Bioorganic & Medicinal Chemistry Letters* (1999) 9:2583-2586.
Chen et. al., "Optimization of 3-phyenylpyrazolo[1,5-alpha]pyrimidines as potent corticotrophin-release factor-1 antagonists with adequate lipophilicity and water solubility," *Bioorganic & Medicinal Chemistry Letters* (2004) 14:3669-3673.
Chen et al., "Design and Synthesis of a Series of Non-Peptide High-Affinity Human Corticotropin-Releasing Factor 1 Receptor Antagonists," *J. Med. Chem.* (1996) 39:4358-4360.
Chen et al., "Free Radical Method for the Synthesis of Spiro-Piperidinyl Heterocycles," *Tetrahedron Letters* (1996) 37(30):5233-5234.
Chorvat et al., "Synthesis, Corticotropin-Releasing Factor Receptor Binding Affinity, and Pharmacokineitc Properties of Triazolo-, Imidazo-, and Pyrrolopyrimidines and -pyridines," *J. Med. Chem.* (1999) 42:833-848.
Clark et al., "Synthesis and Analgesic Activity of 1,3-Dihydro-3-(Substituted phenyl)imidazo[4,5-b]pyridine-2-ones and 3-(Substituted phenyl)-1,2,3-triazolo(4,5-b)pyridines," *J. Med. Chem.* (1978) 21(9):965-978.
Cocuzza et al., "Use of the Suzuki Reaction for the Synthesis of Aryl-Substituted Heterocycles as Corticotropin-Releasing Hormone (CRH) Antagonists," *Bioorganic &Medicinal Chemistry Letters* (1999) 9:1063-1066.

Cohen et al., "The Preparation and Properties of 6-Halomethylpurines," *Div. of Nucleoprotein Chemistry, Sloan-Kettering Institute for Cancer Research, and Sloan Kettering Div. Grad. School of Med. Sci.*, Cornell Uiv. Med. College (1962) 27:3545-3549.

Colandrea et al., "Synthesis and regioselective alkylation of 1,6- and 1,7-naphythridines," *Tetrahedron Letters* (2000) 41:8053-8057.

Collier et al., "Radiosynthesis and in-vivo evaluation of the pseudopeptide δ-opioid antagonist [$^{125}$I]-ITIPP (ψ)," *J. Labeled Compd. Radiopharm.*, (1999) 42(Suppl. 1):S264-S266.

Cossey et al., "Amide-acid chloride adducts. VI. Pyridines and pyridinium salts from cyanoacetamides," *Australian Journal of Chemistry* (1976) 29(5):1039-1050.

Cryan et al., "Behavioral characterization of the novel GABAB receptor-positive modulator GS39783 (N,N'-dicyclopentyl-2-methylsulfanyl-5-nitropyrimidine-4,6-diamine): Anxiolytic-like activity without side effects associated with baclofen or benzodiazepines," *Journal of Pharmacology and Experimental Therapeutics* (2004) 310(3):952-963.

Dai et al., "The first general method for palladium-catalyzed Negishi cross-coupling of aryl and vinyl chlorides: use of commercially available Pd(P(t-Bu)$_3$)$_2$ as a catalyst," *J Am Chem Soc* (2001) 123(12):2719-2724.

Desimoni et al., "Polynuclear isoxazole Types-I—Isoxazolo[4,5-d]Pyrimidines," *Tetrahedron* (1967) 23:675-680.

Devita et al., "Identification and initial structure-activity relationships of a novel non-peptide quinolone GnRH receptor antagonist," *Bioorg & Med Chem Ltrs* (1999) 9(17):2615-2620.

Di Braccio et al., "Synthesis and preliminary pharmacological examination of 2,4-disubstituted N,N-dialkyl-1,8-naphthyridine-3-carboxamides," *Farmaco* (1989) 44(9):865-881.

Dzierba et al., "Synthesis, Structure-Activity Relationships, and in Vivo Properties of 3,4-Dihydro-1H-pyrido[2,3-b]pyrazin-2-ones as Corticotropin-Releasing Factor-1 Receptor Antagonists," *Journal of Medicinal Chemistry* (2004) 47(23):5783-5790.

Eicher et al., "Reaction of triafulvenes with isonitriles. A simple synthesis of diphenyl-substituted functionalized cyclobutene derivatives and related products," *Synthesis* (1987) (7):619-626.

Escher et al., "Cyclopentylamine Substituted Triazolo[4,5-D]Pyrimidine: Implications for Binding to the Adenosine Receptor," *Tetrahedron Letters* (1991) 32(29):3583-3584.

Gangloff et al., "Synthesis of 3,5-disubstituted-1,2,4-oxadiazoles using tetrabutylammonium fluoride as a mild and efficient catalyst," *Tetrahedron Letters* (2001) 42:1441-1443.

Gilligan et al., "Corticotropin-releasing factor antagonists: Recent advances and exciting prospects for the treatment of human diseases," *Current Opinion in Drug Discovery & Development* (2004) 7(4):487-497.

Gilligan, et al., "Corticotropin Releasing Factor (CRF) Receptor Modulators Progress and Opportunities for New Therapeutic Agents," *J. Med. Chem.* (2000) 43(9):1641-1660.

Goldner et al., "Die Darstellung 2,9-; 2,6,9- und 6,9-substituierter Purine," *Journal fuer Praktische Chemie (Leipzig)* (1961) 12:242-252.

Giner-Sorolla et al., "The Synthesis and Properties of 6-Mercaptomethylpurine and Derivatives," *Cornell University Medical College* (1965) 8:667-672.

Gomtsyan et al., "Design, synthesis, and structure-activity relationship of 6-alkynylpyrimidines as potent adenosine kinase inhibitors," *J Med Chem.* (2002) 45(17):3639-3648.

Hamada et al., "An improved synthesis of arylsulfonyl chlorides from arylhalides," *Synthesis* (1986) pp. 852-854.

He et al., "4-(1,3-Dimethozyprop-2-ylamino)-2,7-dimethyl-8-(2,4-dichlorophenyl)-pyrazolo[1,5-a]-1,3,5-triazine: A Potent, Orally Bioavailable CRF1 Receptor Antagonist," *J. Med. Chem.* (2000) 43:449-456.

Hecht et al., "On the "activation" of cytokins*," *J of Biological Chemistry* (1975) 250(18):7343-7351.

Hersperger et al., "Palladium-Catalyzed Cross-Coupling Rtions for the Synthesis of 6,8-Disubstituted 1,7-Naphthyridines: A Novel Class of Potent and Selective Phosphodiesterase Type 4D Inhibitors," *J. Med. Chem.* (2000) 43:675-682.

Higuchi et al., "Pro-drugs as novel delivery systems," *A.C.S. Symposium Series*, vol. 14.

Hill et al., "Environmental contributions to the obesity epidemic," *Science* (1998) 280(5368):1371-4.

Hocek et al., "An Efficient Synthesis of 2-Substituted 6-Methylpurine Bases and Nucleosides by Fe- or Pd-Catalyzed C ross-Coupling Reactions of 2,6-Dichloropurines," *J. Org. Chem.* (2003) 68:5773-5776.

Huang et al., "Synthesis and Antiplatelet Activity of Phenyl Quinolones," *Bioorganic & Medicinal Chemistry* (1998) 6:1657-1662.

Berge et al., "Pharmaceutical Salts," *Journal of Pharmaceutical Sciences* (1977) 66(1):1-19.

Jia, et al., "Design, Synthesis and Biological Activity of Novel Non-Amidine Factor Xa Inhibitors. Part 1: P1 Structure-Activity Relationships of the Substituted 1-(2-Naphtyl)-1H-pyrazole-5-carboxylamides," *Bioorganic & Medicinal Chemistry Letters* (2002) 12:1651-1655.

Jogie et al., "Unusual protein-binding specificity and capacity of aza-arenophilic gels," *Journal of Molecular Recognition* (1998) 11:261-262.

Kawase et al., "α-trifluoromethylated acyloins induce apoptosis in human oral tumor cell lines," *Bioorg & Med Chem Ltrs* (1999) 9(21):3113-3118.

Kelly et al., "A Synthesis of Aaptamine," *Tetrahedron* (1985) 41(15):3033-3066.

Kelley et al., "Benzodiazepine receptor binding activity of 8-substituted-9-(3-substituted-benzyl)-6-(dimethylamino)-9H-purines," *J Med Chem* (1990) 33(1):196-202.

Kempson et al., "Fused pyrimidine based inhibitors of phosphodiesterase 7 (PDE7): synthesis and initial structure-activity relationships," *Bioorganic & Medicinal Chemistry Letters* (2005) 15:1829-1833.

Khattab et al., "Quinolines with heteroatom substituents in position 2 and 4. Nucleophilic substitution of 2,4-dichloro-3-phenylquinolines," *ACH—Models in Chemistry* (1994) 131(3-4):521-527.

Kloetzer et al., "Chlorierende formylierungsreaktionen an pyrimidinen," *Monatshefte fuer Chemie*, (1965) 96(5):1567-1572.

Kotian et al., "Synthesis, ligand binding, and quantitative structure-activity relationship study of 3β-(4'-substituted phenyl)-2β-heterocyclic tropanes: evidence for an electrostatic interaction at the 2β-position," *J Med Chem* (1996) 39(14):2753-2763.

Krauze et al., "Derivatives of 3-cyano-6-phenyl-4-(3'-pyridyl)-pyridine-2(1H)-thione and their neurotropic activity," *European Journal of Medicinal Chemistry* (1999) 34(4):301-310.

Krauze et al., "Synthesis of 3-oxoisothiazolo[5,4-b]pyridines," *Khimiya Geterotsiklicheskikh Soedinenii* (1982) (4):508-512.

Kumegai et al., "Synthesis, SAR and biological activities of CRH1 Receptor: Novel 3- or 4-carbamoyl-1,2,5,6-tetrahydropyridinopyrrolopyrimidine derivative," 4$^{th}$ ACS National Meeting, Aug. 18-22, 2002, Boston, MA. Poster #259.

Lai et al., "A one-pot method for the efficient conversion of aryl- and acyl-substituted methyl alcohols into chlorides," *Synthetic Communications* (2003) 33(10):1727-1732.

Lanier et al., "Small molecule corticotrophin-releasing factor antagonists," *Expert Opinion* (2002) 12(11):1619-1630.

Leadbeater et al., "First Examples Of Transition-Metal Free Sonogashira-Type Couplings," *Organic Letters* (2003) 5(21):3919-3922.

Leadbeater et al., "Transition-metal free sonogashira-type couplings," *Department of Chemistry, King's College London*, Supplementary Information, pp. S1-S4.

Lee et al., "Synthesis and biological evaluation of clitocine analogues as adenosine kinase inhibitors," *Bioorg & Med Chem Ltrs* (2001) 11(18):2419-2422.

Leese et al., "Potential antipurines. II. Synthesis of 6- and 9-substituted purines and 8-azapurines," *Journal of the Chemical Society* (1958) 4107-4110.

Le Bas et al., "Radioiodinated analogs of EP 00652218 for the exploration of the tachykinin NK1 receptor by spect," *J. Labeled Compd. Radiopharm.* (2001) 44:S280-S282.

Le Stunff et al., "Early changes in postprandial insulin secretion, not in insulin sensitivity, characterize juvenile obesity," *Diabetes* (1989) 43:696-702.

Lin, et al., "Synthesis and Antitumor Activity of Halogen-Substituted 4-(3,3-Dimethyl-1-triazeno)quinolines," *J. Med. Chem.* (1978) 21(3):268-272.

Litvak et al., "Polynucleotides and Their Components in the Processes of Aromatic Nucleophilic Substitution: II.1 Nucleophilic Modification of 3',5'-Bis-O-(α,β,α',β'-tetrafluoropyrid-γ-yl)thymidine," *Russian Journal of Bioorganic Chemistry* (2004) 30(4):337-343.

Litvinov et al., "Naphythyridines. Structure, physicochemical properties and general methods of synthesis," *Russian Chemical Reviews* (2000) 69(3):201-220.

Loupy et al., "Easy and efficient $S_NAr$ Reactions on halopyridines in solvent free conditions," *Heterocycles* (1991) 32(10):1947-1952.

Luo et al., "Microwave-assisted synthesis of aminopyrimidines," *Tetrahedron Letters* (2002) 43:5739-5742.

Groger "Moderne methoden der Suzuki-kreuzkupplung: die langerwarteten universellen synthesevarianten mit arylchloriden," *J Prakt Chem* (2000) 342(4):334-339.

Ma, et al. "Mild Method for Ullmann Coupling Reaction of Amines and Aryl Halides," *Organic Letters* (2003) 5(14):2453-2455.

Macchia et al., "New N-n-propyl-substituted 3-aryl- and 3-cyclohexylpiperidines as partial agonists at the D4 dopamine receptor," *J Med Chem* (2003) 46(1):161-168.

Mackman et al., "2-(2-Hydroxy-3-alkoxyphenyl)-1*H*-benzimidazole-5-carboxamidine derivatives as potent and selective urokinase-type plasminogen activator inhibitors," *Bioorganic & Medicinal Chemistry Letters* (2002) 12(15):2019-2022.

Majeed, et al, "Stannylation Reactions and Cross-Couplings in Pyrimidines," *Tetrahedron* (1989) 45(4):993-1006.

Matsui et al., "Highly potent inhibitors of TNF-α production. Part II: metabolic stabilization of a newly found chemical lead and conformational analysis of an active diastereoisomer," *Bioorg Med Chem.* (2002) 10(12):3787-805.

Matsuno et al., "Potent and selective inhibitors of platelet-derived growth factor receptor phosphorylation. 3. Replacement of quinazoline moiety and improvement of metabolic polymorphism of 4-[4-(*N*-substituted (thio)carbamoyl)-1-piperazinyl]-6,7-dimethoxyquinzoline derivatives," *J Med Chem* (2003) 46(23):4910-4925.

Mesguiche et al., "4-Alkoxy-2,6-diaminopyrimidine derivatives: inhibitors of cyclin dependent kinases 1 and 2," *Bioorganic & Medicinal Chemistry Letters* (2003) 13(2):217-222.

Metzger et al., "Einstufensynthese von 2,4-Bis(*sec*-alkylamino-6-halogen-3-pyridincarbonitrilen**)," *Liebigs Annalen der Chemie* (1980) (6):946-953.

Mittelbach et al., "Syntheses with nitriles. 60. Preparation of 4-amino-5-cyano-6-phenylpyrimidines from 2-amino-1,1-dicyano-2-phenylethene," *Journal of Heterocyclic Chemistry* (1980) 17(7):1385-1387.

Miyashita et al., "Preparation of Heterarenecarbonitriles by Reaction of Haloheteroarenes with Potassium Cyanide Atalyzied by Sodium *p*-Toluenesulfinate," *Heterocycles* (1994) 39(1):345-350.

Mohan et al., "Solid-phase synthesis of N-substituted amidinophenoxy pyridines as factor Xa inhibitors," *Bioorganic & Medicinal Chemistry Letters* (1998) 8(14):1877-1882.

Mombereau et al., "Genetic and Pharmacological Evidence of a Role for GABAB Receptors in the Modulation of Anxiety- and Antidepressant-Like Behavior," *Neuropsychopharmacology* (2004) 29(6):1050-1062.

Mongin et al., "Advances in the directed metallation of azines and diazines (pyridines, pyrimidines, pyrazines, pyridazines, quinolines, benzodiazines and carbolines). Part 1: Metallation of pyridines, quinolines and carbolines," *Tetrahedron* (2001) 57(19):4059-4090.

Montgomery et al., "Isonucleosides. I. Preparation of methyl 2-deoxy-2-(purin-9-yl)arabinofuranosides and methyl 3-deoxy-3-(purin-9-yl)xylofuranosides," *Journal of Organic Chemistry* (1975) 40(13):1923-1927.

Morimoto et al., "Potent and selective ET-A antagonists. 1. Syntheses and structure-activity relationships of *N*-(6-(2-(aryloxy)ethoxy)-4-pyrimidinyl)sulfonamide derivatives," *J Med Chem* (2001) 44(21):3355-3368.

Moschitskii et al., Translation of "reaction of 2,3,5,6-tetrachloro-4-pyridyl-vinyl sulfone with nuleophilic agents," *Khimiya Geterotsiklicheskikh Soedinenii* (1972) pp. 1634-1637, (Translated pp. 1482-1485).

Muller et al., "7-Deaza-2-phenyladenines: Structure-Activity Relationships of Potent A1 Selective adenosine Receptor Antagonists," *J. Med. Chem.* (1990) 33:2822-2828.

Nakazato et al., "Synthesis, SAR and biological activities of CRH1 Receptor: Novel 3- or 4-carbamoyl-1,2,5,6-tetrahydropyridinoquinoline derivative," 24th ACS National Meeting, Aug. 18-22, 2002, Boston, MA. Poster #258.

Nakazato et al., "Design, synthesis and structure-affinity relationships of 4-methylidenepiperidine and 4-aryl-1,2,3,6-tetrahydropyridine derivatives as corticotropin-releasing factor receptor antagonists," *Bioorganic & Medicinal Chemistry* (2000) 8(5):1183-1193.

Nesi et al., "New Difunctionalized 4-Nitroisoxazoles from Alpha-Nitroacetophenone Oxime," *Heterocycles* (1985) 23(6):1465-1469.

Nicewonger et al., "Microwave-assisted acylation of 7-amino-5-aryl-6-cyanopyrido[2,3-d]pyrimidines," *Molecular Diversity* (2003) 7(2-4):247-252.

Norman et al., "Strucutre -activity relationships of a series of pyrrolo(3,2-*d*) pyrimidine derivatives and related compounds as neuropeptide Y5 receptor antagonists" *J. Med. Chem.* (2000) 43(22):4288-4312.

Norman et al., "Strucutre -activity relationships of a series of pyrrolo(3,2-*d*) pyrimidine derivatives and related compounds as neuropeptide Y5 receptor antagonists" *J. Med. Chem.* (2000) 43(22):4288-4312, JM000269T, Supplemental Material, pp. 1-11.

Olesen et al., "The use of bioisosteric groups in lead optimization," *Current Opinion in Drug Discovery & Development* (2001) 4(4):471-478.

Parlow et al., "Design, synthesis, and crystal structure of selective 2-pyridone tissue factor VIIa inhibitors," *J Med Chem* (2003) 46(22):4696-4701.

Paulsen et al., "Darstellung von Bausteinen zur Synthese carbocyclischer furanose-analoga," *Chemische Berichte* (1981) 114(1):346-358.

Pederson, "The impact of obesity on the pathogenesis of non-insulin-dependent diabetes mellitus: a review of current hypotheses," *Diab. Metab. Rev.*, (1989) 5(6):495-509.

Perry et al., "Prospective study of risk factors for development of non-insulin dependent diabetes in middle aged British men," *BMJ* (1995) 310(6979):560-4.

Phillips et al., "Discovery of *N*-[2-[5-[Amino(imino)methyl]-2-hydroxyphenoxyl]-3,5-difluoro-6-[3-(4,5-dihydro-1-methyl-1H-imidazol-2-yl)phenoxy]pyridine-4-yl]-*N*-methylglycine(ZK-807834): A Potent, Selective, and Orally Active Inhibitor of the Blood Coagulation Enzyme Factor Xa," *J. Med. Chem.* (1998) 41(19):3557-3562.

Pomorski "Synthesis of Acids, Derivatives of 4-Hydroxy-1,5-Naphthyridine," *Roczniki Chemii, Ann. Soc. Chim. Polonorum* (1974) 48:321-325.

Potenza et al., "A rapid quantitative bioassay for evaluating the effects of ligands upon receptors that modulate cAMP levels in a melanophore cell line," *Pigment Cell Res.* (1992) 5(6):372-8.

Prasad, et al., "Convenient Methods for the Reduction of Amides, Nitriles, Carboxylic Esters, Acids and Hydroboration of Alkenes Using $NaBH_4/I_2$ System," *Tetrahedron* (1992) 48(22):4623-4628.

Press et al., "Synthesis and SAR of 6-Substituted Purine Derivatives as Novel Selective Positive Inotropes," *J. Med. Chem* (1992) 35(24):4509-4515.

Quintela et al., "6-Dimethylamino 1H-Pyrazolo[3,4-*d*]pyrimidine Derivatives as New Inhibitors of Inflammatory Mediators in Intact Cells," *Bioorganic &Medicinal Chemistry* (2003) 11:863-868.

Quintela et al., "Pyrazolopyrimidines: synthesis, effect on histamine release from rat peritoneal mast cells and cytotoxic activity," *Eur. J. Med. Chem.* (2001) 36:321-332.

Ram et al., "Chemotherapeutic agents. Part XXII. Synthesis of π-deficient pyrimidines as leishmanicides," *Indian Journal of Chemistry, Section B* (1991) 30B(10):962-965.

Reed et al., "In-vivo and in-vitro models of type 2 diabetes in pharmaceutical drug discovery," *Diabetes Obes Metab*, (1999) 1(2):75-86.

Rehwald et al., "Syntheses of thieno[2,3-d]pyrimidines and aminopyrimidines from 2-alkoxy-5-cyano-4-thioxopyrimidine intermediates," *Heterocycles* (1998) 48(6):1157-1167.

*Remington's Pharmaceutical Sciences*, 17th Ed., (1985), Mack Publishing Company, Easton, PA, p. 1418-1419.

*Remington's Pharmaceutical Sciences*, 16th Ed., (1980), Mack Publishing Company, Easton, PA.

Rewcastle, et al., "Tyrosine Kinase Inhibitors. 10. Isomeric 4-[(3-Bromophenyl)amino]pyrido[*d*]pyrimidines are Potent ATP Binding Site Inhibitors of the Tyrosine Kinase Function of the Epidermal Growth Factor Receptor," *J. Med. Chem.* (1996) 39:1823-1835.

Raffel et al., "Diabetes Mellitus," *Principles And Practice Of Medical Genetics*, 3rd Ed. 1:1401-1440 (1996).

Roberts et al., "Peroxy-acid oxidation of N,N-disubstituted aminotetrafluoro-, amino-3-chlorotrifluoro-, and amino-3,5-dichlorodifluoro-pyridines," *Journal of the Chemical Society [Section] C: Organic* (1969) (11):1485-1491.

Roberts et al., "Polychloroaromatic compounds. I. Oxidation of pentachloropyridine and its N,N-disubstituted amino derivatives with peroxyacids," *Journal of the Chemical Society [Section] C: Organic* (1968) (12):1537-1541.

Robins, et al., "Potential Purine Antagonists. IV. Synthesis of Some 9-Methyl-6-substituted-purines," (1957) 79:490-494.

Robev et al., "4-Cyclopropylamino- and 4-cyclobutylamino derivatives of some aryl-substituted 5-cyanopyrimidines," *Doklady Bolgarskoi Akademii Nauk* (1981) 34(12):1677-1680.

Roche, *Bioreversible Carriers in Drug Design, ed.*, American Pharmaceutical Association and Pergamon Press (1987).

Rotwein et al., "Polymorphism in the 5' flanking region of the human insulin gene: a genetic marker for non-insulin-dependent diabetes," *N Engl J Med.* (1983) 308(2):65-71.

Showell et al., "Tetrahydropyridyloxadiazoles: semirigid muscarinic ligands," *J Med Chem* (1991) 34(3):1086-1094.

Silhar et al., "Facile and Efficient Synthesis of 6-(Hydroxymethyl)purines," *Org. Lett.* (2004) 6(19):3225-3228.

Smith et al., "Effects of positive allosteric modulators of the GABAB receptor on cocaine self-administration in rats," *Psychopharmacology* (2004) 173(1-2):105-111.

Silvestri et al., "Novel indolyl aryl sulfones active against HIV-1 carrying NNRTI resistance mutations: synthesis and SAR studies," *J Med Chem* (2003) 46(12):2482-2493.

Steensma et al., "A novel method for the synthesis of aryl sulfones," *Tetrahedron Ltrs* (2001) 42:2281-2283.

Sternfeld et al., "Synthesis and serotonergic activity of 3-[2-(pyrrolidin-1-yl)ethyl]indoles: potent agonist for the h5-HT1D receptor with high selectivity over the h5-HT1B receptor," *J Med Chem* (1999) 42(4):677-690.

Strupczewski et al., "Synthesis and neuroleptic activity of 3-(1-substituted-4-piperidinyl)-1,2-benzisoxazoles," *J Med Chem* (1985) 28(6):761-769.

Suami et al., "Nucleoside analogs. I. Synthesis of 1,3-dihydroxy-2-(6-substituted-9-purinyl)cyclohexane," *Journal of Heterocyclic Chemistry* (1969) 6(5):663-665.

Sugimoto et al., "Preparation of Nitrogen-Containing π—Deficient Heteroaromatic Grignard Reagents: Oxidative Magnesiation of Nitrogen-Containing π-Deficient Halgenoheteroaromatics Using Active Magnesium," *J. Org. Chem.* (2003) 68:2054-2057.

Sugimoto et al., "Lithiation of 1H-Pyrazolo[3,4-*d*]pyrimidine Derivative Using Lithium Alkanetellurolate," *Tetrahedron Letters* (1999) 40:2139-2140.

Terashima et al., "Inhibition of human O6-alkylguanine-DNA alkyltransferase and potentiation of the cytotoxicity of chloroethylnitrosourea by 4(6)-(benzyloxy)-2,6(4)-diamino-5-(nitro or nitroso)pyrimidine derivatives and analogues," *J Med Chem* (1998) 41(4):503-508.

Thompson et al., "$N^6$,9-Disubstituted Adenines: Potent, Selective Antagonists at the A1 Adenosine Receptor," *J. Med. Chem.* (1991) 34:2877-2882.

Thompson et al., "Synthesis and evaluation of 6-(dibromomethyl)-5-nitropyrimidines as potential antitumor agents," *J Med Chem* (1997) 40(5):766-770.

Turck et al., "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines," *Tetrahedron* (2001) 57(21):4489-4505.

Urgaonkar et al., "Pd/P(*i*-BuNCH$_2$CH$_2$)$_3$N: an efficient catalyst for Suzuki cross-coupling of aryl bromides and chlorides with arylboronic acids," *Tetrahedron Letters* (2002) 43(49):8921-8924.

Urwyler et al., "*N,N'*—Dicyclopentyl-2-methylsulfanyl-5-nitropyrimidine-4,6-diamine (GS39783) and structurally related compounds: Novel allosteric enhancers of γ-aminobutyric acidB receptor function," *Journal of Pharmacology and Experimental Therapeutics* (2003) 307(1):322-330.

Vaughan et al., "The Reformatsky Reaction. I. Zinc and Ethyl Alpha-Bromoisobutyrate," *Dept. of Chem., The Univ. of Michigan*, Ann Arbor, MI., (1964) 30:1790-1795.

Vice,et al., "Concise Formation of 4-Benzyl Piperidines and Related Derivatives Using a Suzuki Protocol," *J. Org. Chem.* (2001) 66:2487-2492.

Vice,et al., "Concise Formation of 4-Benzyl Piperidines and Related Derivatives Using a Suzuki Protocol," *J. Org. Chem.* (2001) 66:2487-2492, Supporting Information, pp. S1-A32.

Wang et al., "Improving the oral efficacy of CNS drug candidates: discovery of highly orally efficacious piperidinyl piperidine M2 muscarinic receptor antagonists," *J Med Chem* (2002) 45(25):5415-5418.

Wells et al., "Regioselective nucleophilic substitutions of fluorobenzene derivatives," *Tetrahedron Letters* (1996) 37(36):6439-6442.

Werbel et al., "Synthesis and antimalarial effects of 5,6-dichloro-2-[(4-[[ [4—(diethylamino) 1-methylbutyl]amino [[-6-methyl-2-pyrimidinyl)amino] benzimidazole and related benzimidazoles and I,*H*-Imidazo[4,5-*b*]pyridines," *J. Het. Chem* (1973) vol. 10, 363-382.

Wilson et al., "Microwave-assisted synthesis of 2-aminoquinolines," *Tetrahedron Letters* (2002) 43(4):581-583.

Wolfe et al., "Scope and limitations of the Pd/BINAP-catalyzed amination of aryl bromides," *J Org Chem* (2000) 65(4):1144-1157.

Wolfe et al., "Simple, efficient catalyst system for the palladium-catalyzed amination of aryl chlorides, bromides, and triflates," *J Org Chem* (2000) 65(4):1158-1174.

Wolter et al., "Copper-Catalyzed Coupling of Aryl Iodides with Aliphatic Alcohols," *Organic Letters* (2002) 4(6):973-976.

Wolter et al., "Copper-Catalyzed Coupling of Aryl Iodides with Aliphatic Alcohols," *Organic Letters* (2002) 4(6):973-976, Supporting Information, pp. S1-S16.

Wu et al., "One-Pot Two-Step Microwave-Assisted Reaction in Constructing 4,5-Disubstituted Pyrazolopyrimidines," *Org. Lett.*, (2003) 5(20):3587-3590.

Yarovenko et al., "New method for the preparation of 5-amino-1,2,4-oxadiazoles," *Bull Acad Sci, USSR Div Chem Sci*, (1991) 40:1924.

Yoon et al., "Reaction of Dissobutylaluminum Hydride with Selected Organic Compounds Containing Representative Functional Groups," *J. Org. Chem.* (1985) 50:2443-2450.

Zamponi et al., "Unique structure-activity relationship for 4-isoxazolyl-1,4-dihydropyridines," *J Med Chem* (2003) 46:87-96.

Zamponi et al., "Unique structure-activity relationship for 4-isoxazolyl-1,4-dihydropyridines," *J Med Chem* (2003), Supporting Information., pp. 1-31.

Zhang, et al., "Preparation of 1-(Tri-n-Butylstannyl) Furanoid Glycals and Their Use in Palladium-Mediated Coupling Reactions," *Tetrahedron Letters* (1993) 34(10):1571-1574.

Zhu et al., Synthesis and mode of action of (125)I- and (3)H-labeled thieno[2,3-c]pyridine antagonists of cell adhesion molecule expression, *J Org Chem.* (2002) 67(3):943-8.

Accession No. 2003:2415108 Chemcats, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1.

Accession No. 2003:2415906 Chemcats, Interbioscreen Compound Library, Chemical Name: 1H-Pyrazolo[3,4-d]pyrimidine-4-amine, N-cyclohexyl-1-1-(4-methylphenyl)-, XP-002311325, 2003, CAS Registry No. 393844-89-8.

Accession No. 2003:2416398 Chemcats, Interbioscreen Compound Library, Chemical Name: 1H-Pyrazolo[3,4-d]pyrimidine-4-amine, N-cyclohexyl-1-1-(2,4-dimethylphenyl)-N-methyl-, XP-002311324, 2003, CAS Registry No. 393844-91-2.

Accession No. 2003:2417080 Chemcats, Interbioscreen Compound Library, Chemical Name: 1H-Pyrazolo[3,4-d]pyrimidine-4-amine, N-cyclohexyl-N-methyl-1-phenyl)-, XP-002311323, 2003, CAS Registry No. 393844-87-6.

Cover Sheet and 54 Compounds—CAS Registry file (23 pp.), 2001.

Cover Sheet and 18 Compounds—CAS Registry file (9 pp.), 2004.

Cover Sheet and 2534 Compounds—CAS Registry and ChemCats file (817pp.), 2006.

Cover Sheet and 1185 Compounds—CAS Registry and ChemCats Files (391pp.), 2005.

23 Compounds—ChemCats File (11pp.), 2003.

Greene et al., *Protective Groups in Organic Synthesis*, 3rd Ed., John Wiley & Sons, New York (1999).

Remington, *The Science and Practice of Pharmacy*, 20th Ed., Lippincott Williams & Wilkins (2000).

Oae, *Organic Chemistry of Sulfur*, Ed., Plenum Press: New York (1977).

Chu et al., "A role for B-cell-expressed G protein receptor 119 in glycemic control by enhancing glucose-dependent insulin release", *Endocrinology*, 148:2601-2609 (2007).

Overton et al., Deorphanization of a G protein-coupled receptor for oleoylethanolamide and its use in the discovery of small-molecule hypophagic agents, *Cell Metabolism*, 3:167-175 (2006).

Soga et al., Lysophosphatidylcholine enhances glucose-dependent insulin secretion via an orphan G-protein-coupled receptor, *Biochem. Biophys. Res. Commun.*, 326:744-751 (2005).

Abstract #107, p. 56, *Toward Understanding Islet Biology*, Jan. 21, 2003-Jan. 26, 2003, Keystone, Colorado.

Abstract #112, p. 42, *Diabetes Mellitus: Molecular Mechanisms Genetics and New Therapies*, Jan. 27, 2005-Feb. 2, 2005, Keystone, Colorado.

Abstract #228, p. 54, *Diabetes Mellitus: Molecular Mechanisms Genetics and New Therapies*, Jan. 27, 2005-Feb. 2, 2005, Keystone, Colorado.

Abstract #117 & Poster, *Diabetes: Molecular Genetics, Signaling Pathways and Integrated Physiology*, Jan. 14, 2007-Jan. 19, 2007, Keystone, Colorado.

Abstract #230 & Poster, *Diabetes: Molecular Genetics, Signaling Pathways and Integrated Physiology*, Jan. 14, 2007-Jan. 19, 2007, Keystone, Colorado.

Fyfe et al., *Diabetes*, 56 (Supplement 1):A142 (Abstract #532-P) (2007).

Chu et al., "A role for intestinal endocrine cell-expressed GPR119 in glycemic control by enhancing GLP-1 and GIP release", Arena Pharmaceuticals pre-publication document.

Hocek et al., "An efficient synthesis of 2-substituted 6-methylpurine bases and nucleosides by Fe- or Pd-catalyzed cross-coupling reactions of 2,6-dichloropurines", *Journal of Organic Chemistry*, 68:5773-6 (2003).

Lin et al., "Synthesis and antitumor activity of halogen-substituted 4-(3,3-dimethyl-1-1triazeno)quinolines", *Journal of Medicinal Chemistry*, 21(3):268-72 (1978).

Litvinov et al., "Naphthyridines. Structure, physicochemical properties and general methods of synthesis", *Russian Chemical Reviews*, 69(3):201-220 (2000).

\* cited by examiner

TRISUBSTITUTED ARYL AND HETEROARYL DERIVATIVES AS MODULATORS OF METABOLISM AND THE PROPHYLAXIS AND TREATMENT OF DISORDERS RELATED THERETO

CROSS REFERENCE TO RELATED APPLICATIONS

This application claims the benefit of U.S. Ser. No. 60/486,728, filed Jul. 11, 2003 and U.S. Ser. No. 60/487,370, filed Jul. 14, 2003, the disclosures of each of which are herein incorporated by reference in their entireties.

FIELD OF THE INVENTION

The present invention relates to certain trisubstituted aryl and heteroaryl derivatives that are modulators of glucose metabolism. Accordingly, compounds of the present invention are useful in the prophylaxis or treatment of metabolic disorders and complications thereof, such as, diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either don't produce insulin or can't efficiently use the insulin they produce; therefore, they can't move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

People with IDDM, which accounts for about 5% to 10% of those who have diabetes, don't produce insulin and therefore must inject insulin to keep their blood glucose levels normal. IDDM is characterized by low or undetectable levels of endogenous insulin production caused by destruction of the insulin-producing β cells of the pancreas, the characteristic that most readily distinguishes IDDM from NIDDM. IDDM, once termed juvenile-onset diabetes, strikes young and older adults alike.

Approximately 90 to 95% of people with diabetes have Type II (or NIDDM). NIDDM subjects produce insulin, but the cells in their bodies are insulin resistant: the cells don't respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NIDDM; many NIDDM patients have normal or even elevated blood insulin levels, while other NIDDM patients have inadequate insulin production (Rotwein, R. et al. *N. Engl. J. Med.* 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically inapparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. Emery and Rimoin's Principles and Practice of Medical Genetics $3^{rd}$ Ed. 1:1401-1402 (1996)).

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity and diabetes are among the most common human health problems in industrialized societies. In industrialized countries a third of the population is at least 20% overweight. In the United States, the percentage of obese people has increased from 25% at the end of the 1970s, to 33% at the beginning the 1990s. Obesity is one of the most important risk factors for NIDDM. Definitions of obesity differ, but in general, a subject weighing at least 20% more than the recommended weight for his/her height and build is considered obese. The risk of developing NIDDM is tripled in subjects 30% overweight, and three-quarters with NIDDM are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increase insulin secretion balances insulin resistance and protects patients from hyperglycemia (Le Stunff, et al. *Diabetes* 43, 696-702 (1989)). However, after several decades, β cell function deteriorates and non-insulin-dependent diabetes develops in about 20% of the obese population (Pederson, P. *Diab. Metab. Rev.* 5, 505-509 (1989)) and (Brancati, F. L., et al., *Arch. Intern. Med.* 159, 957-963 (1999)). Given its high prevalence in modern societies, obesity has thus become the leading risk factor for NIDDM (Hill, J. O., et al., *Science* 280, 1371-1374 (1998)). However, the factors which predispose a fraction of patients to alteration of insulin secretion in response to fat accumulation remain unknown.

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25-30 kg/m$^2$, and obesity as a BMI greater than 30 kg/m$^2$ (see TABLE below). There are problems with this definition in that it does not take into account the proportion of body mass that is muscle in relation to fat (adipose tissue). To account for this, obesity can also be defined on the basis of body fat content: greater than 25% and 30% in males and females, respectively.

| CLASSIFICATION OF WEIGHT BY BODY MASS INDEX (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL™) and Sibutramine. Orlistat (a lipase inhibitor) inhibits fat absorption directly and tends to produce a high incidence of unpleasant (though relatively harmless) side-effects such as diarrhea. Sibutramine (a mixed 5-HT/noradrenaline reuptake inhibitor) can increase blood pressure and heart rate in some patients. The serotonin releaser/reuptake inhibitors fenfluramine (Pondimin™) and dexfenfluramine (Redux™) have been reported to decrease food intake and body weight over a prolonged period (greater than 6 months). However, both products were withdrawn after reports of preliminary evidence of heart valve abnormalities associated with their use. Accordingly, there is a need for the development of a safer anti-obesity agent.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM and coronary heart disease and the potential value of an integrated approach to the prevention of these conditions based on the prevention of these conditions based on the prevention of obesity (Perry, I. J., et al., *BMJ* 310, 560-564 (1995)).

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

SUMMARY OF THE INVENTION

The present invention is drawn to compounds which bind to and modulate the activity of a GPCR, referred to herein as RUP3, and uses thereof. The term RUP3 as used herein includes the human sequences found in GeneBank accession numbers XM_066873 and AY288416, and naturally-occurring allelic variants, mammalian orthologs, and recombinant mutants thereof. A preferred human RUP3 for use in screening and testing of the compounds of the invention is provided in the nucleotide sequence of Seq. ID. No:1 and the corresponding amino acid sequence in Seq. ID. No:2.

One aspect of the present invention encompasses trisubstituted aryl and heteroaryl derivatives as shown in Formula (I):

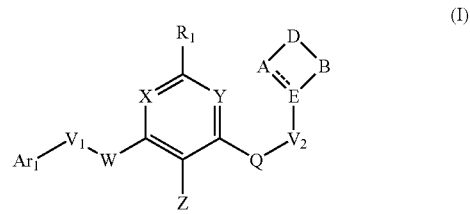

or a pharmaceutically acceptable salt, hydrate or solvate, or N-oxide thereof;

wherein:

A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;

D is O, S, S(O), S(O)$_2$, CR$_2$R$_3$ or N—R$_2$;

E is N, C or CR$_4$;

---is a single bond when E is N or CR$_4$, or a double bond when E is C;

$V_1$ is selected from the group consisting of $C_{1-3}$ alkylene, ethynylene and $C_{1-2}$ heteroalkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or $V_1$ is a bond;

$V_2$ is $C_{3-6}$ cycloalkylene or $C_{1-3}$ alkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or $V_2$ is a bond;

W is NR$_5$, O, S, S(O) or S(O)$_2$; or W is absent;

Q is NR$_6$, O, S, S(O) or S(O)$_2$;

X is N or CR$_7$;

Y is N or CR$_8$;

Z is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$- alkoxy, carboxamide, carboxy, cyano, $C_{3-7}$ cycloalkyl, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxycarbamimidoyl, hydroxylamino, nitro and tetrazolyl, wherein $C_{1-8}$ alkyl, $C_{3-7}$ cycloalkyl, and heterocyclic are each optionally substituted with 1, 2, 3 or 4 groups selected from the group consisting of $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro, and wherein said $C_{1-7}$ alkyl is optionally substituted with amino; or Z is a group of Formula (A):

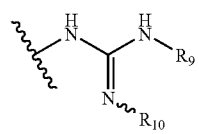

(A)

wherein:

$R_9$ is H, $C_{1-8}$ alkyl or $C_{3-7}$ cycloalkyl; and $R_{10}$ is H, nitro or nitrile;

$Ar_1$ is aryl or heteroaryl each optionally substituted with $R_{11}$, $R_{12}$, $R_{13}$, $R_{14}$, and $R_{15}$; wherein $R_{11}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein $C_{1-5}$ acyl, $C_{1-6}$ acylsulfonamide, $C_{1-4}$ alkoxy, $C_{1-8}$ alkyl, $C_{1-4}$ alkylamino, $C_{1-4}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, wherein said $C_{1-7}$ alkyl and $C_{1-4}$ alkylcarboxamide are each optionally substituted with 1 to 5 substituents selected from the group consisting of $C_{1-4}$ alkoxy and hydroxy; or $R_{11}$ is a group of Formula (B):

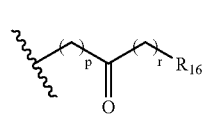

(B)

wherein:

"p" and "r" are each independently 0, 1, 2 or 3; and $R_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{12}$, $R_{13}$, $R_{14}$, and $R_{15}$ are each independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent groups selected from the group consisting of $R_{12}$, $R_{13}$, $R_{14}$ and $R_{15}$ together with the atoms to which they are attached form a 5-, 6- or 7-membered cycloalkyl, cycloalkenyl or heterocyclic group fused with $Ar_1$, wherein the 5-, 6- or 7-membered group is optionally substituted with halogen;

$R_1$, $R_7$ and $R_8$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;

$R_2$ is selected from the group consisting of $C_{1-8}$ alkyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo- $C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (C):

wherein:

$R_{17}$ is H, $C_{1-8}$ alkyl, $C_{3-7}$ cycloalkyl, aryl, heteroaryl or $OR_{19}$; and $R_{18}$ is F, Cl, Br, CN or $NR_{20}R_{21}$; where $R_{19}$ is H, $C_{1-8}$ alkyl or $C_{3-7}$ cycloalkyl, and $R_{20}$ and $R_{21}$ are each independently H, $C_{1-8}$ alkyl, $C_{3-7}$ cycloalkyl, aryl or heteroaryl; or $R_2$ is a group of Formula (D):

wherein:

G is:

i) —C(O)—, —C(O)NR$_{23}$—, —C(O)O—, —OC(O)NR$_{23}$—, —NR$_{23}$C(O)O—, —OC(O)—, —C(S)—, —C(S)NR$_{23}$—, —C(S)O—, —OC(S)—, —CR$_{23}$R$_{24}$—, —O—, —S—, —S(O)— or —S(O)$_2$— when D is CR$_2$R$_3$, or ii) —CR$_{23}$R$_{24}$C(O)—, —C(O)—, —CR$_{23}$R$_{24}$C(O)NR$_{25}$—, —C(O)NR$_{23}$—, —C(O)O—, —C(S)—, —C(S)NR$_{23}$—, —C(S)O—, —CR$_{23}$R$_{24}$—, —S(O)$_2$—, or a bond when D is NR$_2$, wherein $R_{23}$, $R_{24}$ and $R_{25}$ are each independently H or $C_{1-8}$ alkyl; and $R_{22}$ is H, $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$R_3$ is H, $C_{1-8}$ alkyl, $C_{1-4}$ alkoxy or hydroxyl; and $R_4$, $R_5$ and $R_6$ are each independently H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl.

One aspect of the present invention pertains to pharmaceutical compositions comprising at least one compound of the present invention and a pharmaceutically acceptable carrier.

One aspect of the present invention pertains to methods for the treatment of a metabolic-related disorder in an individual comprising administering to the individual in need of such treatment a therapeutically effective amount of a compound of the present invention or a pharmaceutical composition thereof.

One aspect of the present invention pertains to methods of decreasing food intake of an individual comprising administering to the individual in need thereof a therapeutically effective amount of a compound of the present invention or pharmaceutical composition thereof.

One aspect of the present invention pertains to methods of inducing satiety in an individual comprising administering to the individual in need thereof a therapeutically effective amount of a compound of the present invention or pharmaceutical composition thereof.

One aspect of the present invention pertains to methods of controlling or decreasing weight gain of an individual comprising administering to the individual in need thereof a therapeutically effective amount of a compound of the present invention or pharmaceutical composition thereof.

One aspect of the present invention pertains to methods of modulating a RUP3 receptor in an individual comprising contacting the receptor with a compound of the present invention. In some embodiments, the compound is an agonist for the RUP3 receptor. In some embodiments, the modulation of the RUP3 receptor is the treatment of a metabolic-related disorder.

Some embodiments of the present invention include a method of modulating a RUP3 receptor in an individual comprising contacting the receptor with a compound of the present invention wherein the modulation of the RUP3 receptor reduces food intake of the individual.

Some embodiments of the present invention include a method of modulating a RUP3 receptor in an individual comprising contacting the receptor with a compound of the present invention wherein the modulation of the RUP3 receptor induces satiety in the individual.

Some embodiments of the present invention include a method of modulating a RUP3 receptor in an individual comprising contacting the receptor with a compound of the present invention wherein the modulation of the RUP3 receptor controls or reduces weight gain of the individual.

One aspect of the present invention pertains to use of a compound of the present invention for production of a medicament for use in the treatment of a metabolic-related disorder.

One aspect of the present invention pertains to use of a compound of the present invention for production of a medicament for use in decreasing food intake in an individual.

One aspect of the present invention pertains to use of a compound of the present invention for production of a medicament for use of inducing satiety in an individual.

One aspect of the present invention pertains to use of a compound of the present invention for production of a medicament for use in controlling or decreasing weight gain in an individual.

One aspect of the present invention pertains to a compound of the present invention for use in a method of treatment of the human or animal body by therapy.

One aspect of the present invention pertains to a compound of the present invention for use in a method of treatment of a metabolic-related disorder of the human or animal body by therapy.

One aspect of the present invention pertains to a compound of the present invention for use in a method of decreasing food intake of the human or animal body by therapy.

One aspect of the present invention pertains to a compound of the present invention for use in a method of inducing satiety of the human or animal body by therapy.

One aspect of the present invention pertains to a compound of the present invention for use in a method of controlling or decreasing weight gain of the human or animal body by therapy.

Some embodiments of the present invention pertain to methods wherein the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

In some embodiments the individual is a mammal. In some embodiments the mammal is a human.

In some embodiments, the metabolic-related disorder is hyperlipidemia, type 1 diabetes, type 2 diabetes mellitus, idiopathic type 1 diabetes (Type 1b), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertryglyceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

In some embodiments, the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments, the metabolic-related disorder is type II diabetes. In some embodiments, the metabolic-related disorder is hyperglycemia. In some embodiments, the metabolic-related disorder is hyperlipidemia. In some embodiments, the metabolic-related disorder is hypertriglyceridemia. In some embodiments, the metabolic-related disorder is type I diabetes. In some embodiments, the metabolic-related disorder is dyslipidemia. In some embodiments, the metabolic-related disorder is syndrome X.

One aspect of the present invention pertains to a method of producing a pharmaceutical composition comprising admixing at least one compound, as described herein, and a pharmaceutically acceptable carrier.

This application is related to two U.S. Provisional Patent Applications, Ser. No. 60/486,728 filed Jul. 11, 2003; and 60/487,370 filed Jul. 14, 2003, both which are incorporated by reference in their entirety.

Applicant reserves the right to exclude any one or more of the compounds from any of the embodiments of the invention. Applicant additionally reserves the right to exclude any disease, condition or disorder from any of the embodiments of the invention.

DETAILED DESCRIPTION OF THE INVENTION

Definitions

Figure 1:
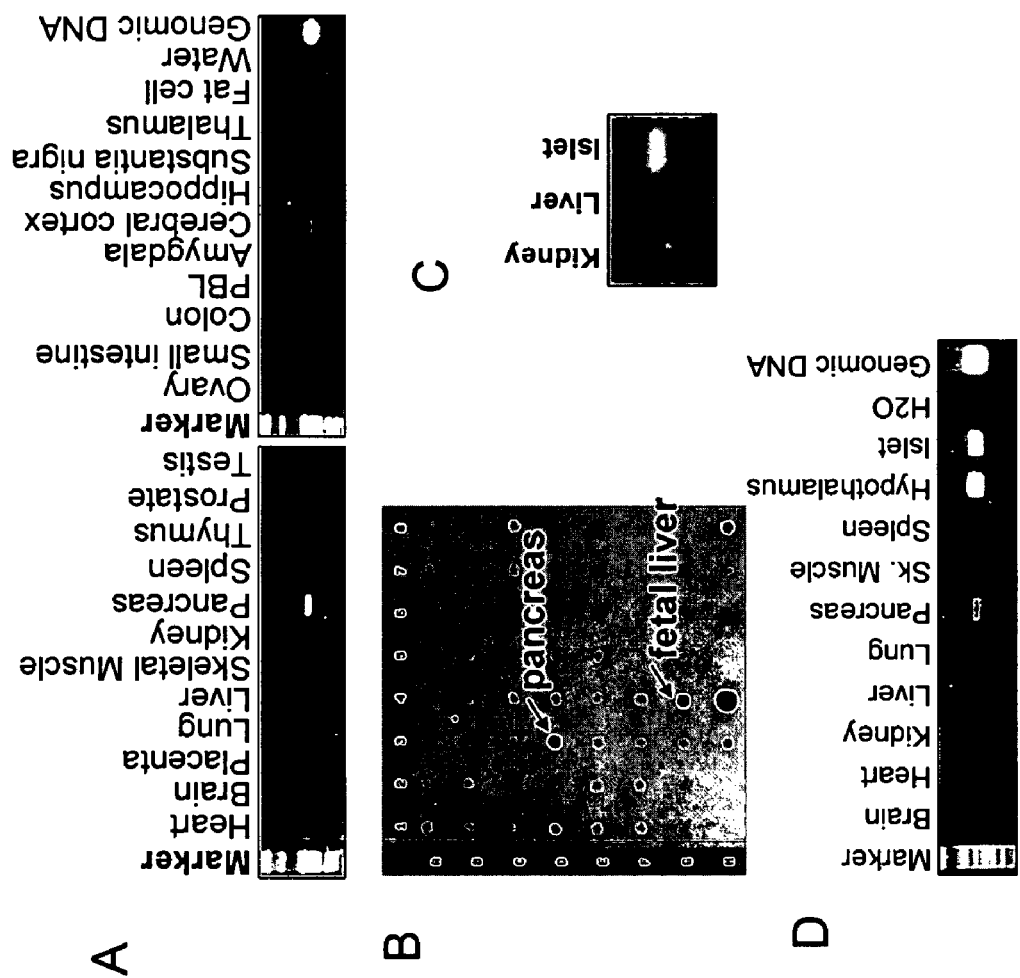
FIG. 1A shows RT-PCR analysis of RUP3 expression in human tissues. A total of twenty-two (22) human tissues were analyzed.
FIG. 1B shows the cDNA Dot-Blot analysis of RUP3 expression in human tissues.
FIG. 1C shows analysis of RUP3 by RT-PCR with isolated human pancreatic islets of Langerhans.
FIG. 1D shows analysis of RUP3 expression with cDNAs of rat origin by RT-PCR.

The scientific literature that has evolved around receptors has adopted a number of terms to refer to ligands having various effects on receptors. For clarity and consistency, the following definitions will be used throughout this patent document.

AGONISTS shall mean moieties that interact and activate the receptor, such as the RUP3 receptor and initiates a physiological or pharmacological response characteristic of that receptor. For example, when moieties activate the intracellular response upon binding to the receptor, or enhance GTP binding to membranes.

AMINO ACID ABBREVIATIONS used herein are set out in TABLE 1:

TABLE 1

| ALANINE | ALA | A |
|---|---|---|
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |
| ALANINE | ALA | A |

The term ANTAGONISTS is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

Chemical Group, Moiety or Radical:

The term "$C_{1-5}$ acyl" denotes a $C_{1-5}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-5}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{1-6}$ acylsulfonamide" refers to a $C_{1-6}$ acyl attached directly to the nitrogen of the sulfonamide, wherein the definitions for $C_{1-6}$ acyl and sulfonamide have the same meaning as described herein, and a $C_{1-6}$ acylsulfonamide can be represented by the following formula:

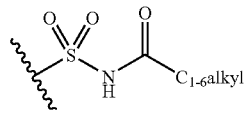

Some embodiments of the present invention are when acyl-sulfonamide is a $C_{1-5}$ acylsulfonamide, some embodiments are $C_{1-4}$ acylsulfonamide, some embodiments are $C_{1-3}$ acylsulfonamide, and some embodiments are $C_{1-2}$ acylsulfonamide. Examples of an acylsulfonamide include, but not limited to, acetylsulfamoyl [—S(=O)$_2$NHC(=O)Me], propionylsulfamoyl [—S(=O)$_2$NHC(=O)Et], isobutyryl-sulfamoyl, butyrylsulfamoyl, 2-methyl-butyrylsulfamoyl, 3-methyl-butyrylsulfamoyl, 2,2-dimethyl-propionylsulfamoyl, pentanoylsulfamoyl, 2-methyl-pentanoylsulfamoyl, 3-methyl-pentanoylsulfamoyl, 4-methyl-pentanoylsulfamoyl, and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "$C_{1-4}$ alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "alkyl" denotes a straight or branched carbon radical containing 1 to 8 carbons, some embodiments are 1 to 7 carbons, some embodiments are 1 to 6 carbons, some embodiments are 1 to 3 carbons, and some embodiments are 1 or 2 carbons. Examples of an alkyl include, but not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term $C_{1-6}$ or $C_{1-4}$ "alkylcarboxamido" or "alkylcarboxamide" denotes a single $C_{1-6}$ or $C_{1-4}$ alkyl group attached to the nitrogen or carbon of an amide group, wherein alkyl has the same definition as found herein. The alkylcarboxamide may be represented by the following:

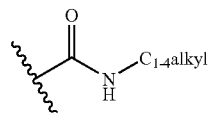 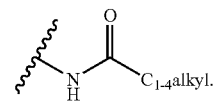

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —CH$_2$—, —CH$_2$CH$_2$—, —CH$_2$CH$_2$CH$_2$—, and the like. In some embodiments, $C_{1-3}$ alkylene refers to —CH—, —CHCH$_2$—, —CHCH$_2$CH$_2$—, and the like wherein these examples relate generally to "A".

The term "$C_{1-4}$ alkylsulfinyl" denotes a $C_{1-4}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-4}$ alkylsuffonamide" refers to the groups

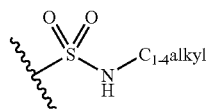 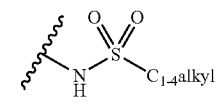

wherein $C_{1-4}$ alkyl has the same definition as described herein.

The term "$C_{1-4}$ alkylsulfonyl" denotes a $C_{1-4}$ alkyl radical attached to a sulfone radical of the formula: —S(O)$_2$— wherein the alkyl radical has the same definiti+on as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butyl, and the like.

The term "$C_{1-4}$ alkylthio" denotes a $C_{1-4}$ alkyl radical attached to a sulfide of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{1-4}$ alkylthiocarboxamide" denotes a thioamide of the following formulae:

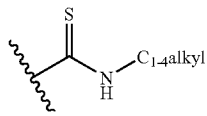 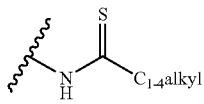

wherein $C_{1-4}$ alkyl has the same definition as described herein.

The term "$C_{1-4}$ alkylthioureyl" denotes the group of the formula: —NC(S)N— wherein one are both of the nitrogens are substituted with the same or different $C_{1-4}$ alkyl groups and alkyl has the same definition as described herein. Examples of an alkylthioureyl include, but not limited to, $CH_3NHC(S)NH—$, $NH_2C(S)NCH_3—$, $(CH_3)_2N(S)NH—$, $(CH_3)_2N(S)NH—$, $(CH_3)_2N(S)NCH_3—$, $CH_3CH_2NHC(S)NH—$, $CH_3CH_2NHC(S)NCH_3—$, and the like.

The term "$C_{1-4}$ alkylureyl" denotes the group of the formula: —NC(O)N— wherein one are both of the nitrogens are substituted with the same or different $C_{1-4}$ alkyl group wherein alkyl has the same definition as described herein. Examples of an alkylureyl include, but not limited to, $CH_3NHC(O)NH—$, $NH_2C(O)NCH_3—$, $(CH_3)_2N(O)NH—$, $(CH_3)_2N(O)NH—$, $(CH_3)_2N(O)NCH_3—$, $CH_3CH_2NHC(O)NH—$, $CH_3CH_2NHC(O)NCH_3—$, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" denotes the group —$NH_2$.

The term "$C_{1-4}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —$CH_2$—, —$CH_2CH_2$— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. The example is N-phenylcarboxamide.

The term "arylureyl" denotes the group —NC(O)N— where one of the nitrogens are substituted with an aryl.

The term "benzyl" denotes the group —$CH_2C_6H_5$.

The term "carbamimidoyl" refers to a group of the following chemical formula:

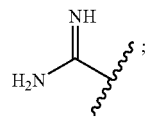

and in some embodiments, one or both hydrogens are replaced with another group. For example, one hydrogen can be replaced with a hydroxyl group to give a N-hydroxycarbamimidoyl group, or one hydrogen can be replaced with an alkyl group to give N-methylcarbamimidoyl, N-ethylcarbamimidoyl, N-propylcarbamimidoyl, N-butylcarbamimidoyl, and the like.

The term "carbo-$C_{1-6}$-alkoxy" refers to a $C_{1-6}$ alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neopentoxy, carbo-n-hexyloxy, and the like.

The term "carboxamide" refers to the group —$CONH_2$.

The term "carboxy" or "carboxyl" denotes the group —$CO_2H$; also referred to as a carboxylic acid group.

The term "cyano" denotes the group —CN.

The term "$C_{3-7}$ cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "$C_{3-7}$ cycloalkyl" denotes a saturated ring radical containing 3 to 6 carbons; some embodiments contain 3 to 5 carbons; some embodiments contain 3 to 4 carbons. Examples include cyclopropyl, cyclobutyl, cyclopentyl, cyclopenyl, cyclohexyl, cycloheptyl and the like.

The term "$C_{3-6}$ cycloalkylene" refers to a divalent cycloalkyl radical, where cycloalkyl is as defined herein, containing 3 to 6 carbons; some embodiments contain 3 to 5 carbons; some embodiments contain 3 to 4 carbons. In some embodiments, the two bonding groups are on the same carbon, for example:

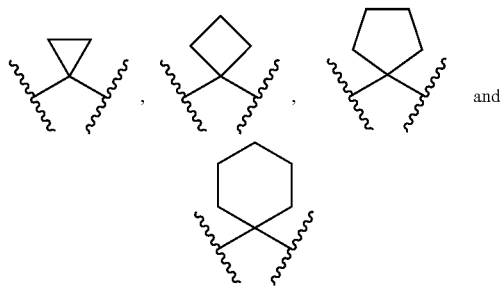

In some embodiments, the two bonding groups are on different carbons.

The term "$C_{4-8}$ diacylamino" denotes an amino group bonded with two acyl groups defined herein wherein the acyl groups may be the same or different, such as:

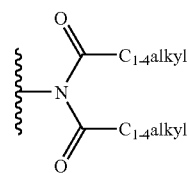

Examples of $C_{4-8}$ diacylamino groups include, but limited to, diacetylamino, dipropionylamino, acetylpropionylamino and the like.

The term "$C_{2-6}$ dialkylamino" denotes an amino substituted with two of the same or different alkyl radicals wherein alkyl radical has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like. Some embodiments are "$C_{2-4}$ dialkylamino."

The term "$C_{1-4}$ dialkylcarboxamido" or "$C_{1-4}$ dialkylcarboxamide" denotes two alkyl radicals, that are the same or different, attached to an amide group, wherein alkyl has the same definition as described herein. A $C_{1-4}$ dialkylcarboxamido may be represented by the following groups:

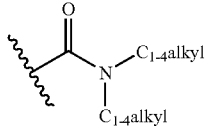 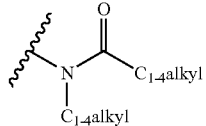

wherein $C_{1-4}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "$C_{2-6}$ dialkylsulfonamide" refers to one of the following groups shown below:

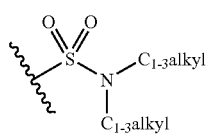 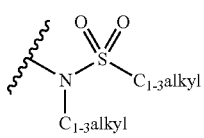

wherein $C_{1-3}$ has the same definition as described herein, for example but not limited to, methyl, ethyl, n-propyl, isopropyl, and the like.

The term "$C_{2-6}$ dialkylthiocarboxamido" or "$C_{2-6}$ dialkylthiocarboxamido" denotes two alkyl radicals, that are the same or different, attached to a thioamide group, wherein alkyl has the same definition as described herein. A $C_{1-4}$ dialkylthiocarboxamido may be represented by the following groups:

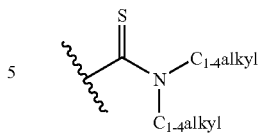 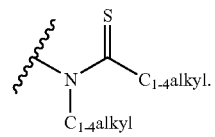

Examples of a dialkylthiocarboxamide include, but not limited to, N,N-dimethylthiocarboxamide, N-methyl-N-ethylthiocarboxamide and the like.

The term "$C_{2-6}$ dialkylsulfonylamino" refers to an amino group bonded with two $C_{1-3}$ alkylsulfonyl groups as defined herein.

The term "ethynylene" refers to the carbon-carbon triple bond group as represented below:

The term "formyl" refers to the group —CHO.
The term "guanidine" refers to a group of the following chemical formula:

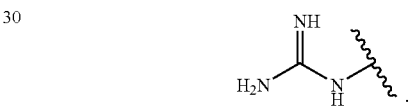

The term "$C_{1-4}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy and the like.

The term "$C_{1-4}$ haloalkyl" denotes an $C_{1-4}$ alkyl group, defined herein, wherein the alkyl is substituted with one halogen up to fully substituted and a fully substituted $C_{1-4}$ haloalkyl can be represented by the formula $C_nL_{2n+1}$ wherein L is a halogen and "n" is 1, 2, 3 or 4; when more than one halogen is present then they may be the same or different and selected from the group consisting of F, Cl, Br and I, preferably F. Examples of $C_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "$C_{1-4}$ haloalkylcarboxamide" denotes an alkylcarboxamide group, defined herein, wherein the alkyl is substituted with one halogen up to fully substituted represented by the formula $C_nL_{2n+1}$ wherein L is a halogen and "n" is 1, 2, 3 or 4. When more than one halogen is present they may be the same or different and selected from the group consisting of F, Cl, Br and I, preferably F.

The term "$C_{1-4}$ haloalkylsulfinyl" denotes a haloalkyl radical attached to a sulfoxide group of the formula: —S(O)— wherein the haloalkyl radical has the same definition as described herein. Examples include, but not limited to, trifluoromethylsulfinyl, 2,2,2-trifluoroethylsulfinyl, 2,2-difluoroethylsulfinyl and the like.

The term "$C_{1-4}$ haloalkylsulfonyl" denotes a haloalkyl radical attached to a sulfone group of the formula: —S(O)$_2$— wherein haloalkyl has the same definition as described herein.

Examples include, but not limited to, trifluoromethylsulfonyl, 2,2,2-trifluoroethylsulfonyl, 2,2-difluoroethylsulfonyl and the like.

The term "$C_{1-4}$ haloalkylthio" denotes a haloalkyl radicaol directly attached to a sulfur wherein the haloalkyl has the same meaning as described herein. Examples include, but not limited to, trifluoromethylthio (i.e., $CF_3S—$), 1,1-difluoroethylthio, 2,2,2-trifluoroethylthio and the like.

The term "halogen" or "halo" denotes to a fluoro, chloro, bromo or iodo group.

The term "$C_{1-2}$ heteroalkylene" refers to a $C_{1-2}$ alkylene bonded to a heteroatom selected from O, S, S(O), $S(O)_2$ and NH. Some represented examples include, but not limited to, the groups of the following formulae:

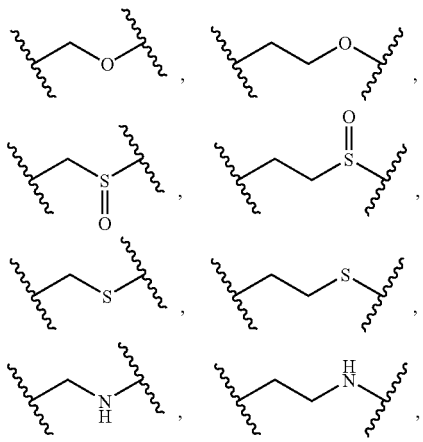

and the like.

The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, $C_{1-4}$ acyl or $C_{1-4}$ alkyl. Examples of heteroaryl groups include, but not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH, examples include, but not limited to, pyrrole, indole, and the like. Other examples include, but not limited to, those in TABLE 2A, TABLE 4, and the like.

The term "heterocyclic" denotes a non-aromatic carbon ring (i.e., cycloalkyl or cycloalkenyl as defined herein) wherein one, two or three ring carbons are replaced by a heteroatom selected from, but not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like. Additional examples of heterocyclic groups are shown in TABLES 2B, 2C, 2D, 2E, 2F and 2G, infra.

The term "heterocyclic-carbonyl" denotes a heterocyclic group, as defined herein, directly bonded to the carbon of a carbonyl group (i.e., C=O). In some embodiments, a ring nitrogen of the heterocyclic group is bonded to the carbonyl group forming an amide. Examples include, but not limited to,

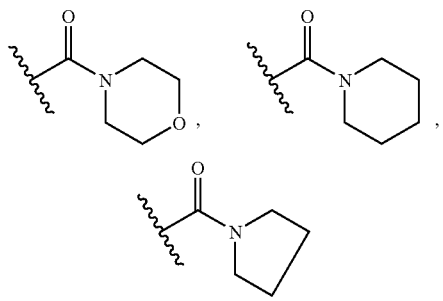

and the like.

In some embodiments, a ring carbon is bonded to the carbonyl group forming a ketone group. Examples include, but not limited to,

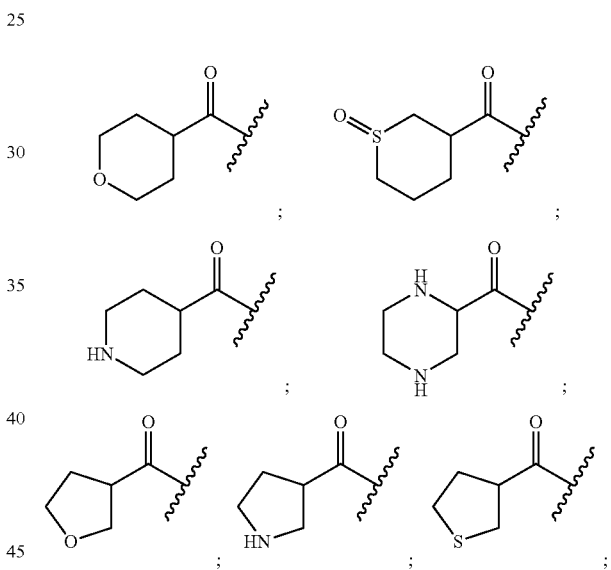

and the like.

The term "heterocyclic-oxy" refers to a heterocyclic group, as defined herein, that is directly bonded to an oxygen atom. Examples include the following:

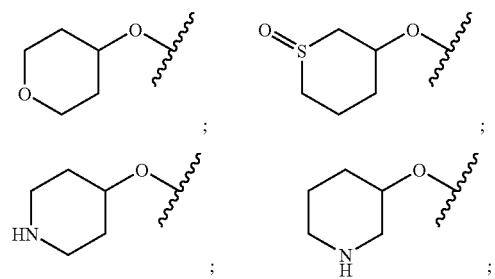

-continued

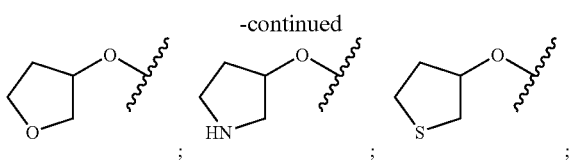

;

and the like.

The term "heterocyclicsulfonyl" denotes a heterocyclic group, as defined herein, with a ring nitrogen where the ring nitrogen is bonded directly to an $SO_2$ group forming an sulfonamide. Examples include, but not limited to,

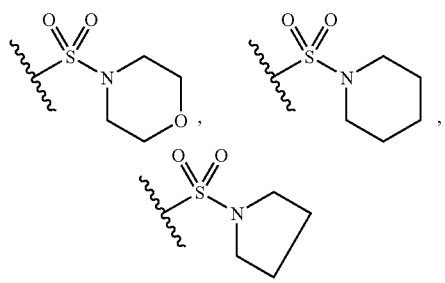

and the like.

The term "hydroxyl" refers to the group —OH.

The term "hydroxylamino" refers to the group —NHOH.

The term "nitro" refers to the group —$NO_2$.

The term "$C_{4-7}$ oxo-cycloalkyl" refers to a $C_{4-7}$ cycloalkyl, as defined herein, wherein one of the ring carbons is replaced with a carbonyl. Examples of $C_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

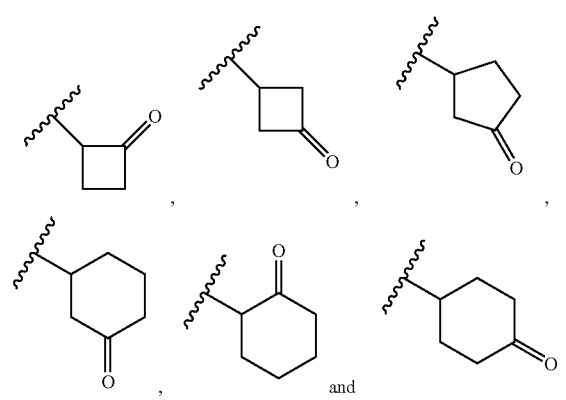

and

The term "perfluoroalkyl" denotes the group of the formula —$C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "phenoxy" refers to the group $C_6H_5O$—.

The term "phenyl" refers to the group $C_6H_5$—.

The term "phosphonooxy" refers to a group with the following chemical structure:

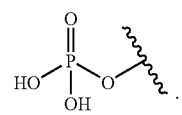

The term "sulfonamide" refers to the group —$SO_2NH_2$.

The term "sulfonic acid" refers to the group —$SO_3H$.

The term "tetrazolyl" refers to the five membered heteroaryl of the following formulae:

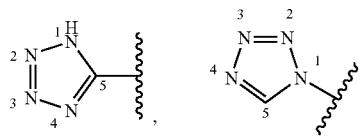

In some embodiments, the tetrazolyl group is further substituted at either the 1 or 5 position resepectively with a group selected from the group consisting of $C_{1-3}$ alkyl, $C_{1-3}$ haloalkyl and $C_{1-3}$ alkoxy.

The term "thiol" denotes the group —SH.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

COMPOSITION shall mean a material comprising at least two compounds or two components; for example, and without limitation, a Pharmaceutical Composition is a Composition comprising a compound of the present invention and a pharmaceutically acceptable carrier.

CONTACT or CONTACTING shall mean bringing the indicated moieties together, whether in an in vitro system or an in vivo system. Thus, "contacting" a RUP3 receptor with a compound of the invention includes the administration of a compound of the present invention to an individual, preferably a human, having a RUP3 receptor, as well as, for example, introducing a compound of the invention into a sample containing a cellular or more purified preparation containing a RUP3 receptor.

IN NEED OF PROPHYLAXIS OR TREATMENT as used herein refers to a judgment made by a caregiver (e.g. physician, nurse, nurse practitioner, etc. in the case of humans; veterinarian in the case of animals, including non-human mammals) that an individual or animal requires or will benefit from prophylaxis or treatment. This judgment is made based on a variety of factors that are in the realm of a caregiver's expertise, but that includes the knowledge that the individual or animal is ill, or will be ill, as the result of a disease, condition or disorder that is treatable by the compounds of the invention. In general, "in need of prophylaxis" refers to the judgment made by the caregiver that the individual will become ill. In this context, the compounds of the invention are used in a protective or preventive manner. However, "in need of treatment" refers to the judgment of the caregiver that the individual is already ill, therefore, the compounds of the present invention are used to alleviate, inhibit or ameliorate the disease, condition or disorder.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

As used herein, the terms MODULATE or MODULATING shall mean to refer to an increase or decrease in the amount, quality, response or effect of a particular activity, function or molecule.

PHARMACEUTICAL COMPOSITION shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Present Invention:

One aspect of the present invention encompasses trisubstituted aryl and heteroaryl derivatives as shown in Formula (I):

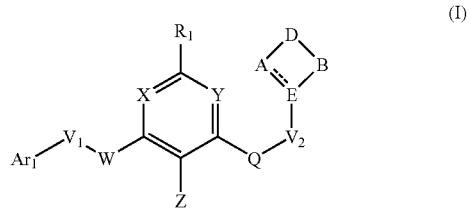

or a pharmaceutically acceptable salt, or N-oxide thereof; wherein $Ar_1$, $V_1$, $V_2$, W, Q, X, Y, Z, A, B, D, E, --- and $R_1$ have the same definitions as described herein, supra and infra.

Some embodiments of the present invention encompass trisubstituted aryl and heteroaryl derivatives as shown in Formula (I) wherein:

A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;

D is O, S, S(O), S(O)$_2$, $CR_2R_3$ or N—$R_2$;

E is N, C or $CR_4$;

--- is a single bond when E is N or $CR_4$, or a double bond when E is C;

$V_1$ is selected from the group consisting of $C_{1-3}$ alkylene, ethynylene and $C_{1-2}$ heteroalkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or $V_1$ is a bond;

$V_2$ is selected from the group consisting of $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or $V_2$ is a bond;

W is $NR_5$, O, S, S(O) or S(O)$_2$; or W is absent;

Q is $NR_6$, O, S, S(O) or S(O)$_2$;

X is N or $CR_7$;

Y is N or $CR_8$;

Z is selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbo-$C_{1-6}$-alkoxy, carboxamide, carboxy, cyano, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxylamino, nitro and tetrazolyl, wherein $C_{1-8}$ alkyl is optionally substituted with 1, 2, 3 or 4 groups selected from the group consisting of $C_{1-5}$ acyl, $C_{1-5}$ acyloxy, $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro; or Z is a group of Formula (A):

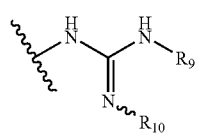

wherein:
$R_9$ is H, $C_{1-8}$ alkyl or $C_{3-7}$ cycloalkyl; and
$R_{10}$ is H, nitro or nitrile;
$Ar_1$ is aryl or heteroaryl each optionally substituted with $R_{11}$, $R_{12}$, $R_{13}$, $R_{14}$, and $R_{15}$; where $R_{11}$ is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy or phenyl optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or
$R_{11}$ is a group of Formula (B):

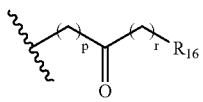

wherein:
"p" and "r" are each independently 0, 1, 2 or 3; and
$R_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;
$R_{12}$, $R_{13}$, $R_{14}$, and $R_{15}$ are each independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent groups selected from the group consisting of $R_{12}$, $R_{13}$, $R_{14}$ and $R_{15}$ form a 5, 6 or 7 membered cycloalkyl, cycloalkenyl or heterocyclic group with $Ar_1$ wherein the 5, 6 or 7 membered group is optionally substituted with halogen;
$R_1$, $R_7$ and $R_8$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;
$R_2$ is selected from the group consisting of H, $C_{1-8}$ alkyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or
$R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or
$R_2$ is a group of Formula (C):

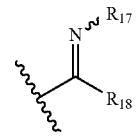

wherein:
$R_{17}$ is H, $C_{1-8}$ alkyl, $C_{3-7}$ cycloalkyl, aryl, heteroaryl or $OR_{19}$; and $R_{18}$ is F, Cl, Br, CN or $NR_{20}R_{21}$; where $R_{19}$ is H, $C_{1-8}$ alkyl or $C_{3-7}$ cycloalkyl, and $R_{20}$ and $R_{21}$ are each independently H, $C_{1-8}$ alkyl, $C_{3-7}$ cycloalkyl, aryl or heteroaryl; or
$R_2$ is a group of Formula (D):

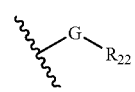

wherein:

G is:
i) C(O), C(O)NR$_{23}$, C(O)O, OC(O), C(S), C(S)NR$_{23}$, C(S)O, OC(S), CR$_{23}$R$_{24}$, O, S, S(O) or S(O)$_2$ when D is CR$_2$R$_3$, or
ii) C(O), C(O)NR$_{23}$, C(O)O, C(S), C(S)NR$_{23}$, C(S)O, CR$_{23}$R$_{24}$ or S(O)$_2$ when D is NR$_2$, where R$_{23}$ and R$_{24}$ are each independently H or C$_{1-8}$ alkyl; and R$_{22}$ is C$_{1-8}$ alkyl, C$_{3-7}$ cycloalkyl, phenyl or heteroaryl optionally substituted with 1 to 5 substituents selected from the group consisting of C$_{1-5}$ acyl, C$_{1-5}$ acyloxy, C$_{1-4}$ alkoxy, C$_{1-7}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-6}$-cycloalkyl, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, hydroxyl, hydroxylamino and nitro;

R$_3$ is H, C$_{1-8}$ alkyl, C$_{1-4}$ alkoxy or hydroxyl; and

R$_4$, R$_5$ and R$_6$ are each independently H, or C$_{1-8}$ alkyl; or a pharmaceutically acceptable salt, hydrate or solvate thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

It is understood and appreciated that compounds of Formula (I) may have one or more chiral centers, and therefore can exist as enantiomers and/or diastereomers. The invention is understood to extend to and embrace all such enantiomers, diastereomers and mixtures thereof, including but not limited, to racemates. Accordingly, some embodiments of the present invention pertain to compounds of Formula (I) and formulae used throughout this disclosure that are R enantiomers. Further, some embodiments of the present invention pertain to compounds of Formula (I) and formulae used throughout this disclosure that are S enantiomers. In examples where more than one chiral center is present, then, some embodiments of the present invention include compounds that are RS or SR enantiomers. In further embodiments, compounds of the present invention are RR or SS enantiomers. It is understood that compounds of Formula (I) and formulae used throughout this disclosure are intended to represent all individual enantiomers and mixtures thereof, unless stated or shown otherwise.

Many geometric isomers of olefins, C=N double bonds, disubstituted cycloalkyl (i.e., 1,4-cyclohexyl groups), and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

In some embodiments, X and Y are each independently N or CH, provided that if either X or Y is CH then the other is N.

Some embodiments of the present invention pertain to compounds of Formula (I) wherein W is NR$_5$. In some embodiments, R$_5$ is H.

In some embodiments, W is NH.

In some embodiments compounds of the present invention can be represented by Formula (Ia) as illustrated below:

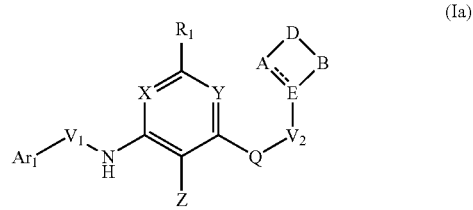

(Ia)

wherein each variable in Formula (Ia) has the same meaning as described herein, supra and infra. In some embodiments, V$_1$ is a bond. In still further embodiments, both V$_1$ and V$_2$ are bonds.

In some embodiments, W is O.

Some embodiments of the present invention pertain to compounds of Formula (I) wherein W is O and can be represented by Formula (Ic) as illustrated below:

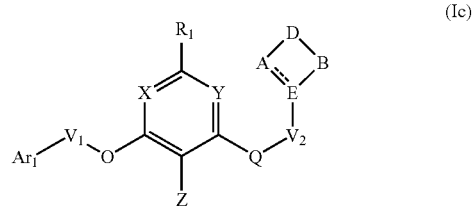

(Ic)

wherein each variable in Formula (Ic) has the same meaning as described herein, supra and infra. Some embodiments of the present invention pertain to compounds of Formula (Ic) wherein V$_1$ is absent. In some embodiments, Q is an oxygen atom. In still further embodiments, Q is an oxygen atom and both V$_1$ and V$_2$ are bonds.

Some embodiments of the present invention pertain to compounds of Formula (I) wherein W is S, S(O) or $S(O)_2$.

Some embodiments of the present invention pertain to compounds of Formula (I) wherein W is absent.

Some embodiments of the present invention pertain to compounds of Formula (I) wherein Q is $NR_6$.

In some embodiments, $R_6$ is H.

In some embodiments, $R_6$ is $C_{1-8}$ alkyl.

In some embodiments, $R_6$ is selected from the group consisting of methyl, ethyl, isopropyl, and n-propyl.

In some embodiments, $R_6$ is isopropyl.

In some embodiments, $R_6$ is $C_{3-7}$ cycloalkyl.

In some embodiments, $R_6$ is selected from the group consisting of cyclopropyl, cyclobutyl, and cyclopentyl.

In some embodiments, $R_6$ is cyclopropyl

In some embodiments, Q is NH.

In some embodiments, $R_6$ is cyclopropylmethyl.

Some embodiments of the present invention pertain to compounds of Formula (I) wherein Q is NH and can be represented by Formula (Ie) as illustrated below:

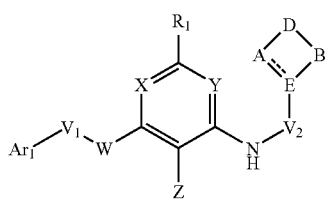

(Ie)

wherein each variable in Formula (Ie) has the same meaning as described herein, supra and infra. In some embodiments, $V_2$ is a bond.

In some embodiments, Q is O.

Some embodiments of the present invention pertain to compounds of Formula (I) wherein Q is O (i.e., an oxygen atom) and can be represented by Formula (Ig) as illustrated below:

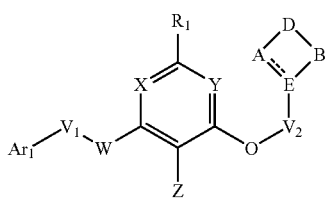

(Ig)

wherein each variable in Formula (Ig) has the same meaning as described herein, supra and infra. In some embodiments, $V_2$ is a bond. In some embodiments, $V_2$ is —$CH_2$—. In still further embodiments, $V_2$ is —$CH_2CH_2$—.

Some embodiments of the present invention pertain to compounds of Formula (I) wherein Q is S, S(O) or $S(O)_2$.

In some embodiments, Q is S.

Some embodiments of the present invention pertain to compounds of Formula (I) wherein $V_1$ is a bond.

Some embodiments of the present invention pertain to compounds of Formula (I) wherein $V_2$ is a bond.

In some embodiments, $V_1$ and $V_2$ are both a bond.

Some embodiments of the present invention pertain to compounds of Formula (I) wherein $V_2$ is —$CH_2$—.

Some embodiments of the present invention pertain to compounds of Formula (I) wherein $V_2$ is —$CH_2CH_2$—.

Some embodiments of the present invention pertain to compounds of Formula (I) wherein A and B are independently $C_{1-2}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen.

Some embodiments of the present invention pertain to compounds of Formula (I) wherein both A and B are $C_1$ alkylene groups wherein A and B are optionally substituted with 1 to 2 methyl groups.

In some embodiments, A and B are both —$CH_2$—. In some embodiments, compounds of the present invention can be represented by Formula (Ik) as shown below:

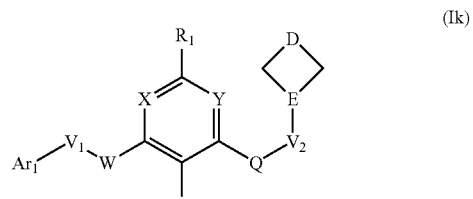

(Ik)

wherein each variable in Formula (Ik) has the same meaning as described herein, supra and infra.

In some embodiments, both A and B are —$CH_2$— and E is CH.

In some embodiments, both A and B are —$CH_2$—, E is CH, and D is N—$R_2$.

In some embodiments, A is —$CH_2CH_2$— and B is —$CH_2$—.

In some embodiments, A is —$CH_2CH_2$— and B is —$CH_2$—, and E is CH.

In some embodiments, A is —$CH_2CH_2$— and B is —$CH_2$—, E is CH and D is N—$R_2$.

Some embodiments of the present invention pertain to compounds of Formula (I) wherein A is a $C_1$ alkylene group and B is a $C_2$ alkylene group wherein A is optionally substituted with 1 to 2 methyl groups and B is optionally substituted with 1 to 4 methyl groups.

In some embodiments, compounds of the present invention can be represented by Formulae (Im) and (In) respectively as shown below:

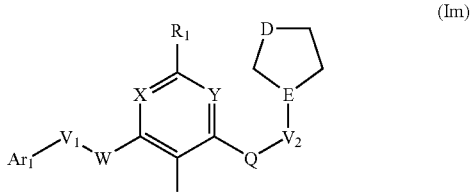

(Im)

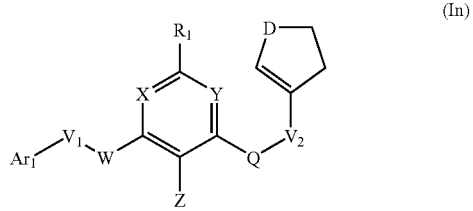

(In)

wherein each variable in Formulae (Im) and (In) has the same meaning as described herein, supra and infra. In some embodiments, A is —CH$_2$— and B is —CH$_2$CH$_2$—. In further embodiments, A is —CH$_2$—, B is —CH$_2$CH$_2$—, and V$_2$ is —CH$_2$— or —CH$_2$CH$_2$—.

Some embodiments of the present invention pertain to compounds of Formula (I) wherein A is a C$_1$ alkylene group and B is a C$_3$ alkylene group wherein A is optionally substituted with 1 to 2 methyl groups and B is optionally substituted with 1 to 4 methyl groups. In some embodiments, A is —CH$_2$— or —CH— and B is —CH$_2$CH$_2$CH$_2$— and can be represented by Formulae (Ip) and (Iq) respectively as shown below:

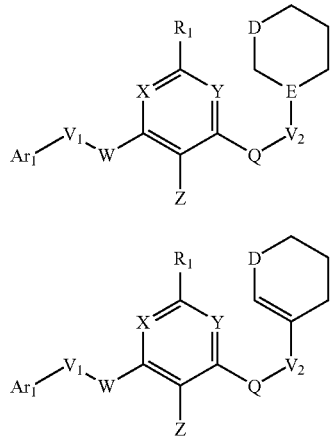

wherein each variable in Formulae (Ip) and (Iq) has the same meaning as described herein, supra and infra.

Some embodiments of the present invention pertain to compounds of Formula (I) wherein A is a C$_2$ alkylene group and B is a C$_1$ alkylene group wherein A is optionally substituted with 1 to 4 methyl groups and B is optionally substituted with 1 to 2 methyl groups. In some embodiments, A is —CHCH$_2$— and B is —CH$_2$—; these embodiments can be represented by Formula (It) as shown below:

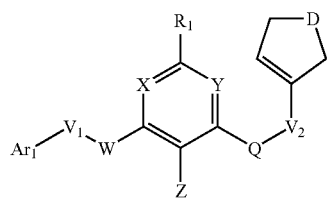

wherein each variable in Formula (It) has the same meaning as described herein, supra and infra.

Some embodiments of the present invention pertain to compounds of Formula (I) wherein A is CH$_2$ and B is —CH$_2$CH$_2$—, —CH$_2$CH(CH$_3$)—, —CH(CH$_3$)CH$_2$—, —CH$_2$CH(CF$_3$)— or —CH(CF$_3$)CH$_2$—. In some embodiments, compounds of the invention are represented by Formulae (Iv), (Iw) and (Ix) as shown below:

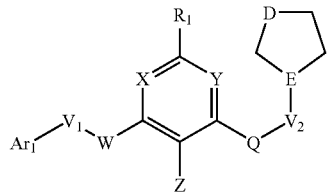

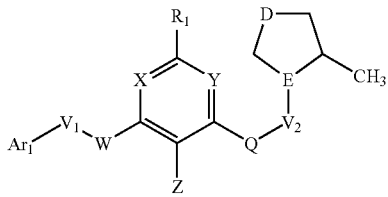

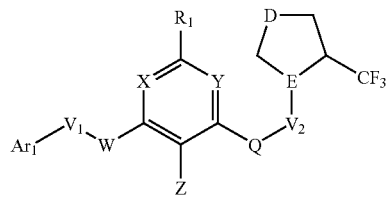

wherein each variable in Formulae (Iv), (Iw) and (Ix) has the same meaning as described herein, supra and infra. In some embodiments, D is N—R$_2$. In further embodiments, D is N—R$_2$ wherein R$_2$ is represented by Formula (D). In still further embodiments, D is N—R$_2$ wherein R$_2$ is —C(O)OC$_{1-8}$ alkyl.

Some embodiments of the present invention pertain to compounds of Formula (I) wherein A is a C$_3$ alkylene group and B is a C$_1$ alkylene group wherein A is optionally substituted with 1 to 4 methyl groups and B is optionally substituted with 1 to 2 methyl groups. In some embodiments, A is —CHCH$_2$CH$_2$— and B is —CH$_2$— and represented by Formulae (IIa) as shown below:

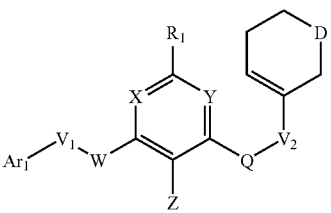

wherein each variable in Formulae (IIa) has the same meaning as described herein, supra and infra.

In some embodiments, both A and B are —CH$_2$CH$_2$—.

In some embodiments, both A and B are —CH$_2$CH$_2$— and E is CH.

In some embodiments, both A and B are —CH$_2$CH$_2$—, E is CH, and D is N—R$_2$.

Some embodiments of the present invention pertain to compounds of Formula (I) wherein both A and B are C$_2$ alkylene groups wherein A and B are optionally substituted with 1 to 4 methyl groups.

In some embodiments, A is —CH$_2$CH$_2$— or —CHCH$_2$— and B is —CH$_2$CH$_2$—. In some embodiments, compounds of the present invention can be represented by Formulae (IIc) and (IId) as shown below:

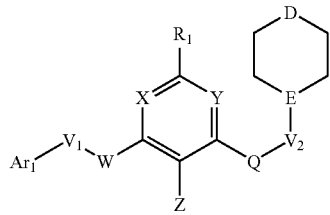
(IIc)

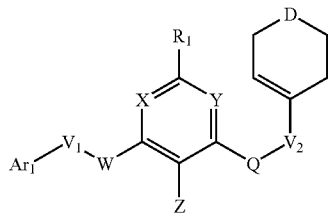
(IId)

wherein each variable in Formulae (IIc) and (IId) has the same meaning as described herein, supra and infra. In some embodiments, A and B are both —CH$_2$CH$_2$—, D is N—R$_2$, and E is CR$_4$; these embodiments are represented by Formula (IIf) as shown below:

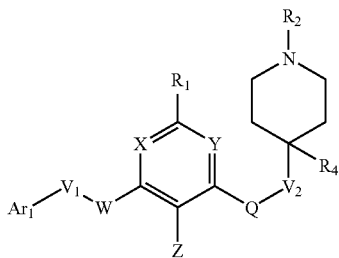
(IIf)

wherein each variable in Formula (IIf) has the same meaning as described herein, supra and infra. In some embodiments, compounds have the Formula (IIf) and R$_4$ is H. In further embodiment, V$_2$ is a bond. In still further embodiments, V$_2$ is —CH$_2$— or —CH$_2$CH$_2$—.

Some embodiments of the present invention pertain to compounds of Formula (I) wherein A is a C$_2$ alkylene group and B is a C$_3$ alkylene group wherein A and B are optionally substituted with 1 to 4 methyl groups. In some embodiments, A is —CH$_2$CH$_2$— or —CHCH$_2$— and B is —CH$_2$CH$_2$CH$_2$— and can be represented by Formulae (IIh) and (IIi) as shown below:

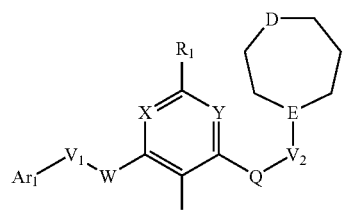
(IIh)

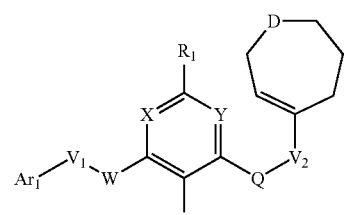
(IIi)

wherein each variable in Formulae (IIh) and (IIi) has the same meaning as described herein, supra and infra.

Some embodiments of the present invention pertain to compounds of Formula (I) wherein A is a C$_3$ alkylene group and B is a C$_2$ alkylene group wherein A and B are optionally substituted with 1 to 4 methyl groups. In some embodiments, A is —CHCH$_2$CH$_2$— and B is —CH$_2$CH$_2$—; these embodiments can be represented by Formula (IIk) as shown below:

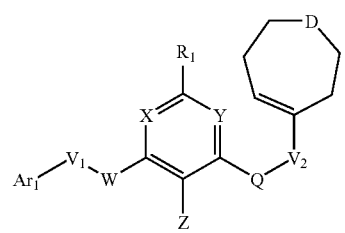
(IIk)

wherein each variable in Formula (IIk) has the same meaning as described herein, supra and infra.

Some embodiments of the present invention pertain to compounds of Formula (I) wherein both A and B are C$_3$ alkylene groups wherein A and B are optionally substituted with 1 to 4 methyl groups. In some embodiments, A is —CH$_2$CH$_2$CH$_2$— or —CHCH$_2$CH$_2$— and B is —CH$_2$CH$_2$CH$_2$— and are represented by Formula (IIm) and (IIn) respectively as shown below:

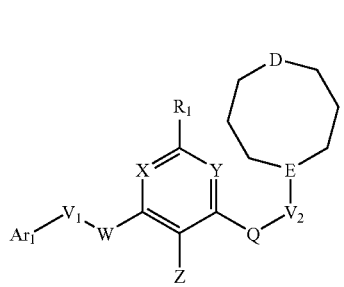
(IIm)

-continued (IIn)

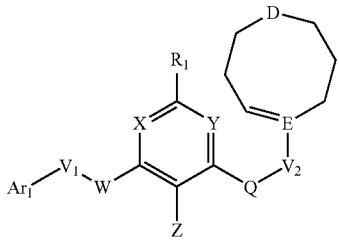

wherein each variable in Formulae (IIm) and (IIn) has the same meaning as described herein, supra and infra.

Some embodiments of the present invention pertain to compounds of Formula (I) wherein --- is a single bond.

Some embodiments of the present invention pertain to compounds of Formula (I) wherein E is a nitrogen atom (i.e., N).

Some embodiments of the present invention pertain to compounds of Formula (I) wherein E is $CR_4$. In some embodiments, $R_4$ is H and can be represented by Formula (IIp) as shown below:

(IIp)

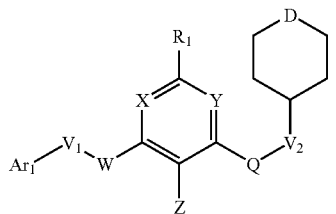

wherein each variable in Formula (IIp) has the same meaning as described herein, supra and infra. In further embodiments, $V_2$ is a bond and represented by Formula (IIr):

(IIr)

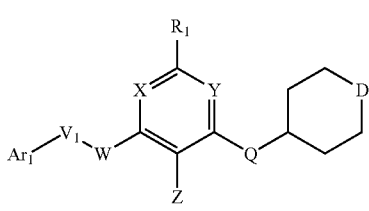

wherein each variable in Formula (IIr) has the same meaning as described herein, supra and infra. In some embodiments, compounds of the present invention are of Formula (IIr) and Q is NH. In some embodiments, compounds are of Formula (IIr) and Q is O (i.e., an oxygen atom).

Some embodiments of the present invention pertain to compounds of Formula (I) wherein --- a double bond. It is understood that when --- is a double bond then E is C (i.e., a carbon atom) and not N (i.e., a nitrogen atom).

Some embodiments of the present invention pertain to compounds of Formula (I) wherein $V_2$ is a $CH_2$ or $CH_2CH_2$ group.

Some embodiments of the present invention pertain to compounds of Formula (I) wherein $V_1$ is a bond and $V_2$ is a $CH_2$ or $CH_2CH_2$ group.

Some embodiments of the present invention pertain to compounds of Formula (I) wherein D is $CR_2R_3$ and can be represented by Formula (IIt) as shown below:

(IIt)

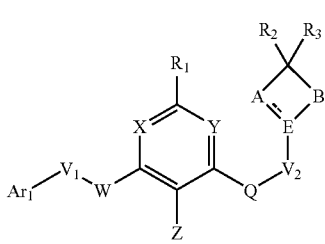

wherein each variable in Formula (IIt) has the same meaning as described herein, supra and infra. In some embodiments, compounds of the invention are of Formula (IIt) and $R_2$ is selected from the group consisting of H, amino, carboxamide, carboxy, cyano, $C_{3-6}$-cycloalkyl, $C_{1-4}$ haloalkoxy, $C_{1-4}$ haloalkyl, halogen and hydroxyl. In some embodiments, $R_2$ is —$NR_{23}C(O)O$—($C_{1-8}$alkyl) or —$OC(O)NR_{23}$—($C_{1-8}$ alkyl). In some embodiments, $R_2$ is selected from the group consisting of $OCH_3$, $OCH_2CH_3$, $OCH_2CH_2CH_3$, $OCH(CH_3)_2$, $OCH_2(CH_2)_2CH_3$, amino, carboxamide, carboxy, cyano, cyclopropyl, cyclobutyl, cyclopentyl, cyclohexyl, $OCF_3$, $OCHF_2$, $CF_3$, $CHF_2$ and F. In some embodiments, $R_2$ is $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro. In some embodiments, $R_2$ is selected from the group consisting of $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$. In some embodiments, $R_2$ is selected from the group consisting of $CH_2OCH_3$, $CH_2CH_2OCH_3$, $CH_2OCH_2CH_3$, $CH_2OCH_2CH_2CH_3$, $CH_2CH_2OCH_2CH_3$, $CH_2CH_2OCH_2CH_2CH_3$, $CH_2OCH(CH_3)_2$, $CH_2OCH_2CH(CH_3)_2$, $CH_2CO_2H$, $CH_2CH_2CO_2H$, $CH_2OH$, $CH_2CH_2OH$ and $CH_2CH_2CH_2OH$. In some embodiments, $R_2$ is selected from the group consisting of $CH_2SCH_3$, $CH_2SCH_2CH_3$, $CH_2SCH_2CH_2CH_3$, $CH_2SCH(CH_3)_2$, $CH_2SCH_2(CH_2)_2CH_3$, $CH_2CH_2SCH_3$, $CH_2CH_2SCH_2CH_3$, $CH_2CH_2SCH_2CH_2CH_3$, $CH_2CH_2SCH(CH_3)_2$, $CH_2CH_2SCH_2(CH_2)_2CH_3$, $CH_2S(O)CH_3$, $CH_2S(O)CH_2CH_3$, $CH_2S(O)CH_2CH_2CH_3$, $CH_2S(O)CH(CH_3)_2$, $CH_2S(O)CH_2(CH_2)_2CH_3$, $CH_2CH_2S(O)CH_3$, $CH_2CH_2S(O)CH_2CH_3$, $CH_2CH_2S(O)CH_2CH_2CH_3$, $CH_2CH_2S(O)CH(CH_3)_2$, $CH_2CH_2S(O)CH_2(CH_2)_2CH_3$, $CH_2S(O)_2CH_3$, $CH_2S(O)_2CH_2CH_3$, $CH_2S(O)_2CH_2CH_2CH_3$, $CH_2S(O)_2CH(CH_3)_2$, $CH_2S(O)_2CH_2(CH_2)_2CH_3$, $CH_2CH_2S(O)_2CH_3$, $CH_2CH_2S(O)_2CH_2CH_3$, $CH_2CH_2S(O)_2CH_2CH_2CH_3$, $CH_2CH_2S(O)_2CH(CH_3)_2$ and $CH_2CH_2S(O)_2CH_2(CH_2)_2CH_3$. In some embodiments, $R_2$ is selected from the group consisting of $CH_2OCH_2$-cyclopropyl, $CH_2OCH_2$-cyclobutyl, $CH_2OCH_2$-cyclopentyl, $CH_2OCH_2$-cyclohexyl, $CH_2OCH_2CH_2$-cyclopropyl, $CH_2OCH_2CH_2$-cyclobutyl, $CH_2OCH_2CH_2$-cyclopentyl, $CH_2OCH_2CH_2$-cyclohexyl, CH₂CH₂OCH₂-cyclopropyl, CH₂CH₂OCH₂-cyclobutyl, CH₂CH₂OCH₂-cyclopentyl, CH₂CH₂OCH₂-cyclohexyl, CH₂CH₂OCH₂CH₂-cyclopropyl, CH₂CH₂OCH₂CH₂-cyclobutyl, CH₂CH₂OCH₂CH₂-cyclopentyl and CH₂CH₂OCH₂CH₂-cyclohexyl. In some embodiments, $R_2$ is selected from the group consisting of 1,2,4-oxadiazol-3-yl, 1,2,4-oxadiazol-5-yl, 1,3,4-oxadiazol-2-yl, 1,2,4-triazol-5-yl and 1,2,4-triazol-1-yl, 3-methyl-1,2,4-oxadiazol-5-yl, 3-methyl-1,2,4-oxadiazol-5-yl, 3-ethyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 3-methyl-1,2,4-triazol-5-yl, 3-ethyl-1,2,4-triazol-5-yl, 3-methyl-1,2,4-triazol-1-yl, 3-ethyl-1,2,4-triazol-1-yl, 5-methyl-1,2,4-triazol-1-yl and 5-ethyl-1,2,4-triazol-1-yl.

In some embodiments $R_2$ is a heteroaryl comprising 5-atoms in the aromatic ring and are represented by the following formulae:

TABLE 2A

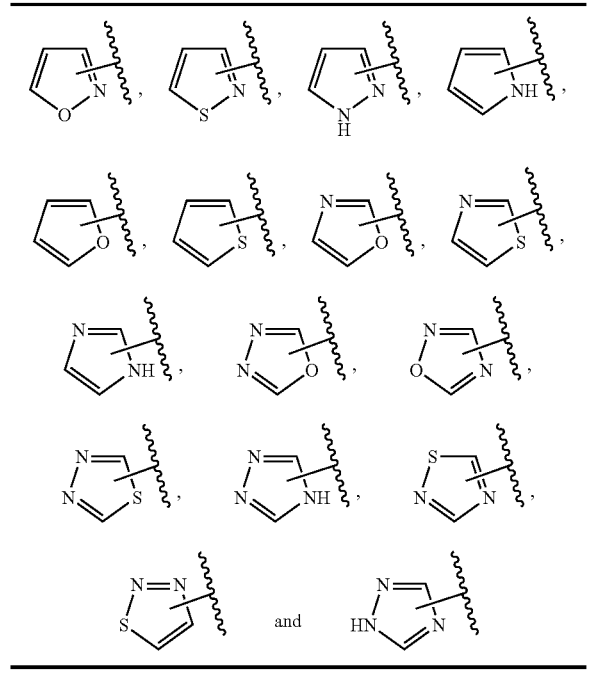

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imiadazol-5-yl group). In some embodiments $R_2$ is a 5-membered heteroaryl, for example but not limited to those shown in TABLE 2A, optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro.

In some embodiments $R_2$ is a heteroaryl comprising 5-atoms in the aromatic ring and are represented by the following formulae:

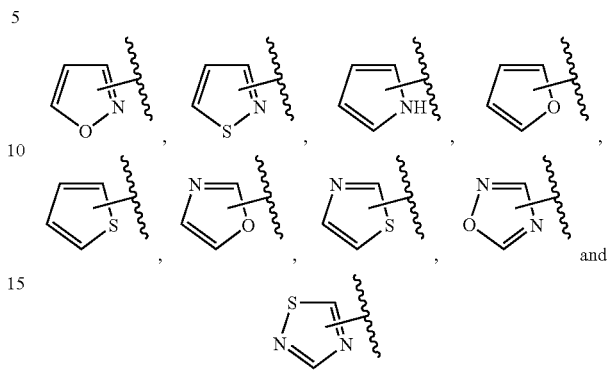

and wherein the 5-membered heteroaryl is bonded at any available position of the ring as described above. In some embodiments, $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro.

In some embodiments $R_2$ is a heterocyclic group represented, for example, by the formulae in TABLE 2B.

TABLE 2B

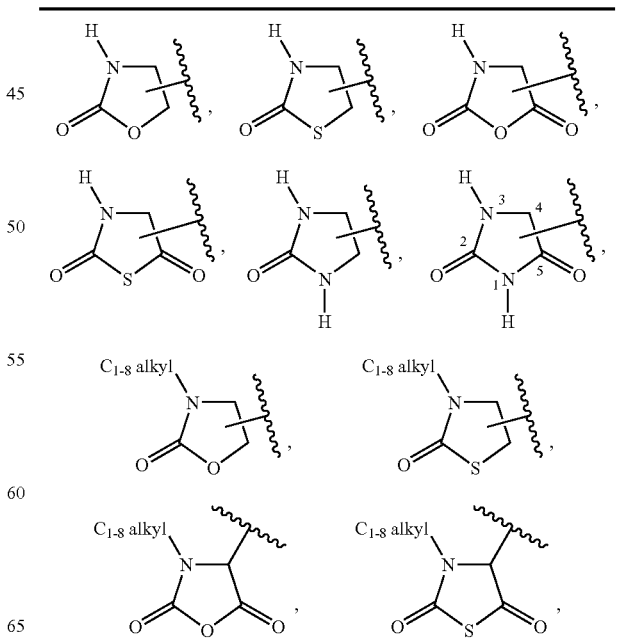

TABLE 2B-continued

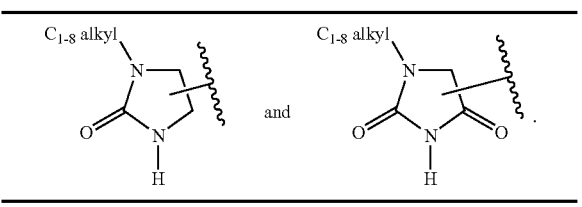

It is understood that any one of the heterocyclic groups shown in TABLES 2B to 2E may be bonded at any ring carbon or ring nitrogen as allowed by the respective formula unless otherwise specified. For example, a 2,5-dioxo-imidazolidinyl group may be bonded at the ring carbon or at either of the two ring nitrogens to give the following formulae respectively:

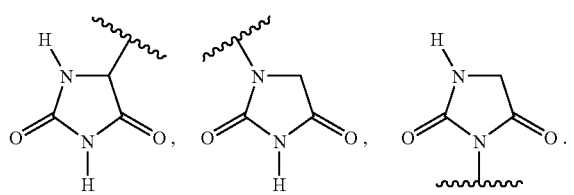

In some embodiments $R_2$ is a heterocyclic represented, for example, by the formulae in TABLE 2C.

TABLE 2C

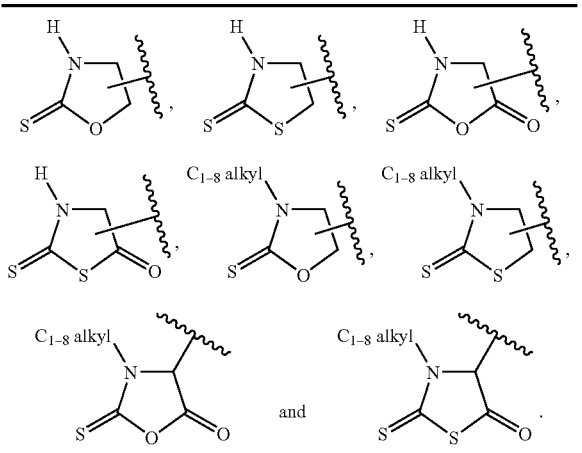

In some embodiments $R_2$ is a heterocyclic represented, for example, by the formulae in TABLE 2D.

TABLE 2D

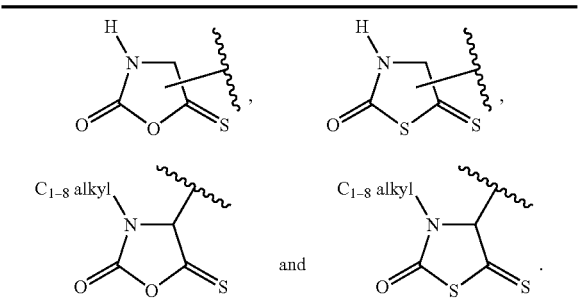

In some embodiments $R_2$ is a heterocyclic represented, for example, by the formulae in TABLE 2E.

TABLE 2E

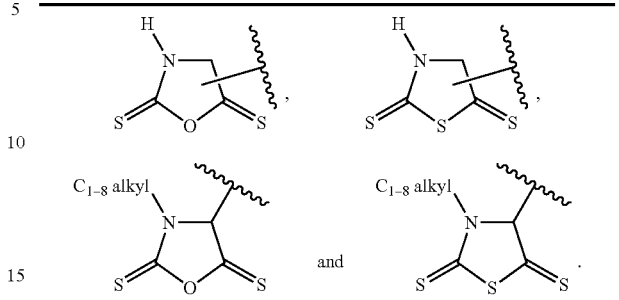

In some embodiments $R_2$ is a heterocyclic represented, for example, by the formulae in TABLE 2F wherein the $C_{1-6}$ alkyl group on the respective ring nitrogen atoms may be the same or different.

TABLE 2F

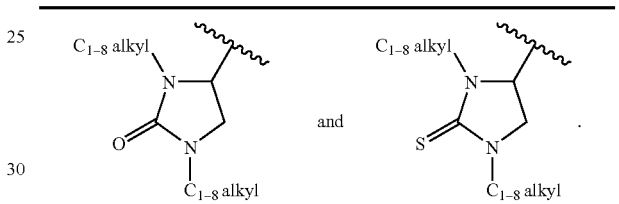

In some embodiments $R_2$ is a heterocyclic represented, for example, by the formulae in TABLE 2G wherein the $C_{1-6}$ alkyl group on the respective ring nitrogen atoms may be the same or different.

TABLE 2G

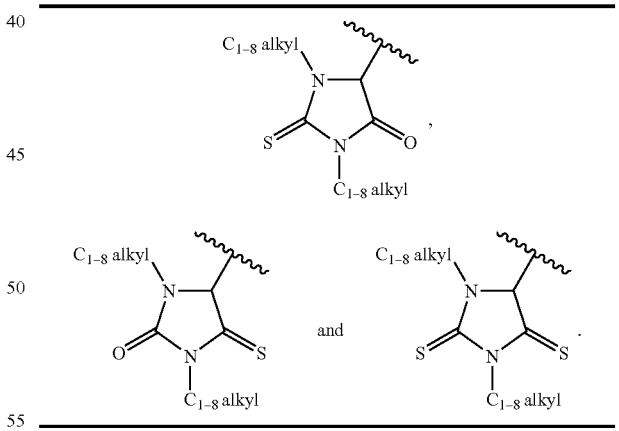

Some embodiments of the present invention pertain to compounds of Formula (IIt) and $R_2$ is —$Ar_2$—$Ar_3$ wherein $Ar_2$ and $Ar_3$ are independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro. In some embodiments, $Ar_2$ is a heteroaryl and $Ar_3$ is phenyl. In some embodiments, the heteroaryl and said phenyl are optionally substituted with 1 to 5 substituents selected from the group consisting of $C_{1-4}$ alkoxy, $C_{1-8}$ alkyl, $C_{1-4}$ alkylcarboxamide, $C_{1-4}$ alkylsulfinyl, $C_{1-4}$ alkylsulfonyl, $C_{1-4}$ alkylthio, cyano, $C_{1-4}$ haloalkoxy, $C_{1-4}$ haloalkyl, halogen, hydroxyl and nitro.

In some embodiments $Ar_2$ is a heteroaryl comprising 5-atoms in the aromatic ring and are represented by the following formulae shown in TABLE 3.

TABLE 3

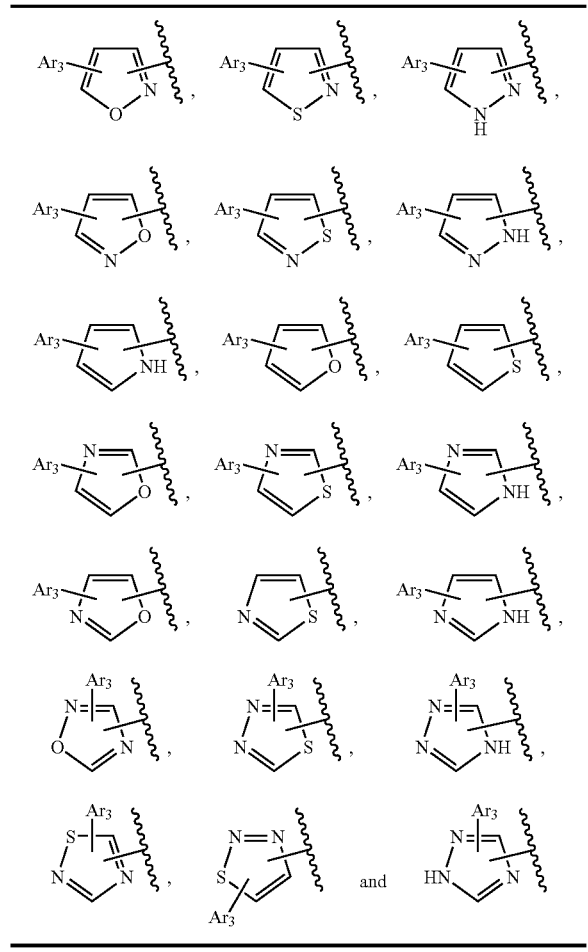

wherein the 5-membered heteroaryl is bonded at any position of the ring, for example, a imidazolyl ring can be bonded at one of the ring nitrogens (i.e., imidazol-1-yl group) or at one of the ring carbons (i.e., imidazol-2-yl, imidazol-4-yl or imiadazol-5-yl group) and $Ar_3$ is bonded to any remaining available ring atom. In some embodiments $Ar_2$ is a heteroaryl and $Ar_3$ is phenyl. In some embodiments, $Ar_2$ is a phenyl and $Ar_3$ is heteroaryl (such as a heteroaryl selected from TABLE 2A, supra). In some embodiments the heteroaryl and phenyl are optionally substituted with 1 to 5 substituents selected from the group consisting of H, $C_{1-4}$ alkoxy, $C_{1-8}$ alkyl, $C_{1-4}$ alkylcarboxamide, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, halogen, hydroxyl and nitro.

Some embodiments of the present invention pertain to compounds of Formula (I) wherein D is $CR_2R_3$, or $R_2$ is Formula (C):

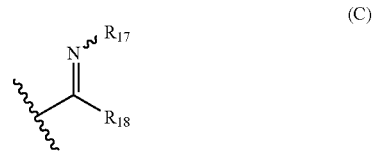

(C)

wherein:
$R_{17}$ is $C_{1-8}$ alkyl or $C_{3-7}$ cycloalkyl; and $R_{18}$ is F, Cl, Br or CN. In some embodiments, $R_{17}$ is $C_{1-8}$ alkyl and $R_{18}$ is F, Cl or CN.

Some embodiments of the present invention pertain to compounds of Formula (I) wherein D is $CR_2R_3$ and $R_2$ is Formula (D):

(D)

wherein:
G is C(O), C(O)$NR_{23}$, C(O)O, OC(O), C(S), C(S)$NR_{23}$, C(S)O, OC(S), $CR_{23}R_{24}$, O, S, S(O) or S(O)$_2$; where $R_{23}$ and $R_{24}$ are independently H or $C_{1-8}$ alkyl; and $R_{22}$ is $C_{1-8}$ alkyl, $C_{3-7}$ cycloalkyl, phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

Some embodiments of the present invention pertain to compounds of Formula (I) wherein $R_2$ is Formula (D) and G is C(O), C(O)$NR_{23}$, C(O)O, OC(O), C(S), C(S)$NR_{23}$, C(S)O, OC(S) or $CR_{23}R_{24}$. In some embodiments, $R_{22}$ is $C_{1-8}$ alkyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, Formula (D) (i.e., -G-$R_{22}$) is selected from the group consisting of C(O)$CH_3$, C(O)$CH_2CH_3$, C(O)$CH_2CH_2CH_3$, C(O)$CH(CH_3)_2$, C(O)$CH_2CH_2CH_2CH_3$, C(O)C($CH_3)_3$, C(O)$CH_2C(CH_3)_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, C($CH_3)_3$, $CH_2(CH_2)_3CH_3$, C(O)NH$CH_3$, C(O)NH$CH_2CH_3$, C(O)NH$CH_2CH_2CH_3$, C(O)NH$CH(CH_3)_2$, C(O)NH$CH_2(CH_2)_2CH_3$, C(O)N($CH_3)_2$, C(O)N($CH_3$)$CH_2CH_3$, C(O)NH($CH_2CH_3)_2$, $CO_2CH_3$, $CO_2CH_2CH_3$, $CO_2CH_2CH_2CH_3$, $CO_2CH(CH_3)_2$ and $CO_2CH_2(CH_2)_2CH_3$.

Some embodiments of the present invention pertain to compounds of Formula (I) wherein $R_2$ is Formula (D) and G is C(O), C(O)$NR_{23}$, C(O)O, OC(O), C(S), C(S)$NR_{23}$, C(S)O, OC(S) or $CR_{23}R_{24}$. In some embodiments, $R_{22}$ is phenyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (I) wherein $R_2$ is Formula (D) and G is C(O), C(O)NR$_{23}$, C(O)O, OC(O), C(S), C(S)NR$_{23}$, C(S)O, OC(S) or CR$_{23}$R$_{24}$. In some embodiments, $R_{22}$ is heteroaryl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $R_{22}$ is a 5-membered heteroaryl, for example, as shown in TABLE 2A supra. In some embodiments, $R_{22}$ is 1-methyl-1H-imidazole-4-yl or 2,4-dimethylthiazole-5-yl.

In some embodiments, $R_{22}$ is a 6-membered heteroaryl, for example, the 6-membered heteroaryls as shown in TABLE 4:

TABLE 4

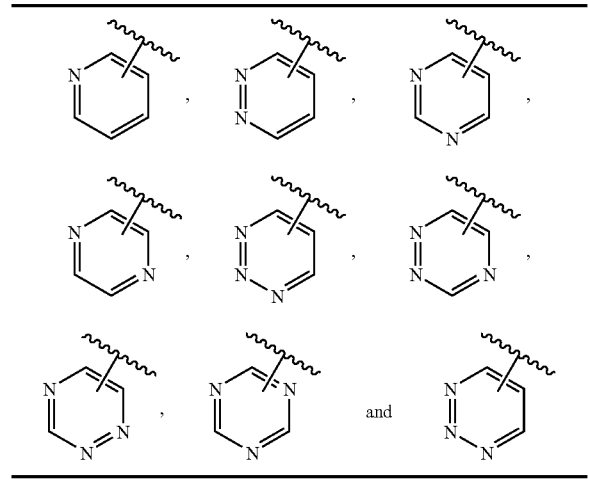

wherein the heteroaryl group is bonded at any ring carbon. In some embodiments $R_{22}$ is selected from the group consisting of pyridinyl, pyridazinyl, pyrimidinyl and pyrazinyl. In some embodiments, $R_{22}$ is pyridinyl.

Some embodiments of the present invention pertain to compounds of Formula (I) wherein $R_{23}$ and $R_{24}$ are independently H or $C_{1-2}$ alkyl.

Some embodiments of the present invention pertain to compounds of Formula (I) wherein $R_2$ is Formula (D) and G is O, S, S(O) or S(O)$_2$. In some embodiments, $R_{22}$ is $C_{1-8}$ alkyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, Formula (D) (i.e., -G-R$_{22}$) is selected from the group consisting of: OCH$_3$, OCH$_2$CH$_3$, OCH$_2$CH$_2$CH$_3$, OCH(CH$_3$)$_2$, OCH$_2$(CH$_2$)$_2$CH$_3$, SCH$_3$, SCH$_2$CH$_3$, SCH$_2$CH$_2$CH$_3$, SCH(CH$_3$)$_2$, SCH$_2$(CH$_2$)$_2$CH$_3$, S(O)CH$_3$, S(O)CH$_2$CH$_3$, S(O)CH$_2$CH$_2$CH$_3$, S(O)CH(CH$_3$)$_2$, S(O)CH$_2$(CH$_2$)$_2$CH$_3$, S(O)$_2$CH$_3$, S(O)$_2$CH$_2$CH$_3$, S(O)$_2$CH$_2$CH$_2$CH$_3$, S(O)$_2$CH(CH$_3$)$_2$ and S(O)$_2$CH$_2$(CH$_2$)$_2$CH$_3$.

Some embodiments of the present invention pertain to compounds of Formula (I) wherein $R_2$ is Formula (D) and G is O, S, S(O) or S(O)$_2$. In some embodiments, $R_{22}$ is phenyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (I) wherein $R_2$ is Formula (D) and G is O, S, S(O) or S(O)$_2$. In some embodiments, $R_{22}$ is heteroaryl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $R_{22}$ is a 5-membered heteroaryl, for example, as shown in TABLE 2A supra. In some embodiments, $R_{22}$ is a 6-membered heteroaryl, as shown in TABLE 4 supra. In some embodiments $R_{22}$ is selected from the group consisting of pyridinyl, pyridazinyl, pyrimidinyl and pyrazinyl. In some embodiments, $R_{22}$ is pyridinyl.

Some embodiments of the present invention pertain to compounds of Formula (I) wherein $R_3$ is H.

In some embodiments, D is N—R$_2$.

Some embodiments of the present invention pertain to compounds wherein D is N—R$_2$ and is represented by Formula (IIv):

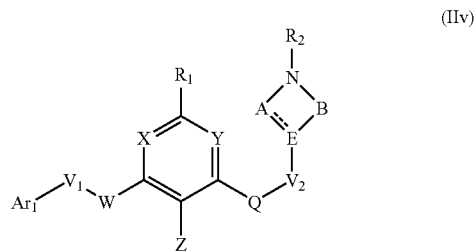

(IIv)

wherein each variable in Formula (IIv) has the same meaning as described herein, supra and infra.

In some embodiments, $R_2$ is $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro. In some embodiments, $R_2$ is pyridyl. In some embodiments, $R_2$ is 2-pyridyl. In some embodiments, $R_2$ is selected from the group consisting of CH$_2$CH$_2$C(CH$_3$)$_3$, CH$_2$CH$_2$CH(CH$_3$)$_2$ and CH$_2$(CH$_2$)$_4$CH$_3$. In some embodiments, $R_2$ is selected from the group consisting of: CH$_3$, CH$_2$CH$_3$, CH$_2$CH$_2$CH$_3$, CH(CH$_3$)$_2$, CH(CH$_3$)(CH$_2$CH$_3$), CH$_2$(CH$_2$)$_2$CH$_3$ and CH$_2$(CH$_2$)$_3$CH$_3$. In some embodiments, $R_2$ is selected from the group consisting of CH$_2$OCH$_3$, CH$_2$CH$_2$OCH$_3$, CH$_2$OCH$_2$CH$_3$, CH$_2$OCH$_2$CH$_2$CH$_3$, CH$_2$CH$_2$OCH$_2$CH$_3$, CH$_2$CH$_2$OCH$_2$CH$_2$CH$_3$, CH$_2$OCH (CH₃)₂, CH₂OCH₂CH(CH₃)₂, CH₂CO₂H, CH₂CH₂CO₂H, CH₂OH, CH₂CH₂OH and CH₂CH₂CH₂OH. In some embodiments, R₂ is selected from the group consisting of CH₂SCH₃, CH₂SCH₂CH₃, CH₂SCH₂CH₂CH₃, CH₂SCH(CH₃)₂, CH₂SCH₂(CH₂)₂CH₃, CH₂CH₂SCH₃, CH₂CH₂SCH₂CH₃, CH₂CH₂SCH₂CH₂CH₃, CH₂CH₂SCH(CH₃)₂, CH₂CH₂SCH₂(CH₂)₂CH₃, CH₂S(O)CH₃, CH₂S(O)CH₂CH₃, CH₂S(O)CH₂CH₂CH₃, CH₂S(O)CH(CH₃)₂, CH₂S(O)CH₂(CH₂)₂CH₃, CH₂CH₂S(O)CH₃, CH₂CH₂S(O)CH₂CH₃, CH₂CH₂S(O)CH₂CH₂CH₃, CH₂CH₂S(O)CH(CH₃)₂, CH₂CH₂S(O)CH₂(CH₂)₂CH₃, CH₂S(O)₂CH₃, CH₂S(O)₂CH₂CH₃, CH₂S(O)₂CH₂CH₂CH₃, CH₂S(O)₂CH(CH₃)₂, CH₂S(O)₂CH₂(CH₂)₂CH₃, CH₂CH₂S(O)₂CH₃, CH₂CH₂S(O)₂CH₂CH₃, CH₂CH₂S(O)₂CH₂CH₂CH₃, CH₂CH₂S(O)₂CH(CH₃)₂ and CH₂CH₂S(O)₂CH₂(CH₂)₂CH₃. In some embodiments, R₂ is CH₂-cyclopropyl. In some embodiments, R₂ is selected from the group consisting of CH₂OCH₂-cyclopropyl, CH₂OCH₂-cyclobutyl, CH₂OCH₂-cyclopentyl, CH₂OCH₂-cyclohexyl, CH₂OCH₂CH₂-cyclopropyl, CH₂OCH₂CH₂-cyclobutyl, CH₂OCH₂CH₂-cyclopentyl, CH₂OCH₂CH₂-cyclohexyl, CH₂CH₂OCH₂-cyclopropyl, CH₂CH₂OCH₂-cyclobutyl, CH₂CH₂OCH₂-cyclopentyl, CH₂CH₂OCH₂-cyclohexyl, CH₂CH₂OCH₂CH₂-cyclopropyl, CH₂CH₂OCH₂CH₂-cyclobutyl, CH₂CH₂OCH₂CH₂-cyclopentyl and CH₂CH₂OCH₂CH₂-cyclohexyl. In some embodiments, R₂ is selected from the group consisting of 1,2,4-oxadiazol-3-yl, 1,2,4-oxadiazol-5-yl, 1,3,4-oxadiazol-2-yl, 1,2,4-triazol-5-yl and 1,2,4-triazol-1-yl, 3-methyl-1,2,4-oxadiazol-5-yl, 3-methyl-1,2,4-oxadiazol-5-yl, 3-ethyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 3-methyl-1,2,4-triazol-5-yl, 3-ethyl-1,2,4-triazol-5-yl, 3-methyl-1,2,4-triazol-1-yl, 3-ethyl-1,2,4-triazol-1-yl, 5-methyl-1,2,4-triazol-1-yl and 5-ethyl-1,2,4-triazol-1-yl.

In some embodiments, compounds are of Formula (IIv) and R₂ is a heteroaryl comprising 5-atoms in the aromatic ring selected from the group shown in Table 2A. In some embodiments R₂ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro. In some embodiments R₂ is a heteroaryl selected from the group, but not limited to the group, in TABLE 2A. In some embodiments, R₂ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro. In some embodiments R₂ is a heterocyclic group selected from the groups shown in TABLE 2B to TABLE 2G.

Some embodiments of the present invention pertain to compounds of Formula (IIv) and R₂ is —Ar₂—Ar₃ wherein Ar₂ and Ar₃ are independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_1$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro. In some embodiments Ar₂ is a heteroaryl comprising 5-atoms in the aromatic ring and selected from the group shown in TABLE 3. In some embodiments Ar₂ is a heteroaryl and Ar₃ is phenyl. In some embodiments, Ar₂ is a phenyl and Ar₃ is heteroaryl (such as a heteroaryl selected from TABLE 2A or TABLE 4, supra). In some embodiments, the heteroaryl and phenyl are optionally substituted with 1 to 5 substituents selected from the group consisting of H, $C_{1-4}$ alkoxy, $C_{1-8}$ alkyl, $C_{1-4}$ alkylcarboxamide, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, halogen, hydroxyl and nitro.

Some embodiments of the present invention pertain to compounds of Formula (I) wherein D is N—R₂. In some embodiments, R₂ is Formula (C):

(C)

wherein:

$R_{17}$ is $C_{1-8}$ alkyl or $C_{3-7}$ cycloalkyl; and $R_{18}$ is F, Cl, Br or CN. In some embodiments, $R_{17}$ is $C_{1-8}$ alkyl and $R_{18}$ is F, Cl or CN.

In some embodiments, R₂ is selected from the group consisting of methoxycarbonyl, ethoxycarbonyl, iso-propoxycarbonyl, n-propoxycarbonyl, n-butoxycarbonyl, tert-butoxycarbonyl, iso-butoxycarbonyl, and n-pentyloxycarbonyl. In some embodiments, R₂ is iso-propoxycarbonyl or tert-butoxycarbonyl.

Some embodiments of the present invention pertain to compounds of Formula (I) wherein D is N—R₂. In some embodiments, R₂ is Formula (D):

(D)

wherein:

G is C(O), C(O)NR₂₃, C(O)O, C(S), C(S)NR₂₃, C(S)O, CR₂₃R₂₄ or S(O)₂; where R₂₃ and R₂₄ are independently H or $C_{1-8}$ alkyl; and R₂₂ is $C_{1-8}$ alkyl, $C_{3-7}$ cycloalkyl, phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

Some embodiments of the present invention pertain to compounds of Formula (I) wherein D is N—$R_2$. In some embodiments, $R_2$ is Formula (D) and $R_{22}$ is $C_{1-8}$ alkyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, D is N—$R_2$ where $R_2$ is of Formula (D) (i.e., -G-$R_{22}$) and -G-$R_{22}$ is selected from the group consisting of C(O)CH$_3$, C(O)CH$_2$CH$_3$, C(O)CH$_2$CH$_2$CH$_3$, C(O)CH(CH$_3$)$_2$, C(O)CH$_2$CH$_2$CH$_2$CH$_3$, C(O)C(CH$_3$)$_3$, C(O)CH$_2$C(CH$_3$)$_3$, CH3, CH$_2$CH$_3$, CH$_2$CH$_2$CH$_3$, CH(CH$_3$)$_2$, CH(CH$_3$)(CH$_2$CH$_3$), CH$_2$(CH$_2$)$_2$CH$_3$, C(CH$_3$)$_3$, CH$_2$(CH$_2$)$_3$CH$_3$, C(O)NHCH$_3$, C(O)NHCH$_2$CH$_3$, C(O)NHCH$_2$CH$_2$CH$_3$, C(O)NHCH(CH$_3$)$_2$, C(O)NHCH$_2$(CH$_2$)$_2$CH$_3$, C(O)N(CH$_3$)$_2$, C(O)N(CH$_3$)CH$_2$CH$_3$, C(O)NH(CH$_2$CH$_3$)$_2$, CO$_2$CH$_3$, CO$_2$CH$_2$CH$_3$, CO$_2$CH$_2$CH$_2$CH$_3$, CO$_2$CH(CH$_3$)$_2$ and CO$_2$CH$_2$(CH$_2$)$_2$CH$_3$.

Some embodiments of the present invention pertain to compounds of Formula (I) wherein D is N—$R_2$. In some embodiments, $R_2$ is Formula (D) and $R_{22}$ is phenyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (I) wherein D is N—$R_2$. In some embodiments, $R_2$ is Formula (D) and $R_{22}$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $R_{22}$ is selected from the group consisting of pyridinyl, pyridazinyl, pyrimidinyl and pyrazinyl. In some embodiments, $R_{22}$ is pyridinyl.

In some embodiments, $R_2$ is a group of Formula (D):

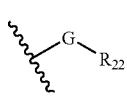

(D)

wherein:

G is —CR$_{23}$R$_{24}$C(O)—, —C(O)—, —CR$_{23}$R$_{24}$C(O)NR$_{23}$—, —C(O)NR$_{23}$—, —C(O)O—, —C(S)—, —C(S)NR$_{23}$—, —C(S)O—, —CR$_{23}$R$_{24}$—, —S(O)$_2$—, or a bond; wherein R$_{23}$ and R$_{24}$ are each independently H or C$_{1-8}$ alkyl; and $R_{22}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro.

In some embodiments, Formula (D) is —C(O)OR$_{22}$.

In some embodiments, Formula (D) is —C(O)R$_{22}$.

In some embodiments, Formula (D) is —CR$_{23}$R$_{24}$—R$_{22}$.

In some embodiments, Formula (D) is —R$_{22}$ (i.e., -G- is a bond).

In some embodiments, Formula (D) is —S(O)$_2$R$_{22}$.

In some embodiments, Formula (D) is —CR$_{23}$R$_{24}$C(O)R$_{22}$.

In some embodiments, Formula (D) is —CR$_{23}$R$_{24}$C(O)NR$_{25}$R$_{22}$.

In some embodiments, $R_2$ is —C(O)OR$_{22}$ and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

In some embodiments, $R_2$ is —C(O)OR$_{22}$ and $R_{22}$ is $C_{1-8}$ alkyl, or $C_{3-7}$ cycloalkyl each optionally substituted with 1 to 5 substituents selected from the group consisting of $C_{1-4}$ alkoxy, $C_{1-7}$ alkyl, $C_{1-4}$ alkylsulfonyl, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid.

In some embodiments, $R_2$ is —C(O)OR$_{22}$ and $R_{22}$ is $C_{1-8}$ alkyl, or $C_{3-7}$ cycloalkyl wherein said $C_{3-7}$ cycloalkyl is optionally substituted with 1 to 5 substituents selected from the group consisting of $C_{1-4}$ alkoxy, $C_{1-7}$ alkyl, carboxy, $C_{2-8}$ dialkylamino, and halogen.

In some embodiments, $R_2$ is —C(O)OR$_{22}$ and $R_{22}$ is $C_{1-8}$ alkyl, or $C_{3-7}$ cycloalkyl.

In some embodiments, $R_2$ is —C(O)R$_{22}$ and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

In some embodiments, $R_2$ is $-C(O)R_{22}$ and $R_{22}$ is $C_{1-8}$ alkyl, heteroaryl, or heterocyclic each optionally substituted with 1 to 5 substituents selected from the group consisting of H, $C_{1-4}$ alkoxy, $C_{1-7}$ alkyl, amino, carboxy, halogen, heteroaryl, hydroxyl, phenoxy, and sulfonic acid, wherein said $C_{1-7}$ alkyl and phenoxy are optionally substituted with 1 to 5 substituents selected from the group consisting of amino, $C_{1-4}$ haloalkoxy, and heterocyclic.

In some embodiments, $R_2$ is $-CH_2R_{22}$, or $-R_{22}$ and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{2-6}$ alkenyl, $C_{1-4}$ alkoxy, $C_{1-7}$ alkyl, $C_{1-4}$ alkylsulfonyl, amino, carbo-$C_{1-6}$- alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

In some embodiments, $R_2$ is $-CH_2R_{22}$, or $-R_{22}$, and $R_{22}$ is $C_{1-8}$ alkyl, $C_{3-7}$ cycloalkyl, or heteroaryl each optionally substituted with 1 to 5 substituents selected from the group consisting of $C_{1-5}$ acyl, $C_{2-6}$ alkenyl, $C_{1-4}$ alkoxy, carbo-$C_{1-6}$-alkoxy, carboxy, cyano, $C_{3-7}$ cycloalkyl, and hydroxyl.

$R_2$ is $-S(O)_2R_{22}$ and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

In some embodiments, $R_2$ is $-S(O)_2R_{22}$ and $R_{22}$ is $C_{1-8}$ alkyl, or heteroaryl and said heteroaryl is optionally substituted with 1 to 5 $C_{1-7}$ alkyl.

In some embodiments, $R_2$ is $-CR_{23}R_{24}C(O)R_{22}$ and wherein $R_{23}$ and $R_{24}$ are each independently H or $C_{1-8}$ alkyl; and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

In some embodiments, $R_2$ is $-CR_{23}R_{24}C(O)R_{22}$ and wherein $R_{23}$ and $R_{24}$ are each independently H or $C_{1-8}$ alkyl; and $R_{22}$ is phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylsulfonyl, cyano, $C_{2-8}$ dialkylamino, $C_{1-4}$ haloalkoxy, $C_{1-4}$ haloalkyl, halogen, heteroaryl, and phenyl.

$R_2$ is $-CR_{23}R_{24}C(O)NR_{25}R_{22}$ and wherein $R_{23}$, $R_{24}$ and $R_{25}$ are each independently H or $C_{1-8}$ alkyl; and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

In some embodiments, $R_2$ is $-CH_2C(O)NHR_{22}$ and wherein $R_{22}$ is phenyl optionally substituted with 1 to 5 substituents selected from the group consisting of $C_{1-4}$ alkoxy, $C_{1-7}$ alkyl, $C_{1-4}$ haloalkyl, and halogen.

In some embodiments, A and B are both $-CH_2CH_2-$, D is $NR_2$, E is $CR_4$, ---is a single bond and $V_1$ and $V_2$ are both single bonds; these embodiments can be represented by Formula (IIx) as shown below:

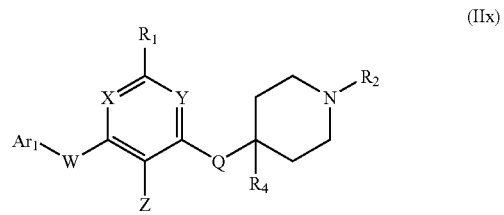

(IIx)

wherein each variable in Formula (IIx) has the same meaning as described herein, supra and infra. In some embodiments, compounds are of Formula (IIx) and W is $NR_5$. In some embodiments, $R_5$ is H. In some embodiments, Z is cyano. In further embodiments, Q is $NR_6$, O, S, S(O) or $S(O)_2$. In still further embodiments, Q is NH or O.

In some embodiments, compounds of the present invention are of Formula (IIx) wherein $R_2$ is Formula (D); these embodiments can be represented by Formula (IIy) as shown below:

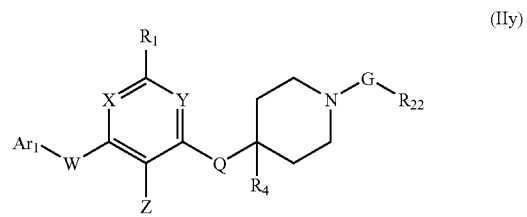

(IIy)

wherein each variable in Formula (IIy) has the same meaning as described herein, supra and infra. In some embodiments, G is C(O), C(O)$NR_{23}$, C(O)O, C(S), C(S)$NR_{23}$, C(S)O, $CR_{23}R_{24}$ or $S(O)_2$. In some embodiments, G is C(O) and can be represented by Formula (IIz) as shown below:

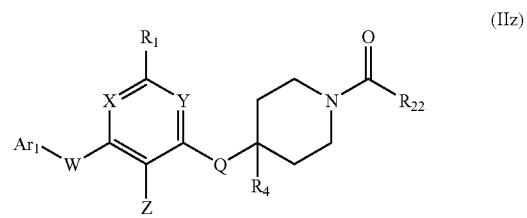

(IIz)

wherein each variable in Formula (IIz) has the same meaning as described herein, supra and infra. In some embodiments, G is C(O)O and can be represented by Formula (IIIa) as shown below:

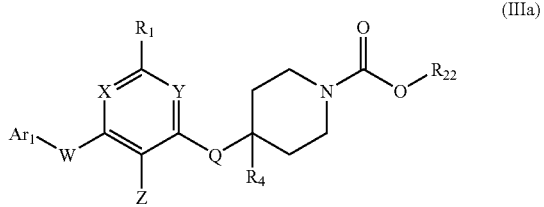

(IIIa)

wherein each variable in Formula (IIIa) has the same meaning as described herein, supra and infra.

In some embodiments, compounds are of either Formula (IIz) or (IIIa) and $R_{22}$ is $C_{1-8}$ alkyl, $C_{3-7}$ cycloalkyl, phenyl or heteroaryl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

In some embodiments, compounds are of either Formula (IIz) or (IIIa) and $R_{22}$ is $C_{1-8}$ alkyl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

In some embodiments, compounds are of either Formula (IIz) or (IIIa) and $R_{22}$ is phenyl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-4}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro. In some embodiments, the phenyl is substituted with 1 to 4 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, carboxamide, carboxy, $C_{3-7}$ cycloalkyl, $C_{2-8}$ dialkylamino, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio and halogen. In some embodiments, the phenyl is substituted with 1 to 4 substituents selected from the group consisting of $C_{1-4}$ alkylsulfonyl, $C_{1-4}$ haloalkylsulfonyl and halogen.

In some embodiments, compounds are of either Formula (IIz) or (IIIa) and $R_{22}$ is heteroaryl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro. In some embodiments, the heteroaryl is substituted with 1 to 4 substituents selected from the group consisting of $C_{1-5}$ acyl, $C_{1-4}$ alkoxy, $C_{1-7}$ alkyl, $C_{1-4}$ alkylsulfinyl, $C_{1-4}$ alkylsulfonyl, $C_{1-4}$ alkylthio, carboxamide, carboxy, $C_{3-7}$ cycloalkyl, $C_{2-8}$ dialkylamino, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio and halogen. In some embodiments, the heteroaryl is substituted with 1 to 4 substituents selected from the group consisting of $C_{1-4}$ alkylsulfonyl, $C_{1-4}$ haloalkylsulfonyl and halogen. In some embodiments, the heteroaryl is a 5-memebered heteroaryl, for example, as shown in TABLE 2A, supra. In some embodiments, the heteroaryl is a 6-membered heteroaryl, for example, as shown in TABLE 4, supra. In some embodiments, the heteroaryl is selected from the group consisting of pyridinyl, pyridazinyl, pyrimidinyl and pyrazinyl. In some embodiments, the heteroaryl is pyridinyl.

In some embodiments, $R_{22}$ is 1-methyl-1H-imidazole-4-yl, or 2,4-dimethyl-thiazole-5-yl.

In some embodiments, compounds are of Formula (IIy), (IIx) or (IIIa) and W is $NR_5$. In some embodiments, $R_5$ is H. In some embodiments, Z is cyano. In further embodiments, Q is $NR_6$, O, S, S(O) or $S(O)_2$. In still further embodiments, Q is NH or O.

Some embodiments of the present invention pertain to compounds of Formula (I) wherein D is O, S, S(O) or $S(O)_2$.

Some embodiments of the present invention pertain to compounds of Formula (I) wherein $R_{23}$ and $R_{24}$ are independently H or $C_{1-2}$ alkyl. In some embodiments, $R_{23}$ and $R_{24}$ are H.

In some embodiments, Z is selected from the group consisting of $C_{1-5}$ acyl, $C_{1-8}$ alkyl, $C_{2-6}$ alkynyl, $C_{1-4}$ alkylsulfonamide, amino, carbamimidoyl, cyano, $C_{3-7}$ cycloalkyl, heterocyclic, and hydroxycarbamimidoyl, wherein $C_{1-8}$ alkyl, $C_{3-7}$ cycloalkyl, and heterocyclic are each optionally substituted with 1, 2, 3 or 4 groups selected from the group consisting of $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro, and wherein said $C_{1-7}$ alkyl is optionally substituted with amino.

In some embodiments, Z is selected from the group consisting of $C_{1-5}$ acyl, $C_{1-8}$ alkyl, $C_{2-6}$ alkynyl, $C_{1-4}$ alkylsulfonamide, amino, carbamimidoyl, cyano, $C_{3-7}$ cycloalkyl, heterocyclic, and hydroxycarbamimidoyl, wherein said heterocyclic is optionally substituted with a —$CH_2NH_2$ group.

In some embodiments, Z is selected from the group consisting of $C(O)CH_3$, $C(O)CH_2CH_3$, $CH_3$, $CH_2CH_3$, C≡CH, $NHS(O)_2CH_3$, amino, carbamimidoyl, cyano, cyclopropyl, 4,5-dihydro-1H-imidazol-2-yl, 5-aminomethyl-4,5-dihydrooxazol-2-yl, and hydroxycarbamimidoyl.

Some embodiments of the present invention pertain to compounds of Formula (I) wherein Z is selected from the group consisting of $C_{1-5}$ acyl, $C_{1-4}$ alkoxy, $C_{1-8}$ alkyl, $C_{1-4}$ alkylcarboxamide, $C_{1-4}$ alkylthiocarboxamide, $C_{1-4}$ alkylthioureyl, $C_{1-4}$ alkylureyl, carboxamide, carboxy, cyano, formyl, aryl, $C_{1-4}$ haloalkyl, $C_{1-4}$ haloalkylcarboxamide, heteroaryl, hydroxyl, hydroxylamino, nitro and tetrazolyl. In some embodiments, Z is selected from the group consisting of formyl, $NHC(O)CH_3$, $NHC(O)CH_2CH_3$, $NHC(O)CH(CH_3)_2$, $CH_3$, $CH_2CH_3$, $CH(CH_3)_2$, $CH_2CH_2CH_2CH_3$, $NHC(O)CF_3$, carboxy, cyano, $CF_3$, $CF_2CF_3$, nitro and 1H-tetrazol-5-yl. In some embodiments, Z is selected from the group consisting of carboxy, $CF_3$, nitro and 1H-tetrazol-5-yl. In some embodiments, Z is cyano. In still further embodiments, Z is formyl [i.e. —C(O)H].

Some embodiments of the present invention pertain to compounds of Formula (I) wherein Z is Formula (A):

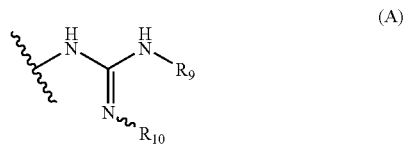

wherein:

$R_9$ is H, $C_{1-8}$ alkyl or $C_{3-7}$ cycloalkyl; and $R_{10}$ is H, nitro or nitrile. In some embodiments, $R_9$ is H or $C_{1-8}$ alkyl.

Some embodiments of the present invention pertain to compounds of Formula (I) wherein $R_1$, $R_7$ and $R_8$ are independently selected from the group consisting of H, $C_{1-4}$ alkoxy, $C_{1-8}$ alkyl, $C_{2-6}$ alkynyl, amino, $C_{3-7}$ cycloalkyl and $C_{1-4}$ haloalkyl. In some embodiments, $R_1$, $R_7$ and $R_8$ are independently H, halogen or amino. In still further embodiments, $R_1$, $R_7$ and $R_8$ are H.

In some embodiments, $Ar_1$ is aryl or heteroaryl each optionally substituted with $R_{11}$, $R_{12}$, $R_{13}$, $R_{14}$, and $R_{15}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

In some embodiments, $Ar_1$ is aryl.

In some embodiments, $Ar_1$ is phenyl optionally substituted with $R_{11}$, $R_{12}$, $R_{13}$, $R_{14}$, and $R_{15}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocy- clic-carbonyl, heteroaryl, heteroarylcarbonyl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

In some embodiments, $Ar_1$ is phenyl optionally substituted with $R_{11}$, $R_{12}$, $R_{13}$, $R_{14}$, and $R_{15}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-8}$ alkyl, and halogen.

Some embodiments of the present invention pertain to compounds of Formula (I) wherein $Ar_1$ is phenyl. In some embodiments, the phenyl is optionally substituted with $R_{11}$. In some embodiments, $R_{11}$ is selected from the group consisting of H, $C_{1-5}$ acyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, carboxamide, $C_{3-7}$ cycloalkyl, halogen and sulfonamide. In some embodiments, $R_{11}$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OCH_3$, $OCH_2CH_3$, $OCH_2CH_2CH_3$, $OCH(CH_3)_2$, $OCH_2CH_2CH_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $CH_2(CH_2)_4CH_3$, $CH_2(CH_2)_5CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, CCH, $S(O)_2NHCH_3$, $S(O)_2NHCH_2CH_3$, $S(O)_2NHCH_2CH_2CH_3$, $S(O)_2NHCH(CH_3)_2$, $S(O)_2NHCH_2(CH_2)_2CH_3$, $S(O)_2NHCH(CH_3)CH_2CH_3$, $S(O)CH_3$, $S(O)CH_2CH_3$, $S(O)CH_2CH_2CH_3$, $S(O)CH(CH_3)_2$, $S(O)CH_2(CH_2)_2CH_3$, $S(O)CH(CH_3)CH_2CH_3$, $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, $S(O)_2CH(CH_3)CH_2CH_3$, $SCH_3$, $SCH_2CH_3$, $SCH_2CH_2CH_3$, $SCH(CH_3)_2$ and $SCH_2(CH_2)_2CH_3$. In some embodiments, $R_{11}$ is selected from the group consisting of amino, arylsulfonyl, carboxy, cyano, $C_{3-7}$ cycloalkyl, halogen, $C_{1-4}$ haloalkoxy, $C_{1-4}$ haloalkyl and $C_{1-4}$ haloalkylthio. In some embodiments, $R_{11}$ is selected from the group consisting of phenylsulfonyl, cyclopropyl, cyclobutyl, cyclopentyl, cyclohexyl, Cl, F, Br, $OCF_3$, $OCHF_2$, $OCH_2CF_3$, $CF_3$, $CHF_2$, $CH_2CF_3$, $SCF_3$, $SCHF_2$ and $SCH_2CF_3$. In some embodiments, $R_{11}$ is selected from the group consisting of heterocyclic, heteroaryl, $C_{4-7}$ oxo-cycloalkyl, phenoxy and phenyl. In some embodiments, $R_{11}$ is selected from the group consisting of morpholin-4-yl, thiomorpholin-4-yl, 1-oxo-$1\lambda^4$-thiomorpholin-4-yl, 1,1-Dioxo-$1\lambda^6$-thiomorpholin-4-yl, piperazin-1-yl, 4-methyl-piperazin-1-yl, 4-ethyl-piperazin-1-yl, 4-propyl-piperazin-1-yl, piperidin-1-yl, pyrrolidin-1-yl, 2,5-dioxo-imidazolidin-4-yl, 2,4-dioxo-thiazolidin-5-yl, 4-oxo-2-thioxo-thiazolidin-5-yl, 3-methyl-2,5-dioxo-imidazolidin-4-yl, 3-methyl-2,4-dioxo-thiazolidin-5-yl, 3-methyl-4-oxo-2-thioxo-thiazolidin-5-yl, 3-ethyl-2,5-dioxo-imidazolidin-4-yl, 3-ethyl-2,4-dioxo-thiazolidin-5-yl, and 3-ethyl-4-oxo-2-thioxo-thiazolidin-5-yl. In some embodiments, $R_{11}$ is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, $R_{11}$ is $C_{1-8}$ alkyl or $C_{1-4}$ alkoxy optionally substituted with 1 to 5 substituents selected independently from the group consisting of $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carbo-$C_{1-6}$-alkoxy, carboxamide, carboxy, cyano, heterocyclic, hydroxyl and phenyl. In some embodiments, $R_{11}$ is $C_{1-4}$ alkylsulfonyl optionally substituted with 1 to 5 substituents selected independently from the group consisting of $C_{1-4}$ alkoxy, carboxamide, heteroaryl, heterocyclic and phenyl. In some embodiments, the $C_{1-4}$ alkylsulfonyl is substituted with the heteroaryl group. In some embodiments, the heteroaryl group is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4] thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3] thiadiazol-4-yl. In some embodiments, $R_{11}$ is arylsulfonyl, heteroaryl, phenoxy or phenyl optionally substituted with 1 to 5 substituents selected independently from the group consisting of $C_{1-5}$ acyl, $C_{1-4}$ alkoxy, $C_{1-8}$ alkyl, $C_{1-4}$ alkylsulfonamide, $C_{1-4}$ alkylsulfinyl, $C_{1-4}$ alkylsulfonyl, $C_{1-4}$ alkylthio, carboxamide, carboxy, cyano, halogen, $C_{1-4}$ haloalkoxy, $C_{1-4}$ haloalkyl, $C_{1-4}$ haloalkylthio and hydroxyl. In some embodiments, $R_{11}$ is arylsulfonyl, heteroaryl, phenoxy or phenyl optionally substituted with 1 to 5 substituents selected independently from the group consisting of $C_{1-4}$ alkoxy, $C_{1-8}$ alkyl, cyano, halogen, $C_{1-4}$ haloalkoxy, $C_{1-4}$ haloalkyl and hydroxyl.

Some embodiments of the present invention pertain to compounds of Formula (I) wherein $Ar_1$ is phenyl. In some embodiments, the phenyl is optionally substituted with $R_{11}$. In some embodiments, $R_{11}$ is a group of Formula (B):

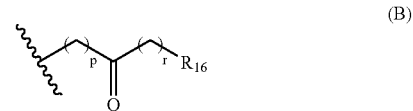

(B)

wherein:

"p" and "r" are independently 0, 1, 2 or 3; and $R_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl may be optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, p=0 and r=0. In some embodiments, $R_{16}$ is heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, p=0 and r=1. In some embodiments, $R_{16}$ is carbo-$C_{1-6}$-alkoxy or carboxy. In some embodiments, p=2 and r=1. In some embodiments, $R_{16}$ is H, $C_{1-5}$ acyl or $C_{1-8}$ alkyl.

Some embodiments of the present invention pertain to compounds of Formula (I) wherein $Ar_1$ is phenyl. In some embodiments, the phenyl is optionally substituted with $R_{11}$, $R_{12}$, $R_{13}$, $R_{14}$, and $R_{15}$. In some embodiments, $R_{11}$, $R_{12}$, $R_{13}$, $R_{14}$, and $R_{15}$ are independently selected from the group consisting of H, $C_{1-5}$ acyl, $C_{1-4}$ alkoxy, $C_{1-8}$ alkyl, $C_{1-4}$ alkylcarboxamide, $C_{1-4}$ alkylureyl, carbo-$C_{1-6}$-alkoxy, carboxamide, carboxy, cyano, $C_{3-7}$ cycloalkyl, halogen, $C_{1-4}$ haloalkoxy and $C_{1-4}$ haloalkyl.

Some embodiments of the present invention pertain to compounds of Formula (I) wherein $Ar_1$ is phenyl and $R_{11}$ is substituted at the para position on the phenyl; these embodiments can be represented by Formula (IIIc) as shown below:

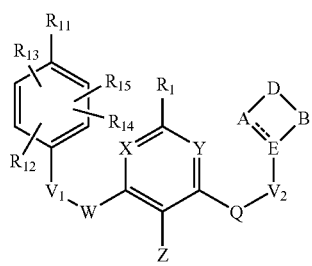

wherein each variable in Formula (IIIc) has the same meaning as described herein, supra and infra.

Some embodiments of the present invention pertain to compounds of Formula (I) wherein $Ar_1$ is phenyl and two adjacent $R_{11}$, $R_{12}$, $R_{13}$, $R_{14}$, and $R_{15}$ groups together with the atoms to which they are attached form a 5-, 6- or 7-membered cycloalkyl, cycloalkenyl or heterocyclic group fused with $Ar_1$, wherein the 5-, 6- or 7-membered group is optionally substituted with halogen. In some embodiments, the phenyl and two adjacent $R_{11}$, $R_{12}$, $R_{13}$, $R_{14}$, and $R_{15}$ groups form a 5-, 6- or 7-membered cycloalkyl as represented in TABLE 5:

TABLE 5

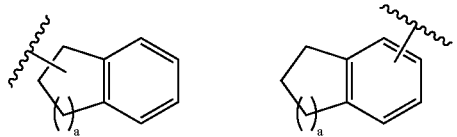

wherein "a" is 1, 2 or 3 to give a 5-, 6- or 7-membered cycloalkyl fused together with the phenyl group where two of the ring carbons are shared between the cycloalkyl and phenyl group. In some embodiments, 1, 2, or 3 ring carbons are replaced by a heteroatom selected from, but not limited to, O, S, and N, wherein N is substituted with H or $C_{1-4}$ alkyl. In some embodiments, the two adjacent groups form a 5 membered heterocyclic group with the phenyl group. In some embodiments, the 5 membered heterocyclic group with the phenyl group together is a 2,3-dihydro-benzofuran-5-yl or benzo[1,3]dioxol-5-yl group. In some embodiments, the two adjacent groups form a 6 membered heterocyclic group with the phenyl group. In some embodiments, the 6 membered heterocyclic group with the phenyl group together is a 2,3-dihydro-benzo[1,4]dioxin-6-yl or 2,3-dihydro-benzo[1,4]dioxin-2-yl group. In some embodiments, the two adjacent groups form a 7 membered heterocyclic group with the phenyl group. In some embodiments, the 7 membered heterocyclic group with the phenyl group together is a 3,4-dihydro-2H-benzo[b][1,4]dioxepin-7-yl group.

In some embodiments, $Ar_1$ is heteroaryl.

In some embodiments, $Ar_1$ is pyridyl optionally substituted with $R_{11}$, $R_{12}$, $R_{13}$, and $R_{14}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting Of $C_{1-4}$ alkoxy and hydroxy; and $R_{12}$, $R_{13}$, and $R_{14}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

In some embodiments, $Ar_1$ is pyridyl optionally substituted with $R_{11}$, $R_{12}$, $R_{13}$, and $R_{14}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-4}$ alkylsulfonyl, $C_{1-4}$ alkylthio, amino, $C_{2-6}$ dialkylamino, halogen, heterocyclic, and sulfonamide, and wherein $C_{1-4}$ alkoxy, $C_{1-8}$ alkyl, $C_{1-4}$ alkylamino, alkylsulfonyl, $C_{1-4}$ alkylthio, $C_{2-6}$ dialkylamino, and heterocyclic are each optionally substituted with 1 to 5 substituents selected independently from the group consisting of $C_{1-6}$ acylsulfonamide, $C_{1-4}$ alkoxy, $C_{1-4}$ alkylsulfonyl, $C_{3-7}$ cycloalkyloxy, heteroaryl, hydroxyl, phenyl, and phosphonooxy; and $R_{12}$, $R_{13}$, and $R_{14}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

In some embodiments, $Ar_1$ is pyridyl optionally substituted with $R_{11}$, $R_{12}$, $R_{13}$, and $R_{14}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-4}$ alkylsulfonyl, $C_{1-4}$ alkylthio, amino, $C_{2-6}$ dialkylamino, halogen, heterocyclic, and sulfonamide, and wherein $C_{1-4}$ alkoxy, $C_{1-8}$ alkyl, $C_{1-4}$ alkylamino, alkylsulfonyl, $C_{1-4}$ alkylthio, $C_{2-6}$ dialkylamino, and heterocyclic are each optionally substituted with 1 to 5 substituents selected independently from the group consisting of $C_{1-6}$ acylsulfonamide, $C_{1-4}$ alkoxy, $C_{1-4}$ alkylsulfonyl, $C_{3-7}$ cycloalkyloxy, heteroaryl, hydroxyl, phenyl, and phosphonooxy; and $R_{12}$, $R_{13}$, and $R_{14}$ are each independently selected form the group consisting of $C_{1-8}$ alkyl, and halogen.

Some embodiments of the present invention pertain to compounds of Formula (I) wherein $Ar_1$ is heteroaryl. In some embodiments, the heteroaryl is optionally substituted with $R_{11}$. In some embodiments, $R_{11}$ is selected from the group consisting of $C_{1-5}$ acyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, carboxamide, $C_{3-7}$ cycloalkyl, halogen and sulfonamide. In some embodiments, $R_{11}$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OCH_3$, $OCH_2CH_3$, $OCH_2CH_2CH_3$, $OCH(CH_3)_2$, $OCH_2CH_2CH_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $CH_2(CH_2)_4CH_3$, $CH_2(CH_2)_5CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, $CCH$, $S(O)_2NHCH_3$, $S(O)_2NHCH_2CH_3$, $S(O)_2NHCH_2CH_2CH_3$, $S(O)_2NHCH(CH_3)_2$, $S(O)_2NHCH_2(CH_2)_2CH_3$, $S(O)_2NHCH(CH_3)CH_2CH_3$, $S(O)CH_3$, $S(O)CH_2CH_3$, $S(O)CH_2CH_2CH_3$, $S(O)$ $CH(CH_3)_2$, $S(O)CH_2(CH_2)_2CH_3$, $S(O)CH(CH_3)CH_2CH_3$, $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, $S(O)_2CH(CH_3)CH_2CH_3$, $SCH_3$, $SCH_2CH_3$, $SCH_2CH_2CH_3$, $SCH(CH_3)_2$ and $SCH_2(CH_2)_2CH_3$. In some embodiments, $R_{11}$ is selected from the group consisting of amino, arylsulfonyl, carboxy, cyano, $C_{3-7}$ cycloalkyl, halogen, $C_{1-4}$ haloalkoxy, $C_{1-4}$ haloalkyl and $C_{1-4}$ haloalkylthio. In some embodiments, $R_{11}$ is selected from the group consisting of phenylsulfonyl, cyclopropyl, cyclobutyl, cyclopentyl, cyclohexyl, Cl, F, Br, $OCF_3$, $OCHF_2$, $OCH_2CF_3$, $CF_3$, $CHF_2$, $CH_2CF_3$, $SCF_3$, $SCHF_2$ and $SCH_2CF_3$. In some embodiments, $R_{11}$ is selected from the group consisting of heterocyclic, heteroaryl, $C_{4-7}$ oxo-cycloalkyl, phenoxy and phenyl. In some embodiments, $R_{11}$ is selected from the group consisting of morpholin-4-yl, thiomorpholin-4-yl, 1-oxo-$1\lambda^4$-thiomorpholin-4-yl, 1,1-Dioxo-$1\lambda^6$-thiomorpholin-4-yl, piperazin-1-yl, 4-methyl-piperazin-1-yl, 4-ethyl-piperazin-1-yl, 4-propyl-piperazin-1-yl, piperidin-1-yl, pyrrolidin-1-yl, 2,5-dioxo-imidazolidin-4-yl, 2,4-dioxo-thiazolidin-5-yl, 4-oxo-2-thioxo-thiazolidin-5-yl, 3-methyl-2,5-dioxo-imidazolidin-4-yl, 3-methyl-2,4-dioxo-thiazolidin-5-yl, 3-methyl-4-oxo-2-thioxo-thiazolidin-5-yl, 3-ethyl-2,5-dioxo-imidazolidin-4-yl, 3-ethyl-2,4-dioxo-thiazolidin-5-yl, and 3-ethyl-4-oxo-2-thioxo-thiazolidin-5-yl. In some embodiments, $R_{11}$ is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, $R_{11}$ is $C_{1-8}$ alkyl or $C_{1-4}$ alkoxy, optionally substituted with 1 to 5 substituents selected independently from the group consisting of $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carbo-$C_{1-6}$-alkoxy, carboxamide, carboxy, cyano, heterocyclic, hydroxyl and phenyl. In some embodiments, $R_{11}$ is $C_{1-4}$ alkylsulfonyl optionally substituted with 1 to 5 substituents selected independently from the group consisting of $C_{1-4}$ alkoxy, carboxamide, heteroaryl, heterocyclic and phenyl. In some embodiments, the $C_{1-4}$ alkylsulfonyl is substituted with the heteroaryl group. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, $R_{11}$ is arylsulfonyl, heteroaryl, phenoxy or phenyl optionally substituted with 1 to 5 substituents selected independently from the group consisting of $C_{1-5}$ acyl, $C_{1-4}$ alkoxy, $C_{1-8}$ alkyl, $C_{1-4}$ alkylsulfonamide, $C_{1-4}$ alkylsulfinyl, $C_{1-4}$ alkylsulfonyl, $C_{1-4}$ alkylthio, carboxamide, carboxy, cyano, halogen, $C_{1-4}$ haloalkoxy, $C_{1-4}$ haloalkyl, $C_{1-4}$ haloalkylthio and hydroxyl. In some embodiments, $R_{11}$ is arylsulfonyl, heteroaryl, phenoxy or phenyl optionally substituted with 1 to 5 substituents selected independently from the group consisting of $C_{1-4}$ alkoxy, $C_{1-8}$ alkyl, cyano, halogen, $C_{1-4}$ haloalkoxy, $C_{1-4}$ haloalkyl and hydroxyl.

Some embodiments of the present invention pertain to compounds of Formula (I) wherein $Ar_1$ is heteroaryl. In some embodiments, the heteroaryl is optionally substituted with $R_{11}$. In some embodiments, $R_{11}$ is of Formula (B):

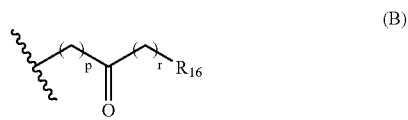

wherein:
"p" and "r" are independently 0, 1, 2 or 3; and $R_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl may be optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, p=0 and r=0. In some embodiments, $R_{16}$ is heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, p=0 and r=1. In some embodiments, $R_{16}$ is carbo-$C_{1-6}$-alkoxy or carboxy. In some embodiments, p=2 and r=1. In some embodiments, $R_{16}$ is H, $C_{1-5}$ acyl or $C_{1-8}$ alkyl.

Some embodiments of the present invention pertain to compounds of Formula (I) wherein $Ar_1$ is heteroaryl. In some embodiments, the heteroaryl is optionally substituted with $R_{11}$, $R_{12}$, $R_{13}$, $R_{14}$, and $R_{15}$. In some embodiments, $R_{11}$, $R_{12}$, $R_{13}$, $R_{14}$, and $R_{15}$ are independently selected from the group consisting of H, $C_{1-5}$ acyl, $C_{1-4}$ alkoxy, $C_{1-8}$ alkyl, $C_{1-4}$ alkylcarboxamide, $C_{1-4}$ alkylureyl, carbo-$C_{1-6}$-alkoxy, carboxamide, carboxy, cyano, $C_{3-7}$ cycloalkyl, halogen, $C_{1-4}$ haloalkoxy and $C_{1-4}$ haloalkyl.

Some embodiments of the present invention pertain to compounds of Formula (I) wherein $Ar_1$ is heteroaryl. In some embodiments, the heteroaryl is optionally substituted with $R_{11}$, $R_{12}$, $R_{13}$, $R_{14}$, and $R_{15}$ wherein two adjacent $R_{11}$, $R_{12}$, $R_{13}$, $R_{14}$, and $R_{15}$ groups together with the atoms to which they are attached form a 5-, 6- or 7-membered cycloalkyl, cycloalkenyl or heterocyclic group fused with $Ar_1$, wherein the 5-, 6- or 7-membered group is optionally substituted with halogen. In some embodiments, the two adjacent groups form a 5-membered heterocyclic group with the heteroaryl group. In some embodiments, the two adjacent groups form a 6-membered heterocyclic group with the heteroaryl group. In some embodiments, the two adjacent groups form a 7-membered heterocyclic group with the heteroaryl group.

Some embodiments of the present invention pertain to compounds of Formula (I) wherein $R_4$, $R_5$ and $R_6$ are independently H or $CH_3$.

Some embodiments of the present invention pertain to compounds of Formula (I) wherein X is N.

Some embodiments of the present invention pertain to compounds of Formula (I) wherein Y is N.

Some embodiments of the present invention pertain to compounds of Formula (I) wherein X is N and Y is CH.

Some embodiments of the present invention pertain to compounds of Formula (I) wherein X is CH and Y is N.

Some embodiments of the present invention pertain to compounds of Formula (I) wherein X and Y are N.

Some embodiments of the present invention pertain to compounds of Formula (I) wherein X and Y are CH.

Some embodiments of the present invention pertain to compounds of Formula (I) wherein:

A and B are each independently —CH$_2$CH$_2$— or —CH$_2$—;

D is N—R$_2$;

V$_1$ is a bond;

V$_2$ is —CH$_2$—, —CH$_2$CH$_2$—, or a bond;

W and Q are each independently NH or O;

X and Y are each independently N or CH, provided that if either X or Y is CH then the other is N;

Z is selected from the group consisting of nitro, C$_{1-5}$ acyl, C$_{1-8}$ alkyl, C$_{2-6}$ alkynyl, C$_{1-4}$ alkylsulfonamide, amino, carbamimidoyl, cyano, C$_{3-7}$ cycloalkyl, heterocyclic, and hydroxycarbamimidoyl, wherein said heterocyclic is optionally substituted with a —CH$_2$NH$_2$ group;

R$_2$ is —C(O)OR$_{22}$, —C(O)R$_{22}$, —CH$_2$R$_{22}$, —R$_{22}$, —S(O)$_2$ R$_{22}$, —CR$_{23}$R$_{24}$C(O)R$_{22}$, or

—CR$_{23}$R$_{24}$C(O)NR$_{25}$R$_{22}$, wherein R$_{22}$ is C$_{1-8}$ alkyl, C$_{3-7}$ cycloalkyl, phenyl, heteroaryl, or heterocyclic each optionally substituted with 1 to 5 substituents selected from the group consisting of C$_{2-6}$ alkenyl, C$_{1-4}$ alkoxy, C$_{1-7}$ alkyl, C$_{1-4}$ alkylsulfonyl, amino, carbo-C$_{1-6}$-alkoxy, carboxy, cyano, C$_{3-7}$ cycloalkyl, C$_{2-8}$ dialkylamino, C$_{1-4}$ haloalkoxy, C$_{1-4}$ haloalkyl, halogen, heteroaryl, heterocyclic, hydroxyl, phenyl, phenoxy, and sulfonic acid, wherein said C$_{1-7}$ alkyl, phenyl and phenoxy are each optionally substituted with 1 to 5 substituents selected from the group consisting of amino, C$_{1-4}$ haloalkoxy, and heterocyclic; and R$_{23}$ and R$_{24}$ are each independently H or C$_{1-8}$ alkyl;

Ar$_1$ is aryl or heteroaryl each optionally substituted with R$_{11}$, R$_{12}$, R$_{13}$, R$_{14}$, and R$_{15}$; wherein R$_{11}$ is selected from the group consisting of C$_{1-6}$ acylsulfonamide, C$_{1-4}$ alkoxy, C$_{1-8}$ alkyl, C$_{2-6}$ alkynyl, C$_{1-4}$ alkylamino, C$_{1-6}$ alkylcarboxamide, C$_{1-4}$ alkylsulfonamide, C$_{1-4}$ alkylsulfonyl, C$_{1-4}$ alkylthio, amino, carbamimidoyl, carboxamide, carboxy, cyano, C$_{2-6}$ dialkylamino, halogen, heterocyclic, heterocyclic-oxy, heterocyclic-carbonyl, heteroaryl, and sulfonamide, and wherein C$_{1-6}$ acylsulfonamide, C$_{1-4}$ alkoxy, C$_{1-8}$ alkyl, C$_{1-4}$ alkylamino, C$_{1-4}$ alkylsulfonamide, alkylsulfonyl, C$_{1-4}$ alkylthio, carbamimidoyl, C$_{2-6}$ dialkylamino, heterocyclic, heterocyclic-carbonyl, and heteroaryl are each optionally substituted with 1 to 5 substituents selected independently from the group consisting of C$_{1-6}$ acylsulfonamide, C$_{1-4}$ alkoxy, C$_{1-7}$ alkyl, C$_{1-4}$ alkylcarboxamide, C$_{1-4}$ alkylsulfonyl, carboxy, C$_{3-7}$ cycloalkyloxy, C$_{2-6}$ dialkylamino, C$_{2-6}$ dialkylcarboxamide, heteroaryl, heterocyclic, hydroxyl, phenyl, and phosphonooxy wherein said C$_{1-7}$ alkyl and C$_{1-4}$ alkylcarboxamide are each optionally substituted with 1 to 5 substituents selected from the group consisting of C$_{1-4}$ alkoxy and hydroxy; and R$_{12}$, R$_{13}$, R$_{14}$, and R$_{15}$ are each independently selected form the group consisting of C$_{1-6}$ acylsulfonamide, C$_{1-4}$ alkoxy, C$_{1-8}$ alkyl, C$_{1-4}$ alkylamino, C$_{1-4}$ alkylcarboxamide, C$_{1-4}$ alkylsulfonamide, C$_{1-4}$ alkylsulfonyl, C$_{1-4}$ alkylthio, amino, carbamimidoyl, carboxamide, cyano, C$_{2-6}$ dialkylamino, and halogen.

Some embodiments of the present invention pertain to compounds of Formula (I) wherein:

A and B are both —CH$_2$CH$_2$—;

D is N—R$_2$;

V$_1$ and V$_2$ are both a bond;

W and Q are each independently NH or O;

X and Y are both N;

Z is selected from the group consisting of nitro, C(O)CH$_3$, C(O)CH$_2$CH$_3$, CH$_3$, CH$_2$CH$_3$, C≡CH, NHS(O)$_2$CH$_3$, amino, carbamimidoyl, cyano, cyclopropyl, 4,5-dihydro-1H-imidazol-2-yl, 5-aminomethyl-4,5-dihydro-oxazol-2-yl, and hydroxycarbamimidoyl;

R$_2$ is —C(O)OR$_{22}$, wherein R$_{22}$ is C$_{1-8}$ alkyl, or C$_{3-7}$ cycloalkyl each optionally substituted with 1 to 5 substituents selected from the group consisting of C$_{1-4}$ alkoxy, C$_{1-8}$ alkyl, C$_{1-4}$ alkylsulfonyl, amino, carboxy, cyano, C$_{3-7}$ cycloalkyl, C$_{2-8}$ dialkylamino, C$_{1-4}$ haloalkoxy, C$_{1-4}$ haloalkyl, halogen, and hydroxyl;

Ar$_1$ is phenyl optionally substituted with R$_{11}$, R$_{12}$, R$_{13}$, R$_{14}$, and R$_{15}$;

wherein R$_{11}$ is selected from the group consisting Of C$_{1-6}$ acylsulfonamide, C$_{1-4}$ alkoxy, C$_{1-8}$ alkyl, C$_{1-4}$ alkylamino, C$_{1-6}$ alkylcarboxamide, C$_{1-4}$ alkylsulfonamide, C$_{1-4}$ alkylsulfonyl, C$_{1-4}$ alkylthio, carbamimidoyl, carboxamide, carboxy, cyano, C$_{2-6}$ dialkylamino, halogen, heterocyclic, heterocyclic-oxy, heterocyclic-carbonyl, heteroaryl, heteroarylcarbonyl, and sulfonamide, and wherein C$_{1-4}$ alkoxy, C$_{1-8}$ alkyl, C$_{1-4}$ alkylamino, C$_{1-16}$ alkylcarboxamide, C$_{1-4}$ alkylsulfonamide, C$_{1-4}$ alkylsulfonyl, C$_{1-4}$ alkylthio, carbamimidoyl, C$_{2-6}$ dialkylamino, heterocyclic, heterocyclic-carbonyl, and heteroaryl are each optionally substituted with 1 to 5 substituents selected independently from the group consisting of C$_{1-6}$ acylsulfonamide, C$_{1-4}$ alkoxy, C$_{1-7}$ alkyl, C$_{1-4}$ alkylcarboxamide, C$_{1-4}$ alkylsulfonyl, carboxy, C$_{2-6}$ dialkylamino, C$_{2-6}$ dialkylcarboxamide, heteroaryl, heterocyclic, hydroxyl, phenyl, and phosphonooxy wherein said C$_{1-7}$ alkyl and C$_{1-4}$ alkylcarboxamide are each optionally substituted with 1 to 5 substituents selected from the group consisting of C$_{1-4}$ alkoxy and hydroxy; and R$_{12}$, R$_{13}$, R$_{14}$, and R$_{15}$ are each independently selected form the group consisting Of C$_{1-8}$ alkyl, and halogen.

Some embodiments of the present invention pertain to compounds of Formula (I) wherein:

A and B are both —CH$_2$CH$_2$—;

D is N—R$_2$;

V$_1$ and V$_2$ are both a bond;

W is NH;

Q is O;

X and Y are both N;

Z is nitro, cyano, C(O)CH$_3$, amino, CH$_3$, CH$_2$CH$_3$, or C≡CH;

R$_2$ is —C(O)OR$_{22}$, —C(O)R$_{22}$, —R$_{22}$, or —S(O)$_2$R$_{22}$ wherein R$_{22}$ is C$_{1-8}$ alkyl, C$_{3-7}$ cycloalkyl, phenyl, heteroaryl, or heterocyclic each optionally substituted with 1 to 5 substituents selected from the group consisting of C$_{1-5}$ acyl, C$_{2-6}$ alkenyl, C$_{1-4}$ alkoxy, C$_{1-7}$ alkyl, C$_{1-4}$ alkylsulfonyl, amino, carbo-C$_{1-6}$-alkoxy, carboxy, cyano, C$_{3-7}$ cycloalkyl, C$_{2-8}$ dialkylamino, C$_{1-4}$ haloalkoxy, C$_{1-4}$ haloalkyl, halogen, heteroaryl, heterocyclic, hydroxyl, phenyl, phenoxy, and sulfonic acid, wherein said C$_{1-7}$ alkyl, phenyl and phenoxy are each optionally substituted with 1 to 5 substituents selected from the group consisting of amino, C$_{1-4}$ haloalkoxy, and heterocyclic;

Ar$_1$ is phenyl, 3-pyridyl, or 2-pyridyl each optionally substituted with R$_{11}$, R$_{12}$, R$_{13}$, R$_{14}$, and R$_{15}$, wherein R$_{11}$ is selected from the group consisting Of C$_{1-6}$ acylsulfonamide, C$_{1-4}$ alkoxy, C$_{1-8}$ alkyl, C$_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting Of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently $CH_3$, or F.

Some embodiments of the present invention pertain to compounds of Formula (I) wherein:

A and B are both —$CH_2CH_2$—;
D is N—$R_2$;
$V_1$ and $V_2$ are both a bond;
W and Q are both O;
X and Y are both N;
Z is selected from the group consisting of $CH_3$, $CH_2CH_3$, cyclopropyl, or C≡CH;
$R_2$ is —C(O)O$R_{22}$, —C(O)$R_{22}$, —$R_{22}$, —$CH_2$C(O)$R_{22}$, or —$CH_2$C(O)NH$R_{22}$, wherein $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylsulfonyl, amino, carboxy, cyano, $C_{2-8}$ dialkylamino, $C_{1-4}$ haloalkoxy, $C_{1-4}$ haloalkyl, halogen, heteroaryl, hydroxyl, phenyl, and phenoxy, wherein said $C_{1-7}$ alkyl, is optionally substituted with 1 or 2 substituents selected from the group consisting of $C_{1-4}$ haloalkoxy, and heterocyclic;

$Ar_1$ is phenyl, 2-pyridyl, or 3-pyridyl each optionally substituted with $R_{11}$, $R_{12}$, $R_{13}$, $R_{14}$, and $R_{15}$, wherein $R_{11}$ is selected from the group consisting of $C_{1-6}$ acylsulfonamide, $C_{1-4}$ alkoxy, $C_{1-8}$ alkyl, $C_{2-6}$ alkynyl $C_{1-4}$ alkylamino, $C_{1-6}$ alkylcarboxamide, $C_{1-4}$ alkylsulfonyl, $C_{1-4}$ alkylthio, amino, carbamimidoyl, carboxy, cyano, $C_{2-6}$ dialkylamino, halogen, heterocyclic, heterocyclic-oxy, heterocyclic-carbonyl, heteroaryl, and sulfonamide, and wherein $C_{1-4}$ alkoxy, $C_{1-8}$ alkyl, $C_{1-4}$ alkylamino, $C_{1-6}$ alkylcarboxamide, $C_{1-4}$ alkylsulfonyl, $C_{1-4}$ alkylthio, $C_{2-6}$ dialkylamino, and heteroaryl are each optionally substituted with 1 to 5 substituents selected independently from the group consisting of $C_{1-4}$ alkoxy, $C_{1-7}$ alkyl, $C_{1-4}$ alkylcarboxamide, heteroaryl, hydroxyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-8}$ alkyl, and halogen.

In some embodiments, compounds of the present invention are when $R_{11}$ is selected from the group consisting of:
sulfamoyl [—S(O)$_2$NH$_2$],
acetylsulfamoyl [—S(O)$_2$NHC(O)CH$_3$],
propionylsulfamoyl [—S(O)$_2$NHC(O)CH$_2$CH$_3$],
butyrylsulfamoyl [—S(O)$_2$NHC(O)CH$_2$CH$_2$CH$_3$],
pentanoylsulfamoyl [—S(O)$_2$NHC(O)CH$_2$CH$_2$CH$_2$CH$_3$],
methanesulfonyl [—S(O)$_2$CH$_3$],
ethanesulfonyl [—S(O)$_2$CH$_2$CH$_3$],
propane-1-sulfonyl [—S(O)$_2$CH$_2$CH$_2$CH$_3$],
hydroxymethyl (—CH$_2$OH);
2-hydroxyethyl (—CH$_2$CH$_2$OH);
3-hydroxypropyl (—CH$_2$CH$_2$CH$_2$OH);
4-hydroxy-butyl (—CH$_2$CH$_2$CH$_2$CH$_2$OH);
phosphonooxymethyl [—CH$_2$OP(O)(OH)$_2$];
2-phosphonooxy-ethyl [—CH$_2$CH$_2$OP(O)(OH)$_2$];
3-phosphonooxy-propyl [—CH$_2$CH$_2$CH$_2$OP(O)(OH)$_2$]; and
4-phosphonooxy-butyl [—CH$_2$CH$_2$CH$_2$CH$_2$OP(O)(OH)$_2$].

In some embodiments, $R_{11}$ is methoxy, ethoxy, isobutoxy or 3-methyl-butoxy.

In some embodiments, $R_{11}$ is pyridyl optionally substituted with $C_{1-4}$ alkoxy, $C_{1-8}$ alkyl, $C_{1-4}$ alkylamino, halogen or hydroxyl.

In some embodiments, $R_{11}$ is 2-pyridyl optionally substituted with $C_{1-4}$ alkoxy, $C_{1-8}$ alkyl, $C_{1-4}$ alkylamino, halogen or hydroxyl.

In some embodiments, $R_{11}$ is 3-pyridyl optionally substituted with $C_{1-4}$ alkoxy, $C_{1-8}$ alkyl, $C_{1-4}$ alkylamino, halogen or hydroxyl.

Some embodiments of the present invention include one of more of the compounds illustrated in TABLES A, B, C, D and E; these TABLES are shown below.

TABLE A

| Cmpd # | Structure | Chemical Name |
| --- | --- | --- |
| A1 | 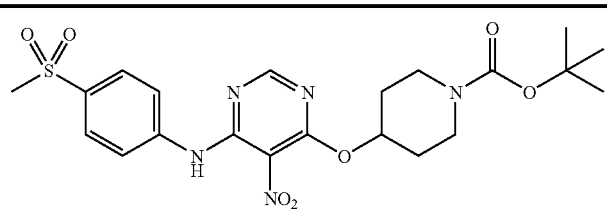 | 4-[6-(4-Methanesulfonyl-phenyl-amino)-5-nitro-pyrimidin-4-yloxy]-piperidine-1-carboxylic acid tert-butyl ester |
| A2 | 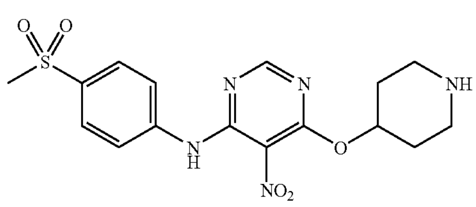 | (4-Methanesulfonyl-phenyl)-[5-nitro-6-(piperidin-4-yloxy)-pyrimidin-4-yl]-amine |

TABLE A-continued

| Cmpd # | Structure | Chemical Name |
|---|---|---|
| A3 | 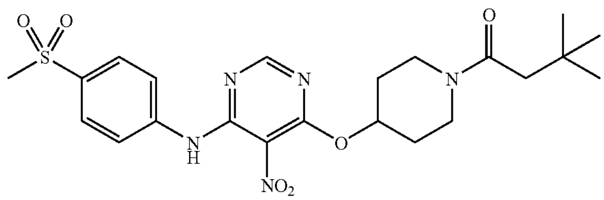 | 1-{4-[6-(4-Methanesulfonyl-phenyl-amino)-5-nitro-pyrimidin-4-yl-oxy]-piperidin-1-yl}-3,3-dimethyl-butan-1-one |
| A4 | 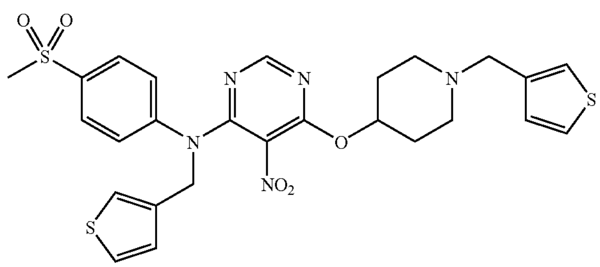 | (4-Methanesulfonyl-phenyl)-[5-nitro-6-(1-thiophen-3-ylmethyl-piperidin-4-yloxy)-pyrimidin-4-yl]-thiophen-3-ylmethyl-amine |
| A5 | 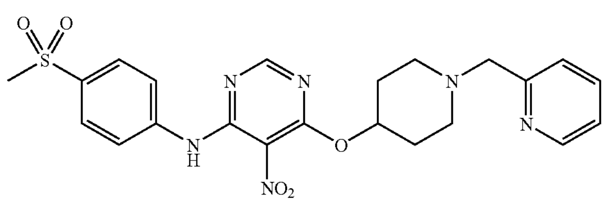 | (4-Methanesulfonyl-phenyl)-[5-nitro-6-(1-pyridin-2-ylmethyl-piperidin-4-yloxy)-pyrimidin-4-yl]-amine |
| A6 | 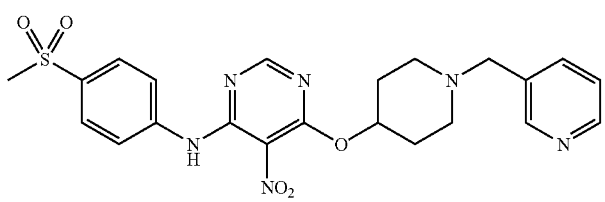 | (4-Methanesulfonyl-phenyl)-[5-nitro-6-(1-pyridin-3-ylmethyl-piperidin-4-yloxy)-pyrimidin-4-yl]-amine |
| A7 | 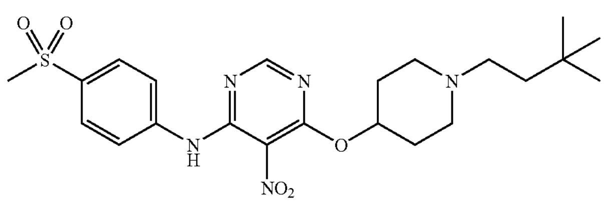 | {6-[1-(3,3-Dimethyl-butyl)-piperidin-4-yloxy]-5-nitro-pyrimidin-4-yl}-(4-methanesulfonyl-phenyl)-amine |
| A8 | 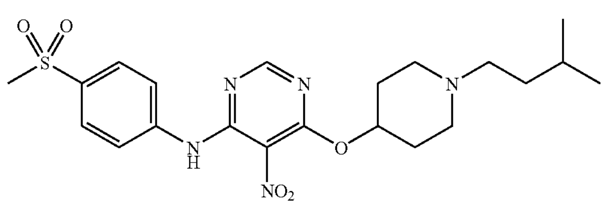 | (4-Methanesulfonyl-phenyl)-{6-[1-(3-methyl-butyl)-piperidin-4-yloxy]-5-nitro-pyrimidin-4-yl}-amine |
| A9 | 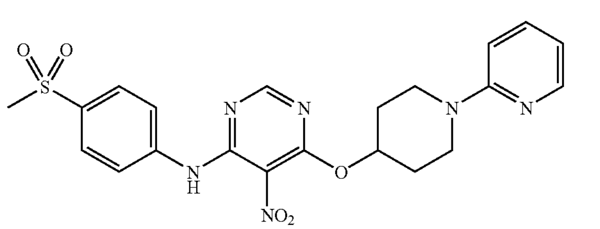 | (4-Methanesulfonyl-phenyl)-[5-nitro-6-(3,4,5,6-tetrahydro-2H-[1,2']bipyridinyl-4-yloxy)-pyrimidin-4-yl]-amine |

TABLE A-continued

| Cmpd # | Structure | Chemical Name |
|---|---|---|
| A10 | 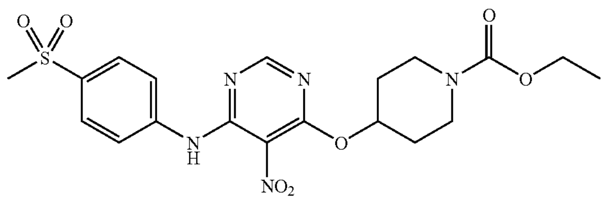 | 4-[6-(4-Methanesulfonyl-phenyl-amino)-5-nitro-pyrimidin-4-yl-oxy]-piperidine-1-carboxylic acid ethyl ester |
| A11 | 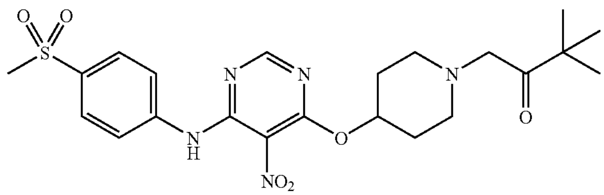 | 1-{4-[6-(4-Methanesulfonyl-phenyl-amino)-5-nitro-pyrimidin-4-yl-oxy]-piperidin-1-yl}-3,3-dimethyl-butan-2-one |
| A12 | 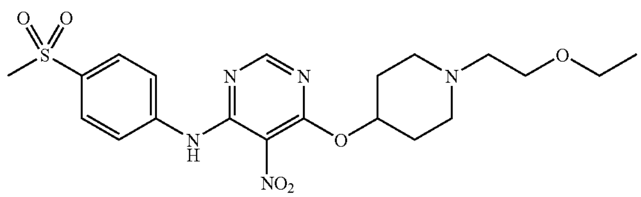 | {6-[1-(2-Ethoxy-ethyl)-piperidin-4-yl-oxy]-5-nitro-pyrimidin-4-yl}-(4-methanesulfonyl-phenyl)-amine |
| A13 | 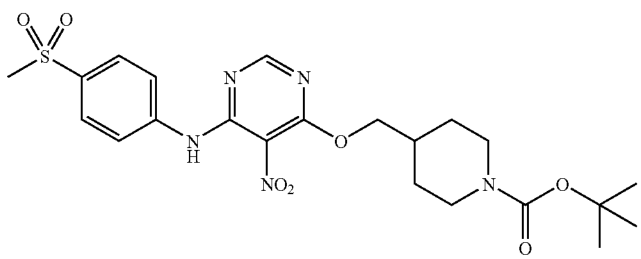 | 4-[6-(4-Methanesulfonyl-phenyl-amino)-5-nitro-pyrimidin-4-yl-oxymethyl]-piperidine-1-carboxylic acid tert-butyl ester |
| A14 | 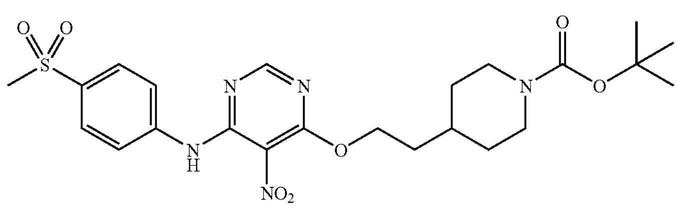 | 4-{2-[6-(4-Methanesulfonyl-phenyl-amino)-5-nitro-pyrimidin-4-yl-oxy]-ethyl}-piperidine-1-carboxylic acid tert-butyl ester |
| A15 | 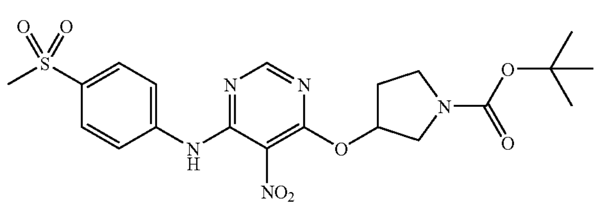 | 3-[6-(4-Methanesulfonyl-phenyl-amino)-5-nitro-pyrimidin-4-yl-oxy]-pyrrolidine-1-carboxylic acid tert-butyl ester |
| A16 | 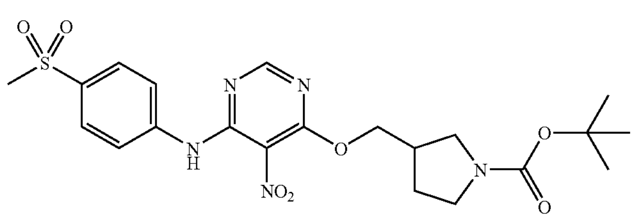 | 3-[6-(4-Methanesulfonyl-phenyl-amino)-5-nitro-pyrimidin-4-yl-oxymethyl]-pyrrolidine-1-carboxylic acid tert-butyl ester |

TABLE A-continued

| Cmpd # | Structure | Chemical Name |
|---|---|---|
| A17 | 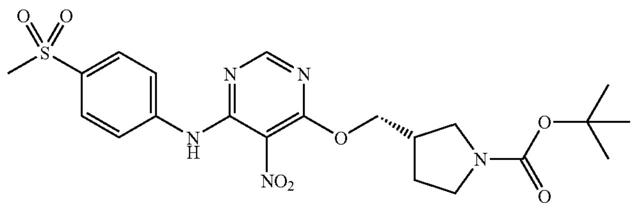 | 3-[6-(4-Methanesulfonyl-phenyl-amino)-5-nitro-pyrimidin-4-yl-oxymethyl]-pyrrolidine-1-carboxylic acid tert-butyl ester |
| A18 | 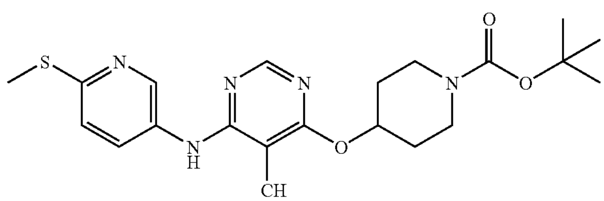 | 4-[5-Cyano-6-(6-methylsulfanyl-pyridin-3-ylamino)-pyrimidin-4-yl-oxy]-piperidine-1-carboxylic acid tert-butyl ester |
| A19 | 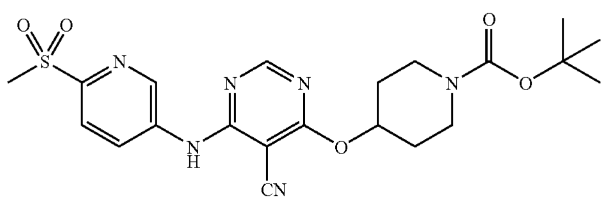 | 4-[5-Cyano-6-(6-methanesulfonyl-pyridin-3-ylamino)-pyrimidin-4-yl-oxy]-piperidine-1-carboxylic acid tert-butyl ester |
| A20 | 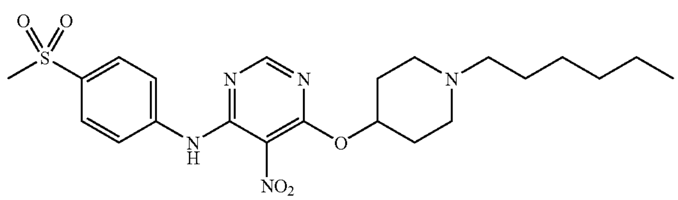 | [6-(1-Hexyl-piperidin-4-yloxy)-5-nitro-pyrimidin-4-yl]-(4-methanesulfonyl-phenyl)-amine |
| A21 | 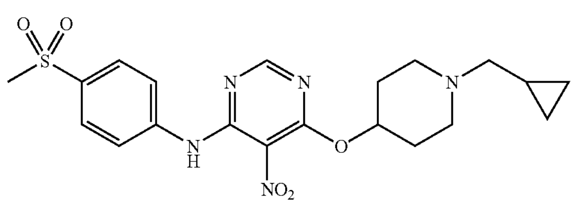 | [6-(1-Cyclopropylmethyl-piperidin-4-yloxy)-5-nitro-pyrimidin-4-yl]-(4-methanesulfonyl-phenyl)-amine |
| A22 | 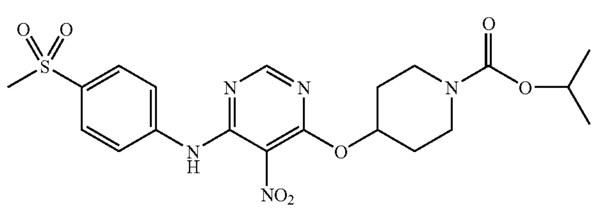 | 4-[6-(4-Methanesulfonyl-phenyl-amino)-5-nitro-pyrimidin-4-yl-oxy]-piperidine-1-carboxylic acid isopropyl ester |
| A23 | 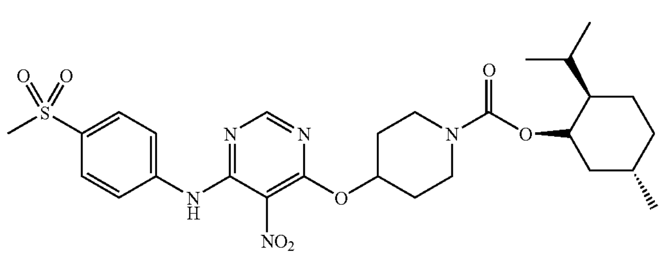 | 4-[6-(4-Methanesulfonyl-phenyl-amino)-5-nitro-pyrimidin-4-yl-oxy]-piperidine-1-carboxylic acid 2-isopropyl-5-methyl-cyclohexyl ester |

TABLE A-continued

| Cmpd # | Structure | Chemical Name |
|---|---|---|
| A24 | 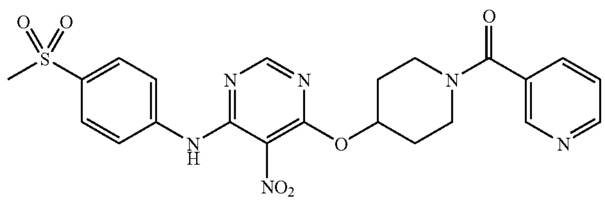 | {4-[6-(4-Methanesulfonyl-phenyl-amino)-5-nitro-pyrimidin-4-yl-oxy]-piperidin-1-yl}-pyridin-3-yl-methanone |
| A25 | 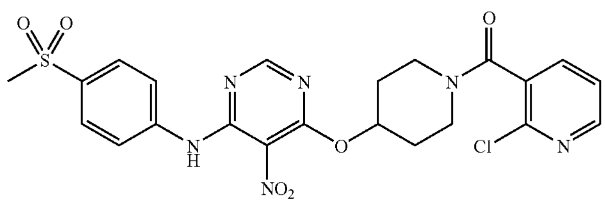 | (2-Chloro-pyridin-3-yl)-{4-[6-(4-methane-sulfonyl-phenylamino)-5-nitro-pyrimidin-4-yloxy]-piperidin-1-yl}-methanone |
| A26 | 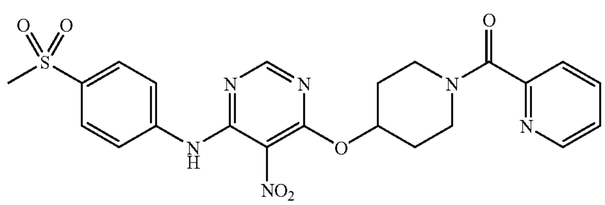 | {4-[6-(4-Methanesulfonyl-phenyl-amino)-5-nitro-pyrimidine-4-yl-oxy]-piperidin-1-yl}-pyridin-2-yl-methanone |
| A27 | 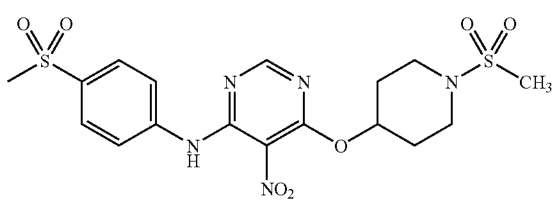 | (4-Methane-sulfonyl-phenyl)-[6-(1-methane-sulfonyl-piperidin-4-yl-oxy)-5-nitro-pyrimidin-4-yl]-amine |
| A28 | 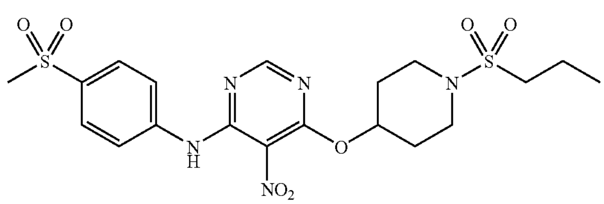 | (4-Methanesulfonyl-phenyl)-{5-nitro-6-[1-(propane-1-sulfonyl)-piperidin-4-yloxy]-pyrimidin-4-yl}-amine |
| A29 | 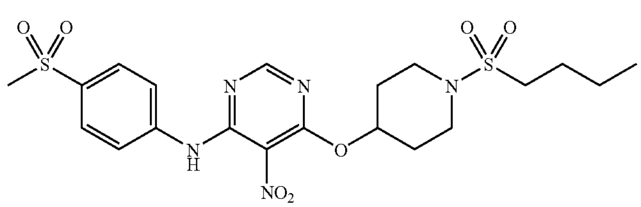 | {6-[1-(Butane-1-sulfonyl)-piperidin-4-yloxy]-5-nitro-pyrimidin-4-yl}-(4-methane-sulfonyl-phenyl)-amine |
| A30 | 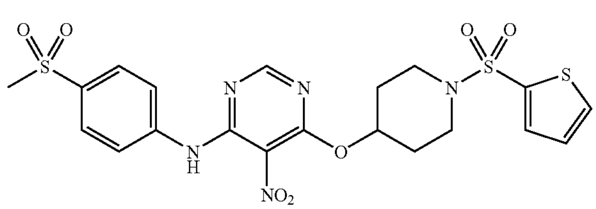 | (4-Methanesulfonyl-phenyl)-{5-nitro-6-[1-(thiophene-2-sulfonyl)-piperidin-4-yloxy]-pyrimidin-4-yl}-amine |

TABLE A-continued

| Cmpd # | Structure | Chemical Name |
|---|---|---|
| A31 | 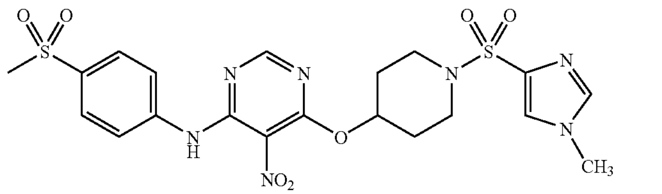 | (4-Methane-sulfonyl-phenyl)-{6-[1-(1-methyl-1H-imidazole-4-sulfonyl)-piperidin-4-yloxy]-5-nitro-pyrimidin-4-yl}-amine |
| A32 | 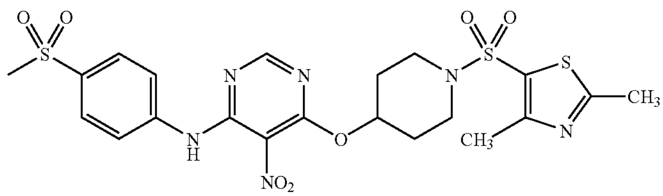 | {6-[1-(2,4-Dimethyl-thiazole-5-sulfonyl)-piperidin-4-yloxy]-5-nitro-pyrimidin-4-yl}-(4-methane-sulfonyl-phenyl)-amine |
| A33 | 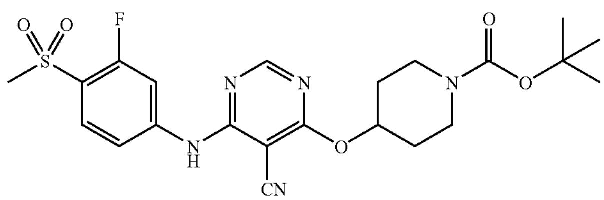 | 4-[5-Cyano-6-(3-fluoro-4-methane-sulfonyl-phenylamino)-pyrimidin-4-yloxy]-piperidine-1-carboxylic acid tert-butyl ester |
| A34 | 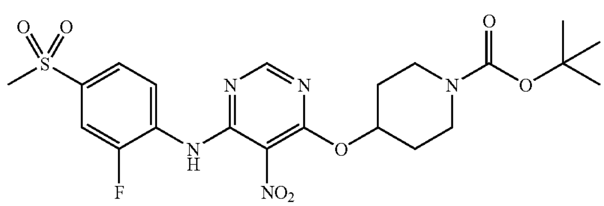 | 4-[6-(2-Fluoro-4-methanesulfonyl-phenyl-amino)-5-nitro-pyrimidin-4-yl-oxy]-piperidine-1-carboxylic acid tert-butyl ester |
| A35 | 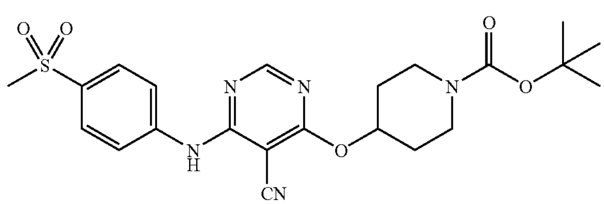 | 4-[5-Cyano-6-(4-methanesulfonyl-phenyl-amino)-pyrimidin-4-yloxy]-piperidine-1-carboxylic acid tert-butyl ester |
| A36 | 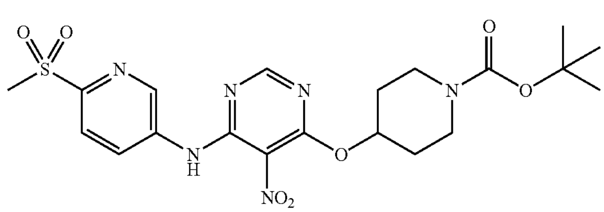 | 4-[6-(6-Methanesulfonyl-pyridin-3-yl-amino)-5-nitro-pyrimidin-4-yl-oxy]-piperidine-1-carboxylic acid tert-butyl ester |
| A37 | 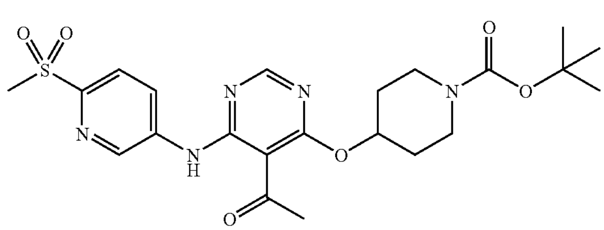 | 4-[5-Acetyl-6-(6-methanesulfonyl-pyridin-3-ylamino)-pyrimidin-4-yl-oxy]-piperidine-1-carboxylic acid tert-butyl ester |

TABLE A-continued

| Cmpd # | Structure | Chemical Name |
|---|---|---|
| A38 | 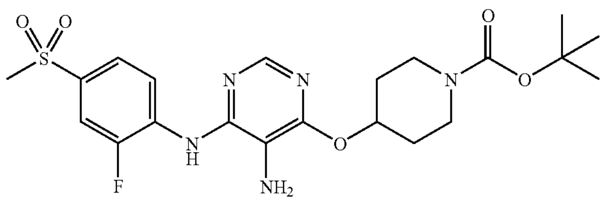 | 4-[5-Amino-6-(2-fluoro-4-methane-sulfonyl-phenylamino)-pyrimidin-4-yloxy]-piperidine-1-carboxylic acid tert-butyl ester |
| A39 | 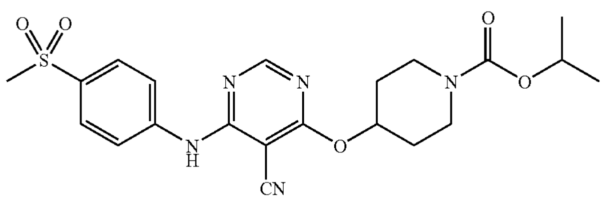 | 4-[5-Cyano-6-(4-methanesulfonyl-phenyl-amino)-pyrimidin-4-yloxy]-piperidine-1-carboxylic acid isopropyl ester |
| A40 | 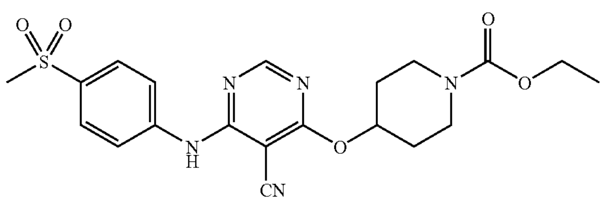 | 4-[5-Cyano-6-(4-methanesulfonyl-phenyl-amino)-pyrimidin-4-yloxy]-piperidine-1-carboxylic acid ethyl ester |
| A41 | 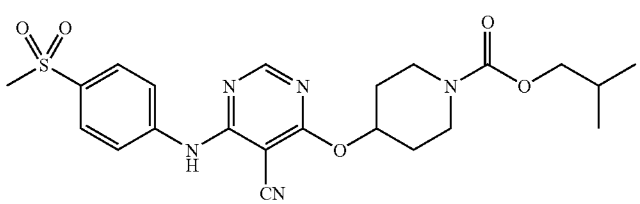 | 4-[5-Cyano-6-(4-methanesulfonyl-phenyl-amino)-pyrimidin-4-yloxy]-piperidine-1-carboxylic acid isobutyl ester |
| A42 | 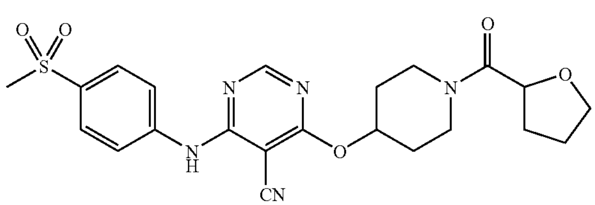 | 4-(4-Methanesulfonyl-phenyl-amino)-6-[1-(tetrahydro-furan-2-carbonyl)-piperidin-4-yloxy]-pyrimidine-5-carbonitrile |
| A43 | 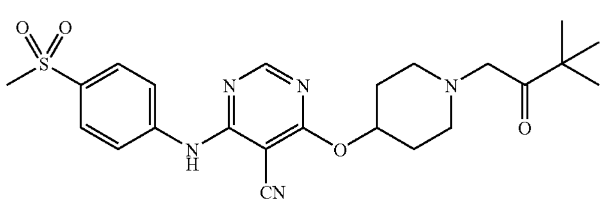 | 4-[1-(3,3-Dimethyl-2-oxo-butyl)-piperidin-4-yloxy]-6-(4-methane-sulfonyl-phenylamino)-pyrimidine-5-carbonitrile |
| A44 | 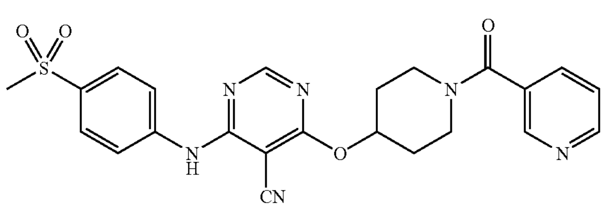 | 4-(4-Methanesulfonyl-phenyl-amino)-6-[1-(pyridine-3-carbonyl)-piperidin-4-yloxy]-pyrimidine-5-carbonitrile |

TABLE A-continued

| Cmpd # | Structure | Chemical Name |
| --- | --- | --- |
| A45 | 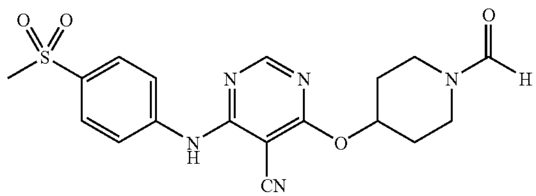 | 4-(1-Formyl-piperidin-4-yloxy)-6-(4-methanesulfonyl-phenylamino)-pyrimidine-5-carbonitrile |
| A46 | 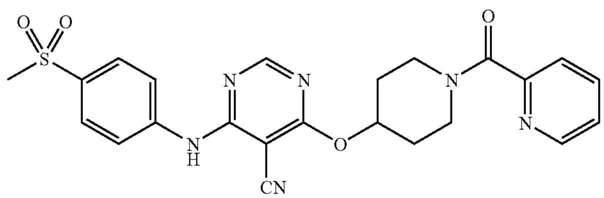 | 4-(4-Methanesulfonyl-phenylamino)-6-[1-(pyridine-2-carbonyl)-piperidin-4-yloxy]-pyrimidine-5-carbonitrile |
| A47 | 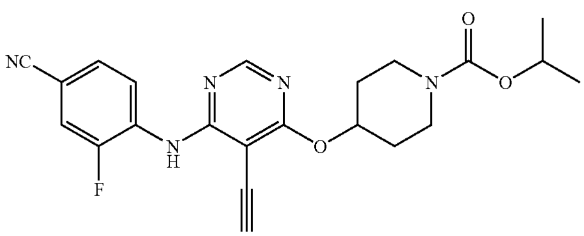 | 4-[6-(4-Cyano-2-fluoro-phenylamino)-5-ethynyl-pyrimidin-4-yloxy]-piperidine-1-carboxylic acid isopropyl ester |
| A48 | 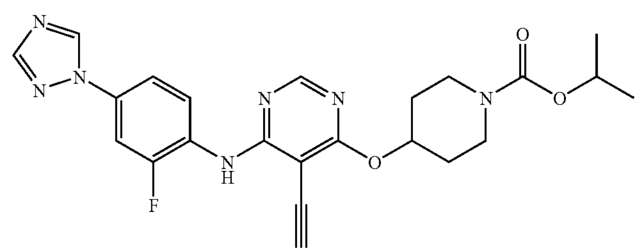 | 4-[5-Ethynyl-6-(2-fluoro-4-[1,2,4]triazol-1-yl-phenylamino)-pyrimidin-4-yloxy]-piperidine-1-carboxylic acid isopropyl ester |
| A49 | 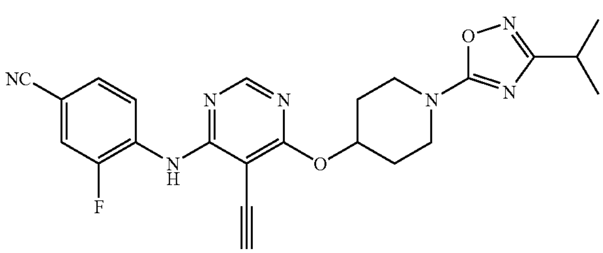 | 4-{5-Ethynyl-6-[1-(3-isopropyl-[1,2,4]oxadiazol-5-yl)-piperidin-4-yloxy]-pyrimidin-4-ylamino}-3-fluoro-benzonitrile |
| A50 | 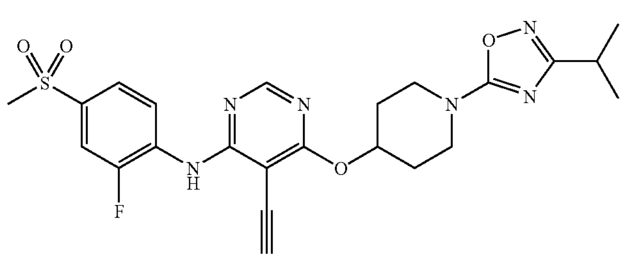 | {5-Ethynyl-6-[1-(3-isopropyl-[1,2,4]oxadiazol-5-yl)-piperidin-4-yloxy]-pyrimidin-4-yl}-(2-fluoro-4-methanesulfonyl-phenyl)-amine |

TABLE A-continued

| Cmpd # | Structure | Chemical Name |
|---|---|---|
| A51 | 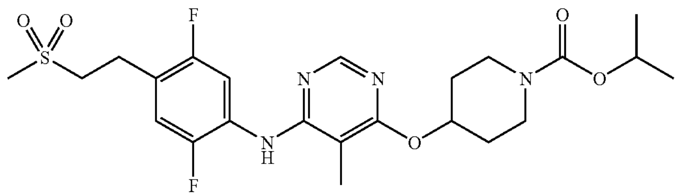 | 4-{6-[2,5-Difluoro-4-(2-methane-sulfonyl-ethyl)-phenyl-amino]-5-methyl-pyrimidin-4-yl-oxy}-piperidine-1-carboxylic acid isopropyl ester |
| A52 | 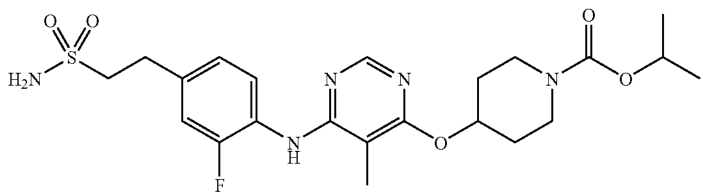 | 4-{6-[2-Fluoro-4-(2-sulfamoyl-ethyl)-phenylamino]-5-methyl-pyrimidin-4-yloxy}-piperidine-1-carboxylic acid isopropyl ester |
| A53 | 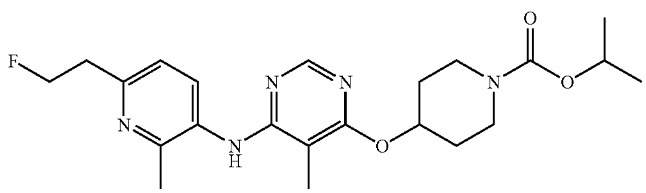 | 4-{6-[6-(2-Fluoro-ethyl)-2-methyl-pyridin-3-ylamino]-5-methyl-pyrimidin-4-yloxy}-piperidine-1-carboxylic acid isopropyl ester |
| A54 | 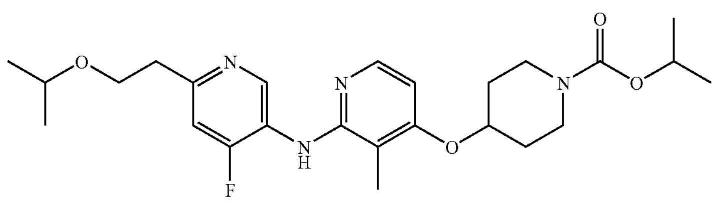 | 4-{2-[4-Fluoro-6-(2-isopropoxy-ethyl)-pyridin-3-ylamino]-3-methyl-pyridin-4-yloxy}-piperidine-1-carboxylic acid isopropyl ester |
| A55 | 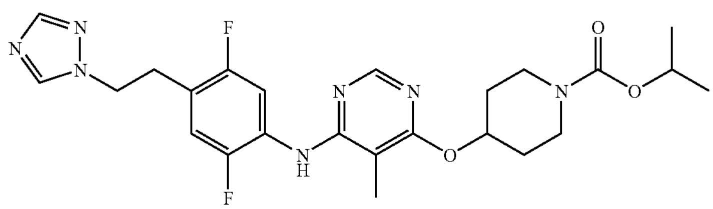 | 4-{6-[2,5-Difluoro-4-(2-[1,2,4]triazol-1-yl-ethyl)-phenyl-amino]-5-methyl-pyrimidin-4-yloxy}-piperidine-1-carboxylic acid isopropyl ester |
| A56 | 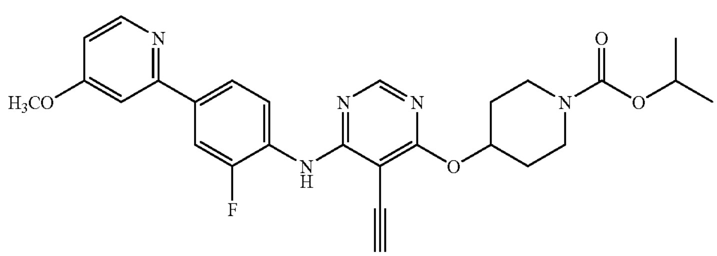 | 4-{5-Ethynyl-6-[2-fluoro-4-(4-methoxy-pyridin-2-yl)-phenyl-amino]-pyrimidin-4-yloxy}-piperidine-1-carboxylic acid isopropyl ester |
| A57 | 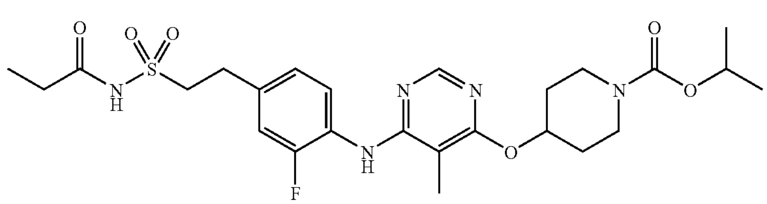 | 4-{6-[2-Fluoro-4-(2-propionylsulfamoyl-ethyl)-phenyl-amino]-5-methyl-pyrimidin-4-yloxy}-piperidine-1-carboxylic acid isopropyl ester |

TABLE A-continued

| Cmpd # | Structure | Chemical Name |
|---|---|---|
| A58 | 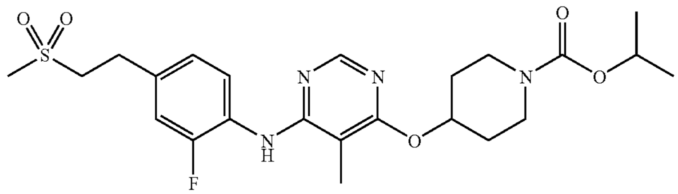 | 4-{6-[2-Fluoro-4-(2-methane-sulfonyl-ethyl)-phenyl-amino]-5-methyl-pyrimidin-4-yl-oxy}-piperidine-1-carboxylic acid isopropyl ester |
| A59 | 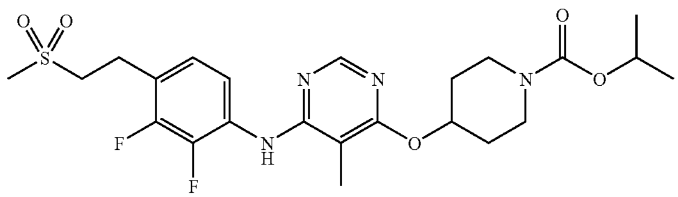 | 4-{6-[2,3-Difluoro-4-(2-methane-sulfonyl-ethyl)-phenyl-amino]-5-methyl-pyrimidin-4-yl-oxy}-piperidine-1-carboxylic acid isopropyl ester |
| A60 | 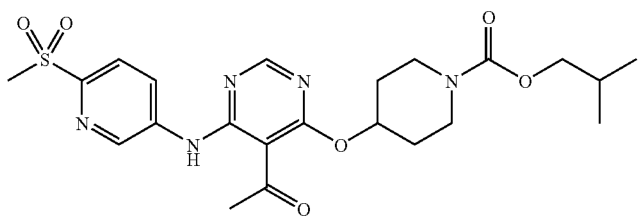 | 4-[5-Acetyl-6-(6-methanesulfonyl-pyridin-3-ylamino)-pyrimidin-4-yl-oxy]-piperidine-1-carboxylic acid isobutyl ester |
| A61 | 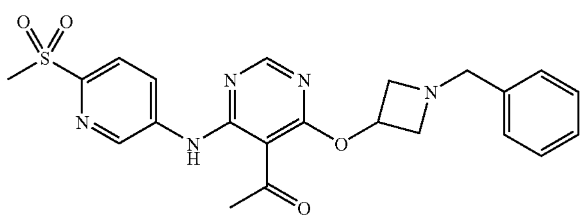 | 1-[4-(1-Benzyl-azetidin-3-yloxy)-6-(6-methane-sulfonyl-pyridin-3-yl-amino)-pyrimidin-5-yl]-ethanone |
| A62 | 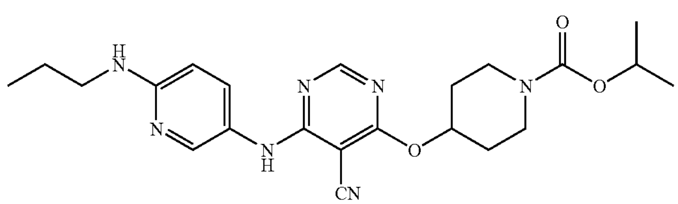 | 4-[5-Cyano-6-(6-propylamino-pyridin-3-ylamino)-pyrimidin-4-yl-oxy]-piperidine-1-carboxylic acid isopropyl ester |
| A63 | 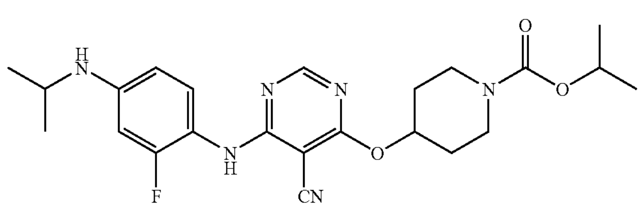 | 4-[5-Cyano-6-(2-fluoro-4-iso-propylamino-phenylamino)-pyrimidin-4-yloxy]-piperidine-1-carboxylic acid isopropyl ester |
| A64 | 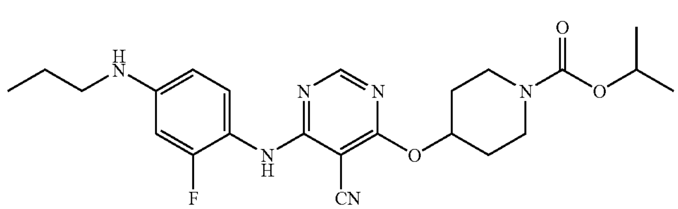 | 4-[5-Cyano-6-(2-fluoro-4-propyl-amino-phenylamino)-pyrimidin-4-yloxy]-piperidine-1-carboxylic acid isopropyl ester |

TABLE A-continued

| Cmpd # | Structure | Chemical Name |
| --- | --- | --- |
| A65 | 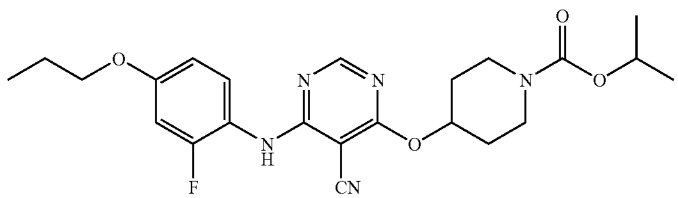 | 4-[5-Cyano-6-(2-fluoro-4-propoxy-phenyl-amino)-pyrimidin-4-yloxy]-piperidine-1-carboxylic acid isopropyl ester |
| A66 | 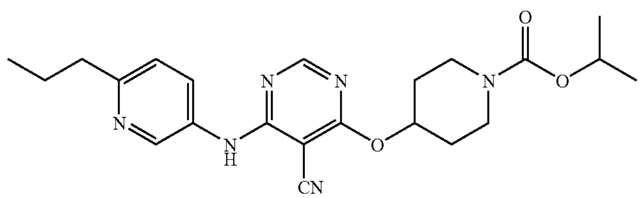 | 4-[5-Cyano-6-(6-propyl-pyridin-3-yl-amino)-pyrimidin-4-yloxy]-piperidine-1-carboxylic acid isopropyl ester |
| A67 | 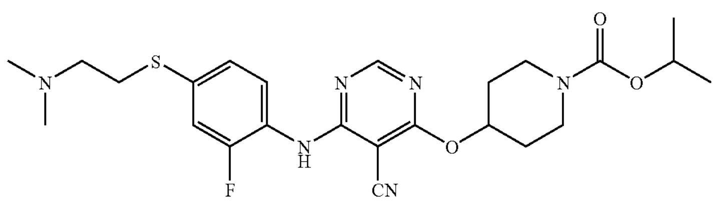 | 4-{5-Cyano-6-[4-(2-di-methylamino-ethylsulfanyl)-2-fluoro-phenylamino]-pyrimidin-4-yl-oxy}-piperidine-1-carboxylic acid isopropyl ester |
| A68 | 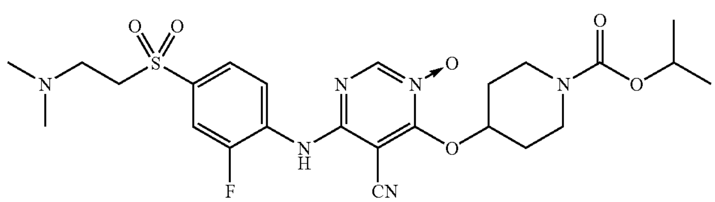 | 4-{5-Cyano-6-[4-(2-di-methylamino-ethanesulfonyl)-2-fluoro-phenylamino]-3-oxy-pyrimidin-4-yloxy}-piperidine-1-carboxylic acid isopropyl ester |
| A69 | 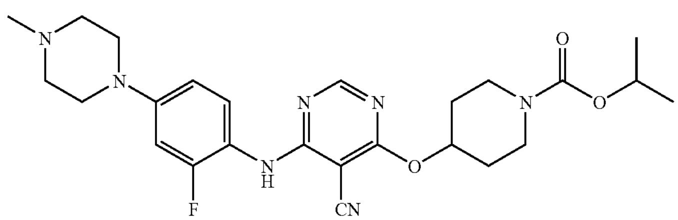 | 4-{5-Cyano-6-[2-fluoro-4-(4-methyl-piperazin-1-yl)-phenyl-amino]-pyrimidin-4-yloxy}-piperidine-1-carboxylic acid isopropyl ester |
| A70 | 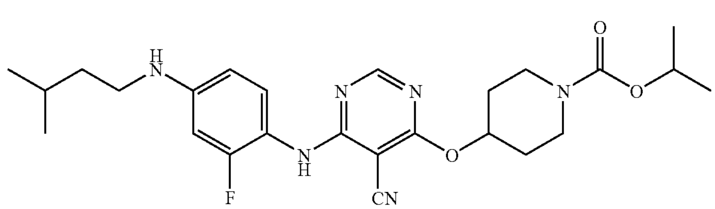 | 4-{5-Cyano-6-[2-fluoro-4-(3-methyl-butylamino)-phenylamino]-pyrimidin-4-yloxy}-piperidine-1-carboxylic acid isopropyl ester |
| A71 | 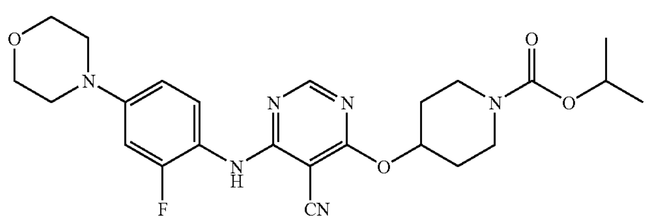 | 4-[5-Cyano-6-(2-fluoro-4-morpholin-4-yl-phenylamino)-pyrimidin-4-yloxy]-piperidine-1-carboxylic acid isopropyl ester |

TABLE A-continued

| Cmpd # | Structure | Chemical Name |
| --- | --- | --- |
| A72 | 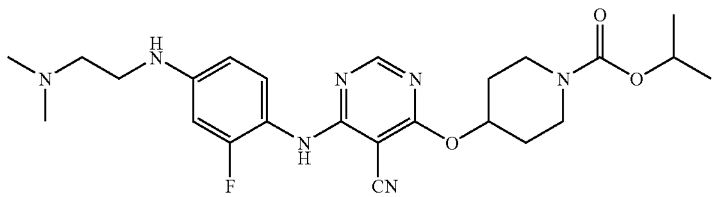 | 4-{5-Cyano-6-[4-(2-di-methylamino-ethylamino)-2-fluoro-phenylamino]-pyrimidin-4-yl-oxy}-piperidine-1-carboxylic acid isopropyl ester |
| A73 | 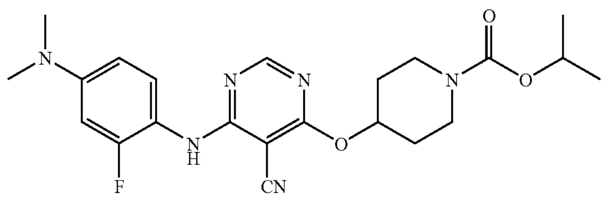 | 4-[5-Cyano-6-(4-dimethylamino-2-fluoro-phenylamino)-pyrimidin-4-yl-oxy]-piperidine-1-carboxylic acid isopropyl ester |
| A74 | 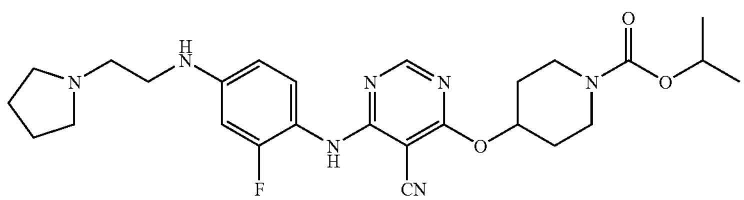 | 4-{5-Cyano-6-[2-fluoro-4-(2-pyrrolidin-1-yl-ethylamino)-phenylamino]-pyrimidin-4-yloxy}-piperidine-1-carboxylic acid isopropyl ester |
| A75 | 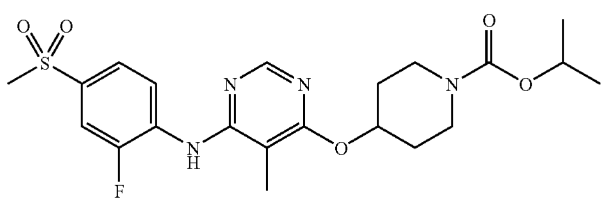 | 4-[6-(2-Fluoro-4-methanesulfonyl-phenylamino)-5-methyl-pyrimidin-4-yl-oxy]-piperidine-1-carboxylic acid isopropyl ester |
| A76 | 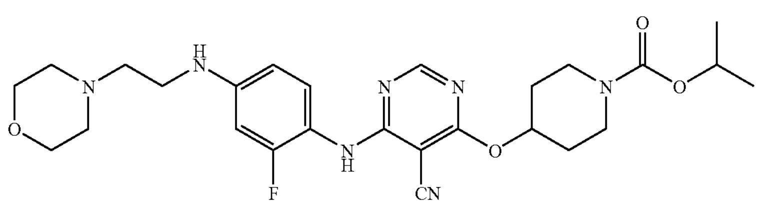 | 4-{5-Cyano-6-[2-fluoro-4-(2-morpholin-4-yl-ethylamino)-phenylamino]-pyrimidin-4-yloxy}-piperidine-1-carboxylic acid isopropyl ester |
| A77 | 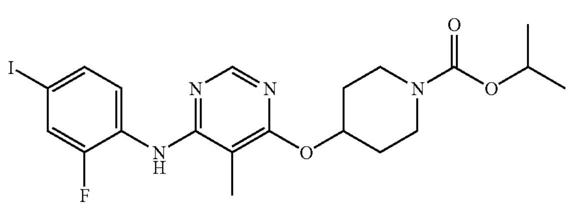 | 4-[6-(2-Fluoro-4-iodo-phenylamino)-5-methyl-pyrimidin-4-yl-oxy]-piperidine-1-carboxylic acid isopropyl ester |
| A78 | 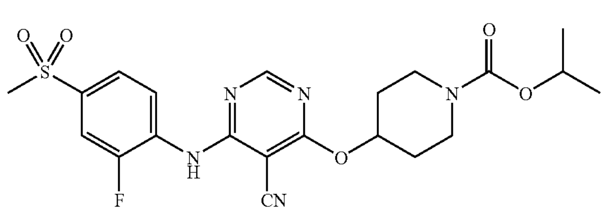 | 4-[5-Cyano-6-(2-fluoro-4-methanesulfonyl-phenylamino)-pyrimidin-4-yloxy]-piperidine-1-carboxylic acid isopropyl ester |

TABLE A-continued

| Cmpd # | Structure | Chemical Name |
| --- | --- | --- |
| A79 | 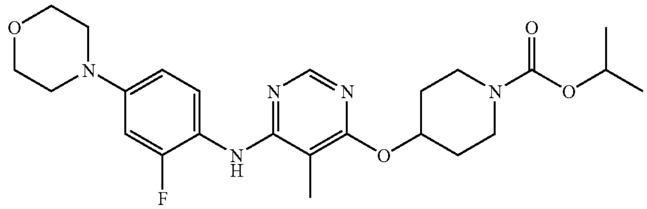 | 4-[6-(2-Fluoro-4-morpholin-4-yl-phenyl-amino)-5-methyl-pyrimidin-4-yl-oxy]-piperidine-1-carboxylic acid isopropyl ester |
| A80 | 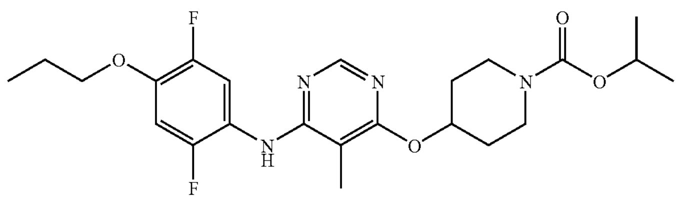 | 4-[6-(2,5-Difluoro-4-propoxy-phenyl-amino)-5-methyl-pyrimidin-4-yl-oxy]-piperidine-1-carboxylic acid isopropyl ester |
| A81 | 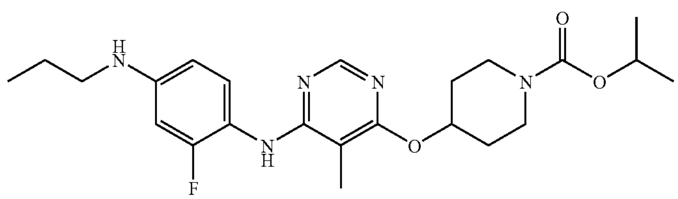 | 4-[6-(2-Fluoro-4-propylamino-phenyl-amino)-5-methyl-pyrimidin-4-yl-oxy]-piperidine-1-carboxylic acid isopropyl ester |
| A82 | 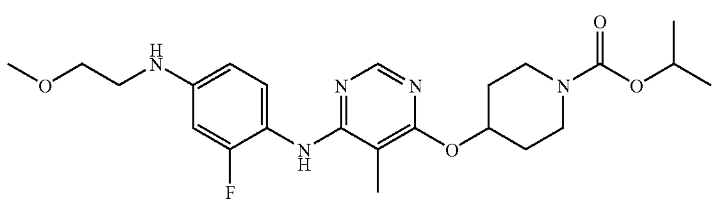 | 4-{6-[2-Fluoro-4-(2-methoxy-ethylamino)-phenylamino]-5-methyl-pyrimidin-4-yloxy}-piperidine-1-carboxylic acid isopropyl ester |
| A83 | 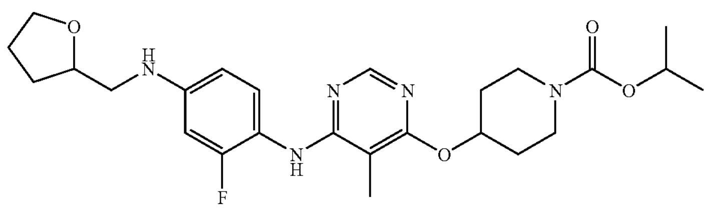 | 4-(6-{2-Fluoro-4-[(tetrahydro-furan-2-ylmethyl)-amino]-phenyl-amino}-5-methyl-pyrimidin-4-yl-oxy)-piperidine-1-carboxylic acid isopropyl ester |
| A84 | 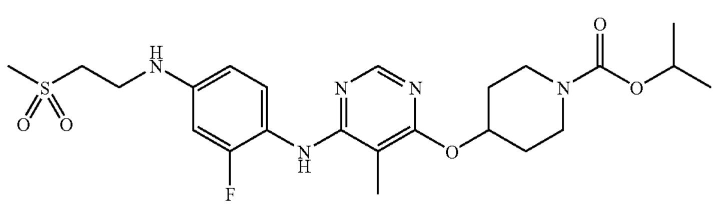 | 4-{6-[2-Fluoro-4-(2-methane-sulfonyl-ethylamino)-phenyl-amino]-5-methyl-pyrimidin-4-yl-oxy}-piperidine-1-carboxylic acid isopropyl ester |
| A85 | 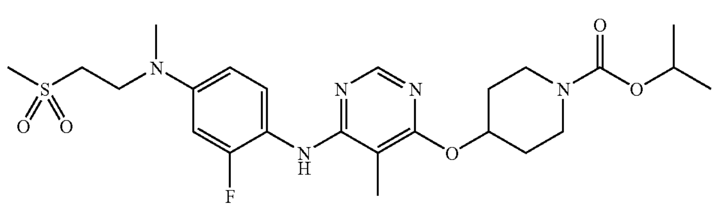 | 4-(6-{2-Fluoro-4-[(2-methane-sulfonyl-ethyl)-methyl-amino]-phenylamino}-5-methyl-pyrimidin-4-yloxy)-piperidine-1-carboxylic acid isopropyl ester |

TABLE A-continued

| Cmpd # | Structure | Chemical Name |
|---|---|---|
| A86 | 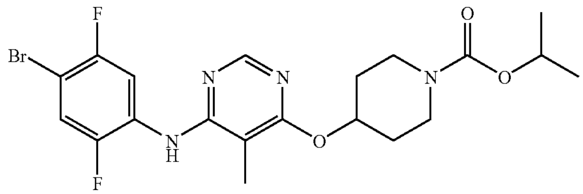 | 4-[6-(4-Bromo-2,5-difluoro-phenylamino)-5-methyl-pyrimidin-4-yloxy]-piperidine-1-carboxylic acid isopropyl ester |
| A87 | 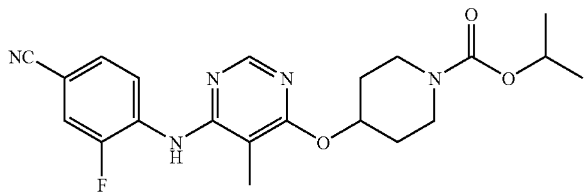 | 4-[6-(4-Cyano-2-fluoro-phenylamino)-5-methyl-pyrimidin-4-yloxy]-piperidine-1-carboxylic acid isopropyl ester |
| A88 | 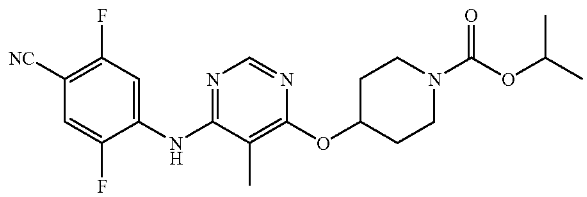 | 4-[6-(4-Cyano-2,5-difluoro-phenylamino)-5-methyl-pyrimidin-4-yloxy]-piperidine-1-carboxylic acid isopropyl ester |
| A89 | 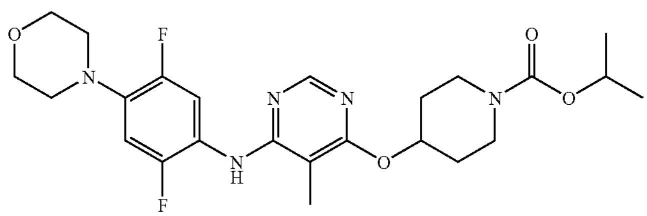 | 4-[6-(2,5-Difluoro-4-morpholin-4-yl-phenylamino)-5-methyl-pyrimidin-4-yloxy]-piperidine-1-carboxylic acid isopropyl ester |
| A90 | 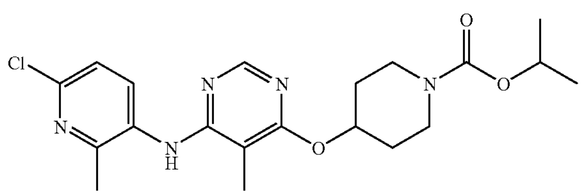 | 4-[6-(6-Chloro-2-methyl-pyridin-3-ylamino)-5-methyl-pyrimidin-4-yloxy]-piperidine-1-carboxylic acid isopropyl ester |
| A91 | 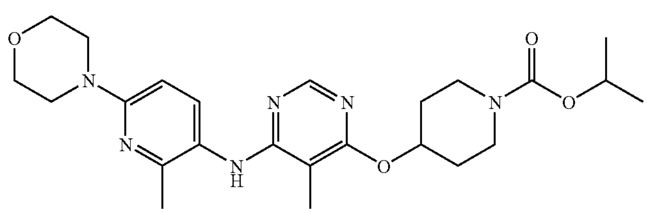 | 4-[5-Methyl-6-(2-methyl-6-morpholin-4-yl-pyridin-3-ylamino)-pyrimidin-4-yloxy]-piperidine-1-carboxylic acid isopropyl ester |
| A92 | 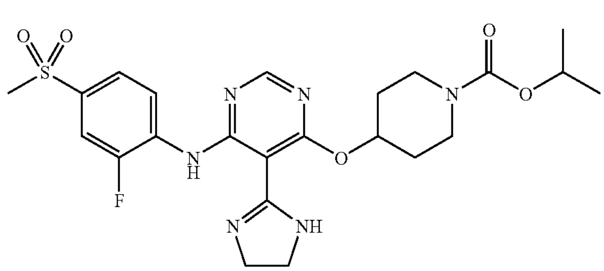 | 4-[5-(4,5-Dihydro-1H-imidazol-2-yl)-6-(2-fluoro-4-methanesulfonyl-phenylamino)-pyrimidin-4-yloxy]-piperidine-1-carboxylic acid isopropyl ester |

TABLE A-continued

| Cmpd # | Structure | Chemical Name |
|---|---|---|
| A93 | 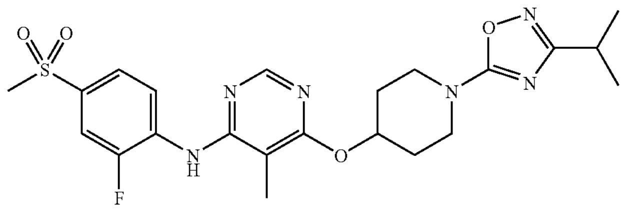 | (2-Fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine |
| A94 | 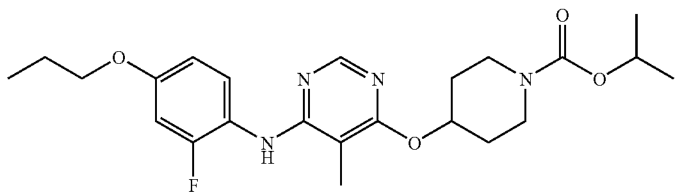 | 4-[6-(2-Fluoro-4-propoxy-phenylamino)-5-methyl-pyrimidin-4-yloxy]-piperidine-1-carboxylic acid isopropyl ester |
| A95 | 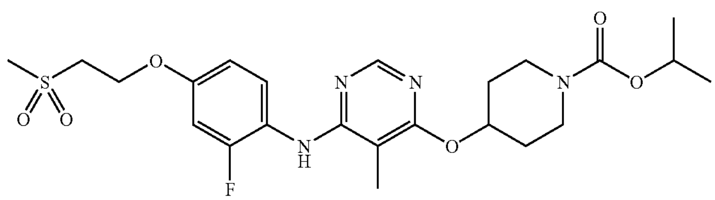 | 4-{6-[2-Fluoro-4-(2-methanesulfonyl-ethoxy)-phenylamino]-5-methyl-pyrimidin-4-yloxy}-piperidine-1-carboxylic acid isopropyl ester |
| A96 | 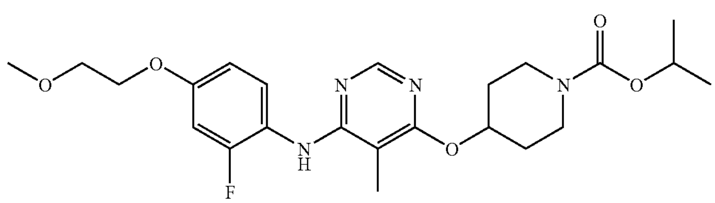 | 4-{6-[2-Fluoro-4-(2-methoxy-ethoxy)-phenylamino]-5-methyl-pyrimidin-4-yloxy}-piperidine-1-carboxylic acid isopropyl ester |
| A97 | 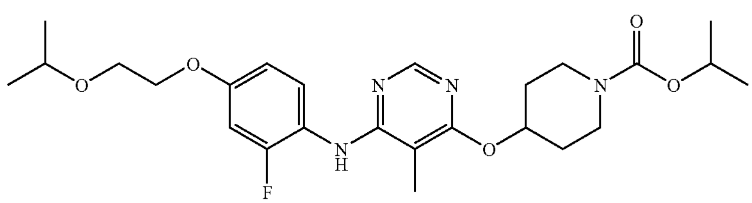 | 4-{6-[2-Fluoro-4-(2-isopropoxy-ethoxy)-phenylamino]-5-methyl-pyrimidin-4-yloxy}-piperidine-1-carboxylic acid isopropyl ester |
| A98 | 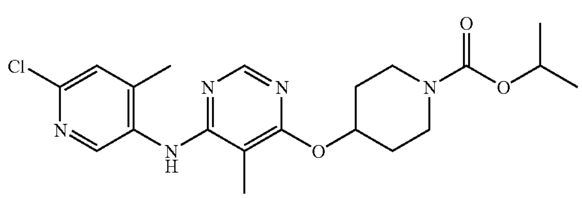 | 4-[6-(6-Chloro-4-methyl-pyridin-3-yl-amino)-5-methyl-pyrimidin-4-yloxy]-piperidine-1-carboxylic acid isopropyl ester |
| A99 | 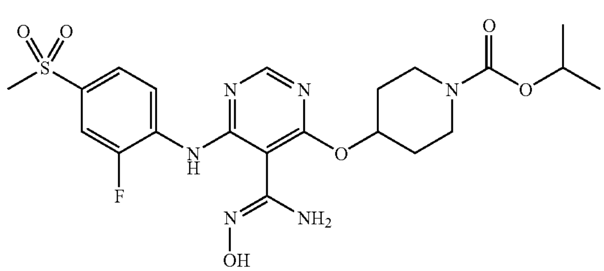 | 4-[6-(2-Fluoro-4-methanesulfonyl-phenyl-amino)-5-(N-hydroxycarbamimidoyl)-pyrimidin-4-yloxy]-piperidine-1-carboxylic acid isopropyl ester |

TABLE A-continued

| Cmpd # | Structure | Chemical Name |
|---|---|---|
| A100 | 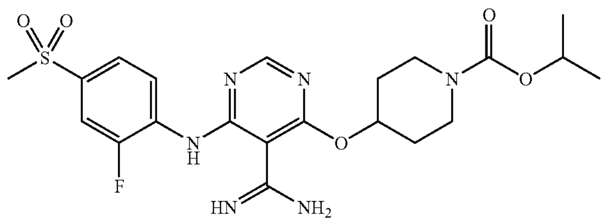 | 4-[5-Carbamimi-doyl-6-(2-fluoro-4-methane-sulfonyl-phenylamino)-pyrimidin-4-yloxy]-piperidine-1-carboxylic acid isopropyl ester |
| A101 | 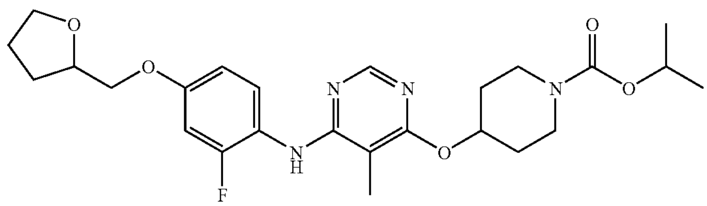 | 4-{6-[2-Fluoro-4-(tetrahydro-furan-2-yl-methoxy)-phenylamino]-5-methyl-pyrimidin-4-yloxy}-piperidine-1-carboxylic acid isopropyl ester |
| A102 | 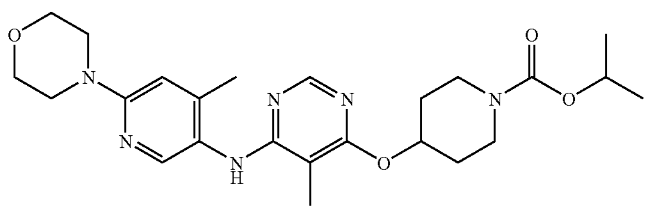 | 4-[5-Methyl-6-(4-methyl-6-morpholin-4-yl-pyridin-3-ylamino)-pyrimidin-4-yloxy]-piperidine-1-carboxylic acid isopropyl ester |
| A103 | 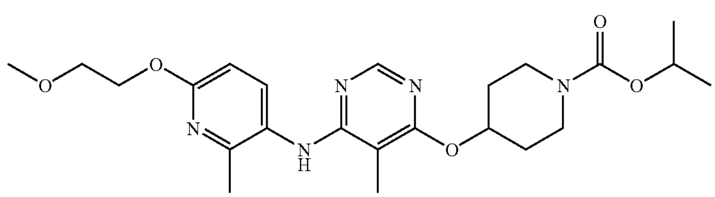 | 4-{6-[6-(2-Methoxy-ethoxy)-2-methyl-pyridin-3-ylamino]-5-methyl-pyrimidin-4-yloxy}-piperidine-1-carboxylic acid isopropyl ester |
| A104 | 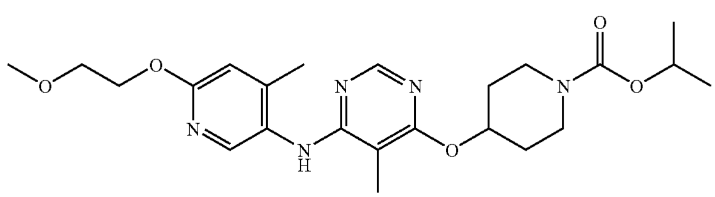 | 4-{6-[6-(2-Methoxy-ethoxy)-4-methyl-pyridin-3-ylamino]-5-methyl-pyrimidin-4-yloxy}-piperidine-1-carboxylic acid isopropyl ester |
| A105 | 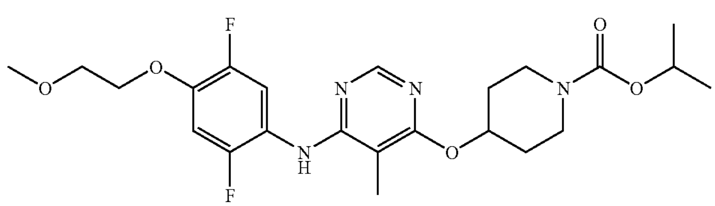 | 4-{6-[2,5-Difluoro-4-(2-methoxy-ethoxy)-phenylamino]-5-methyl-pyrimidin-4-yloxy}-piperidine-1-carboxylic acid isopropyl ester |
| A106 | 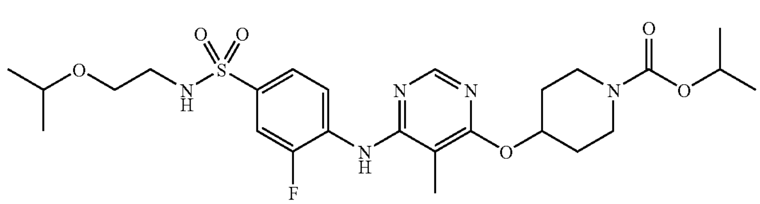 | 4-{6-[2-Fluoro-4-(2-isopropoxy-ethylsulfamoyl)-phenylamino]-5-methyl-pyrimidin-4-yloxy}-piperidine-1-carboxylic acid isopropyl ester |

TABLE A-continued

| Cmpd # | Structure | Chemical Name |
| --- | --- | --- |
| A107 | 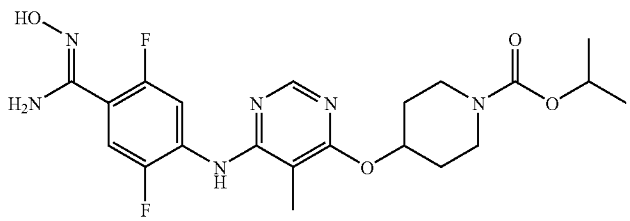 | 4-{6-[2,5-Difluoro-4-(N-hydroxycarbamimidoyl)-phenylamino]-5-methyl-pyrimidin-4-yloxy}-piperidine-1-carboxylic acid isopropyl ester |
| A108 | 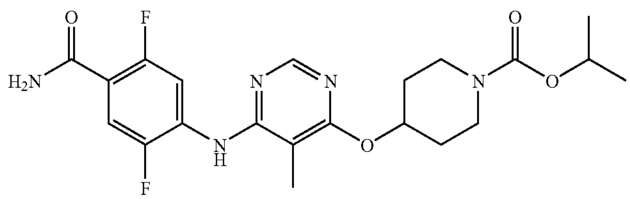 | 4-[6-(4-Carbamoyl-2,5-difluoro-phenylamino)-5-methyl-pyrimidin-4-yloxy]-piperidine-1-carboxylic acid isopropyl ester |
| A109 | 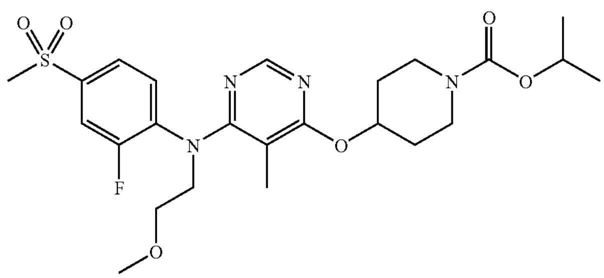 | 4-{6-[(2-Fluoro-4-methanesulfonyl-phenyl)-(2-methoxy-ethyl)-amino]-5-methyl-pyrimidin-4-yloxy}-piperidine-1-carboxylic acid isopropyl ester |
| A110 | 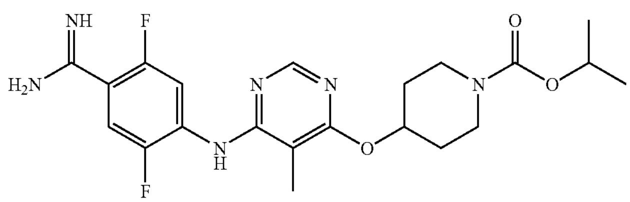 | 4-[6-(4-Carbamimidoyl-2,5-difluoro-phenylamino)-5-methyl-pyrimidin-4-yloxy]-piperidine-1-carboxylic acid isopropyl ester |
| A111 | 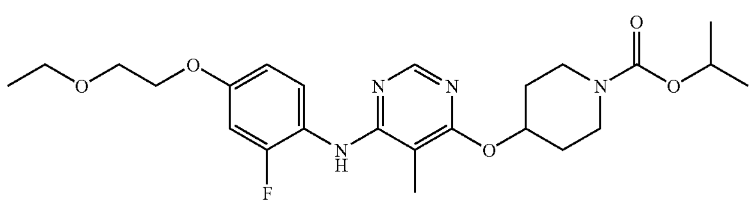 | 4-{6-[4-(2-Ethoxy-ethoxy)-2-fluoro-phenylamino]-5-methyl-pyrimidin-4-yloxy}-piperidine-1-carboxylic acid isopropyl ester |
| A112 | 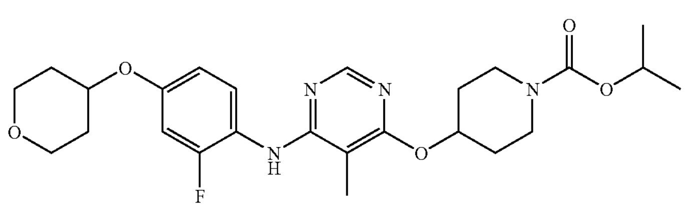 | 4-{6-[2-Fluoro-4-(tetrahydro-pyran-4-yloxy)-phenylamino]-5-methyl-pyrimidin-4-yloxy}-piperidine-1-carboxylic acid isopropyl ester |
| A113 | 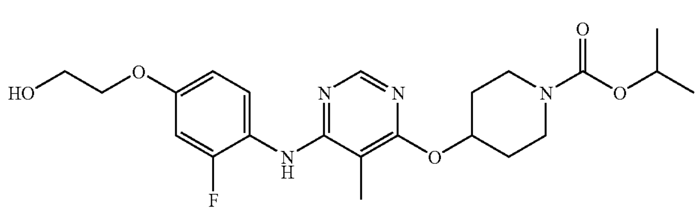 | 4-{6-[2-Fluoro-4-(2-hydroxy-ethoxy)-phenylamino]-5-methyl-pyrimidin-4-yloxy}-piperidine-1-carboxylic acid isopropyl ester |

TABLE A-continued

| Cmpd # | Structure | Chemical Name |
| --- | --- | --- |
| A114 | 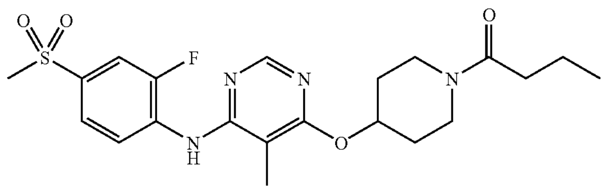 | 1-{4-[6-(2-Fluoro-4-methane-sulfonyl-phenylamino)-5-methyl-pyrimidin-4-yloxy]-piperidin-1-yl}-butan-1-one |
| A115 | 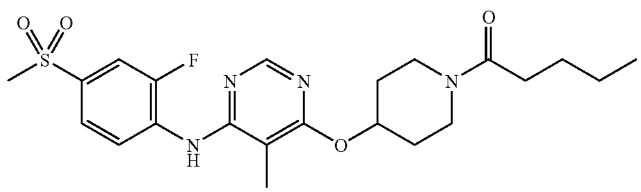 | 1-{4-[6-(2-Fluoro-4-methane-sulfonyl-phenylamino)-5-methyl-pyrimidin-4-yloxy]-piperidin-1-yl}-pentan-1-one |
| A116 | 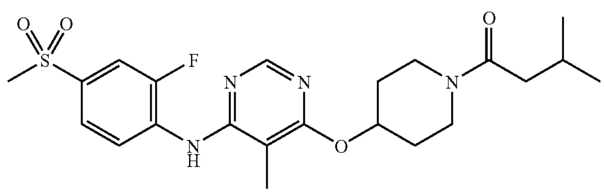 | 1-{4-[6-(2-Fluoro-4-methane-sulfonyl-phenylamino)-5-methyl-pyrimidin-4-yloxy]-piperidin-1-yl}-3-methyl-butan-1-one |
| A117 | 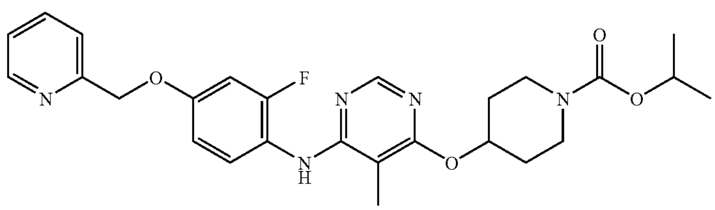 | 4-{6-[2-Fluoro-4-(pyridin-2-yl-methoxy)-phenylamino]-5-methyl-pyrimidin-4-yloxy}-piperidine-1-carboxylic acid isopropyl ester |
| A118 | 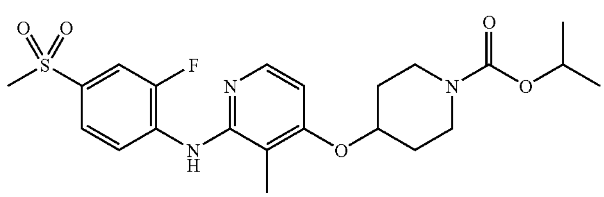 | 4-[2-(2-Fluoro-4-methanesulfonyl-phenylamino)-3-methyl-pyridin-4-yloxy]-piperidine-1-carboxylic acid isopropyl ester |
| A119 | 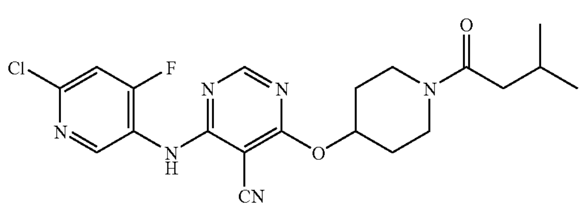 | 4-[6-(6-Chloro-4-fluoro-pyridin-3-yl-amino)-5-cyano-pyrimidin-4-yloxy]-piperidine-1-carboxylic acid isopropyl ester |
| A120 | 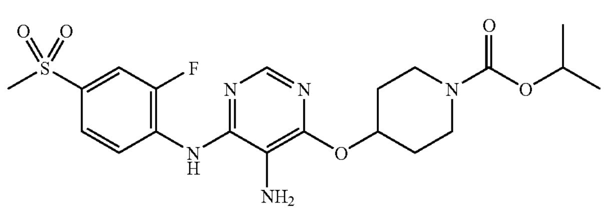 | 4-[5-Amino-6-(2-fluoro-4-methane-sulfonyl-phenylamino)-pyrimidin-4-yloxy]-piperidine-1-carboxylic acid isopropyl ester |

TABLE B

| Cmpd # | Structure | Chemical Name |
|---|---|---|
| B1 | 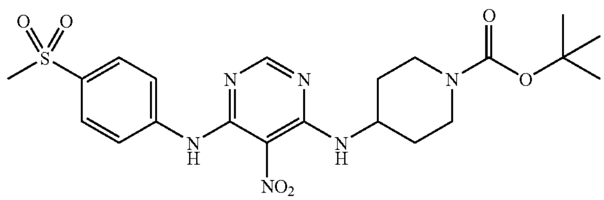 | 4-[6-(4-Methanesulfonyl-phenyl-amino)-5-nitro-pyrimidin-4-yl-amino]-piperidine-1-carboxylic acid tert-butyl ester |
| B2 | 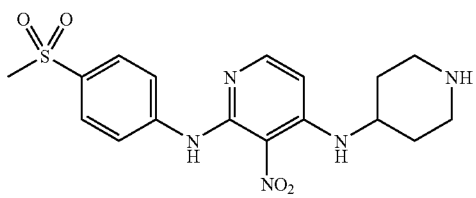 | N-(4-Methanesulfonyl-phenyl)-5-nitro-N'-piperidin-4-yl-pyrimidine-4,6-diamine |
| B3 | 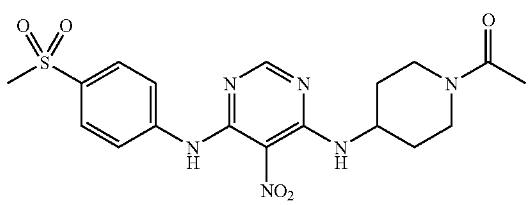 | 1-{4-[6-(4-Methanesulfonyl-phenyl-amino)-5-nitro-pyrimidin-4-yl-amino]-piperidin-1-yl}-ethanone |
| B4 | 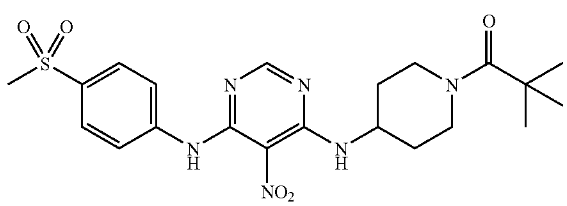 | 1-{4-[6-(4-Methanesulfonyl-phenyl-amino)-5-nitro-pyrimidin-4-yl-amino]-piperidin-1-yl}-2,2-dimethyl-propan-1-one |
| B5 | 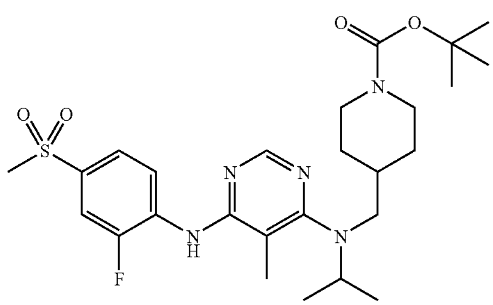 | 4-({[6-(2-Fluoro-4-methane-sulfonyl-phenylamino)-5-methyl-pyrimidin-4-yl]-isopropyl-amino}-methyl)-piperidine-1-carboxylic acid tert-butyl ester |

TABLE C

| Cmpd # | Structure | Chemical Name |
|---|---|---|
| C1 | 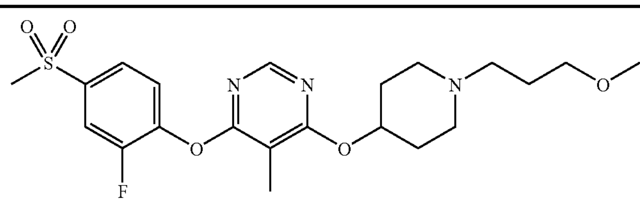 | 4-(2-Fluoro-4-methanesulfonyl-phenoxy)-6-[1-(3-methoxy-propyl)-piperidin-4-yloxy]-5-methyl-pyrimidine |

TABLE C-continued

| Cmpd # | Structure | Chemical Name |
|---|---|---|
| C2 | 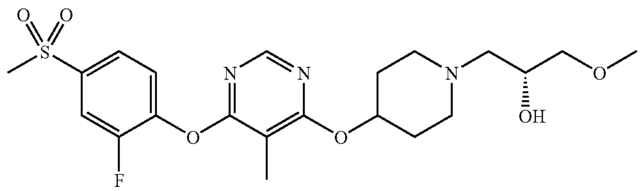 | 1-{4-[6-(2-Fluoro-4-methane-sulfonyl-phenoxy)-5-methyl-pyrimidin-4-yloxy]-piperidin-1-yl}-3-methoxy-propan-2-ol |
| C3 | 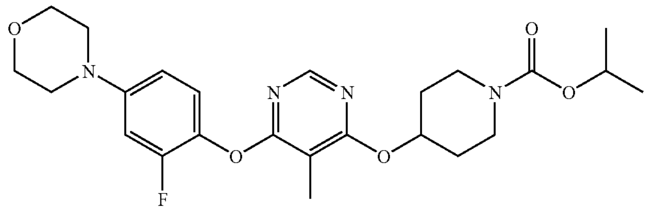 | 4-[6-(2-Fluoro-4-morpholin-4-yl-phenoxy)-5-methyl-pyrimidin-4-yloxy]-piperidine-1-carboxylic acid isopropyl ester |
| C4 | 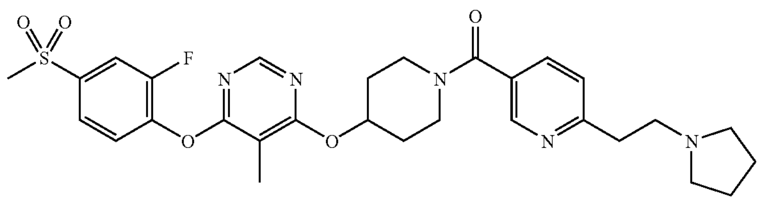 | {4-[6-(2-Fluoro-4-methanesulfonyl-phenoxy)-5-methyl-pyrimidin-4-yloxy]-piperidin-1-yl}-[6-(2-pyrrolidin-1-yl-ethyl)-pyridin-3-yl]-methanone |
| C5 | 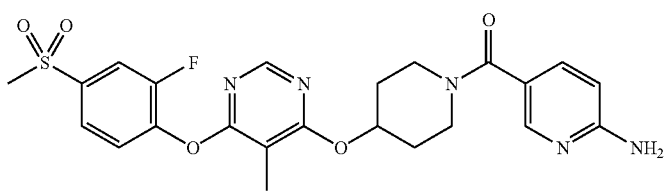 | (6-Amino-pyridin-3-yl)-{4-[6-(2-fluoro-4-methanesulfonyl-phenoxy)-5-methyl-pyrimidin-4-yloxy]-piperidin-1-yl}-methanone |
| C6 | 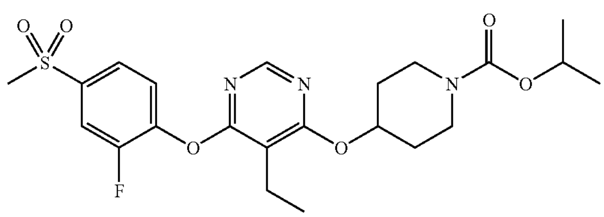 | 4-[5-Ethyl-6-(2-fluoro-4-methane-sulfonyl-phenoxy)-pyrimidin-4-yloxy]-piperidine-1-carboxylic acid isopropyl ester |
| C7 | 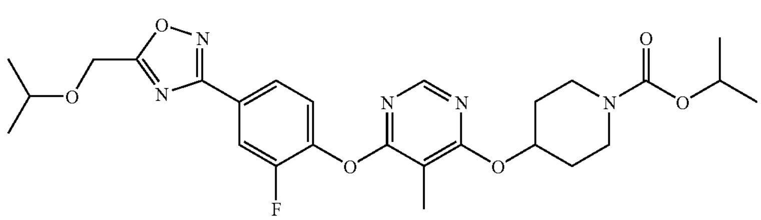 | 4-{6-[2-Fluoro-4-(5-isopropoxymethyl-[1,2,4]oxadiazol-3-yl)-phenoxy]-5-methyl-pyrimidin-4-yloxy}-piperidine-1-carboxylic acid isopropyl ester |
| C8 | 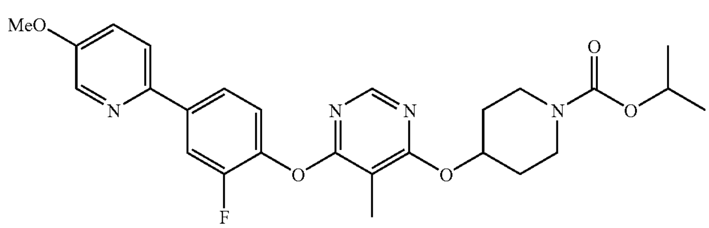 | 4-{6-[2-Fluoro-4-(5-methoxy-pyridin-2-yl)-phenoxy]-5-methyl-pyrimidin-4-yloxy}-piperidine-1-carboxylic acid isopropyl ester |

TABLE C-continued

| Cmpd # | Structure | Chemical Name |
|---|---|---|
| C9 | 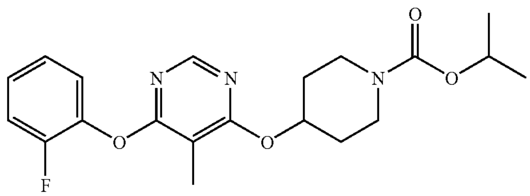 | 4-[6-(2-Fluoro-phenoxy)-5-methyl-pyrimidin-4-yloxy]-piperidine-1-carboxylic acid isopropyl ester |
| C10 | 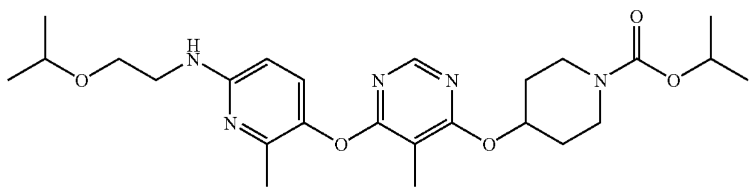 | 4-{6-[6-(2-Isopropoxy-ethylamino)-2-methyl-pyridin-3-yloxy]-5-methyl-pyrimidin-4-yloxy}-piperidine-1-carboxylic acid isopropyl ester |
| C11 | 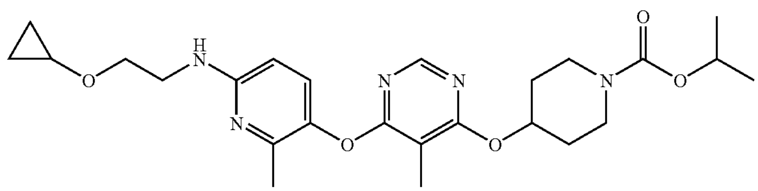 | 4-{6-[6-(2-Cyclopropoxy-ethylamino)-2-methyl-pyridin-3-yloxy]-5-methyl-pyrimidin-4-yloxy}-piperidine-1-carboxylic acid isopropyl ester |
| C12 | 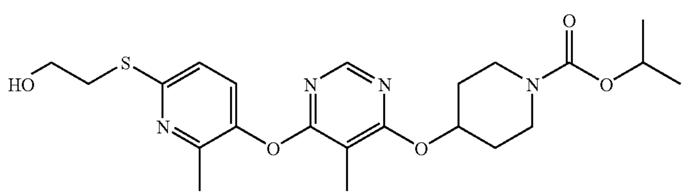 | 4-{6-[6-(2-Hydroxy-ethylsulfanyl)-2-methyl-pyridin-3-yloxy]-5-methyl-pyrimidin-4-yloxy}-piperidine-1-carboxylic acid isopropyl ester |
| C13 | 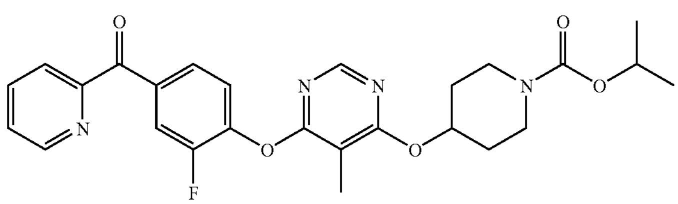 | 4-{6-[2-Fluoro-4-(pyridine-2-carbonyl)-phenoxy]-5-methyl-pyrimidin-4-yloxy}-piperidine-1-carboxylic acid isopropyl ester |
| C14 | 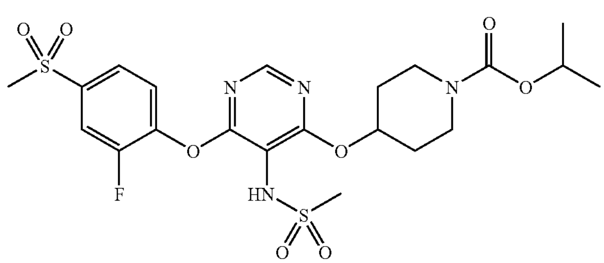 | 4-[6-(2-Fluoro-4-methanesulfonyl-phenoxy)-5-methanesulfonylamino-pyrimidin-4-yloxy]-piperidine-1-carboxylic acid isopropyl ester |
| C15 | 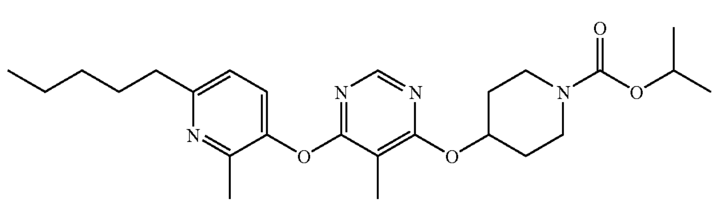 | 4-[5-Methyl-6-(2-methyl-6-pentyl-pyridin-3-yloxy)-pyrimidin-4-yloxy]-piperidine-1-carboxylic acid isopropyl ester |

TABLE C-continued

| Cmpd # | Structure | Chemical Name |
|---|---|---|
| C16 | 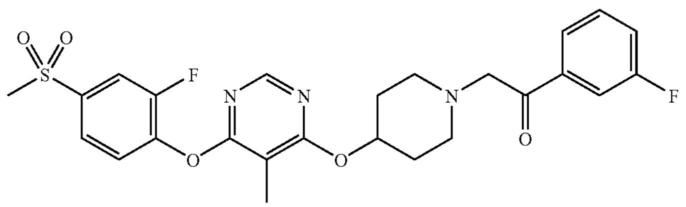 | 2-{4-[6-(2-Fluoro-4-methane-sulfonyl-phenoxy)-5-methyl-pyrimidin-4-yloxy]-piperidin-1-yl}-1-(3-fluoro-phenyl)-ethanone |
| C17 | 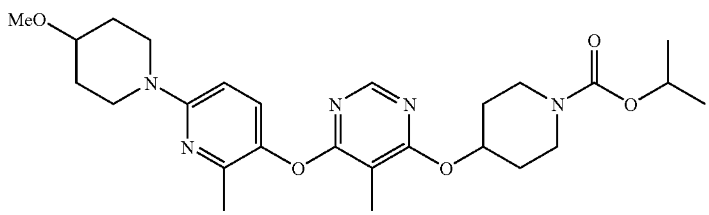 | 4-[6-(4-Methoxy-6'-methyl-3,4,5,6-tetrahydro-2H-[1,2']bipyridinyl-5'-yloxy)-5-methyl-pyrimidin-4-yloxy]-piperidine-1-carboxylic acid isopropyl ester |
| C18 | 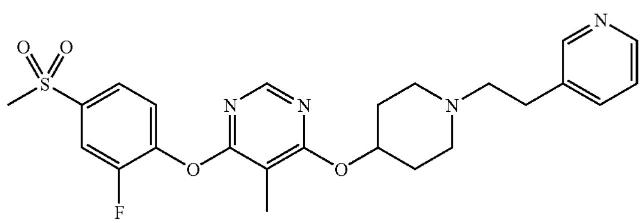 | 4-(2-Fluoro-4-methanesulfonyl-phenoxy)-5-methyl-6-[1-(2-pyridin-3-yl-ethyl)-piperidin-4-yloxy]-pyrimidine |
| C19 | 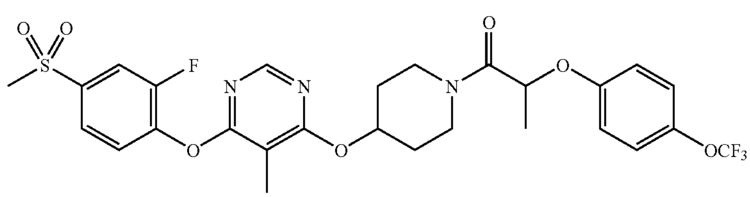 | 1-{4-[6-(2-Fluoro-4-methane-sulfonyl-phenoxy)-5-methyl-pyrimidin-4-yloxy]-piperidin-1-yl}-2-(4-trifluoromethoxy-phenoxy)-propan-1-one |
| C20 | 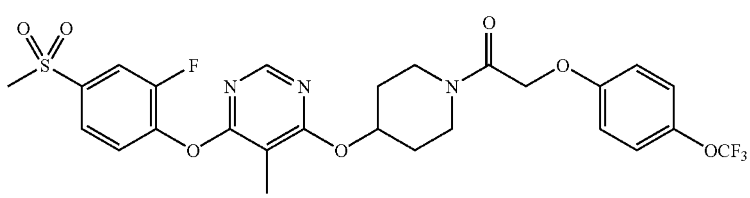 | 1-{4-[6-(2-Fluoro-4-methane-sulfonyl-phenoxy)-5-methyl-pyrimidin-4-yloxy]-piperidin-1-yl}-2-(4-trifluoromethoxy-phenoxy)-ethanone |
| C21 | 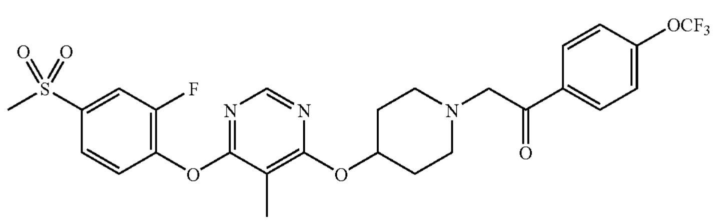 | 2-{4-[6-(2-Fluoro-4-methane-sulfonyl-phenoxy)-5-methyl-pyrimidin-4-yloxy]-piperidin-1-yl}-1-(4-trifluoromethoxy-phenyl)-ethanone |
| C22 | 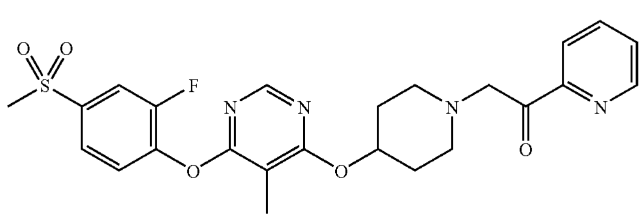 | 2-{4-[6-(2-Fluoro-4-methane-sulfonyl-phenoxy)-5-methyl-pyrimidin-4-yloxy]-piperidin-1-yl}-1-pyridin-2-yl-ethanone |

TABLE C-continued

| Cmpd # | Structure | Chemical Name |
|---|---|---|
| C23 | 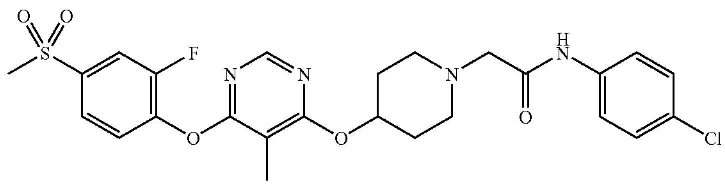 | N-(4-Chloro-phenyl)-2-{4-[6-(2-fluor-o-4-methanesulfonyl-phe-noxy)-5-methyl-pyrimidin-4-yl-oxy]-piperidin-1-yl}-acetamide |
| C24 | 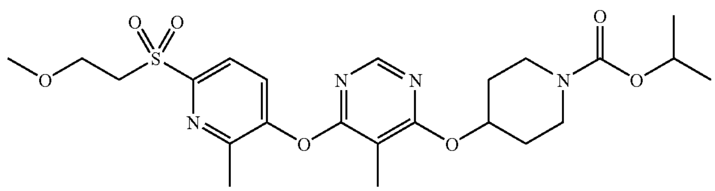 | 4-{6-[6-(2-Methoxy-ethane-sulfonyl)-2-methyl-pyridin-3-yl-oxy]-5-methyl-pyrimidin-4-yl-oxy}-piperidine-1-carboxylic acid isopropyl ester |
| C25 | 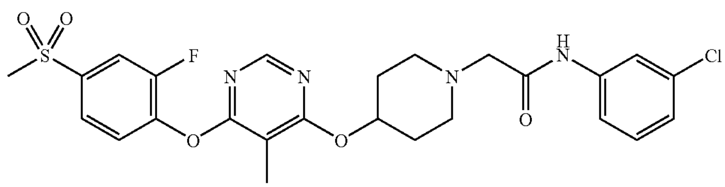 | N-(3-Chloro-phenyl)-2-{4-[6-(2-fluor-o-4-methanesulfonyl-phe-noxy)-5-methyl-pyrimidin-4-yl-oxy]-piperidin-1-yl}-acetamide |
| C26 | 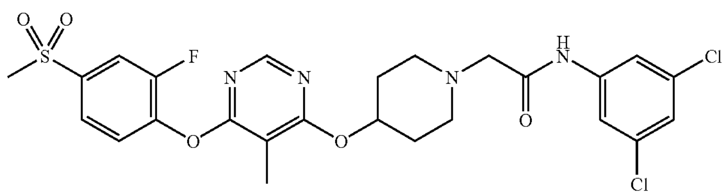 | N-(3,5-Dichloro-phe-nyl)-2-{4-[6-(2-fluoro-4-methane-sulfonyl-phe-noxy)-5-methyl-pyrimidin-4-yl-oxy]-piperidin-1-yl}-acetamide |
| C27 | 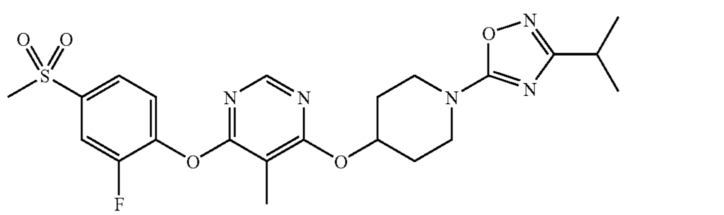 | 4-(2-Fluoro-4-methanesulfonyl-phe-noxy)-6-[1-(3-isopropyl-[1,2,4]oxa-diazol-5-yl)-piperidin-4-yl-oxy]-5-methyl-pyrimidine |
| C28 | 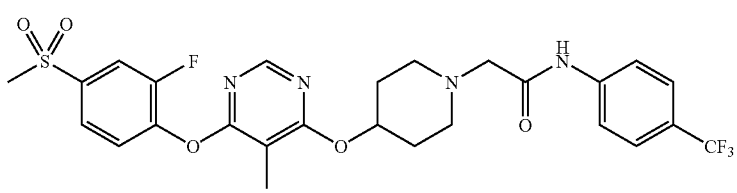 | 2-(4-[6-(2-Fluoro-4-methane-sulfonyl-phenoxy)-5-meth-yl-pyrimidin-4-yloxy]-pipe-ridin-1-yl}-N-(4-tri-fluoromethyl-phenyl)-acetamide |
| C29 | 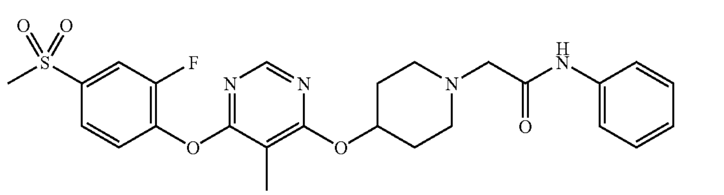 | 2-{4-[6-(2-Fluoro-4-methane-sulfonyl-phenoxy)-5-meth-yl-pyrimidin-4-yloxy]-pipe-ridin-1-yl}-N-phenyl-acetamide |
| C30 | 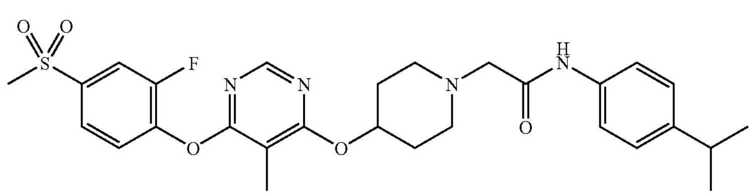 | 2-{4-[6-(2-Fluoro-4-methane-sulfonyl-phenoxy)-5-meth-yl-pyrimidin-4-yloxy]-pipe-ridin-1-yl}-N-(4-isopropyl-phe-nyl)-acetamide |

TABLE C-continued

| Cmpd # | Structure | Chemical Name |
| --- | --- | --- |
| C31 | 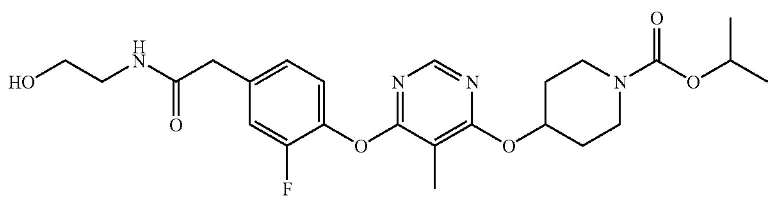 | 4-(6-{2-Fluoro-4-[(2-hydroxy-ethyl-carbamoyl)-methyl]-phenoxy}-5-methyl-pyrimidin-4-yloxy)-piperidine-1-carboxylic acid isopropyl ester |
| C32 | 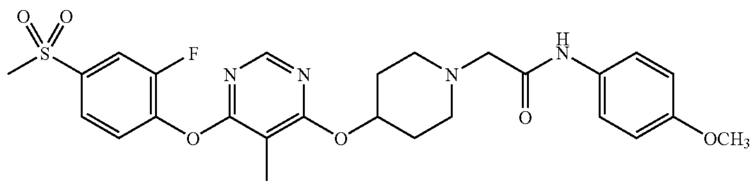 | 2-{4-[6-(2-Fluoro-4-methanesulfonyl-phenoxy)-5-methyl-pyrimidin-4-yloxy]-piperidin-1-yl}-N-(4-methoxy-phenyl)-acetamide |
| C33 | 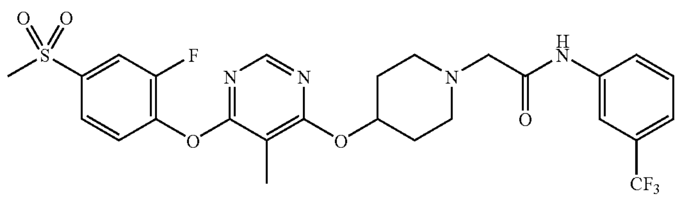 | 2-{4-[6-(2-Fluoro-4-methanesulfonyl-phenoxy)-5-methyl-pyrimidin-4-yloxy]-piperidin-1-yl}-N-(3-trifluoromethyl-phenyl)-acetamide |
| C34 | 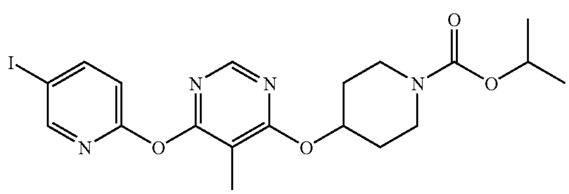 | 4-[6-(5-Iodo-pyridin-2-yloxy)-5-methyl-pyrimidin-4-yloxy]-piperidine-1-carboxylic acid isopropyl ester |
| C35 | 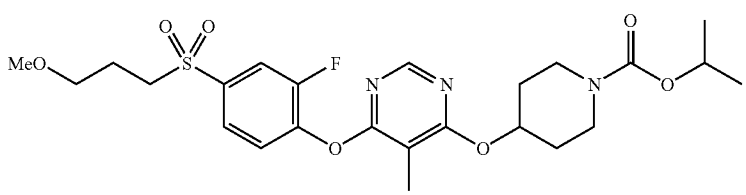 | 4-{6-[2-Fluoro-4-(3-methoxy-propane-1-sulfonyl)-phenoxy]-5-methyl-pyrimidin-4-yloxy}-piperidine-1-carboxylic acid isopropyl ester |
| C36 | 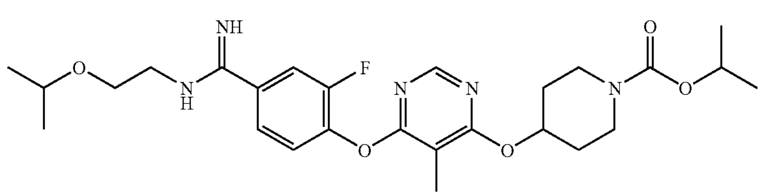 | 4-(6-{2-Fluoro-4-[N-(2-isopropoxy-ethyl)-carbamimidoyl]-phenoxy}-5-methyl-pyrimidin-4-yloxy)-piperidine-1-carboxylic acid isopropyl ester |
| C37 | 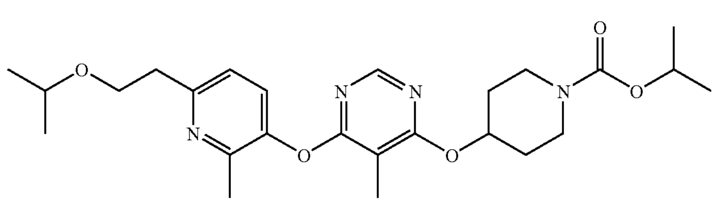 | 4-{6-[6-(2-Isopropoxy-ethyl)-2-methyl-pyridin-3-yloxy]-5-methyl-pyrimidin-4-yloxy}-piperidine-1-carboxylic acid isopropyl ester |

TABLE C-continued

| Cmpd # | Structure | Chemical Name |
|---|---|---|
| C38 | 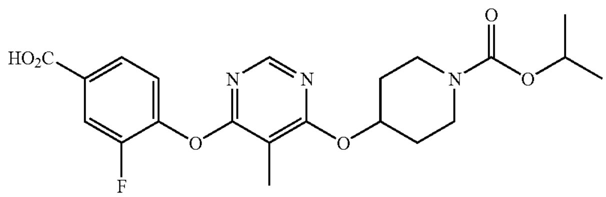 | 4-[6-(4-Carboxy-2-fluoro-phenoxy)-5-methyl-pyrimidin-4-yloxy]-piperidine-1-carboxylic acid isopropyl ester |
| C39 | 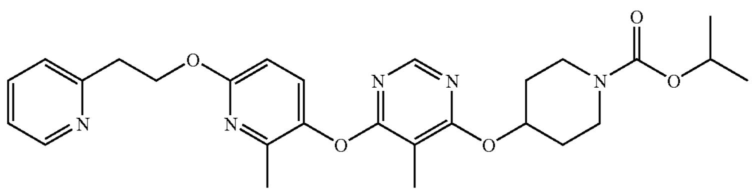 | 4-{5-Methyl-6-[2-methyl-6-(2-pyridin-2-yl-ethoxy)-pyridin-3-yloxy]-pyrimidin-4-yloxy}-piperidine-1-carboxylic acid isopropyl ester |
| C40 | 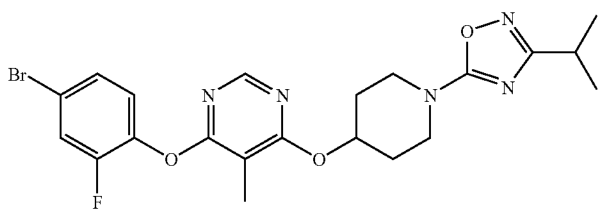 | 4-(4-Bromo-2-fluoro-phenoxy)-6-[1-(3-isopropyl-[1,2,4]oxadiazol-5-yl)-piperidin-4-yloxy]-5-methyl-pyrimidine |
| C41 | 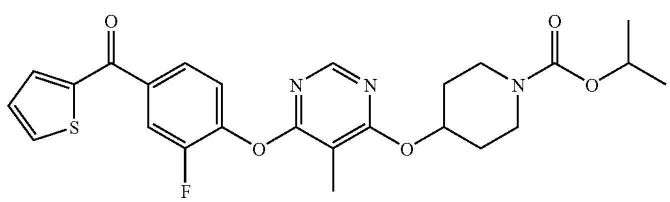 | 4-{6-[2-Fluoro-4-(thiophene-2-carbonyl)-phenoxy]-5-methyl-pyrimidin-4-yloxy}-piperidine-1-carboxylic acid isopropyl ester |
| C42 | 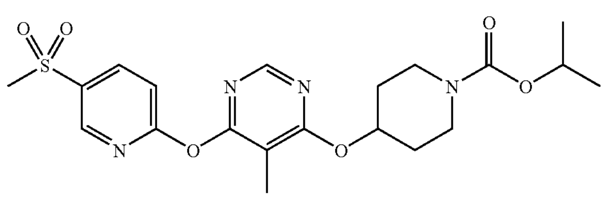 | 4-[6-(5-Methanesulfonyl-pyridin-2-yloxy)-5-methyl-pyrimidin-4-yloxy]-piperidine-1-carboxylic acid isopropyl ester |
| C43 | 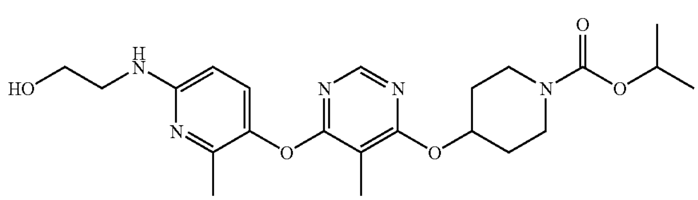 | 4-{6-[6-(2-Hydroxy-ethylamino)-2-methyl-pyridin-3-yloxy]-5-methyl-pyrimidin-4-yloxy}-piperidine-1-carboxylic acid isopropyl ester |
| C44 | 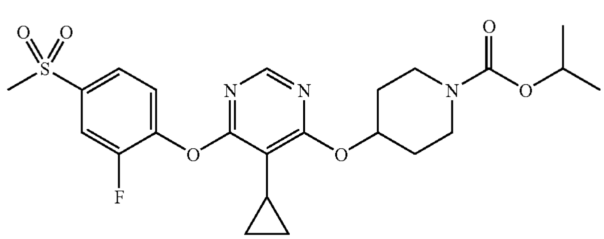 | 4-[5-Cyclopropyl-6-(2-fluoro-4-methanesulfonyl-phenoxy)-pyrimidin-4-yloxy]-piperidine-1-carboxylic acid isopropyl ester |

TABLE C-continued

| Cmpd # | Structure | Chemical Name |
|---|---|---|
| C45 | 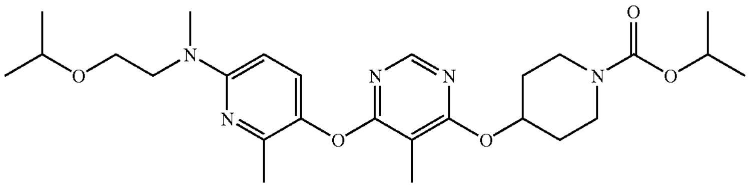 | 4-(6-{6-[(2-Isopropoxy-ethyl)-methyl-amino]-2-methyl-pyridin-3-yl-oxy}-5-methyl-pyrimidin-4-yl-oxy)-piperidine-1-carboxylic acid isopropyl ester |
| C46 | 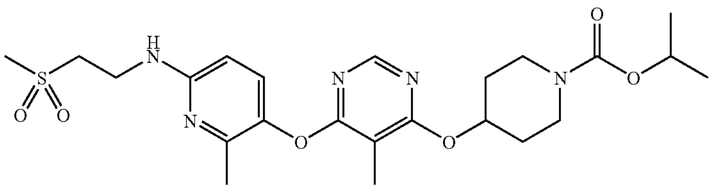 | 4-{6-[6-(2-Methanesulfonyl-ethylamino)-2-methyl-pyridin-3-yl-oxy]-5-methyl-pyrimidin-4-yl-oxy}-piperidine-1-carboxylic acid isopropyl ester |
| C47 | 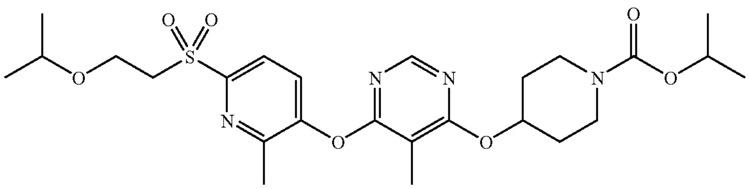 | 4-{6-[6-(2-Isopropoxy-ethanesulfonyl)-2-methyl-pyridin-3-yl-oxy]-5-methyl-pyrimidin-4-yl-oxy}-piperidine-1-carboxylic acid isopropyl ester |
| C48 | 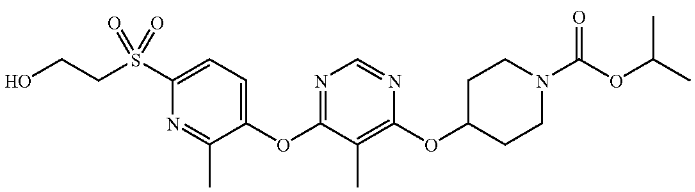 | 4-{6-[6-(2-Hydroxy-ethanesulfonyl)-2-methyl-pyridin-3-yl-oxy]-5-methyl-pyrimidin-4-yl-oxy}-piperidine-1-carboxylic acid isopropyl ester |
| C49 | 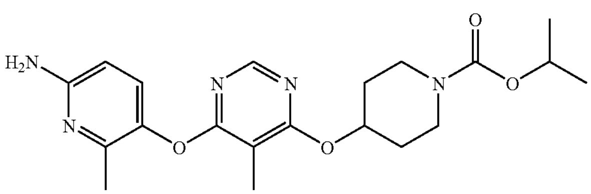 | 4-[6-(6-Amino-2-methyl-pyridin-3-yl-oxy)-5-methyl-pyrimidin-4-yl-oxy]-piperidine-1-carboxylic acid isopropyl ester |
| C50 | 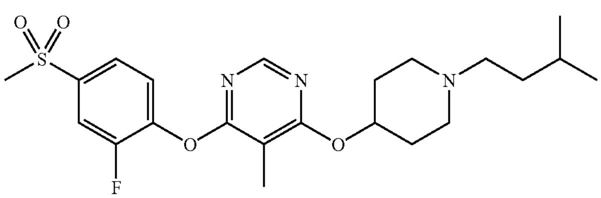 | 4-(2-Fluoro-4-methanesulfonyl-phenoxy)-5-methyl-6-[1-(3-methyl-butyl)-piperidin-4-yloxy]-pyrimidine |
| C51 | 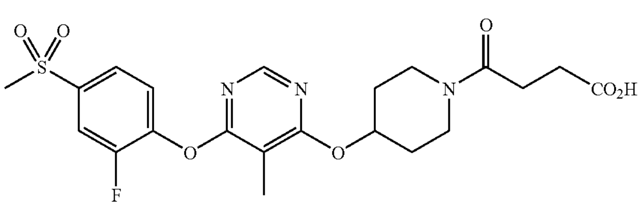 | 4-{4-[6-(2-Fluoro-4-methanesulfonyl-phenoxy)-5-methyl-pyrimidin-4-yloxy]-piperidin-1-yl}-4-oxo-butyric acid |

TABLE C-continued

| Cmpd # | Structure | Chemical Name |
| --- | --- | --- |
| C52 | 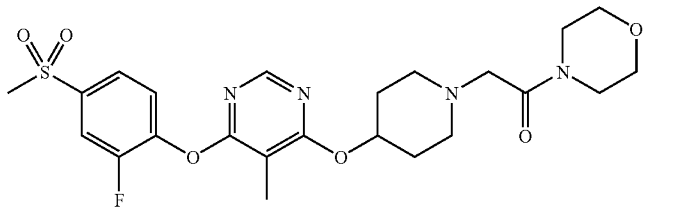 | 2-{4-[6-(2-Fluoro-4-methane-sulfonyl-phenoxy)-5-methyl-pyrimidin-4-yloxy]-piperidin-1-yl}-1-morpholin-4-yl-ethanone |
| C53 | 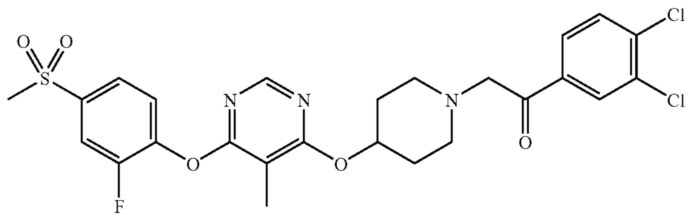 | 1-(3,4-Dichloro-phenyl)-2-{4-[6-(2-fluoro-4-methanesulfonyl-phenoxy)-5-methyl-pyrimidin-4-yloxy]-piperidin-1-yl}-ethanone |
| C54 | 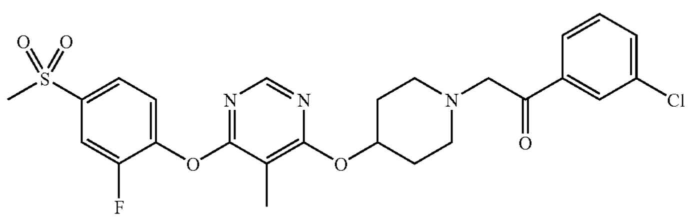 | 1-(3-Chloro-phenyl)-2-{4-[6-(2-fluoro-4-methanesulfonyl-phenoxy)-5-methyl-pyrimidin-4-yloxy]-piperidin-1-yl}-ethanone |
| C55 | 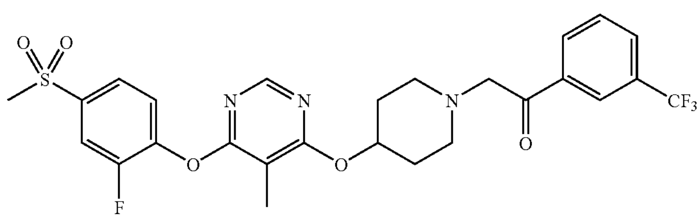 | 2-{4-[6-(2-Fluoro-4-methane-sulfonyl-phenoxy)-5-methyl-pyrimidin-4-yloxy]-piperidin-1-yl}-1-(3-trifluoromethyl-phenyl)-ethanone |
| C56 | 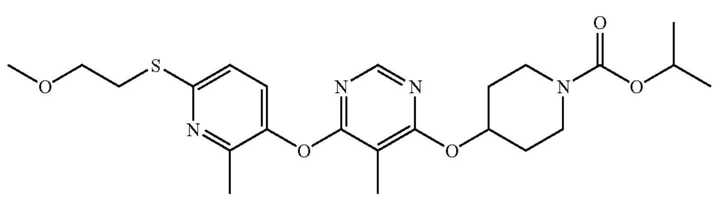 | 4-{6-[6-(2-Methoxy-ethylsulfanyl)-2-methyl-pyridin-3-yloxy]-5-methyl-pyrimidin-4-yloxy}-piperidine-1-carboxylic acid isopropyl ester |
| C57 | 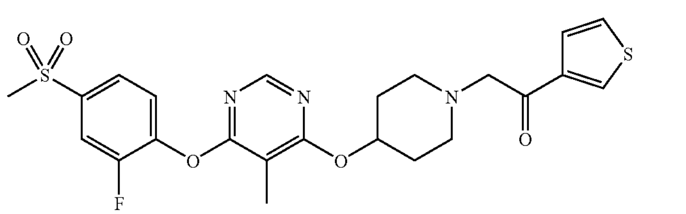 | 2-{4-[6-(2-Fluoro-4-methane-sulfonyl-phenoxy)-5-methyl-pyrimidin-4-yloxy]-piperidin-1-yl}-1-thiophen-3-yl-ethanone |
| C58 | 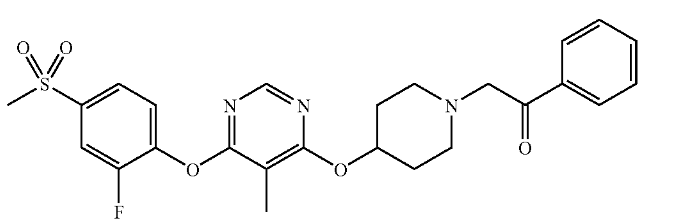 | 2-{4-[6-(2-Fluoro-4-methanesulfonyl-phenoxy)-5-methyl-pyrimidin-4-yloxy]-piperidin-1-yl}-1-phenyl-ethanone |

TABLE C-continued

| Cmpd # | Structure | Chemical Name |
|---|---|---|
| C59 | 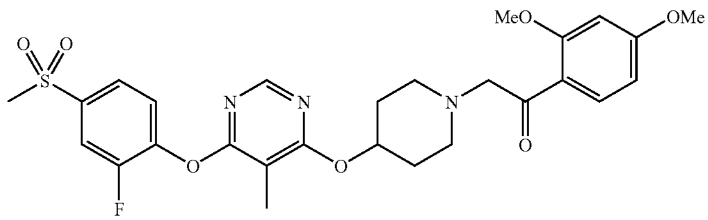 | 1-(2,4-Dimethoxy-phenyl)-2-{4-[6-(2-fluoro-4-methanesulfonyl-phenoxy)-5-methyl-pyrimidin-4-yloxy]-piperidin-1-yl}-ethanone |
| C60 | 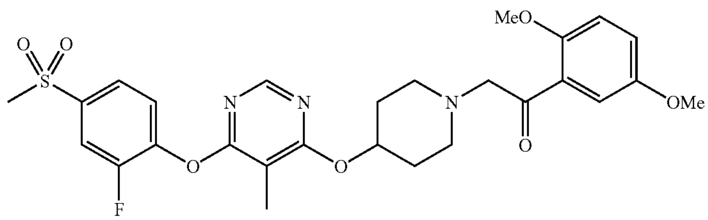 | 1-(2,5-Dimethoxy-phenyl)-2-{4-[6-(2-fluoro-4-methanesulfonyl-phenoxy)-5-methyl-pyrimidin-4-yloxy]-piperidin-1-yl}-ethanone |
| C61 | 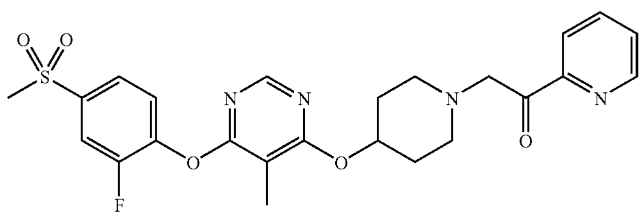 | 2-{4-[6-(2-Fluoro-4-methanesulfonyl-phenoxy)-5-methyl-pyrimidin-4-yloxy]-piperidin-1-yl}-1-pyridin-2-yl-ethanone |
| C62 | 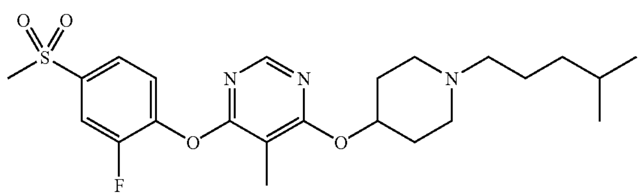 | 4-(2-Fluoro-4-methanesulfonyl-phenoxy)-5-methyl-6-[1-(4-methyl-pentyl)-piperidin-4-yloxy]-pyrimidine |
| C63 | 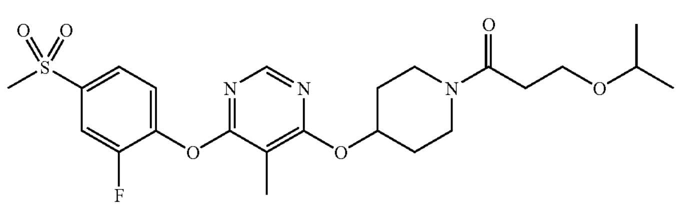 | 1-{4-[6-(2-Fluoro-4-methanesulfonyl-phenoxy)-5-methyl-pyrimidin-4-yloxy]-piperidin-1-yl}-3-isopropoxy-propan-1-one |
| C64 | 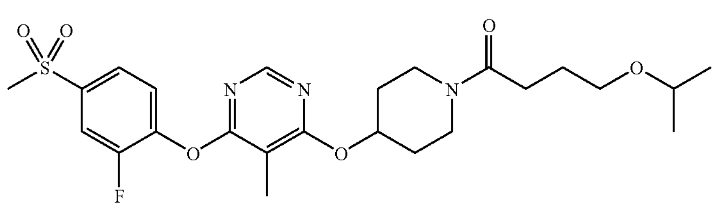 | 1-{4-[6-(2-Fluoro-4-methanesulfonyl-phenoxy)-5-methyl-pyrimidin-4-yloxy]-piperidin-1-yl}-4-isopropoxy-butan-1-one |
| C65 | 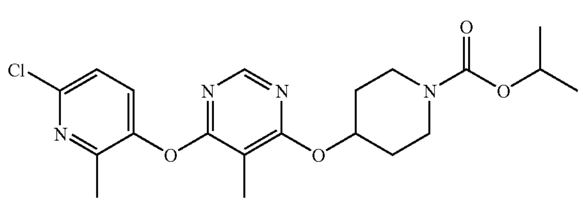 | 4-[6-(6-Chloro-2-methyl-pyridin-3-yloxy)-5-methyl-pyrimidin-4-yloxy]-piperidine-1-carboxylic acid isopropyl ester |

| Cmpd # | Structure | Chemical Name |
|---|---|---|
| C66 | 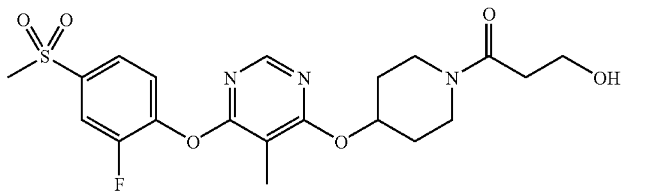 | 1-{4-[6-(2-Fluoro-4-methanesulfonyl-phenoxy)-5-methyl-pyrimidin-4-yloxy]-piperidin-1-yl}-3-hydroxy-propan-1-one |
| C67 | 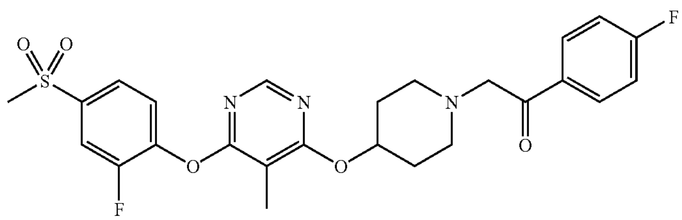 | 2-{4-[6-(2-Fluoro-4-methanesulfonyl-phenoxy)-5-methyl-pyrimidin-4-yloxy]-piperidin-1-yl}-1-(4-fluoro-phenyl)-ethanone |
| C68 | 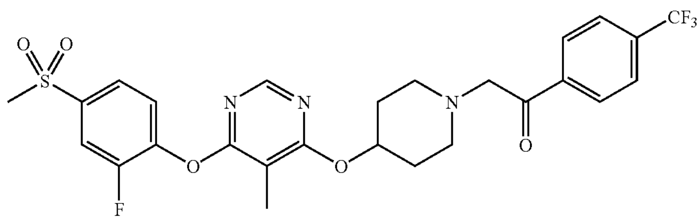 | 2-{4-[6-(2-Fluoro-4-methanesulfonyl-phenoxy)-5-methyl-pyrimidin-4-yloxy]-piperidin-1-yl}-1-(4-trifluoromethyl-phenyl)-ethanone |
| C69 | 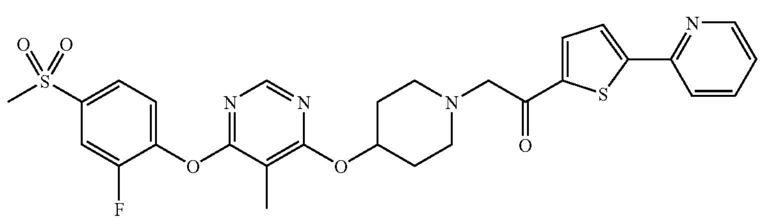 | 2-{4-[6-(2-Fluoro-4-methanesulfonyl-phenoxy)-5-methyl-pyrimidin-4-yloxy]-piperidin-1-yl}-1-(5-pyridin-2-yl-thiophen-2-yl)-ethanone |
| C70 | 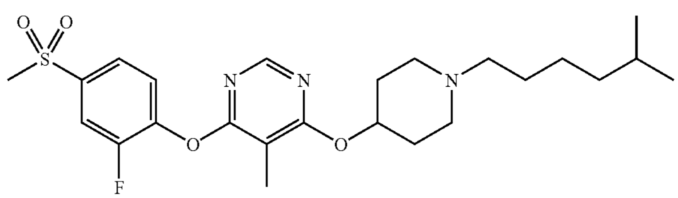 | 4-(2-Fluoro-4-methanesulfonyl-phenoxy)-5-methyl-6-[1-(5-methyl-hexyl)-piperidin-4-yloxy]-pyrimidine |
| C71 | 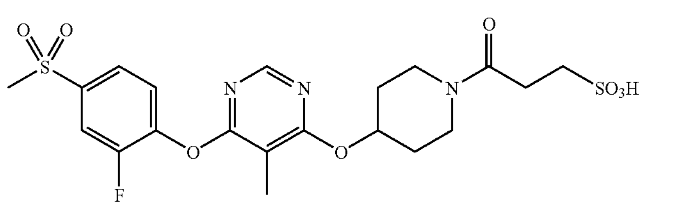 | 3-{4-[6-(2-Fluoro-4-methanesulfonyl-phenoxy)-5-methyl-pyrimidin-4-yloxy]-piperidin-1-yl}-3-oxo-propane-1-sulfonic acid |
| C72 | 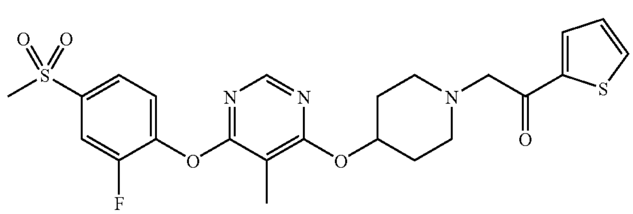 | 2-{4-[6-(2-Fluoro-4-methanesulfonyl-phenoxy)-5-methyl-pyrimidin-4-yloxy]-piperidin-1-yl}-1-thiophen-2-yl-ethanone |

TABLE C-continued

| Cmpd # | Structure | Chemical Name |
|---|---|---|
| C73 | 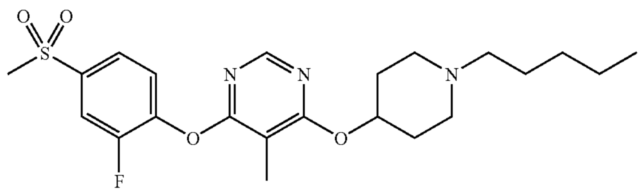 | 4-(2-Fluoro-4-methanesulfonyl-phenoxy)-5-methyl-6-(1-pentyl-piperidin-4-yloxy)-pyrimidine |
| C74 | 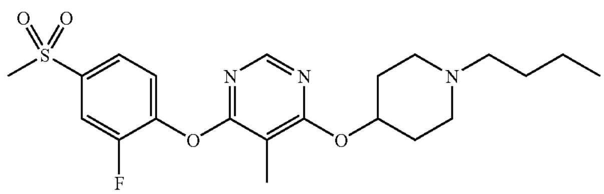 | 4-(1-Butyl-piperidin-4-yloxy)-6-(2-fluoro-4-methanesulfonyl-phenoxy)-5-methyl-pyrimidine |
| C75 | 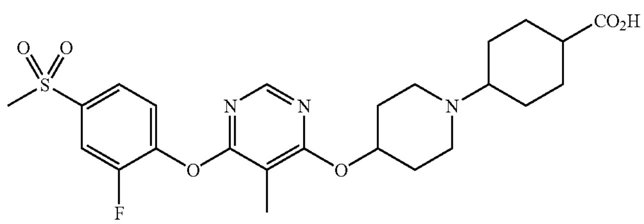 | 4-{4-[6-(2-Fluoro-4-methanesulfonyl-phenoxy)-5-methyl-pyrimidin-4-yloxy]-piperidin-1-yl}-cyclohexanecarboxylic acid |
| C76 | 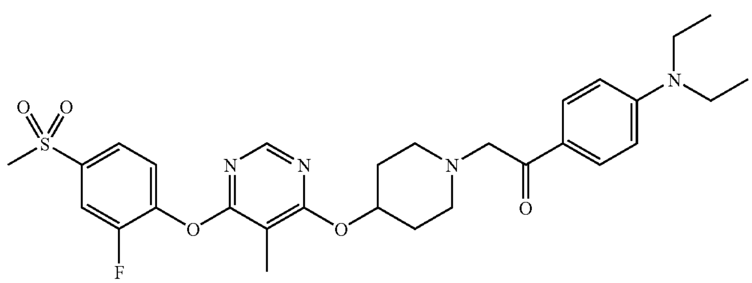 | 1-(4-Diethylamino-phenyl)-2-{4-[6-(2-fluoro-4-methanesulfonyl-phenoxy)-5-methyl-pyrimidin-4-yloxy]-piperidin-1-yl}-ethanone |
| C77 | 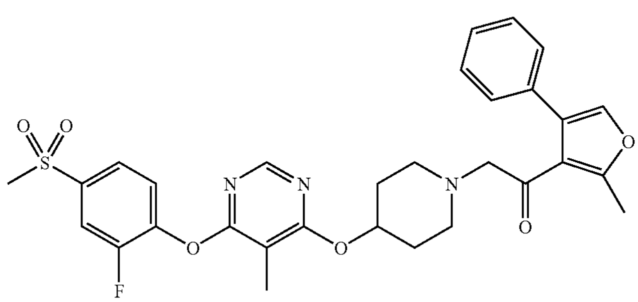 | 2-{4-[6-(2-Fluoro-4-methanesulfonyl-phenoxy)-5-methyl-pyrimidin-4-yloxy]-piperidin-1-yl}-1-(2-methyl-4-phenyl-furan-3-yl)-ethanone |
| C78 | 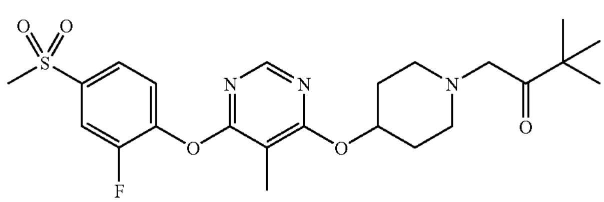 | 1-{4-[6-(2-Fluoro-4-methanesulfonyl-phenoxy)-5-methyl-pyrimidin-4-yloxy]-piperidin-1-yl}-3,3-dimethyl-butan-2-one |

TABLE C-continued

| Cmpd # | Structure | Chemical Name |
|---|---|---|
| C79 | 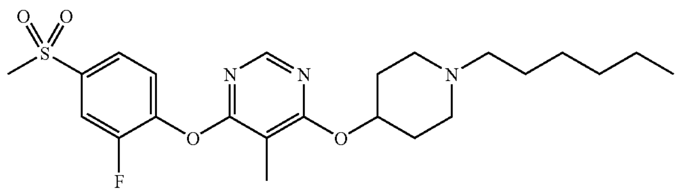 | 4-(2-Fluoro-4-methanesulfonyl-phenoxy)-6-(1-hexyl-piperidin-4-yloxy)-5-methyl-pyrimidine |
| C80 | 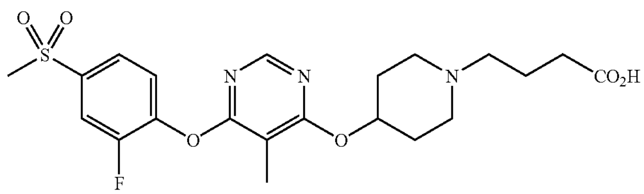 | 4-{4-[6-(2-Fluoro-4-methanesulfonyl-phenoxy)-5-methyl-pyrimidin-4-yloxy]-piperidin-1-yl}-butyric acid |
| C81 | 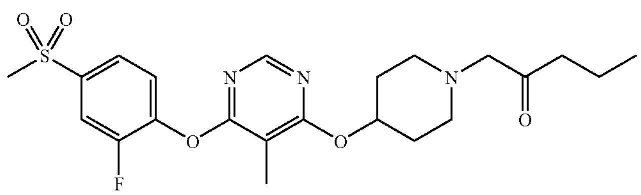 | 1-{4-[6-(2-Fluoro-4-methanesulfonyl-phenoxy)-5-methyl-pyrimidin-4-yloxy]-piperidin-1-yl}-pentan-2-one |
| C82 | 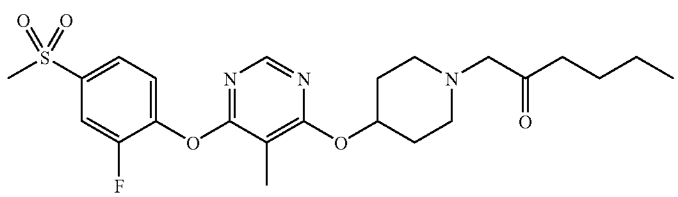 | 1-{4-[6-(2-Fluoro-4-methanesulfonyl-phenoxy)-5-methyl-pyrimidin-4-yloxy]-piperidin-1-yl}-hexan-2-one |
| C83 | 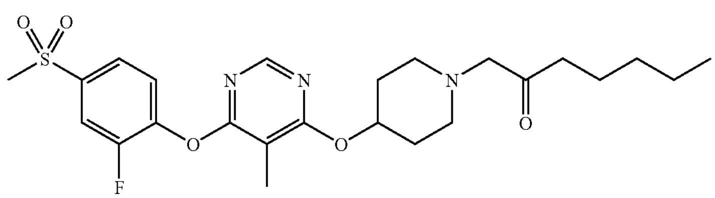 | 1-{4-[6-(2-Fluoro-4-methanesulfonyl-phenoxy)-5-methyl-pyrimidin-4-yloxy]-piperidin-1-yl}-heptan-2-one |
| C84 | 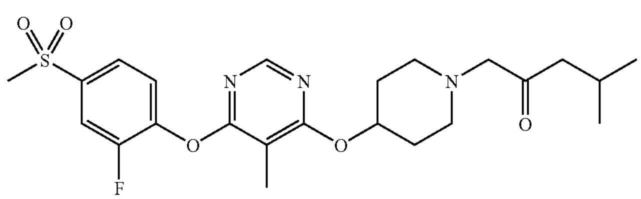 | 1-{4-[6-(2-Fluoro-4-methanesulfonyl-phenoxy)-5-methyl-pyrimidin-4-yloxy]-piperidin-1-yl}-4-methyl-pentan-2-one |
| C85 | 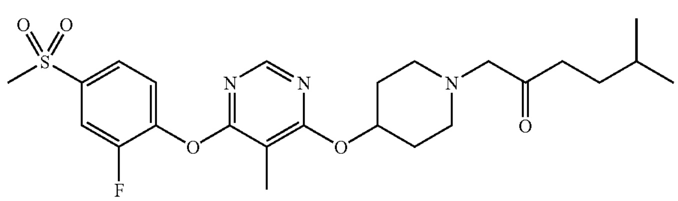 | 1-{4-[6-(2-Fluoro-4-methanesulfonyl-phenoxy)-5-methyl-pyrimidin-4-yloxy]-piperidin-1-yl}-5-methyl-hexan-2-one |
| C86 | 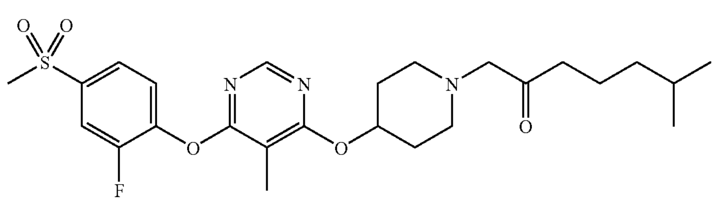 | 1-{4-[6-(2-Fluoro-4-methanesulfonyl-phenoxy)-5-methyl-pyrimidin-4-yloxy]-piperidin-1-yl}-6-methyl-heptan-2-one |

TABLE C-continued

| Cmpd # | Structure | Chemical Name |
|---|---|---|
| C87 | 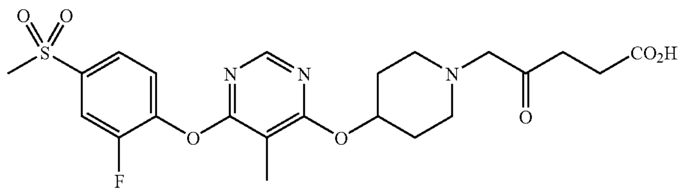 | 5-{4-[6-(2-Fluoro-4-methanesulfonyl-phenoxy)-5-methyl-pyrimidin-4-yloxy]-piperidin-1-yl}-4-oxo-pentanoic acid |
| C88 | 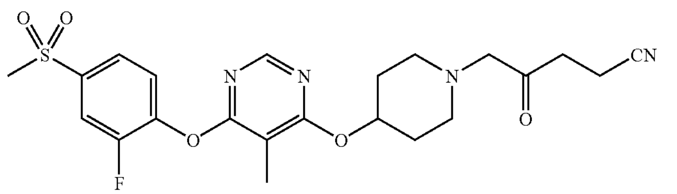 | 5-{4-[6-(2-Fluoro-4-methanesulfonyl-phenoxy)-5-methyl-pyrimidin-4-yloxy]-piperidin-1-yl}-4-oxo-pentanenitrile |
| C89 | 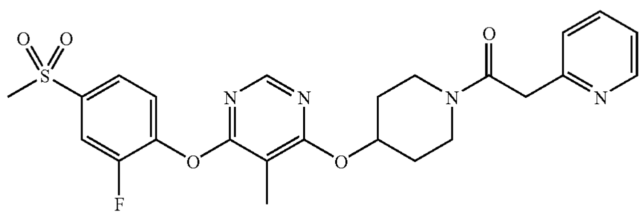 | 1-{4-[6-(2-Fluoro-4-methanesulfonyl-phenoxy)-5-methyl-pyrimidin-4-yloxy]-pipedin-1-yl}-2-pyridin-2-yl-ethanone |
| C90 | 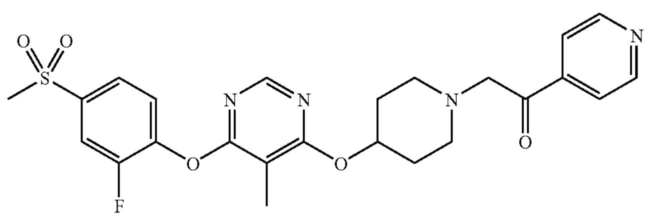 | 2-{4-[6-(2-Fluoro-4-methanesulfonyl-phenoxy)-5-methyl-pyrimidin-4-yloxy]-piperidin-1-yl}-1-pyridin-4-yl-ethanone |
| C91 | 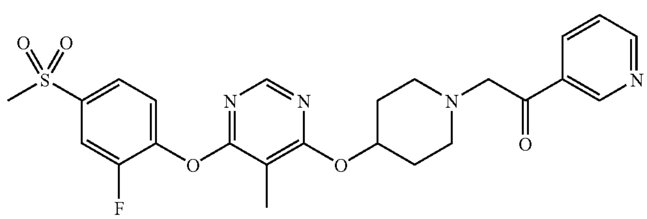 | 2-{4-[6-(2-Fluoro-4-methanesulfonyl-phenoxy)-5-methyl-pyrimidin-4-yloxy]-piperidin-1-yl}-1-pyridin-3-yl-ethanone |
| C92 | 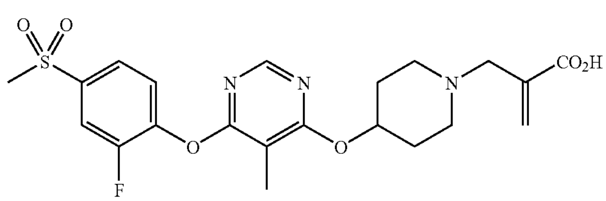 | 2-{4-[6-(2-Fluoro-4-methanesulfonyl-phenoxy)-5-methyl-pyrimidin-4-yloxy]-piperidin-1-ylmethyl}-acrylic acid |
| C93 | 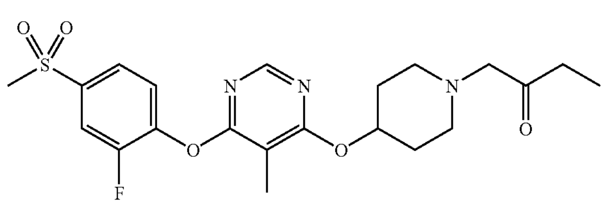 | 1-{4-[6-(2-Fluoro-4-methanesulfonyl-phenoxy)-5-methyl-pyrimidin-4-yloxy]-piperidin-1-yl}-butan-2-one |

TABLE C-continued

| Cmpd # | Structure | Chemical Name |
|---|---|---|
| C94 | 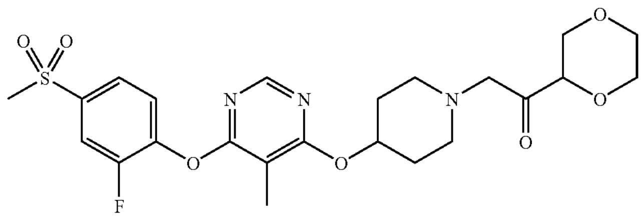 | 1-[1,4]Dioxan-2-yl-2-{4-[6-(2-fluoro-4-methanesulfonyl-phenoxy)-5-methyl-pyrimidin-4-yloxy]-piperidin-1-yl}-ethanone |
| C95 | 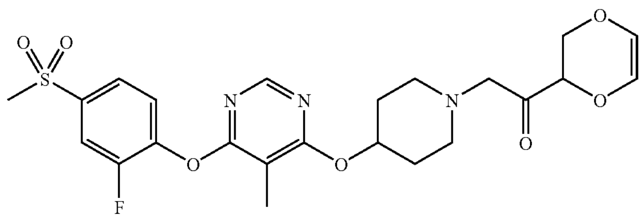 | 1-(2,3-Dihydro-[1,4]dioxin-2-yl)-2-{4-[6-(2-fluoro-4-methanesulfonyl-phenoxy)-5-methyl-pyrimidin-4-yloxy]-piperidin-1-yl}-ethanone |
| C96 | 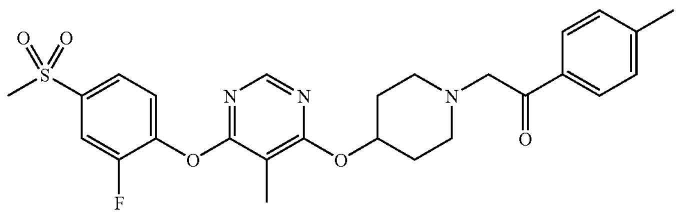 | 2-{4-[6-(2-Fluoro-4-methanesulfonyl-phenoxy)-5-methyl-pyrimidin-4-yloxy]-piperidin-1-yl}-1-p-tolyl-ethanone |
| C97 | 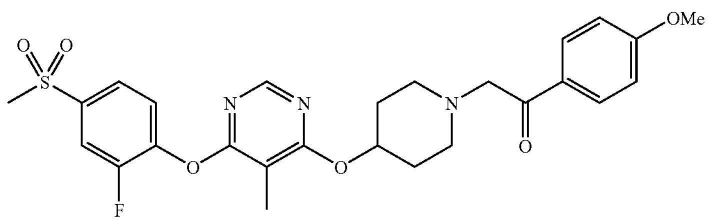 | 2-{4-[6-(2-Fluoro-4-methanesulfonyl-phenoxy)-5-methyl-pyrimidin-4-yloxy]-piperidin-1-yl}-1-(4-methoxy-phenyl)-ethanone |
| C98 | 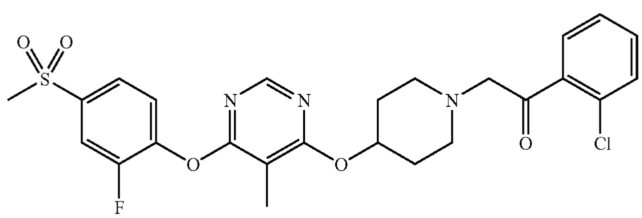 | 1-(2-Chloro-phenyl)-2-{4-[6-(2-fluoro-4-methanesulfonyl-phenoxy)-5-methyl-pyrimidin-4-yloxy]-piperidin-1-yl}-ethanone |
| C99 | 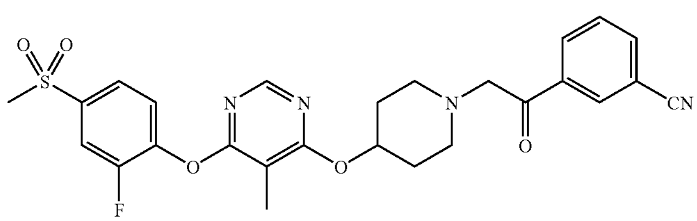 | 3-(2-{4-[6-(2-Fluoro-4-methanesulfonyl-phenoxy)-5-methyl-pyrimidin-4-yloxy]-piperidin-1-yl}-acetyl)-benzonitrile |
| C100 | 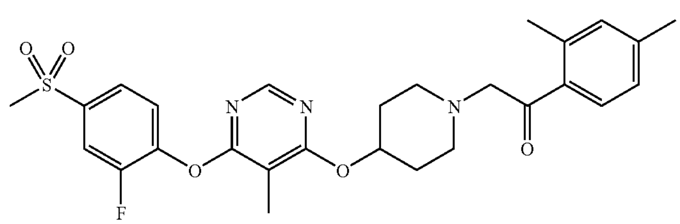 | 1-(2,4-Dimethyl-phenyl)-2-{4-[6-(2-fluoro-4-methanesulfonyl-phenoxy)-5-methyl-pyrimidin-4-yloxy]-piperidin-1-yl}-ethanone |

TABLE C-continued

| Cmpd # | Structure | Chemical Name |
|---|---|---|
| C101 | 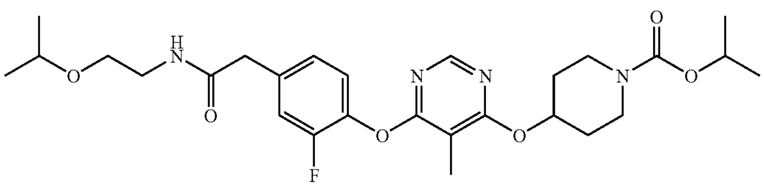 | 4-(6-{2-Fluoro-4-[(2-isopropoxy-ethylcarbamoyl)-methyl]-phenoxy}-5-methyl-pyrimidin-4-yloxy)-piperidine-1-carboxylic acid isopropyl ester |
| C102 | 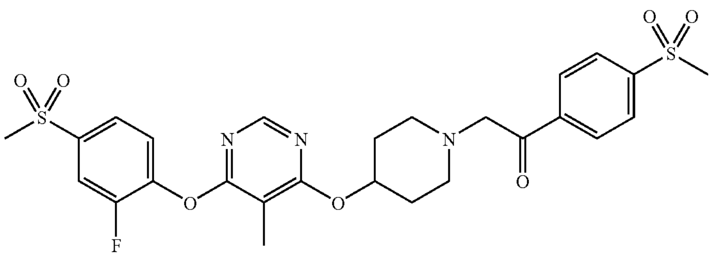 | 2-{4-[6-(2-Fluoro-4-methanesulfonyl-phenoxy)-5-methyl-pyrimidin-4-yloxy]-piperidin-1-yl}-1-(4-methanesulfonyl-phenyl)-ethanone |
| C103 | 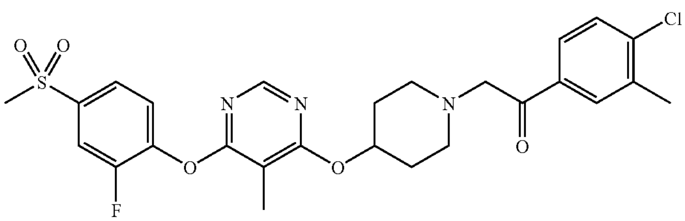 | 1-(4-Chloro-3-methyl-phenyl)-2-{4-[6-(2-fluoro-4-methanesulfonyl-phenoxy)-5-methyl-pyrimidin-4-yloxy]-piperidin-1-yl}-ethanone |
| C104 | 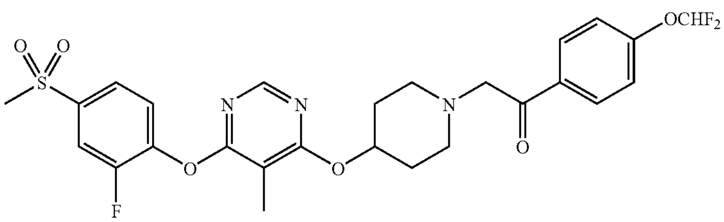 | 1-(4-Difluoromethoxy-phenyl)-2-{4-[6-(2-fluoro-4-methanesulfonyl-phenoxy)-5-methyl-pyrimidin-4-yloxy]-piperidin-1-yl}-ethanone |
| C105 | 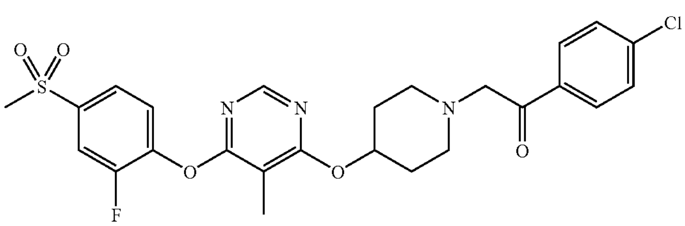 | 1-(4-Chloro-phenyl)-2-{4-[6-(2-fluoro-4-methanesulfonyl-phenoxy)-5-methyl-pyrimidin-4-yloxy]-piperidin-1-yl}-ethanone |
| C106 | 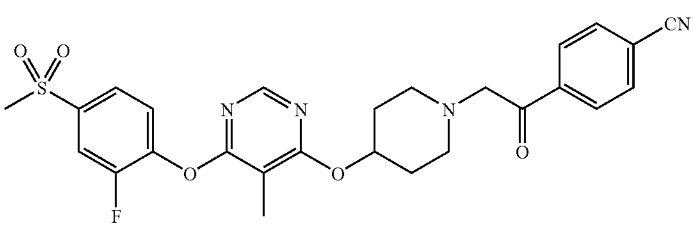 | 4-(2-{4-[6-(2-Fluoro-4-methanesulfonyl-phenoxy)-5-methyl-pyrimidin-4-yloxy]-piperidin-1-yl}-acetyl)-benzonitrile |
| C107 | 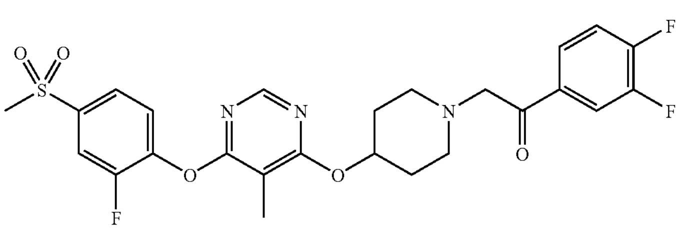 | 1-(3,4-Difluoro-phenyl)-2-{4-[6-(2-fluoro-4-methanesulfonyl-phenoxy)-5-methyl-pyrimidin-4-yloxy]-piperidin-1-yl}-ethanone |

TABLE C-continued

| Cmpd # | Structure | Chemical Name |
| --- | --- | --- |
| C108 | 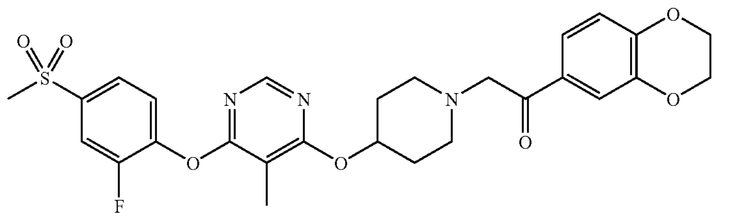 | 1-(2,3-Dihydro-benzo[1,4]dioxin-6-yl)-2-{4-[6-(2-fluoro-4-methanesulfonyl-phenoxy)-5-methyl-pyrimidin-4-yloxy]-piperidin-1-yl}-ethanone |
| C109 | 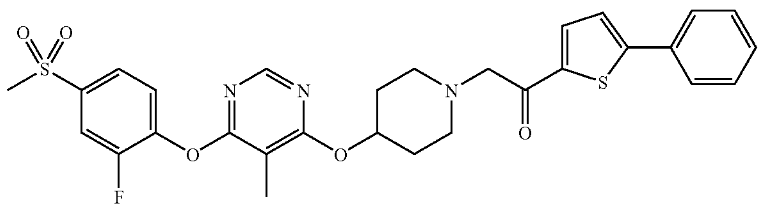 | 2-{4-[6-(2-Fluoro-4-methanesulfonyl-phenoxy)-5-methyl-pyrimidin-4-yloxy]-piperidin-1-yl}-1-(5-phenyl-thiophen-2-yl)-ethanone |
| C110 | 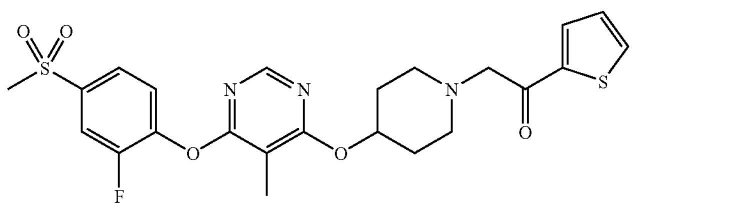 | 2-{4-[6-(2-Fluoro-4-methanesulfonyl-phenoxy)-5-methyl-pyrimidin-4-yloxy]-piperidin-1-yl}-1-thiophen-2-yl-ethanone |
| C111 | 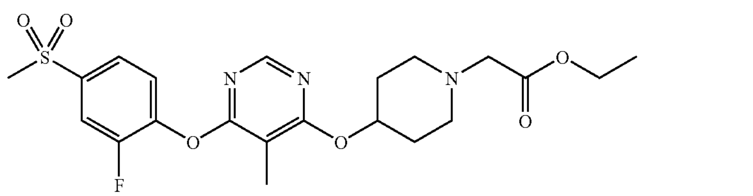 | {4-[6-(2-Fluoro-4-methanesulfonyl-phenoxy)-5-methyl-pyrimidin-4-yloxy]-piperidin-1-yl}-acetic acid ethyl ester |
| C112 | 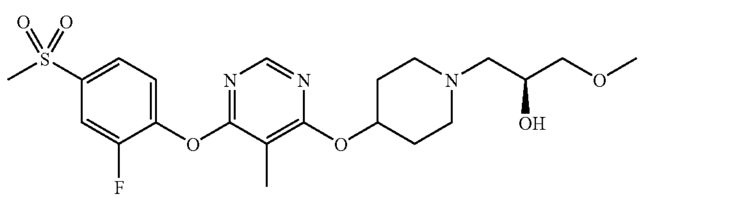 | 1-{4-[6-(2-Fluoro-4-methanesulfonyl-phenoxy)-5-methyl-pyrimidin-4-yloxy]-piperidin-1-yl}-3-methoxy-propan-2-ol |
| C113 | 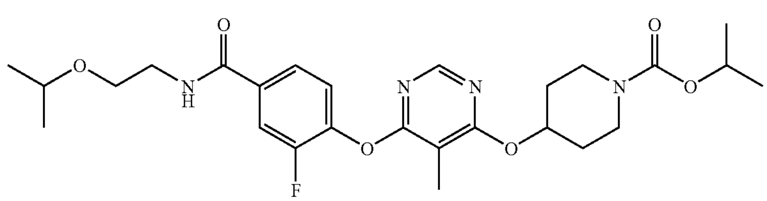 | 4-{6-[2-Fluoro-4-(2-isopropoxy-ethylcarbamoyl)-phenoxy]-5-methyl-pyrimidin-4-yloxy}-piperidine-1-carboxylic acid isopropyl ester |
| C114 | 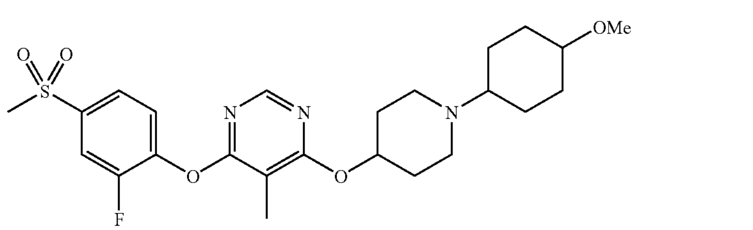 | 4-(2-Fluoro-4-methanesulfonyl-phenoxy)-6-[1-(4-methoxy-cyclohexyl)-piperidin-4-yloxy]-5-methyl-pyrimidine |

TABLE C-continued

| Cmpd # | Structure | Chemical Name |
|---|---|---|
| C115 | 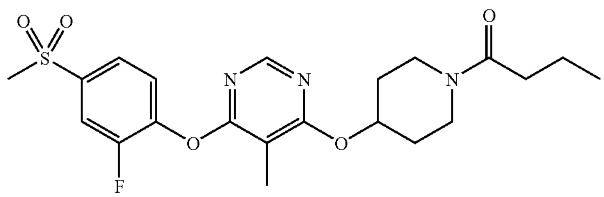 | 1-{4-[6-(2-Fluoro-4-methanesulfonyl-phenoxy)-5-methyl-pyrimidin-4-yloxy]-piperidin-1-yl}-butan-1-one |
| C116 | 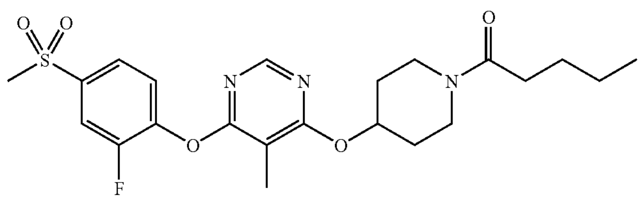 | 1-{4-[6-(2-Fluoro-4-methanesulfonyl-phenoxy)-5-methyl-pyrimidin-4-yloxy]-piperidin-1-yl}-pentan-1-one |
| C117 | 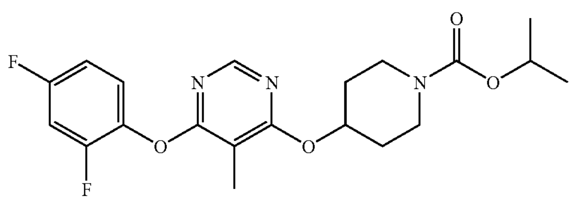 | 4-[6-(2,4-Difluoro-phenoxy)-5-methyl-pyrimidin-4-yloxy]-piperidine-1-carboxylic acid isopropyl ester |
| C118 | 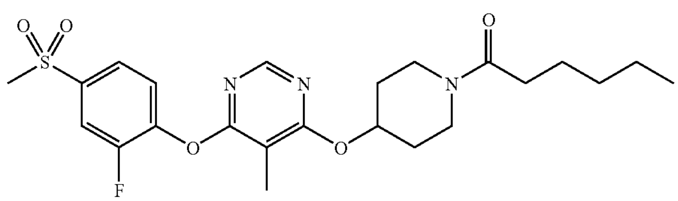 | 1-{4-[6-(2-Fluoro-4-methanesulfonyl-phenoxy)-5-methyl-pyrimidin-4-yloxy]-piperidin-1-yl}-hexan-1-one |
| C119 | 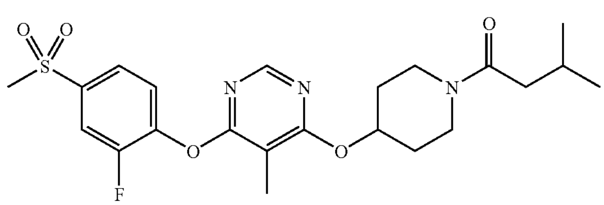 | 1-{4-[6-(2-Fluoro-4-methanesulfonyl-phenoxy)-5-methyl-pyrimidin-4-yloxy]-piperidin-1-yl}-3-methyl-butan-1-one |
| C120 | 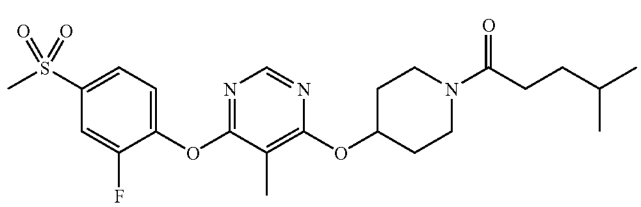 | 1-{4-[6-(2-Fluoro-4-methanesulfonyl-phenoxy)-5-methyl-pyrimidin-4-yloxy]-piperidin-1-yl}-4-methyl-pentan-1-one |
| C121 | 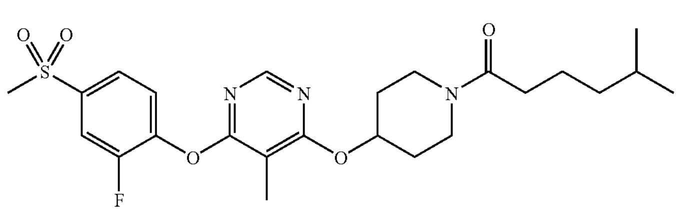 | 1-{4-[6-(2-Fluoro-4-methanesulfonyl-phenoxy)-5-methyl-pyrimidin-4-yloxy]-piperidin-1-yl}-5-methyl-hexan-1-one |

TABLE C-continued

| Cmpd # | Structure | Chemical Name |
|---|---|---|
| C122 | 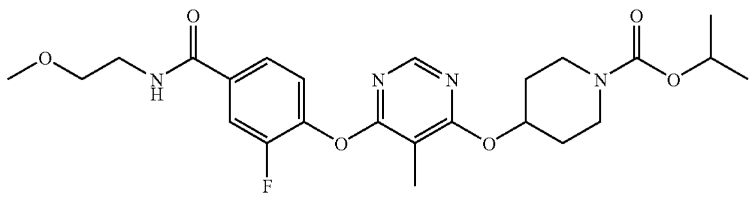 | 4-{6-[2-Fluoro-4-(2-methoxy-ethylcarbamoyl)-phenoxy]-5-methyl-pyrimidin-4-yloxy}-piperidine-1-carboxylic acid isopropyl ester |
| C123 | 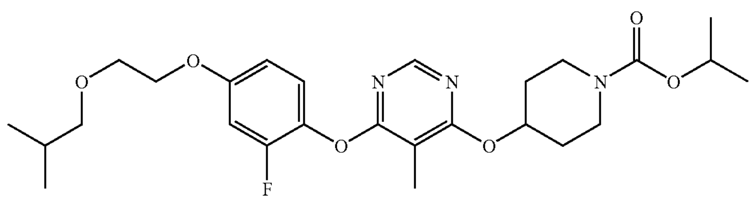 | 4-{6-[2-Fluoro-4-(2-isobutoxy-ethoxy)-phenoxy]-5-methyl-pyrimidin-4-yloxy}-piperidine-1-carboxylic acid isopropyl ester |
| C124 | 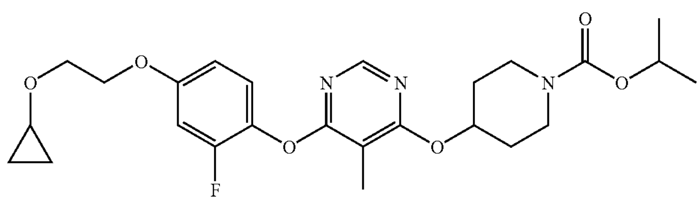 | 4-{6-[4-(2-Cyclopropoxy-ethoxy)-2-fluoro-phenoxy]-5-methyl-pyrimidin-4-yloxy}-piperidine-1-carboxylic acid isopropyl ester |
| C125 | 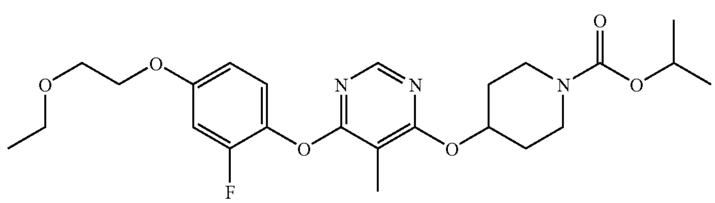 | 4-{6-[4-(2-Ethoxy-ethoxy)-2-fluoro-phenoxy]-5-methyl-pyrimidin-4-yloxy}-piperidine-1-carboxylic acid isopropyl ester |
| C126 | 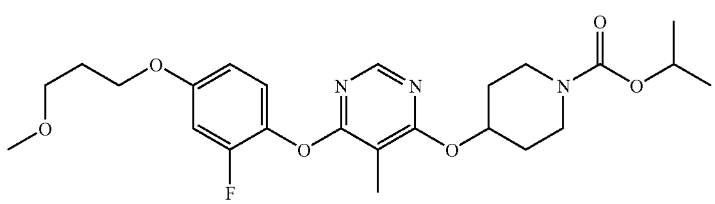 | 4-{6-[2-Fluoro-4-(3-methoxy-propoxy)-phenoxy]-5-methyl-pyrimidin-4-yloxy}-piperidine-1-carboxylic acid isopropyl ester |
| C127 | 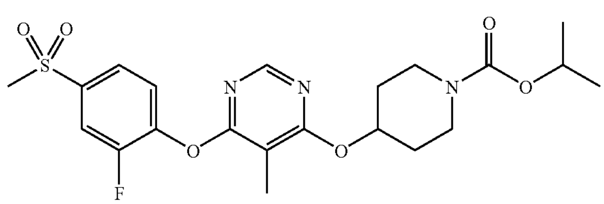 | 4-[6-(2-Fluoro-4-methanesulfonyl-phenoxy)-5-methyl-pyrimidin-4-yloxy]-piperidine-1-carboxylic acid isopropyl ester |
| C128 | 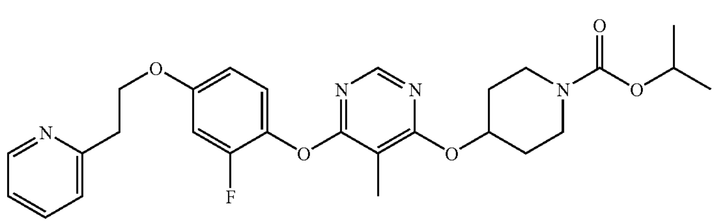 | 4-{6-[2-Fluoro-4-(2-pyridin-2-yl-ethoxy)-phenoxy]-5-methyl-pyrimidin-4-yloxy}-piperidine-1-carboxylic acid isopropyl ester |

TABLE C-continued

| Cmpd # | Structure | Chemical Name |
|---|---|---|
| C129 | 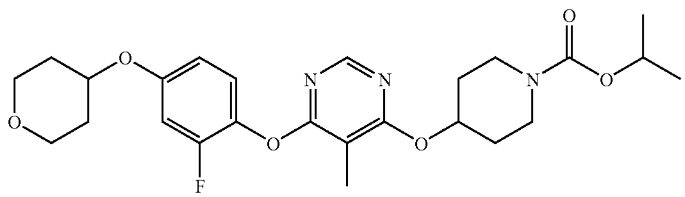 | 4-{6-[2-Fluoro-4-(tetrahydro-pyran-4-yl-oxy)-phenoxy]-5-methyl-py-rimidin-4-yloxy}-piperidine-1-carboxylic acid isopropyl ester |
| C130 | 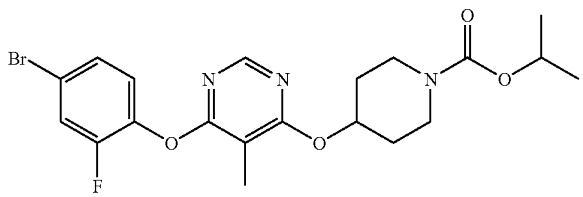 | 4-[6-(4-Bromo-2-fluoro-phenoxy)-5-methyl-pyrimidin-4-yloxy]-piperidine-1-carboxylic acid isopropyl ester |
| C131 | 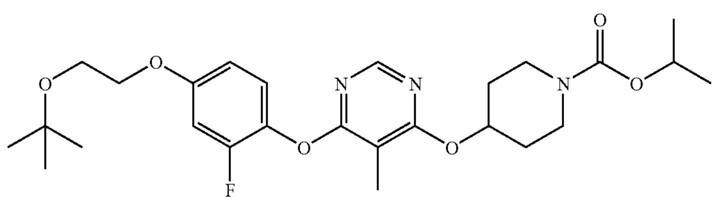 | 4-{6-[4-(2-tert-Butoxy-ethoxy)-2-fluoro-phenoxy]-5-methyl-pyrimidin-4-yloxy}-piperidine-1-carboxylic acid isopropyl ester |
| C132 | 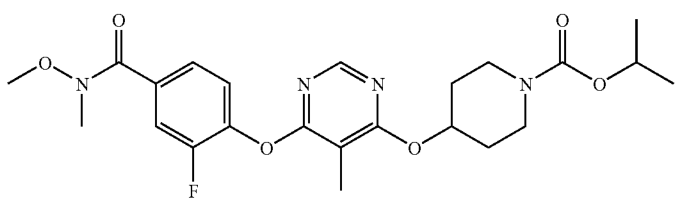 | 4-{6-[2-Fluoro-4-(methoxy-methyl-carbamoyl)-phenoxy]-5-methyl-pyrimidin-4-yloxy}-piperidine-1-carboxylic acid isopropyl ester |
| C133 | 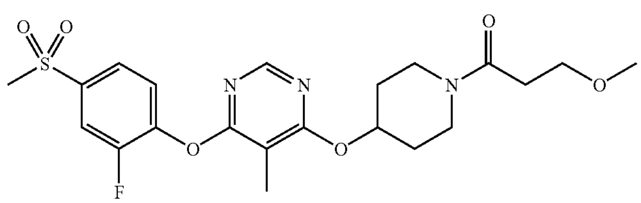 | 1-{4-[6-(2-Fluoro-4-methanesulfonyl-phenoxy)-5-methyl-pyrimidin-4-yloxy]-piperidin-1-yl}-3-methoxy-propan-1-one |
| C134 | 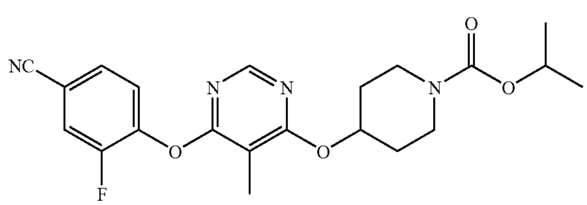 | 4-[6-(4-Cyano-2-fluoro-phenoxy)-5-methyl-pyrimidin-4-yloxy]-piperidine-1-carboxylic acid isopropyl ester |
| C135 | 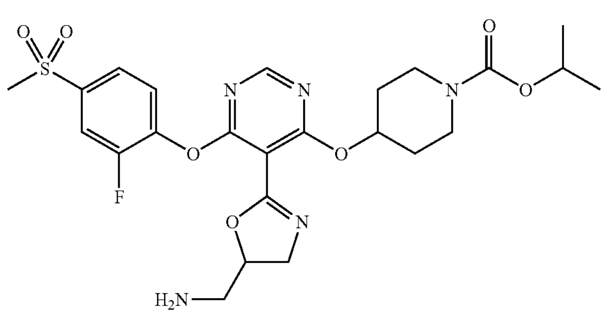 | 4-[5-(5-Aminomethyl-4,5-dihydro-oxazol-2-yl)-6-(2-fluoro-4-methanesulfonyl-phenoxy)-pyrimidin-4-yloxy]-piperidine-1-carboxylic acid isopropyl ester |

TABLE C-continued

| Cmpd # | Structure | Chemical Name |
|---|---|---|
| C136 | 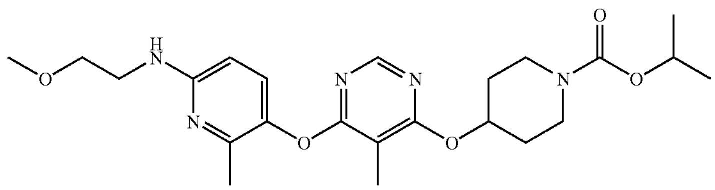 | 4-{6-[6-(2-Methoxy-ethylamino)-2-methyl-pyridin-3-yloxy]-5-methyl-pyrimidin-4-yloxy}-piperidine-1-carboxylic acid isopropyl ester |
| C137 | 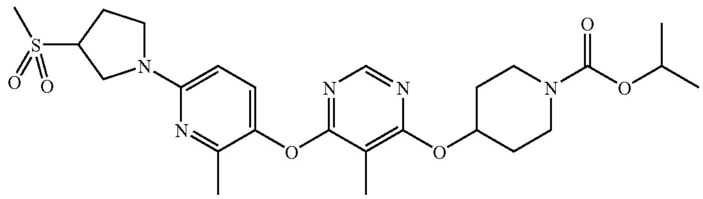 | 4-{6-[6-(3-Methanesulfonyl-pyrrolidin-1-yl)-2-methyl-pyridin-3-yloxy]-5-methyl-pyrimidin-4-yloxy}-piperidine-1-carboxylic acid isopropyl ester |
| C138 | 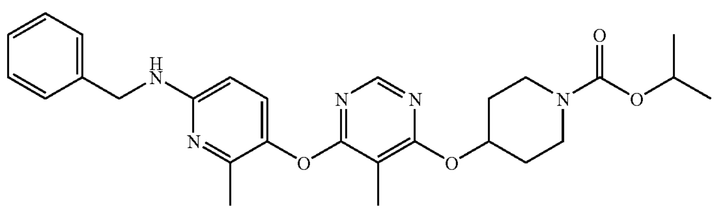 | 4-[6-(6-Benzylamino-2-methyl-pyridin-3-yloxy)-5-methyl-pyrimidin-4-yloxy]-piperidine-1-carboxylic acid isopropyl ester |
| C139 | 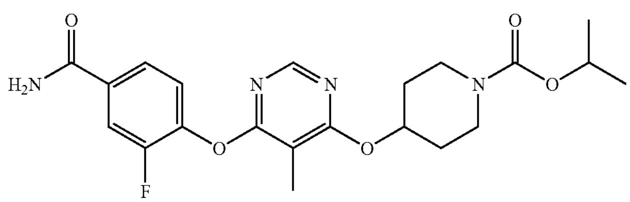 | 4-[6-(4-Carbamoyl-2-fluoro-phenoxy)-5-methyl-pyrimidin-4-yloxy]-piperidine-1-carboxylic acid isopropyl ester |
| C140 | 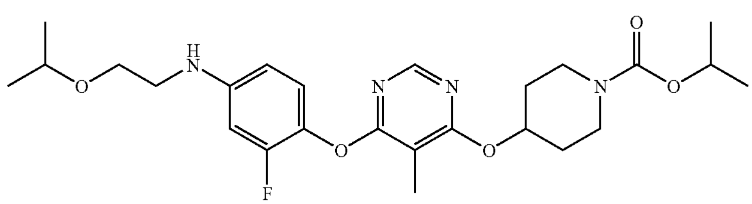 | 4-{6-[2-Fluoro-4-(2-isopropoxy-ethylamino)-phenoxy]-5-methyl-pyrimidin-4-yloxy}-piperidine-1-carboxylic acid isopropyl ester |
| C141 | 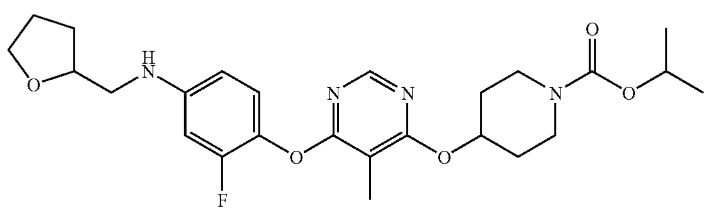 | 4-(6-{2-Fluoro-4-[(tetrahydro-furan-2-ylmethyl)-amino]-phenoxy}-5-methyl-pyrimidin-4-yloxy)-piperidine-1-carboxylic acid isopropyl ester |
| C142 | 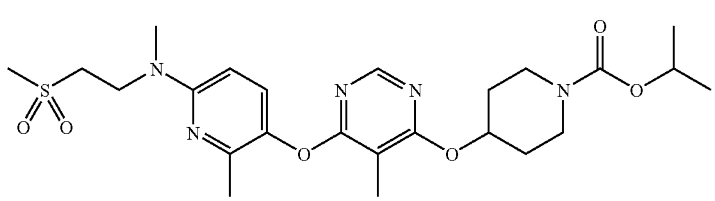 | 4-(6-{6-[(2-Methanesulfonyl-ethyl)-methyl-amino]-2-methyl-pyridin-3-yloxy}-5-methyl-pyrimidin-4-yloxy)-piperidine-1-carboxylic acid isopropyl ester |

TABLE C-continued

| Cmpd # | Chemical Name |
|---|---|
| C143 | 4-[6-(2-Fluoro-4-hydroxycarbamoyl-phenoxy)-5-methyl-pyrimidine-4-yloxy]-piperidin-1-carboxylic acid isopropyl ester |
| C144 | 4-{6-[2-Fluoro-4-(2-pyrrolidin-1-yl-ethylcarbamoyl)-phenoxy]-5-methyl-pyrimidin-4-yloxy}-piperidine-1-carboxylic acid isopropyl ester |
| C145 | 4-{6-[2-Fluoro-4-(4-isopropyl-piperazine-1-carbonyl)-phenoxy]-5-methyl-pyrimidin-4-yloxy}-piperidine-1-carboxylic acid isopropyl ester |
| C146 | 4-{6-[2-Fluoro-4-(2-morpholin-4-yl-ethyl)-phenoxy]-5-methyl-pyrimidin-4-yloxy}-piperidine-1-carboxylic acid isopropyl ester |
| C147 | 4-{6-[2-Fluoro-4-(2-methanesulfonyl-ethyl)-phenoxy]-5-methyl-pyrimidin-4-yloxy}-piperidine-1-carboxylic acid isopropyl ester |
| C148 | 4-{6-[2-Fluoro-4-(2-hydroxy-ethyl)-phenoxy]-5-methyl-pyrimidin-4-yloxy}-piperidine-1-carboxylic acid isopropyl ester |
| C149 | 4-[6-(4-Carboxylmethyl-2-fluoro-phenoxy)-5-methyl-pyrimidin-4-yloxy]-piperidine-1-carboxylic acid isopropyl ester |

TABLE C-continued

| Cmpd # | Structure | Chemical Name |
|---|---|---|
| C150 | 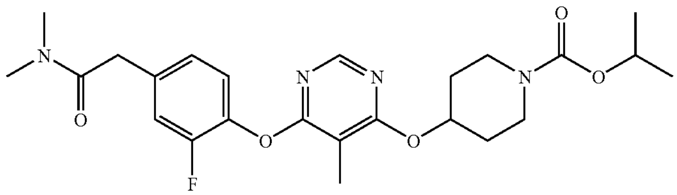 | 4-[6-(4-Dimethylcarbamoylmethyl-2-fluoro-phenoxy)-5-methyl-pyrimidin-4-yloxy]-piperidine-1-carboxylic acid isopropyl ester |
| C151 | 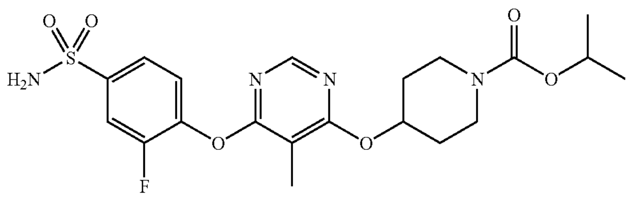 | 4-[6-(2-Fluoro-4-sulfamoyl-phenoxy)-5-methyl-pyrimidin-4-yloxy]-piperidine-1-carboxylic acid isopropyl ester |
| C152 | 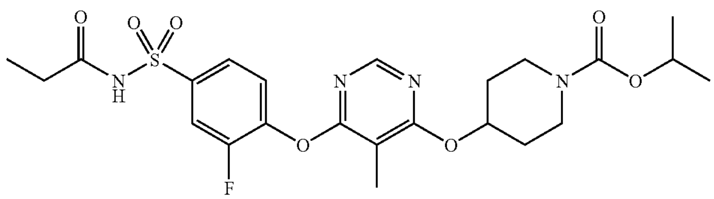 | 4-[6-(2-Fluoro-4-propionylsulfamoyl-phenoxy)-5-methyl-pyrimidin-4-yloxy]-piperidine-1-carboxylic acid isopropyl ester |
| C153 | 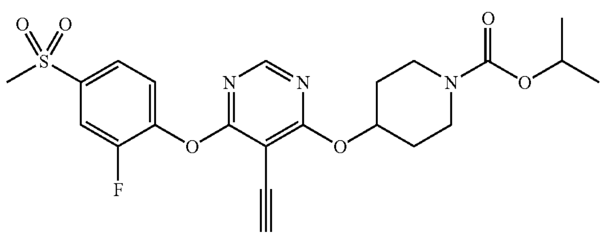 | 4-[5-Ethynyl-6-(2-fluoro-4-methanesulfonyl-phenoxy)-pyrimidin-4-yloxy]-piperidine-1-carboxylic acid isopropyl ester |
| C154 | 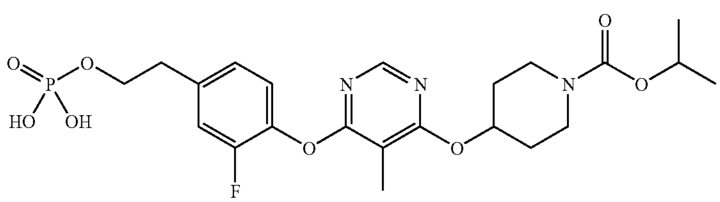 | 4-{6-[2-Fluoro-4-(2-phosphonooxy-ethyl)-phenoxy]-5-methyl-pyrimidin-4-yloxy}-piperidine-1-carboxylic acid isopropyl ester |
| C155 | 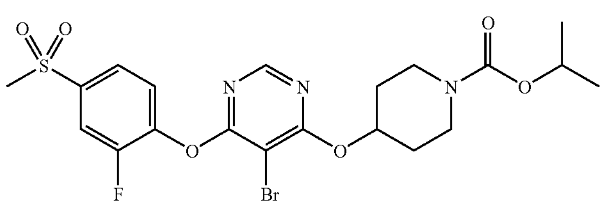 | 4-[5-Bromo-6-(2-fluoro-4-methanesulfonyl-phenoxy)-pyrimidin-4-yloxy]-piperidine-1-carboxylic acid isopropyl ester |
| C156 | 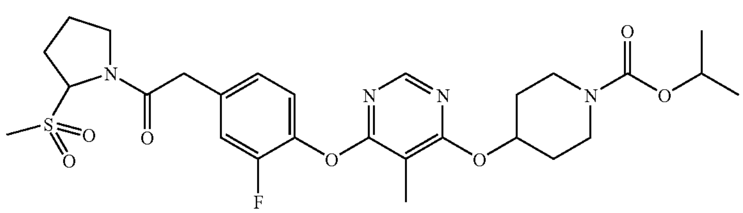 | 4-(6-{2-Fluoro-4-[2-(2-methanesulfonyl-pyrrolidin-1-yl)-2-oxo-ethyl]-phenoxy}-5-methyl-pyrimidin-4-yloxy)-piperidine-1-carboxylic acid isopropyl ester |

| Cmpd # | Structure | Chemical Name |
|---|---|---|
| C157 | 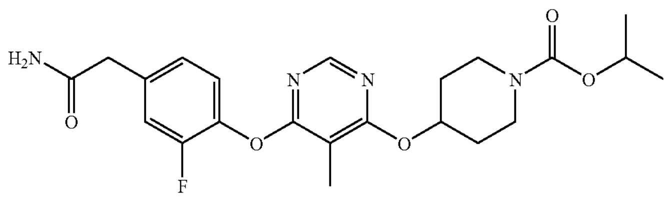 | 4-[6-(4-Carbamoylmethyl-2-fluoro-phenoxy)-5-methyl-pyrimidin-4-yloxy]-piperidine-1-carboxylic acid isopropyl ester |
| C158 | 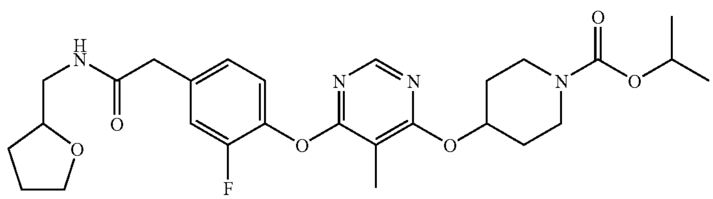 | 4-[6-(2-Fluoro-4-{[(tetrahydro-furan-2-ylmethyl)-carbamoyl]-methyl}-phenoxy)-5-methyl-pyrimidin-4-yloxy]-piperidine-1-carboxylic acid isopropyl ester |
| C159 | 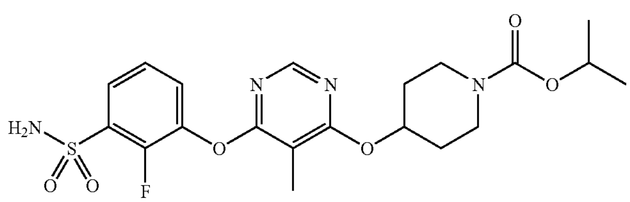 | 4-[6-(2-Fluoro-3-sulfamoyl-phenoxy)-5-methyl-pyrimidin-4-yloxy]-piperidine-1-carboxylic acid isopropyl ester |
| C160 | 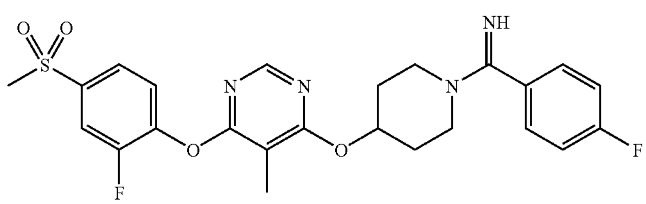 | C-{4-[6-(2-Fluoro-4-methanesulfonyl-phenoxy)-5-methyl-pyrimidin-4-yloxy]-piperidin-1-yl}-C-(4-fluoro-phenyl)-methyleneamine |
| C161 | 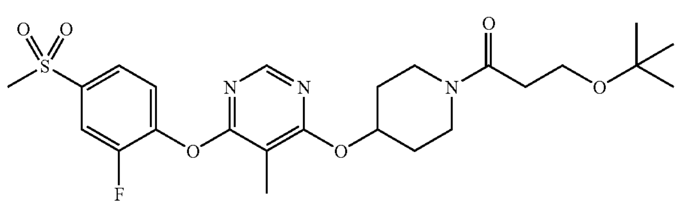 | 3-tert-Butoxy-1-{4-[6-(2-fluoro-4-methanesulfonyl-phenoxy)-5-methyl-pyrimidin-4-yloxy]-piperidin-1-yl}-propan-1-one |
| C162 | 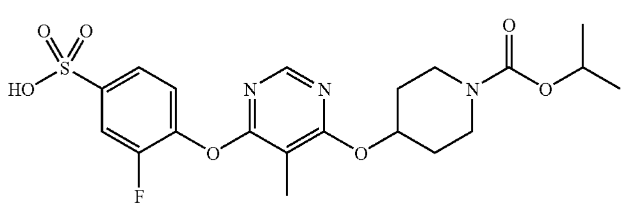 | 4-[6-(2-Fluoro-4-sulfo-phenoxy)-5-methyl-pyrimidin-4-yloxy]-piperidine-1-carboxylic acid isopropyl ester |
| C163 | 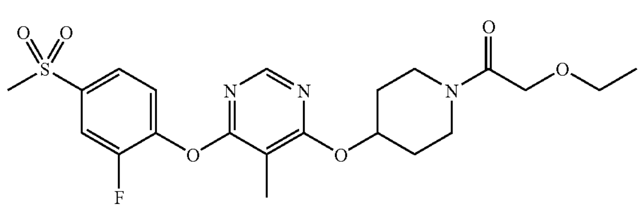 | 2-Ethoxy-1-{4-[6-(2-fluoro-4-methanesulfonyl-phenoxy)-5-methyl-pyrimidin-4-yloxy]-piperidin-1-yl}-ethanone |

TABLE C-continued

| Cmpd # | Structure | Chemical Name |
|---|---|---|
| C164 | 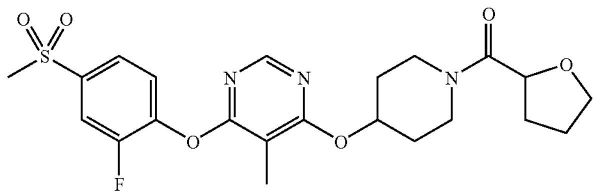 | {4-[6-(2-Fluoro-4-methanesulfonyl-phenoxy)-5-methyl-pyrimidin-4-yloxy]-piperidin-1-yl}-(tetrahydro-furan-2-yl)-methanone |
| C165 | 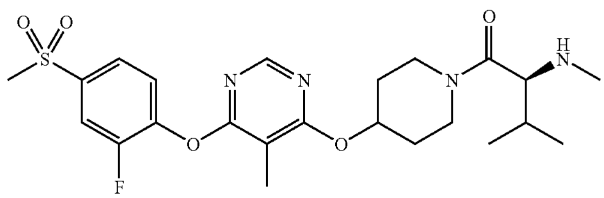 | (S)-1-{4-[6-(2-Fluoro-4-methanesulfonyl-phenoxy)-5-methyl-pyrimidin-4-yloxy]-piperidin-1-yl}-3-methyl-2-methylamino-butan-1-one |
| C166 | 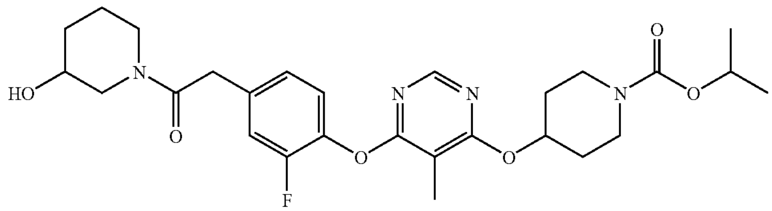 | 4-(6-{2-Fluoro-4-[2-(3-hydroxy-piperidin-1-yl)-2-oxo-ethyl]-phenoxy}-5-methyl-pyrimidin-4-yloxy)-piperidine-1-carboxylic acid isopropyl ester |
| C167 | 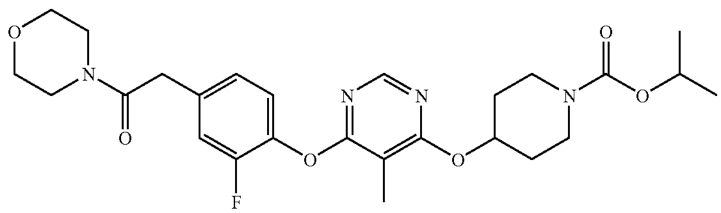 | 4-{6-[2-Fluoro-4-(2-morpholin-4-yl-2-oxo-ethyl)-phenoxy]-5-methyl-pyrimidin-4-yloxy}-piperidine-1-carboxylic acid isopropyl ester |
| C168 | 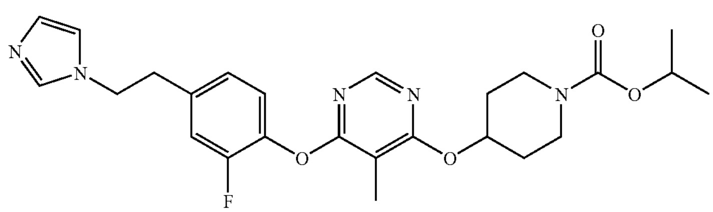 | 4-{6-[2-Fluoro-4-(2-imidazol-1-yl-ethyl)-phenoxy]-5-methyl-pyrimidin-4-yloxy}-piperidine-1-carboxylic acid isopropyl ester |
| C169 | 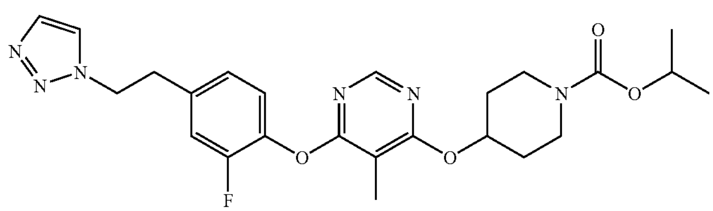 | 4-{6-[2-Fluoro-4-(2-[1,2,3]triazol-1-yl-ethyl)-phenoxy]-5-methyl-pyrimidin-4-yloxy}-piperidine-1-carboxylic acid isopropyl ester |
| C170 | 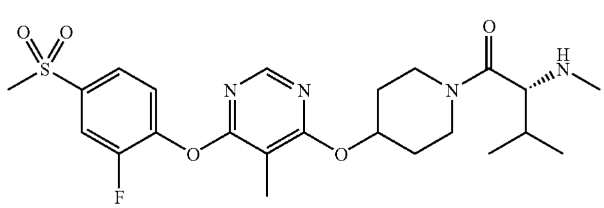 | (R)-1-{4-[6-(2-Fluoro-4-methanesulfonyl-phenoxy)-5-methyl-pyrimidin-4-yloxy]-piperidin-1-yl}-3-methyl-2-methylamino-butan-1-one |

TABLE C-continued

| Cmpd # | Structure | Chemical Name |
|---|---|---|
| C171 | 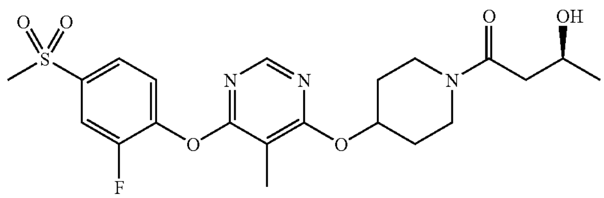 | (S)-1-{4-[6-(2-Fluoro-4-methanesulfonyl-phenoxy)-5-methyl-pyrimidin-4-yloxy]-piperidin-1-yl}-3-hydroxy-butan-1-one |
| C172 | 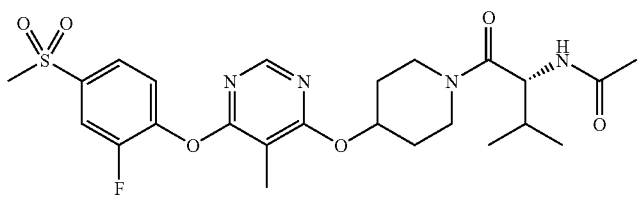 | (R)-N-(1-{4-[6-(2-Fluoro-4-methanesulfonyl-phenoxy)-5-methyl-pyrimidin-4-yloxy]-piperidine-1-carbonyl}-2-methyl-propyl)-acetamide |
| C173 | 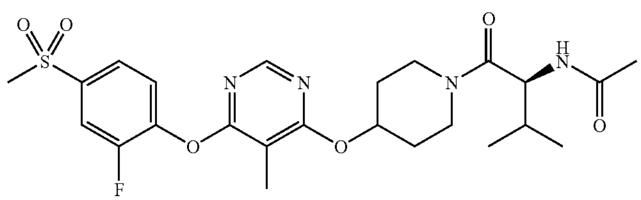 | (S)-N-(1-{4-[6-(2-Fluoro-4-methanesulfonyl-phenoxy)-5-methyl-pyrimidin-4-yloxy]-piperidine-1-carbonyl}-2-methyl-propyl)-acetamide |
| C174 | 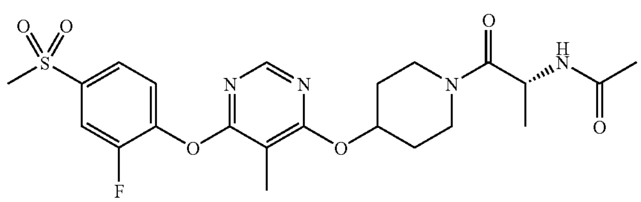 | (R)-N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide |
| C175 | 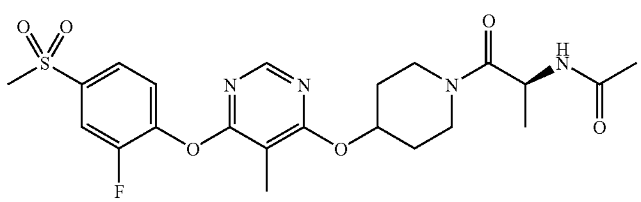 | (S)-N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide |
| C176 | 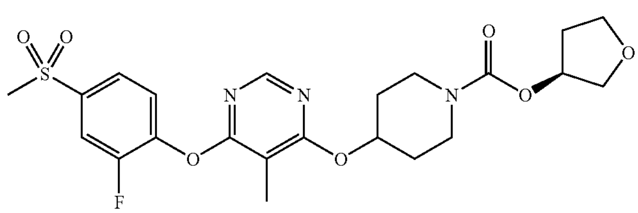 | 4-[6-(2-Fluoro-4-methanesulfonyl-phenoxy)-5-methyl-pyrimidin-4-yloxy]-piperidine-1-carboxylic acid (S)-tetrahydro-furan-3-yl ester |
| C177 | 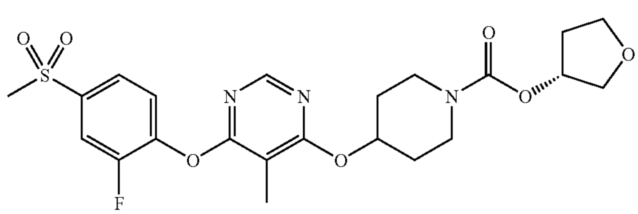 | 4-[6-(2-Fluoro-4-methanesulfonyl-phenoxy)-5-methyl-pyrimidin-4-yloxy]-piperidine-1-carboxylic acid (R)-tetrahydro-furan-3-yl ester |

TABLE C-continued

| Cmpd # | Structure | Chemical Name |
|---|---|---|
| C178 | 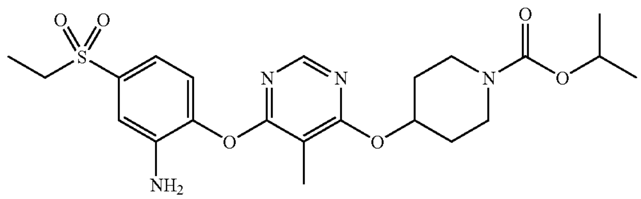 | 4-[6-(2-Amino-4-ethanesulfonyl-phenoxy)-5-methyl-pyrimidin-4-yloxy]-piperidine-1-carboxylic acid isopropyl ester |
| C179 | 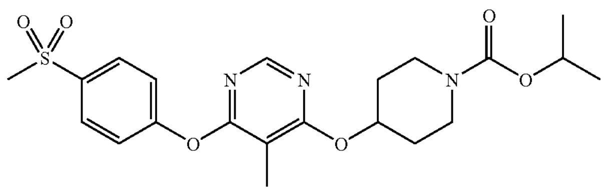 | 4-[6-(4-Methanesulfonyl-phenoxy)-5-methyl-pyrimidin-4-yloxy]-piperidine-1-carboxylic acid isopropyl ester |
| C180 | 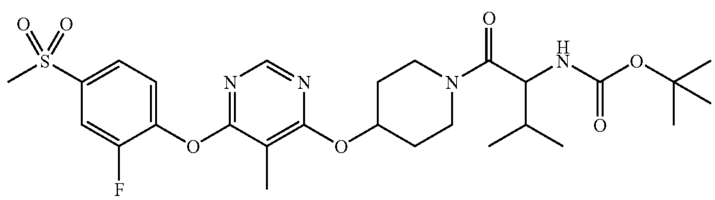 | (1-{4-[6-(2-Fluoro-4-methanesulfonyl-phenoxy)-5-methyl-pyrimidin-4-yloxy]-piperidine-1-carbonyl}-2-methyl-propyl)-carbamic acid tert-butyl ester |
| C181 | 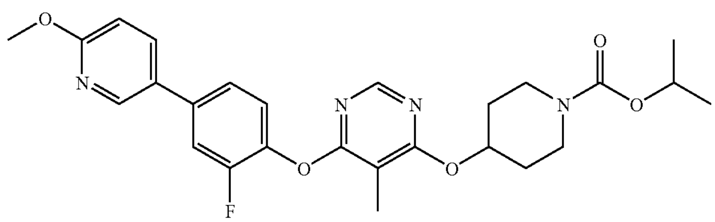 | 4-{6-[2-Fluoro-4-(6-methoxy-pyridin-3-yl)-phenoxy]-5-methyl-pyrimidin-4-yloxy}-piperidine-1-carboxylic acid isopropyl ester |
| C182 | 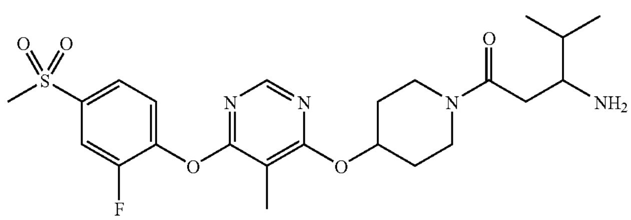 | 3-Amino-1-{4-[6-(2-fluoro-4-methanesulfonyl-phenoxy)-5-methyl-pyrimidin-4-yloxy]-piperidin-1-yl}-4-methyl-pentan-1-one |
| C183 | 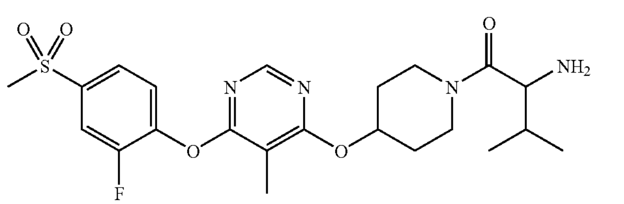 | 2-Amino-1-{4-[6-(2-fluoro-4-methanesulfonyl-phenoxy)-5-methyl-pyrimidin-4-yloxy]-piperidin-1-yl}-3-methyl-butan-1-one |
| C184 | 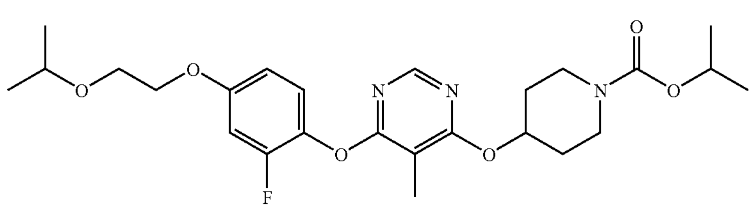 | 4-{6-[2-Fluoro-4-(2-isopropoxy-ethoxy)-phenoxy]-5-methyl-pyrimidin-4-yloxy}-piperidine-1-carboxylic acid isopropyl ester |

TABLE C-continued

| Cmpd # | Structure | Chemical Name |
|---|---|---|
| C185 | 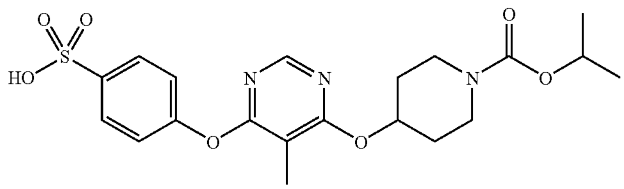 | 4-[5-Methyl-6-(4-sulfo-phenoxy)-pyrimidin-4-yloxy]-piperidine-1-carboxylic acid isopropyl ester |
| C186 | 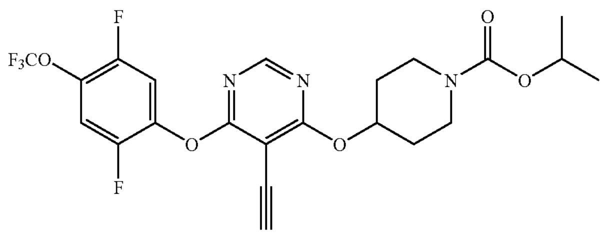 | 4-[6-(2,5-Difluoro-4-trifluoromethoxy-phenoxy)-5-ethynyl-pyrimidin-4-yloxy]-piperidine-1-carboxylic acid isopropyl ester |
| C187 | 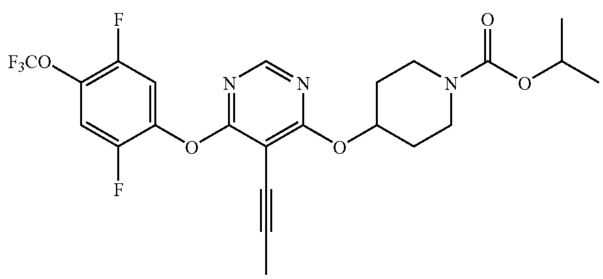 | 4-[6-(2,5-Difluoro-4-trifluoromethoxy-phenoxy)-5-prop-1-ynyl-pyrimidin-4-yloxy]-piperidine-1-carboxylic acid isopropyl ester |
| C188 | 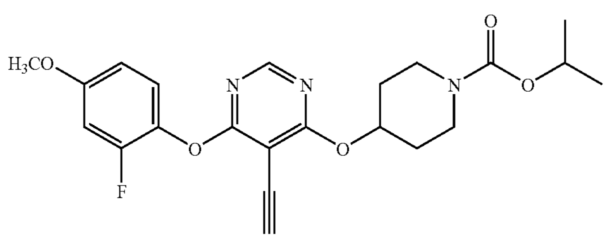 | 4-[5-Ethynyl-6-(2-fluoro-4-methoxy-phenoxy)-pyrimidin-4-yloxy]-piperidine-1-carboxylic acid isopropyl ester |
| C189 | 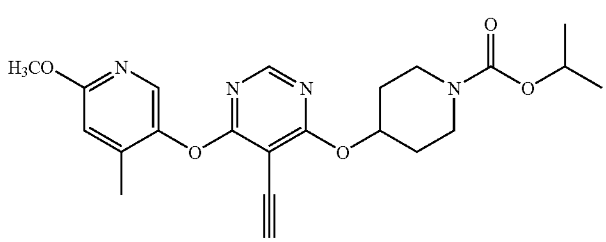 | 4-[5-Ethynyl-6-(6-methoxy-4-methyl-pyridin-3-yloxy)-pyrimidin-4-yloxy]-piperidine-1-carboxylic acid isopropyl ester |
| C190 | 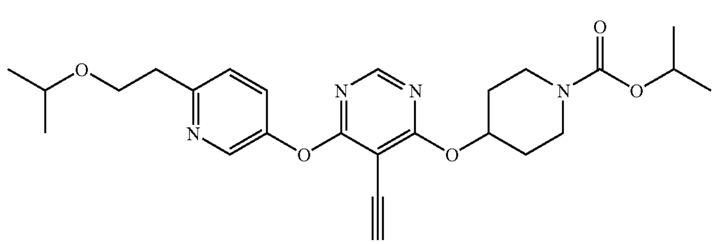 | 4-{5-Ethynyl-6-[6-(2-isopropoxy-ethyl)-2-methyl-pyridin-3-yloxy]-pyrimidin-4-yloxy}-piperidine-1-carboxylic acid isopropyl ester |

TABLE C-continued

| Cmpd # | Structure | Chemical Name |
| --- | --- | --- |
| C191 | 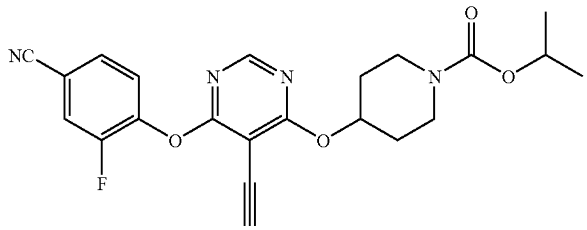 | 4-[6-(4-Cyano-2-fluoro-phenoxy)-5-ethynyl-pyrimidin-4-yloxy]-piperidine-1-carboxylic acid isopropyl ester |
| C192 | 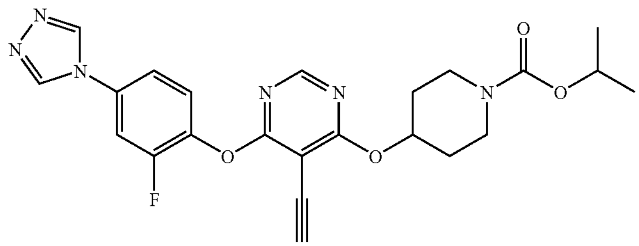 | 4-[5-Ethynyl-6-(2-fluoro-4-[1,2,4]triazol-4-yl-phenoxy)-pyrimidin-4-yloxy]-piperidine-1-carboxylic acid isopropyl ester |
| C193 | 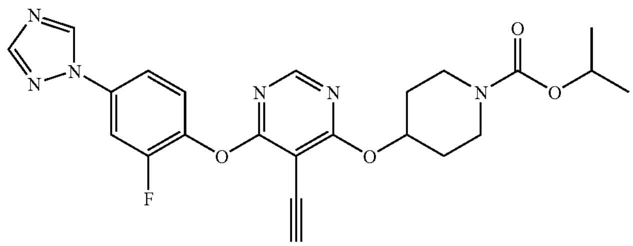 | 4-[5-Ethynyl-6-(2-fluoro-4-[1,2,4]triazol-1-yl-phenoxy)-pyrimidin-4-yloxy]-piperidine-1-carboxylic acid isopropyl ester |
| C194 | 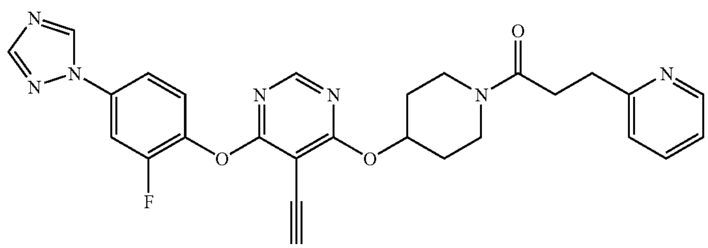 | 1-{4-[5-Ethynyl-6-(2-fluoro-4-[1,2,4]triazol-1-yl-phenoxy)-pyrimidin-4-yloxy]-piperidin-1-yl}-3-pyridin-2-yl-propan-1-one |
| C195 | 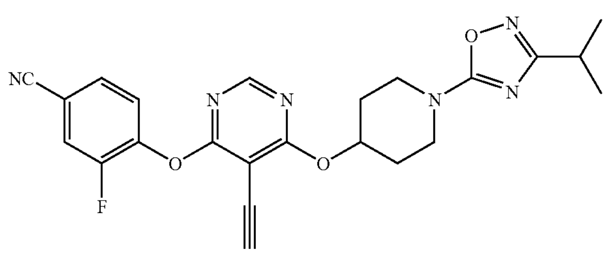 | 4-{5-Ethynyl-6-[1-(3-isopropyl-[1,2,4]oxadiazol-5-yl)-piperidin-4-yloxy]-pyrimidin-4-yloxy}-3-fluoro-benzonitrile |
| C196 | 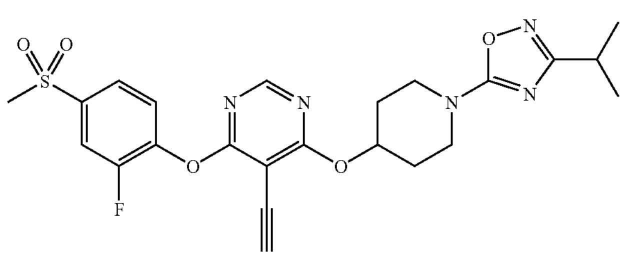 | 5-Ethynyl-4-(2-fluoro-4-methanesulfonyl-phenoxy)-6-[1-(3-isopropyl-[1,2,4]oxadiazol-5-yl)-piperidin-4-yloxy]-pyrimidine |

TABLE C-continued

| Cmpd # | Structure | Chemical Name |
|---|---|---|
| C197 | 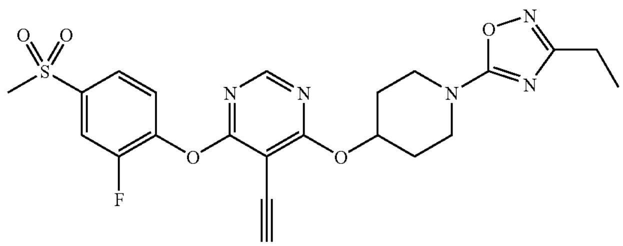 | 4-[1-(3-Ethyl-[1,2,4]oxadiazol-5-yl)-piperidin-4-yloxy]-5-ethynyl-6-(2-fluoro-4-methanesulfonyl-phenoxy)-pyrimidine |
| C198 | 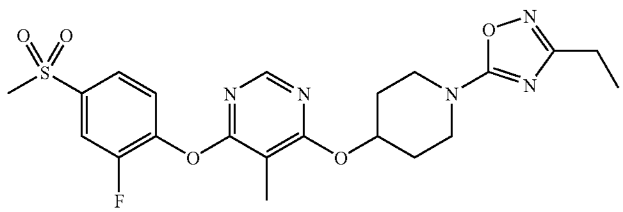 | 4-[1-(3-Ethyl-[1,2,4]oxadiazol-5-yl)-piperidin-4-yloxy]-6-(2-fluoro-4-methanesulfonyl-phenoxy)-5-methyl-pyrimidine |
| C199 | 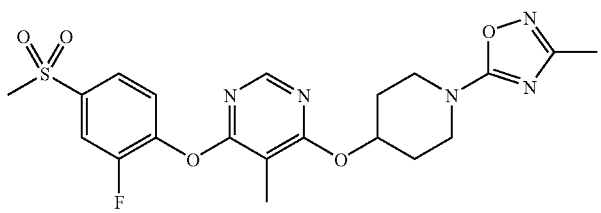 | 4-(2-Fluoro-4-methanesulfonyl-phenoxy)-5-methyl-6-[1-(3-methyl-[1,2,4]oxadiazol-5-yl)-piperidin-4-yloxy]-pyrimidine |
| C200 | 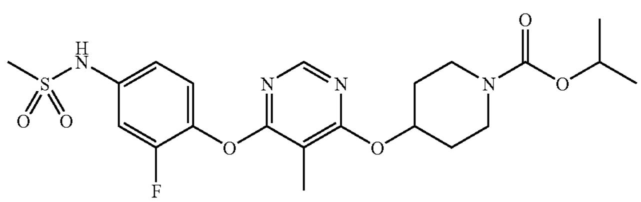 | 4-[6-(2-Fluoro-4-methanesulfonylamino-phenoxy)-5-methyl-pyrimidin-4-yloxy]-piperidine-1-carboxylic acid isopropyl ester |
| C201 | 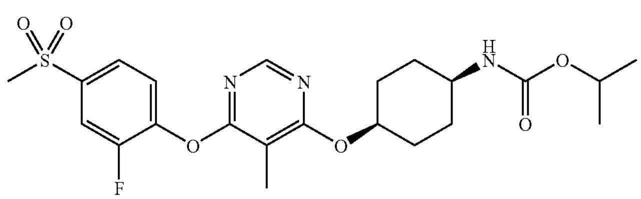 | cis-{4-[6-(2-Fluoro-4-methanesulfonyl-phenoxy)-5-methyl-pyrimidin-4-yloxy]-cyclohexyl}-carbamic acid isopropyl ester |
| C202 | 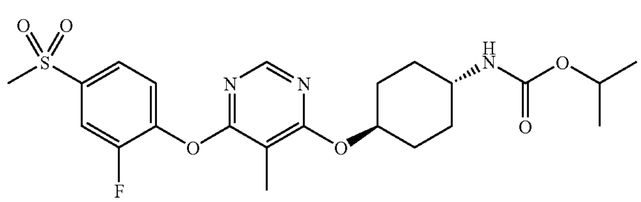 | trans-{4-[6-(2-Fluoro-4-methanesulfonyl-phenoxy)-5-methyl-pyrimidin-4-yloxy]-cyclohexyl}-carbamic acid isopropyl ester |
| C203 | 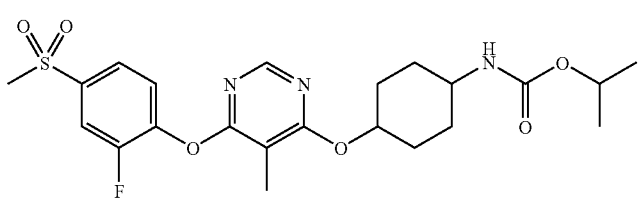 | N-{4-[6-(2-Fluoro-4-methanesulfonyl-phenoxy)-5-methyl-pyrimidin-4-yloxy]-cyclohexyl}-3-methyl-butyramide |

TABLE C-continued

| Cmpd # | Structure | Chemical Name |
| --- | --- | --- |
| C204 | 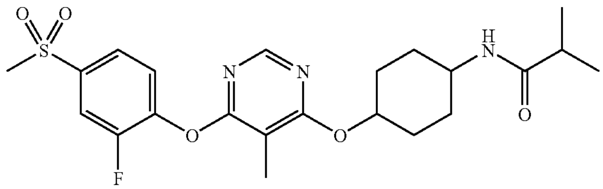 | N-{4-[6-(2-Fluoro-4-methanesulfonyl-phenoxy)-5-methyl-pyrimidin-4-yloxy]-cyclohexyl}-isobutyramide |
| C205 | 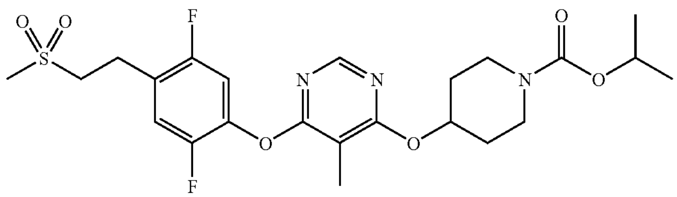 | 4-{6-[2,5-Difluoro-4-(2-methanesulfonyl-ethyl)-phenoxy]-5-methyl-pyrimidin-4-yloxy}-piperidine-1-carboxylic acid isopropyl ester |
| C206 | 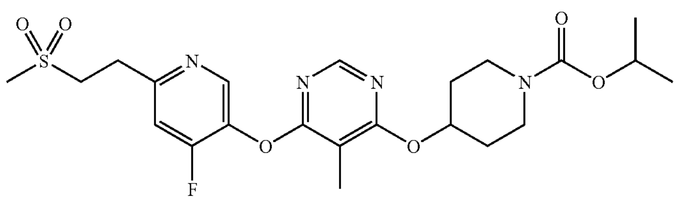 | 4-{6-[4-Fluoro-6-(2-methanesulfonyl-ethyl)-pyridin-3-yloxy]-5-methyl-pyrimidin-4-yloxy}-piperidine-1-carboxylic acid isopropyl ester |
| C207 | 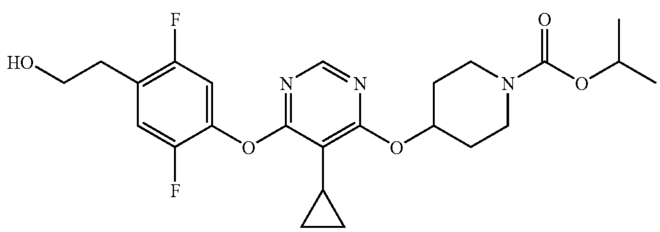 | 4-{5-Cyclopropyl-6-[2,5-difluoro-4-(2-hydroxy-ethyl)-phenoxy]-pyrimidin-4-yloxy}-piperidine-1-carboxylic acid isopropyl ester |
| C208 | 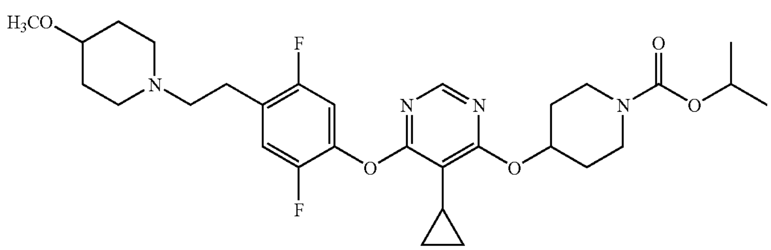 | 4-(5-Cyclopropyl-6-{2,5-difluoro-4-[2-(4-methoxy-piperidin-1-yl)-ethyl]-phenoxy}-pyrimidin-4-yloxy)-piperidine-1-carboxylic acid isopropyl ester |
| C209 | 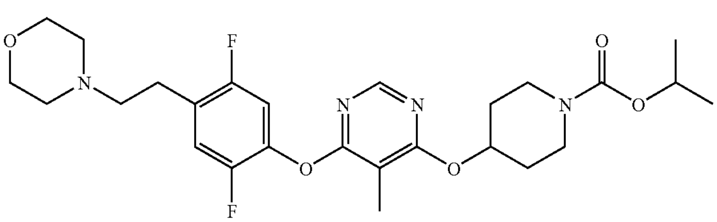 | 4-{6-[2,5-Difluoro-4-(2-morpholin-4-yl-ethyl)-phenoxy]-5-methyl-pyrimidin-4-yloxy}-piperidine-1-carboxylic acid isopropyl ester |
| C210 | 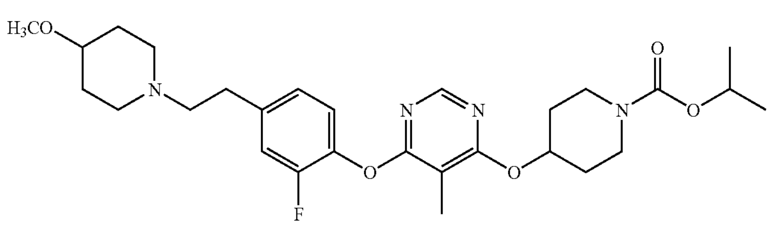 | 4-(6-{2-Fluoro-4-[2-(4-methoxy-piperidin-1-yl)-ethyl]-phenoxy}-5-methyl-pyrimidin-4-yloxy)-piperidine-1-carboxylic acid isopropyl ester |

TABLE C-continued

| Cmpd # | Structure | Chemical Name |
|---|---|---|
| C211 | 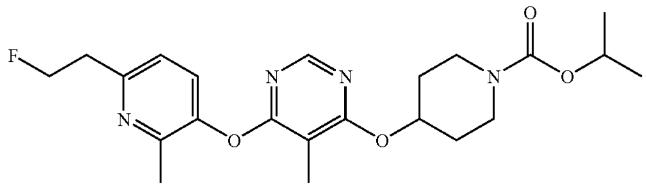 | 4-{6-[6-(2-Fluoro-ethyl)-2-methyl-pyridin-3-yloxy]-5-methyl-pyrimidin-4-yloxy}-piperidine-1-carboxylic acid isopropyl ester |
| C212 | 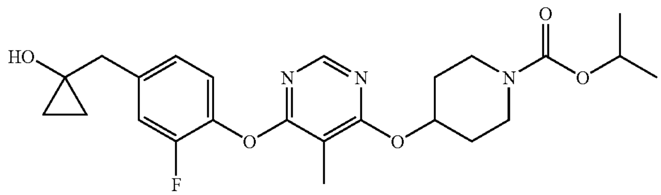 | 4-{6-[2-Fluoro-4-(1-hydroxy-cyclopropylmethyl)-phenoxy]-5-methyl-pyrimidin-4-yloxy}-piperidine-1-carboxylic acid isopropyl ester |
| C213 | 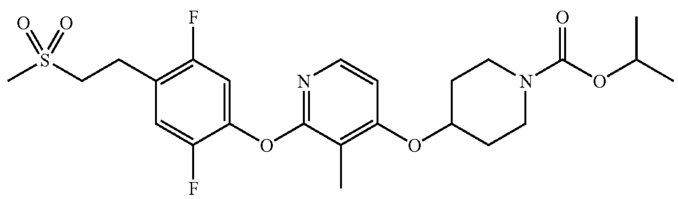 | 4-{2-[2,5-Difluoro-4-(2-methanesulfonyl-ethyl)-phenoxy]-3-methyl-pyridin-4-yloxy}-piperidine-1-carboxylic acid isopropyl ester |
| C214 | 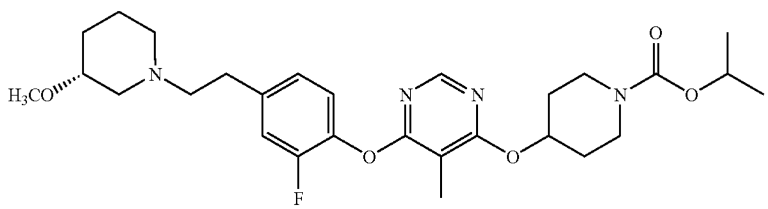 | (R)-4-(6-{2-Fluoro-4-[2-(3-methoxy-piperidin-1-yl)-ethyl]-phenoxy}-5-methyl-pyrimidin-4-yloxy)-piperidine-1-carboxylic acid isopropyl ester |
| C215 | 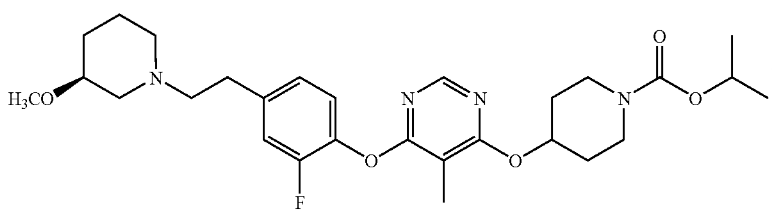 | (S)-4-(6-{2-Fluoro-4-[2-(3-methoxy-piperidin-1-yl)-ethyl]-phenoxy}-5-methyl-pyrimidin-4-yloxy)-piperidine-1-carboxylic acid isopropyl ester |
| C216 | 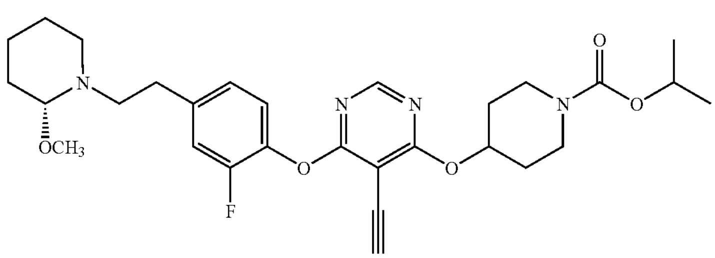 | (R)-4-(5-Ethynyl-6-{2-fluoro-4-[2-(2-methoxy-piperidin-1-yl)-ethyl]-phenoxy}-pyrimidin-4-yloxy)-piperidine-1-carboxylic acid isopropyl ester |
| C217 | 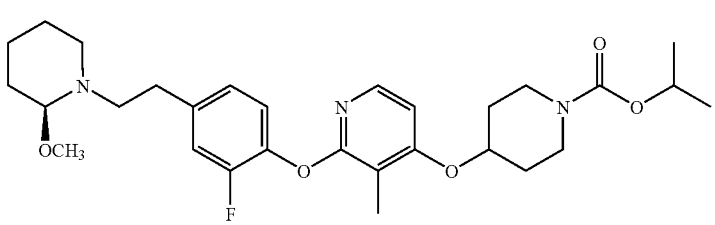 | (S)-4-(2-{2-Fluoro-4-[2-(2-methoxy-piperidin-1-yl)-ethyl]-phenoxy}-3-methyl-pyridin-4-yloxy)-piperidine-1-carboxylic acid isopropyl ester |

TABLE C-continued

| Cmpd # | Structure | Chemical Name |
|---|---|---|
| C218 | 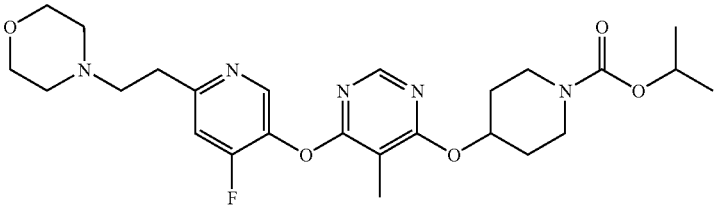 | 4-{6-[4-Fluoro-6-(2-morpholin-4-yl-ethyl)-pyridin-3-yloxy]-5-methyl-pyrimidin-4-yloxy}-piperidine-1-carboxylic acid isopropyl ester |
| C219 | 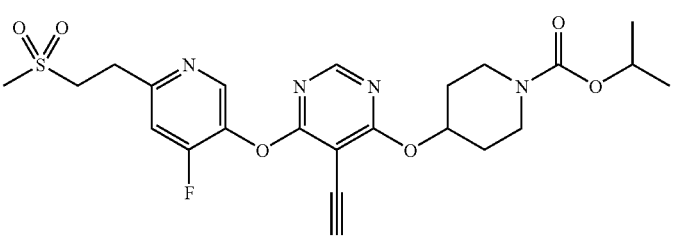 | 4-{5-Ethynyl-6-[4-fluoro-6-(2-methanesulfonyl-ethyl)-pyridin-3-yloxy]-pyrimidin-4-yloxy}-piperidine-1-carboxylic acid isopropyl ester |
| C220 | 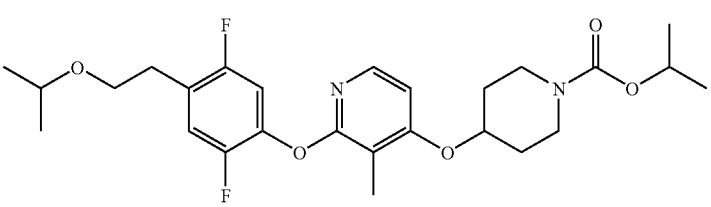 | 4-{2-[2,5-Difluoro-4-(2-isopropoxy-ethyl)-phenoxy]-3-methyl-pyridin-4-yloxy}-piperidine-1-carboxylic acid isopropyl ester |
| C221 | 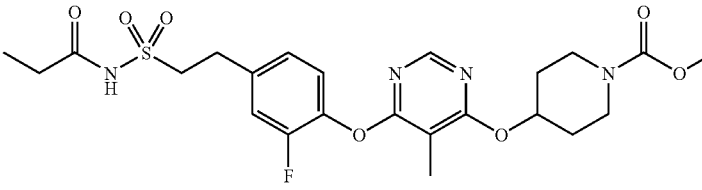 | 4-{6-[2-Fluoro-4-(2-propionylsulfamoyl-ethyl)-phenoxy]-5-methyl-pyrimidin-4-yloxy}-piperidine-1-carboxylic acid isopropyl ester |
| C222 | 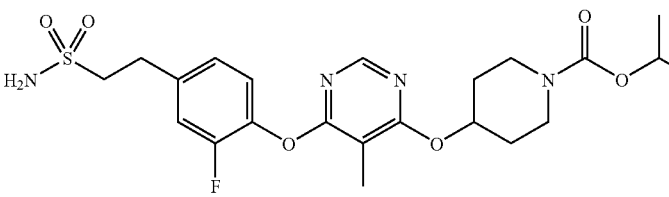 | 4-{6-[2-Fluoro-4-(2-sulfamoyl-ethyl)-phenoxy]-5-methyl-pyrimidin-4-yloxy}-piperidine-1-carboxylic acid isopropyl ester |
| C223 | 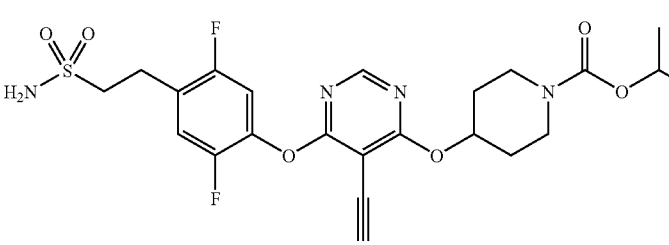 | 4-{6-[2,5-Difluoro-4-(2-sulfamoyl-ethyl)-phenoxy]-5-ethynyl-pyrimidin-4-yloxy}-piperidine-1-carboxylic acid isopropyl ester |
| C224 | 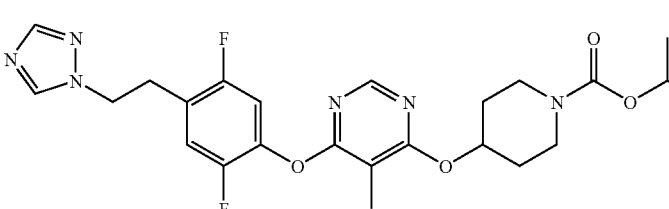 | 4-{6-[2,5-Difluoro-4-(2-[1,2,4]triazol-1-yl-ethyl)-phenoxy]-5-methyl-pyrimidin-4-yloxy}-piperidine-1-carboxylic acid isopropyl ester |

TABLE C-continued

| Cmpd # | Structure | Chemical Name |
|---|---|---|
| C225 | 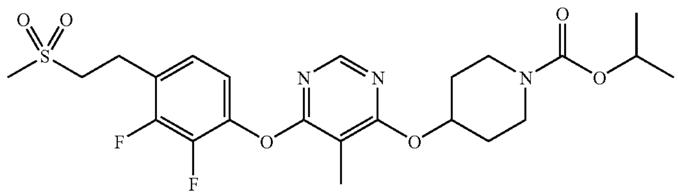 | 4-{6-[2,3-Difluoro-4-(2-methanesulfonyl-ethyl)-phenoxy]-5-methyl-pyrimidin-4-yloxy}-piperidine-1-carboxylic acid isopropyl ester |
| C226 | 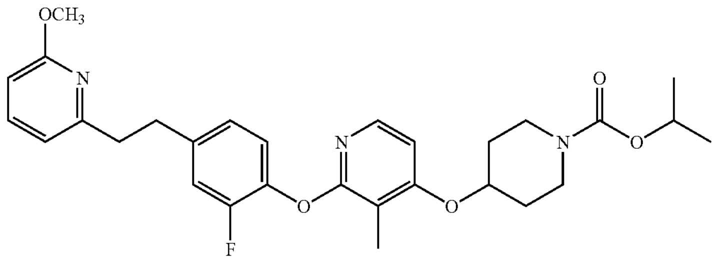 | 4-(2-{2-Fluoro-4-[2-(6-methoxy-pyridin-2-yl)-ethyl]-phenoxy}-3-methyl-pyridin-4-yloxy)-piperidine-1-carboxylic acid isopropyl ester |
| C227 | 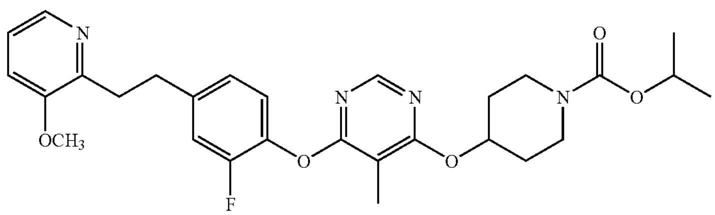 | 4-(6-{2-Fluoro-4-[2-(3-methoxy-pyridin-2-yl)-ethyl]-phenoxy}-5-methyl-pyrimidin-4-yloxy)-piperidine-1-carboxylic acid isopropyl ester |
| C228 | 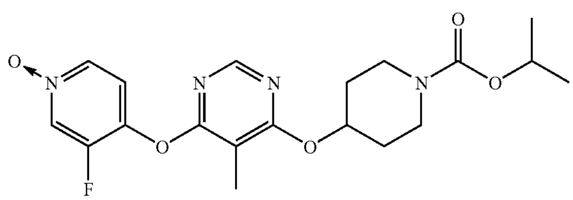 | 4-[6-(3-Fluoro-1-oxy-pyridin-4-yloxy)-5-methyl-pyrimidin-4-yloxy]-piperidine-1-carboxylic acid isopropyl ester |
| C229 | 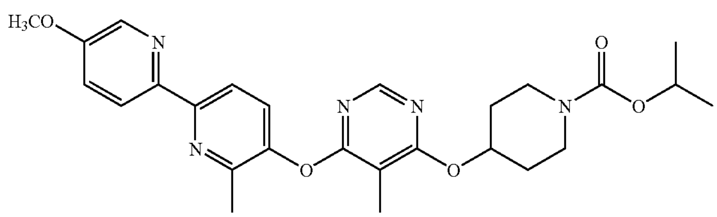 | 4-[6-(5'-Methoxy-6-methyl-[2,2']bipyridinyl-5-yloxy)-5-methyl-pyrimidin-4-yloxy]-piperidine-1-carboxylic acid isopropyl ester |
| C230 | 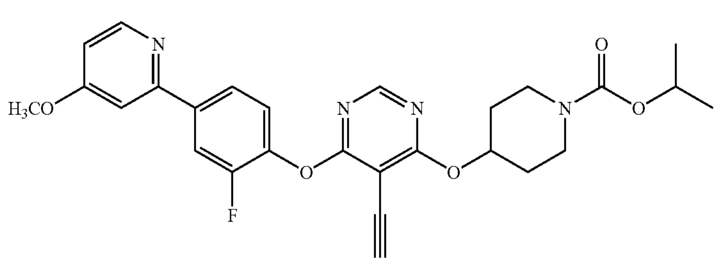 | 4-{5-Ethynyl-6-[2-fluoro-4-(4-methoxy-pyridin-2-yl)-phenoxy]-pyrimidin-4-yloxy}-piperidine-1-carboxylic acid isopropyl ester |
| C231 | 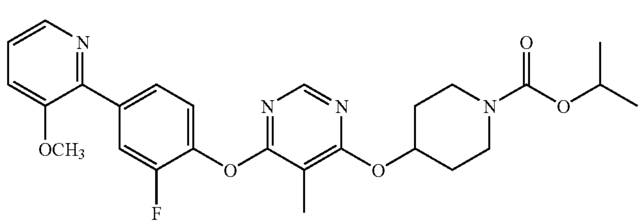 | 4-{6-[2-Fluoro-4-(3-methoxy-pyridin-2-yl)-phenoxy]-5-methyl-pyrimidin-4-yloxy}-piperidine-1-carboxylic acid isopropyl ester |

TABLE C-continued

| Cmpd # | Structure | Chemical Name |
|---|---|---|
| C232 | 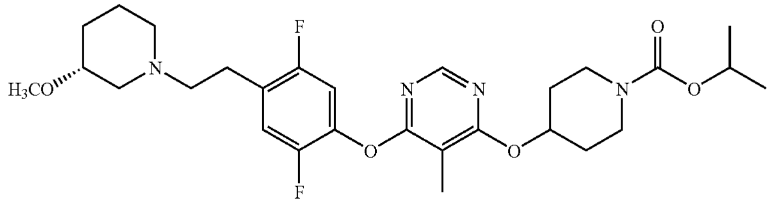 | 4-(6-{2,5-Difluoro-4-[2-(3-methoxy-piperidin-1-yl)-ethyl]-phenoxy}-5-methyl-pyrimidin-4-yloxy)-piperidine-1-carboxylic acid isopropyl ester |
| C233 | 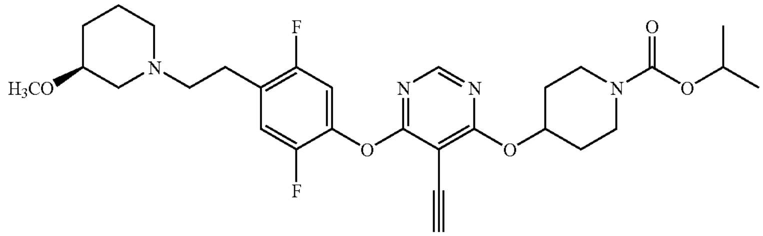 | 4-(6-{2,5-Difluoro-4-[2-(3-methoxy-piperidin-1-yl)-ethyl]-phenoxy}-5-ethynyl-pyrimidin-4-yloxy)-piperidine-1-carboxylic acid isopropyl ester |
| C234 | 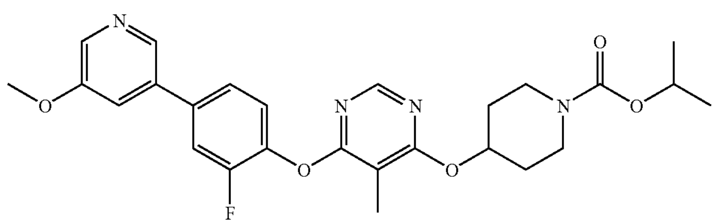 | 4-{6-[2-Fluoro-4-(5-methoxy-pyridin-3-yl)-phenoxy]-5-methyl-pyrimidin-4-yloxy}-piperidine-1-carboxylic acid isopropyl ester |
| C235 | 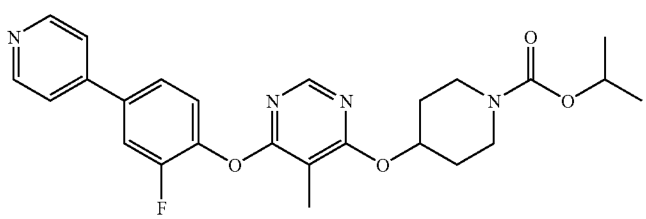 | 4-[6-(2-Fluoro-4-pyridin-4-yl-phenoxy)-5-methyl-pyrimidin-4-yloxy]-piperidine-1-carboxylic acid isopropyl ester |
| C236 | 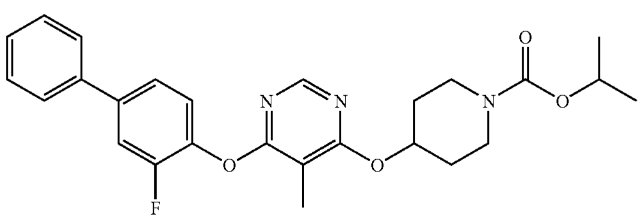 | 4-[6-(3-Fluoro-biphenyl-4-yloxy)-5-methyl-pyrimidin-4-yloxy]-piperidine-1-carboxylic acid isopropyl ester |
| C237 | 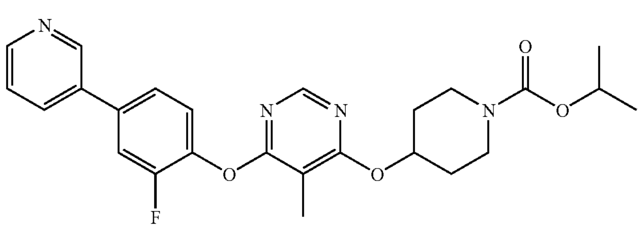 | 4-[6-(2-Fluoro-4-pyridin-3-yl-phenoxy)-5-methyl-pyrimidin-4-yloxy]-piperidine-1-carboxylic acid isopropyl ester |
| C238 | 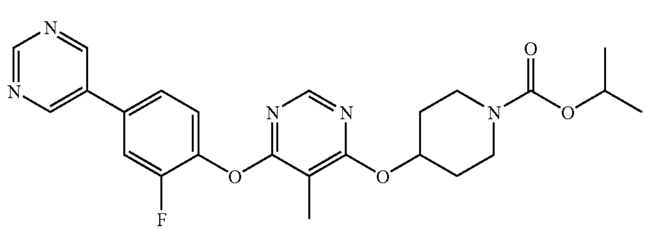 | 4-[6-(2-Fluoro-4-pyrimidin-5-yl-phenoxy)-5-methyl-pyrimidin-4-yloxy]-piperidine-1-carboxylic acid isopropyl ester |

TABLE C-continued

| Cmpd # | Structure | Chemical Name |
|---|---|---|
| C239 | 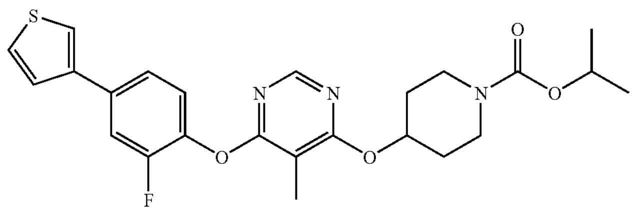 | 4-[6-(2-Fluoro-4-thiophen-3-yl-phenoxy)-5-methyl-pyrimidin-4-yloxy]-piperidine-1-carboxylic acid isopropyl ester |
| C240 | 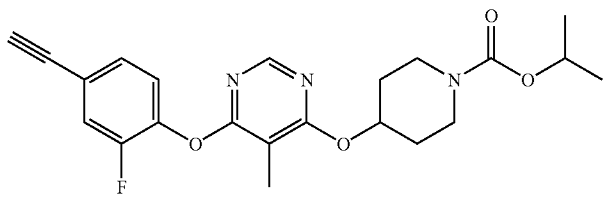 | 4-[6-(4-Ethynyl-2-fluoro-phenoxy)-5-methyl-pyrimidin-4-yloxy]-piperidine-1-carboxylic acid isopropyl ester |
| C241 | 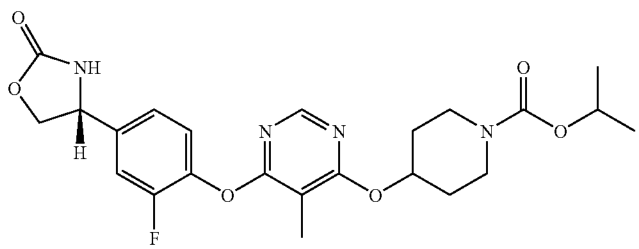 | (R)-4-{6-[2-Fluoro-4-(2-oxo-oxazolidin-4-yl)-phenoxy]-5-methyl-pyrimidin-4-yloxy}-piperidine-1-carboxylic acid isopropyl ester |
| C242 | 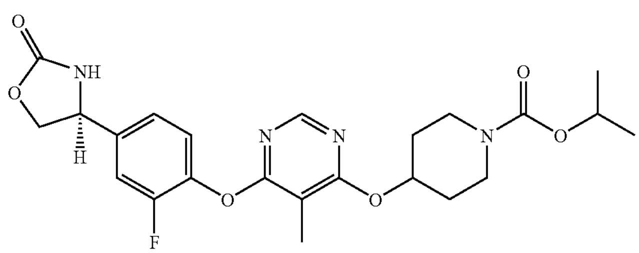 | (S)-4-{6-[2-Fluoro-4-(2-oxo-oxazolidin-4-yl)-phenoxy]-5-methyl-pyrimidin-4-yloxy}-piperidine-1-carboxylic acid isopropyl ester |

TABLE D

| Cmpd# | Structure | Chemical Name |
|---|---|---|
| D1 | 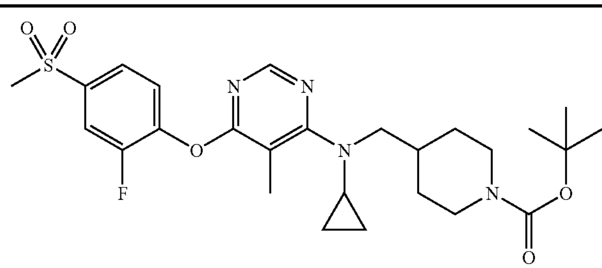 | 4-({Cyclopropyl-[6-(2-fluoro-4-methanesulfonyl-phenoxy)-5-methyl-pyrimidin-4-yl]-amino}-methyl)-piperidine-1-carboxylic acid tert-butyl ester |

TABLE D-continued

| Cmpd# | Structure | Chemical Name |
|---|---|---|
| D2 | 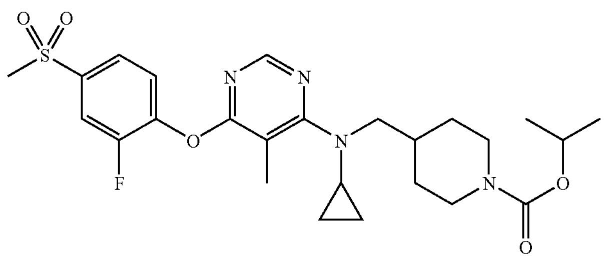 | 4-({Cyclopropyl-[6-(2-fluoro-4-methanesulfonyl-phenoxy)-5-methyl-pyrimidin-4-yl]-amino}-methyl)-piperidine-1-carboxylic acid isopropyl ester |
| D3 | 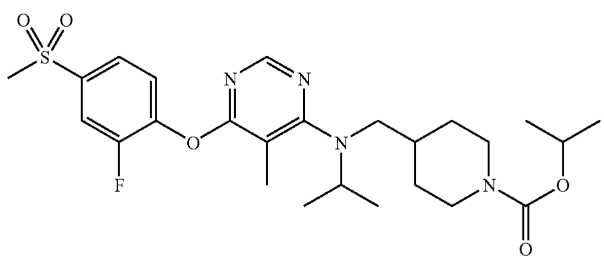 | 4-({[6-(2-Fluoro-4-methanesulfonyl-phenoxy)-5-methyl-primidin-4-yl]-isopropyl-amino}-methyl)-piperidine-1-carboxylic acid isopropyl ester |
| D4 | 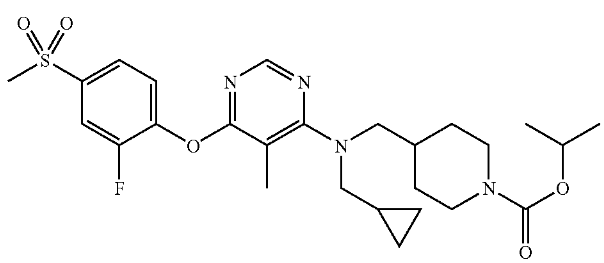 | 4-({Cyclopropylmethyl-[6-(2-fluoro-4-methanesulfonyl-phenoxy)-5-methyl-pyrimidin-4-yl]-amino}-methyl)-piperidine-1-carboxylic acid isopropyl ester |

TABLE E

| Cmpd# | Structure | Chemical Name |
|---|---|---|
| E1 | 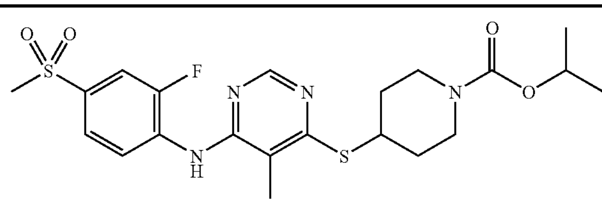 | 4-[6-(2-Fluoro-4-methanesulfonyl-phenylamino)-5-methyl-pyrimidin-4-ylsulfanyl]-piperidine-1-carboxylic acid isopropyl ester |

Additionally, compounds of the present invention encompass all pharmaceutically acceptable salts, solvates, and particularly hydrates, thereof.

General Synthetic Methods

As a result of their profound biological significance in higher eukaryotes and utilization of the pyrimidine core in a number of marketed drugs (Scheme 1) and other medicinally relevant compounds, pyrimidines and pyridines play pivotal roles as chemotypes in drug discovery campaigns. As a direct consequence of this there is a wealth of scientific literature describing synthetic construction, as well as chemical modification and elaboration of these classes of heterocycles.

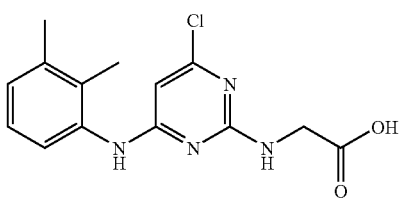

Scheme 1 aronixil 1

-continued

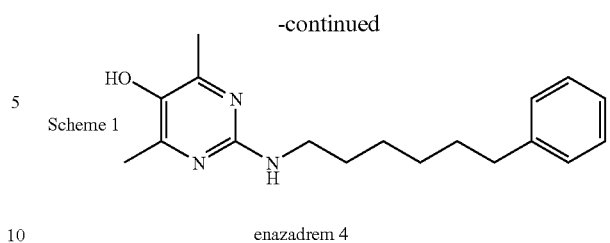

Scheme 1 enazadrem 4

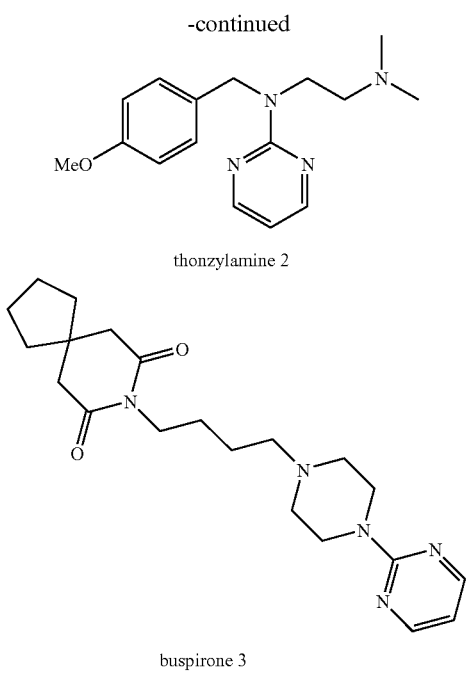

thonzylamine 2 buspirone 3

The novel substituted pyrimidines and pyridines of the present invention can be prepared according to a variety of synthetic manipulations, all of which would be familiar to one skilled in the art of synthetic organic chemistry. Certain methods for the preparation of compounds of the present invention include, but are not limited to, those described in Schemes 2-13 set forth in this section of the specification and in the Examples, infra.

Common dihalo-substituted intermediates 9.1 and 9.2, used as a starting point for the synthesis of compounds of the present invention are commercially available or can be prepared by methods know in the art, for example as depicted in Scheme 2a.

Scheme 2a

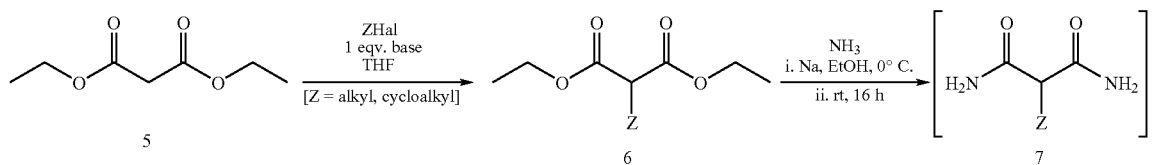

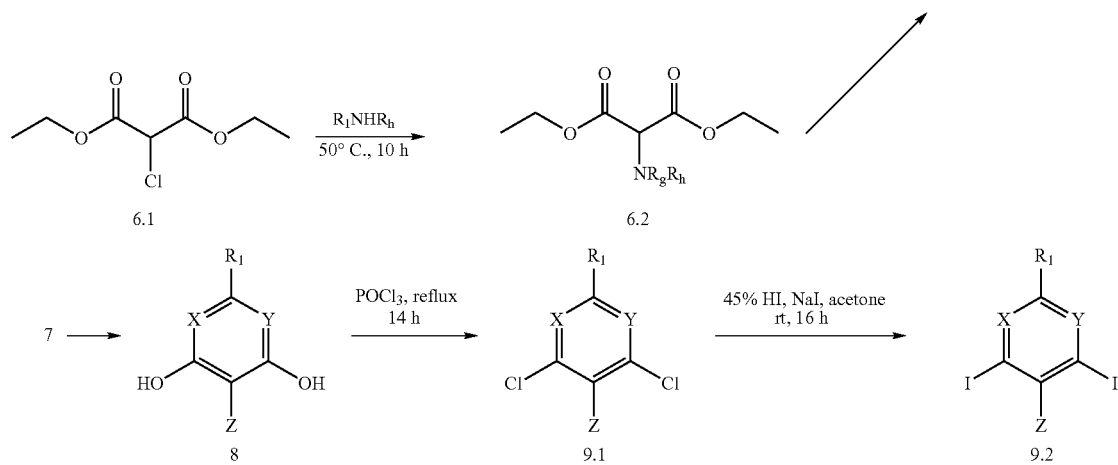

This is accomplished in two steps from a di-$C_{1-6}$-alkylmalonate, one particularly useful di-$C_{1-6}$-alkylmalonate is diethyl malonate 5. Cyclization to the C5-Z-substituted-4,6-dihydroxypyrimidine 8 is achieved via an initial alkali metal base catalysed deprotonation, alkylation strategy or via generation of the monoanion using sodium/EtOH followed by alkylation using Z-Hal, subsequent reaction of monoalkyl species 6 with formamidine in the presence of an alkali metal alkoxide, by mixing the malonate and all or part of the formamidine with the alkoxide or with the alkoxide and the rest of the formamide. Alternative reagents such as dimethylmalonate, sodium methoxide, formamide, in low molecular weight alcoholic solvents, including methanol, ethanol, 2-propanol and the like, may be utilized in the synthesis by heating at a temperature range between about 80° C. to about 100® C. for about 30 mins to about 90 mins followed by a mineral acid work up. In a preferred variation chlorinated intermediate 6.1 may be used as a starting point to obtain pyrimidines wherein alternate C5 substituents such as $R_gR_hN$ are introduced by performing thermal nucleophilic displacements. Preparation of dihydroxypyrimidines can also be achieved using microorganisms such as Rhodococcus (see for reference WO97008152 A1). An ortho metallation strategy can be utilized to facilitate C3-alkylation of the corresponding 2,4-dichloropyridyl core 15. Using n-BuLi at −78° C. under anhydrous/inert conditions followed by trapping of the resulting monoanion with an appropriate alkyl bromide or iodide (Scheme 2c) [for references see Mongin, F.; Queguiner, G. Advances in the directed metallation of azines and diazines (pyridines, pyrimidines, pyrazines, pyridazines, quinolines, benzodiazines and carbolines). Part 1: Metallation of pyridines, quinolines and carbolines. Tetrahedron (2001), 57(19), 40594090. Turck, A.; Ple, N.; Mongin, F.; Queguiner, G. Advances in the directed metalation of azines and diazines (pyridines, pyrimidines, pyrazines, pyridazines, quinolines, benzodiazines and carbolines). Part 2. Metalation of pyrimidines, pyrazines, pyridazines and benzodiazines. Tetrahedron (2001), 57(21), 4489-4505]

Chlorination of the 4 and 6 ring positions to produce intermediate 8 maybe carried out by reacting 8 with a chlorinating reagent, such as, phosgene, $POCl_3$ (for reference see A. Gomtsyan et al., J. Med. Chem. 2002, 45, 3639-3648), thionyl chloride, oxalyl chloride and by mixtures of the above reagents including $PCl_3/POCl_3$ at elevated reaction temperatures.

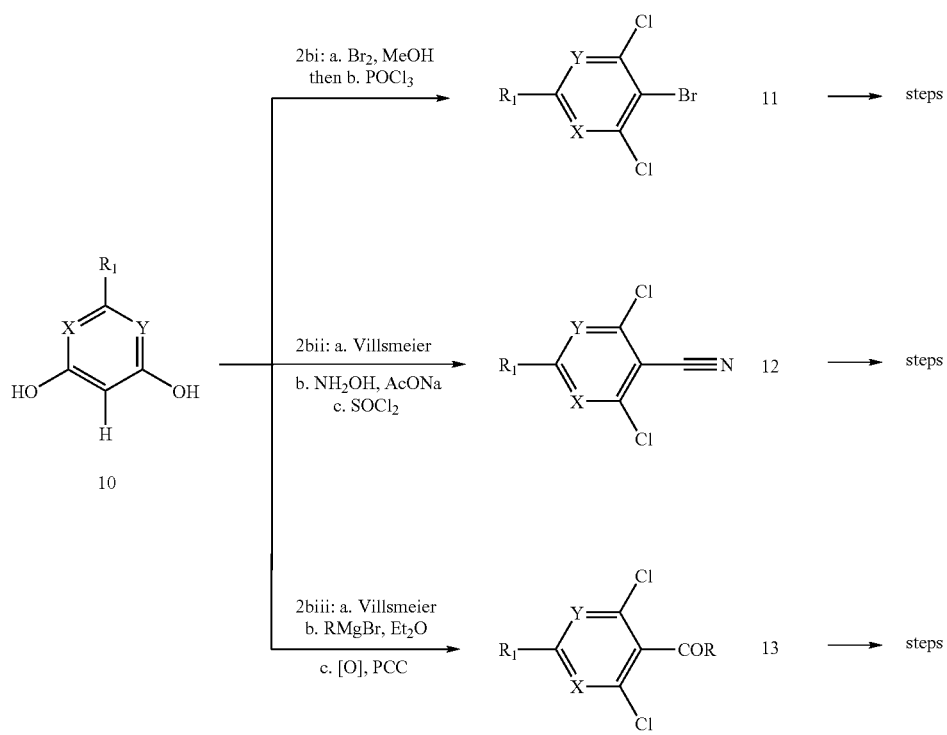

Scheme 2b

In some embodiments of the current invention alternate functionalities are required at the C5 pyrimidinyl position to achieve the desired biological outcome. Such functionality may be introduced via a broad range of organic synthetic procedures. Some examples are depicted in Scheme 2b, wherein common intermediate 10 can be converted to intermediates such as 11, 12, 13 by synthetic chemistries familiar to those in the art. Schemes 2bii and 2biii are initially reliant upon the one pot chlorinating formylation variant of the Villsmeier-Haack reaction which introduces "synthetic handles" at ring positions 3, 4 and 5 of the core simultaneously (for references see; Chlorinating formylation reactions with pyrimidines. Kloetzer, W.; Herberz, M., Monatshefte fuer Chemie (1965), 96(5), 1567-72. Also see Gontsyan et al Journal of Medicinal Chemistry, 2002, 45, 3639-3648 and references therein). Wherein Z=nitro, commercially available 2,6-dichlor-5-nitropyrimidine was utilized. Where necessary all dichloro intermediate pyrimidines (9.1, 11, 12, 13 etc) that are used as core building blocks in the present invention may be optionally converted to 4,6-diiodopyrimidines by halo exchange using sodium iodide and 45% hydroiodic acid as depicted in Scheme 2a.

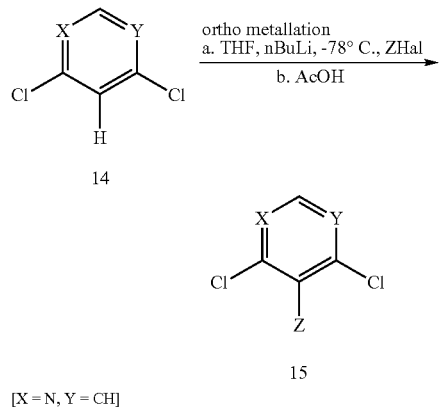

Conventional thermal aromatic substitution reactions of amines and alcohols with halogenated pyrimidines have been well documented (see for example A. G. Arvanitis et al., J. Medicinal Chemistry, 1999, 42, 805-818 and references therein). Nucleophilic aromatic ($SN_{Ar}$) substitution reactions of electron deficient halogenated pyrimidines are usually rapid and high yielding. However, in certain cases, such as electron rich or neutral halogenated heterocycles, successful substitution is afforded by prolonged heating.

To facilitate rapid entry into many of the compounds of the invention microwave synthesis was utilized (Schemes 3 and 4). The Smith synthesizer from Personal Chemistry is a commercially available focused field heating instrument that provides safer and more uniform conditions for performing the base catalyzed substitution reactions depicted in Schemes 3a, 3b and 3c. Bases employed for such conversions (whereby Q=N) include tertiary amines such as triethylamine, Hunig's base (i.e. diisopropyl-ethylamine), N-methylmorpholine and the like. Alternatively, one skilled in the art can employ alkali metal hydrides, alkali metal carbonates (such as, $Li_2CO_3$, $Na_2CO_3$, $K_2CO_3$ and the like), an alkali metal hydrogencarbonate (such as, $LiHCO_3$, $NaHCO_3$, $KHCO_3$ and the like). Wherein Q=N, inert lower alkyl alcoholic solvent can be emplyed (such as, MeOH, EtOH, i-PrOH, n-BuOH and the like) or wherein Q=O, an ethereal solvent such as tetrahydrofuran, 1,4-dioxane, and the like can be used. Reaction times to access typical monosubstituted intermediates such as, 15 and 16, can range from about 300 s to about 3000 s and when conventional thermal methods are employed (wherein Q=O) about 20 mins to about 120 mins.

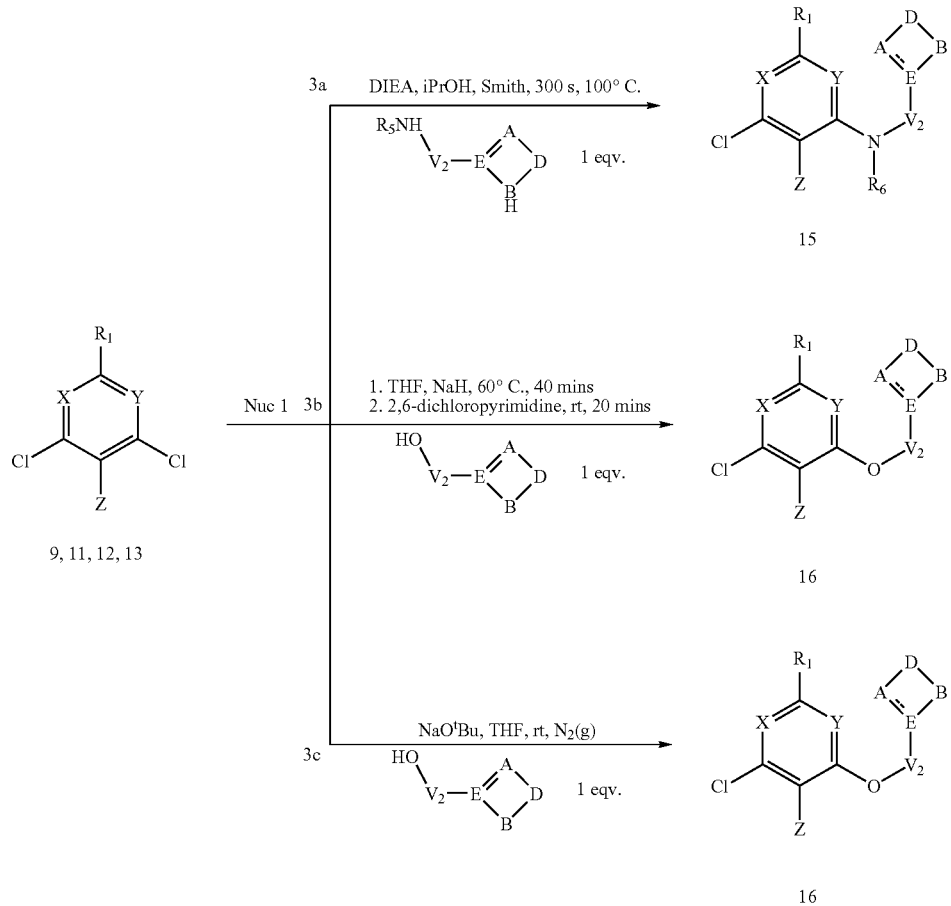

Methods for conversion of intermediate monosubstituted pyrimidines and pyridines 15 and 16 are illustrated in Scheme 4. Examples wherein Q=NR$_6$ (Schemes 4a, 4b and 4d) were obtained using palladium catalysed aminations. This synthetic strategy has emerged as a powerful tool for synthesis of substituted aryl and heteroaryl anilines in recent times (for reference see S. L. Buchwald., Top. Curr. Chem., 2002, 219, 131 and references therein). Reaction of a suitably substituted amine (such as, intermediate 17) in the presence of a palladium or alternative transition metal catalyst selected from but not limited to Pd$_2$(dba)$_3$, Pd(OAc)$_2$, CuI, Cu(OTf)$_2$, Ni(COD)$_2$, Ni(acac)$_2$ in a suitable anhydrous solvent (such as, THF, 1,4-dioxane, and the like) with as strong alkali metal alkoxide base (such as, NaO$^t$Bu, KO$^t$Bu and the like). A suitable ligand employed in this step can be selected from BINAP, P(o-tolyl)$_3$, tBu$_3$P, DPPF, P[N($^t$Bu)CH$_2$CH$_3$]$_3$N and the like when the catalyst is a palladium derived complex.

Alternatively, for "Ullman-type" aryl aminations catalysed by copper derived complexes the base employed maybe selected from an alkali metal carbonate in an aprotic polar solvent (such as N,N-dimethylacetamide, DMF, DMSO, and the like) with L-proline, N-methylglycine or diethylsalicyclamide as the ligand (for reference see D. Ma, Organic Lett., 2003, 5, 14, 2453-2455).

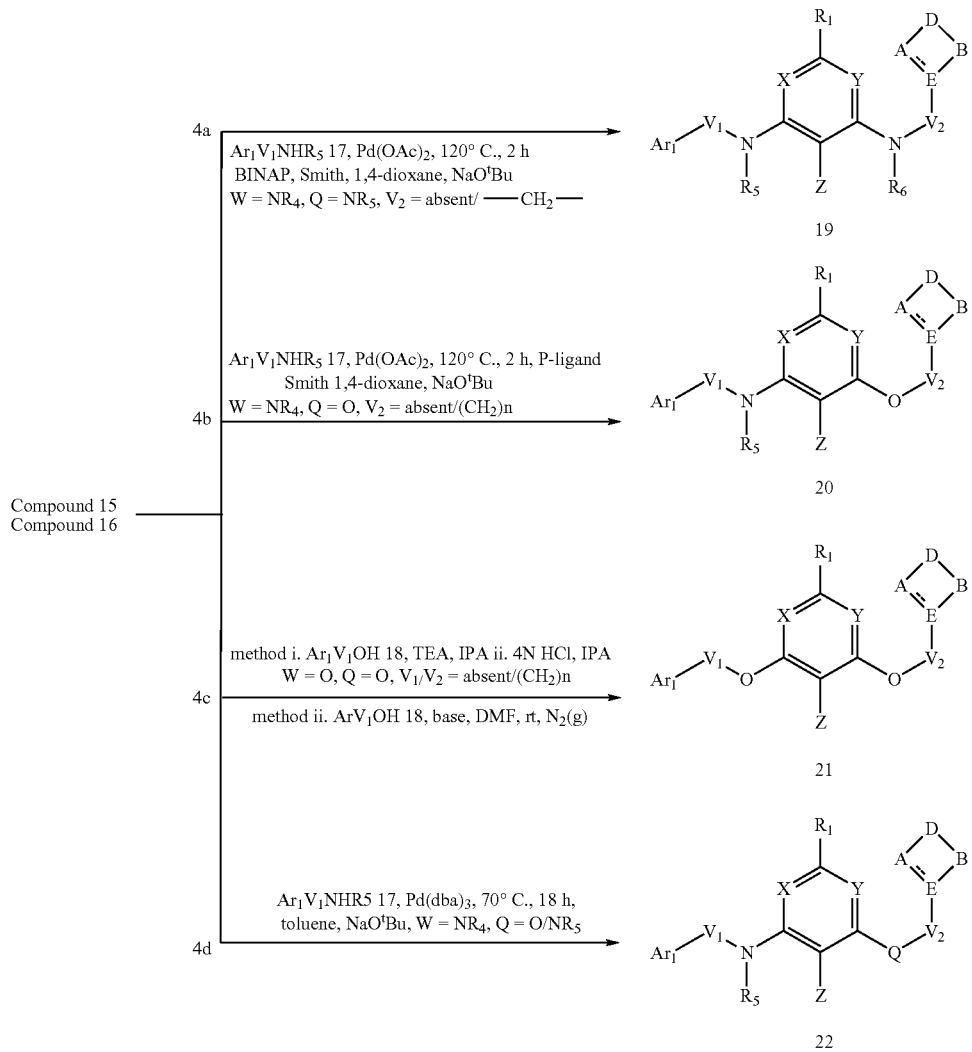

Scheme 4

Compounds of general formula 19 to 22 may also be obtained by reversing the order of the reaction steps (i.e. introduction of W followed by Q), wherein the initial step comprises of introduction of either Intermediate 17 or 18 by using base in $^i$PrOH followed by addition of 4N HCl in dioxane.

As illustrated in Scheme 5, a similar transition metal catalysed couplings were utilized to obtain molecules of general formula 24 and 27 (Scheme 5.1) wherein the Ar$_1$ substituent (Hal=Br, I) of intermediate 23 is modified to give analogs with alkyl amino substituents (i.e., NR$_a$R$_b$, wherein R$_a$ and R$_b$ are each independently H, C$_{1-6}$ alkyl or a substituted C$_{1-6}$ alkyl, or R$_a$ and R$_b$ together with the nitrogen form a heterocyclic ring, as described herein). Alternatively, the linker atom can be oxygen by utilizing the CuI catalysed method for aromatic C—O formation described by Buchwald (see for reference S. L. Buchwald; Organic Lett., 2002, 4, 6, 973-976) by utilizing, for example, 10 mol % CuI, 20 mol % 1,10-phenanthroline, 2 equivalents of $Cs_2CO_3$, at 110° C. for 18 h (Scheme 5d), with an $Ar_1$ iodo substitution in the substrate. Additional important organometallic transformations from halo intermediates 23 to active analogues of the current invention include the well know palladium catalyzed couplings of appropriately substituted aryl boronic acids via the "Suzuki coupling reaction" (Scheme 5e).

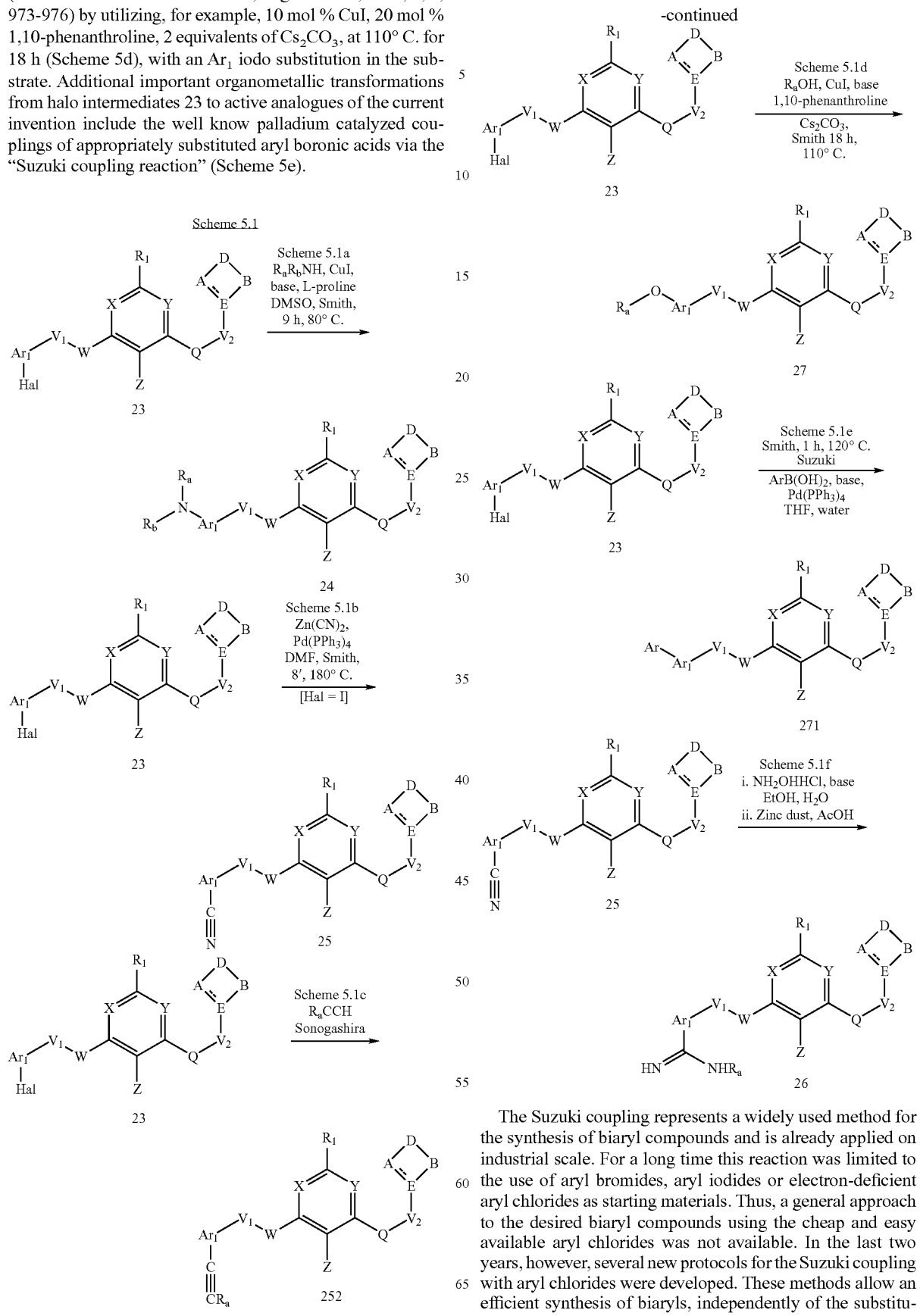

The Suzuki coupling represents a widely used method for the synthesis of biaryl compounds and is already applied on industrial scale. For a long time this reaction was limited to the use of aryl bromides, aryl iodides or electron-deficient aryl chlorides as starting materials. Thus, a general approach to the desired biaryl compounds using the cheap and easy available aryl chlorides was not available. In the last two years, however, several new protocols for the Suzuki coupling with aryl chlorides were developed. These methods allow an efficient synthesis of biaryls, independently of the substitution pattern and electronic properties of the starting materials.

These concepts which were developed by the research groups of Fu, Buchwald, Guram, Beller as well as Trudell and Nolan are highlighted in "Modern methods of the Suzuki cross coupling: the long expected general synthetic routes using aryl chlorides. Groger, Harald, Journal fuer Praktische Chemie (Weinheim, Germany) (2000), 342(4), 334-339. Alternatively additional functionality maybe introduced using other metal catalyzed transformations such as cyanation using zinc (II)cyanide under microwave irradiation conditions to obtain compounds of general formula 25 or the well documented Pd catalyzed "Sonogashira reaction" (Scheme 5c) for introduction of terminal alkynes. Most recently the Sonogashira Coupling has been described to produce almost quantitative yields of desired product using appropriate reaction conditions in the complete absence of palladium catalysts (for ref see "First Examples of Transition-Metal Free Sonogashira-Type Couplings" Leadbeater, Nicholas E.; Marco, Maria; Tominack, Bonnie J, Organic Letters (2003), 5(21), 3919-3922, and also also Transition-metal-free Sonogashira-type coupling reactions in water, Appukkuttan, Prasad; Dehaen, Wim; Van der Eycken, Erik, European Journal of Organic Chemistry (2003), (24), 4713-4716. In other preferred embodiments of the present invention, such organotransition metal chemistries may be used to introduce similar functional groups to the C5 position or the C3 position of the respective pyrimidine and pyridyl cores. For example C5 bromo or iodo intermediates may be cyanated or alkynylated as depicted in Schemes 5.2 and 5.3. Indeed, advanced nitrile derivatives of the present invention may be optionally modified via synthetic manipulations outlined in Schemes 5.1f and Schemes 5.2a-c.

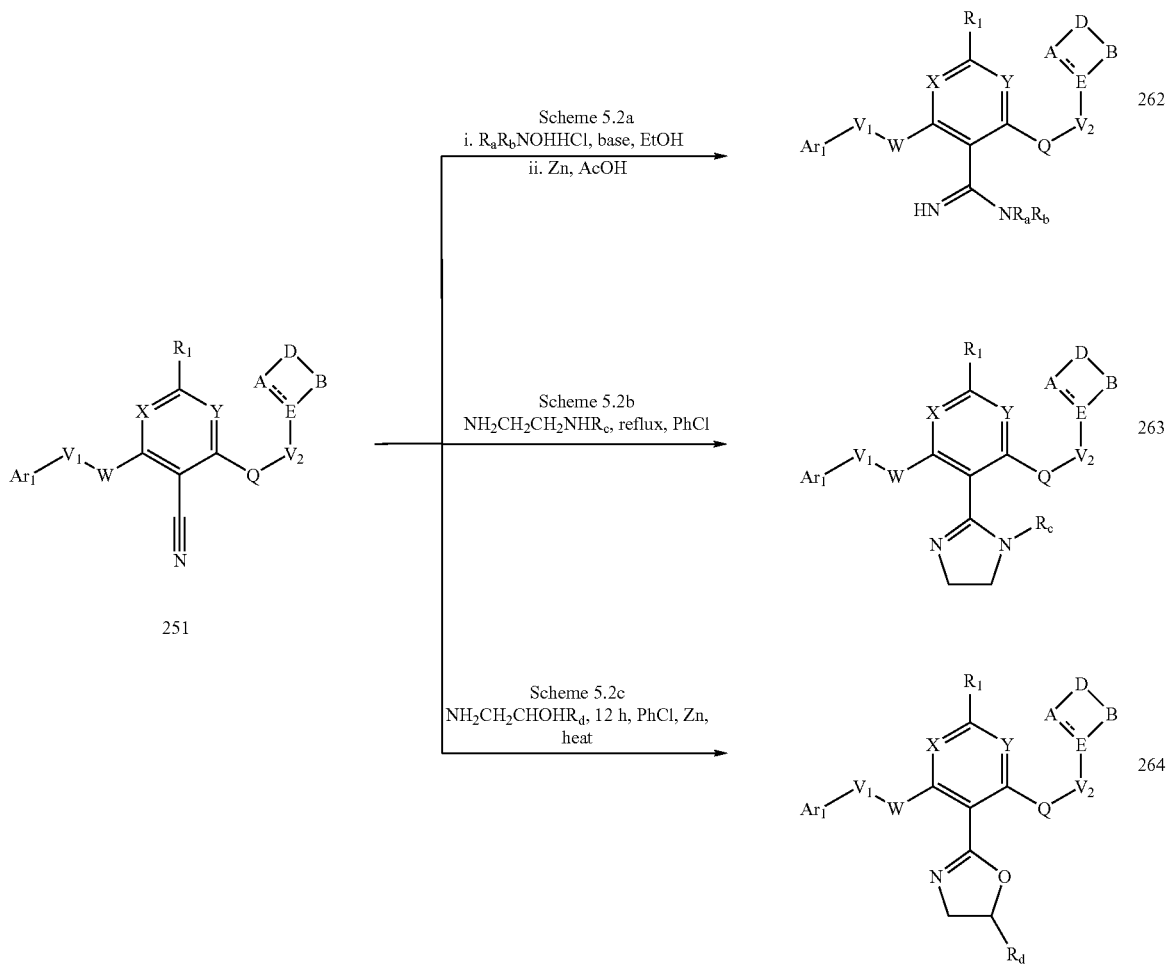

One particular embodiment is when the Hal group on Ar is located at the para position of a phenyl ring (Ar). In another particular emdodiment of the invention, the Hal group is chloro at the 2 position of a trisubstituted pyridyl moiety (intermediate 28). Organotransition metal catalysed methods for substitution of this halogen are depicted in Scheme 6.

Scheme 5.3

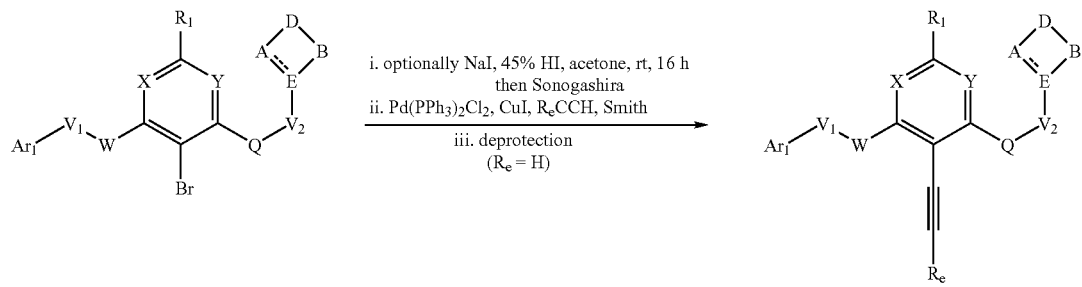

A particular substitution for compounds 19-29 is wherein D=NCOOR$_c$ wherein R$_c$ is C$_{1-6}$ alkyl, or C$_{3-7}$ cycloalkyl and each can be further substituted. Urethanes of this type can be prepared directly from intermediates depicted in Schemes 3 and 4 when D=NH. In certain reactions, use of a suitable nitrogen protecting group (such as, 'Boc, Cbz, Moz, Alloc, Fmoc and the like) may be necessary during further chemical modification of the core. Deprotection maybe achieved using standard reagents familiar to one skilled in the art (these might include TFA, mineral acid, Palladium/hydrogen gas and the like in an alcoholic or ethereal solvent system chosen from methanol, ethanol, tert-butanol, THF, 1,4-dioxane, and the like). On occasion wherein the target molecule contains 2 protecting groups, an orthogonal protection strategy may be adopted. The deprotected secondary amine (D=NH) can subsequently be modified accordingly.

Scheme 6

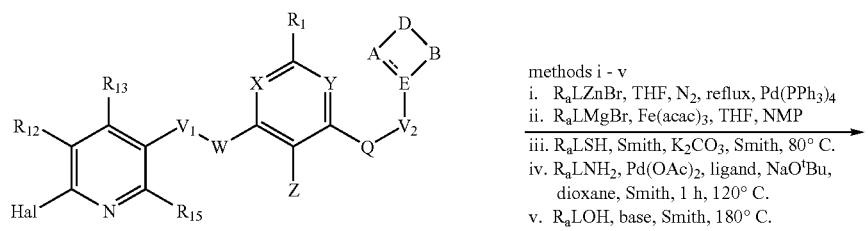

methods i - v
i. R$_a$LZnBr, THF, N$_2$, reflux, Pd(PPh$_3$)$_4$
ii. R$_a$LMgBr, Fe(acac)$_3$, THF, NMP
iii. R$_a$LSH, Smith, K$_2$CO$_3$, Smith, 80° C.
iv. R$_a$LNH$_2$, Pd(OAc)$_2$, ligand, NaO$^t$Bu, dioxane, Smith, 1 h, 120° C.
v. R$_a$LOH, base, Smith, 180° C.

28

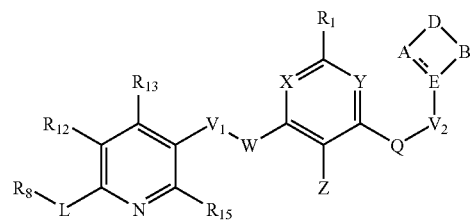

29

Schemes 7 and 8 and 9 illustrate such chemistries wherein generation of a carbamate, urea or amide can be executed using an appropriate reaction in the presence of a base, for example, a tertiary amine base such as TEA, DIEA and the like, in an inert solvent system.

As illustrated in Scheme 7, urethane 19 can be obtained by a urethane reaction using $R_cOCO$-halide (wherein $R_a$ is as described supra, and halide is chloro, bromo, or iodo, particularly useful is chloro) in an inert solvent with or without a base. Suitable bases include an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide, potassium hydroxide, and the like), a tertiary amine (such as, N,N-diisopropylethylamine, triethylamine, N-methylmorpholine, and the like), or an aromatic amine (such as, pyridine, imidazole, poly-(4-vinylpyridine), and the like). The inert solvent includes lower halocarbon solvents (such as, dichloromethane, dichloroethane, chloroform, and the like), ethereal solvents (such as, tetrahydrofuran, dioxane, and the like), aromatic solvents (such as, benzene, toluene, and the like), or polar solvents (such as, N,N-dimethylformamide, dimethyl sulfoxide, and the like). Reaction temperature ranges from about $-20°$ C. to $120°$ C., preferably about $0°$ C. to $100°$ C.

As shown in Scheme 8a, the amine intermediate obtained from acidic deprotection of 30 can be functionalized to amides represented by species 32. Carbamate 20 is first reacted with 4N HCl in dioxane or alternatively TFA in dichloromethane and further reacted with a carboxylic acid ($R_dCO_2H$, wherein as used in Scheme 8a, $R_d$ is Ar, or a $C_{1-6}$-alkylene-Ar; Ar can be substituted or unsubstituted and has the same meaning as described herein) with a dehydrating condensing agent in an inert solvent with or without a base to provide the amide 23 of the present invention. The dehydrating condensing agent includes dicyclohexylcarbodiimide (DCC), 1,3-diisopropylcarbodiimide (DIC), 1-ethyl-3-(3-dimethylaminopropyl)carbodiimide hydrochloride (EDC.HCl), bromo-tris-pyrrolidino-phosphonium hexafluorophosphate (PyBroP), benzotriazoloyloxytris (dimethylamino)-phosphonium hexafluorophosphate (BOP), O-(7-azabenzo triazol-1-yl)-1,1,3,3-tetramethyluronium hexafluorophosphate (HATU), or 1-cyclohexyl-3-methylpolystyrene-carbodiimide. The base includes a tertiary amine (such as, N,N-diisopropylethylamine, triethylamine, and the like). The inert solvent includes lower halocarbon solvents (such as, dichloromethane, dichloroethane, chloroform, and the like), ethereal solvents (such as, tetrahydrofuran, dioxane, and the like), nitrile solvents (such as, acetonitrile, and the like), amide solvents (N,N-dimethylformamide, N,N-dimethylacetamide, and the like) and mixtures thereof. Optionally, 1-hydroxybenzotriazole (HOBT), HOBT-6-carboxaamidomethyl polystyrene, or 1-hydroxy-7-azabenzotriazole (HOAT) can be used as a reactant agent. Reaction temperature ranges from about $-20°$ C. to $50°$ C., preferably about $0°$ C. to $40°$ C.

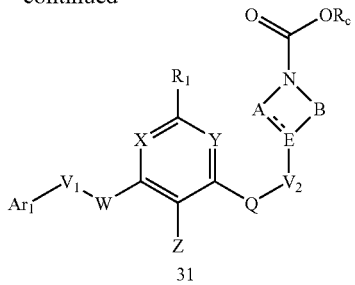

31

Scheme 7

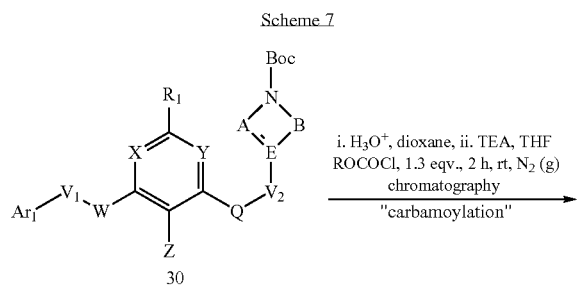

Scheme 8

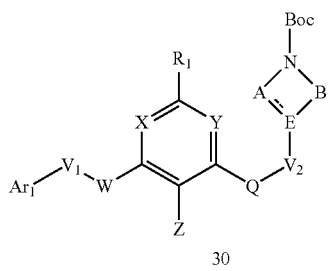

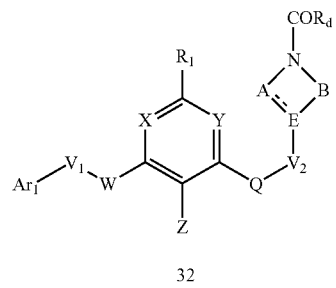

32

Reducing agent

-continued

Scheme 8b
i. H₃O⁺, dioxane ii. TEA, THF
R_d halide, 1.3 eqv., 2 h, rt, N₂ (g)
or R_d CHO / BH4⁻

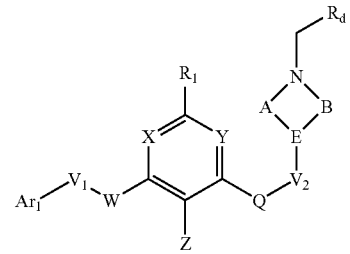

33

Alternatively, amides 32 of the present invention can be obtained by an amidation reaction using an acid halide (such as, $R_aCOCl$) and a base in an inert solvent (Scheme 8a). The base includes an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide or potassium hydroxide, and like), a tertiary amine (such as, N,N-diisopropylethylamine, triethylamine, N-methylmorpholine, and the like), or an aromatic amine (such as, pyridine, imidazole, poly-(4-vinylpyridine), and the like). The inert solvent includes lower halocarbon solvents (such as, dichloromethane, dichloroethane, chloroform, and the like), ethereal solvents (such as, tetrahydrofuran, dioxane, and the like), amide solvents (such as, N,N-dimethylacetamide, N,N-dimethylformamide, and the like), aromatic solvents (benzene, toluene, pyridine, and the like) and mixtures thereof. Reaction temperature ranges from about −20° C. to 50° C., preferably about 0° C. to 40° C.

Also illustrated in Scheme 8, amide 32 can be reacted with a reducing agent in an inert solvent to provide the amine 33 of the present invention. The reducing agent includes alkali metal aluminum hydrides (such as, lithium aluminum hydride, and the like), alkali metal borohydrides (such as, lithium borohydride, and the like), alkali metal trialkoxyaluminum hydrides (such as, lithium tri-tert-butoxyaluminum hydride, and the like), dialkylaluminum hydrides (such as, di-isobutylaluminum hydride, and the like), borane, dialkylboranes (such as, di-isoamyl borane, and the like), alkali metal trialkylboron hydrides (such as, lithium triethylboron hydride, and the like). The inert solvent includes ethereal solvents (such as, tetrahydrofuran, dioxane, and the like), aromatic solvents (such as, toluene, and the like) and mixtures thereof. Reaction temperature ranges from about −78° C. to 200° C., such as, about 50° C. to 120° C.

Alternatively, the amine 33 of the present invention can be obtained by a reductive amination reaction using the acid deprotected secondary amine intermediate with an aldehyde ($R_6CHO$) and a reducing agent in an inert solvent with or without an acid. The reducing agent includes sodium triacetoxyborohydride, sodium cyanoborohydride, sodium borohydride, borane-pyridine complex, and the like. The inert solvent includes lower alkyl alcohol solvents (such as, methanol, ethanol, and the like), lower halocarbon solvents (such as, dichloromethane, dichloroethane, chloroform, and the like), ethereal solvents (such as, tetrahydrofuran, dioxane, and the like), aromatic solvents (such as, benzene, toluene, and the like) and mixtures thereof. The acid includes an inorganic acid (such as, hydrochloric acid, sulfuric acid, and the like) or an organic acid (such as, acetic acid, and the like).

Reaction temperature ranges from about −20° C. to 120° C., preferably about 0° C. to 100° C. In addition, this reaction can optionally be carried out under microwave conditions.

In an alternative manner, the intermediate amine product of acid deprotection of 30 can be alkylated directly with an alkylating agent, such as $R_6$-halide (wherein $R_6$ is substituted or unsubstituted $C_{1-6}$ alkyl, or substituted or unsubstituted $C_{1-6}$ alkyl-Ar, and halide is chloro, bromo and iodo), in the presence of a base and in an inert solvent to provide amine 33. The base includes an alkali metal carbonate (such as, sodium carbonate, potassium carbonate, and the like), an alkali metal hydride (such as, sodium hydride, potassium hydride, and the like), alkali metal alkoxide (such as, potassium tert-butoxide, sodium tert-butoxide, and the like); alkyl lithiums (such as, tert-butyl lithium, n-butyl lithium and the like). The inert solvents include, ethereal solvents (such as, tetrahydrofuran, dioxane), aromatic solvents (such as, benzene, toluene, and the like), amide solvents (such as, N,N-dimethylformamide, and the like) and mixtures thereof. Reaction temperature ranges from about −20° C. to 120° C., preferably about 0° C. to 100° C.

Also shown in Scheme 8 is the preparation of additional compounds of the invention via alkylating the nitrogen of ureas represented by 32 with an alkyl-halide (wherein halide is chloro, bromo and iodo) in the presence of a base in an inert solvent to provide di-substituted urea. The base includes an alkali metal hydride (such as, sodium hydride, potassium hydride, and the like), alkali metal alkoxide (such as, potassium tert-butoxide, sodium tert-butoxide, and the like); alkyl lithiums (such as, tert-butyl lithium, n-butyl lithium and the like). The inert solvents include, ethereal solvents (such as, tetrahydrofuran, dioxane), aromatic solvents (such as, benzene, toluene, and the like), amide solvents (such as, N,N-dimethylformamide, and the like) and mixtures thereof. Reaction temperature ranges from about −20° C. to 120° C., preferably about 0° C. to 100° C.

In addition, as illustrated in Scheme 9a, urea 34 can be obtained from deprotecting common intermediate 30 and allowing the amine (i.e., D=NH) to react with a variety isocyanates ($R_aNCO$, wherein $R_a$ has the same meaning as described herein) in an inert solvent with or without a base. Suitable bases include an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide, potassium hydroxide, and the like), a tertiary amine (such as, N,N-diisopropylethylamine, triethylamine, N-methylmorpholine, and the like), or an aromatic amine (such as, pyridine, imidazole, and the like). The inert solvent includes lower halocarbon solvents (such as, dichloromethane, dichloroethane, chloroform, and the like), ethereal solvents (such as, tetrahydrofuran, dioxane, and the like), aromatic solvents (such as, benzene, toluene, and the like), or polar solvents (such as, N,N-dimethylformamide, dimethyl sulfoxide, and the like). Reaction temperature ranges from about −20° C. to 120° C., preferably about 0° C. to 100° C.

mol % N,N'-dimethylethylenediamine in DMSO by the method of Wang et al (see for reference Wang Z.; Baskin J. M., Org. Lett., 2002, 4, 25, 4423-4425). In some embodiments, $R_{10}$ and $R_{13}$ are each independently H, halogen, or $C_{1-6}$ alkyl; $R_{11}$ and $R_{12}$ are both H; Hal=Br, I; and Q1=OH, or $NH_2$.

Scheme 9

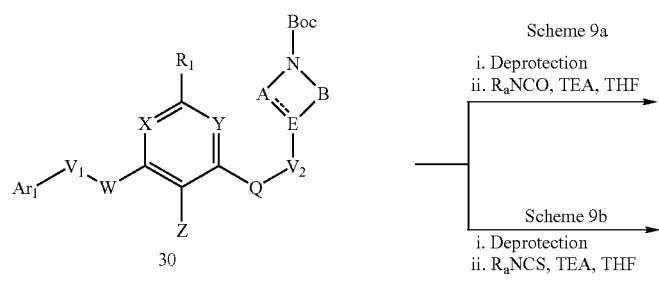
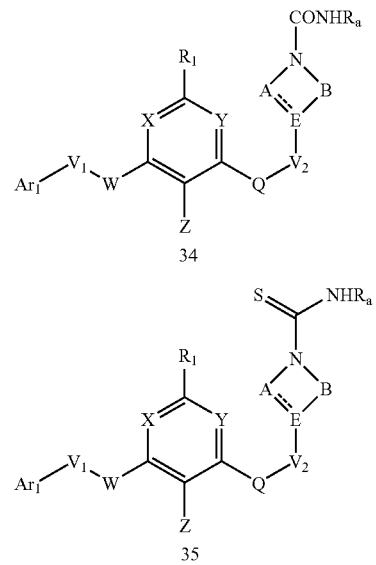

Further, as illustrated in Scheme 9b, thiourea 35 can be obtained from deprotecting common intermediate 30 and allowing the amine (i.e., D=NH) to react with a variety thioisocyanates ($R_aNCS$, wherein $R_a$ has the same meaning as described herein) in an inert solvent with or without a base. Suitable bases include an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide, potassium hydroxide, and the like), a tertiary amine (such as, N,N-diisopropylethylamine, triethylamine, N-methylmorpholine, and the like), or an aromatic amine (such as, pyridine, imidazole, and the like). The inert solvent includes lower halocarbon solvents (such as, dichloromethane, dichloroethane, chloroform, and the like), ethereal solvents (such as, tetrahydrofuran, dioxane, and the like), aromatic solvents (such as, benzene, toluene, and the like), or polar solvents (such as, N,N-dimethylformamide, dimethyl sulfoxide, and the like). Reaction temperature ranges from about −20° C. to 120° C., preferably about 0° C. to 100° C.

Scheme 10 illustrates the synthesis of para-alkyl sulfones (37) which are used as aryl building blocks in Scheme 4 of the present invention, wherein $R_{10}$-$R_{13}$ have the same meaning as described herein. The common methods for preparing these sulfones include the oxidation of sulfides or the sulfonylation of arenes using aryl sulfonyl halides or aryl sulfonic acids in the presence of a strong acid catalyst (see for general reference: the Organic Chemistry of Sulfur; Oae S., Ed.; Plenum Press: New York, 1977). Optimal conversion to the optionally 2,5-disubstituted arene 37 was achieved thermally wherein Hal is preferably iodo using 5 mol % $(CuOTf)_2 \cdot PhH$ and 10

Scheme 10

Alternative standard organic synthetic methods may be used to introduce alternate substituents in to the Ar component. In one example wherein the linker atom is Q=N, the manipulation maybe carried out by protecting the aniline amino functionality using standard FmocCl and CbzCl protection deprotection steps familiar to one skilled in the art (Scheme 11, wherein $R_{10}$-$R_{13}$ have the same meaning as described herein) and subsequently using the deprotected aniline in subsequent steps such as those depicted in Scheme 4. Nitrile 39, maybe alternatively transformed in to amidines (see Table of compounds) by using hydroxylamine HCl followed by reduction using zinc/acetic acid. In some embodiments of the invention $R_{10}$ is halogen, and $R_{13}$ is H or halogen.

Scheme 11

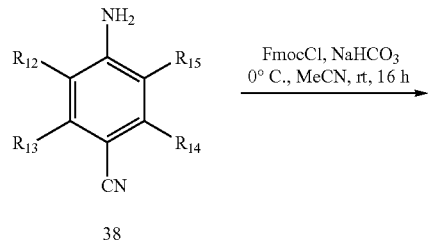

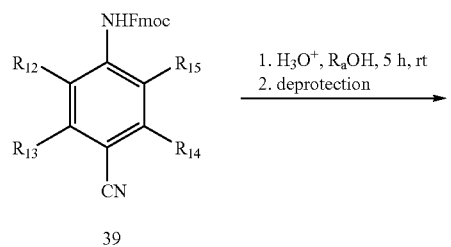

Synthetic scheme 11.1, depicts some of organic synthetic strategies of the current invention for accessing advanced aromatic building blocks required for use in scheme 4c wherein $R_{10}$-$R_{13}$ are preferably halogen, alkoxy or short alkyl. Following incorporation in to analogues of the present invention via methodologies depicted in scheme 4c, intermediates such as those of type 38.3 may be deprotected through use of suitable silyl deprotection agents such as TBAF or HF. Resulting terminal alcohols may be optionally further modified (for ref see T. Matsui et al., Biorg. Med. Chem, 10, 2002, 3787).

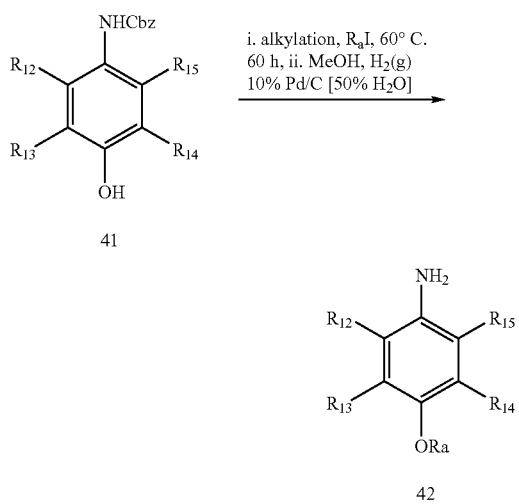

Scheme 11.1

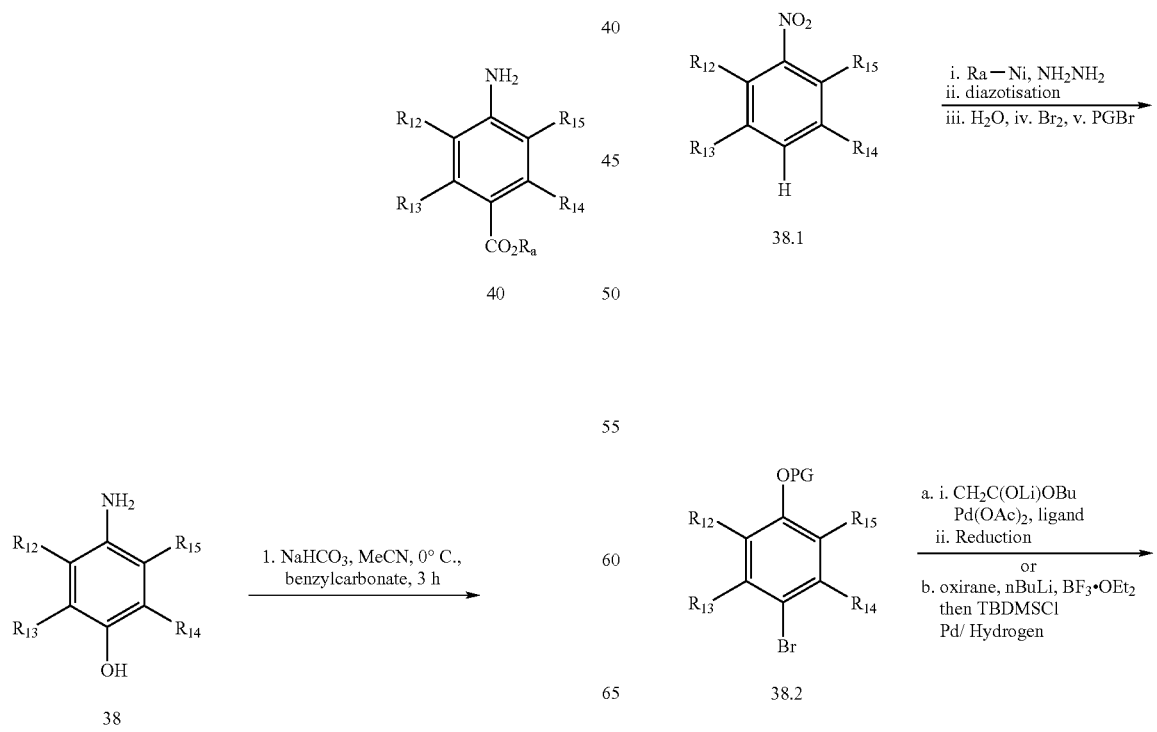

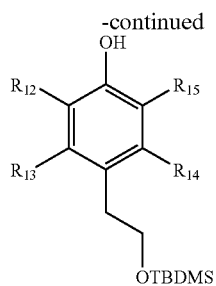
38.3
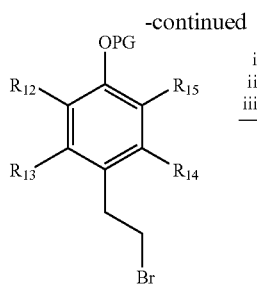
38.5
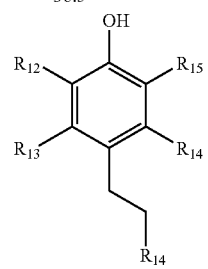
38.5
Scheme 11.2
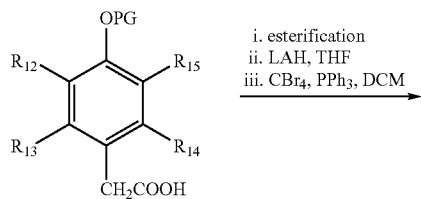
38.4
Synthesis of the 3,5-oxadiazolo variant is depicted in Scheme 12. Zinc(II)chloride catalyzed coupling of amidoxime 44 with 4-hydroxypiperidine, CNBr derived 46 yielded building block 47 after acidic workup, which was subsequently utilized in reaction sequences depicted as illustrated in Scheme 3.
Scheme 12
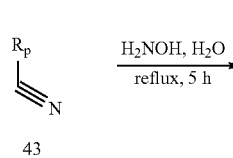
43
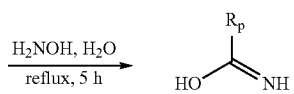
44
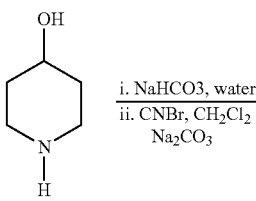
45
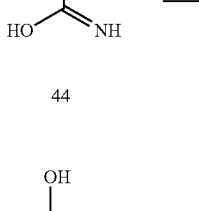
46
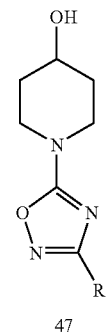
47

In a preferred embodiment of the present invention a sulfonamide group may be introduced into the meta or para Ar position. This can be accomplished via several amenable synthetic multi step manipulations including the reaction of ammonia with sulfonyl chlorides (Scheme 13A) or alternatively sulfonamides can be obtained by reacting sulfinic acid salts with an electrophilic nitrogen source such as hydroxylamine-O-sulfonic acid or bis-(2,2,2-trichloroethyl)-azodicarboxylate. Preferably 3-methoxy-3-oxapropane-1-sulfinate can serve as a sulfinate donor moiety through a simple alkylation and be subsequently removed via a beta-elimination reaction. Reaction of the resulting sulfinate wityh an electrophilic nitrogen source provides the primary sulfonamide analogue of the current invention. Such intermediates may be optionally further modified to amides such as those represented by general formula 49. Acylsulfonamides of this type can be obtained by an amidation reaction using an acid halide or anhydride (such as, $R_gCOCl$ or $(R_gCO)_2O$) and a base in an inert solvent (Scheme 13C). The base includes an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide or potassium hydroxide, and like), a tertiary amine (such as, NtV-diisopropylethylamine, triethylamine, N-methylmorpholine, and the like), or an aromatic amine (such as, pyridine, imidazole, poly-(4-vinylpyridine), and the like). The inert solvent includes lower halocarbon solvents (such as, dichloromethane, dichloroethane, chloroform, and the like), ethereal solvents (such as, tetrahydrofuran, dioxane, and the like), amide solvents (such as, N,N-dimethylacetamide, N,N-dimethylformamide, and the like), aromatic solvents (benzene, toluene, pyridine, and the like) and mixtures thereof. Reaction temperature ranges from about −20° C. to 50° C., preferably about 0° C. to 40° C.

Organic Synthesis, $3^{rd}$ Edition, 1999 [Wiley]; incorporated herein by reference in its entirity).

The present invention also encompasses diastereomers as well as optical isomers, e.g. mixtures of enantiomers including racemic mixtures, as well as individual enantiomers and diastereomers, which arise as a consequence of structural asymmetry in certain compounds of Formula (I). Separation of the individual isomers or selective synthesis of the individual isomers is accomplished by application of various methods which are well known to practitioners in the art.

The present invention also encompasses diastereomers as well as optical isomers, e.g. mixtures of enantiomers including racemic mixtures, as well as individual enantiomers and diastereomers, which arise as a consequence of structural asymmetry in certain compounds of Formula (I). Separation of the individual isomers or selective synthesis of the individual isomers is accomplished by application of various methods which are well known to practitioners in the art.

Indications and Methods of Prophylaxis and/or Treatment

In addition to the foregoing beneficial uses for compounds of the present invention disclosed herein, compounds of the invention are useful in the treatment of additional diseases. Without limitation, these include the following.

The most significant pathologies in Type II diabetes are impaired insulin signaling at its target tissues ("insulin resistance") and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of

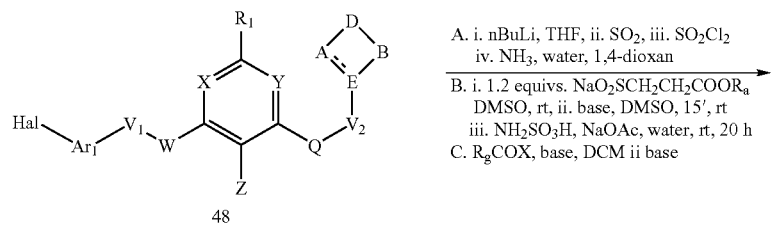

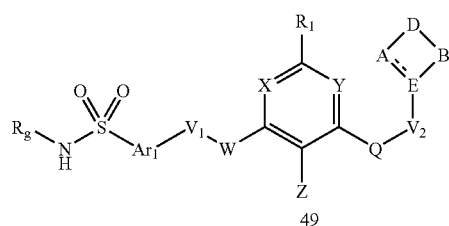

The compounds of the present invention may be prepared according to the general synthetic schemes as described herein as well as relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., Protecting Groups in pharmaceuticals that function in a glucose-dependent action, i.e. potentiators of glucose signaling. Physiological signaling systems which function in this manner are well-characterized and include the gut peptides GLP1, GIP and PACAP. These hormones act via their cognate G-protein coupled receptor to stimulate the production of cAMP in pancreatic β-cells. The increased cAMP does not appear to result in stimulation of insulin release during the fasting or preprandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including RUP3, would also stimulate the release of endogenous insulin and consequently promote normoglycemia in Type II diabetes.

It is also established that increased cAMP, for example as a result of GLP1 stimulation, promotes β-cell proliferation, inhibits β-cell death and thus improves islet mass. This positive effect on β-cell mass is expected to be beneficial in both Type II diabetes, where insufficient insulin is produced, and Type I diabetes, where β-cells are destroyed by an inappropriate autoimmune response.

Some β-cell GPCRs, including RUP3, are also present in the hypothalamus where they modulate hunger, satiety, decrease food intake, controlling or decreasing weight and energy expenditure. Hence, given their function within the hypothalamic circuitry, agonists or inverse agonists of these receptors mitigate hunger, promote satiety and therefore modulate weight.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In some embodiments of the present invention the metabolic-related disorder is hyperlipidemia, type 1 diabetes, type 2 diabetes mellitus, idiopathic type 1 diabetes (Type 1b), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

One aspect of the present invention pertains to methods for treatment of a metabolic-related disorder in an individual comprising administering to the individual in need of such treatment a therapeutically effective amount of a compound as described herein or a pharmaceutical composition thereof.

In some embodiments the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments the metabolic-related disorder is type II diabetes. In some embodiments the metabolic-related disorder is hyperglycemia. In some embodiments the metabolic-related disorder is hyperlipidemia. In some embodiments the metabolic-related disorder is hypertriglyceridemia. In some embodiments the metabolic-related disorder is type I diabetes. In some embodiments the metabolic-related disorder is dyslipidemia. In some embodiments the metabolic-related disorder is syndrome X. In some embodiments the individual is a mammal. In some embodiments the mammal is a human.

One aspect of the present invention pertains to methods of decreasing food intake of an individual comprising administering to the individual in need thereof a therapeutically effective amount of a compound of the present invention or pharmaceutical composition thereof. In some embodiments the individual is a mammal. In some embodiments the mammal is a human.

One aspect of the present invention pertains to methods of inducing satiety in an individual comprising administering to the individual in need of such treatment a therapeutically effective amount of a compound of the present invention or pharmaceutical composition thereof. In some embodiments the individual is a mammal. In some embodiments the mammal is a human.

One aspect of the present invention pertains to methods of controlling or decreasing weight gain of an individual comprising administering to the individual in need of such treatment a therapeutically effective amount of a compound of the present invention or pharmaceutical composition thereof. In some embodiments the individual is a mammal. In some embodiments the mammal is a human.

Some embodiments of the present invention pertain to methods wherein the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to methods of modulating a RUP3 receptor in an individual comprising contacting the receptor with a compound of the present invention or pharmaceutical composition thereof. In some embodiments, the compound is an agonist. In some embodiments, the compound is an inverse agonist. In some embodiments, the compound is an antagonist. In some embodiments, the modulation of the RUP3 receptor is treatment of a metabolic-related disorder and complications thereof. In some embodiments, the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments, the metabolic-related disorder is type II diabetes. In some embodiments, the metabolic-related disorder is hyperglycemia. In some embodiments, the metabolic-related disorder is hyperlipidemia. In some embodiments, the metabolic-related disorder is hypertriglyceridemia. In some embodiments, the metabolic-related disorder is type I diabetes. In some embodiments, the metabolic-related disorder is dyslipidemia. In some embodiments, the metabolic-related disorder is syndrome X. In some embodiments, the individual is a mammal. In some embodiments, the mammal is a human.

Some embodiments of the present invention include a method of modulating a RUP3 receptor in an individual comprising contacting the receptor with a compound of the present invention wherein the modulation of the RUP3 receptor reduces food intake of the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

Some embodiments of the present invention include a method of modulating a RUP3 receptor in an individual comprising contacting the receptor with a compound of the present invention wherein the modulation of the RUP3 receptor induces satiety in the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

Some embodiments of the present invention include a method of modulating a RUP3 receptor in an individual comprising contacting the receptor with a compound of the present invention wherein the modulation of the RUP3 receptor controls or reduces weight gain of the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

One aspect of the present invention pertains to use of a compound as described herein, for production of a medicament for use in treatment of a metabolic-related disorder. In some embodiments, the metabolic-related disorder is type II diabetes, inadequate glucose tolerance, insulin resistance, hyperglycemia, hyperlipidemia, hypertriglyceridemia, hypercholesterolemia, dyslipidemia or syndrome X.

One aspect of the present invention pertains to use of a compound as described herein, for production of a medicament for use in decreasing food intake of an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to use of a compound as described herein, for production of a medicament for use of inducing satiety in an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to use of a compound as described herein, for production of a medicament for use in controlling or decreasing weight gain in an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to a compound, as described herein, for use in a method of treatment of the human or animal body by therapy.

One aspect of the present invention pertains to a compound, as described herein, for use in a method of treatment of a metabolic-related disorder of the human or animal body by therapy.

One aspect of the present invention pertains to a compound, as described herein, for use in a method of decreasing food intake of the human or animal body by therapy.

One aspect of the present invention pertains to a compound, as described herein, for use in a method of inducing satiety of the human or animal body by therapy.

One aspect of the present invention pertains to a compound, as described herein, for use in a method of controlling or decreasing weight gain of the human or animal body by therapy.

Pharmaceutical Compositions

A further aspect of the present invention pertains to pharmaceutical compositions comprising one or more compounds of Formula (I) or any formula disclosed herein, and one or more pharmaceutically acceptable carriers. Some embodiments of the present invention pertain to pharmaceutical compositions comprising a compound of Formula (I) and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insulation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as RUP3 receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 to about 2500 mg, about 0.001 to about 1000 mg, 0.001 to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. Typically, animal models include, but are not limited to, the rodents diabetes models as described in Example 5, infra (as well as other animal models known in the art, such as those reported by Reed and Scribner in Diabetes, Obesity and Metabolism, 1, 1999, 75-86). In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the Formula (I) and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the Formula (I) or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the Formula (I) as an aerosol can be prepared by processes well-known to the person skilled in the art. For their preparation, for example, solutions or dispersions of the compounds of the Formula (I) in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, "Pro-drugs as Novel Delivery Systems,"Vol. 14 of the A.C.S. Symposium Series; and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

In some embodiments the pharmaceutical agents is selected from the group consisting of: apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agensts, $\beta_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like), appetite suppressants (for example, bupropion) and the like. In further embodiments, the pharmaceutical agent is selected from the group consisting of orlistat, sibutramine, bromocriptine, ephedrine, leptin, and pseudoephedrine.

In some embodiments the pharmaceutical agents is selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin.

It is noted that when the RUP3 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as RUP3 receptor modulators, for the treatment of obesity in domestic animals (e.g., cats and dogs), and RUP3 receptor modulators in other domestic animals where no disease or disorder is evident (e.g., food-oriented animals such as cows, chickens, fish, etc.). Those of ordinary skill in the art are readily credited with understanding the utility of such compounds in such settings.

Combination Therapy—Prophylaxis and Treatment

In the context of the present invention, a compound of Formula (I) or pharmaceutical composition thereof can be utilized for modulating the activity of RUP3 receptor mediated diseases, conditions and/or disorders as described herein. Examples of modulating the activity of RUP3 receptor mediated diseases include the prophylaxis or treatment of metabolic related disorders such as, but not limited to, type I diabetes, type II diabetes, inadequate glucose tolerance, insulin resistance, hyperglycemia, hyperlipidemia, hypertriglyceridemia, hypercholesterolemia, dyslipidemia and syndrome X. Other examples of modulating the activity of RUP3 receptor mediated diseases include the prophylaxis or treatment of obesity and/or overweight by decreasing food intake, inducing satiation (i.e., the feeling of fullness), controlling weight gain, decreasing body weight and/or affecting metabolism such that the recipient loses weight and/or maintains weight.

While the compounds of the invention can be administered as the sole active pharmaceutical agent (i.e., mono-therapy), they can also be used in combination with other pharmaceutical agents (i.e., combination-therapy) for the treatment of the diseases/conditions/disorders described herein. Therefore, another aspect of the present invention includes methods of prophylaxis and/or treatment of a metabolic related disorder or a weight related disorder, such as obesity, comprising administering to an individual in need of prophylaxis and/or treatment a therapeutically effective amount of a compound of the present invention, for example Formula (I), in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

It will be understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of metabolic related disorders and/or concomitant diseases thereof. For example, but not limited to, congestive heart failure, type I diabetes, type II diabetes, inadequate glucose tolerance, insulin resistance, hyperglycemia, hyperlipidemia, hypertriglyceridemia, hypercholesterolemia, dyslipidemia, syndrome X, retinopathy, nephropathy and neuropathy. Prophylaxis or treatment of one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists, adiponectin and the like. In accordance to one aspect of the present invention, a compound of the present can be used in combination with a pharmaceutical agent or agents belonging to one or more of the classes of drugs cited herein.

It will be understood that the scope of combination-therapy of the compounds of the present invention with other pharmaceutical agents is not limited to those listed herein, supra or infra, but includes in principle any combination with any pharmaceutical agent or pharmaceutical composition useful for the prophylaxis or treatment of diseases, conditions or disorders that are linked to metabolic related disorders.

Some embodiments of the present invention include methods of prophylaxis or treatment of a disease, disorder, condition or complication thereof as described herein, comprising administering to an individual in need of such prophylaxis or treatment a therapeutically effective amount or dose of a compound of the present invention in combination with at least one pharmaceutical agent selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, methods of the present invention include compounds of the present invention and the pharmaceutical agents are administered separately. In further embodiments, compounds of the present invention and the pharmaceutical agents are administered together.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to sulfonylureas in reducing HbA1c. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of the present invention include the α-glucosidase inhibitors. The α-glucosidase inhibitors competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Suitable pharmaceutical agents that can be used in conjunction with compounds of the present invention include the Fibrates. Fibrate compounds belong to a class of drugs that lower blood cholesterol levels by inhibiting synthesis and secretion of triglycerides in the liver and activating a lipoprotein lipase. Fibrates have been known to activate peroxisome proliferators-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form), and angiotensin II receptor antagonists known in the art.

Other treatments for one or more of the diseases cited herein include the use of pharmaceutical agents known in the art belonging to the classes of drugs referred to, but not limited to, the following: amylin agonists (for example, pramlintide), insulin secretagogues (for example, GLP-1 agonists; exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds) and squalene synthase inhibitors.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy]phosphinyl]-3-phenoxybenzenebutanesulfonic acid, mono potassium salt (BMS-188494) and squalene synthesis inhibitors known in the art.

In accordance with the present invention, the combination can be used by mixing the respective active components either all together or independently with a physiologically acceptable carrier, excipient, binder, diluent, etc., as described herein above, and administering the mixture or mixtures either orally or non-orally as a pharmaceutical composition. When a compound or a mixture of compounds of Formula (I) are administered as a combination therapy with another active compound the therapeutic agents can be formulated as a separate pharmaceutical compositions given at the same time or at different times, or the therapeutic agents can be given as a single composition.

Other Utilities

Another object of the present invention relates to radio-labeled compounds of Formula (I) that would be useful not only in radio-imaging but also in assays, both in vitro and in vivo, for localizing and quantitating the RUP3 receptor in tissue samples, including human, and for identifying RUP3 receptor ligands by inhibition binding of a radio-labeled compound. It is a further object of this invention to develop novel RUP3 receptor assays of which comprise such radio-labeled compounds.

The present invention embraces isotopically-labeled compounds of Formula (I) and any subgenera herein, such as but not limited to, Formula (Ia) through Formula (Is). An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, 13N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro RUP3 receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of Formula (I) that has incorporated at least one radionuclide; in some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]— This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$ I. A represented procedure was reported by Zhu, D.-G. and co-workers in J. Org. Chem. 2002, 67, 943-948.

B. Ortho $^{125}$Iodination of phenols—This procedure allows for the incorporation of $^{125}$I at the ortho position of a phenol as reported by Collier, T. L. and co-workers in J. Labeled Compd Radiopharm. 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)4] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in J. Labeled Compd Radiopharm. 2001, 44, S280-S282.

A radio-labeled RUP3 receptor compound of Formula (1) can be used in a screening assay to identify/evaluate compounds. In general terms, a newly synthesized or identified compound (i.e., test compound) can be evaluated for its ability to reduce binding of the "radio-labeled compound of Formula (I)" to the RUP3 receptor. Accordingly, the ability of a test compound to compete with the "radio-labeled compound of Formula (I)" for the binding to the RUP3 receptor directly correlates to its binding affinity.

The labeled compounds of the present invention bind to the RUP3 receptor. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM, and in still yet another embodiment the labeled inhibitor has an IC$_{50}$ less than about 0.1 μM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

The examples are provided to further define the invention without, however, limiting the invention to the specifics of these examples.

Example 1

96-Well Cyclic AMP Membrane Assay for RUP3

Materials:
1) Adenlyl cyclase Activation Flashplate Assay kit from Perkin Elmer—96 wells (SMP004B) and $^{125}$I tracer (NEX 130) which comes with the kit. Keep in refrigerator, in a box, and do not expose the Flashplates to light.
2) Phosphocreatine—Sigma P-7936
3) Creatine Phosphokinase—Sigma C-3755
4) GTP—Sigma G-8877
5) ATP—Sigma A-2383
6) IBMX—Sigma I-7018
7) Hepes—1M solution in distilled water—Gibco #15630080
8) MgCl$_2$—Sigma M-1028—1M Solution
9) NaCl—Sigma —S6546—5M Solution
10) Bradford Protein Assay Kit—Biorad # 5000001
11) Proclin 300—Sigma #4-8126

Binding Buffer—filter through 45-micron Nalgene filter and keep in refrigerator. All buffers and membranes should be kept cold (in ice bucket) while performing assay.
20 mM Hepes, pH7.4
1 mM MgCl2
100 mM NaCl
2× Regeneration Buffer (make in binding buffer):
20 mM Phosphocreatine (1.02 gm/200 ml binding buffer)
20 units Creatine phosphokinase (4 mg/200 ml)
20 uM GTP (make up 10.46 mg/ml in binding buffer and add 200 μL/200 ml)
0.2 mM ATP (22.04 mg/200 ml)
100 mM IBMX (44.4 mg IBMX dissolved in 1 ml 100% DMSO first and then add the entire amount to 200 ml of buffer).

Regeneration buffer can be aliquotted into 40-45 ml portions (in 50 ml sterile tubes) and kept frozen for up to 2 months. Simply put the tube in a beaker with room temperature water to thaw out the regeneration buffer on the day of the assay.

A. Assay Procedure
1) Pipet 50 μL regeneration buffer in all 96 wells using Matrix 1250 8-channel pipettor.
2) Pipet 5 μL DMSO in columns 1 and columns 11 and 12.
3) Pipet 50 μL cAMP standards in columns 11 and 12 in this format: 50 pmole/well for row A, 25 pmole/well for row B, 12.5 pmole/well for row C, 5 picomol/well for row D, 2.5 pmole/well for row E, 1.25 pmole/well for row F, 0.5 pmole/well for row G, and 0 pmole/well (buffer only) for row H.
4) Pipet 5 μL compounds from each well of a compound dilution plate, for IC50s, using the following dilution scheme:
Well H: 400 uM compound (final concentration of compound in reaction mix=5/100×400 uM=20 uM
Well G: 1:10 dilution of Well H (i.e. 5 mL compound from well H+45 μL 100% DMSO) (final concentration=2 uM)
Well F: 1:10 dilution of well G (final concentration=0.2 uM)
Well E: 1:10 dilution of well F (final concentration=0.02 uM)
Well D: 1:10 dilution of well E (final concentration=0.002 uM)
Well C: 1:10 dilution of well D (final concentration=0.0002 uM
Well B: 1:10 dilution of well C (final concentration=0.00002 uM)
Well A: 1:10 dilution of well B (final concentration=0.000002 uM)
IC$_{50}$s or EC$_{50}$s are done in triplicate. One Flashplate can therefore be set up to handle 3 compounds. (i.e., columns 2, 3, and 4 are for compound #1, columns 5, 6, and 7 are for compound #2, and columns 8, 9, and 10 are for compound #3.)
5) Add 50 μL of RUP3 membranes to all wells in Columns 2 to 10. (Prior to the start of the assay, the frozen membrane pellets for both RUP3 and CMV (cells transfected with an expression plasmid containing no RUP3 sequences), are suspended in binding buffer, usually 1 ml binding buffer for 1 plate of membranes. The membranes are kept in ice all the time, and a polytron (Brinkmann polytron, model # PT-3100) is used (setting 6-7, for 15-20 seconds) to obtain a homogeneous membrane suspension.) Protein concentration is determined by Bradford protein assay kit using instructions given in the kit, using the standard supplied with the kit as a reference. The protein concentration of the membranes is adjusted with binding buffer, so that 50 μL membranes=15 ug protein (i.e. 0.3 mg/ml protein).
6) In column 1, Wells A, B, C, and D, add 50 μL RUP3 membranes. To wells E, F, G, and H, add 50 μL CMV membranes, (CMV membranes being of the same protein concentration as the RUP3 membranes).
7) Incubate 1 hour at room temperature with agitation on a rotating platform shaker. Cover with foil while shaking.
8) After 1 hour, add (to all 96 wells), 100 μL of the $^{125}$I tracer in detection buffer supplied with the Flashplate kit plus proclin, made up in the following manner:
Pipet per 10 ml per Flashplate: 100 ml of detection buffer+ 1 ml $^{125}$I+0.2 ml of Proclin (the proclin helps to stop the production of cAMP). Make a smaller quantity of detection buffer mix if you have fewer plates.
9) Shake the plates on a rotating platform shaker for 2 hours, covering the plates with lead sheeting.
10) Seal the plates with the plastic film sealers provided with the Flashplate kit.
11) Count the plates using a TRILUX 1450 Microbeta Counter. See the door of the counter to determine which counting protocol to use.
12) Data is analyzed on the Arena Database according to the RUP3 non-fusion, IC$_{50}$ EC$_{50}$ for 96-well cAMP membrane assay, and the compound numbers and the concentrations of compounds must be entered by the user.

B. Membrane Cyclase Criteria
1) Signal to Noise:
An acceptable signal-to-noise ratio for RUP3 can vary from 4 to 6. The raw cpms are approximately 1800 to 2500 for RUP3 and 3500-4500 for CMV. The cpm (or ultimately pmoles of cAMP/well) cannot be outside the standard curve, and should not approach well A of the standard curve (50 pmole/well) and well H (no cAMP). Generally, the pmoles of cAMP produced by RUP3 receptor are around 11 to 13 pmole/well (for 15 ug/well protein), and for CMV are between 2 to 3 pmole/well (for 15 ug protein/well).

2) Standard Curve:

The slope should be linear and the error bars for duplicates should be very small. The receptor and CMV controls cannot be off scale of the standard curve, as described above. If the receptor controls are off the high end of the standard curve, i.e. 50 pmole/well or higher, one must repeat the experiment using less protein. However, such a case has not been observed with transiently transfected RUP3 membranes (10 ug DNA/15 cm plate, using 60 µL Lipofectamine, and preparing membranes after 24 hour of transfection.)

3) The $IC_{50}$ or $EC_{50}$ curve should be at 100% (+ or −20%) of control RUP3 membranes at the top, and should go down to 0 (or up to 20%) at the bottom. The standard error of the triplicate determinations should be + or −10%.

C. Stimulation of cAMP in HIT-T15 Cells

HIT-T15 (ATCC CRL#1777) is an immortalized hamster insulin-producing cell line. These cells express RUP3 and therefore can be used to assess the ability of RUP3 ligands to stimulate or inhibit cAMP accumulation via its endogenously expressed receptor. In this assay, cells are grown to 80% confluence and then distributed into a 96-well Flashplate (50,000 cells/well) for detection of cAMP via a "cAMP Flashplate Assay" (NEN, Cat # SMP004). Briefly, cells are placed into anti-cAMP antibody-coated wells that contain either vehicle, the test ligand(s) at a concentration of interest, or 1 uM forskolin. The latter is a direct activator of adenylyl cyclase and serves as a positive control for stimulation of cAMP in HIT-TIS cells. All conditions are tested in triplicate. After a 1 hour incubation to allow for stimulation of cAMP, a Detection Mix containing $^{125}$I-cAMP is added to each well and the plate is allowed to incubate for another 1 hour. The wells are then aspirated to remove unbound $^{125}$I-cAMP. Bound $^{125}$I-cAMP is detected using a Wallac Microbeta Counter. The amount of cAMP in each sample is determined by comparison to a standard curve, obtained by placing known concentrations of cAMP in some wells on the plate.

A number of the compounds disclosed herein were screened using the above described assay. Representative compounds and their corresponding $EC_{50}$ values are shown in the Table 6 below:

TABLE 6

| Compound | RUP3 ($EC_{50}$) (µM) |
|---|---|
| A1 | 0.020 |
| A34 | 0.027 |
| A35 | 0.059 |

D. Stimulation of Insulin Secretion in HIT-T15 Cells

It is known that stimulation of cAMP in HIT-T15 cells causes an increase in insulin secretion when the glucose concentration in the culture media is changed from 3 mM to 15 mM. Thus, RUP3 ligands can also be tested for their ability to stimulate glucose-dependent insulin secretion (GSIS) in HIT-T15 cells. In this assay, 30,000 cells/well in a 12-well plate are incubated in culture media containing 3 mM glucose and no serum for 2 hours. The media is then changed; wells receive media containing either 3 mM or 15 mM glucose, and in both cases the media contains either vehicle (DMSO) or RUP3 ligand at a concentration of interest. Some wells receive media containing 1 uM forskolin as a positive control. All conditions are tested in triplicate. Cells are incubated for 30 minutes, and the amount of insulin secreted into the media is determined by ELISA, using a kit from either Peninsula Laboratories (Cat # ELIS-7536) or Crystal Chem Inc. (Cat # 90060).

E. Stimulation of Insulin Secretion in Isolated Rat Islets

As with HIT-T15 cells, it is known that stimulation of cAMP in isolated rat islets causes an increase in insulin secretion when the glucose concentration in the culture media is changed from 60 mg/dl to 300 mg/dl. RUP3 is an endogenously expressed GPCR in the insulin-producing cells of rat islets. Thus, RUP3 ligands can also be tested for their ability to stimulate GSIS in rat islet cultures. This assay is performed as follows:

A. Select 75-150 islet equivalents (IEQ) for each assay condition using a dissecting microscope. Incubate overnight in low-glucose culture medium. (Optional.)

B. Divide the islets evenly into triplicate samples of 25-40 islet equivalents per sample. Transfer to 40 µm mesh sterile cell strainers in wells of a 6-well plate with 5 ml of low (60 mg/dl) glucose Krebs-Ringers Buffer (KRB) assay medium.

C. Incubate 30 minutes (1 hour if overnight step skipped) at 37° C. and 5% $CO_2$. Save the supernatants if a positive control for the RIA is desired.

D. Move strainers with islets to new wells with 5 ml/well low glucose KRB. This is the second pre-incubation and serves to remove residual or carryover insulin from the culture medium. Incubate 30 minutes.

E. Move strainers to next wells (Low 1) with 4 or 5 ml low glucose KRB. Incubate @ 37° C. for 30 minutes. Collect supernatants into low-binding polypropylene tubes prelabelled for identification and keep cold.

F. Move strainers to high glucose wells (300 mg/dl, which is equivalent to 16.7 mM). Incubate and collect supernatants as before. Rinse islets in their strainers in low-glucose to remove residual insulin. If the rinse if to be collected for analysis, use one rinse well for each condition (i.e. set of triplicates.)

G. Move strainers to final wells with low-glucose assay medium (Low 2). Incubate and collect supernatants as before.

H. Keeping cold, centrifuge supernatants at 1800 rpm for 5 minutes @ 4-8° C. to remove small islets/islet pieces that escape the 40 mm mesh. Remove all but lower 0.5-1 ml and distribute in duplicate to pre-labelled low-binding tubes. Freeze and store at <−20° C. until insulin concentrations can be determined.

I. Insulin determinations are done as above, or by Linco Labs as a custom service, using their rat insulin RIA (Cat. # RI-13K).

Example 2

A. RT-PCR Analysis of RUP3 Expression in Human Tissues (FIG. 1A).

RT-PCR was applied to determine the tissue distribution of RUP3. Oligonucleotides used for PCR had the following sequences:

ZC47: 5'-CATTGCCGGGCTGTGGTTAGTGTC-3' (forward primer), (SEQ ID NO:3);

ZC48: 5'-GGCATAGATGAGTGGGTTGAGCAG-3' (reverse primer), (SEQ ID NO:4);

and the human multiple tissue cDNA panels (MTC, Clontech) were used as templates (1 ng cDNA per PCR amplification). Twenty-two (22) human tissues were analyzed. PCR was performed using Platinum PCR SuperMix (Life Technologies, Inc.; manufacture instructions were followed) in a 50 µl reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 µl) were loaded on a 1.5% agarose gel to analyze the RT-PCR products, and a specific 466 base-pair DNA fragment representing RUP3 was specifically amplified from cDNA of pancreas origin. Low expression was also evident in subregions of brain.

B. cDNA Dot-Blot Analysis of RUP3 Expression in Human Tissues (FIG. 1B).

Results from RT-PCR analysis were further confirmed in cDNA dot-blot analysis. In this assay, a dot-blot membrane containing cDNA from 50 human tissues (Clontech) was hybridized with a $^{32}$P-radiolabelled DNA probe having sequences derived from human RUP3. Hybridyzation signals were seen in pancreas and fetal liver, suggesting these tissues express RUP3. No significant expression was detected in other tissues analyzed.

C. Analysis of RUP3 by RT-PCR With Isolated Human Pancreatic Islets of Langerhans (FIG. 1C).

Further analysis of RUP3 by RT-PCR with isolated human pancreatic islets of Langerhans showed robust expression of RUP3 in islet cells but not in control samples.

D. Analysis of RUP3 Expression With cDNAs of Rat Origin by RT-PCR (FIG. 1D).

RUP3 expression was further analyzed with cDNAs of rat origin by RT-PCR technique. Tissue cDNAs used for this assay were obtained from Clontech except those for hypothalamus and islets, which were prepared in house. Concentrations of each cDNA sample were normalized via a control RT-PCR analysis of the house-keeping gene GAPDH before assaying for RUP3 expression. Oligonucleotides used for PCR had the following sequences:

rat RUP3 ("rRUP3") forward: 5'-CATGGGCCCTGCAC-CTTCTTTG-3' (SEQ ID NO:5);

rRUP3 reverse: 5'-GCTCCGGATGGCTGATGAT-AGTGA-3' (SEQ ID NO:6).

PCR was performed using Platinum PCR SuperMix (Life Technologies, Inc.; manufacture instructions were followed) in a 50 µl reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 µl) were loaded on a 1.5% agarose gel to analyze the RT-PCR products, and a specific 547 base-pair DNA fragment representing rat RUP3 was specifically amplified from cDNA of pancreas origin, revealing a similar expression profile with human. Of particular note, robust expression was seen in isolated islets and hypothalamus.

Example 3

Figure 2:
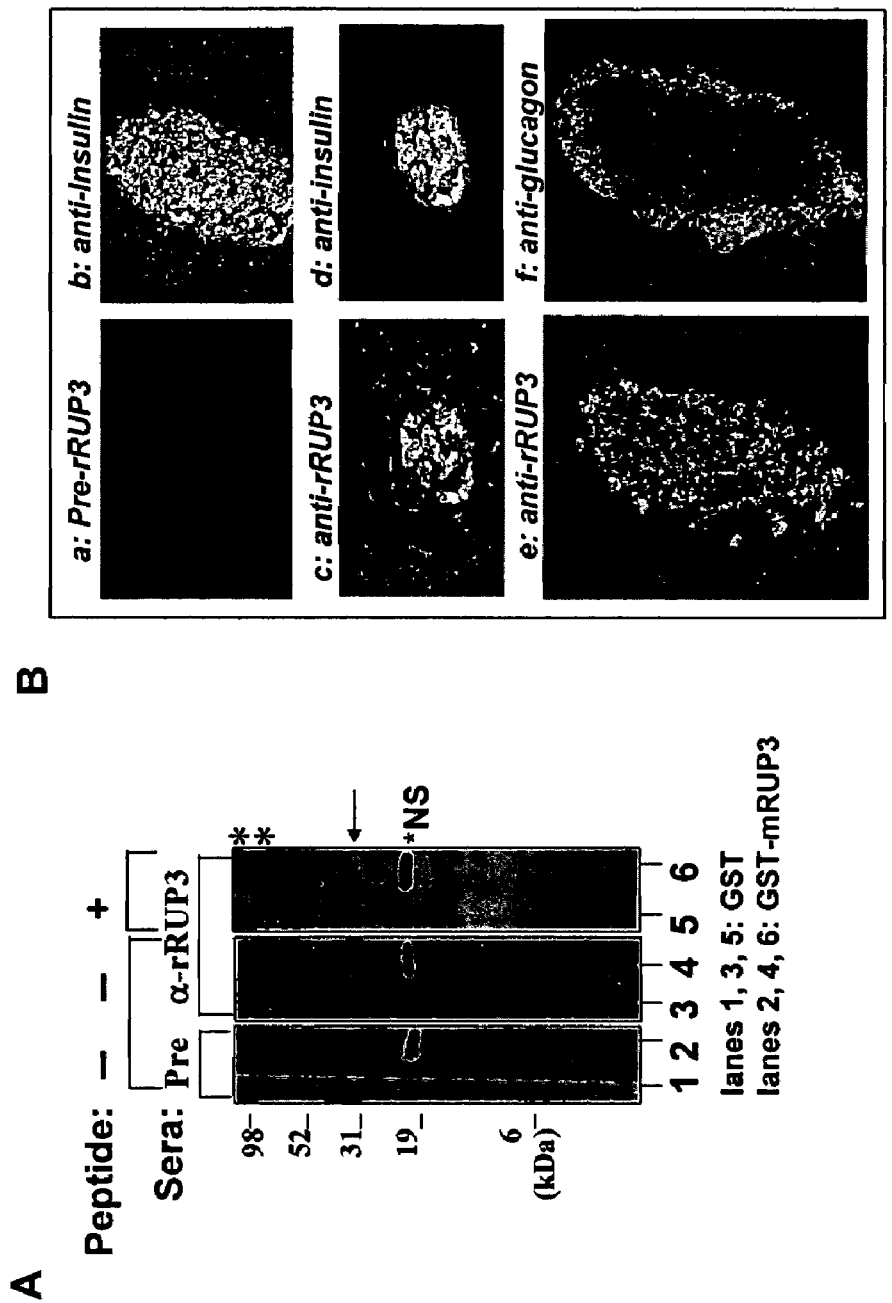
FIG. 2A shows a polyclonal anti-RUP3 antibody prepared in Rabbits.
FIG. 2B shows the expression of RUP3 in insulin-producing β cells of pancreatic islets.

RUP3 Protein Expression is Restricted to β Cell Lineage of Pancreatic Islets (FIG. 2).

A. A Polyclonal Anti-RUP3 Antibody Was Prepared in Rabbits (FIG. 2A).

Rabbits were immunized with an antigenic peptide with sequence derived from rat RUP3 ("rRUP3"). The peptide sequence was RGPERTRESAYHIVTISHPELDG and shared 100% identity with mouse RUP3 in the corresponding region. A cysteine residue was incorporated at the N-terminal end of this antigenic peptide to facilitate KLH crosslinking before injecting into rabbits. The resulting antisera ("anti-rRUP3") and the corresponding preimmune sera ("pre-rRUP3") were tested for immune reactivity to mouse RUP3 in immunobloting assays (lanes 1 though 4). In this assay, the GST-RUP3 fusion protein was readily recognized by the anti-rRUP3 antisera (lane 4), but not by the preimmune sera (lane 2). The immunoreactive signal could be efficiently eliminated when the immunobloting assay was performed in the presence of excess antigenic peptide (lane 6).

B. RUP3 Expression in Insulin-Producing β Cells of Pancreatic Islets (FIG. 2B). Rat pancreas was perfused with 4% paraformaldehyde (PFA) in PBS and embedded in OCT embedding medium. Ten micron sections were prepared, fixed on glass slides, and immunostained with either pre-rRUP3 (FIG. 2B, panel a) or with anti-rRUP3 antisera (FIG. 2B, panels c and e) followed by secondary staining with donkey anti-rabbit IgG conjugated to the fluorochrome Cy-3. Each section was also co-immunostained with a monoclonal anti-insulin antibody (Santa Cruz, FIG. 2B, panels b and d) in primary staining followed by a secondary staining with donkey anti-mouse IgG conjugated with FITC, or with a goat anti-glucagon antibody (Santa Cruz, FIG. 2B, panel f) and donkey anti-goat IgG coupled to FITC. Immunofluorescent signals were examined under a fluorescent microscope. RUP3 was found expressed in insulin producing cells (panels c and d), but not in glucagons producing cells (panels e and f). These data demonstrated that RUP3 is expressed in β cells but not in β cells of the rat pancreatic islets. Analogous results were obtained when mouse pancreatic sections were investigated for RUP3 expression.

Example 4

Figure 3:
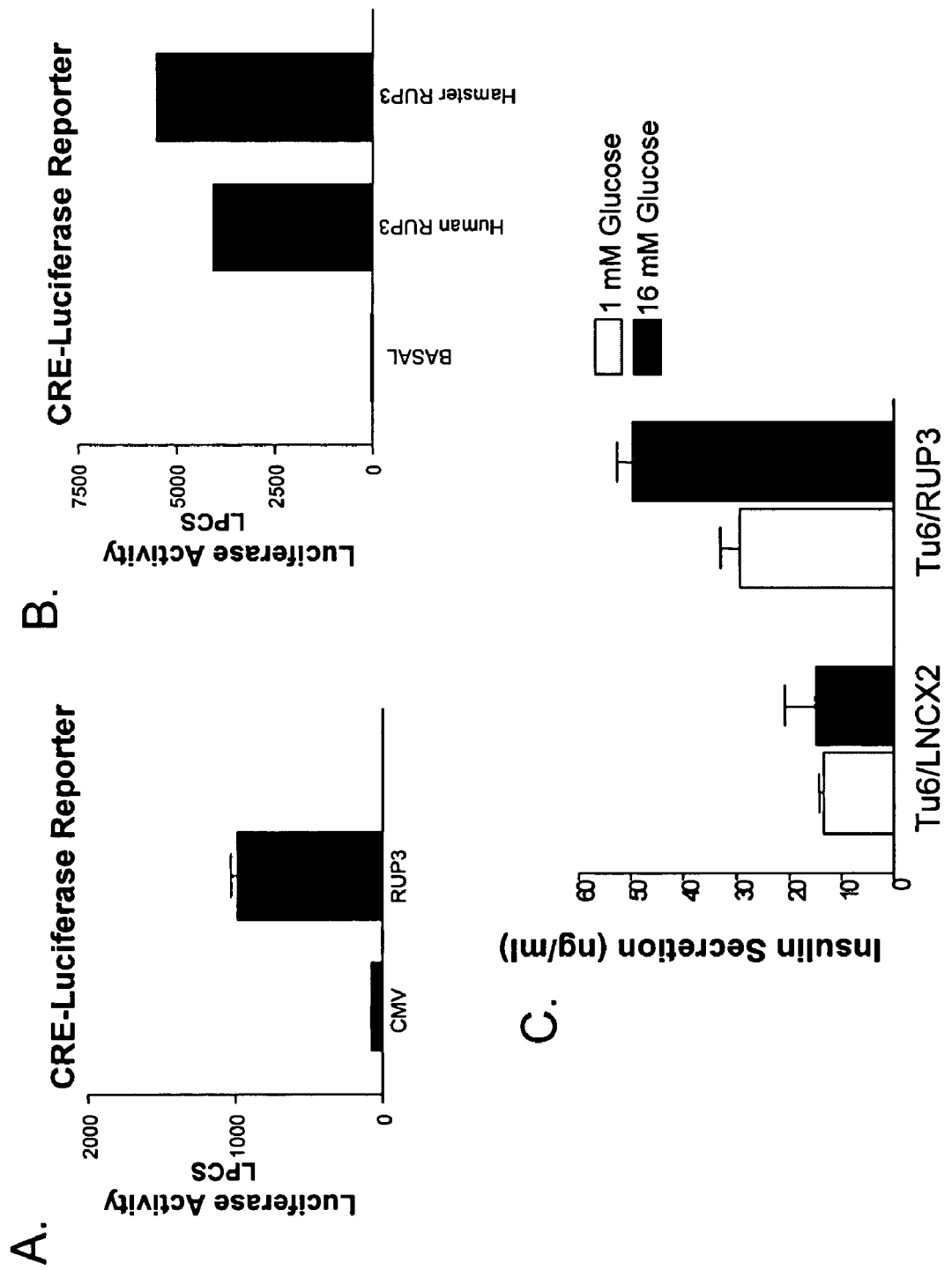
FIG. 3 shows in vitro functional activities of RUP3.
Figure 4:
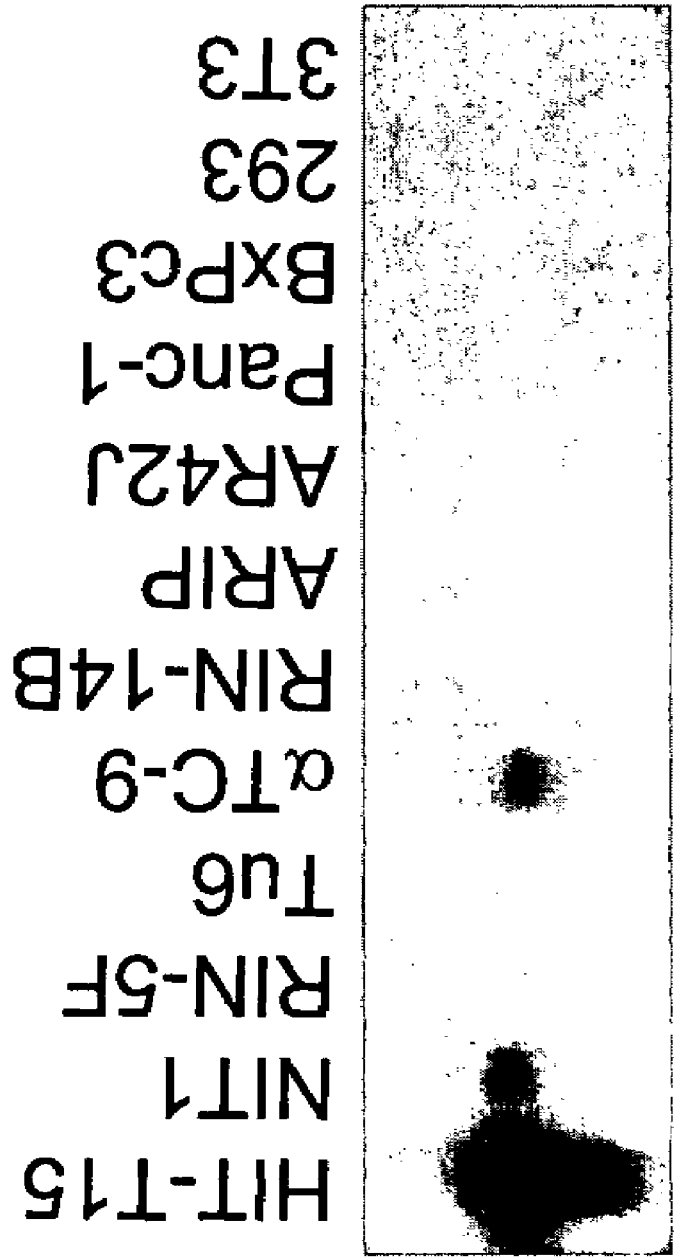
FIG. 4 shows a RUP3 RNA blot.

Functional Activities of RUP3 In Vitro (FIG. 3).

It was established that RUP3 stimulates the production of cAMP by cotransfection of 293 cells with: (1) a CRE-Luciferase reporter, wherein the ability to stimulate the production of firefly luciferase depends on increased cAMP in cells, and (2) an expression plasmid encoding the human form of RUP3 (FIG. 3A). Note that cells co-transfected with an expression plasmid containing no RUP3 sequences ("CMV" in FIG. 3A) produce very little luciferase activity, whereas cells transfected with an expression plasmid encoding RUP3 ("RUP3" in FIG. 3A) have at least a 10-fold increase in luciferase activity. This indicates that RUP3 stimulates the production of cAMP when introduced into 293 cells. This property of RUP3 is conserved across species, because hamster RUP3 stimulates luciferase activity when introduced into 293 cells in a manner analogous to that described for human RUP3 (FIG. 3B).

It is established that, when cAMP is increased in insulin-producing cells of the pancreas, these cells exhibit an enhanced ability to secrete insulin when glucose concentrations rise. To test whether RUP3 might impart enhanced glucose-dependent insulin release, retrovirus containing human RUP3 was used to generate Tu6 cells that express high levels of RUP3. Tu6 cells produce insulin, but do not express appreciable levels of RUP3 and do not normally exhibit an increase in insulin release when increased glucose is present in the culture media. As shown in FIG. 3C, Tu6 cells transduced with a control virus that contains no receptor are still able to produce insulin, but do not show an increase in insulin secretion when the concentration of glucose in the culture media is shifted from 1 mM to 16 mM. By contrast, Tu6 cells transduced with RUP3-containing retrovirus display significant glucose-dependent insulin secretion (FIG. 3C).

Example 5

In Vivo Effects of RUP3 Agonists on Glucose Homeostasis in Rats.

A. Oral Glucose Tolerance Test (oGTT)

Male Sprague Dawley rats weighing approximately 200 g-250 g were fasted for 15 hours and randomly grouped (n=6) to receive a RUP3 agonist (Compounds A78, A88 or A118) at 3, 10 or 30 mg/kg. Compounds were delivered orally via a gavage needle (p.o., volume 3 ml/kg). At time 0, levels of blood glucose were assessed using a glucometer (Elite XL, Bayer), and rats were administered either vehicle (20% hydroxypropyl-beta-cyclodextrin) or test compound. Thirty minutes after administration of test compound, levels of blood glucose were again assessed, and rats were administered dextrose orally at a dose of 2 g/kg. Blood glucose measurements were then taken 30 min, 60 min, and 120 min after this time. Table 7 shows the mean percentage inhibition of glucose excursion for each test compound, averaged across the six animals in the treatment group. These results demonstrated that the RUP3 agonists, Compounds A78, A88 and A118 lowered blood glucose after challenge with glucose.

TABLE 7

Mean % Inhibition of Glucose Excursion

| Compound | % inhibition of glucose excursion, (dose, mg/kg) |
|---|---|
| A78 | 39%, (10) |
| A88 | 38%, (30) |
| A118 | 43%, (30) |

Example 6

Generation of Tu6/RUP3 Stable Lines

To produce Tu6 cells that express RUP3 at high levels, a retrovirus bearing an expression cassette for RUP3 was generated. Briefly, RUP3 coding sequence was cloned into the retroviral vector pLNCX2 (Clontech, Cat # 6102-1). The amphotropic packaging cell line PT-67 (Clontech, K1060-D) was then transfected with either the parental vector pLNCX2 or pLNCX2/RUP3 using Lipofectamine and stable lines were established using guidelines provided by the PT-67 vendor. Retrovirus-containing supernatant was obtained by collecting media from the resultant stables according to the manufacturer's directions. Tu6 cells, in a 10 cm dish, were then infected with retrovirus by incubating in a solution of 1 ml viral supernatant/9 ml culture media containing 40 ug/ml polybrene for 24 hours. The medium was then changed to culture media containing 300 ug/ml G418. G418-resistant clones were ultimately created by virtue of the neomycin-resistance gene cassette present in the pLNCX2 vector, thus indicating the successful integration of retrovirus into the Tu6 genome. The expression of RUP3 in the Tu6/RUP3 G418-resistant colonies was confirmed by Northern blot.

Example 7

Insulin Secretion, Tu6 Stables

To measure insulin secretion from rodent insulin-producing cell lines, cells were first cultured overnight in serum-free, glucose-deficient media. The following morning, the cells were then placed in the same media supplemented with either 1 mM or 16 mM glucose. After an incubation of 4 hours, the media was collected and analyzed for insulin content using a Rat Insulin Enzyme-Immunoassay (EIA) System (Amersham Pharmacia Biotech, Cat. # RPN 2567). Typically, the assay was performed using multiple dilutions of sample media in order to ensure that the sample measurements fell within the boundaries of the standard curve (generated using known amounts of insulin), as recommended by the manufacturer.

Example 8

Receptor Binding Assay

In addition to the methods described herein, another means for evaluating a test compound is by determining binding affinities to the RUP3 receptor. This type of assay generally requires a radiolabelled ligand to the RUP3 receptor. Absent the use of known ligands for the RUP3 receptor and radiolabels thereof, compounds of Formula (I) can be labelled with a radioisotope and used in an assay for evaluating the affinity of a test compound to the RUP3 receptor.

A radiolabelled RUP3 compound of Formula (I) can be used in a screening assay to identify/evaluate compounds. In general terms, a newly synthesized or identified compound (i.e., test compound) can be evaluated for its ability to reduce binding of the "radiolabelled compound of Formula (I)" to the RUP3 receptor. Accordingly, the ability to compete with the "radio-labelled compound of Formula (I)" or Radiolabelled RUP3 Ligand for the binding to the RUP3 receptor directly correlates to its binding affinity of the test compound to the RUP3 receptor.

Assay Protocol for Determining Receptor Binding for RUP3:

A. RUP3 Receptor Preparation 293 cells (human kidney, ATCC), transiently transfected with 10 ug human RUP3 receptor and 60 µL Lipofectamine (per 15-cm dish), were grown in the dish for 24 hours (75% confluency) with a media change and removed with 10 ml/dish of Hepes-EDTA buffer (20 mM Hepes+10 mM EDTA, pH 7.4). The cells were then centrifuged in a Beckman Coulter centrifuge for 20 minutes, 17,000 rpm (JA-25.50 rotor). Subsequently, the pellet was resuspended in 20 mM Hepes+1 mM EDTA, pH 7.4 and homogenized with a 50-ml Dounce homogenizer and again centrifuged. After removing the supernatant, the pellets were stored at −80° C., until used in binding assay. When used in the assay, membranes were thawed on ice for 20 minutes and then 10 mL of incubation buffer (20 mM Hepes, 1 mM $MgCl_2$, 100 mM NaCl, pH 7.4) added. The membranes were then vortexed to resuspend the crude membrane pellet and homogenized with a Brinkmann PT-3100 Polytron homogenizer for 15 seconds at setting 6. The concentration of membrane protein was determined using the BRL Bradford protein assay.

B. Binding Assay

For total binding, a total volume of 50 µL of appropriately diluted membranes (diluted in assay buffer containing 50 mM Tris HCl (pH 7.4), 10 mM $MgCl_2$, and 1 mM EDTA; 5-50 µg protein) is added to 96-well polyproylene microtiter plates followed by addition of 100 µL of assay buffer and 50 µL of Radiolabelled RUP3 Ligand. For nonspecific binding, 50 µL of assay buffer is added instead of 100 µL and an additional 50 µL of 10 µM cold RUP3 is added before 50 µL of Radiolabelled RUP3 Ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 μL of Optiphase Supermix is added to each well, the top of the plates are sealed, and plates are counted in a Trilux MicroBeta scintillation counter. For compound competition studies, instead of adding 100 μL of assay buffer, 100 μL of appropriately diluted test compound is added to appropriate wells followed by addition of 50 μL of Radiolabelled RUP3 Ligand.

C. Calculations

The test compounds are initially assayed at 1 and 0.1 μM and then at a range of concentrations chosen such that the middle dose would cause about 50% inhibition of a Radio-RUP3 Ligand binding (i.e., $IC_{50}$). Specific binding in the absence of test compound ($B_O$) is the difference of total binding ($B_T$) minus non-specific binding (NSB) and similarly specific binding (in the presence of test compound) (B) is the difference of displacement binding ($B_D$) minus non-specific binding (NSB). $IC_{50}$ is determined from an inhibition response curve, logit-log plot of % $B/B_O$ vs concentration of test compound.

$K_i$ is calculated by the Cheng and Prustoff transformation:

$$K_i = IC_{50}/(1+[L]/K_D)$$

where [L] is the concentration of a Radio-RUP3 Ligand used in the assay and $K_D$ is the dissociation constant of a Radio-RUP3 Ligand determined independently under the same binding conditions.

Chemistry

Syntheses of Compounds of the Present Invention

Example 9

The compounds of the invention and their synthesis are further illustrated by the following examples. The following examples are provided to further define the invention without, however, limiting the invention to the particulars of these examples. The compounds described herein, supra and infra, are named according to the CS Chem Draw Ultra Version 7.0.1, AutoNom version 2.2. In certain instances common names are used and it is understood that these common names would be recognized by those skilled in the art.

Chemistry: Proton nuclear magnetic resonance ($^1H$ NMR) spectra were recorded on a Varian Mercury Vx-400 equipped with a 4 nucleus auto switchable probe and z-gradient or a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, t=triplet, q=quartet, m=multiplet, br=broad. Microwave irradiations were carried out using the Emyrs Synthesizer (Personal Chemistry). Thin-layer chromatography (TLC) was performed on silica gel 60 $F_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063-0.200 mm (Merck). Evaporation was done in vacuo on a Buchi rotary evaporator. Celite 545® was used during palladium filtrations.

LCMS specs: 1) PC: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2. 2) Mac: HPLC-pumps: LC-8A VP, Shimadzu Inc; HPLC system controller: SCL-10A VP, Shimadzu Inc. UV-Detector: SPD-10A VP, Shimadzu Inc; Autosampler: 215 Liquid Handler, Gilson Inc; Mass spectrometer: API 150EX with Turbo Ion Spray source, AB/MDS Sciex Software: Masschrom 1.5.2.

Example 9.1

Preparation of 4-[6-(4-Methanesulfonyl-phenylamino)-5-nitro-pyrimidin-4-yloxy]-piperidine-1-carboxylic acid tert-butyl ester (Compound A1)

4-Hydroxy-piperidine-1-carboxylic acid tert-butyl ester (3.03 mmol, 610 mg) and sodium hydride (10.6 mmol, 255 mg) were dissolved in dry THF (20 mL) and stirred for 30 minutes at room temperature. Then, (6-chloro-5-nitro-pyrimidin-4-yl)-(4-methanesulfonyl-phenyl)-amine (3.03 mmol, 1.0 g) was added. The reaction was stirred at room temperature for 30 minutes. Its progress was monitored by thin layer chromatography and LCMS. Sodium hydride was quenched with water and the desired compound was extracted in ethyl acetate. Organic solvents were evaporated in vacuo. Flash chromatography (Silica gel 60; 30/70 EtOAc/Hexanes) provided Compound A1 as a yellow solid (1.2 g, 68%). $^1H$ NMR (400 MHz, CDCl$_3$) δ (ppm): 10.10 (s, 1H), 8.33 (s, 1H), 7.90 (d, 2H), 7.79 (d, 2H), 5.51 (heptet, 1H), 3.58 (m, 2H), 3.46 (m, 2H), 2.97 (s, 3H), 1.84 (m, 4H), 1.36 (s, 9H). LCMS (ESI), m/z 494.4 (M+H+, 100%).

Example 9.2

Preparation of (4-Methanesulfonyl-phenyl)-[5-nitro-6-(piperidin-4-yloxy)-pyrimidin-4-yl]-amine (Compound A2)

Compound A1 (1.42 mmol, 700 mg) was dissolved in a commercially available 4M HCl solution in 1,4-dioxane (25 mL). The mixture was stirred at 40° C. for 1.0 hour. Removal of organic solvents in vacuo provided compound A2 as a yellow solid (580 mg, 100%). $^1H$ NMR (400 MHz, MeOH-d$_4$) δ (ppm): 8.29 (s, 1H), 7.81 (quartet, 4H), 5.56 (m, 1H), 3.21 (m, 4H), 3.00 (s, 3H), 2.07 (m, 4H). LCMS (ESI), m/z 394.1 (M+H+, 100%).

Example 9.3

Preparation of 1-{4-[6-(4-Methanesulfonyl-phenylamino)-5-nitro-pyrimidin-4-yloxy]-piperidin-1-yl}-3,3-dimethyl-butan-1-one (Compound A3)

Compound A2 (0.12 mmol, 50 mg), 3,3-dimethyl-butyryl chloride (0.18 mmol, 24 mg) and triethylamine (0.63 mmol, 88 L) were dissolved in DMF and microwaved at 80° C. for 5 minutes. The reaction mixture was quenched with water and extracted with ethyl acetate. Removal of organic solvents in vacuo provided Compound A3 as a yellow solid (46 mg, 78%). $^1H$ NMR (400 MHz, CDCl$_3$) δ (ppm): 9.98 (s, 1H), 8.20 (s, 1H), 7.77 (d, 2H), 7.64 (d, 2H), 5.44 (heptet, 1H), 3.71 (m, 1H), 3.48 (m, 3H), 2.75 (s, 3H), 2.11 (quartet, 2H), 1.76 (m, 4H), 0.85 (s, 9H). LCMS (ESI), m/z 492.4 (M+H+, 100%).

Example 9.4

Preparation of (4-Methanesulfonyl-phenyl)-[5-nitro-6-(1-thiophen-3-ylmethyl-piperidin-4-yloxy)-pyrimidin-4-yl]-thiophen-3-ylmethyl-amine (Compound A4)

Compound A2 (0.12 mmol, 50 mg), 3-chloromethyl-thiophene (0.12 mmol, 16 mg) and triethylamine (0.63 mmol, 88 µL) were dissolved in DMF and microwaved at 80° C. for 10 minutes. The reaction mixture was quenched with water and extracted with ethyl acetate. Purification by HPLC provided Compound A4 as a yellow solid (24 mg, 34%). $^1$H NMR (400 MHz, CDCl$_3$) δ (ppm): 8.35 (s, 1H), 7.93 (m, 2H), 7.79 (m, 2H), 7.22 (m, 1H), 7.19 (m, 2H), 7.08 (m, 1H), 6.98 (m, 1H), 6.84 (m, 1H), 5.68 (m, 1H), 4.08 (m, 4H), 3.36 (m, 2H), 3.04 (s, 3H), 2.86 (m, 2H), 2.34 (m, 2H), 2.07 (m, 2H). LCMS (ESI), m/z 586.1 (M+H+, 100%).

Example 9.5

Preparation of (4-Methanesulfonyl-phenyl)-[5-nitro-6-(1-pyridin-2-ylmethyl-piperidin-4-yloxy)-pyrimidin-4-yl]-amine (Compound A5)

Compound A2 (0.12 mmol, 50 mg), 2-chloromethyl-pyridine (0.12 mmol, 20 mg) and triethylamine (0.63 mmol, 88 µL) were dissolved in DMF and microwaved at 80° C. for 10 minutes. The reaction mixture was quenched with water and extracted with ethyl acetate. Removal of organic solvent in vacuo provided Compound A5 pure as a yellow solid (27 mg, 47%). $^1$H NMR (400 MHz, CDCl$_3$) δ (ppm): 10.09 (s, 1H), 8.51 (m, 1H), 8.32 (s, 1H), 7.89 (d, 2H), 7.78 (d, 2H), 7.60 (t, 1H), 7.36 (m, 1H), 7.13 (t, 1H), 5.40 (m, 1H), 3.65 (m, 2H), 3.07 (s, 3H), 2.72 (m, 2H), 2.45 (m, 2H), 2.02 (m, 2H), 1.91 (m, 2H). LCMS (ESI), m/z 484.5 (M+H+, 100%).

Example 9.6

Preparation of (4-Methanesulfonyl-phenyl)-[5-nitro-6-(1-pyridin-3-ylmethyl-piperidin-4-yloxy)-pyrimidin-4-yl]-amine (Compound A6)

Compound A2 (0.12 mmol, 50 mg), 3-chloromethyl-pyridine (0.12 mmol, 20 mg) and triethylamine (0.63 mmol, 88 µL) were dissolved in DMF and microwaved at 80° C. for 10 minutes. The reaction mixture was quenched with water and extracted with ethyl acetate. Removal of organic solvent in vacuo provided Compound A6 pure as a yellow solid (39 mg, 66%). $^1$H NMR (400 MHz, CDCl$_3$) δ (ppm): 10.09 (s, 1H), 8.45 (m, 2H), 8.33 (s, 1H), 7.90 (d, 2H), 7.78 (d, 2H), 7.65 (m, 1H), 7.21 (m, 1H), 5.41 (heptet, 1H), 3.52 (m, 2H), 3.01 (s, 3H), 2.65 (m, 2H), 2.47 (m, 2H), 1.98 (m, 2H), 1.94 (m, 2H). LCMS (ESI), m/z 484.3 (M+H+, 100%).

Example 9.7

Preparation of {6-[1-(3,3-Dimethyl-butyl)-piperidin-4-yloxy]-5-nitro-pyrimidin-4-yl}-(4-methanesulfonyl-phenyl)-amine (Compound A7)

Compound A2 (0.20 mmol, 80 mg), and 3,3-dimethyl-butyraldehyde (0.24 mmol, 30 PL) were dissolved in methanol (2 mL) and stirred for 5 minutes at room temperature. Then, added sodium borohydride (0.25 mmol, 8.7 mg) and stirred for 10 minutes at room temperature. The reaction mixture was quenched with saturated ammonium chloride solution (1 mL) followed by an extraction with dichloromethane. Removal of organic solvent in vacuo and purification by prep-LCMS provided Compound A7 as a yellow solid (12 mg, 13%). $^1$H NMR (400 MHz, CDCl$_3$) δ (ppm): 10.17 (s, 1H), 8.36 (s, 1H), 7.90 (d, 2H), 7.78 (d, 2H), 5.71 (s broad, 1H), 3.51 (d, 2H), 3.08 (m, 2H), 2.97 (m, 5H), 2.38 (m, 2H), 2.14 (m, 2H), 1.60 (m, 2H), 0.85 (s, 9H). LCMS (ESI), m/z 478.3 (M+H+, 100%).

Example 9.8

Preparation of (4-Methanesulfonyl-phenyl)-{6-[1-(3-methyl-butyl)-piperidin-4-yloxy]-5-nitro-pyrimidin-4-yl}-amine (Compound A8)

Compound A2 (0.15 mmol, 60 mg), and 3-methyl-butyraldehyde (0.15 mmol, 13 mg) were dissolved in methanol (2 mL) and stirred for 5 minutes at room temperature. Then, sodium borohydride (0.18 mmol, 6.3 mg) was added at 0° C. The reaction was complete immediately upon addition of sodium borohydride. The mixture was quenched with saturated ammonium chloride solution (1 mL) followed by an extraction with dichloromethane. Removal of organic solvent in vacuo and purification by HPLC provided Compound A8 as a yellow solid (25 mg, 36%). $^1$H NMR (400 MHz, CDCl$_3$) δ (ppm): 10.17 (s, 1H), 8.35 (s, 1H), 7.90 (d, 2H), 7.80 (d, 2H), 5.72 (s broad, 1H), 3.65 (m, 2H), 3.11 (m, 2H), 2.96 (m, 5H), 2.40 (m, 2H), 2.15 (m, 2H), 1.60 (m, 3H), 0.85 (d, 6H). LCMS (ESI), m/z 464.4 (M+H+, 100%).

Example 9.9

Preparation of (4-Methanesulfonyl-phenyl)-[5-nitro-6-(3,4,5,6-tetrahydro-2H-[1,2'] bipyridinyl-4-yloxy)-pyrimidin-4-yl]-amine (Compound A9)

Compound A2 (0.13 mmol, 50 mg), and 2-bromo-pyridine (0.53 mmol, 53 µL) were dissolved in DMF (1 mL) and triethylamine (0.46 mmol, 63 µL). The reaction was heated in a microwave at 165° C. for 40 minutes. The mixture was quenched with water and extracted with ethyl acetate. Removal of organic solvent in vacuo and purification by prep-TLC provided Compound A9 as a yellow solid (12 mg, 20%). $^1$H NMR (400 MHz, CDCl$_3$) δ (ppm): 10.10 (s, 1H), 8.35 (s, 1H), 8.13 (m, 1H), 7.89 (d, 2H), 7.81 (d, 2H), 7.42 (m, 1H), 6.64 (d, 1H), 6.55 (m, 1H), 5.58 (heptet, 1H), 3.78 (m, 2H), 3.60 (m, 2H), 3.00 (s, 3H), 2.02 (m, 2H), 1.91 (m, 2H). LCMS (ESI), m/z 471.4 (M+H+, 100%).

Example 9.10

Preparation of 4-[6-(4-Methanesulfonyl-phenylamino)-5-nitro-pyrimidin-4-yloxy]-piperidine-1-carboxylic acid ethyl ester (Compound A10)

Compound A2 (0.13 mmol, 50 mg), and ethyl chloroformate (0.13 mmol, 13 µL) were dissolved in DMF (1 mL) and triethylamine (0.36 mmol, 50 µL). The reaction was heated in a microwave at 80° C. for 4 minutes. The mixture was quenched with water and extracted with ethyl acetate. Removal of organic solvent in vacuo provided Compound A10 as a yellow solid (50 mg, 89%). $^1$H NMR (400 MHz, CDCl$_3$) δ (ppm): 9.97 (s, 1H), 8.20 (s, 1H), 7.77 (d, 2H), 7.66

(d, 2H), 5.41 (heptet, 1H), 3.96 (q, 2H), 3.47 (m, 4H), 2.88 (s, 3H), 1.72 (m, 4H), 1.08 (t, 3H). LCMS (ESI), m/z 466.3 (M+H+, 100%).

Example 9.11

Preparation of 1-{4-[6-(4-Methanesulfonyl-phenylamino)-5-nitro-pyrimidin-4-yloxy]-piperidin-1-yl}-3,3-dimethyl-butan-2-one (Compound A11)

Compound A2 (0.12 mmol, 50 mg), and 1-bromo-3,3-dimethyl-butan-2-one (0.12 mmol, 16 µL) were dissolved in DMF (1 mL) and triethylamine (0.36 mmol, 50 µL). The reaction was heated in a microwave at 80° C. for 4 minutes. The mixture was quenched with water and extracted with ethyl acetate. Removal of organic solvent in vacuo and purification by HPLC provided Compound A11 as a yellow solid (15 mg, 25%). $^1$H NMR (400 MHz, CDCl$_3$) δ (ppm): 10.11 (s, 1H), 8.32 (s, 1H), 7.89 (d, 2H), 7.78 (d, 2H), 5.49 (s broad, 1H), 3.53 (s broad, 2H), 3.01 (s, 3H), 2.78 (m, 4H), 2.18 (m, 2H), 1.96 (m, 2H), 1.20 (s, 9H). LCMS (ESI), m/z 492.3 (M+H+, 100%).

Example 9.12

Preparation of {6-[1-(2-Ethoxy-ethyl)-piperidin-4-yloxy]-5-nitro-pyrimidin-4-yl}-(4-methanesulfonyl-phenyl)-amine (Compound A12)

Compound A2 (0.13 mmol, 50 mg), and 1-bromo-2-ethoxy-ethane (0.65 mmol, 99 mg) were dissolved in DMF (1 mL) and triethylamine (0.91 mmol, 127 µL). The reaction was heated in a microwave at 80° C. for 20 minutes. The mixture was quenched with water and extracted with ethyl acetate. Removal of organic solvent in vacuo and purification by prep-TLC provided Compound A12 as a yellow solid (20 mg, 33%). $^1$H NMR (400 MHz, CDCl$_3$) δ (ppm): 10.06 (s, 1H), 8.29 (s, 1H), 7.84 (d, 2H), 7.74 (d, 2H), 5.39 (s broad, 1H), 3.53 (m, 2H), 3.39 (q, 2H), 2.86 (s, 3H), 2.77 (m, 2H), 2.65 (m, 3H), 2.04 (m, 2H), 1.92 (m, 3H), 1.09 (m 3H). LCMS (ESI), m/z 466.3 (M+H+, 100%).

Example 9.13

Preparation of 4-[6-(4-Methanesulfonyl-phenylamino)-5-nitro-pyrimidin-4-yloxymethyl]-piperidine-1-carboxylic acid tert-butyl ester (Compound A13)

4-Hydroxymethyl-piperidine-1-carboxylic acid tert-butyl ester (1.0 mmol, 226 mg) and sodium hydride (1.0 mmol, 25 mg) were dissolved in dimethyl acetamide (1.0 mL) and stirred for 30 minutes at room temperature. Then, (6-chloro-5-nitro-pyrimidin-4-yl)-(4-methanesulfonyl-phenyl)-amine (0.21 mmol, 70 mg) was added. The reaction was stirred at 70° C. for 20 minutes and the progress of the reaction was monitored by thin layer chromatography and LCMS. Sodium hydride was quenched with water and the desired compound was extracted in ethyl acetate. Organic solvents were evaporated in vacuo. Flash chromatography (Silica gel 60; 40/60 EtOAc/Hexanes) provided Compound A13 as a yellow solid (10 mg, 10%). $^1$H NMR (400 MHz, CDCl$_3$) δ (ppm): 10.21 (s, 1H), 8.41 (s, 1H), 7.97 (d, 2H), 7.86 (d, 2H), 4.39 (d, 2H), 4.17 (m, 2H), 3.07 (s, 3H), 2.76 (m, 2H), 1.83 (m, 2H), 1.59 (m, 1H), 1.45 (s, 9H), 1.30 (m, 2H). LCMS (ESI), m/z 408.2 (M+H+, 100%).

Example 9.14

Preparation of 4-{2-[6-(4-Methanesulfonyl-phenylamino)-5-nitro-pyrimidin-4-yloxy]-ethyl}-piperidine-1-carboxylic acid tert-butyl ester (Compound A14)

4-(2-Hydroxy-ethyl)-piperidine-1-carboxylic acid tert-butyl ester (1.0 mmol, 230 µL) and sodium hydride (1.0 mmol, 26 mg) were dissolved in dimethyl acetamide (1.0 mL) and stirred for 30 minutes at room temperature. Then, (6-chloro-5-nitro-pyrimidin-4-yl)-(4-methanesulfonyl-phenyl)-amine (0.21 mmol, 70 mg) was added. The reaction was stirred at 70° C. for 20 minutes. Its progress was monitored by thin layer chromatography and LCMS. Sodium hydride was quenched with water and the desired compound was extracted in ethyl acetate. Organic solvents were evaporated in vacuo. Flash chromatography (Silica gel 60; 40/60 EtoAc/Hexanes) provided Compound A14 as a yellow oil (90 mg, 82%). $^1$H NMR (400 MHz, CDCl$_3$) δ (ppm): 10.26 (s, 1H), 8.40 (s, 1H), 7.98 (d, 2H), 7.86 (d, 2H), 4.51 (t, 2H), 4.09 (m, 2H), 3.73 (t, 2H), 3.07 (s, 3H), 2.72 (m, 2H), 1.76 (m,1H), 1.55 (q, 2H), 1.46 (s, 9H), 1.15 (m, 2H). LCMS (ESI), m/z 422.2 (M+H+, 100%).

Example 9.15

Preparation of 3-[6-(4-Methanesulfonyl-phenylamino)-5-nitro-pyrimidin-4-yloxy]-pyrrolidine-1-carboxylic acid tert-butyl ester (Compound A15)

3-Hydroxy-pyrrolidine-1-carboxylic acid tert-butyl ester (1.0 mmol, 197 mg) and sodium hydride (1.0 mmol, 26 mg) were dissolved in THF (1.5 mL) and stirred for 30 minutes at room temperature. Then, (6-chloro-5-nitro-pyrimidin-4-yl)-(4-methanesulfonyl-phenyl)-amine (0.21 mmol, 70 mg) was added. The reaction was stirred at 0° C. for 30 minutes. Its progress was monitored by thin layer chromatography and LCMS. Sodium hydride was quenched with water and the desired compound was extracted in ethyl acetate. Organic solvents were evaporated in vacuo. Flash chromatography (Silica gel 60; 50/50 EtOAc/Hexanes) provided Compound A15 as a yellow oil (60 mg, 60%). $^1$H NMR (400 MHz, CDCl$_3$) δ (ppm): 10.18 (s, 1H), 8.47 (s, 1H), 7.98 (d, 2H), 5.78 (m, 2H), 5.78 (m,1H), 4.46 (m, 2H), 3.08 (s, 3H), 2.26 (m, 2H), 1.63 (m, 2H), 1.48 (s, 9H). LCMS (ESI), m/z 480.4 (M+H+, 100%).

Example 9.16

Preparation of 3-[6-(4-Methanesulfonyl-phenylamino)-5-nitro-pyrimidin-4-yloxymethyl]-pyrrolidine-1-carboxylic acid tert-butyl ester (Compound A16)

3-Hydroxymethyl-pyrrolidine-1-carboxylic acid tert-butyl ester (0.65 mmol, 131 mg) and sodium hydride (1.3 mmol, 31 mg) were dissolved in N,N-dimethyl acetamide (1.5 mL) and stirred for 30 minutes at room temperature. Then, (6-chloro-5-nitro-pyrimidin-4-yl)-(4-methanesulfonyl-phenyl)-amine (0.26 mmol, 84 mg) was added. The reaction was stirred at 70° C. for 30 minutes. Its progress was monitored by thin layer chromatography and LCMS. Sodium hydride was quenched with water and the desired compound was extracted in ethyl acetate. Organic solvents were evaporated in vacuo. Flash chromatography (Silica gel 60; 50/50 EtoAc/Hexanes) provided Compound A16 as a yellow solid (96 mg, 54%). $^1$H NMR (400 MHz, CDCl$_3$) δ (ppm): 10.21 (s, 1H), 8.41 (s, 1H), 7.97 (d, 2H), 7.86 (d, 2H), 4.52 (m, 2H), 3.49 (m, 2H), 3.11 (s, 3H), 2.75 (m, 1H), 1.84 (m, 2H), 1.65 (m, 2H), 1.46 (s, 9H). LCMS (ESI), m/z 394.1 (M+H+, 100%).

Example 9.17

Preparation of 3-[6-(4-Methanesulfonyl-phenylamino)-5-nitro-pyrimidin-4-yloxymethyl]-pyrrolidine-1-carboxylic acid tert-butyl ester (Compound A17)

(S)-3-Hydroxymethyl-pyrrolidine-1-carboxylic acid tert-butyl ester (0.65 mmol, 131 mg) and sodium hydride (1.3 mmol, 31 mg) were dissolved in N,N-dimethyl acetamide (1.5 mL) and stirred for 30 minutes at room temperature. Then, (6-chloro-5-nitro-pyrimidin-4-yl)-(4-methanesulfonyl-phenyl)-amine (0.26 mmol, 84 mg) was added. The reaction was stirred at 70° C. for 30 minutes. Its progress was monitored by thin layer chromatography and LCMS. Sodium hydride was quenched with water and the desired compound was extracted in ethyl acetate. Organic solvents were evaporated in vacuo. Flash chromatography (Silica gel 60; 50/50 EtoAc/Hexanes) provided Compound A17 as a yellow solid (26 mg, 15%). $^1$H NMR (400 MHz, CDCl$_3$) δ (ppm): 10.22 (s, 1H), 8.41 (s, 1H), 7.97 (d, 2H), 7.87 (d, 2H), 4.52 (m, 2H), 3.49 (m, 2H), 3.09 (s, 3H), 2.75 (m, 1H), 1.97 (m, 2H), 1.67 (m, 2H), 1.49 (s, 9H). LCMS (ESI), m/z 394.1 (M+H+, 100%).

Example 9.18

Preparation of 4-[5-Cyano-6-(6-methylsulfanyl-pyridin-3-ylamino)-pyrimidin-4-yloxy]-piperidine-1-carboxylic acid tert-butyl ester (Compound A18)

To a solution of 4-hydroxy-piperidine-1-carboxylic acid tert-butyl ester (304 mg, 1.51 mmol) in DMF was added sodium hydride (36 mg, 1.51 mmol) and allowed the resulting mixture was allowed to stir at room temperature. After 30 minutes, 4-chloro-6-(6-methylsulfanyl-pyridin-3-ylamino)-pyrimidine-5-carbonitrile was added and the resulting mixture was heated at 70° C. for 1 hour. Worked up with Ethyl acetate, sodium bicarbonate, dried with magnesium sulfate and evaporated to afford a white solid as Compound A18 (80.0 mg, 59.8%). $^1$H NMR 400 MHz DMSO-d$_6$ δ (ppm): 9.90 (s, 1H), 8.54 (d, 1H), 8.40 (s, 1H, pyrimidine), 7.78 (m, 1H), 7.29 (d, 1H), 5.75 (s, 3H), 5.35 (m, 1H), 3.58 (m, 2H), 3.27 (m, 2H), 1.93 (m, 2H), 1.63 (m, 2H), 1.38 (s, 9H), LCMS (ESI) for $C_{21}H_{26}ClN_6OS$: m/z 443.4 (M+H$^+$, 100%).

The intermediate 4-chloro-6-(6-methylsulfanyl-pyridin-3-ylamino)-pyrimidine-5-carbonitrile was prepared in the following manner:

A. 4,6-Dichloro-pyrimidine-5-carbaldehyde

Phosphorus oxychoride (200 mL, 2184.8 mmol) was added drop wise (via additional funnel) to DMF cooled to 0° C. After for 1 hour, 4,6 dihydroxypyridimidine (50.0 g, 446.1 mmol) was added and the mixture was allowed to warm to room temperature. The resulting heterogeneous mixture was refluxed for 3 hours. The volatiles were removed at reduce pressure, and the residue was poured in ice water and extract with CHCl$_3$/Et$_2$O, wash with sodium bicarbonate and concentrate under high vacuum. Final product was purified by silica plug using CH$_2$Cl$_2$ to afford a yellow solid (54.0 g), $^1$H NMR 400 MHz CDCl$_3$ δ (ppm): 10.3 (s, 1H, aldehyde), 8.7 (s, 1H, pyrimidine).

B. 4,6-Dichloro-pyrimidine-5-carbonitrile 4,6-Dichloro-pyrimidine-5-carbaldehyde (15.0 g, 84,75 mmol, 1.0 equivalent) was dissolved in ethyl acetate (150 mL), mixed with hydroxylamine hydrochloride in water (30 mL) and added sodium acetate. Reaction was at left room temperature for 1.5 hours. Worked up with ethyl acetate, sodium bicarbonate, dried with magnesium sulfate, rotovaped and dried and high vacuum to afford a white solid (14.593 g). The white solid (iminohydroxy intermediate) was added to thionyl chloride (100 mL) at 0° C. with stirring and allowed to warm to room temperature for 3 hours. The reaction was quenched in ice (500 g), and the precipitated was filtered off, washed with cold water, and dried under high vacuum to afford a white solid as product (10.739 g, 72.8%). $^1$H NMR 400 MHz CDCl$_3$ 6 (ppm): 8.95 (s, 1H, pyrimidine).

C. 4-Chloro-6-(6-methylsulfanyl-pyridin-3-ylamino)-pyrimidine-5-carbonitrile

6-Methylsulfanyl-pyridin-3-ylamine (500.0 mg, 3.57 mmol, 1.0 equivalent) in DMF (1 mL) was added drop wise to a suspension of 4,6-dichloro-pyrimidine-5-carbonitrile (616.9 mg, 3.57 mmol, 1.0 equivalent), potassium carbonate (542.1 mg, 3.92 mmol, 1.1 equivalent) at 0° C. under stirring. The reaction was left reacting at room temperature for 1.5 hours. Product was crystallized using ethyl acetate, hexane getting a yellow solid as product (650.00 mg, 65.62%). LCMS (ESI) for C, 1H$_8$ClN$_5$S: m/z 278.0 (M+H$^+$, 100%).

Example 9.19

Preparation of 4-[5-Cyano-6-(6-methanesulfonyl-pyridin-3-ylamino)-pyrimidin-4-yloxy]-piperidine-1-carboxylic acid tert-butyl ester (Compound A19)

To a solution of Compound A18 (52.0 mg, 0.11 mmol) in CH$_2$Cl$_2$ (5 mL) was added mCPBA (101.5 mg, 0.59 mmol) and the resulting mixture was heated to reflux. After 30 minutes, the mixture was worked up with water (basic conditions using ammonium hydroxide, pH=10), dichloromethane, and sodium bicarbonate, dried with magnesium sulfate and evaporated to afford Compound A19 as a white solid (24.9 mg, 43.9%). $^1$H NMR 400 MHz CDCl$_3$ δ (ppm): 8.92 (d, 1H), 8.52 (d, 1H), 8.46 (s, 1H, pyrimidine), 8.10 (d, 1H), 7.47 (s, 1H), 5.45 (m, 1H), 3.77 (m, 2H), 3.37 (m, 2H), 3.24 (m,3H), 1.98 (m, 2H), 1.84 (m, 2H), 1.48 (s, 9H), LCMS (ESI) for $C_{21}H_{26}ClN_6OS$: m/z 474.9 (M+H$^+$, 100%).

Example 9.20

Preparation of [6-(1-Hexyl-piperidin-4-yloxy)-5-nitro-pyrimidin-4-yl]-(4-methanesulfonyl-phenyl)-amine (Compound A20)

General procedure; alkoxide substitution of (6-Chloro-5-nitro-pyrimidin-4-yl)-(4-methanesulfonyl-phenyl)-amine: In a 16 mL reaction vial was placed sodium hydride (25 mg, 60% in oil, 0.625 mmol) and 1.5 mL of THF. 1-Hexyl-piperidin-4-ol (30 mg, 0.162 mmol) was added to the suspension and the mixture was stirred for 20 min under N$_2$ at room temperature, followed by the addition of (6-chloro-5-nitro-pyrimidin-4-yl)-(4-methanesulfonyl-phenyl)-amine (41 mg, 0.125 mmol). After stirring overnight under $N_2$ at room temperature, all of the starting chloropyrimidines was completely converted as indicated by LCMS. The reaction mixture was then concentrated under vacuum and purified by preparative HPLC to give Compound A20. $^1$H NMR (CDCl$_3$, 400 MHz) δ 0.89 (m,2H), 1.37 (m, 6H), 1.80 (m, 2H), 2.21 (m,2H), 2.56 (m, 2H), 3.03 (m, 2H), 3.08 (s, 3H), 3.18 (m, 2H), 3.56 (m, 2H), 5.79 (m, 1H), 7.86 (d, 2H), 7.98 (d, 2H), 8.40 (s, 1H), 10.23 (s, 1H), 12.5 (s, 1H). Exact mass calculated for $C_{22}H_{31}N_5O_5S$ 477.20, found 478.4 (MH$^+$).

Example 9.21

Preparation of [6-(1-Cyclopropylmethyl-piperidin-4-yloxy)-5-nitro-pyrimidin-4-yl]-(4-methanesulfonyl-phenyl)-amine (Compound A21)

Compound A21 was prepared in a similar manner as described above using N-cyclopropanyl-4-hydroxy-piperidine. $^1$H NMR (CDCl$_3$, 400 MHz) δ 0.43 (m, 2H), 0.82 (m, 2H), 1.18 (m, 1H), 2.26 (m,2H), 2.56 (m, 2H), 3.01 (m, 2H), 3.08 (s, 3H), 3.25 (m, 2H), 3.69 (m, 2H), 5.80 (m, 1H), 7.87 (d, 2H), 7.97 (d, 2H), 8.44 (s, 1H), 10.24 (s, 1H), 12.0 (s, 1H). Exact mass calculated for $C_{20}H_{25}N_5O_5S$ 447.16, found 448.3 (MH$^+$).

Example 9.22

Preparation of 4-[6-(4-Methanesulfonyl-phenylamino)-5-nitro-pyrimidin-4-yloxy]-piperidine-1-carboxylic acid isopropyl ester (Compound A22)

General procedure for the syntheses of carbamates, pyridinamides, and sulfonamides. In a 16 mL reaction vessel was placed (4-methanesulfonyl-phenyl)-[5-nitro-6-(piperidin-4-yloxy)-pyrimidin-4-yl]-amine (i.e., Comound A2) (42 mg, 0.1 mmol), triethylamine (90 µl) and DMF (1.5 mL) was added to completely dissolve the solid material. Isopropyl chloroformate (0.15 mL, 1.0M in toluene) was added to the solution and the mixture was stirred 30 min under $N_2$ at room temperature. After all of the starting amine was completely converted as indicated by LCMS, the reaction was stopped by quenching with water. The reaction mixture was concentrated under vacuum and purified by preparative HPLC to give Compound A22, $^1$H NMR (CDCl$_3$, 400 MHz) δ 1.26 (d,6H), 1.89 (m, 2H), 1.93 (m,2H), 3.07 (s, 3H), 3.63 (m, 2H), 3.67 (m, 2H), 4.94 (m, 1H), 5.61 (m, 1H), 7.87 (d, 2H), 7.97 (d, 2H), 8.40 (s, 1H), 10.18 (s, 1H). Exact mass calculated for $C_{20}H_{25}N_5O_7S$ 479.15, found 480.4 (MH$^+$).

Example 9.23

Preparation of 4-[6-(4-Methanesulfonyl-phenylamino)-5-nitro-pyrimidin-4-yloxy]-piperidine-1-carboxylic Acid 2-isopropyl-5-methyl-cyclohexyl ester (Compound A23)

Compound A23 was prepared in a similar manner as described above using (4-methanesulfonyl-phenyl)-[5-nitro-6-(piperidin-4-yloxy)-pyrimidin-4-yl]-amine (i.e., Comound A2) (15 mg, 0.035 mmol), triethylamine (501 µl), menthyl chloroformate (10 mg, 0.046 mmol), DMF (0.6 mL), $^1$H NMR (CDCl$_3$, 400 MHz) δ 0.81 (d, 3H), 0.92 (d, 6H), 1.06 (m, 1H), 1.10 (m, 1H), 1.41 (m, 1H), 1.51 (m, 1H), 1.67 (m,2H), 1.94 (m, 4H), 2.08 (m, 2H), 3.08 (s, 3H), 3.65 (m, 4H), 4.58 (m, 1H), 5.60 (m, 1H), 7.86 (d, 2H), 7.97 (d, 2H), 8.41 (s, 1H), 10.18 (s, 1H). Exact mass calculated for $C_{27}H_{37}N_5O_7S$ 575.24, found 576.4 (MH$^+$).

Example 9.24

Preparation of {4-[6-(4-Methanesulfonyl-phenylamino)-5-nitro-pyrimidin-4-yloxy]-piperidin-1-yl}-pyridin-3-yl-methanone (Compound A24)

Compound A24 was prepared in a similar manner as described above using (4-methanesulfonyl-phenyl)-[5-nitro-6-(piperidin-4-yloxy)-pyrimidin-4-yl]-amine (i.e., Comound A2) (16 mg, 0.037 mmol), triethylamine (50 µl), nicotinoyl chloride (10 mg, 0.046 mmol), DMF (1 mL), $^1$H NMR (CDCl$_3$, 400 MHz) δ 1.95 (m, 2H), 2.14 (m,2H), 3.07 (s, 3H), 3.55 (m, 1H), 3.65 (m, 2H), 4.13 (m, 1H), 5.72 (m, 1H), 7.40 (m, 1H), 7.79 (m, 1H), 7.87 (d, 2H), 7.97 (d, 2H), 8.41 (s, 1H), 8.70 (m, 2H), 10.20 (s, 1H). Exact mass calculated for $C_{22}H_{22}N_6O_6S$ 498.13, found 499.3 (MH$^+$).

Example 9.25

Preparation of (2-Chloro-pyridin-3-yl)-{4-[6-(4-methanesulfonyl-phenylamino)-5-nitro-pyrimidin-4-yloxy]-piperidin-1-yl}-methanone (Compound A25)

Compound A25 was prepared in a similar manner as described above using (4-methanesulfonyl-phenyl)-[5-nitro-6-(piperidin-4-yloxy)-pyrimidin-4-yl]-amine (i.e., Comound A2) (16 mg, 0.037 mmol), triethylamine (50 µl), 2-chloro-nicotinoyl chloride (10 mg, 0.046 mmol), DMF (1 mL), $^1$H NMR (CDCl$_3$, 400 MHz) δ 1.91 (m,1H), 2.00 (m, 1H), 2.14 (m, 2H), 3.08 (s, 3H), 3.36 (m, 1H), 3.65 (m, 2H), 4.13 (m, 1H), 4.31 (m, 1H), 5.72 (m, 1H), 7.36 (m,1H), 7.69 (m, 1H), 7.87 (d, 2H), 7.97 (d, 2H), 8.41 (m, 1H), 8.47 (m, 1H), 10.20 (s, 1H). Exact mass calculated for $C_{22}H_{21}ClN_6O_6S$ 532.09, found 533.3 (MH$^+$).

Example 9.26

Preparation of {4-[6-(4-Methanesulfonyl-phenylamino)-5-nitro-pyrimidin-4-yloxy]-piperidin-1-yl}-pyridin-2-yl-methanone (Compound A26)

Compound A26 was prepared in a similar manner as described above using (4-methanesulfonyl-phenyl)-[5-nitro-6-(piperidin-4-yloxy)-pyrimidin-4-yl]-amine (i.e., Compound A2) (16 mg, 0.037 mmol), triethylamine (50 µl), pyridine-2-carbonyl chloride (10 mg, 0.046 mmol)[Pyridine-2-carbonyl chloride was prepared by refluxing picolinic acid with SOCl$_2$ for 3 hours and worked up in general method], DMF (1 mL), $^1$H NMR (CDCl$_3$, 400 MHz) δ 1.95 (m,2H), 2.13 (m,2H), 3.07 (s, 3H), 3.65 (m, 2H), 3.79 (m, 2H), 4.13 (m, 1H), 5.72 (m, 1H), 7.37 (m,1H), 7.67 (m, 1H), 7.81 (m, 1H), 7.87 (d, 2H), 7.97 (d, 2H), 8.41 (s, 1H), 8.60 (m, 2H), 10.19 (s, 1H). Exact mass calculated for $C_{22}H_{22}N_6O_6S$ 498.13, found 499.3 (MH$^+$).

Example 9.27

Preparation of (4-Methanesulfonyl-phenyl)-[6-(1-methanesulfonyl-piperidin-4-yloxy)-5-nitro-pyrimidin-4-yl]-amine (Compound A27)

Compound A27 was prepared in a similar manner as described above using (4-methanesulfonyl-phenyl)-[5-nitro- 6-(piperidin-4-yloxy)-pyrimidin-4-yl]-amine (i.e., Comound A2) (15 mg, 0.035 mmol), triethylamine (50 µl), methanesulfonyl chloride (10 mg, 0.087 mmol), DMF (1 mL), $^1$H NMR (CDCl$_3$, 400 MHz) δ 2.13 (m, 4H), 2.85 (s, 3H), 3.08 (s, 3H), 3.31 (m, 2H), 3.57 (m, 2H), 4.13 (m, 1H), 5.69 (m, 1H), 7.87 (d,2H), 7.98 (d, 2H), 8.42 (s, 1H), 10.21 (s, 1H). Exact mass calculated for C$_{17}$H$_{21}$N$_5$O$_7$S$_2$ 471.09, found 472.3 (MH$^+$).

Example 9.28

Preparation of (4-Methanesulfonyl-phenyl)-{5-nitro-6-[1-(propane-1-sulfonyl)-piperidin-4-yloxy]-pyrimidin-4-yl}-amine (Compound A28)

Compound A28 was prepared in a similar manner as described above using (4-methanesulfonyl-phenyl)-[5-nitro-6-(piperidin-4-yloxy)-pyrimidin-4-yl]-amine (i.e., Comound A2) (15 mg, 0.035 mmol), triethylamine (20 µl), propane-1-sulfonyl chloride (8 mg, 0.056 mmol), DMF (0.6 mL), $^1$H NMR (CDCl$_3$, 400 MHz) δ 1.09 (t,3H), 1.90 (m,2H), 2.07 (m,4H), 2.95 (m, 2H), 3.08 (s, 3H), 3.40 (m, 2H), 3.57 (m, 2H), 5.67 (m, 1H), 7.87 (d, 2H), 7.98 (d, 2H), 8.41 (s, 1H), 10.21 (s, 1H). Exact mass calculated for C$_{19}$H$_{25}$N$_5$O$_7$S$_2$ 499.12, found 500.3 (MH$^+$).

Example 9.29

Preparation of {6-[1-(Butane-1-sulfonyl)-piperidin-4-yloxy]-5-nitro-pyrimidin-4-yl}-(4-methanesulfonyl-phenyl)-amine (Compound A29)

Compound A29 was prepared in a similar manner as described above using (4-methanesulfonyl-phenyl)-[5-nitro-6-(piperidin-4-yloxy)-pyrimidin-4-yl]-amine (i.e., Comound A2) (15 mg, 0.035 mmol), triethylamine (20 µl), butane-1-sulfonyl chloride (8 mg, 0.056 mmol), DMF (0.6 mL), $^1$H NMR (CDCl$_3$, 400 MHz) δ 0.98 (t,3H), 1.51 (m,2H), 1.83 (m,2H), 2.07 (m,4H), 2.97 (m, 2H), 3.08 (s, 3H), 3.40 (m, 2H), 3.58 (m, 2H), 5.68 (m, 1H), 7.87 (d, 2H), 7.98 (d, 2H), 8.41 (s, 1H), 10.21 (s, 1H). Exact mass calculated for C$_{20}$H$_{27}$N$_5$O$_7$S$_2$ 513.14, found 514.4 (MH$^+$).

Example 9.30

Preparation of (4-Methanesulfonyl-phenyl)-{5-nitro-6-[1-(thiophene-2-sulfonyl)-piperidin-4-yloxy]-pyrimidin-4-yl}-amine (Compound A30)

Compound A30 was prepared in a similar manner as described above using (4-methanesulfonyl-phenyl)-[5-nitro-6-(piperidin-4-yloxy)-pyrimidin-4-yl]-amine (i.e., Comound A2) (15 mg, 0.035 mmol), triethylamine (20 µl), thiophene-2-sulfonyl chloride (9 mg, 0.049 mmol), DMF (0.6 mL), $^1$H NMR (CDCl$_3$, 400 MHz) δ 2.07 (m,4H), 3.08 (s, 3H), 3.14 (m, 2H), 3.41 (m, 2H), 5.53 (m, 1H), 7.31 (m, 1H), 7.50 (m, 1H), 7.55 (m, 1H), 7.83 (m,2H), 7.95 (m, 2H), 8.37 (s, 1H), 10.14 (s, 1H). Exact mass calculated for C$_{20}$H$_{21}$N$_5$O$_7$S$_3$ 539.06, found 540.2 (MH$^+$).

Example 9.31

Preparation of (4-Methanesulfonyl-phenyl)-{6-[1-(1-methyl-1H-imidazole-4-sulfonyl)-piperidin-4-yloxy]-5-nitro-pyrimidin-4-yl}-amine (Compound A31)

Compound A31 was prepared in a similar manner as described above using (4-methanesulfonyl-phenyl)-[5-nitro-6-(piperidin-4-yloxy)-pyrimidin-4-yl]-amine (i.e., Comound A2) (15 mg, 0.035 mmol), triethylamine (20 EL), 1-methyl-1H-imidazole-4-sulfonyl chloride (9 mg, 0.050 mmol), DMF (0.6 mL), $^1$H NMR (CDCl$_3$, 400 MHz) δ 2.07 (m, 4H), 3.08 (s, 3H), 3.32 (m, 2H), 3.53 (m, 2H), 3.79 (s,3H), 5.55 (m, 1H), 7.46 (s, 1H), 7.53 (s,1H), 7.85 (d,2H), 7.97 (d, 2H), 8.38 (s, 1H), 10.16 (s, 1H). Exact mass calculated for C$_{20}$H$_{23}$N$_7$O$_7$S$_2$ 537.11, found 538.4 (MH$^+$).

Example 9.32

Preparation of {6-[1-(2,4-Dimethyl-thiazole-5-sulfonyl)piperidin-4-yloxy]-5-nitro-pyrimidin-4-yl}-(4-methanesulfonyl-phenyl)-amine (Compound A32)

Compound A32 was prepared in a similar manner as described above using (4-methanesulfonyl-phenyl)-[5-nitro-6-(piperidin-4-yloxy)-pyrimidin-4-yl]-amine (i.e., Comound A2) (15 mg, 0.035 mmol), triethylamine (20 µL), 2,4-dimethyl-thiazole-5-sulfonyl chloride (10 mg, 0.047 mmol), DMF (0.6 mL), $^1$H NMR (CDCl$_3$, 400 MHz) δ 2.09 (m, 4H), 2.67 (s, 3H), 2.75 (s,3H), 3.08 (s, 3H), 3.21 (m, 2H), 3.50 (m, 2H), 5.58 (m, 1H), 7.85 (d, 2H), 7.97 (d, 2H), 8.38 (s, 1H), 10.14 (s, 1H). Exact mass calculated for C$_{21}$H$_{24}$N$_6$O$_7$S$_3$ 568.09, found 569.4 (MH$^+$).

Example 9.33

Preparation of 4-[5-Cyano-6-(3-fluoro-4-methanesulfonyl-phenylamino)-pyrimidin-4-yloxy]-piperidine-1-carboxylic acid tert-butyl ester (Compound A33)

Compound A33 was prepared in a similar manner as described in Example 9.1 as a yellow solid (78%). $^1$H NMR (CDCl$_3$, 400 MHz) δ 1.48 (s, 9H), 1.80-1.86 (m, 2H), 1.90-1.98 (m, 2H), 3.23 (s, 3H), 3.34-3.40 (m, 2H), 3.73-3.78 (m, 2H), 5.44-5.46 (m, 1H), 7.34-7.37 (m, 2H), 7.92-7.96 (m, 1H), 8.04-8.07 (m, 1H), 8.55 (s, 1H). Exact mass calculated for C$_{22}$H$_{26}$FN$_5$O$_5$S 491.1, found 492.3 (MH$^+$).

Example 9.34

Preparation of 4-[6-(2-Fluoro-4-methanesulfonyl-phenylamino)-5-nitro-pyrimidin-4-yloxy]-piperidine-1-carboxylic acid tert-butyl ester (Compound A34)

Compound A34 was prepared in a similar manner as described in Example 9.1 as a yellow solid (287 mg, 93%). $^1$H NMR 400 MHz CDCl$_3$ δ (ppm): 10.3 (s, NH), 8.69 (t, 1H), 8.45 (s, 1H), 7.78 (t, 2H), 5.60 (m,1H), 3.64-3.61 (m,2H), 3.56 (m,2H), 3.09 (s,3H), 1.97 (m,2H), 1.88-1.84 (m, 2H), 1.48 (s, 9H). Exact mass calculated for C$_{21}$H$_{26}$FN$_5$O$_7$S 511.15, LCMS (ESI) m/z 534.3 (M+H$^+$+Na, 100%).

Example 9.35

Preparation of 4-[5-Cyano-6-(4-methanesulfonyl-phenylamino)-pyrimidin-4-yloxy]-piperidine-1-carboxylic acid tert-butyl ester (Compound A35)

Compound A35 was prepared in a similar manner as described in Example 9.1 as a white solid (1.930 g, 72%). $^1$H NMR 400 MHz CDCl$_3$ δ (ppm): 8.51 (s, 1H), 7.96 (d, 2H), 7.86 (d, 2H), 7.37 (s, NH), 5.44 (m,1H), 3.78-3.73 (m,2H), 3.40-3.33 (m,2H), 3.07 (s,3H), 1.99 (m,2H), 1.85-1.82 (m, 2H), 1.48 (s, 9H). Exact mass calculated for $C_{22}H_{27}N_5O_5S$ 473.17, LCMS (ESI) m/z 474.1 (M+H$^+$, 100%).

Example 9.36

Preparation of 4-[6-(6-Methanesulfonyl-pyridin-3-ylamino)-5-nitro-pyrimidin-4-yloxy]-piperidine-1-carboxylic acid tert-butyl ester (Compound A36)

Compound A36 was prepared in a similar manner as described in Example 9.1 as a yellow solid (1.848 g, 76%). $^1$H NMR 400 MHz CDCl$_3$ δ (ppm): 10.2 (s, NH), 8.92 (s, 1H), 8.43 (d, 1H), 8.42 (s,1H), 8.13 (d,1H), 5.61 (m,1H), 3.64-3.61 (m,2H), 3.56-3.51 (m,2H), 3.24 (s, 3H), 1.96 (m,2H), 1.91-1.88 (m,2H), 1.48 (s,9H), Exact mass calculated for $C_{20}H_{26}N_6O_7S$ 494.16, LCMS (ESI) m/z 495.1 (M+H$^+$, 100%).

Example 9.37

Preparation of 4-[5-Acetyl-6-(6-methanesulfonyl-pyridin-3-ylamino)-pyrimidin-4-yloxy]-piperidine-1-carboxylic acid tert-butyl ester (Compound A37)

4-Hydroxy-piperidine-1-carboxylic acid tert-butyl ester (3.2 mmol, 633 mg) and sodium hydride (3.2 mmol, 76 mg) were dissolved in N,N-dimethyl acetamide (1.5 mL) and stirred for 30 minutes at room temperature. Subsequently, compound 1-[4-chloro-6-(6-methanesulfonyl-pyridin-3-ylamino)-pyrimidin-5-yl]-ethanone (0.63 mmol, 207 mg) was added. The reaction was stirred at 70° C. for 30 minutes. Progress of the reaction was monitored by thin layer chromatography and LCMS. Sodium hydride was carefully quenched with water and the desired compound was extracted with ethyl acetate. Organic solvents were evaporated in vacuo and purified by flash chromatography (Silica gel 60; 50/50 EtoAc/Hexanes) to afford Compound A37 as a yellow solid (156 mg, 50%). $^1$H NMR (400 MHz, CDCl$_3$) δ (ppm): 12.19 (s, 1H), 8.95 (s, 1H), 8.56 (d, 1H), 8.44 (s, 1H), 8.07 (d, 1H), 5.56 (h, 1H), 3.82 (m, 2H), 3.31 (m, 2H), 3.23 (s, 3H), 2.70 (s, 3H), 2.11 (m, 2H), 1.85 (m, 2H), 1.48 (s, 9H). LCMS (ESI), m/z 492.4 (M+H+, 100%).

Example 9.38

Preparation of 4-[5-Amino-6-(2-fluoro-4-methanesulfonyl-phenylamino)-pyrimidin-4-yloxy]-piperidine-1-carboxylic acid tert-butyl ester (Compound A38)

Compound A34 was subjected to hydrogenation conditions, H$_2$ in the presence of 10% Pd/C and ethyl acetate to provide compound A38 as a yellow solid (503 mg, 89%). $^1$H NMR 400 MHz CDCl$_3$ δ (ppm): 8.63 (t, 1H), 8.18 (s, 1H), 7.72 (d, 1H), 7.69 (d, 1H), 7.16 (s, NH), 5.32 (m,1H), 3.82 (m,2H), 3.30-3.24 (m,2H), 3.05 (s,3H), 2.03 (m,2H), 1.76 (m, 2H), 1.48 (s, 9H). Exact mass calculated for $C_{21}H_{28}FN_5O_5S$ 481.18, LCMS (ESI) m/z 482.3 (M+H$^+$, 100%).

Example 9.39

Preparation of 4-[5-Cyano-6-(4-methanesulfonyl-phenylamino)-pyrimidin-4-yloxy]-piperidine-1-carboxylic acid isopropyl ester (Compound A39)

Compound A39 was obtained in a similar manner as described in Example 9.10 as a solid (80%). $^1$H NMR (CDCl$_3$, 400 MHz) δ 1.26 (d, 6H), 1.82-1.86 (m, 2H), 1.90-1.99 (m, 2H), 3.07 (s, 3H), 3.39-3.45 (m, 2H), 3.76-3.82 (m, 2H), 4.94 (sept, 1H), 5.44-5.48 (m, 1H), 7.37 (s, 1H), 7.85-7.87 (m, 2H), 7.95-7.97 (m, 2H), 8.52 (s, 1H). Exact mass calculated for $C_{21}H_{25}N_5O_5S$ 459.2, found 460.2 (MH$^+$).

Example 9.40

Preparation of 4-[5-Cyano-6-(4-methanesulfonyl-phenylamino)-pyrimidin-4-yloxy]-piperidine-1-carboxylic Acid Ethyl Ester (Compound A40)

Compound A40 was obtained in a similar manner as described in Example 9.10 as a solid (75%). $^1$H NMR (CDCl$_3$, 400 MHz) δ 1.28 (t, 3H), 1.82-1.86 (m, 2H), 1.90-1.99 (m, 2H), 3.07 (s, 3H), 3.39-3.45 (m, 2H), 3.76-3.82 (m, 2H), 4.16 (q, 2H), 5.44-5.48 (m, 1H), 7.37 (s, 1H), 7.85-7.87 (m, 2H), 7.95-7.97 (m, 2H), 8.52 (s, 1H). Exact mass calculated for $C_{20}H_{23}N_5O_5S$ 445.1, found 446.2 (MH$^+$).

Example 9.41

Preparation of 4-[5-Cyano-6-(4-methanesulfonyl-phenylamino)-pyrimidin-4-yloxy]-piperidine-1-carboxylic Acid Isobutyl Ester (Compound A41)

Compound A41 was obtained in a similar manner as described in Example 9.10 as a solid (76%). $^1$H NMR (CDCl$_3$, 400 MHz) δ 0.95 (d, 6H), 1.82-1.86 (m, 2H), 1.90-1.99 (m, 2H), 3.07 (s, 3H), 3.42-3.48 (m, 2H), 3.76-3.82 (m, 2H), 3.89 (d, 2H), 5.44-5.48 (m, 1H), 7.37 (s, 11H), 7.85-7.87 (m, 2H), 7.95-7.97 (m, 2H), 8.52 (s, 1H). Exact mass calculated for $C_{22}H_{27}N_5O_5S$ 473.2, found 474.3 (MH$^+$).

Example 9.42

Preparation of 4-(4-Methanesulfonyl-phenylamino)-6-[1-(tetrahydro-furan-2-carbonyl)-piperidin-4-yloxy]-pyrimidine-5-carbonitrile (Compound A42)

Compound A42 was obtained in a similar manner as described in Example 9.24 as a solid (75%). $^1$H NMR (CDCl$_3$, 400 MHz) δ 1.87-2.06 (m, 8H), 2.31-2.34 (m, 1H), 3.07 (s, 3H), 3.49-3.50 (m, 1H), 3.74-3.99 (m, 4H), 4.64 (t, 1H), 5.54-5.56 (m, 1H), 7.40-7.42 (m, 1H), 7.85-7.88 (m, 2H), 7.95-7.97 (m, 2H), 8.52 (s, 1H). Exact mass calculated for $C_{22}H_{25}N_5O_5S$ 471.2, found 472.2 (MH$^+$).

Example 9.43

Preparation of 4-[1-(3,3-Dimethyl-2-oxo-butyl)-piperidin-4-yloxy]-6-(4-methanesulfonyl-phenylamino)-pyrimidine-5-carbonitrile (Compound A43)

Compound A43 was obtained in a similar manner as described in Example 9.5 as a solid (70%). $^1$H NMR (CDCl$_3$, 400 MHz) δ 1.17 (s, 9H), 1.95-1.99 (m, 2H), 2.00-2.11 (m, 2H), 2.48-2.52 (m, 2H), 2.70-2.75 (m, 2H), 3.07 (s, 3H), 3.48 (s, 2H), 5.44-5.48 (m, 1H), 7.37 (s, 1H), 7.85-7.87 (m, 2H), 7.95-7.97 (m, 2H), 8.52 (s, 1H). Exact mass calculated for $C_{23}H_{29}N_5O_4S$ 471.2, found 472.2 ($MH^+$).

Example 9.44

Preparation of 4-(4-Methanesulfonyl-phenylamino)-6-[1-(pyridine-3-carbonyl)-piperidin-4-yloxy]-pyrimidine-5-carbonitrile (Compound A44)

Compound A44 was obtained in a similar manner as described in Example 9.24 as a solid (88%). $^1$H NMR (CDCl$_3$, 400 MHz) δ 1.80-2.14 (m, 4H), 3.07 (s, 3H), 3.40-4.01 (m, 4H), 5.56-5.60 (m, 1H), 7.38-7.44 (m, 2H), 7.79-7.81 (m, 1H), 7.85-7.87 (m, 2H), 7.95-7.97 (m, 2H), 8.52 (s, 1H), 8.70 (s, 1H). Exact mass calculated for $C_{23}H_{22}N_6O_4S$ 478.1, found 479.3 ($MH^+$).

Example 9.45

Preparation of 4-(1-Formyl-piperidin-4-yloxy)-6-(4-methanesulfonyl-phenylamino)-pyrimidine-5-carbonitrile (Compound A45)

Compound A45 was obtained in a similar manner as described in Example 9.24 as a solid (60%). $^1$H NMR (CDCl$_3$, 400 MHz) δ 1.93-2.07 (m, 4H), 3.07 (s, 3H), 3.42-3.48 (m, 1H), 3.66-3.76 (m, 3H), 5.56-5.60 (m, 1H), 7.36 (s, 1H), 7.85-7.87 (m, 2H), 7.96-7.98 (m, 2H), 8.13 (s, 1H), 8.53 (s, 1H). Exact mass calculated for $C_{18}H_{19}N_5O_4S$ 401.1, found 402.4 ($MH^+$).

Example 9.46

Preparation of 4-(4-Methanesulfonyl-phenylamino)-6-[1-(pyridine-2-carbonyl)-piperidin-4-yloxy]-pyrimidine-5-carbonitrile (Compound A46)

Compound A46 was obtained in a similar manner as described in Example 9.24 as a solid (23%). $^1$H NMR (CDCl$_3$, 400 MHz) δ 1.90-2.14 (m, 4H), 3.07 (s, 3H), 3.46-3.48 (m, 1H), 3.69-3.97 (m, 3H), 5.56-5.60 (m, 1H), 7.47 (s, 1H), 7.54-7.58 (m, 1H), 7.70-7.72 (m, 1H), 7.85-7.87 (m, 2H), 7.95-7.97 (m, 2H), 8.01-8.03 (m, 1H), 8.52 (s, 1H), 8.73-8.74 (m, 1H). Exact mass calculated for $C_{23}H_{22}N_6O_4S$ 478.1, found 479.2 ($MH^+$).

Example 9.47

Preparation of 4-[5-Cyano-6-(2-fluoro-4-isopropylamino-phenylamino)-pyrimidin-4-yloxy]-piperidine-1-carboxylic acid isopropyl ester (Compound A63)

4-[5-Cyano-6-(2-fluoro-4-iodo-phenylamino)-pyrimidin-4-yloxy]-piperidine-1-carboxylic acid isopropyl ester (250 mg, 0.48 mmol), isopropylamine (408 µL, 4.8 mmol), proline (99 mg, 0.86 mmol), copper iodide (92 mg, 0.48 mmol) and potassium carbonate (152 mg, 1.1 mmol) were mixed together in DMSO (4 mL). The reaction vessel was heated in a microwave at 80° C. for 1.0 hour. Progress of the reaction was monitored by TLC and LCMS. Purification by HPLC afforded compound A63 as a white solid (50 mg, 23%). $^1$H NMR (CDCl$_3$, 400 MHz) δ 8.37 (s, 1H), 7.99 (t, 1H), 7.12 (s, 1H), 6.93 (t, 2H), 5.38 (h, 1H), 4.87 (h, 1H), 3.72 (m, 2H), 3.52 (m, 1H), 1.91 (m, 2H), 1.77 (m, 2H), 1.92 (m, 2H), 1.26 (d, 6H), 1.13 (d, 6H). Exact mass calculated for $C_{23}H_{29}FN_6O_3$ 456.51, found 457.1 ($MH^+$).

Example 9.48

Preparation of 4-[5-Cyano-6-(2-fluoro-4-propylamino-phenylamino)-pyrimidin-4-yloxy]-piperidine-1-carboxylic acid isopropyl ester (Compound A64)

4-[5-Cyano-6-(2-fluoro-4-iodo-phenylamino)-pyrimidin-4-yloxy]-piperidine-1-carboxylic acid isopropyl ester (250 mg, 0.48 mmol), n-propylamine (408 µL, 4.8 mmol), proline (99 mg, 0.86 mmol), copper iodide (92 mg, 0.48 mmol) and potassium carbonate (152 mg, 1.1 mmol) were mixed together in DMSO (4 mL). The reaction vessel was heated in a microwave at 80° C. for 30 minutes. Progress of the reaction was monitored by TLC and LCMS. Purification by HPLC afforded compound A64 as a white solid (80 mg, 37%). $^1$H NMR (CDCl$_3$, 400 MHz) δ 9.37 (s, 1H), 8.22 (s, 1H), 6.91 (t, 1H), 6.91 (m, 2H), 5.27 (h, 1H), 4.71 (h, 1H), 3.53 (m, 2H), 3.23 (m, 2H), 2.91 (m, 2H), 1.85 (m, 2H), 1.54 (m, 4H), 1.13 (d, 6H), 0.88 (t, 3H). Exact mass calculated for $C_{23}H_{29}FN_6O_3$ 456.51, found 457.4 ($MH^+$).

Example 9.49

Preparation of 4-[5-Cyano-6-(2-fluoro-4-propoxy-phenylamino)-pyrimidin-4-yloxy]-piperidine-1-carboxylic acid isopropyl ester (Compound A65)

A mixture of 4-[5-cyano-6-(2-fluoro-4-iodo-phenylamino)-pyrimidin-4-yloxy]-piperidine-1-carboxylic acid isopropyl ester (250 mg, 0.48 mmol), propan-1-ol (2 mL, excess), copper iodide (9.1 mg, 0.048 mmol), 1,10-phenanthroline (18.1 mg, 0.096 mmol) and cesium carbonate (313 mg, 0.96 mmol) in dioxane (3.5 mL) was heated under microwave irradiation for 30 min at 90° C. The crude mixture was concentrated in vacuo and purified by HPLC to provide compound A65 as a white solid (10 mg, 12%). Exact mass calculated for $C_{23}H_{28}FN_5O_4$ 457.50, found 458.8 ($MH^+$).

Example 9.50

Preparation of 4-[5-Cyano-6-(6-propyl-pyridin-3-ylamino)-pyrimidin-4-yloxy]-piperidine-1-carboxylic acid isopropyl ester (Compound A66)

In a 25 mL round-bottomed flask fitted with a condenser and $N_2$ inlet was placed 4-[6-(6-chloro-pyridin-3-ylamino)-5-cyano-pyrimidin-4-yloxy]-piperidine-1-carboxylic acid isopropyl ester (100 mg, 1.3 mmol), n-propylzinc bromide (0.5M in THF, 0.72 mL), tetrakis (triphenylphosphino)palladium (28 mg, 0.024 mmol), and THF (3.5 mL). The reaction mixture was refluxed overnight under $N_2$ atmosphere. The product was purified by preparative HPLC. $^1$H NMR (CDCl$_3$, 400 MHz) δ 1.03 (t, 3H), 1.26 (d, 6H), 1.85 (m, 4H), 1.98 (m, 2H), 3.04 (t, 2H), 3.44 (m, 2H), 3.77 (m, 2H), 4.94 (m, 1H), 5.46 (m, 1H), 7.57 (d, 1H), 8.34 (s, 1H), 8.51 (s, 1H), 8.56 (d, 1H), 9.42 (s, 1H). Exact mass calculated for $C_{22}H_{28}N_6O_3$ 424.22, found 425.2 ($MH^+$).

Example 9.51

Preparation of 4-{5-Cyano-6-[4-(2-dimethylamino-ethylsulfanyl)-2-fluoro-phenylamino]-pyrimidin-4-yloxy}-piperidine-1-carboxylic acid isopropyl ester (Compound A67)

In a microwave reaction tube was placed 4-[5-cyano-6-(2-fluoro-4-iodo-phenylamino)-pyrimidin-4-yloxy]-piperidine-1-carboxylic acid isopropyl ester (10 mg, 0.19 mmol), 2-dimethylamino-ethanethiol (27 mg, 0.19 mmol), di-m-bromobis (tri-t-butylphosphino)dipalladium (I) (8 mg, 0.0095 mmol), sodium t-butoxide (55 mg, 0.57 mmol), and DMSO (0.5 mL). The reaction mixture was heated at 120° C. under microwave for 4 hours. The resulting mixture was filtered through a syringe filter and purified by preparative HPLC. $^1$H NMR (CDCl$_3$, 400 MHz) δ 1.26 (d, 6H), 1.86 (m, 2H), 2.00 (m, 2H), 2.86 (s, 6H), 3.20 (m, 2H), 3.30 (m, 2H), 3.43 (m, 2H), 3.78 (m, 2H), 4.94 (m, 1H), 5.44 (m, 1H), 7.22 (s, 1H), 7.24 (s, 1H), 7.35 (s, 1H), 8.11 (t, 1H), 8.45 (s, 1H). Exact mass calculated for $C_{24}H_{31}FN_6O_3S$ 502.22, found 503.2 (MH$^+$).

Example 9.52

Preparation of 4-{5-Cyano-6-[4-(2-dimethylamino-ethanesulfonyl)-2-fluoro-phenylamino]-3-oxy-pyrimidin-4-yloxy}-piperidine-1-carboxylic acid isopropyl ester (Compound A68)

In a 50 mL round-bottomed flask immersed in an ice-bath was place a stir bar, 4-{5-cyano-6-[4-(2-dimethylamino-ethylsulfanyl)-2-fluoro-phenylamino]-pyrimidin-4-yloxy}-piperidine-1-carboxylic acid isopropyl ester (25 mg, 0.04 mmol) and CH$_2$Cl$_2$ (15 mL). mCPBA (20 mg, 0.089 mmol) dissolved in CH$_2$Cl$_2$ (2 mL) was added dropwise at 0° C. The resulting mixture was stirred at 0° C. for 1 h and subsequently quenched with sodium bisulfite solution. The organic layer was separated. The aqueous layer was extracted with CH$_2$Cl$_2$. The combined organic extracts was dried and concentrated under vacuum to give the crude product. The crude was purified by preparative HPLC. Exact mass calculated for $C_{24}H_{31}FN_6O_6S$ 550.20, found 551.2 (MH$^+$).

Example 9.53

Preparation of 4-[5-Cyano-6-(2-fluoro-4-morpholin-4-yl-phenylamino)-pyrimidin-4-yloxy]-piperidine-1-carboxylic acid isopropyl ester (Compound A71)

A mixture of 4-[5-cyano-6-(2-fluoro-4-iodo-phenylamino)-pyrimidin-4-yloxy]-piperidine-1-carboxylic acid isopropyl ester (60 mg, 0.114 mmol), morpholine (50 µL, 0.571 mmol), CuI (21 mg, 0.114 mmol), proline (23 mg, 0.205 mmol) and potassium carbonate (36 mg, 0.262 mmol) in DMSO (1 mL) was heated in microwave for 30 minutes at 80° C. The mixture was purified by HPLC to give Compound A71 as a solid (25.1 mg, 45%). $^1$H NMR (CDCl$_3$, 400 MHz) δ (ppm): 8.31 (s, 1H), 7.61 (t, 1H), 7.08 (s, 1H), 6.69 (m, 2H), 5.35 (m, 1H), 4.86 (m, 1H), 3.82 (m, 4H), 3.68 (m, 2H), 3.38 (m, 2H), 3.19 (m, 4H), 1.90 (m, 2H), 1.75 (m, 2H), 1.18 (d, 6H). Exact mass calculated for $C_{24}H_{29}FN_6O_4$ 484.22, found 485.2 (MH$^+$).

Example 9.54

Preparation of 4-[5-Cyano-6-(4-dimethylamino-2-fluoro-phenylamino)-pyrimidin-4-yloxy]-piperidine-1-carboxylic acid isopropyl ester (Compound A73)

Compound A73 was prepared in a similar procedure as described in Example 9.53 as a brownish solid (20 mg, 39.6%). $^1$H NMR (CDCl$_3$, 400 MHz) δ (ppm): 8.41 (s, 1H), 7.97 (t, 1H), 7.37 (s, 1H), 6.99 (m, 2H), 5.42 (m, 1H), 4.92 (m, 1H), 3.73 (m, 2H), 3.44 (m, 2H), 3.09 (s, 6H), 1.95 (m, 2H), 1.85 (m, 2H), 1.23 (d, 6H). Exact mass calculated for $C_{22}H_{27}FN_6O_3$ 442.49, found 443.3 (MH$^+$).

Example 9.55

Preparation of 4-[6-(2-Fluoro-4-methanesulfonyl-phenylamino)-5-methyl-pyrimidin-4-yloxy]-piperidine-1-carboxylic acid isopropyl ester (Compound A75)

Compound A75 was obtains as a tan solid (HCl salt, 219 mg, 21%). $^1$H NMR (MeOH-d$_4$, 400 MHz) δ 1.17-1.18 (d, 6H), 1.66-1.78 (m, 2H), 1.87-2.01 (m, 2H), 2.12 (s, 3H), 3.10 (s, 3H), 3.18-3.234 (m, 1H), 3.36 (m, 2H), 3.53-3.73 (m, 2H), 5.28-5.39 (m, 1H), 7.73-7.88 (m, 3H), 8.25 (s, 1H). Exact mass calculated for $C_{21}H_{27}FN_4O_5S$ 466.17, found 467.5 (MH$^+$).

Example 9.56

Preparation of 4-[6-(2-Fluoro-4-iodo-phenylamino)-5-methyl-pyrimidin-4-yloxy]-piperidine-1-carboxylic acid isopropyl ester (Compound A77)

Step 1: Preparation of the 4-(6-Chloro-5-methyl-pyrimidin-4-yloxy)-piperidine-1-carboxylic acid isopropyl ester To a solution of 4-hydroxy-piperidine-1-carboxylic acid isopropyl ester (6.26 g, 33.4 mmol) and 4,6-dichloro-5-methyl-pyrimidine (5.45 g, 33.4 mmol) in 100 mL THF, 1M potassium tert-butoxide in THF (40 mL, 40 mmol) were added slowly by syringe pump. After 1 hour, everything had been added and mixture was concentrated. Residue was extracted with methylene chloride and water. Organic phases were dried over magnesium sulfate, filtered, and concentrated to give 4-(6-chloro-5-methyl-pyrimidin-4-yloxy)-piperidine-1-carboxylic acid isopropyl ester as a pale yellow solid (10.3 g, 98%). $^1$H NMR (CDCl$_3$, 400 MHz) δ 1.22-1.24 (d, 6H), 1.74-1.81 (m, 2H), 1.95-2.04 (m, 2H), 2.24 (s, 3H), 3.40-3.45 (m, 2H), 3.74-3.81 (m, 2H), 4.90-4.98 (m, 1H), 5.31-5.37 (m, 1H), 8.40 (s, 1H).

Step 2: Preparation of 4-[6-(2-Fluoro-4-iodo-phenylamino)-5-methyl-pyrimidin-4-yloxy]-piperidine-1-carboxylic acid isopropyl ester (Compound A77)

A mixture of 4-(6-chloro-5-methyl-pyrimidin-4-yloxy)-piperidine-1-carboxylic acid isopropyl ester (2.58 g, 8.22 mmol), palladium acetate (185 mg, 0.82 mmol), biphenyl-3-yl-di-tert-butyl-phosphane (25 mg, 0.08 mmol), sodium tert-butoxide (2.4 g, 21.2 mmol), and 4-iodo-2-fluoro aniline (2.0 g, 8.4 mmol) in 15 mL dioxane was heated in microwave for 1 hour at 120° C. Solids were filtered off and mixture was purified by column chromatography and precipitating out of hexane/AcOEt to give compound A77 as a tanned solid (1.99 g, 47%). $^1$H NMR (CDCl$_3$, 400 MHz) δ 1.15-1.16 (d, 6H), 1.61-1.71 (m, 2H), 1.85-1.90 (m, 2H), 1.99 (s, 3H), 3.27-3.33 (m, 2H), 3.63-3.66 (m, 2H), 4.82-4.85 (m, 1H), 5.20-5.23 (m, 1H), 6.35-6.36 (d, 1H), 7.33-7.36 (m, 2H), 8.08-8.13 (m, 1H), 8.22 (s, 1H). Exact mass calculated for C$_{20}$H$_{24}$F$_1$N$_4$O$_3$ 514.09, found 515.2 (MH$^+$).

Example 9.57

Preparation of 4-[6-(2-Fluoro-4-morpholin-4-yl-phenylamino)-5-methyl-pyrimidin-4-yloxy]-piperidine-1-carboxylic acid isopropyl ester (Compound A79)

Compound A79 was obtained in a similar manner as described in Example 9.47 as a white solid (HCl salt, 401 mg, 38%). $^1$H NMR (MeOH-d$_4$, 400 MHz) δ 1.03-1.05 (d, 6H), 1.53-1.68 (m, 3H), 1.79-1.88 (m, 2H), 1.98 (s, 3H), 3.05-3.09 (m, 3H), 3.15-3.25 (m, 2H), 3.49-3.57 (m, 3H), 3.62-3.65 (m, 4H), 4.69-4.63 (m, 1H), 5.24-5.28 (m, 1H), 6.74-6.80 (m, 1H), 7.08-7.12 (m, 1H), 8.06 (s, 1H). Exact mass calculated for C$_{25}$H$_{32}$FN$_5$O$_4$ 473.24, found 474.7 (MH$^+$).

Example 9.58

Preparation of 4-[6-(2,5-Difluoro-4-propoxy-phenylamino)-5-methyl-pyrimidin-4-yloxy]-piperidine-1-carboxylic acid isopropyl ester (Compound A80)

A mixture of 4-(6-chloro-5-methyl-pyrimidin-4-yloxy)-piperidine-1-carboxylic acid isopropyl ester (330 mg, 1.05 mmol), palladium acetate (23.6 mg, 0.01 mmol), biphenyl-3-yl-di-tert-butyl-phosphane (4 mg, 0.013 mmol), sodium tert-butoxide (330 mg, 3.43 mmol), and 2,5-difluoro-4-propoxy-phenylamine (HCl salt, 235 mg, 1.05 mmol) in 15 mL dioxane was heated in microwave for 1 hour at 120° C. Mixture was purified by HPLC and treated with THF to give compound A80 as a white solid (HCl salt, 140 mg, 27%). $^1$H NMR (CDCl$_3$, 400 MHz) δ 0.88-0.92 (t, 3H), 1.08-1.09 (d, 6H), 1.62-1.73 (m, 4H), 1.83-1.91 (m, 2H), 2.02 (s, 3H), 3.22-3.30 (m, 2H), 3.53-3.60 (m, 2H), 3.88-3.91 (t, 2H), 4.70-4.74 (m, 1H), 5.29-5.30 (m, 1H), 6.99-7.04 (m, 1H), 7.10-7.15 (m, 1H), 8.12 (s, 1H). Exact mass calculated for C$_{23}$H$_{30}$F$_2$N$_4$O$_4$ 464.22, found 465.4 (MH$^+$).

Example 9.59

Preparation of 4-[6-(2-Fluoro-4-propylamino-phenylamino)-5-methyl-pyrimidin-4-yloxy]-piperidine-1-carboxylic acid isopropyl ester (Compound A81)

A mixture of 4-[6-(2-fluoro-4-iodo-phenylamino)-5-methyl-pyrimidin-4-yloxy]-piperidine-1-carboxylic acid isopropyl ester (100 mg, 196 mmol), L-proline (45 mg, 0.39 mmol), copper iodide (37.6 mg, 0.198 mmol), and propylamine (321 µl, 3.91 mmol) in 4 mL DMSO was heated in microwave for 1 hour at 80° C. Mixture was purified by HPLC to give Compound A81 as a white solid (TFA salt, 108.6 mg, 99%). $^1$H NMR (MeOH-d$_4$, 400 MHz) δ 0.80-0.84 (t, 3H), 1.06-1.07 (d, 6H), 1.44-1.50 (m, 2H), 1.57-1.62 (m, 2H), 1.79-1.97 (m, 2H), 1.97 (s, 3H), 2.90-2.93 (m, 2H), 3.20-3.29 (m, 2H), 3.54-3.58 (m, 2H), 4.684.72 (m, 1H), 5.23-5.26 (m, 1H), 6.37-6.41 (m, 1H), 6.96-7.00 (m, 1H), 8.01 (s, 1H). Exact mass calculated for C$_{22}$H$_{32}$FN$_5$O$_3$ 445.25, found 446.3 (MH$^+$).

Example 9.60

Preparation of 4-{6-[2-Fluoro-4-(2-methoxy-ethylamino)-phenylamino]-5-methyl-pyrimidin-4-yloxy}-piperidine-1-carboxylic acid isopropyl ester (Compound A82)

A mixture of 4-[6-(2-fluoro-4-iodo-phenylamino)-5-methyl-pyrimidin-4-yloxy]-piperidine-1-carboxylic acid isopropyl ester (100 mg, 196 mmol), 1-proline (45 mg, 0.39 mmol), copper iodide (37.6 mg, 0.198 mmol), and 2-methoxyethylamine (340 µl, 3.91 mmol) in 4 mL DMSO was heated in microwave for 1 hour at 80° C. Mixture was purified by HPLC to give Compound A82 as a white solid (TFA salt, 101.7 mg, 90%). $^1$H NMR (MeOH-d$_4$, 400 MHz) δ 1.21-1.22 (d, 6H), 1.71-1.78 (m, 2H), 1.96-2.01 (m, 2H), 2.13 (s, 3H), 3.34 (s, 3H), 3.34-3.45 (m, 2H), 3.53-3.56 (t, 2H), 3.70-3.73 (m, 2H), 4.81-4.87 (m, 1H), 5.38-5.42 (m, 1H), 6.64-6.57 (m, 1H), 7.09-7.13 (m, 1H), 8.17 (s, 1H). Exact mass calculated for C$_{22}$H$_{32}$FN$_5$O$_3$ 461.24, found 462.4 (MH$^+$).

Example 9.61

Preparation of 4-(6-{2-Fluoro-4-[(tetrahydro-furan-2-ylmethyl)-amino]-phenylamino}-5-methyl-pyrimidin-4-yloxy)-piperidine-1-carboxylic acid isopropyl ester (Compound A83)

A mixture of 4-[6-(2-fluoro-4-iodo-phenylamino)-5-methyl-pyrimidin-4-yloxy]-piperidine-1-carboxylic acid isopropyl ester (100 mg, 196 mmol), L-proline (45 mg, 0.39 mmol), copper iodide (37.6 mg, 0.198 mmol), and C-(tetrahydro-furan-2-yl)-methylamine (404 µl, 3.91 mmol) in 4 mL DMSO was heated in microwave for 1 hour at 80° C. Mixture was purified by HPLC to give Compound A83 as a white solid (TFA salt, 119 mg, 100%). $^1$H NMR (MeOH-d$_4$, 400 MHz) δ 1.51-1.53 (d, 6H), 1.90-2.10 (m, 3H), 2.12-2.38 (m, 5H), 2.43 (s, 3H), 3.40-3.49 (m, 2H), 3.75-3.83 (m, 2H), 3.98-4.06 (m, 3H), 4.10-4.19 (m, 1H), 4.30-4.38 (m, 1H), 5.13-5.17 (m, 1H), 5.69-5.72 (m, 1H), 6.85-6.87 (m, 2H), 7.37-7.41 (m, 1H), 8.47 (s, 1H). Exact mass calculated for C$_{22}$H$_{32}$FN$_5$O$_3$ 487.26, found 488.3 (MH$^+$).

Example 9.62

Preparation of 4-{6-[2-Fluoro-4-(2-methanesulfonyl-ethylamino)-phenylamino]-5-methyl-pyrimidin-4-yloxy}-piperidine-1-carboxylic acid isopropyl ester (Compound A84)

A mixture of 4-[6-(2-fluoro-4-iodo-phenylamino)-5-methyl-pyrimidin-4-yloxy]-piperidine-1-carboxylic acid isopropyl ester (100 mg, 196 mmol), 1-proline (45 mg, 0.39 mmol), copper iodide (37.6 mg, 0.198 mmol), and 2-methanesulfonyl-ethylamine (307 µl, 2.5 mmol) in 4 mL DMSO was heated in microwave for 1 hour at 80° C. Mixture was purified by HPLC to give Compound A84 as a white solid (TFA salt, 52.9 mg, 44%). $^1$H NMR (MeOH-d$_4$, 400 MHz) δ 1.17-1.18 (d, 6H), 1.68-1.72 (m, 2H), 1.91-1.95 (m, 2H), 2.08 (s, 3H), 2.93 (s, 3H), 3.28-3.37 (m, 4H), 3.58-3.67 (m, 4H), 4.78-4.82 (m, 1H), 5.32-5.36 (m, 1H), 6.48-6.53 (s, 2H), 7.06-7.10 (m, 1H), 8.11 (s, 1H). Exact mass calculated for C$_{23}$H$_{32}$FN$_5$O$_5$S 509.21, found 510.5 (MH$^+$).

Example 9.63

Preparation of 4-(6-{2-Fluoro-4-[(2-methanesulfonyl-ethyl)-methyl-amino]-phenylamino}-5-methyl-pyrimidin-4-yloxy)-piperidine-1-carboxylic acid isopropyl ester (Compound A85)

A mixture of 4-[6-(2-fluoro-4-iodo-phenylamino)-5-methyl-pyrimidin-4-yloxy]-piperidine-1-carboxylic acid isopropyl ester (100 mg, 196 mmol), L-proline (45 mg, 0.39 mmol), copper iodide (37.6 mg, 0.198 mmol), and (2-Methanesulfonyl-ethyl)-methyl-amine (268 µl, 1.95 mmol) in 4 mL DMSO was heated in microwave for 3 hours at 80° C. and for 2 hours at 90° C. Mixture was purified by HPLC to give Compound A85 as a white solid (TFA salt, 22.4 mg, 18%). $^1$H NMR (MeOH-d$_4$, 400 MHz) δ 1.04-1.06 (d, 6H), 1.51-1.62 (m, 2H), 1.78-1.89 (m, 2H), 1.95 (s, 3H), 2.79 (s, 3H), 2.82 (s, 3H), 3.19-3.23 (m, 4H), 3.50-3.60 (m, 2H), 3.68-3.72 (t, 2H), 4.66-4.70 (m, 1H), 5.19-5.22 (m, 1H), 6.50-6.53 (m, 2H), 7.01-7.06 (m, 1H), 7.96 (s, 1H). Exact mass calculated for $C_{24}H_{34}FN_5O_5S$ 523.23, found 524.4 (MH$^+$).

Example 9.64

Preparation of 4-[6-(4-Bromo-2,5-difluoro-phenylamino)-5-methyl-pyrimidin-4-yloxy]-piperidine-1-carboxylic acid isopropyl ester (Compound A86)

A mixture of 4-(6-chloro-5-methyl-pyrimidin-4-yloxy)-piperidine-1-carboxylic acid isopropyl ester (1.03 g, 3.28 mmol), palladium acetate (74 mg, 0.33 mmol), biphenyl-3-yl-di-tert-butyl-phosphane (9.7 mg, 0.033 mmol), sodium tert-butoxide (708 mg, 7.36 mmol), and 4-bromo-2,5-difluoro-phenylamine (706 mg, 3.39 mmol) in 15 mL dioxane was heated in microwave for 1 hour at 120° C. Solids were filtered off and mixture was purified by column chromatography (hexane/AcOEt) and crystallized from hexane/AcOEt to give compound A86 as a tanned solid (652 mg, 41%). $^1$H NMR (CDCl$_3$, 400 MHz) δ 1.04-1.05 (d, 6H), 1.50-1.61 (m, 2H), 1.74-1.82 (m, 2H), 1.89 (s, 3H), 3.16-3.22 (m, 2H), 3.51-3.60 (m, 2H), 4.69-4.76 (m, 1H), 5.09-5.15 (m, 1H), 6.34-6.36 (m, 1H), 7.07-7.11 (m, 1H), 8.15(s, 1H), 8.34-8.38 (m, 1H). Exact mass calculated for $C_{20}H_{23}BrF_2N_4O_3$ 484.09, found 485.2 (MH$^+$).

Example 9.65

Preparation of 4-[6-(4-Cyano-2-fluoro-phenylamino)-5-methyl-pyrimidin-4-yloxy]-piperidine-1-carboxylic acid isopropyl ester (Compound A87)

Compound A87 was obtains as a tanned solid (TFA salt, 387.1 mg, 28%). $^1$H NMR (MeOH-d$_4$, 400 MHz) δ 1.118-1.221 (d, J=6.32 Hz, 6H), 1.608-1.724 (m, 2H), 1.859-1.966 (m, 2H), 2.064 (s, 3H), 3.289-3.404 (m, 2H), 3.607-3.727 (m, 2H), 4.73-4.82 (m, 1H), 5.220-5.310 (m, 1H), 7.409 (d, 1H), 7.545 (d, 1H), 7.954-8.031 (t, J=8.08 Hz, 1H), 8.145 (s, 1H). Exact mass calculated for $C_{21}H_{24}FN_5O_3$ 413.19, found 414.4 (MH$^+$).

Example 9.66

Preparation of 4-[6-(4-Cyano-2,5-difluoro-phenylamino)-5-methyl-pyrimidin-4-yloxy]-piperidine-1-carboxylic acid isopropyl ester (Compound A88)

Compound A88 was obtains as a white solid (TFA salt, 309.8 mg, 22%). $^1$H NMR (DMSO-d$_6$, 400 MHz) δ 1.18-1.20 (d, J=6.32 Hz, 6H), 1.57-1.66 (m, 2H), 1.89-1.94 (m, 2H), 2.1 (s, 3H), 3.30-3.35 (m, 2H), 3.59-3.65 (m, 1H), 4.73-4.82 (m, J=6.32 Hz, 2H), 5.24-5.30 (m, J=3.79 Hz, 1H), 7.88-7.93 (dd, J=11.37, 6.57 Hz, 1H), 7.93-7.98 (dd, J=10.36, 6.06 Hz, 1H), 8.31 (s, 1H), 8.72 (s, 1H). Exact mass calculated for $C_{21}H_{23}F_2N_5O_3$ 431.18, found 432.3 (MH$^+$).

Example 9.67

Preparation of 4-[6-(2,5-Difluoro-4-morpholin-4-yl-phenylamino)-5-methyl-pyrimidin-4-yloxy]-piperidine-1-carboxylic acid isopropyl ester (Compound A89)

A mixture of 4-[6-(4-bromo-2,5-difluoro-phenylamino)-5-methyl-pyrimidin-4-yloxy]-piperidine-1-carboxylic acid isopropyl ester (645 mg, 1.33 mmol), L-proline (306 mg, 2.66 mmol), copper iodide (253 mg, 1.33 mmol), potassium carbonate (211 mg, 1.53 mmol), and morpholine (2.3 mL, 26 mmol) in 15 mL DMSO was heated in microwave for 18 hours at 80° C. Mixture was purified by HPLC to give Compound A89 as a tanned solid (HCl salt, 251 mg, 30%). $^1$H NMR (MeOH-d$_4$, 400 MHz) δ 1.05-1.07 (d, 6H), 1.52-1.63 (m, 2H), 1.80-1.89 (m, 2H), 1.99 (s, 3H), 2.94-2.96 (m, 4H), 3.21-3.29 (m, 2H), 3.54-3.70 (m, 6H), 5.22-5.29 (m, 1H), 6.82-6.86 (m, 1H), 7.03-7.08 (m, 1H), 8.10 (s, 1H). Exact mass calculated for $C_{24}H_{31}F_2N_5O_4$ 491.23, found 492.5 (MH$^+$).

Example 9.68

Preparation of 4-[6-(6-Chloro-2-methyl-pyridin-3-ylamino)-5-methyl-pyrimidin-4-yloxy]-piperidine-1-carboxylic acid isopropyl ester (Compound A90)

A mixture of 4-(6-chloro-5-methyl-pyrimidin-4-yloxy)-piperidine-1-carboxylic acid isopropyl ester (1.546 g, 4.93 mmol), palladium acetate (110 mg, 0.49 mmol), biphenyl-3-yl-di-tert-butyl-phosphane (18.5 mg, 0.062 mmol), sodium tert-butoxide (1.20 g, 12.5 mmol), and 6-chloro-2-methyl-pyridin-3-ylamine (709 mg, 4.97 mmol) in 15 mL dioxane was heated in microwave for 2 hour at 120° C. Solids were filtered off and mixture was purified to give Compound A90 as a tanned solid (640 mg, 31%). $^1$H NMR (CDCl$_3$, 400 MHz) δ 1.11-1.12 (d, 6H), 1.52-1.62 (m, 2H), 1.81-1.89 (m, 2H), 1.98 (s, 3H), 2.23 (m, 3H), 3.21-3.30 (m, 2H), 3.59-3.70 (m, 3H), 5.14-5.17 (m, 1H), 6.83-6.91 (m, 1H), 7.14-7.16 (d, 1H), 7.55-7.57 (d, 1H), 7.87 (s, 1H). Exact mass calculated for $C_{20}H_{26}ClN_5O_3$ 419.17, found 419.9 (MH$^+$).

Example 9.69

Preparation of 4-[5-(4,5-Dihydro-1H-imidazol-2-yl)-6-(2-fluoro-4-methanesulfonyl-phenylamino)-pyrimidin-4-yloxy]-piperidine-1-carboxylic acid isopropyl ester (Compound A92)

To a solution of zinc chloride (28 mg, 0.149 mmol) and 4-[5-cyano-6-(2-fluoro-4-methanesulfonyl-phenylamino)-pyrimidin-4-yloxy]-piperidine-1-carboxylic acid isopropyl ester (1 g, 2.09 mmol) in chlorobenzene (15 mL), ethane-1,2-diamine (0.100 mL, 1.463 mmol) was added. The mixture was heated under reflux for 24 h., LCMS indicated desired product. The crude was concentrated under vacuo and purified by HPLC to afford compound A92 as a yellow solid (303 mg, 23%). $^1$H NMR (CDCl$_3$, 400 MHz) δ 1.23 (d, 6H), 1.68-1.77 (m, 2H), 2.05-2.09 (m, 2H), 3.07 (s, 3H), 3.16-3.23

(m, 2H), 3.84-3.92 (m, 2H), 4.07 (s, 4H), 4.87-4.92 (m, 1H), 5.42-5.47 (m, 1H), 7.50-7.62 (m, 2H), 7.79-7.83 (m, 1H), 8.35 (s, 1H). Exact mass calculated for $C_{23}H_{29}FN_6O_5S$ 520.19, found 521.5 (MH$^+$).

Example 9.70

Preparation of (2-Fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine (Compound A93)

A mixture of (6-chloro-5-methyl-pyrimidin-4-yl)-(2-fluoro-4-methanesulfonyl-phenyl)-amine (HCl salt, 1.76 g, 5.0 mmol) and 1-(3-isopropyl-[1,2,4]oxadiazol-5-yl)-piperidin-4-ol (1.05 g, 5.0 mmol) in anhydrous THF (10 mL) was treated with potassium t-butoxide (20 mL, 20 mmol), placed under inert atmosphere, and refluxed for 4 hours, at which point the reaction had stalled at 60% conversion. The reaction mixture was cooled, quenched with water (30 mL), and extracted with ether (2×50 mL). The combined organic extract was rinsed with water (20 mL), followed by brine (20 mL), and was dried over MgSO$_4$. After solvent removal, the residue was rinsed with boiling ether (2×20 mL), and the combined rinses were set aside to cool. Crystallization yielded a white solid (91% pure by LCMS) which was triturated in hot ether and filtered hot to furnish Compound A93 as a white solid in >95% purity (731 mg, 30% yield). This material was taken up in CH$_2$Cl$_2$ (10 mL), to which was added 1 N HCl/ether (1.5 mL). Upon solvent removal, a light gray foam was obtained (800 mg): $^1$H NMR (DMSO-d$_6$) δ 10.26 (brs, 1 H), 8.77 (s, 1 H), 8.22 (s, 1 H), 7.83-7.71 (m, 3 H), 5.33 (m, 1 H), 3.75 (m, 2 H), 3.57 (m, 2 H), 3.37 (s, 3 H), 2.83 (m 1 H), 2.13 (s, 3 H), 2.04 (m, 2 H), 1.78 (m, 2 H), 1.20 (d, 6 H, J=6.9 Hz), MS m/z 491.2 (M$^+$).

Example 9.71

Preparation of 4-{6-[2-Fluoro-4-(2-methanesulfonyl-ethoxy)-phenylamino]-5-methyl-pyrimidin-4-yloxy}-piperidine-1-carboxylic acid isopropyl ester (Compound A95)

General procedure of coupling alcohol to aryl halides: A mixture of 4-[6-(2-fluoro-4-iodo-phenylamino)-5-methyl-pyrimidin-4-yloxy]-piperidine-1-carboxylic acid isopropyl ester (103 mg, 0.2 mmole), cesium carbonate (130 mg, 0.4 mmole), copper iodide (8 mg, 0.04 mmole), and 1,10-phenanthroline (14 mg, 0.08 mmole) in 2-methanesulfonyl-ethanol (3 mL) was heated under microwave irradiation at 150° C. for 1 hour. The crude mixture was purified by HPLC to provide Compound A95 as a yellow solid (3 mg, 3%). Exact mass calculated for $C_{23}H_{31}FN_4O_6S$ 510.2, found 511.3 (MH$^+$).

Example 9.72

Preparation of 4-[6-(2-Fluoro-4-propoxy-phenylamino)-5-methyl-pyrimidin-4-yloxy]-piperidine-1-carboxylic acid isopropyl ester (Compound A94)

Compound A94 was obtained in a similar manner as described in Example 9.71 as a solid (38 mg, 84%). $^1$H NMR (CDCl$_3$, 400 MHz) δ 1.04 (t, 3H), 1.26 (d, 6H), 1.75-1.84 (m, 7H), 1.97-2.02 (m, 2H), 3.35-3.41 (m, 2H), 3.74-3.77 (m, 2H), 3.91 (t, 2H), 4.93 (sept, 1H), 5.37-5.40 (m, 1H), 6.67-6.72 (m, 2H), 7.27-7.30 (m, 1H), 8.32 (s, 1H), 9.30 (s, 1H). Exact mass calculated for $C_{23}H_{31}FN_4O_4$ 446.2, found 447.3 (MH$^+$).

Example 9.73

Preparation of 4-{6-[2-Fluoro-4-(2-methoxy-ethoxy)-phenylamino]-5-methyl-pyrimidin-4-yloxy}-piperidine-1-carboxylic acid isopropyl ester (Compound A96)

Compound A96 was obtained in a similar manner as described in Example 9.71 as a tan solid (76 mg, 83%). $^1$H NMR (CDCl$_3$, 400 MHz) δ 1.25 (d, J=6.3 Hz, 6H), 1.74-1.79 (m, 2H), 1.81 (s, 3H), 1.97-2.05 (m, 2H), 3.35-3.41 (m, 2H), 3.45 (s, 3H), 3.75-3.77 (m, 4H), 4.10-4.12 (m, 2H), 4.93 (sep, J=6.3 Hz, 1H), 5.36-5.41 (m, 1H), 6.72-6.75 (m, 2H), 7.36 (t, J=9.1 Hz, 1H), 8.31 (s, 1H), 9.15 (s, NH). Exact mass calculated for $C_{23}H_{31}FN_4O_5$ 462.2, found 463.5 (MH$^+$).

Example 9.74

Preparation of 4-{6-[2-Fluoro-4-(2-isopropoxy-ethoxy)-phenylamino]-5-methyl-pyrimidin-4-yloxy}-piperidine-1-carboxylic acid isopropyl ester (Compound A97)

Compound A97 was obtained in a similar manner as described in Example 9.71 as a yellow solid (86 mg, 88%). $^1$H NMR (CDCl$_3$, 400 MHz) δ 1.21 (d, J=6.1 Hz, 6H), 1.25 (d, J=6.3 Hz, 6H), 1.75-1.79 (m, 2H), 1.80 (s, 3H), 1.97-2.02 (m, 2H), 3.35-3.42 (m, 2H), 3.70 (sep, J=6.3 Hz, 1H), 3.76 (dd, J=4.0 Hz, 4.8 Hz, 4H), 4.09 (t, J=4.8 Hz, 2H), 4.93 (sep, J=6.3 Hz, 1H), 5.37-5.41 (m, 1H), 6.73 (dd, J=11.6 Hz, 2H), 7.26 (t, J=8.6 Hz, 1H), 8.32 (s, 1H), 9.36 (s, NH). Exact mass calculated for $C_{25}H_{35}FN_4O_5$ 490.3, found 491.4 (MH$^+$).

Example 9.75

Preparation of 4-[6-(6-Chloro-4-methyl-pyridin-3-ylamino)-5-methyl-pyrimidin-4-yloxy]-piperidine-1-carboxylic acid isopropyl ester (Compound A98)

A mixture of 4-(6-chloro-5-methyl-pyrimidin-4-yloxy)-piperidine-1-carboxylic acid isopropyl ester (1.80 g, 5.74 mmol), palladium acetate (155 mg, 0.69 mmol), biphenyl-3-yl-di-tert-butyl-phosphane (21.5 mg, 0.072 mmol), sodium tert-butoxide (1.38 g, 14.4 mmol), and 6-chloro-4-methyl-pyridin-3-ylamine (838 mg, 5.80 mmol) in 20 mL dioxane was heated in microwave for 1 hour at 120° C. Solids were filtered off and mixture was purified by column chromatography (hexane/AcOEt) to give Compound A98 as a tanned solid (702 mg, 29%). $^1$H NMR (CDCl$_3$, 400 MHz) δ 1.24-1.26 (d, 6H), 1.72-1.81 (m, 2H), 1.95-2.02 (m, 2H), 2.10 (s, 3H), 2.27 (s, 3H), 3.37-3.43 (m, 2H), 3.74-3.77 (m, 2H), 4.90-4.97 (m, 1H), 5.29-5.34 (m, 1H), 5.91 (s, 1H), 7.00 (s, 1H), 8.22 (s, 1H), 8.57 (s, 1H). Exact mass calculated for $C_{20}H_{26}ClN_5O_3$ 419.17, found 420.4 (MH$^+$).

Example 9.76

Preparation of 4-[6-(2-Fluoro-4-methanesulfonyl-phenylamino)-5-(N-hydroxycarbamimidoyl)-pyrimidin-4-yloxy]-piperidine-1-carboxylic acid isopropyl ester (Compound A99)

4-[5-Cyano-6-(2-fluoro-4-methanesulfonyl-phenylamino)-pyrimidin-4-yloxy]-piperidine-1-carboxylic acid isopropyl ester (0.5 g, 1.04 mmol) was dissolved in the mixture ethanol/water (30 mL/14 mL) and heated to 80° C. Hydroxylamine hydrochloride (7.22 g, 104 mmol) and potassium carbonate (14.5 g, 105 mmol) were slowly added and the mixture kept stirring at 80° C. for 1 h. The crude was filtered and the retrieved solid was thoroughly washed with acetonitrile. The filtrate was concentrated under reduced pressure, yielding a yellow solid residue, which was purified by HPLC to afford Compound A99 (0.51 g, 78%). Exact mass calculated for $C_{21}H_{27}FN_6O_6S$ 510.17, found 511.2 (MH$^+$).

Example 9.77

Preparation of 4-[5-Carbamimidoyl-6-(2-fluoro-4-methanesulfonyl-phenylamino)-pyrimidin-4-yloxy]-piperidine-1-carboxylic acid isopropyl ester (Compound A100)

4-[6-(2-Fluoro-4-methanesulfonyl-phenylamino)-5-(N-hydroxycarbarimidoyl)-pyrimidin-4-yloxy]-piperidine-1-carboxylic acid isopropyl ester (0.510 g, 0816 mmol) was dissolved in acetic acid glacial (20 mL) and zinc dust (1 g, 16.32 mmol) was added. The reaction mixture was heated at 70° C. for 40 min. The crude was filtered, the filtrate was concentrated under reduced pressure and the residue was purified by HPLC to afford Compound A100 (43 mg, 8.65%). Exact mass calculated for $C_{21}H_{27}FN_6O_5S$ 494.17, found 495.5 (MH$^+$).

Example 9.78

Preparation of 4-{6-[2-Fluoro-4-(tetrahydro-furan-2-ylmethoxy)-phenylamino]-5-methyl-pyrimidin-4-yloxy}-piperidine-1-carboxylic acid isopropyl ester (Compound A101)

Compound A101 was obtained in a similar manner as described in Example 9.71 as a solid (35 mg, 24%). $^1$H NMR (CDCl$_3$, 400 MHz) δ 1.15 (d, 6H), 1.66-1.73 (m, 5H), 1.87-2.02 (m, 6H), 3.27-3.34 (m, 2H), 3.66-3.89 (m, 6H), 4.19-4.21 (m, 1H), 4.85 (sept, 1H), 5.28-5.30 (m, 1H), 6.64-6.67 (m, 2H), 7.32 (t, 1H), 8.22 (s, 1H), 8.90 (s, 1H). Exact mass calculated for $C_{25}H_{33}FN_4O_5$ 488.2, found 489.5 (MH$^+$).

Example 9.79

Preparation of 4-{6-[6-(2-Methoxy-ethoxy)-2-methyl-pyridin-3-ylamino]-5-methyl-pyrimidin-4-yloxy}-piperidine-1-carboxylic acid isopropyl ester (Compound A103)

A mixture of 4-[6-(6-chloro-2-methyl-pyridin-3-ylamino)-5-methyl-pyrimidin-4-yloxy]-piperidine-1-carboxylic acid isopropyl ester (507 mg, 1.21 mmol) and potassium carbonate (1.62 g, 12 mmol) in 4.5 mL 2-methoxyethanol was heated in microwave for 16.5 hours at 180° C. Mixture was purified by HPLC to give Compound A103 as a tanned solid (HCl salt, 103.5 mg, 17%). $^1$H NMR (MeOH-d$_4$, 400 MHz) δ 1.15-1.17 (d, 6H), 1.68-1.74 (m, 2H), 1.92-1.96 (m, 2H), 2.12 (s, 3H), 2.44 (s, 3H), 3.28-3.37 (m, 5H), 3.64-3.70 (m, 4H), 4.43-4.46 (m, 2H), 4.74-4.79 (m, 1H), 5.35-5.39 (m, 1H), 6.92-6.94 (d, 1H), 7.70-7.73 (d, 1H), 8.16 (s, 1H). Exact mass calculated for $C_{23}H_{33}N_5O_5$ 459.25, found 460.5 (MH$^+$).

Example 9.80

Preparation of 4-{6-[6-(2-Methoxy-ethoxy)-4-methyl-pyridin-3-ylamino]-5-methyl-pyrimidin-4-yloxy}-piperidine-1-carboxylic acid isopropyl ester (Compound A104)

A mixture of 4-[6-(6-chloro-4-methyl-pyridin-3-ylamino)-5-methyl-pyrimidin-4-yloxy]-piperidine-1-carboxylic acid isopropyl ester (353 mg, 0.84 mmol) and potassium carbonate (1.1 g, 7.96 mmol) in 4 mL 2-methoxyethanol was heated in microwave for 17 hours at 180° C. Mixture was purified by HPLC to give Compound A104 as a tanned solid (HCl salt, 61.8 mg, 15%). $^1$H NMR (MeOH-d$_4$, 400 MHz) δ 1.07-1.08 (d, 6H), 1.60-1.65 (m, 2H), 1.83-1.87 (m, 2H), 2.05 (s, 3H), 2.15 (s, 3H), 3.21-3.32 (m, 5H), 3.54-3.61 (m, 4H), 4.34-4.36 (m, 2H), 4.67-4.73 (m, 1H), 5.27-5.31 (m, 1H), 6.98 (s, 1H), 8.04 (s, 1H), 8.09 (s, 1H). Exact mass calculated for $C_{23}H_{33}N_5O_5$ 459.25, found 460.3 (MH$^+$).

Example 9.81

Preparation of 4-{6-[2-Fluoro-4-(2-isopropoxy-ethylsulfamoyl)-phenylamino]-5-methyl-pyrimidin-4-yloxy}-piperidine-1-carboxylic acid isopropyl ester (Compound A106)

A mixture of 4-amino-3-fluoro-N-(2-isopropoxy-ethyl)-benzenesulfonamide (116 mg, 0.42 mmol), 4-(6-chloro-5-methyl-pyrimidin-4-yloxy)-piperidine-1-carboxylic acid isopropyl ester (100 mg, 0.3 mmol), palladium acetate (3 mg, 0.017 mmol), biphenyl-2-yl-di-tert-butyl-phosphane (7.1 mg, 0.034 mmol), and sodium t-butoxide (87 mg, 0.90 mmol) in dioxane (2 mL) was heated under microwave irradiation for 60 min at 150° C. The crude mixture was concentrated in vacuo and purified by HPLC to provide Compound A106 as a brown solid (50 mg, 22%). $^1$H NMR (CDCl$_3$, 400 MHz) δ 1.04 (d, 6H), 1.19 (d, 6H), 1.67-1.78 (m, 2H), 1.89-1.99 (m, 5H), 3.05 (t, 2H), 3.30-3.40 (m, 4H), 3.42-3.52 (m, 1H), 3.66-3.76 (m, 1H), 4.87 (h, 1H), 5.19-5.38 (m, 2H), 7.58 (t, 3H), 7.90-7.98 (s broad, 1H), 8.24 (t, 1H), 8.35 (s, 1H). Exact mass calculated for $C_{23}H_{36}FN_5O_6S$ 553.65, found 554.6 (MH$^+$).

Example 9.82

Preparation of 4-{6-[2,5-Difluoro-4-(N-hydroxycarbamimidoyl)-phenylamino]-5-methyl-pyrimidin-4-yloxy}-piperidine-1-carboxylic acid isopropyl ester (Compound A107) 4-[6-(4-Carbamoyl-2,5-difluoro-phenylamino)-5-methyl-pyrimidin-4-yloxy]-piperidine-1-carboxylic acid isopropyl ester (Compound A108)

A mixture of 4-[6-(4-cyano-2,5-difluoro-phenylamino)-5-methyl-pyrimidin-4-yloxy]-piperidine-1-carboxylic acid isopropyl ester (TFA salt, 181 mg, 0.332 mmol), hydroxylamine (283.8 mg, 4.08 mmol), and potassium carbonate (283.9 mg, 2.05 mmol in 6 mL EtOH/H$_2$O (2:1 v/v) was stirred at 75° C. for 45 min. The crude mixture was purified by HPLC to give Compound A107 as an oil (TFA salt, 111 mg, 58%) and Compound A108 as an oil as a by-product (TFA salt, 74 mg, 40%). $^1$H NMR of A107 (DMSO-d$_6$, 400 MHz) δ 1.19-1.20 (d, J=6.32 Hz, 6H), 1.61-1.63 (m, 2H), 1.88-1.95 (m, 2H), 2.1 (s, 3H), 3.30-3.37 (m, 2H), 3.61-3.63 (m, 2H), 4.75-4.82 (m, J=6.32 Hz, 1H), 5.25-5.29 (m, J=3.79 Hz, 1H), 7.64-7.68 (dd, J=10.36, 6.32 Hz, 1H), 7.72-7.76 (dd, J=11.62, 6.32 Hz, 1H), 8.23 (s, 1H), 8.66 (s, 1H), 9.11 (s, 1H). Exact mass calculated for A107, $C_{21}H_{26}F_2N_6O_4$ 464.2, found 465.5 (MH$^+$) and for A108, $C_{21}H_{25}F_2N_5O_4$ 449.19, found 450.3 (MH$^+$).

Example 9.83

Preparation of 4-[6-(4-Carbamimidoyl-2,5-difluoro-phenylamino)-5-methyl-pyrimidin-4-yloxy]-piperidine-1-carboxylic acid isopropyl ester (Compound A110)

A mixture of Compound A107 (TFA salt, 107.5 mg, 0.186 mmol) and zinc dust (242.6 mg, 3.71 mmol) in acetic acid (3 mL) was stirred at 75° C. for 45 min. The crude mixture was purified by HPLC to provide Compound A110 as a solid (TFA salt, 97.4 mg, 93%). $^1$H NMR (CDCl$_3$, 400 MHz) δ 1.24-1.26 (d, J=6.32 Hz, 6H), 1.76-1.78 (m, 2H), 1.97-1.98 (m, 2H), 2.14 (s, 3H), 3.37-3.43 (m, 2H), 3.75-3.77 (m) 2H), 4.89-4.96 (m, 1H), 5.33-5.37 (m, 1H), 7.16 (s, 1H), 7.48 (s, 1H), 7.59-7.64 (dd, J=10.61, 6.82 Hz, 1H), 8.36 (s, 1H), 8.62-8.68 (m, 1H), 10.42 (s, 2H). Exact mass calculated for $C_{21}H_{26}F_2N_6O_3$ 448.2, found 449.2 (MH$^+$).

Example 9.84

Preparation of 4-{6-[4-(2-Ethoxy-ethoxy)-2-fluoro-phenylamino]-5-methyl-pyrimidin-4-yloxy}-piperidine-1-carboxylic acid isopropyl ester (Compound A111)

Compound A111 was obtained in a similar manner as described in Example 9.71 as a brown solid (52 mg, 55%). $^1$H NMR (CDCl$_3$, 400 MHz) δ 1.25 (t, J=7.1 Hz, 3H), 1.25 (d, J=6.3 Hz, 6H), 1.75-1.79 (m, 2H), 1.79 (s, 3H), 1.97-2.02 (m, 2H), 3.35-3.42 (m, 2H), 3.61 (q, J=7.1 Hz, 2H), 3.75-3.76 (m, 2H), 3.80 (t, J=4.8 Hz, 2H), 4.11 (t, J=4.8 Hz, 2H), 4.93 (sep, J=6.3 Hz, 1H), 5.36-5.40 (m, 1H), 6.72 (d, J=2.02 Hz, 1H), 6.75 (d, J=2.02 Hz, 1H), 7.32 (t, J=8.6 Hz, 1H), 8.30 (s, 1H), 9.41 (s, NH). Exact mass calculated for $C_{24}H_{33}FN_4O_5$ 476.2, found 477.4 (MH$^+$).

Example 9.85

Preparation of 4-{6-[2-Fluoro-4-(tetrahydro-pyran-4-yloxy)-phenylamino]-5-methyl-pyrimidin-4-yloxy}-piperidine-1-carboxylic acid isopropyl ester (Compound A112)

Compound A112 was obtained in a similar manner as described in Example 9.71 as an orange solid (71 mg, 49%). $^1$H NMR (CDCl$_3$, 400 MHz) δ 1.26 (d, J=6.1 Hz, 6H), 1.78-1.86 (m, 4H), 1.90 (s, 3H), 1.99-2.07 (m, 4H), 3.37-3.44 (m, 2H), 3.62-3.68 (m, 2H), 3.76-3.79 (m, 2H), 3.98-4.04 (m, 2H), 4.49 (m, 1H), 4.94 (sep, J=6.1 Hz, 1H), 5.42-5.44 (m, 1H), 6.72-6.74 (m, 1H), 6.74-6.76 (m, 1H), 7.25 (t, J=8.8 Hz, 1H), 8.37 (s, 1H), 8.75 (s, NH). Exact mass calculated for $C_2H_{33}FN_4O_5$ 488.2, found 489.5 (MH$^+$).

Example 9.86

Preparation of 4-{6-[2-Fluoro-4-(2-hydroxy-ethoxy)-phenylamino]-5-methyl-pyrimidin-4-yloxy}-piperidine-1-carboxylic acid isopropyl ester (Compound A113)

Compound A113 was obtained in a similar manner as described in Example 9.71 as an orange solid (76 mg, 84%). $^1$H NMR (CDCl$_3$, 400 MHz) δ 1.25 (d, J=6.3 Hz, 6H), 1.75-1.79 (m, 2H), 1.84 (s, 3H), 1.97-2.02 (m, 2H), 3.35-3.42 (m, 2H), 3.74-3.78 (m, 2H), 3.98 (t, J=4.6 Hz, 2H), 4.09 (t, J=4.6 Hz, 2H), 4.93 (sep, J=6.3 Hz, 1H), 5.36-5.40 (m, 1H), 6.72-6.74 (m, 1H), 6.75 (s, 1H), 7.35 (t, J=9.1 Hz, 1H), 8.31 (s, 1H), 9.15 (s, NH). Exact mass calculated for $C_{22}H_{29}FN_4O_5$ 448.2, found 449.3 (MH$^+$).

Example 9.87

Preparation of 4-{6-[2-Fluoro-4-(pyridin-2-yl-methoxy)-phenylamino]-5-methyl-pyrimidin-4-yloxy}-piperidine-1-carboxylic acid isopropyl ester (Compound A117)

Compound A117 was obtained in a similar manner as described in Example 9.71 as a white solid (11 mg, 11%). Exact mass calculated for $C_{26}H_{30}FN_5O_4$ 495.2, found 496.3 (MH$^+$).

Example 9.88

Preparation of 4-[2-(2-Fluoro-4-methanesulfonyl-phenylamino)-3-methyl-pyridin-4-yloxy]-piperidine-1-carboxylic acid isopropyl ester (Compound A118)

Step 1: Preparation of 2,4-dichloro-3-methyl-pyridine 1.6 M n-Butyl lithium in hexanes (3.75 mL, 6.0 mmol) and anhydrous THF (5 mL) were added to a flame-dried flask under nitrogen atmosphere. This solution was cooled to −78C, 2,4-Dichloro-pyridine was added dropwise while stirring and the mixture was stirred at −78C for 30 min after which time methyliodide (0.374 mL, 6.0 mmol) was added dropwise at −78C. This mixture was stirred at −78C for 1 h under nitrogen atmosphere after which time glacial AcOH (0.114 mL, 2.0 mmol) was added to give a reaction mixture pH (wet pH paper) of 5-6. The reaction mixture was dissolved in Et$_2$O (100 mL), the organic layer was washed with water (10 mL), then brine (10 mL), dried with MgSO$_4$, and the solvent was evaporated in vacuo to give an oil which was purified by flash chromatography using hexanes:CH$_2$Cl$_2$ (50:50 v/v) to hexanes:CH$_2$Cl$_2$:EtOAc (50:47:3 v/v/v) to give 2,4-dichloro-3-methyl-pyridine as a white solid (589 mg, 72%). It was noted that 2,4-dichloro-3-methyl-pyridine readily sublimates in vacuo. $^1$H NMR (CD$_3$OD, 400 MHz) δ 8.15 (d, 1H), 7.46 (d, 1H), 2.50 (s, 3H). LRMS calculated for $C_6H_5Cl_2N$: 160.98, found: (MH)$^+$ 161.9.

Step 2: Preparation of 4-(2-chloro-3-methyl-pyridin-4-yloxy)-piperidine-1-carboxylic acid isopropyl ester 4-Hydroxy-piperidine-1-carboxylic acid isopropyl ester (0.496 mL, 2.90 mmol) was dissolved in anhydrous dimethylacetamide (DMA, 5 mL), NaH (60% oil dispersion, 116 mg, 2.90 mmol) was added and this mixture was stirred at 23° C. for 45 min, then this mixture was added dropwise to 2,4-dichloro-3-methyl-pyridine, which was dissolved in anhydrous DMA (4 mL). This mixture was stirred at 23° C. for 2 h then heated at 50° C. for 15 h, after which time the mixture was diluted with $Et_2O$ (140 mL), washed with water (14 mL), then brine twice (2×14 mL). The organic layer was separated, dried with $MgSO_4$, and the solvent was evaporated in vacuo to give an oil which was purified by flash chromatography using hexanes-EtOAc, 75:25, v/v, then hexanes-EtOAc, 50:50, v/v, to give 4-(2-chloro-3-methyl-pyridin-4-yloxy)-piperidine-1-carboxylic acid isopropyl ester as a solid (223 mg, 27%). $^1$H NMR ($CDCl_3$, 400 MHz) δ 8.09 (d, 11H), 6.69 (d, 11H), 4.91 (m, 1H), 4.60 (m, 1H), 3.61 (m, 2H), 3.52 (m, 2H), 2.24 (s, 3H), 1.91 (m, 2H), 1.80 (m, 2H), 1.24 d, 6H). LRMS calculated for $C_{15}H_{21}ClN_2O_3$: 312.12, Found: $(MH)^+$ 313.4.

Step 3: Preparation of 4-[2-(2-fluoro-4-methane-sulfonyl-phenylamino)-3-methyl-pyridin-4-yloxy]-piperidine-1-carboxylic acid isopropyl ester (Compound A118)

The free base form of Compound A118 was prepared in a similar manner as described in Example 9.64 with modifications, wherein $Pd_2$ $dba_3$, was used instead of Pd $(OAc)_2$, toluene instead of dioxane, and the reaction was heated for 4 h instead of 2 h. Furthermore, no workup was performed and the reaction mixture was applied directly to flash chromatography using hexanes:$CH_2Cl_2$:EtOAc (10:30:60, v/v/v) to give the free base form of Compound A118 as a solid (166 mg, 51%). $^1$H NMR ($CDCl_3$, 400 MHz) δ 1.24 (d, J=6.2 Hz, 6H), 1.86 (m, 2H), 2.00 (m, 2H), 2.05 (s, 3H), 3.05 (s, 3H), 3.50 (m, 2H), 3.70 (m, 2H), 4.75 (septet, J=6.3 Hz, 11H), 4.92 (m, 1H), 6.74 (d, J=6.1 Hz, 11H), 7.65 (m, 3H), 8.00 (d, J=6.5 Hz, 1H). LRMS calculated for $C_{22}H_{28}FN_3O_5S$: 465.17, found: 466.5 $(MH)^+$.

Example 9.89

Preparation of 1-[4-(1-Benzyl-azetidin-3-yloxy)-6-(6-methanesulfonyl-pyridin-3-ylamino)-pyrimidin-5-yl]-ethanone (Compound A61)

Compound A61 was prepared in a manner similar as described in Example 9.37 using 1-benzyl-azetidin-3-ol. Exact mass calculated for $C_{22}H_{23}N_5O_4S$ 453.15, found 489.6 $(MH^+)$.

Example 9.90

Preparation of 4-[5-Acetyl-6-(6-methanesulfonyl-pyridin-3-ylamino)-pyrimidin-4-yloxy]-piperidine-1-carboxylic acid isobutyl ester (Compound A60)

A mixture of 1-[4-(6-methanesulfonyl-pyridin-3-ylamino)-6-(piperidin-4-yloxy)-pyrimidin-5-yl]-ethanone (48 mg, 0.11 mmol), isobutylchloroformate (14.0 μL, 0.11 mmol), and triethylamine (45 μL, 0.34 mmol) in DMF (1.0 mL) was heated under microwave irradiation for 3 minutes at 80° C. The crude mixture was purified by HPLC to provide Compound A60 as a white solid (35 mg, 65%). $^1$H NMR ($CDCl_3$, 400 MHz) δ 0.97 (d, 6H), 1.82-1.92 (m, 2H), 2.10-2.19 (m, 2H), 2.70 (s, 3H), 3.22 (s, 3H), 3.37 (m, 2H), 3.89-3.96 (m, 5H), 5.59 (h, 1H), 8.10 (d, 1H), 8.49-8.57 (m, 2H), 8.92 (d, 2H). Exact mass calculated for $C_{22}H_{29}N_5O_6S$ 491.18, found 492.3 $(MH^+)$.

Example 9.91

Preparation of 4-[5-Methyl-6-(4-methyl-6-morpholin-4-yl-pyridin-3-ylamino)-pyrimidin-4-yloxy]-piperidine-1-carboxylic acid isopropyl ester (Compound A102)

A solution of 4-[6-(6-chloro-4-methyl-pyridin-3-ylamino)-5-methyl-pyrimidin-4-yloxy]-piperidine-1-carboxylic acid isopropyl ester (223 mg, 0.53 mmol) in 4.5 mL morpholine was reacted under microwave irradiation at 180° C. for 16 hours. Mixture was concentrated and purified by HPLC to give Compound A102 as a white solid (200 mg, 74%). $^1$H NMR (MeOH-$d_4$, 400 MHz) δ 1.16-1.18 (d, 6H), 1.64-1.71 (m, 2H), 1.89-1.98 (m, 2H), 2.10 (s, 3H), 2.28 (s, 3H), 3.31-3.38 (m, 2H), 3.61-3.69 (m, 6H), 3.78-3.80 (m, 4H), 4.77-4.82 (m, 1H), 5.28-5.35 (m, 1H), 7.34 (s, 1H), 7.98 (s, 1H), 8.16 (s, 1H). Exact mass calculated for $C_{24}H_{34}N_6O_4$ 470.26, found 471.4 $(MH^+)$.

Example 9.92

Preparation of 4-[5-Methyl-6-(2-methyl-6-morpholin-4-yl-pyridin-3-ylamino)-pyrimidin-4-yloxy]-piperidine-1-carboxylic acid isopropyl ester (Compound A91)

A solution of 4-[6-(6-chloro-2-methyl-pyridin-3-ylamino)-5-methyl-pyrimidin-4-yloxy]-piperidine-1-carboxylic acid isopropyl ester (613 mg, 1.46 mmol) in 15 mL morpholine was reacted under microwave irradiation at 180° C. for 14 hours. Mixture was concentrated and purified by HPLC to give Compound A91 as a white solid (427 mg, 58%). $^1$H NMR (MeOH-$d_4$, 400 MHz) δ 1.03-1.05 (d, 6H), 1.51-1.60 (m, 2H), 1.78-1.85 (m, 2H), 1.98 (s, 3H), 2.29 (s, 3H), 3.19-3.25 (m, 2H), 3.54-3.58 (m, 6H), 3.65-3.67 (m, 4H), 4.65-4.70 (m, 1H), 5.20-5.25 (m, 1H), 7.08-7.10 (d, 1H), 7.68-7.71 (d, 1H), 8.07 (s, 1H). Exact mass calculated for $C_{24}H_{34}N_6O_4$ 470.26, found 471.3 $(MH^+)$.

Example 9.93

Preparation of 4-[5-Amino-6-(2-fluoro-4-methane-sulfonyl-phenylamino)-pyrimidin-4-yloxy]-piperidine-1-carboxylic acid isopropyl ester (Compound A120)

Mixture of 4-[6-(2-fluoro-4-methanesulfonyl-phenylamino)-5-nitro-pyrimidin-4-yloxy]-piperidine-1-carboxylic acid isopropyl ester (197 mg, 0.3 mmole), Zn Dust (2.4 mmole, 8 eq) and 1 mL of Sat $NH_2Cl$ solution in 2 mL THF and 2 mL $H_2O$ was stirred at room temperature for 25 minutes. Zn Dust was filtered off by celite and washed with ethyl acetate. Crude was purified by column chromatography (Hexane/Ethyl Acetate=½, Rf=0.44) to give compound A120 as a yellow oil (100 mg, 71%). $^1$H NMR (DMSO-$d_6$, 400 MHz) δ 1.19 (d, 6H), 1.62-1.68 (m, 2H), 1.88-1.93 (m, 2H), 3.23 (s, 3H), 3.33-3.39 (m, 2H), 3.64-3.70 (m, 2H), 4.77 (sep, 1H), 5.28-5.29 (m, 1H), 7.68 (d, 1H), 7.77 (d, 1H), 7.88 (s, 1H), 8.06 (t, 1H), 8.41 (sb, NH). Exact mass calculated for $C_{20}H_{26}FN_5O_5S$ 467.2, found 468.5 $(MH^+)$.

Example 9.94

Preparation of 1-{4-[6-(2-Fluoro-4-methanesulfonyl-phenylamino)-5-methyl-pyrimidin-4-yloxy]-piperidin-1-yl}-butan-1-one (Compound A114)

General Procedure of Amide Formation

Dissolve HBTU (1.2 eq, 24 mg) in DMF (0.5 mL), and add butyric acid (1.2 eq, 5.8 μL) followed by diisopropyl ethyl amine (2.2 eq, 20.3 μL). After approximately 3 min, (2-fluoro-4-methanesulfonyl-phenyl)-[5-methyl-6-(piperidin-4-yloxy)-pyrimidin-4-yl]-amine (0.053 mmol) was added, and stirred at room temperature overnight. Reactions were filtered through 0.1 μm syringe filter and purified by Prep-LCMS. Fractions were frozen and lyophilized to solid product. Exact Mass: 450.2, found: 451.3 (MH$^+$).

Example 9.95

Preparation of 1-{4-[6-(2-Fluoro-4-methanesulfonyl-phenylamino)-5-methyl-pyrimidin-4-yloxy]-piperidin-1-yl}-pentan-1-one (Compound A115)

Compound A115 was prepared in a similar manner as described in Example 9.94. Exact Mass: 464.2, found: 465.4 (MH$^+$).

Example 9.96

Preparation of 1-{4-[6-(2-Fluoro-4-methanesulfonyl-phenylamino)-5-methyl-pyrimidin-4-yloxy]-piperidin-1-yl}-3-methyl-butan-1-one (Compound A116)

Compound A116 was prepared in a similar manner as described in Example 9.94. Exact Mass: 464.2, found: 465.6 (MH$^+$).

Example 9.97

Preparation of 4-{6-[2,5-Difluoro-4-(2-methoxy-ethoxy)-phenylamino]-5-methyl-pyrimidin-4-yloxy}-piperidine-1-carboxylic acid isopropyl ester (Compound A105)

Compound A105 was obtained in a similar manner as described in Example 9.71 as a solid (TFA salt, 222.5 mg, 16%). $^1$H NMR (CDCl$_3$, 400 MHz) δ 1.23-1.25 (d, J=6.32 Hz, 6H), 1.72-1.79 (m, 2H), 1.88 (s, 3H), 1.95-2.00 (m, 2H), 3.34-3.41 (m, 2H), 3.44 (s, 3H), 3.71-3.77 (m, 4H), 4.14-4.16 (m, 2H), 4.87-4.96 (sep, J=6.32 Hz, 1H), 5.31-5.37 (m, 1H), 6.79-6.84 (dd, J=11.62, 7.58 Hz, 1H), 7.50-7.55 (dd, J=11.62, 7.58 Hz, 1H), 8.31 (s, 1H), 8.56 (s, 1H). Exact mass calculated for C$_{23}$H$_{30}$F$_2$N$_4$O$_5$ 480.22, found 481.3 (MH$^+$).

Example 10

Syntheses of Compounds of the Present Invention

Example 10.1

Preparation of 4-[6-(4-Methanesulfonyl-phenylamino)-5-nitro-pyrimidin-4-ylamino]-piperidine-1-carboxylic acid tert-butyl ester (Compound B1)

General Procedure for the Addition of Amine to pyrimidine: (6-Chloro-5-nitro-pyrimidin-4-yl)-(4-methanesulfonyl-phenyl)-amine (132 mg, 0.4 mmole), 4-amino-piperidine-1-carboxylic acid tert-butyl ester (0.4 mmole, 1 eq) and K$_2$CO$_3$ (0.4 mmole, 1 eq) were dissolved in DMF, and the mixture was stirred at 60° C. for 1 hour. Final product was precipitated out with water to provide Compound B1 as a yellow solid (152 mg, 77%). $^1$H NMR (400 MHz CDCl$_3$) δ (ppm): 10.8 (s, 1H), 9.18 (d,1H), 8.17 (s,1H), 7.90 (d,2H), 7.85 (d,2H), 4.39-4.32 (m,1H), 4.02 (m,2H), 3.01 (s,3H), 2.95-2.90 (m, 2H), 2.00 (m,2H), 1.57-1.50 (m,2H), 1.46 (s, 9H). Exact mass calculated for C$_{21}$H$_{28}$N$_6$O$_6$S 492.18, LCMS (ESI) m/z 493.4 (M+H$^+$, 100%).

Example 10.2

Preparation of N-(4-Methanesulfonyl-phenyl)-5-nitro-N'-piperidin-4-yl-pyrimidine-4,6-diamine (Compound B2)

General Deprotection Procedure: A mixture of Compound B1 and 4 M HCl in dioxane was stirred at 40° C. overnight and concentrated. Excess HCl was evaporated with isopropyl alcohol provided Compound B2 as yellow solid (261 mg, 97%). $^1$H NMR (400 MHz CDCl$_3$) δ (ppm): 10.9 (s, 1H), 8.96 (d,2H), 8.17 (s,1H), 7.84 (d, 4H), 4.40-4.37 (m,1H), 3.25-3.22 (m,2H), 3.16 (s,3H), 3.01-2.93 (m, 2H), 2.04-2.01 (m,2H), 1.88-1.78 (m,2H). Exact mass calculated for C$_{16}$H$_{20}$N$_6$O$_4$S 392.13, LCMS (ESI) m/z 393.1 (M+H$^+$, 100%).

Example 10.3

Preparation of 1-{4-[6-(4-Methanesulfonyl-phenylamino)-5-nitro-pyrimidin-4-ylamino]-piperidin-1-yl}-ethanone (Compound B3)

General Procedure of Acetylating: Mixture of B2 and acetyl chloride was stirred at 180° C. for 2 hours in microwave to provide Compound B3 as yellow solid (10 mg, 18%). $^1$H (400 MHz CDCl$_3$) δ (ppm): 9.06 (d, 1H), 8.07 (s,1H), 7.78 (d, 2H), 7.70 (d, 2H), 4.42-4.37 (m,1H), 4.35-4.30 (m, 1H), 3.74-3.71 (m,1H), 3.19-3.13 (m, 1H), 2.89 (s, 3H), 2.82-2.76 (m, 1H), 2.04 (s,3H), 2.00-1.97 (m, 2H), 1.46-1.37 (m,2H). Exact mass calculated for C$_{18}$H$_{22}$N$_6$O$_5$S 434.14, LCMS (ESI) m/z 435.4 (M+H$^+$, 100%).

Example 10.4

Preparation of 1-{4-[6-(4-Methanesulfonyl-phenylamino)-5-nitro-pyrimidin-4-ylamino]-piperidin-1-yl}-2,2-dimethyl-propan-1-one (Compound B4)

Compound B4 was prepared in a similar manner as described above as yellow solid (7 mg, 11%). $^1$H NMR (400 MHz CDCl$_3$) δ (ppm): 9.16 (d, 1H), 8.17 (s,1H), 7.89 (d, 2H), 7.82 (d, 2H), 4.48-4.42 (m,1H), 4.35-4.32 (m,2H), 3.07-3.04 (m, 2H), 3.00 (s,3H), 2.10-2.08 (m, 2H), 1.55-1.46 (m, 2H), 1.24 (s, 9H). Exact mass calculated for C$_{21}$H$_{28}$N$_6$O$_5$S 476.18, LCMS (ESI) m/z 477.3 (M+H$^+$, 100%).

4-({[6-(2-Fluoro-4-methanesulfonyl-phenylamino)-5-methyl-pyrimidin-4-yl]-isopropyl-amino}-methyl)-piperidine-1-carboxylic acid tert-butyl ester (Compound B5)

Compound B5 was prepared in a similar manner as described in Example 10.1 as a solid (24 mg, 23%). Exact mass calculated for C$_{26}$H$_{38}$FN$_5$O$_4$S 535.2, found 536.4 (MH+).

Example 11

Syntheses of Compounds of the Present Invention

Example 11.1

Preparation of 4-[6-(2-Fluoro-4-morpholin-4-yl-phenoxy)-5-methyl-pyrimidin-4-yloxy]-piperidine-1-carboxylic acid isopropyl ester (Compound C3)

A mixture of 4-[6-(4-bromo-2-fluoro-phenoxy)-5-methyl-pyrimidin-4-yloxy]-piperidine-1-carboxylic acid isopropyl ester (Compound C130, 500 mg, 1.07 mmole), morpholine (121 mg, 1.39 mmole), palladium acetate (3 mg, 0.011 mmole), biphenyl-2-yl-di-tert-butyl-phosphane (4 mg, 0.012 mmole) and sodium t-butoxide (257 mg, 2.14 mmole) in dioxane (3 mL) was heated under microwave irradiation at 150° C. for 1 hours. The crude mixture was purified by HPLC to provide Compound C3 as a yellow oil (235 mg, 46%). $^1$H NMR (CDCl$_3$, 400 MHz) δ 1.28 (d, J=6.3 Hz, 6H), 1.81-1.85 (m, 2H), 1.99-2.04 (m, 2H), 2.20 (s, 3H), 3.44-3.47 (m, 2H), 3.49-3.51 (m, 4H), 3.73-3.78 (m, 2H), 4.08-4.10 (m, 2H), 4.95 (sep, J=6.3 Hz, 1H), 5.35-5.37 (m, 1H), 7.25 (d, J=10.1 Hz, 2H), 7.32 (t, J=8.6 Hz, 1H), 8.26 (s, 1H). Exact mass calculated for C$_{24}$H$_{31}$FN$_4$O$_5$ 474.2, found 475.4 (MH$^+$).

Example 11.2

Preparation of (6-Amino-pyridin-3-yl)-{4-[6-(2-fluoro-4-methanesulfonyl-phenoxy)-5-methyl-pyrimidin-4-yloxy]-piperidin-1-yl}-methanone (Compound C5)

6-Amino-nicotinic acid (21.5 mg, 0.155 mmol), HATU (59 mg, 0.155 mmol) and triethylamine (0.05 mL, 0.359 mmol) were mixed in DMF and stirred at rt for 20 min. 4-(2-Fluoro-4-methanesulfonyl-phenoxy)-5-methyl-6-(piperidin-4-yloxy)-pyrimidine was then added and the mixture stirred at rt for 2 h. The crude was purified by HPLC to afford Compound C5 as a yellow solid (67 mg, 90.7%). $^1$H NMR (CDCl$_3$, 400 MHz) δ 1.88-1.87 (m, 2H), 1.99-2.01 (m, 2H), 2.15 (s, 3H), 3.03 (s, 3H), 3.58-3.60 (m, 2H), 3.77-3.78 (m, 2H), 5.37-5.41 (m, 1H), 6.78-6.82 (d, 1H), 7.33-7.38 (m, 1H), 7.69-7.74 (m, 2H), 7.87-7.96 (m, 2H), 8.14 (s, 1H). Exact mass calculated for C$_{23}$H$_{24}$FN$_5$O$_5$S 501.15, found 502.4 (MH$^+$).

Example 11.3

Preparation of 4-[5-Ethyl-6-(2-fluoro-4-methanesulfonyl-phenoxy)-pyrimidin-4-yloxy]-piperidine-1-carboxylic acid isopropyl ester (Compound C6)

Step 1: Preparation of 4-(6-chloro-5-ethyl-pyrimidin-4-yloxy)-piperidine-1-carboxylic acid isopropyl ester To a solution of 4,6-dichloro-5-ethyl-pyrimidine (1 g, 5.65 mmol) and 4-hydroxy-piperidine-1-carboxylic acid isopropyl ester (1.05 g, 5.65 mmol) in dry THF under nitrogen at 0° C., potassium tert-butoxide (1M solution in THF, 6.78 mL) was added dropwise. The reaction was stirred at rt for 30 min. The mixture was quenched with water and extracted with EtOAc (3×). The organic layer was washed with water, sat. NH$_4$Cl and brine, followed by drying over sodium sulfate and concentration under vacuo. The resulting oil was purified by HPLC to afford 4-(6-chloro-5-ethyl-pyrimidin-4-yloxy)-piperidine-1-carboxylic acid isopropyl ester (0.74 g, 39.8%) as a colorless oil. Exact mass calculated for C$_{15}$H$_{22}$ClN$_3$O$_3$ 327.13, found 328.2 (MH$^+$).

Step 2: Preparation of 4-[5-ethyl-6-(2-fluoro-4-methanesulfonyl-phenoxy)-pyrimidin-4-yloxy]-piperidine-1-carboxylic acid isopropyl ester (Compound C6)

4-(6-Chloro-5-ethyl-pyrimidin-4-yloxy)-piperidine-1-carboxylic acid isopropyl ester (50 mg, 0.152 mmol), 2-fluoro-4-methanesulfonyl-phenol (43.5 mg, 0.228 mmol) and sodium hydride (60% dispersion in mineral oil, 7.28 mg, 0.182 mmol) were dissolved in DMSO (2 mL) and the mixture was heated under microwave irradiation for 1 h at 150° C. The crude was quenched with water and extracted with ethyl acetate. The organic layer was concentrated and the residue was purified by HPLC to afford Compound C6 (20.3 mg, 27.6%) as a white powder. $^1$H NMR (CDCl$_3$, 400 MHz) δ 1.13 (t, J=7.33 Hz, 3H), 1.18 (d, J=6.32 Hz, 6H), 1.72-1.76 (m, 2H), 1.89-1.94 (d, 2H), 2.64 (q, J=7.33 Hz, 2H), 3.02 (s, 3H), 3.35-3.41 (m, 2H), 3.63-3.66 (m, 2H), 4.85-4.88 (m, 1H), 5.25-5.32 (m, 1H), 7.35-7.37 (m, 1H), 7.69-7.74 (m, 2H), 8.13 (s, 1H). Exact mass calculated for C$_{22}$H$_{28}$FN$_3$O$_6$S 481.17, found 482.4 (MH$^+$).

Example 11.4

Preparation of 4-{6-[6-(2-Isopropoxy-ethylamino)-2-methyl-pyridin-3-yloxy]-5-methyl-pyrimidin-4-yloxy}-piperidine-1-carboxylic acid isopropyl ester (Compound C10)

A mixture of 4-[6-(6-chloro-2-methyl-pyridin-3-yloxy)-5-methyl-pyrimidin-4-yloxy]-piperidine-1-carboxylic acid isopropyl ester (60 mg, 0.143 mmol), palladium acetate (12 mg, 0.05 mmol), 2,8,9-triisobutyl-2,5,8,9-tetraaza-1-phospha-bicyclo[3,3,3]undecane (5 mL, 0.015 mmol), 2-isopropoxy-ethylamine (35 μL, 0.28 mmol), and sodium tert-butoxide in 1.5 mL dioxane were heated under microwave irradiation for 1 hour at 120° C. Mixture was purified by HPLC to give Compound C10 as a tanned solid (TFA salt, 44.1 mg, 51%). $^1$HNMR(MeOH-d$_4$, 400 MHz) δ 1.01-1.03 (d, 6H), 1.09-1.11 (d, 6H), 1.58-1.63 (m, 2H), 1.82-1.90 (m, 2H), 2.05 (s, 3H), 2.20 (s, 3H), 3.22-3.30 (m, 2H), 3.46-3.63 (m, 7H), 4.70-4.75 (m, 1H), 5.21-5.27 (m, 1H), 6.82-6.85 (d, 1H), 7.60-7.62 (d, 1H), 8.01 (s, 1H). Exact mass calculated for C$_{25}$H$_{37}$N$_5$O$_5$ 487.28, found 488.6 (MH$^+$).

Example 11.5

Preparation of 4-{6-[6-(2-Hydroxy-ethylsulfanyl)-2-methyl-pyridin-3-yloxy]-5-methyl-pyrimidin-4-yloxy}-piperidine-1-carboxylic acid isopropyl ester (Compound C12)

A mixture of 4-[6-(6-chloro-2-methyl-pyridin-3-yloxy)-5-methyl-pyrimidin-4-yloxy]-piperidine-1-carboxylic acid isopropyl ester (835 mg, 1.98 mmol) and potassium carbonate (305 mg, 2.2 mmol) in 3 mL of 2-mercapto-ethanol was stirred in microwave at 80° C. After 17 hours, mixture was continued to be stirred at 100° C. for 30 minutes and then 120° C. for 30 minutes. Mixture was purified by HPLC and column chromatography (hexane/AcOEt) to give Compound C12 as a white solid (16.4 mg, 2%). $^1$H NMR (CDCl$_3$, 400 MHz) δ 1.07-1.09 (d, J=6.3 Hz, 6H), 1.68-1.78 (m, 2H), 1.90-1.99 (m, 2H), 2.12 (s, 3H), 2.29 (s, 3H), 3.23-3.25 (t, J=5.1 Hz, 2H), 3.32-3.38 (m, 2H), 3.68-3.71 (m, 2H), 3.91-3.94 (t, J=4.9 Hz, 2H), 4.84-4.90 (m, 1H), 5.24-5.30 (m, 1H), 7.12-7.21 (m, 2H), 8.12 (s, 1H). Exact mass calculated for $C_{22}H_{30}N_4O_5S$ 462.19, found 463.3 (MH$^+$).

Example 11.6

Preparation of 4-[5-Methyl-6-(2-methyl-6-pentyl-pyridin-3-yloxy)-pyrimidin-4-yloxy]-piperidine-1-carboxylic acid isopropyl ester (Compound C15)

To a solution of 4-[6-(6-chloro-2-methyl-pyridin-3-yloxy)-5-methyl-pyrimidin-4-yloxy]-piperidine-1-carboxylic acid isopropyl ester (75.1 mg, 0.140 mmol) and iron (III) acetylacetonate (3.1 mg, 0.0088 mmol) in 1 mL THF and 0.1 mL NMP, 2M pentylmagnesium bromide solution in diethylether (135 µl, 0.275 mol) were added. After stirring at room temperature for several hours, mixture was purified by HPLC to give Compound C15 as an oil (TFA salt, 1.8 mg, 2%). Exact mass calculated for $C_{25}H_{36}N_4O_4$ 456.27, found 457.4 (MH$^+$).

Example 11.7

Preparation of 1-{4-[6-(2-Fluoro-4-methanesulfonyl-phenoxy)-5-methyl-pyrimidin-4-yloxy]-piperidin-1-yl}-butan-2-one (Compound C93)

4-(2-Fluoro-4-methanesulfonyl-phenoxy)-5-methyl-6-(piperidin-4-yloxy)-pyrimidine hydrochloride salt (42 mg, 0.1 mmol), 1-bromo-butan-2-one (0.1 mmol, 1 eq), and triethylamine (0.2 mmol, 2 eq) were dissolved in DMF (1 mL) and then stirred at room temperature overnight. The crude was filtered and then purified via prep-LCMS 5-95% to provide Compound C93 as an oil (39.6 mg, 88%). Exact mass calculated for $C_{21}H_{26}FN_3O_5S$ 451.2, found 452.3 (MH$^+$).

Example 11.8

Preparation of 4-(2-Fluoro-4-methanesulfonyl-phenoxy)-5-methyl-6-[1-(2-pyridin-3-yl-ethyl)-piperidin-4-yloxy]-pyrimidine (Compound C18)

A mixture of 4-(2-fluoro-4-methanesulfonyl-phenoxy)-5-methyl-6-(piperidin-4-yloxy)-pyrimidine (100 mg, 0.24 mmol), toluene-4-sulfonic acid 2-pyridin-3-yl-ethyl ester (133 mg, 0.48 mmol), and triethylamine (167 µL, 1.2 mmol) in DMF (2 mL) was heated under microwave irradiation for 60 min at 150° C. The crude mixture was concentrated in vacuo and purified by HPLC to provide Compound C18 as an oil (15 mg, 13%). $^1$H NMR (CDCl$_3$, 400 MHz) δ 2.15 (s, 3H), 2.18-2.38 (m, 4H), 3.04 (s, 3H), 3.07-3.22 (m, 2H), 3.29-3.43 (m, 4H), 3.44-3.65 (m, 2H), 5.43-5.51 (m, 1H), 7.36 (t, 1H), 7.67-7.79 (m, 3H), 8.11 (s, 1H), 8.35 (d, 1H), 8.58 (d, 1H), 8.91 (s, 1H). Exact mass calculated for $C_{24}H_{27}FN_4O_4S$ 486.56, found 487.4 (MH$^+$).

Example 11.9

Preparation of 2-{4-[6-(2-Fluoro-4-methanesulfonyl-phenoxy)-5-methyl-pyrimidin-4-yloxy]-piperidin-1-yl}-1-(4-trifluoromethoxy-phenyl)-ethanone (Compound C21)

Compound C21 was prepared using a similar procedure as described in Example 11.7 and purified by preparative HPLC. $^1$H NMR (CDCl$_3$, 400 MHz) δ 2.22 (s, 3H), 2.33 (m, 2H), 2.48 (m, 2H), 3.14 (s, 3H), 3.69 (m, 4H), 4.78 (s, 2H), 5.58 (m, 1H), 7.34 (d, 2H), 7.44 (t, 1H), 7.79 (m, 2H), 7.99 (d, 2H), 8.22 (s, 1H). Exact mass calculated for $C_{26}H_{25}F_4N_3O_6S$ 583.14, found 584.3 (MH$^+$).

Example 11.10

Preparation of 4-{6-[6-(2-Methoxy-ethanesulfonyl)-2-methyl-pyridin-3-yloxy]-5-methyl-pyrimidin-4-yloxy}-piperidine-1-carboxylic acid isopropyl ester (Compound C24)

A solution of 4-{6-[6-(2-methoxy-ethylsulfanyl)-2-methyl-pyridin-3-yloxy]-5-methyl-pyrimidin-4-yloxy}-piperidine-1-carboxylic acid isopropyl ester (8.8 mg, 0.0185 mmol) in 1 mL methylene chloride was cooled in an ice bath and 3-chloroperoxybenzoic acid (9.4 mg, 0.038 mmol) was added. After stirring for one hour in an ice-bath, mixture was quenched with a aqueous bicarbonate solution and purified by HPLC to give Compound C24 as a white solid (TFA salt, 7.6 mg, 66%). $^1$H NMR (MeOH-d$_4$, 400 MHz) δ 1.22-1.23 (d, 6H), 1.70-1.80 (m, 2H), 1.95-2.02 (m, 2H), 2.20 (s, 3H), 2.43 (s, 3H), 3.14 (s, 3H), 3.35-4.45 (m, 2H), 3.64-3.66 (t, J=5.9 Hz, 3H), 3.70-3.76 (m, 4H), 4.82-4.88 (m, 1H), 5.35-5.39 (m, 1H), 7.72-7.75 (d, J=8.36 Hz, 1H), 8.13 (s, 1H). Exact mass calculated for $C_{23}H_{32}N_4O_6S$ 508.20, found 509.4 (MH$^+$).

Example 11.11

Preparation of 4-(2-Fluoro-4-methanesulfonyl-phenoxy)-6-[1-(3-isopropyl-[1,2,4]oxadiazol-5-yl)-piperidin-4-yloxy]-5-methyl-pyrimidine (Compound C27)

Step 1: Preparation of N-hydroxy-isobutyramidine

A solution of isobutyronitrile (276 g, 4.0 mol) in EtOH (2.0 L) was combined with hydroxylamine (50% aqueous solution, 1.1 L, 16 mol), and refluxed for 5 h. The solvent was then removed in vacuo, and the residual water was azeotropically removed with toluene. The residue was then taken up in CH$_2$Cl$_2$, dried over MgSO$_4$, and the solvent was removed to afford a white solid (402 g, 98% yield). $^1$H NMR (CDCl$_3$) δ 7.94 (br s, 1 H), 4.55 (br s, 2 H), 2.47 (m, 1 H), 1.20 (d, 6 H, J=7.1 Hz).

Step 2: Preparation of 1-cyano-4-hydroxypiperidine

A 5-liter, 3-neck flask was equipped with mechanical stirring, a reflux condenser, and a powder addition funnel. Sodium bicarbonate (840 g, 10 mmol) was added via the powder funnel while stirring, then water (ca. 300-400 mL) was gradually added while vigorously stirring to form a thick, uniform slurry. The flask was then placed in an ice bath, and a solution of 4-hydroxypiperidine (506 g, 5.00 mol) in CH$_2$Cl$_2$ (1.0 L) was added, and the contents were vigorously mixed while cooling. A solution of cyanogen bromide (640 g, 6.0 mol) in CH$_2$Cl$_2$ (600 mL) was added in a dropwise fashion over 2 h, and stirring was continued for an additional 30 min. The ice bath was removed, and the mechanical stirrer was replaced by a magnetic stirrer, and the reaction mixture was stirred for 16 h. The flask was once again placed under mechanical stirring, and sodium carbonate (100 g) was added in order to ensure complete neutralization. MgSO$_4$ (500 g) was added, and vigorous stirring was continued for 15 min. The resulting suspension was filtered, rinsing with CH$_2$Cl$_2$ (2.0 L). A light amber, viscous oil was obtained upon solvent removal to give 1-cyano-4-hydroxypiperidine (574 g, 91% yield. $^1$H NMR (CDCl$_3$) δ 3.80 (m, 1 H), 3.39 (m, 2 H), 3.05 (m, 2 H), 1.87 (m, 2 H), 1.70 (br s, 1 H), 1.62 (m, 2 H), MS m/z 212.1 (M+).

Step 3: Preparation of 1-(3-isopropyl-[1,2,4]oxadiazol-5-yl)-piperidin-4-ol

In a variation of the method described by Yarovenko et al, (Bull. Acad. Sci. USSR, Div. Chem. Sci. 1991, 40, 1924) ZnCl$_2$ (1 N in ether, 120 mL, 120 mmol) was added in a dropwise fashion over 15 min to a magnetically stirred solution of N-hydroxy-isobutyramidine (12.2 g, 120 mmol) and 4-hydroxy-piperidine-1-carbonitrile (12.6 g, 100 mmol) in ethyl acetate (500 mL). Precipitate formed immediately upon addition, and at a point the stirring bar became immobilized in the matrix, requiring the reaction to be manually shaken for the remainder of addition. After standing for 15 min, the supernatant was decanted and filtered, and the residue was rinsed twice with ether, furnishing a hard white precipitate which was collected by filtration. This material was taken up in conc. HCl (50 mL), diluted to 4 N with EtOH (100 mL), and refluxed for 1 h. Upon cooling, a white precipitate was removed by filtration, then the filtrate was reduced to 50 mL and diluted with 100 mL water. Solid Na$_2$CO$_3$ was added until the mixture was basic, CH$_2$Cl$_2$ was added, and the resulting mixture was filtered, rinsing with CH$_2$Cl$_2$. The organic extract was separated, dried over MgSO$_4$, and the solvent was removed to afford a viscous, amber oil as 1-(3-isopropyl-[1,2,4]oxadiazol-5-yl)-piperidin-4-ol (15.0 g, 71% yield): $^1$H NMR (CDCl$_3$) δ 3.95 (m, 3 H), 3.37 (m, 2 H), 2.88 (m, 1 H), 2.34 (br s, 1 H), 1.93 (m, 2 H), 1.63 (m, 2 H), 1.28 (d, 6 H, J=7.1 Hz), MS m/z 212.3 (M+).

Step 4: Preparation of 4-chloro-6-[1-(3-isopropyl-[1,2,4]oxadiazol-5-yl)-piperidin-4-yloxy]-5-methyl-pyrimidine To a solution of 1-(3-isopropyl-[1,2,4]oxadiazol-5-yl)-piperidin-4-ol (3.65 g, 17 mmol) and 4,6-dichloro-5-methylpyrimidine (2.83 g, 17 mmol) in THF (70 mL), 1M potassium-t-butoxide in THF (16 mL, 16 mmol) was added dropwise. The mixture was stirred at room temperature for 10 min. The crude mixture was purified by column chromatography on silica gel with hexane/ethyl acetate (3:1 v/v) to provide 4-chloro-6-[1-(3-isopropyl-[1,2,4]oxadiazol-5-yl)-piperidin-4-yloxy]-5-methyl-pyrimidine as a solid (4.15 g, 71%). Exact mass calculated for C$_{15}$H$_{20}$ClN$_5$O$_2$ 337.13, found 338.2 (MH$^+$).

Step 5: Preparation of 4-(2-fluoro-4-methanesulfonyl-phenoxy)-6-[1-(3-isopropyl-[1,2,4]oxadiazol-5-yl)-piperidin-4-yloxy]-5-methyl-pyrimidine (Compound C27)

A mixture of 4-chloro-6-[1-(3-isopropyl-[1,2,4]oxadiazol-5-yl)-piperidin-4-yloxy]-5-methyl-pyrimidine (756 mg, 2.24 mmol), 2-fluoro-4-methanesulfonyl-phenol (635 mg, 3.33 mmol), and sodium hydride, 60% dispersion in mineral oil (232 mg, 5.81 mmol) in DMAA (30 mL) was divided into two 20 mL microwave vials and heated under microwave irradiation at 150° C. for 1 hour. The crude mixture was purified by HPLC to provide Compound C27 as a solid (TFA salt, 75.5 mg, 5.6%). $^1$H NMR (CDCl$_3$, 400 MHz) δ 1.28-1.31 (d, J=6.32 Hz, 6H), 1.96-2.02 (m, 2H), 2.08-2.15 (m, 2H), 2.20 (s, 3H), 2.91-2.98 (m, 1H), 3.09 (s, 3H), 3.65-3.71 (m, 2H), 3.82-3.89 (m, 2H), 5.42-5.46 (m, 1H), 7.41-7.44 (m, 1H), 7.77-7.81 (m, 2H) 8.21 (s, 1H). Exact mass calculated for C$_{22}$H$_{26}$FN$_5$O$_5$S 491.16, found 492.3 (MH$^+$).

Example 11.12

Preparation of 4-(6-{2-Fluoro-4-[(2-hydroxy-ethyl-carbamoyl)-methyl]-phenoxy}-5-methyl-pyrimidin-4-yloxy)-piperidine-1-carboxylic acid isopropyl ester (Compound C31)

Compound C31 was obtained in a similar manner as described in Example 11.36 as a solid (39 mg, 24%). $^1$H NMR (MeOH-d$_4$, 400 MHz) δ 1.20 (d, 6H), 1.63-1.72 (m, 2H), 1.89-1.99 (m, 2H), 2.11 (s, 3H), 3.19-3.26 (m, 3H), 3.33-3.43 (m, 2H), 3.44-3.56 (m, 4H), 3.64-3.73 (m, 2H), 4.80 (s, 1H), 5.30 (h, 1H), 7.02-7.16 (m, 31H), 8.03 (s, 1H). Exact mass calculated for C$_{24}$H$_{31}$FN$_4$O$_6$ 490.52, found 491.4 (MH$^+$).

Example 11.13

Preparation of 4-[6-(5-Iodo-pyridin-2-yloxy)-5-methyl-pyrimidin-4-yloxy]-piperidine-1-carboxylic acid isopropyl ester (Compound C34)

A mixture of 4-(6-chloro-5-methyl-pyrimidin-4-yloxy)-piperidine-1-carboxylic acid isopropyl ester (1.02 g, 3.25 mmol), 2-hydroxy-5-iodopyridine, and potassium carbonate (903 mg, 6.53 mmol) in 15 mL DMF were heated under microwave irradiation for 1 hour at 150° C. Mixture was purified by HPLC to give Compound C34 (TFA salt, 177 mg, 9%) as a white solid. $^1$H NMR (CDCl$_3$, 400 MHz) δ 1.24-1.25 (d, 6H), 1.75-1.83 (m, 2H), 1.97-2.03 (m, 2H), 2.20 (s, 3H), 3.40-3.45 (m, 2H), 3.71-3.79 (m, 2H), 4.91-4.97 (m, 1H), 5.33-5.39 (m, 1H), 6.93-6.95 (d, 1H), 8.04-8.07 (dd, 1H), 8.31 (s, 1H), 8.51-8.52 (d, 1H). Exact mass calculated for C$_{19}$H$_{23}$I N$_4$O$_4$ 498.08, found 499.2 (MH$^+$).

Example 11.14

Preparation of 4-(6-{2-Fluoro-4-[N-(2-isopropoxy-ethyl)-carbamimidoyl]-phenoxy}-5-methyl-pyrimidin-4-yloxy)-piperidine-1-carboxylic acid isopropyl ester (Compound C36) and 4-[6-(4-Carbamoyl-2-fluoro-phenoxy)-5-methyl-pyrimidin-4-yloxy]-piperidine-1-carboxylic acid isopropyl ester (Compound C139)

Step 1: Preparation of 4-[6-(2-fluoro-4-phenylsulfanylcarbonimidoyl-phenoxy)-5-methyl-pyrimidin-4-yloxy]-piperidine-1-carboxylic acid isopropyl ester A mixture of 4-[6-(4-cyano-2-fluoro-phenoxy)-5-methyl-pyrimidin-4-yloxy]-piperidine-1-carboxylic acid isopropyl ester (TFA salt, 109 mg, 0.21 mmol) and thiophenol (27 µl, 0.21 mmol) in Et$_2$O (1 mL) was stirred in an ice-bath under HBr atmosphere for 30 min. The crude compound was used for the next step without further purification. Exact mass calculated for C$_{27}$H$_{29}$FN$_4$O$_4$S 524.19, found 525.3 (MH$^+$).

Step 2: Preparation of 4-(6-{2-Fluoro-4-[N-(2-isopropoxy-ethyl)-carbamimidoyl]-phenoxy}-5-methyl-pyrimidin-4-yloxy)-piperidine-1-carboxylic acid isopropyl ester (Compound C36) and 4-[6-(4-Carbamoyl-2-fluoro-phenoxy)-5-methyl-pyrimidin-4-yloxy]-piperidine-1-carboxylic acid isopropyl ester (Compound C139)

A mixture of 4-[6-(2-fluoro-4-phenylsulfanylcarbonimidoyl-phenoxy)-5-methyl-pyrimidin-4-yloxy]-piperidine-1-carboxylic acid isopropyl ester (108.4 mg, 0.21 mmol) and 2-aminoethyl isopropyl ether (101 μl, 0.83 mmol) in MeOH (2 mL) was stirred at room temperature for 30 min. Additional 2-aminoethyl isopropyl ether (2 mL, 16.3 mmol) was added and the mixture was stirred under 70° C. for 10 min. The crude mixture was purified by HPLC to provide Compound C36 as a solid (TFA salt, 19.6 mg, 15%). and Compound C139 in solid as a by-product (TFA salt, 23.7 mg, 21%). Compound C36: $^1$H NMR (CDCl$_3$, 400 MHz) δ 1.13-1.20 (m, 6H), 1.26-1.27 (d, 6H), 1.78-1.80 (m, 2H), 1.98-1.99 (m, 2H), 2.19-2.20 (d, 3H), 2.82 (s, 5H), 3.39-3.46 (m, 3H), 3.68-3.79 (m, 4H), 4.92-4.95 (m, 1H), 5.34-5.35 (m, 1H), 7.38-7.44 (m, 1H), 7.68-7.71 (t, 1H), 8.13-8.19 (d, 1H). Exact mass calculated for Compound C36, $C_{26}H_{36}FN_5O_5$ 517.27, found 518.5 (MH$^+$) and for Compound C139, exact mass calculated for $C_{21}H_{25}FN_4O_5$ 432.18, found 433.1 (MH$^+$).

Example 11.15

Preparation of 4-[6-(4-Carboxy-2-fluoro-phenoxy)-5-methyl-pyrimidin-4-yloxy]-piperidine-1-carboxylic acid isopropyl ester (Compound C38)

A mixture of 4-(6-chloro-5-methyl-pyrimidin-4-yloxy)-piperidine-1-carboxylic acid isopropyl ester (300 mg, 0.96 mmol), 2 (150 mg, 0.96 mmol) and potassium carbonate (160 mg, 1.15 mmol) in DMSO was heated under microwave for 4 hrs at 160° C. The mixture was purified through HPLC to afford Compound C38 (200 mg, 48%) as a solid and Compound C9 as a by product. Compound C38: $^1$H NMR (MeOH-d$_4$, 400 MHz) δ 1.15 (d, 6H), 1.64-1.67 (m, 2H), 1.88-1.92 (m, 2H), 2.09 (s, 3H), 3.29-3.31 (m, 2H), 3.62-3.66 (m, 2H), 4.72-4.78 (m, 1H), 5.25-5.28 (m, 1H), 7.23 (t, 1H), 7.70 (d, 1H), 7.77 (d, 1H), 8.02 (s, 1H). Exact mass calculated for $C_{21}H_{24}FN_3O_6$ 433.2, found 434.3 (MH$^+$). Compound C9: Exact mass calculated for $C_{20}H_{24}FN_3O_4$ 389.2, found 390.3 (MH+).

Example 11.16

Preparation of 4-(4-Bromo-2-fluoro-phenoxy)-6-[1-(3-isopropyl-[1,2,4]oxadiazol-5-yl)-piperidin-4-yloxy]-5-methyl-pyrimidine (Compound C40)

A mixture of 4-chloro-6-[1-(3-isopropyl-[1,2,4]oxadiazol-5-yl)-piperidin-4-yloxy]-5-methyl-pyrimidine (1.51 g, 4.46 mmol), potassium carbonate (1.25 g, 9.03 mmol), and 4-bromo-2-fluorophenol (1.11 g, 5.82 mmol) in 15 mL DMF was heated in microwave for 1 hour at 150° C. The mixture was purified by column chromatography on silica gel with hexane/ethyl acetate (3:1 v/v) to give Compound C40 as an oil (1.05 g, 48%). $^1$H NMR (CDCl$_3$, 400 MHz) δ 1.20-1.22 (d, 6H), 1.83-1.91 (m, 2H), 1.98-2.05 (m, 2H), 2.11 (s, 3H), 2.77-2.87 (m, 1H), 3.53-3.59 (m, 2H), 3.74-3.80 (m, 2H), 5.31-5.36 (m, 1H), 6.99-7.03 (m, 1H), 7.22-7.29 (m, 2H), 8.13 (s, 1H). Exact mass calculated for $C_{21}H_{23}BrFN_5O_3$ 491.1, found 492.4 (MH$^+$).

Example 11.17

Preparation of 4-[6-(5-Methanesulfonyl-pyridin-2-yloxy)-5-methyl-pyrimidin-4-yloxy]-piperidine-1-carboxylic acid isopropyl ester (Compound C42)

A mixture of 4-[6-(5-iodo-pyridin-2-yloxy)-5-methyl-pyrimidin-4-yloxy]-piperidine-1-carboxylic acid isopropyl ester (TFA salt, 35.1 mg, 0.07 mmol), sodium methanesulfinate (21.4 mg, 0.21 mmol), copper (I) trifluoromethanesulfonate benzene complex (3.5 mg, 0.007 mmol), and N,N-dimethyl-ethane-1,2-diamine in 1.5 mL DMSO were heated under microwave irradiation for 30 minutes at 160° C. Mixture was purified by HPLC to give Compound C42 as a white solid (TFA salt, 11.5 mg, 30%). $^1$H NMR (MeOH-d$_4$, 400 MHz) δ 1.21-1.22 (d, 6H), 1.71-1.79 (m, 2H), 1.96-2.07 (m, 5H), 3.16 (s, 3H), 3.35-4.42 (m, 2H), 3.80-3.87 (m, 2H), 4.80-4.86 (m, 1H), 5.38-5.42 (m, 1H), 7.32-7.34 (d, 1H), 8.29 (s, 1H), 8.35-8.37 (dd, 1H), 8.69 (s, 1H). Exact mass calculated for $C_{20}H_{26}N_4O_6S$ 450.16, found 451.4 (MH$^+$).

Example 11.18

Preparation of 4-{6-[6-(2-Hydroxy-ethylamino)-2-methyl-pyridin-3-yloxy]-5-methyl-pyrimidin-4-yloxy}-piperidine-1-carboxylic acid isopropyl ester (Compound C43)

To a solution of 4-{6-[6-(2-methoxy-ethylamino)-2-methyl-pyridin-3-yloxy]-5-methyl-pyrimidin-4-yloxy}-piperidine-1-carboxylic acid isopropyl ester (TFA salt, 87 mg, 0.152 mmol) in methylene chloride, trimethylsilyl iodide (300 μl, 1.5 mmol) was added. After stirring for 3 hours at room temperature, mixture was quenched with methanol and purified by HPLC to give Compound C43 as a white solid (TFA salt, 40.6 mg, 48%). $^1$H NMR (MeOH-d$_4$, 400 MHz) δ 1.22-1.23 (d, J=6.2 Hz, 6H), 1.69-1.77 (m, 2H), 1.94-2.02 (m, 2H), 2.17 (s, 3HR, 2.31 (s, 3H), 3.32-3.40 (m, 2H), 3.52-3.55 (t, J=5.1 Hz, 2H), 3.70-3.80 (m, 4H), 4.84-4.88 (m, 1H), 5.34-5.38 (m, 1H), 6.93-6.95 (d, J=9.6 Hz, 1H), 7.70-7.73 (d, J=9.6 Hz, 1H), 8.13 (s, 1H). Exact mass calculated for $C_{22}H_{31}N_5O_5$ 445.23, found 446.3 (MH$^+$).

Example 11.19

Preparation of 4-[5-Cyclopropyl-6-(2-fluoro-4-methanesulfonyl-phenoxy)-pyrimidin-4-yloxy]-piperidine-1-carboxylic acid isopropyl ester (Compound C44)

Step 1: Preparation of 4-(6-chloro-5-cyclopropyl-pyrimidin-4-yloxy)-piperidine-1-carboxylic acid isopropyl ester To a solution of 4,6-dichloro-5-cyclopropyl-pyrimidine (700 mg, 3.70 mmol) and 4-hydroxy-piperidine-1-carboxylic acid isopropyl ester (636.6 mg, 3.70 mmol) in dry THF under nitrogen at 0° C., potassium tert-butoxide (1M solution in THF, 4.45 mL) was added dropwise. The reaction was stirred at rt for 30 min. The mixture was quenched with water and extracted with EtOAc (3x). The organic layer was washed with water, sat. NH$_4$Cl and brine, followed by drying over sodium sulfate and concentration under vacuo. The resulting oil was purified by flash chromatography (0-20% EtOAc/Hexanes) to afford 4-(6-chloro-5-cyclopropyl-pyrimidin-4-yloxy)-piperidine-1-carboxylic acid isopropyl ester (0.927 g, 73.7%) as colorless oil. Exact mass calculated for $C_{16}H_{22}ClN_3O_3$ 339.13, found 340.3 (MH$^+$).

Step 2: Preparation of 4-[5-Cyclopropyl-6-(2-fluoro-4-methanesulfonyl-phenoxy)-pyrimidin-4-yloxy]-piperidine-1-carboxylic acid isopropyl ester (Compound C44)

4-(6-Chloro-5-cyclopropyl-pyrimidin-4-yloxy)-piperidine-1-carboxylic acid isopropyl ester (200 mg, 0.588 mmol), 2-fluoro-4-methanesulfonyl-phenol (168 mg, 0.883 mmol) and sodium hydride (60% dispersion in mineral oil, 53 mg, 1.325 mmol) were dissolved in DMSO (2 mL) and the mixture stirred under Nitrogen for 10 min at rt. The mixture was then heated under microwave irradiation for 1 h at 150° C. The crude was quenched with water and extracted with EtOAc (3×). The organic layer was concentrated and the residue was purified by HPLC to afford Compound C44 (51 mg, 14.3%) as oil. $^1$H NMR (CDCl$_3$, 400 MHz) δ 0.90-0.97 (m, 2H), 1.01-1.06 (m, 2H), 1.23-1.27 (d, J=6.06 Hz, 6H), 1.76-1.91 (m, 2H), 1.92-2.02 (m, 2H), 3.08 (s, 3H), 3.46-3.55 (m, 2H), 3.63-3.72 (m, 2H), 4.87-4.98 (m, 1H), 5.32-5.39 (m, 1H), 7.36-7.42 (m, 1H), 7.73-7.80 (m, 2H), 8.17 (s, 1H). Exact mass calculated for $C_{23}H_{28}FN_3O_6S$ 493.17, found 494.5 (MH$^+$).

Example 11.20

Preparation of 4-{6-[6-(2-Methanesulfonyl-ethylamino)-2-methyl-pyridin-3-yloxy]-5-methyl-pyrimidin-4-yloxy}-piperidine-1-carboxylic acid isopropyl ester (Compound C46)

Using a similar procedure as described in Example 11.4 for the preparation of Compound C10, Compound C46 was obtained as a tanned solid (TFA salt, 27.0 mg, 30%). $^1$H NMR (MeOH-d$_4$, 400 MHz) δ 1.05-1.06 (d, 6H), 1.64-1.72 (m, 2H), 1.88-1.97 (m, 2H), 2.12 (s, 3H), 2.27 (s, 3H), 2.98 (s, 3H), 3.29-3.37 (m, 2H), 3.43-3.46 (t, 2H), 3.65-3.71 (m, 2H), 3.86-3.89 (t, 2H), 4.78-4.82 (m, 1H), 5.29-5.33 (m, 1H), 6.90-6.92 (d, 1H), 7.72-7.74 (d, 1H), 8.07 (s, 1H). Exact mass calculated for $C_{23}H_{33}N_5O_6S$ 507.22, found 508.6 (MH$^+$).

Example 11.21

Preparation of 1-{4-[6-(2-Fluoro-4-methanesulfonyl-phenoxy)-5-methyl-pyrimidin-4-yloxy]-piperidin-1-yl}-5-methyl-hexan-1-one (Compound C 121)

4-(2-Fluoro-4-methanesulfonyl-phenoxy)-5-methyl-6-(piperidin-4-yloxy)-pyrimidine (42 mg, 0.1 mmol), 5-methyl-hexanoic acid (0.12 mmol, 1.2 eq), HATU (0.12 mmol, 1.2 eq), and triethylamine (0.2 mmol, 2 eq) were dissolved in DMF (1 mL), and then stirred at room temperature for 1 hour. The crude was filtered and then purified via prep-LCMS 5-95% to provide Compound C121 as a white powder (28.2 mg, 57%). Exact mass calculated for $C_{24}H_{32}FN_3O_5S$ 493.2, found LCMS (ESI) mf/z 494.5 (MH$^+$).

Example 11.22

Preparation of 4-{6-[6-(2-Methoxy-ethylsulfanyl)-2-methyl-pyridin-3-yloxy]-5-methyl-pyrimidin-4-yloxy}-piperidine-1-carboxylic acid isopropyl ester (Compound C56)

To a solution of compound C12 (15 mg, 0.0324 mmol) in 1 mL THF, sodium hydride dispersion (8 mg, 0.2 mmol) was added. After 10 minutes, methyl iodide (20 μl, 0.32 mmol) was added and mixture was stirred at room temperature for 17 hours. Mixture was purified by column chromatography (AcOEt/hexane) to give Compound C56 as white solid (10.1 mg, 65%). $^1$H NMR (CDCl$_3$, 400 MHz) δ 1.25-1.27 (d, J=6.3 Hz, 6H), 1.75-1.85 (m, 2H), 1.95-2.05 (m, 2H), 2.19 (s, 3H), 2.34 (s, 3H), 3.37-3.45 (m, 7H), 3.65-3.68 (t, J=6.7 Hz, 2H), 3.75-3.81 (m, 2H), 4.91-4.97 (m, 1H), 5.32-5.36 (m, 1H), 7.07-7.09 (d, J=8.4 Hz, 1H), 7.22-7.20 (d, J=8.4 Hz, 1H), 8.19 (s, 1H). Exact mass calculated for $C_{23}H_{32}N_4O_5S$ 476.21, found 477.4 (MH$^+$).

Example 11.23

Preparation of 1-(2,5-Dimethoxy-phenyl)-2-{4-[6-(2-fluoro-4-methanesulfonyl-phenoxy)-5-methyl-pyrimidin-4-yloxy]-piperidin-1-yl}-ethanone (Compound C60)

Compound C60 was prepared using a similar procedure as described in Example 11.7 and was obtained as an oil (35.9 mg, 64%). Exact mass calculated for $C_{27}H_{30}FN_3O_7S$ 559.2, found LCMS (ESI) m/z 560.4 (MH$^+$).

Example 11.24

Preparation of 4-[6-(6-Chloro-2-methyl-pyridin-3-yloxy)-5-methyl-pyrimidin-4-yloxy]-piperidine-1-carboxylic acid isopropyl ester (Compound C65)

A mixture of 4-(6-chloro-5-methyl-pyrimidin-4-yloxy)-piperidine-1-carboxylic acid isopropyl ester (1.03 g, 3.27 mmol), 6-chloro-2-methyl-pyridin-3-ol (470 mg, 3.27 mmol), and potassium carbonate (903 mg, 6.53 mmol) in 15 mL DMF were heated in microwave for 1 hour at 150° C. The mixture was purified to give Compound C65 as a white solid (0.975 g, 71%). $^1$H NMR (CDCl$_3$, 400 MHz) δ 0.92-0.94 (d, 6H), 1.74-1.82 (m, 2H), 1.95-2.02 (m, 2H), 2.19 (s, 3H), 2.47 (s, 3H), 3.39-3.45 (m, 2H), 3.74-3.79 (m, 2H), 4.91-4.97 (m, 1H), 5.33-5.36 (m, 1H), 7.21-7.23 (d, 1H), 7.36-7.38 (d, 1H), 8.19 (s, 1H). Exact mass calculated for $C_{20}H_{25}ClN_4O_4$ 420.16, found 421.3 (MH$^+$).

Example 11.25

Preparation of 1-{4-[6-(2-Fluoro-4-methanesulfonyl-phenoxy)-5-methyl-pyrimidin-4-yloxy]-piperidin-1-yl}-3,3-dimethyl-butan-2-one (Compound C78)

Compound C78 was prepared using a similar procedure as described in Example 11.7 and was obtained as an oil (26 mg, 54%). Exact mass calculated for $C_{23}H_{30}FN_3O_5S$ 479.2, found LCMS (ESI) m/z 480.4 (MH$^+$).

Example 11.26

Preparation of 2-{4-[6-(2-Fluoro-4-methanesulfonyl-phenoxy)-5-methyl-pyrimidin-4-yloxy]-piperidin-1-yl}-1-pyridin-2-yl-ethanone (Compound C22)

Compound C22 was prepared using a similar procedure as described in Example 11.7 and was purified by preparative HPLC. $^1$H NMR (CDCl$_3$, 400 MHz) δ 2.24 (s, 3H), 2.29 (m, 1H), 2.42 (m, 1H), 2.57 (m, 2H), 3.11 (s, 3H), 3.51 (m, 2H), 3.77 (m, 2H), 4.98 (s, 2H), 5.60 (m, 1H), 7.43 (t, 1H), 7.61 (m, 1H), 7.82 (m, 2H), 7.91 (m, 1H), 8.23 (m, 1H), 8.67 (m, 1H). Exact mass calculated for $C_{24}H_{25}FN_4O_5S$ 500.15, found 501.3 (MH$^+$).

Example 11.27

Preparation of 2-{4-[6-(2-Fluoro-4-methanesulfonyl-phenoxy)-5-methyl-pyrimidin-4-yloxy]-piperidin-1-yl}-1-(3-fluoro-phenyl)-ethanone (Compound C16)

Compound C16 was prepared using a similar procedure as described in Example 11.7 and purified by preparative HPLC. $^1$H NMR (CDCl$_3$, 400 MHz) δ 2.31 (s, 3H), 2.34 (m, 2H), 2.39 (m, 2H), 3.11 (s, 3H), 3.68 (m, 4H), 4.78 (s, 2H), 5.59 (m, 1H), 7.36 (m, 1H), 7.46 (m, 1H), 7.52 (m, 1H), 7.63 (m, 1H), 7.71 (m, 1H), 7.82 (m, 2H), 8.22 (s, 1H). Exact mass calculated for $C_{25}H_{25}F_2N_3O_5S$ 517.15, found 518.3 (MH$^+$).

Example 11.28

Preparation of 4-(6-{2-Fluoro-4-[(2-isopropoxy-ethylcarbamoyl)-methyl]-phenoxy}-5-methyl-pyrimidin-4-yloxy)-piperidine-1-carboxylic acid isopropyl ester (Compound C101)

Compound C101 was obtained in a similar manner as described in Example 11.36 as a solid (30 mg, 20%). $^1$H NMR (DMSO-d$_6$, 400 MHz) δ 1.08 (d, 6H), 1.21 (d, 6H), 1.62-1.73 (m, 2H), 1.92-2.01 (m, 2H), 2.16 (s, 3H), 3.21 (q, 2H), 3.31-3.41 (m, 4H), 3.48 (s, 2H), 3.50-3.60 (m, 1H), 3.61-3.71 (m, 2H), 4.80 (h, 1H), 5.33 (h, 1H), 7.13 (d, 1H), 7.22-7.30 (m, 2H), 8.17 (t, 1H), 8.26 (s, 1H). Exact mass calculated for $C_{27}H_{37}FN_4O_6$ 532.60, found 533.4 (MH$^+$).

Example 11.29

Preparation of 4-{6-[2-Fluoro-4-(2-isopropoxy-ethylcarbamoyl)-phenoxy]-5-methyl-pyrimidin-4-yloxy}-piperidine-1-carboxylic acid isopropyl ester (Compound C113)

Compound C113 was obtained in a similar manner as described in Example 11.36 as a solid (25 mg, 83%). $^1$H NMR (MeOH-d$_4$, 400 MHz) δ 1.03 (d, 6H), 1.12 (d, 6H), 1.62-1.65 (m, 2H), 1.86-1.91 (m, 2H), 2.07 (s, 3H), 3.25-3.31 (m, 2H), 3.38-3.44 (m, 2H), 3.48-3.53 (m, 3H), 3.60-3.68 (m, 2H), 4.74-4.76 (m, 1H), 5.24-5.27 (m, 1H), 7.21 (t, 1H), 4.56-7.59 (m, 2H), 8.00 (s, 1H), 8.43 (t, 1H). Exact mass calculated for $C_{26}H_{35}FN_4O_6$ 518.2, found 519.5 (MH$^+$).

Example 11.30

Preparation of 1-{4-[6-(2-Fluoro-4-methanesulfonyl-phenoxy)-5-methyl-pyrimidin-4-yloxy]-piperidin-1-yl}-butan-1-one (Compound C115)

Compound C115 was prepared in a similar manner as described in Example 11.21 and was obtained as a white powder (27.1 mg, 60%). Exact mass calculated for $C_{21}H_{26}FN_3O_5S$ 451.2, found 452.2 (MH$^+$).

Example 11.31

Preparation of 1-{4-[6-(2-Fluoro-4-methanesulfonyl-phenoxy)-5-methyl-pyrimidin-4-yloxy]-piperidin-1-yl}-pentan-1-one (Compound C116)

Compound C116 was prepared in a similar manner as described in Example 11.21 and was obtained as a white powder (29.9 mg, 64%). Exact mass calculated for $C_{22}H_{28}FN_3O_5S$ 465.2, found 466.4 (MH$^+$).

Example 11.32

Preparation of 4-[6-(2,4-Difluoro-phenoxy)-5-methyl-pyrimidin-4-yloxy]-piperidine-1-carboxylic acid isopropyl ester (Compound C117)

A mixture of 4-(6-chloro-5-methyl-pyrimidin-4-yloxy)-piperidine-1-carboxylic acid isopropyl ester (1.0 g, 3.19 mmol), 2,4-difluoro-phenol (585 mg, 4.5 mmol), and potassium carbonate (882 mg, 6.38 mmol) in DMF (11 mL) was heated under microwave irradiation for 80 min at 150° C. The crude mixture was concentrated in vacuo and purified by HPLC to provide Compound C117 as a beige solid (890 mg, 69%). $^1$H NMR (CDCl$_3$, 400 MHz) δ 1.19 (d, 6H), 1.66-1.76 (m, 2H), 1.86-1.95 (m, 2H), 2.11 (s, 3H), 3.30-3.40 (m, 2H), 3.63-3.73 (m, 2H), 4.86 (m, 1H), 5.26 (m, 1H), 6.80-6.91 (m, 2H), 7.09 (q, 1H), 7.19 (s, 1H). Exact mass calculated for $C_{20}H_{23}F_2N_3O_4$ 407.41, found 408.3 (MH$^+$).

Example 11.33

Preparation of 1-{4-[6-(2-Fluoro-4-methanesulfonyl-phenoxy)-5-methyl-pyrimidin-4-yloxy]-piperidin-1-yl}-3-methyl-butan-1-one (Compound C119)

Compound C119 was obtained in a similar manner as described in Example 11.21 as a white powder (28.5 mg, 61%). Exact mass calculated for $C_{22}H_{28}FN_3O_5S$ 465.2, found 466.4 (MH$^+$).

Example 11.34

Preparation of 1-{4-[6-(2-Fluoro-4-methanesulfonyl-phenoxy)-5-methyl-pyrimidin-4-yloxy]-piperidin-1-yl}-4-methyl-pentan-1-one (Compound C120)

Compound C120 was obtained in a similar manner as described in Example 11.21 as an oil (33.3 mg, 69%). Exact mass calculated for $C_{23}H_{30}FN_3O_5S$ 479.2, found LCMS (ESI) m/z 480.4 (MH$^+$).

Example 11.35

Preparation of 4-{4-[6-(2-Fluoro-4-methanesulfonyl-phenoxy)-5-methyl-pyrimidin-4-yloxy]-piperidin-1-yl}-4-oxo-butyric Acid (Compound C51)

Compound C51 was obtained in a similar manner as described in Example 11.21 as a white powder (11.9 mg, 25%). Exact mass calculated for $C_{21}H_{24}FN_3O_7S_{481.1}$, found LCMS (ESI) m/z 482.2 (MH$^+$).

Example 11.36

Preparation of 4-{6-[2-Fluoro-4-(2-methoxy-ethylcarbamoyl)-phenoxy]-5-methyl-pyrimidin-4-yloxy}-piperidine-1-carboxylic Acid isopropyl ester (Compound C122)

A mixture of 4-[6-(4-Carboxy-2-fluoro-phenoxy)-5-methyl-pyrimidin-4-yloxy]-piperidine-1-carboxylic acid isopropyl ester (150 mg, 0.346 mmol), 2-Methoxy-ethylamine (31 mg, 0.41 mmol), HATU (157 mg, 0.42 mmol) and triethyl amine (70 mg, 0.7 mmol) in DMF (5 mL) was stirred at room temperature for 2 h. The mixture was purified through HPLC to provide Compound C122 (115 mg, 68%) as a solid. $^1$H NMR (MeOH-d$_4$, 400 MHz) δ 1.22 (d, J=6.82 Hz, 6H), 1.71-1.74 (m, 2H), 1.97-2.00 (m, 2H), 2.16 (s, 3H), 3.34 (s, 3H), 3.35-3.39 (m, 2H), 3.53 (s, 4H), 3.71-3.74 (m, 2H), 4.81-4.84 (m, 1H), 5.33-5.36 (m, 1H), 7.30 (t, J=8.1 Hz, 1H), 7.66-7.69 (m, 2H), 8.09 (s, 1H). Exact mass calculated for $C_{24}H_{31}FN_4O_6$ 490.2, found 491.4 (MH$^+$).

Example 11.37

Preparation of 4-[6-(2-Fluoro-4-methanesulfonyl-phenoxy)-5-methyl-pyrimidin-4-yloxy]-piperidine-1-carboxylic acid isopropyl ester (Compound C127)

Step 1: Preparation of 4-[6-(4-bromo-2-fluoro-phenoxy)-5-methyl-pyrimidin-4-yloxy]-piperidine-1-carboxylic acid isopropyl ester A mixture of 4-(6-chloro-5-methyl-pyrimidin-4-yloxy)-piperidine-1-carboxylic acid isopropyl ester (1.0098 g, 3.2 mmol), potassium carbonate (889.5 mg, 6.43 mmol), and 4-bromo-2-fluorophenol (458 μl, 4.18 mmol) in 15 mL DMF was heated in microwave for 1 hour at 150° C. The mixture was purified by HPLC to give 4-[6-(4-bromo-2-fluoro-phenoxy)-5-methyl-pyrimidin-4-yloxy]-piperidine-1-carboxylic acid isopropyl ester as a tanned solid as the TFA salt (Compound C130, 741 mg, 39%). Exact mass calculated for $C_{20}H_{23}BrFN_3O_4$ 467.09, found 468.3 ($MH^+$).

Step 2: 4-[6-(2-Fluoro-4-methanesulfonyl-phenoxy)-5-methyl-pyrimidin-4-yloxy]-piperidine-1-carboxylic acid isopropyl ester (Compound C127)

A mixture of 4-[6-(4-bromo-2-fluoro-phenoxy)-5-methyl-pyrimidin-4-yloxy]-piperidine-1-carboxylic acid isopropyl ester (741 mg, 1.27 mmol), sodium methane sulfinate (288.4 mg, 2.82 mmol), and N,N'-dimethyl-ethylene diamine (28 mg, 0.317 mmol) and copper (I) trifluoromethane sulfonate benzene complex (95.6 mg, 0.190 mmol) in 10 mL DMSO was heated in microwave for 30 min at 160° C. The mixture was purified by HPLC to give Compound C127 as a white solid (TFA salt, 327.1 mg, 44%). $^1$H NMR (CD$_3$CN-d$_3$, 400 MHz) δ 1.21-1.23 (d, J=6.32 Hz, 6H), 1.69-1.77 (m, 2H), 1.93-1.95 (m, 2H), 2.184 (s, 3H), 3.125 (s, 3H), 3.359-3.441 (m, 2H), 3.650-3.734 (m, 2H), 4.84 (hept, J=6.32 Hz, 1H), 5.313-5.380 (m, 1H), 7.470-7.526 (m, 1H), 7.781-7.846 (m, 2H) 8.158 (s, 1H). Exact mass calculated for $C_{21}H_{26}FN_3O_6S$ 467.15, found 468.4 ($MH^+$).

Example 11.38

Preparation of 4-{6-[2-Fluoro-4-(methoxy-methyl-carbamoyl)-phenoxy]-5-methyl-pyrimidin-4-yloxy}-piperidine-1-carboxylic Acid Isopropyl Este (Compound C132)

Compound C132 was obtained in a similar manner as described in Example 11.36 as an oil (40 mg, 85%). $^1$H NMR (CDCl$_3$, 400 MHz) δ 1.26 (d, J=6.32 Hz, 6H), 1.75-1.83 (m, 2H), 1.96-2.02 (m, 2H), 2.18 (s, 3H), 3.38 (s, 3H), 3.39-3.46 (m, 2H), 3.60 (s, 3H), 3.71-3.77 (m, 2H), 4.93 (hept, J=6.32 Hz, 1H), 5.31-5.36 (m, 1H), 7.21-7.26 (m, 1H), 7.58-7.62 (m, 2H), 8.20 (s, 1H). Exact mass calculated for $C_{23}H_{29}FN_4O_6$ 476.2, found 477.3 ($MH^+$).

Example 11.39

Preparation of 1-{4-[6-(2-Fluoro-4-methanesulfonyl-phenoxy)-5-methyl-pyrimidin-4-yloxy]-piperidin-1-yl}-3-methoxy-propan-1-one (Compound C133)

Compound C132 was prepared in a similar manner as described in Example 11.21 and was obtained as a white powder (30.5 mg, 65%). Exact mass calculated for $C_{21}H_{26}FN_3O_6S$ 467.1, found LCMS (ESI) m/z 468.2 ($MH^+$).

Example 11.40

Preparation of 4-[6-(4-Cyano-2-fluoro-phenoxy)-5-methyl-pyrimidin-4-yloxy]-piperidine-1-carboxylic acid isopropyl ester (Compound C134)

A mixture of 4-[6-(4-bromo-2-fluoro-phenoxy)-5-methyl-pyrimidin-4-yloxy]-piperidine-1-carboxylic acid isopropyl ester (Compound C130, 1.14 g, 2.4 mmol), zinc cyanide (290 mg, 2.42 mmol), and tetrakistriphenylphosphinepalladium (0) (281 mg, 0.24 mmol) in DMF (15 mL) was purged with Argon and heated under microwave irradiation at 180° C. for 8 min. The crude mixture was purified by HPLC to provide Compound C134 as a solid (TFA salt, 318 mg, 27%). $^1$H NMR (CDCl$_3$, 400 MHz) δ 1.27-1.28 (d, J=6.32 Hz, 6H), 1.81-1.84 (m, 2H), 1.99-2.02 (m, 2H), 2.20 (s, 3H), 3.43-3.49 (m, 2H), 3.75-3.77 (m, 2H), 4.94-4.97 (m, J=6.32 Hz, 1H), 5.35-5.36 (m, J=3.79 Hz, 1H), 7.33-7.37 (m, 1H), 7.49-7.54 (m, 2H), 8.21 (s, 1H). Exact mass calculated for $C_{21}H_{23}FN_4O_4$ 414.17, found 415.4 ($MH^+$).

Example 11.41

Preparation of 4-[5-(5-Aminomethyl-4,5-dihydro-oxazol-2-yl)-6-(2-fluoro-4-methanesulfonyl-phenoxy)-pyrimidin-4-yloxy]-piperidine-1-carboxylic acid isopropyl ester (Compound C135)

In a 100 mL round-bottomed flask fitted with a condenser and N$_2$ inlet was placed a stir bar, 4-[5-cyano-6-(2-fluoro-4-methanesulfonyl-phenylamino)-pyrimidin-4-yloxy]-piperidine-1-carboxylic acid isopropyl ester (1 g, 2 mmol), ZnCl$_2$ (30 mg, 0.2 mmol), 1,3-diamino-propan-2-ol (180 mg, 2 mmol), and chlorobenzene (20 mL). The reaction mixture was heated under reflux overnight. After it was cooled down to room temperature, the reaction was quenched with H$_2$O. The resulting suspension was extracted with EtOAc. The organic extracts was dried and concentrated under vacuum. The crude residue was purified by preparative HPLC to give Compound C135. $^1$H NMR (CDCl$_3$, 400 MHz) δ 1.25 (d, 6H), 1.73 (m, 2H), 1.94 (m, 2H), 2.98 (s, 3H), 3.31 (m, 2H), 3.46 (m, 2H), 3.69 (m, 4H), 4.48 (m, 1H), 4.83 (m, 1H), 5.36 (m, 1H), 7.40 (d, 1H), 7.49 (d, 1H), 8.36 (t, 1H), 8.44 (s, 1H), 9.52 (m, 2H). Exact mass calculated for $C_{24}H_{31}FN_6O_6S$ 550.20, found 551.3 ($MH^+$).

Example 11.42

Preparation of 4-{6-[6-(2-Methoxy-ethylamino)-2-methyl-pyridin-3-yloxy]-5-methyl-pyrimidin-4-yloxy}-piperidine-1-carboxylic acid isopropyl ester (Compound C136)

Using a similar procedure as described in Example 11.4 for the preparation of Compound C10, Compound C136 was obtained as a tanned solid (TFA salt, 167.8 mg, 65%). $^1$H NMR (MeOH-d$_4$, 400 MHz) δ 1.48-1.49 (d, 6H), 1.95-2.02 (m, 2H), 2.21-2.28 (m, 2H), 2.43 (s, 3H), 2.58 (s, 3H), 3.61-3.67 (m, 5H), 3.85-3.89 (m, 4H), 3.95-4.03 (m, 2H), 5.10-5.13 (m, 1H), 7.20-7.22 (d, 1H), 7.98-8.00 (d, 1H), 7.98-8.00 (d, 1H), 8.40 (s, 1H). Exact mass calculated for $C_{23}H_{33}N_5O_5$ 459.25, found 460.3 ($MH^+$).[1]

Example 11.43

Preparation of 4-{6-[6-(3-Methanesulfonyl-pyrrolidin-1-yl)-2-methyl-pyridin-3-yloxy]-5-methyl-pyrimidin-4-yloxy}-piperidine-1-carboxylic acid isopropyl ester (Compound C137)

Using a similar procedure as described in Example 11.4 for the preparation of Compound C10, Compound C137 was obtained as an oil (TFA salt, 54.4 mg, 58%). $^1$H NMR (MeOH-d$_4$, 400 MHz) δ 1.22-1.23 (d, 6H), 1.69-1.77 (m, 2H), 1.95-2.02 (m, 2H), 2.18 (s, 3H), 2.38 (s, 3H), 2.52-2.70 (m, 2H), 3.07 (s, 3H), 3.32-3.42 (m, 2H), 3.71-4.19 (m, 8H), 5.35-5.38 (m, 1H), 6.97-6.99 (d, 1H), 7.80-7.83 (d, 1H), 8.12 (s, 1H). Exact mass calculated for $C_{25}H_{35}N_5O_6S$ 533.23, found 534.5 (MH$^+$).

Example 11.44

Preparation of 4-[6-(6-Benzylamino-2-methyl-pyridin-3-yloxy)-5-methyl-pyrimidin-4-yloxy]-piperidine-1-carboxylic acid isopropyl ester (Compound C138)

Using a similar procedure as described in Example 11.4 for the preparation of Compound C10, Compound C138 was obtained as an oil (TFA salt, 80.8 mg, 61%). $^1$H NMR (MeOH-d$_4$, 400 MHz) δ 1.07-1.10 (d, 6H), 1.68-1.77 (m, 2H), 1.93-1.91 (m, 2H), 2.17 (s, 3H), 2.34 (s, 3H), 3.31-3.41 (m, 2H), 3.69-3.78 (m, 2H), 3.94 (s, 1H), 4.61 (s, 2H), 5.31-5.36 (m, 1H), 6.89-6.91 (d, 1H), 7.30-7.39 (m, 5H), 7.73-7.75 (d, 1H), 8.13 (s, 1H). Exact mass calculated for $C_{27}H_{33}N_5O_4$ 491.25, found 492.5 (MH$^+$).

Example 11.45

Preparation of 2-{4-[6-(2-Fluoro-4-methanesulfonyl-phenoxy)-5-methyl-pyrimidin-4-yloxy]-piperidin-1-yl}-1-pyridin-2-yl-ethanone (Compound C61)

Compound C61 was prepared in a similar manner as described in Example 11.7. $^1$H NMR (CDCl$_3$, 400 MHz) δ 2.18 (s, 3H), 2.24 (m, 1H), 2.29 (m, 1H), 2.57 (m, 2H), 3.11 (s, 3H), 3.52 (m, 2H), 3.77 (m, 2H), 4.98 (s, 2H), 5.60 (m, 1H), 7.45 (t, 1H), 7.60 (m, 1H), 7.82 (m, 2H), 7.91 (m, 1H), 8.10 (m, 1H), 8.23 (m, 1H), 8.67 (m, 1H). Exact mass calculated for $C_{24}H_{25}FN_4O_5S$ 500.15, found 501.1 (MH$^+$).

Example 11.46

Preparation of 4-{6-[2-Fluoro-4-(2-isopropoxy-ethylamino)-phenoxy]-5-methyl-pyrimidin-4-yloxy}-piperidine-1-carboxylic acid isopropyl ester (Compound C140)

Compound C140 was obtained in a similar manner as described in Example 9.71 (Compound A95) as a orange oil (54 mg, 55%). $^1$H NMR (CDCl$_3$, 400 MHz) δ 1.19 (d, J=6.1 Hz, 6H), 1.27 (d, J=6.1 Hz, 6H), 1.79-1.83 (m, 2H), 1.97-2.02 (m, 2H), 2.20 (s, 3H), 3.41-3.48 (m, 2H), 3.65-3.69 (m, 3H), 3.73-3.78 (m, 2H), 4.95 (sept, J=6.3 Hz, 1H), 5.33-5.36 (m, 1H), 6.91-6.97 (m, 2H), 7.18 (t, J=8.3 Hz, 1H), 8.23 (s, 1H). Exact mass calculated for $C_{25}H_{35}FN_4O_5$ 490.3, found 491.4 (MH$^+$).

Example 11.47

Preparation of 4-(6-{2-Fluoro-4-[(tetrahydro-furan-2-ylmethyl)-amino]-phenoxy}-5-methyl-pyrimidin-4-yloxy)-piperidine-1-carboxylic acid isopropyl ester (Compound C141)

Compound C141 was obtained in a similar manner as described in Example 9.71 as a tan solid (62 mg, 63%). $^1$H NMR (CDCl$_3$, 400 MHz) δ 1.26 (d, J=6.3 Hz, 6H), 1.61-1.70 (m, 1H), 1.76-1.84 (m, 2H), 1.94-1.99 (m, 4H), 2.04-2.11 (m, 1H), 2.18 (s, 3H), 3.11 (dd, J=12.4 Hz, 8.3 Hz 1H), 3.29 (dd, J=12.4 Hz, 3.8 Hz, 1H), 3.41-3.47 (m, 2H), 3.72-3.79 (m, 2H), 3.80-3.84 (m, 2H), 3.88-3.94 (m, 2H), 4.17 (qd, J=8.5 Hz, 3.5 Hz, 1H), 4.94 (sept, J=6.3 Hz, 1H), 5.30-5.36 (m, 1H), 6.64 (dd, J=12.1 Hz, 2.5 Hz, 1H), 6.66 (dd, J=14.9 Hz, 2.5 Hz, 1H), 7.05 (t, J=8.3 Hz, 1H), 8.23 (s, 1H). Exact mass calculated for $C_{25}H_{33}FN_4O_5$ 488.2, found 489.4 (MH$^+$).

Example 11.48

Preparation of 4-(6-{6-[(2-Methanesulfonyl-ethyl)-methyl-amino]-2-methyl-pyridin-3-yloxy}-5-methyl-pyrimidin-4-yloxy)-piperidine-1-carboxylic acid isopropyl ester (Compound C142)

Using a similar procedure as described in Example 11.4 for the preparation of Compound C10, Compound C142 was obtained as an oil (TFA salt, 54.1 mg, 50%). $^1$H NMR (MeOH-d$_4$, 400 MHz) δ 1.00-1.02 (d, 6H), 1.70-1.77 (m, 2H), 1.95-2.02 (m, 2H), 2.17 (s, 3H), 2.33 (s, 3H), 3.00 (s, 3H), 3.19 (s, 3H), 3.34-3.41 (m, 2H), 3.49-3.53 (t, 2H), 3.70-3.76 (m, 2H), 3.94 (s, 1H), 4.09-4.12 (t, 2H), 5.33-5.36 (m, 1H), 6.84-6.86 (d, 1H), 7.53-7.55 (d, 1H), 8.10 (s, 1H). Exact mass calculated for $C_{24}H_{35}N_5O_6S$ 521.23, found 522.5 (MH$^+$).

Example 11.49

Preparation of 4-[6-(2-Fluoro-4-hydroxycarbamoyl-phenoxy)-5-methyl-pyrimidin-4-yloxy]-piperidine-1-carboxylic acid isopropyl ester (Compound C143)

Compound C143 was obtained in a similar manner as described in Example 11.36 as an oil (66 mg, 80%). Exact mass calculated for $C_{21}H_{25}FN_4O_6$ 448.2, found 449.3 (MH$^+$).

Example 11.50

Preparation of 4-{6-[2-Fluoro-4-(2-pyrrolidin-1-yl-ethylcarbamoyl)-phenoxy]-5-methyl-pyrimidin-4-yloxy}-piperidine-1-carboxylic acid isopropyl ester (Compound C144)

Compound C144 was obtained in a similar manner as described in Example 11.36 as a solid (30 mg, 58%). $^1$H NMR (CDCl$_3$, 400 MHz) δ 1.13 (d, 6H), 1.65-1.69 (m, 2H), 1.83-1.87 (m, 2H), 2.06 (s, 3H), 2.13-2.22 (m, 4H), 2.90-2.93 (m, 2H), 3.28-3.37 (m, 4H), 3.58-3.65 (m, 2H), 3.70-3.79 (m, 4H), 4.81 (hept, 1H), 5.18-5.23 (m, 1H), 7.15-7.18 (m, 1H), 7.59-7.65 (m, 2H), 7.82 (t, 1H), 8.05 (s, 1H), 10.0 (s, 1H). Exact mass calculated for $C_{27}H_{36}FN_5O_5$ 529.3, found 530.3 (MH$^+$).

Example 11.51

Preparation of 4-{6-[2-Fluoro-4-(4-isopropyl-piperazine-1-carbonyl)-phenoxy]-5-methyl-pyrimidin-4-yloxy}-piperidine-1-carboxylic acid isopropyl ester (Compound C145)

Compound C145 was obtained in a similar manner as described in Example 11.36 as a solid (29 mg, 53%). $^1$H NMR (CDCl$_3$, 400 MHz) δ 1.17 (d, 6H), 1.33 (d, 6H), 1.62-1.77 (m, 2H), 1.85-1.95 (m, 6H), 2.10 (s, 3H), 2.70-2.80 (m, 1H), 3.31-3.51 (m, 6H), 3.58-3.69 (m, 2H), 4.84 (hept, 1H), 5.23-5.28 (m, 1H), 7.21-7.26 (m, 3H), 8.09 (s, 1H), 10.2 (s, 1H). Exact mass calculated for $C_{28}H_{38}FN_5O_5$ 543.3, found 544.5 (MH$^+$).

Example 11.52

Preparation of 4-{6-[2-Fluoro-4-(2-morpholin-4-yl-ethyl)-phenoxy]-5-methyl-pyrimidin-4-yloxy}-piperidine-1-carboxylic acid isopropyl ester (Compound C146)

Step 1: Preparation of (3-fluoro-4-hydroxy-phenyl)-acetic acid methyl ester To a solution of (3-fluoro-4-hydroxy-phenyl)-acetic acid (20 g, 117.5 mmol) in MeOH (150 mL), was H$_2$SO$_4$ (3 drops) added. The reaction mixture was heated to reflux and maintained for 2 hours. The reaction was cooled to room temperature and 5 g of NaHCO$_3$ was added portionwise. The reaction was concentrated under vacuum and dissolved in ether (200 mL). The ether layer was washed with sat. NaHCO$_3$. The ether layer was dried over MgSO$_4$, and concentrated under vacuum to afford the desired compound (19.9 g, 92%) as an oil. The crude compound was used for the next step without further purification. $^1$H NMR (400 Mz, DMSO-d$_6$) δ 9.92 (s, 1H), 7.01-7.20 (m, 2H), 3.62 (s, 2H), 3.61 (s, 3H). LCMS 185.1 [MH$^+$].

Step 2: Preparation of (4-benzyloxy-3-fluoro-phenyl)-acetic acid methyl ester To a solution of (3-fluoro-4-hydroxy-phenyl)-acetic acid methyl ester (15 g, 54.3 mmol) and benzyl bromide (9.28 g, 54.3 mmol) in DMF (50 mL), was K$_2$CO$_3$ (7.24 g, 54.3 mmol) added at an ambient temperature. The reaction mixture was heated to 60° C. and maintained for 2 hours. The reaction was cooled to room temperature and poured into H$_2$O (150 mL). The organic compound was extracted with ether (150 mL) and washed with sat NaHCO$_3$ (100 mL). The ether layer was dried over MgSO$_4$, and concentrated under vacuum to afford the desired compound (12.9 g, 87.9%) as a white crystal. The crude compound was used for the next step without further purification. $^1$H NMR (400 Mz, DMSO-d$_6$) δ 7.41-7.49 (m, 5H), 7.15-7.23 (m, 2H), 7.02-7.04 (m, 1H), 5.19 (s, 2H), 3.65 (s, 2H), 3.63 (s, 3H). LCMS 273.4 [MH$^+$].

Step 3: Preparation of 2-(4-benzyloxy-3-fluoro-phenyl)-ethanol

To a solution of (4-benzyloxy-3-fluoro-phenyl)-acetic acid methyl ester (7.1 g, 25.7 mmol) in ether (150 mL), was LAH (1.07 g, 28.3 mmol) added portionwise at 0° C. The reaction mixture stirred for 2 hours at the same temperature. The reaction was quenched with H$_2$O (5 mL) at 0° C. The solid material was filtrated off and washed with ether (50 mL). The ether was dried over MgSO$_4$ and concentrated under vacuum to afford the desired compound (5.2 g, 82%) as a white solid. The crude compound was used for the next step without further purification. $^1$H NMR (400 Mz, DMSO-d$_6$) δ 7.34-7.48 (m, 5H), 7.09-7.17 (m, 2H), 6.96-6.98 (m, 1H), 5.17 (s, 2H), 4.66 (s, 1H), 3.60 (b, 2H), 2.68 (m, 2H). LCMS 246.3 [MH$^+$].

Step 4: Preparation of 1-benzyloxy-4-(2-bromo-ethyl)-2-fluoro-benzene

To a solution of 2-(4-benzyloxy-3-fluoro-phenyl)-ethanol (1.0 g, 4.0 mmol) and CBr4 (1.5 g, 4.5 mmol) in CH$_2$Cl$_2$ (10 mL), was PPh$_3$ (1.2 g, 4.5 mmol) added portionwise at 0° C. The reaction mixture stirred for 2 hours at the same temperature. The reaction was concentrated under vacuum and the residue was stirred in ether (10 mmol). The solid, mainly triphenylphosphine oxide, was filtrated off and the filtrate was concentrated under vacuum. The residue was purified over SiO$_2$ to afford the desired compound (1.15 g, 93.5%) as a white crystal. $^1$H NMR (400 Mz, DMSO-d$_6$) δ 7.36-7.49 (m, 5H), 7.17-7.23 (m, 2H), 7.03-7.05 (m, 1H), 5.18 (s, 2H), 3.72 (t, 2H), 3.08 (t, 2H). LCMS 273.4 [MH$^+$].

Step 5: Preparation of 2-fluoro-4-(2-morpholin-4-yl-ethyl)-phenol

To a solution of 1-benzyloxy-4-(2-bromo-ethyl)-2-fluoro-benzene (1.0 g, 3.2 mmol) and morpholine (278 mg, 3.2 mmol) in DMF (5 mL), was K$_2$CO$_3$ (432 mg, 3.2 mmol) added. The reaction mixture was heated to 60° C. and maintained for 6 hours. The reaction was cooled to room temperature and poured into H$_2$O (50 mL). The organic compound was extracted with ethyl acetate (50 mL) and dried over MgSO$_4$. The ethyl acetate layer was concentrated under vacuum and dissolved in methanol (50 mL). The solution was treated with Pd/C (20 mg) and stirred under H$_2$ (1 atm) for 3 hours. The solid material was filtrated off and the filtrate was concentrated under vacuum to afford the desired compound (790 mg, 93%) as a white oil. The crude compound was used for the next step without further purification. $^1$H NMR (400 Mz, DMSO-d$_6$) δ 7.33-7.45 (m, 5H), 7.09-7.15 (m, 2H), 6.97-7.01 (m, 1H), 5.13 (s, 2H), 3.56 (m, 4H), 2.64-2.68 (m, 2H), 2.44-2.50 (m, 2H), 2.39 (b, 2H). LCMS 310.5 [MH$^+$].

Step 6: Preparation of 4-{6-[2-Fluoro-4-(2-morpholin-4-yl-ethyl)-phenoxy]-5-methyl-pyrimidin-4-yloxy}-piperidine-1-carboxylic acid isopropyl ester (Compound C146)

To a solution of 4-(6-chloro-5-methyl-pyrimidin-4-yloxy)-piperidine-1-carboxylic acid isopropyl ester (270 mg, 0.84 mmol) and 2-fluoro-4-(2-morpholin-4-yl-ethyl)-phenol (225 mg, 0.84 mmol) in DMF (5 mL), was K$_2$CO$_3$ (137 mg, 0.84 mmol) added. The reaction mixture was irradiated under microwave for 1 hour at 150° C. The reaction was cooled to room temperature and poured into H$_2$O (50 mL) and extracted with ethyl acetate (50 mL). The ethyl acetate was dried over MgSO$_4$, and concentrated under vacuum and purified over SiO$_2$ to afford Compound C146 (380 mg, 90%) as a white solid. $^1$H NMR (400 Mz, DMSO-d$_6$) δ 8.06 (s, 1H), 7.09~7.02 (m, 1H), 6.93~6.91 (m, 2H), 5.12 (m, 1H), 4.61 (m, 1H), 3.46~3.37 (m, 6H), 3.18~3.13 (m, 2H), 2.61~2.57 (m, 2H), 2.38~2.26 (m, 2H), 2.25 (b, 2H), 1.96 (s, 3H), 1.79~1.74 (m, 2H), 1.49~1.45 (m, 2H), 1.03 (d, 6H). LCMS 503.5 [M+1].

Example 11.53

Preparation of 4-{6-[2-Fluoro-4-(2-methanesulfonyl-ethyl)-phenoxy]-5-methyl-pyrimidin-4-yloxy}-piperidine-1-carboxylic acid isopropyl ester (Compound C147)

Step 1: Preparation of 1-benzyloxy-2-fluoro-4-(2-methanesulfonyl-ethyl)-benzene

To a solution of 1-benzyloxy-4-(2-bromo-ethyl)-2-fluoro-benzene (1.9 g, 6.25 mmol) in MeOH (150 mL), was NaSCH$_3$ (439 mg, 6.25 mmol) added at 0° C. The reaction mixture was warmed to room temperature. After stirring for 5 hours, the reaction was concentrated under vacuum. The residue was dissolved in CH$_2$Cl$_2$ (10 mL) and mCPBA (2.7 g, 15.6 mmol) was added portionwise at 0° C. The reaction was warmed to room temperature and stirred for 3 hours. The reaction was dissolved with ether (20 mL) and washed with sat. NaHCO$_3$. The ether layer was dried over MgSO$_4$, and concentrated under vacuum. The residue was purified over SiO$_2$ to afford the desired compound (1.92 g, 89.6%) as a yellowish crystal. $^1$H NMR (400 Mz, DMSO-d$_6$) δ 7.49~7.33 (m, 5H), 7.23~7.15 (m, 2H), 7.05~7.03 (m, 1H), 5.15 (s, 2H), 3.42~3.36 (m, 2H), 2.96~2.93 (m, 2H), 2.94 (s, 3H). LCMS 309.5 [MH$^+$].

Step 2: Preparation of 2-fluoro-4-(2-methanesulfonyl-ethyl)-phenol

To a solution of 1-benzyloxy-2-fluoro-4-(2-methylsulfonyl-ethyl)-benzene (1.5 g, 4.87 mmol) in MeOH (25 mL) was added Pd/C (50 mg). The reaction was stirred under H$_2$ (1 atm) for 3 hours. The solid material was filtrated off and the filtrate was concentrated under vacuum to afford the desired compound (981 mg, 92.4%) as a yellowish solid. The crude compound was used for the next step without further purification. $^1$H NMR (400 Mz, DMSO-d$_6$) δ 9.73 (s, 1H), 7.14~7.11 (m, 1H), 6.94~6.87 (m, 2H), 3.43~3.37 (m, 2H), 2.98 (s, 3H), 2.95~2.91 (m, 2H). LCMS 228.2 [MH$^+$].

Step 3: Preparation of 4-{6-[2-fluoro-4-(2-methanesulfonyl-ethyl)-phenoxy]-5-methyl-pyrimidin-4-yloxy}-piperidine-1-carboxylic acid isopropyl ester (Compound C147)

To a solution of 4-(6-chloro-5-methyl-pyrimidin-4-yloxy)-piperidine-1-carboxylic acid isopropyl ester (270 mg, 0.84 mmol) and 2-fluoro-4-(2-2-methylsulfonyl-ethyl)-phenol. (218 mg, 0.84 mmol) in DMF (5 mL), was K$_2$CO$_3$ (137 mg, 0.84 mmol) added. The reaction mixture was irradiated under microwave for 1 hour at 150° C. The reaction was cooled to room temperature and poured into H$_2$O (50 mL) and extracted with ethyl acetate (50 mL). The ethyl acetate was dried over MgSO$_4$, and concentrated under vacuum and purified over SiO$_2$ to afford Compound C147 (286 mg, 68%) as a white solid. $^1$H NMR (400 Mz, DMSO-d$_6$) δ 8.25 (s, 1H), 7.39~7.35 (m, 1H), 7.30~7.26 (m, 1H), 7.21~7.18 (m, 1H), 5.31 (m, 1H), 4.79 (m, 1H), 3.67~3.65 (m, 2H), 3.64~3.47 (m, 2H), 3.37~3.31 (m, 2H), 3.08 (m, 2H), 2.97 (s, 3H), 2.15 (s, 3H), 2.00~1.93 (m, 2H), 1.68~1.64 (m, 2H), 1.23 (d, 6H). LCMS 496.5 [MH$^+$].

Example 11.54

Preparation of 4-{6-[2-Fluoro-4-(2-hydroxy-ethyl)-phenoxy]-5-methyl-pyrimidin-4-yloxy}-piperidine-1-carboxylic acid isopropyl ester (Compound C148)

Step 1: Preparation of 4-[2-(tert-butyl-dimethyl-silanyloxy)-ethyl]-2-fluoro-phenol To a solution of 2-(4-benzyloxy-3-fluoro-phenyl)-ethanol (9.2 g, 37.4 mmol) in CH$_2$Cl$_2$ (150 mL) and TBDMS-Cl (5.6 g, 37.4 mmol), was added Et$_3$N (5.2 mmol, 37.4 mmol) portionwise at 0° C. The reaction mixture was warmed to room temperature and stirred for 2 hours at the same temperature. The reaction was washed with H$_2$O (150 mL). The CH$_2$Cl$_2$ was dried over MgSO$_4$ and concentrated under vacuum. To a solution of the residue in MeOH (100 mL), was Pd/C (150 mg) added. The reaction was stirred under H$_2$ (1 atm) for 5 hours. The solid material was filtrated off and the filtrate was concentrated under vacuum to afford the desired compound (8.9 g, 88.3%) as a grayish solid. The crude compound was used for the next step without further purification. $^1$H NMR (400 Mz, DMSO-d$_6$) δ 9.53 (s, 1H), 6.99~6.96 (m, 1H), 6.83~6.81 (m, 2H), 3.70 (t, 2H), 2.63 (t, 2H), 0.83 (s, 9H), 0.01 (s, 6H).

Step 2: Preparation of 4-{6-[2-fluoro-4-(2-hydroxy-ethyl)-phenoxy]-5-methyl-pyrimidin-4-yloxy}-piperidine-1-carboxylic acid isopropyl ester (Compound C148)

To a solution of 4-(6-chloro-5-methyl-pyrimidin-4-yloxy)-piperidine-1-carboxylic acid isopropyl ester (270 mg, 0.84 mmol) and 4-[2-(tert-butyl-dimethyl-silanyloxy)-ethyl]-2-fluoro-phenol (279 mg, 0.84 mmol) in DMF (5 mL), was K$_2$CO$_3$ (137 mg, 0.84 mmol) added. The reaction mixture was irradiated under microwave for 1 hour at 150° C. The reaction was cooled to room temperature and treated with 1.0 M TBAF in THF (0.9 mL). After stirring for 2 hours, the reaction was poured into H$_2$O (50 mL) and extracted with ethyl acetate (50 mL). The ethyl acetate was dried over MgSO$_4$, and concentrated under vacuum and purified over SiO$_2$ to afford the desired compound (321 mg, 89%) as a white solid. $^1$H NMR (400 Mz, DMSO-d$_6$) δ 8.21 (s, 1H), 7.38~7.37 (m, 1H), 7.29~7.28 (m, 1H), 7.21~7.17 (m, 1H), 5.30 (m, 1H), 4.75 (m, 1H), 3.67~3.65 (m, 2H), 3.64~3.41 (m, 2H), 3.33~3.30 (m, 2H), 3.02 (m, 2H), 2.91 (s, 3H), 1.99~1.93 (m, 2H), 1.66~1.64 (m, 2H), 1.22 (d, 6H). LCMS 432.6 [MH$^+$].

Example 11.55

Preparation of 4-[6-(4-Carboxymethyl-2-fluoro-phenoxy)5-methyl-pyrimidin-4-yloxy]-piperidine-1-carboxylic acid isopropyl ester (Compound C149)

A mixture of 4-(6-chloro-5-methyl-pyrimidin-4-yloxy)-piperidine-1-carboxylic acid isopropyl ester (1.6 g, 5.32 mmol), (3-fluoro-4-hydroxy-phenyl)-acetic acid (1.8 g, 10.64 mmol), and sodium hydride (638 mg, 26.61 mmol) in dimethylacetamide (18 mL) was heated under microwave irradiation for 1 hr at 150° C. The reaction was quenched with water and the product extracted in ethyl acetate. The organic layer was concentrated in vacuo and purified by flash chromatography to provide compound C149 as a white solid (3.4 g, 48%). $^1$H NMR (DMSO-d$_6$, 400 MHz) δ 1.12 (d, 6H), 1.53-1.63 (m, 2H), 1.82-1.92 (m, 2H), 2.07 (s, 3H), 3.22-3.31 (m, 2H), 3.37-3.52 (m, 2H), 3.52-3.61 (m, 2H), 4.71 (h, 1H), 5.19-5.28 (h, 1H), 7.06 (d, 1H), 7.16-7.23 (m, 2H), 8.17 (s, 1H). Exact mass calculated for $C_{22}H_{26}FN_3O_6$ 447.46, found 448.3 (MH$^+$).

Example 11.56

Preparation of 4-[6-(4-Dimethylcarbamoylmethyl-2-fluoro-phenoxy)-5-methyl-pyrimidin-4-yloxy]-piperidine-1-carboxylic acid isopropyl ester (Compound C150)

A mixture of 4-[6-(4-carboxymethyl-2-fluoro-phenoxy)-5-methyl-pyrimidin-4-yloxy]-piperidine-1-carboxylic acid isopropyl ester (150 mg, 0.335 mmol) and HATU (178 mg, 0.469 mmol) in DMF (4 mL) was stirred for 30 minutes at room temperature. Then, dimethylamine (235 µL, 0.47 mmol) was added and the reaction was stirred for 24 hours at room temperature. The reaction was quenched with water and the product extracted in ethyl acetate. The organic layer was concentrated in vacuo and purified by HPLC to provide Compound C150 as a white solid (40 mg, 25%). $^1$H NMR (DMSO-d$_6$, 400 MHz) δ 1.21 (d, 6H), 1.62-1.72 (m, 2H), 1.92-2.01 (m, 2H), 2.16 (s, 3H), 2.87 (s, 3H), 3.06 (s, 3H), 3.32-3.41 (m, 2H), 3.61-3.69 (m, 2H), 3.75 (s, 2H), 4.08 (h, 1H), 5.33 (h, 1H), 7.08 (d, 1H), 7.23-7.33 (m, 2H), 8.27 (s, 1H). Exact mass calculated for $C_{24}H_{31}FN_4O_5$ 474.53, found 475.5 (MH$^+$).

Example 11.57

Preparation of 4-[6-(2-Fluoro-4-sulfamoyl-phenoxy)-5-methyl-pyrimidin-4-yloxy]-piperidine-1-carboxylic acid isopropyl ester (Compound C151)

A solution of 4-[6-(4-bromo-2-fluoro-phenoxy)-5-methyl-pyrimidin-4-yloxy]-piperidine-1-carboxylic acid isopropyl ester (475 mg, 1.01 mmol) in 5 mL tetrahydrofuran was cooled to −78° C. and n-butyl lithium was added. After stirring for 30 minutes at −78° C., sulfur dioxide was bubbled vigorously through the solution for 10 minutes. Solution was allowed to warm to room temperature and was concentrated on a rotary evaporator. Residue was dissolved in 2 mL tetrahydrofuran and hexane was added until a white solid precipitated. Solid was filtered and dried under high vacuum (white solid, 265 mg). White solid was dissolved in 15 mL methylene chloride and sulfuryl chloride (100 µl, 1.2 mmol) was added. After stirring for 10 minutes at room temperature, mixture was concentrated and residue was dried under high vacuum. Residue was dissolved in 1 mL dioxane, cooled in an ice bath, and 5 mL ammonium hydroxide (28-30% NH$_3$) was added. After stirring for 5 minutes, mixture was concentrated and purified by HPLC to give Compound C151 as a white solid (46.7 mg, 10%). $^1$H NMR (CDCl$_3$, 400 MHz) δ 1.26-1.27 (d, J=6.3 Hz, 6H), 1.76-1.84 (m, 2H), 1.97-2.02 (m, 2H), 2.20 (s, 3H), 3.39-3.46 (m, 2H), 3.74-3.80 (m, 2H), 4.89 (s, 2H), 4.89-4.97 (m, 1H), 5.32-5.38 (m, 1H), 7.35-7.39 (m, 1H), 7.75-7.79 (m, 2H), 8.19 (s, 1H). Exact mass calculated for $C_{20}H_{25}FN_4O_6S$ 468.15, found 469.4 (MH$^+$).

Example 11.58

Preparation of 4-[6-(2-Fluoro-4-propionylsulfamoyl-phenoxy)-5-methyl-pyrimidin-4-yloxy]-piperidine-1-carboxylic acid isopropyl ester (Compound C152)

To a solution of Compound C151 (33.5 mg, 0.0715 mmol) in 3 mL methylene chloride, triethylamine (30 µl, 0.215 mmol) and propionic anhydride (27.7 µl, 0.215 mmol) were added. After stirring at room temperature for 22 hours, solution was concentrated and purified by HPLC. Fractions which contained intermediate were concentrated and dried under high vacuum. Residue was dissolved in 2 mL methanol and sodium bicarbonate (6.9 mg, 0.082 mmol) was added. After stirring for 18 hours at room temperature, solution was concentrated, dissolved in water/acetonitrile and lyophilized to give Compound C152 as a white solid (34.0 mg, 87%). $^1$H NMR (DMSO-d$_6$, 400 MHz) δ 0.85-0.88 (t, J=7.6, 3H), 1.19-1.20 (d, J=6.2, 6H), 1.61-1.69 (m, 2H), 1.92-1.99 (m, 4H), 2.14 (s, 3H), 3.33-3.38 (m, 2H), 3.61-3.67 (m, 2H), 4.75-4.81 (m, 1H), 5.29-5.34 (m, 1H), 7.32-7.36 (m, 1H), 7.57-7.67 (m, 2H), 8.27 (s, 1H). Exact mass calculated for $C_{23}H_{29}FN_4O_7S$ 524.17, found 525.2 (MH$^+$).

Example 11.59

Preparation of 4-[5-Ethynyl-6-(2-fluoro-4-methanesulfonyl-phenoxy)-pyrimidin-4-yloxy]-piperidine-1-carboxylic acid isopropyl ester (Compound C153)

4-[6-(2-Fluoro-4-methanesulfonyl-phenoxy)-5-trimethylsitanylethynyl-pyrimidin-4-yloxy]-piperidine-1-carboxylic acid isopropyl ester (10 mg, 0.018 mmol) was dissolved in THF (0.60 mL) and MeOH (0.30 mL), 1.0 N NaOH (0.036 mL, 0.036 mmol) was added to the reaction mixture, and it was stirred at room temperature for 1 h. Glacial AcOH (0.0041 mL, 0.072 mmol) was then added to give a pH of 5, then the solvents were evaporated in vacuo to give Compound C153 as a crude solid (11 mg) which contained 2 mol eq of AcONa and was of 80% purity (LCMS). LRMS calculated for $C_{22}H_{24}FN_3O_6S$: 477.14. Found: 478.3 (M+H)$^+$.

Example 11.60

Preparation of 4-{6-[2-Fluoro-4-(2-phosphonooxy-ethyl)-phenoxy]-5-methyl-pyrimidin-4-yloxy}-piperidine-1-carboxylic acid isopropyl ester (Compound C154)

A mixture of 4-{6-[2-fluoro-4-(2-hydroxy-ethyl)-phenoxy]-5-methyl-pyrimidin-4-yloxy}-piperidine-1-carboxylic acid isopropyl ester (100 mg, 0.23 mmol), and phosphorus oxychloride (0.105 mL, 1.15 mmol) in dichloroethane (5 mL) was stirred for 5 hours at room temperature. Upon evaporation of the organic solvent, the reaction was quenched with water and the product extracted in ethyl acetate. The organic layer was concentrated in vacuo and purified by HPLC to provide Compound C154 as a white solid (40 mg, 33%). $^1$H NMR (CDCl$_3$, 400 MHz) δ 1.23 (d, 6H), 1.71-1.81 (m, 2H), 1.90-2.01 (m, 2H), 2.15 (s, 3H), 2.89 (t, 2H), 3.34-3.44 (m, 2H), 3.66-3.77 (m, 2H), 4.16 (q, 2H), 4.90 (h, 1H), 5.31 (h, 1H), 6.96-7.09 (m, 3H), 7.38-7.58 (s broad, 2H), 8.18 (s, 1H). Exact mass calculated for $C_{22}H_{29}FN_3O_8P$ 513.45, found 514.3 (MH$^+$).

Example 11.61

Preparation of 4-(6-{2-Fluoro-4-[2-(2-methanesulfonyl-pyrrolidin-1-yl)-2-oxo-ethyl]-phenoxy}-5-methyl-pyrimidin-4-yloxy)-piperidine-1-carboxylic acid isopropyl ester (Compound C156)

Compound C156 was prepared in a similar manner as described in Example 11.56 as a solid (200 mg, 77%). Exact mass calculated for $C_{27}H_{35}FN_4O_7S$ 578.65, found 579.4 (MH$^+$).

Example 11.62

Preparation of 4-[6-(4-Carbamoylmethyl-2-fluoro-phenoxy)-5-methyl-pyrimidin-4-yloxy]-piperidine-1-carboxylic acid isopropyl ester (Compound C157)

Compound C157 was prepared in a similar manner as described in Example 11.56 as a solid (80 mg, 40%). Exact mass calculated for $C_{22}H_{27}FN_4O_5$ 446.47, found 447.6 (MH+).

Example 11.63

Preparation of 4-[6-(2-Fluoro-4-{[(tetrahydro-furan-2-ylmethyl)-carbamoyl]-methyl}-phenoxy)-5-methyl-pyrimidin-4-yloxy]-piperidine-1-carboxylic acid isopropyl ester (Compound C158)

Compound C158 was prepared in a similar manner as described in Example 11.56 as a solid (230 mg, 97%). Exact mass calculated for $C_{27}H_{35}FN_4O_6$ 530.59, found 531.5 (MH+).

Example 11.64

Preparation of 4-(6-{2-Fluoro-4-[2-(3-hydroxy-piperidin-1-yl)-2-oxo-ethyl]-phenoxy}-5-methyl-pyrimidin-4-yloxy)-piperidine-1-carboxylic acid isopropyl ester (Compound C166)

Compound C166 was prepared in a similar manner as described in Example 11.56 as a solid (150 mg, 62%). Exact mass calculated for $C_{27}H_{35}FN_4O_5$ 530.59, found 531.3 (MH+).

Example 11.65

Preparation of 4-{6-[2-Fluoro-4-(2-morpholin-4-yl-2-oxo-ethyl)-phenoxy]-5-methyl-pyrimidin-4-yloxy}-piperidine-1-carboxylic acid isopropyl ester (Compound C167)

Compound C167 was prepared in a similar manner as described in Example 11.56 as a solid (90 mg, 38%). Exact mass calculated for $C_{26}H_{33}FN_4O_6$ 516.56, found 517.4 (MH+).

Example 11.66

Preparation of 4-{6-[2-Fluoro-4-(2-imidazol-1-yl-ethyl)-phenoxy]-5-methyl-pyrimidin-4-yloxy}-piperidine-1-carboxylic acid isopropyl ester (Compound C168)

General Protocol of Alkylation

A mixture of 4-{6-[4-(2-bromo-ethyl)-2-fluoro-phenoxy]-5-methyl-pyrimidin-4-yloxy}-piperidine-1-carboxylic acid isopropyl ester (30.0 mg, 0.44 mmol) and sodium hydride (11.0 mg, 0.44 mmol) in DMF (4 mL) was stirred for 30 minutes at room temperature. Then, imidazole (200 µL, 0.40 mmol) was added and the reaction was stirred for 2 hours at room temperature. The reaction was quenched with water and the product extracted in ethyl acetate. The organic layer was concentrated in vacuo and purified by HPLC to provide compound C168 as a white solid (28 mg, 15%). $^1$H NMR (CDCl$_3$, 400 MHz) δ 1.17 (d, 6H), 1.66-1.76 (m, 2H), 1.85-1.96 (m, 2H), 2.11 (s, 3H), 3.06-3.14 (m, 2H), 3.30-3.37 (m, 2H), 3.62-3.72 (m, 2H), 3.33-3.40 (m, 2H), 4.86 (h, 1H), 5.24 (h, 1H), 6.80-6.95 (m, 3H), 7.09 (t, 1H), 7.32 (s, 1H), 8.11 (s, 1H), 8.72 (s, 1H). Exact mass calculated for $C_{25}H_{30}FN_5O_4$ 483.54, found 484.4 (MH+).

Example 11.67

Preparation of 4-{6-[2-Fluoro-4-(2-[1,2,3]triazol-1-yl-ethyl)-phenoxy]-5-methyl-pyrimidin-4-yloxy}-piperidine-1-carboxylic acid isopropyl ester (Compound C169)

Compound C169 was prepared in a similar manner as described in Example 11.66 as a solid (105 mg, 54%). Exact mass calculated for $C_{24}H_{29}FN_6O_4$ 484.52 found 485.4 (MH+).

Example 11.68

Preparation of 4-[6-(2-Fluoro-4-methanesulfonyl-phenoxy)-5-methyl-pyrimidin-4-yloxy]-piperidine-1-carboxylic acid (R)tetrahydro-furan-3-yl ester (Compound C177)

To a solution of 1,1'-carbonyldiimidazole (54.8 mg, 0.338 mmol) in 1 mL THF was added (R)-(+)-3-hydroxytetrahydrofuran (32 µl, 0.38 mmol). After stirring for 30 minutes at room temperature, 1 mL triethylamine, 1 mL THF, and 4-(2-fluoro-4-methanesulfonyl-phenoxy)-5-methyl-6-(piperidin-4-yloxy)-pyrimidine (70 mg, 0.166 mmol) were added. The resulting mixture was stirred at 60° C. for 48 hours and purified by HPLC to give Compound C177 as a white solid (35.3 mg, 42%). $^1$H NMR (CDCl3, 400 MHz) δ 1.81-1.88 (m, 2H), 1.96-2.09 (m, 3H), 2.12-2.20 (m, 4H), 3.10 (s, 3H), 3.42-3.48 (m, 2H), 3.75-3.81 (m, 2H), 3.84-3.97 (m, 4H), 5.27-5.31 (m, 1H), 5.34-5.38 (m, 1H), 7.41-7.45 (m, 1H), 7.77-7.82 (m, 2H), 8.20 (s, 1H). Exact mass calculated for $C_{22}H_{26}FN_3O_7S$ 495.15, found 496.3 (MH+).

Example 11.69

Preparation of 4-[6-(2-Fluoro-4-methanesulfonyl-phenoxy)-5-methyl-pyrimidin-4-yloxy]-piperidine-1-carboxylic acid (S)-tetrahydro-furan-3-yl ester (Compound C176)

Compound C176 was prepared in a simper manner as described in Example 11.68 as a white solid (40.8 mg, 46%). $^1$H NMR (CDCl$_3$, 400 MHz) δ 1.81-1.88 (m, 2H), 1.96-2.09 (m, 3H), 2.12-2.20 (m, 4H), 3.10 (s, 3H), 3.42-3.48 (m, 2H), 3.75-3.81 (m, 2H), 3.84-3.97 (m, 4H), 5.27-5.31 (m, 1H), 5.34-5.38 (m, 1H), 7.41-7.45 (m, 1H), 7.77-7.82 (m, 2H), 8.20 (s, 1H). Exact mass calculated for $C_{22}H_{26}FN_3O_7S$ 495.15, found 496.3 (MH+).

Example 11.70

Preparation of 4-{6-[2-Fluoro-4-(6-methoxy-pyridin-3-yl)-phenoxy]-5-methyl-pyrimidin-4-yloxy}-piperidine-1-carboxylic acid isopropyl ester (Compound C181)

A mixture of 4-[6-(4-bromo-2-fluoro-phenoxy)-5-methyl-pyrimidin-4-yloxy]-piperidine-1-carboxylic acid isopropyl ester (184 mg, 0.393 mmol), 6-methoxypyridine-3-boronic acid (67.3, 0.396 mmol), potassium carbonate (164 mg, 1.24 mmol), and tetrakis(triphenylphosphine)palladium (20 mg, 0.046 mmol) in 4 mL THF and 0.4 mL H$_2$O was heated under microwave irradiation for 1 hour at 120° C. The mixture was purified by HPLC to give Compound C181 as a colorless oil (TFA salt, 186 mg, 78%). $^1$H NMR (CDCl$_3$, 400 MHz) δ 1.27-1.29 (d, J=6.3 Hz, 6H), 1.80-1.88 (m, 2H), 1.98-2.05 (m, 2H), 2.23 (s, 3H), 3.44-3.50 (m, 2H), 3.74-3.80 (m, 2H), 4.12 (s, 3H), 4.93-4.99 (m, 1H), 5.34-5.39 (m, 1H), 5.34-5.39 (m, 1H), 7.06-7.08 (m, 1H), 7.33-7.39 (m, 3H), 8.07-8.10 (m, 1H), 8.27 (s, 1H), 8.57-8.58 (d, J=2.4 Hz, 1H). Exact mass calculated for C$_{26}$H$_{29}$FN$_4$O$_5$ 496.21, found 497.4 (MH+).

Example 11.71

Preparation of 4-[5-Bromo-6-(2-fluoro-4-methanesulfonyl-phenoxy)-pyrimidin-4-yloxy]-piperidine-1-carboxylic acid isopropyl ester (Compound C155)

4-[6-(2-fluoro-4-methanesulfonyl-phenoxy)-pyrimidin-4-yloxy]-piperidine-1-carboxylic acid isopropyl ester (1.02 g, 2.25 mmol) and NBS (601 mg, 3.38 mmol) in acetic acid (10 mL) was stirred at 40° C. for three days. The mixture was purified through HPLC to provide compound C155 as a solid (685 mg, 50%). $^1$H NMR (CDCl$_3$, 400 MHz) δ 1.24 (d, 6H), 1.82-1.86 (m, 2H), 1.94-1.98 (m, 2H), 3.08 (s, 3H), 3.46-3.52 (m, 2H), 3.68-3.74 (m, 2H), 4.92 (hept, 1H), 5.38-5.42 (m, 1H), 7.42-7.46 (m, 1H), 7.77-7.81 (m, 2H), 8.18 (s, 1H). Exact mass calculated for C$_{20}$H$_{23}$FBrN$_3$O$_6$S 531.1, found 532.4/534.4 (MH$^+$).

Example 11.72

Preparation of 4-[6-(4-Methanesulfonyl-phenoxy)-5-methyl-pyrimidin-4-yloxy]-piperidine-1-carboxylic acid isopropyl ester (Compound C179)

Compound C179 was prepared in a similar manner as described in Example 11.15 as a solid (60 mg, 67%). $^1$H NMR (CDCl$_3$, 400 MHz) δ 1.26 (d, 6H), 1.77-1.85 (m, 2H), 1.98-2.03 (m, 2H), 2.18 (s, 3H), 3.08 (s, 3H), 3.41-3.47 (m, 2H), 3.74-3.80 (m, 2H), 4.95 (hept, 1H), 5.35-5.39 (m, 1H), 7.30-7.33 (m, 2H), 7.98-8.01 (m, 2H), 8.28 (s, 1H). Exact mass calculated for C$_{21}$H$_{27}$N$_3$O$_6$S$_{449.2}$, found 450.3 (MH$^+$).

Example 11.73

Preparation of 4-[6-(2-Amino-4-ethanesulfonyl-phenoxy)-5-methyl-pyrimidin-4-yloxy]-piperidine-1-carboxylic acid isopropyl ester (Compound C178)

Compound C178 was prepared in a similar manner as described in Example 11.15 as a solid (66 mg, 69%). $^1$H NMR (CDCl$_3$, 400 MHz) δ 1.11 (t, 3H), 1.20 (d, 6H), 1.59-1.66 (m, 2H), 1.90-1.95 (m, 2H), 2.08 (s, 3H), 3.19 (quart, 2H), 3.30-3.35 (m, 2H), 3.60-3.67 (m, 2H), 4.78 (hept, 1H), 5.24-5.30 (m, 1H), 7.10 (d, 1H), 7.48 (dd, 1H), 7.99 (s, 2H), 8.27 (s, 1H), 8.33 (d, 1H). Exact mass calculated for C$_{22}$H$_{30}$N$_4$O$_6$S 478.2, found 479.2 (MH$^+$).

Example 11.74

Preparation of 4-[5-Methyl-6-(4-sulfo-phenoxy)-pyrimidin-4-yloxy]-piperidine-1-carboxylic acid isopropyl ester (Compound C185)

Compound C185 was prepared in a similar manner as described in Example 11.15 as a solid (21 mg, 23%). $^1$H NMR (CDCl$_3$, 400 MHz) δ 1.20 (d, 6H), 1.63-1.67 (m, 2H), 1.91-1.97 (m, 2H), 2.12 (s, 3H), 3.32-3.36 (m, 2H), 3.62-3.67 (m, 2H), 4.78 (quint, 1H), 5.30-5.32 (m, 1H), 7.06-7.09 (m, 2H), 7.61-7.64 (m, 2H), 8.24 (s, 1H). Exact mass calculated for C$_{20}$H$_{25}$N$_3$O$_7$S 451.1, found 452.3 (MH$^+$).

Example 11.75

Preparation of 4-{6-[2-Fluoro-4-(2-isopropoxy-ethoxy)-phenoxy]-5-methyl-pyrimidin-4-yloxy}-piperidine-1-carboxylic acid isopropyl ester (Compound C184)

Mixture of 4-(6-Chloro-5-methyl-pyrimidin-4-yloxy)-piperidine-1-carboxylic acid isopropyl ester (147 mg, 0.47 mmole), 2-fluoro-4-(2-isopropoxy-ethoxy)-phenol (0.47 mmole, 1 eq) and K$_2$CO$_3$ (0.75 mmole, 1.5 eq) in 2 mL DMSO was heated under microwave irradiation at 150° C. for 40 minutes. Mixture was purified by HPLC to give compound C184 as a yellow oil (273 mg, 96%). $^1$H NMR (DMSO-d$_6$, 400 MHz) δ 1.23 (d, 6H), 1.27 (d, 6H), 1.79-1.86 (m, 2H), 1.97-2.04 (m, 1H), 2.20 (s, 3H), 3.43-3.50 (m, 2H), 3.73-3.79 (m, 3H), 3.82 (t, 2H), 4.09 (t, 2H), 4.95 (sep, 1H), 5.33-5.36 (m, 1H), 6.70-6.78 (m, 2H), 7.08 (t, 1H), 8.27 (s, 1H). Exact mass calculated for C$_{25}$H$_{34}$FN$_3$O$_6$ 491.2, found 492.4 (MH$^+$).

Example 11.76

Preparation of 3-tert-Butoxy-1-{4-[6-(2-fluoro-4-methanesulfonyl-phenoxy)-5-methyl-pyrimidin-4-yloxy]-piperidin-1-yl}-propan-1-one (Compound C161)

Mixture of 4-(2-fluoro-4-methanesulfonyl-phenoxy)-5-methyl-6-(piperidin-4-yloxy)-pyrimidine (76 mg, 0.2 mmole), 3-tert-butoxy-propionic acid (0.26 mmole, 1.3 eq), HATU (0.26 mmole, 1.3 eq), and triethylamine (0.4 mmole, 2 eq) in 2 mL DMF was stirred at room temp for 2 hours. Mixture was purified by HPLC to give compound C161 as a white solid (88 mg, 86%). $^1$H NMR (CDCl$_3$, 400 MHz) δ 1.20 (s, 9H), 1.91-1.96 (m, 2H), 2.02-2.10 (m, 2H), 2.22 (s, 3H), 2.72 (t, 2H), 3.11 (s, 3H), 3.62-3.64 (m, 2H), 3.72 (t, 2H), 3.86-3.91 (m, 2H), 5.41-5.46 (m, 1H), 7.44 (t, 1H), 7.78-7.82 (m, 2H), 8.23 (s, 1H). Exact mass calculated for C$_{24}$H$_{32}$FN$_3$O$_6$S 509.2, found 510.6 (MH$^+$).

Example 11.77

Preparation of 2-Ethoxy-1-{4-[6-(2-fluoro-4-methanesulfonyl-phenoxy)-5-methyl-pyrimidin-4-yloxy]-piperidin-1-yl}-ethanone (Compound C163)

Mixture of 4-(2-fluoro-4-methanesulfonyl-phenoxy)-5-methyl-6-(piperidin-4-yloxy)-pyrimidine (76 mg, 0.2 mmole), 2-ethoxyacetic acid (0.26 mmole, 1.3 eq), HATU (0.26 mmole, 1.3 eq), and TEA (0.4 mmole, 2 eq) in 2 mL THF was heated under microwave irradiation at 120° C. for 30 minutes. Mixture was purified by HPLC to give compound C163 as a white solid (55 mg, 59%). $^1$H NMR (CDCl$_3$, 400 MHz) δ 1.25 (t, 3H), 1.86-1.90 (m, 2H), 2.01-2.09 (m, 2H), 2.22 (s, 3H), 3.10 (s, 3H), 3.51-3.69 (m, 2H), 3.59 (q, 2H), 3.76-3.87 (m, 2H), 4.21 (s, 2H), 5.41-5.44 (m, 1H), 7.43 (t, 1H), 7.78-7.82 (m, 2H), 8.21 (s, 1H). Exact mass calculated for C$_{21}$H$_{26}$FN$_3$O$_6$S 467.2, found 468.5 (MH$^+$).

Example 11.78

Preparation of {4-[6-(2-Fluoro-4-methanesulfonyl-phenoxy)-5-methyl-pyrimidin-4-yloxy]-piperidin-1-yl}-(tetrahydro-furan-2-yl)-methanone (Compound C164)

Mixture of 4-(2-fluoro-4-methanesulfonyl-phenoxy)-5-methyl-6-(piperidin-4-yloxy)-pyrimidine (76 mg, 0.2 mmole), tetrahydro-furan-2-carboxylic acid (0.26 mmole, 1.3 eq), HATU (0.26 mmole, 1.3 eq), and TEA (0.4 mmole, 2 eq) in 2 mL THF was heated under microwave irradiation at 120° C. for 30 minutes. Mixture was purified by HPLC to give compound C164 as a yellow solid (78 mg, 81%). $^1$H NMR (CDCl$_3$, 400 MHz) δ 1.85-2.17 (m, 8H), 2.21 (s, 3H), 3.10 (s, 3H), 3.75-3.80 (m, 2H), 3.86-3.91 (m, 2H), 3.96-4.01 (m, 2H), 4.68 (t, 1H), 5.40-5.45 (m, 1H), 7.44 (t, 1H), 7.78-7.82 (m, 2H), 8.21 (s, 1H). Exact mass calculated for C$_{22}$H$_{26}$FN$_3$O$_6$S 479.2, found 480.3 (MH$^+$).

Example 11.79

Preparation of (S)-1-{4-[6-(2-Fluoro-4-methane-sulfonyl-phenoxy)-5-methyl-pyrimidin-4-yloxy]-piperidin-1-yl}-3-methyl-2-methylamino-butan-1-one (Compound C165)

Compound C165 was obtained in a similar manner as described in Example 11.78 as a yellow solid (7 mg, 7%). Exact mass calculated for C$_{23}$H$_{31}$FN$_4$O$_5$S 494.2, found 495.5 (MH$^+$).

Example 11.80

Preparation of (S)-1-{4-[6-(2-Fluoro-4-methane-sulfonyl-phenoxy)-5-methyl-pyrimidin-4-yloxy]-piperidin-1-yl}-3-hydroxy-butan-1-one (Compound C171)

Compound C171 was obtained in a similar manner as described in Example 11.78 as a white solid (31 mg, 33%). Exact mass calculated for C$_{21}$H$_{26}$FN$_3$O$_6$S 467.2, found 468.6 (MH$^+$).

Example 11.81

Preparation of (R)-1-{4-[6-(2-Fluoro-4-methane-sulfonyl-phenoxy)-5-methyl-pyrimidin-4-yloxy]-piperidin-1-yl}-3-methyl-2-methylamino-butan-1-one (Compound C170)

Compound C170 was obtained in a similar manner as described in Example 11.78 as a yellow solid (16 mg, 16%). Exact mass calculated for C$_{23}$H$_{31}$FN$_4$O$_5$S 494.2, found 495.5 (MH$^+$).

Example 11.82

Preparation of (R)-N-(1-{4-[6-(2-Fluoro-4-methane-sulfonyl-phenoxy)-5-methyl-pyrimidin-4-yloxy]-piperidine-1-carbonyl}-2-methyl-propyl)-acetamide (Compound C172)

Compound C172 was obtained in a similar manner as described in Example 11.78 as a white solid (83 mg, 80%). $^1$H NMR (CD$_3$OD, 400 MHz) δ 0.95-0.99 (m, 6H), 1.78-1.91 (m, 2H), 2.00 (s, 3H), 2.04-2.05 (m, 2H), 2.23 (d, 3H), 3.19 (s, 3H), 3.58-3.64 (m, 2H), 3.77 (m, 2H), 4.02 (m, 2H), 4.70 (d, 1H), 5.45-5.47 (m, 1H), 7.54 (t, 1H), 7.84-7.88 (m, 2H), 8.16 (s, 1H). Exact mass calculated for C$_{24}$H$_{31}$FN$_4$O$_6$S 522.2, found 523.5 (MH$^+$).

Example 11.83

Preparation of (S)-N-(1-{4-[6-(2-Fluoro-4-methane-sulfonyl-phenoxy)-5-methyl-pyrimidin-4-yloxy]-piperidine-1-carbonyl}-2-methyl-propyl)-acetamide (Compound C173)

Compound C173 was obtained in a similar manner as described in Example 11.78 as a white solid (89 mg, 80%). $^1$H NMR (CD$_3$OD, 400 MHz) δ 0.96-0.99 (m, 6H), 1.77-1.82 (m, 2H), 2.00 (s, 3H), 2.04-2.10 (m, 2H), 2.23 (d, 3H), 3.19 (s, 3H), 3.75-3.77 (m, 2H), 3.86-3.88 (m, 2H), 4.02 (m, 2H), 4.70 (d, 1H), 5.45-5.47 (m, 1H), 7.55 (t, 1H), 7.85-7.89 (m, 2H), 8.17 (s, 1H). Exact mass calculated for C$_{24}$H$_{31}$FN$_4$O$_6$S 522.2, found 523.5 (MH$^+$).

Example 11.84

Preparation of (R)-N-(2-{4-[6-(2-Fluoro-4-methane-sulfonyl-phenoxy)-5-methyl-pyrimidin-4-yloxy]-piperidin-1-yl}-1-methyl-2-oxo-ethyl)-acetamide (Compound C174)

Compound C174 was obtained in a similar manner as described in Example 11.78 as a white solid (84 mg, 85%). $^1$H NMR (CD$_3$OD, 400 MHz) δ 1.32 (d, 3H), 1.79-1.91 (m, 2H), 1.98 (s, 3H), 2.04-2.10 (m, 2H), 2.23 (d, 3H), 3.20 (s, 3H), 3.75-3.99 (m, 2H), 3.86-3.88 (m, 1H), 4.02 (m, 2H), 5.46-5.48 (m, 1H), 7.55 (t, 1H), 7.85-7.89 (m, 2H), 8.17 (s, 1H). Exact mass calculated for C$_{22}$H$_{27}$FN$_4$O$_6$S 494.2, found 495.5 (MH$^+$).

Example 11.85

Preparation of (S)-N-(2-{4-[6-(2-Fluoro-4-methane-sulfonyl-phenoxy)-5-methyl-pyrimidin-4-yloxy]-piperidin-1-yl}-1-methyl-2-oxo-ethyl)-acetamide (Compound C175)

Compound C175 was obtained in a similar manner as described in Example 11.78 as a white solid (81 mg, 82%). $^1$H NMR (CD$_3$OD, 400 MHz) δ 1.32 (d, 3H), 1.82-1.99 (m, 2H), 2.01 (s, 3H), 2.05-2.15 (m, 2H), 2.24 (d, 3H), 3.20 (s, 3H), 3.46-3.55 (m, 2H), 3.74-3.81 (m, 1H), 3.92-4.02 (m, 2H), 5.45-5.48 (m, 1H), 7.55 (t, 1H), 7.85-7.90 (m, 2H), 8.17 (s, 1H). Exact mass calculated for C$_{22}$H$_{27}$FN$_4$O$_6$S 494.2, found 495.5 (MH$^+$).

Example 11.86

Preparation of 3-Amino-1-{4-[6-(2-fluoro-4-methanesulfonyl-phenoxy)-5-methyl-pyrimidin-4-yloxy]-piperidin-1-yl}-4-methyl-pentan-1-one (Compound C182)

Compound C182 was obtained in a similar manner as described in Example 11.78 as a white solid (3 mg, 3%). Exact mass calculated for C$_{23}$H$_{31}$FN$_4$O$_5$S 494.2, found 495.5 (MH$^+$).

Example 11.87

Preparation of (1-{4-[6-(2-Fluoro-4-methanesulfonyl-phenoxy)-5-methyl-pyrimidin-4-yloxy]-piperidine-1-carbonyl}-2-methyl-propyl)-carbamic acid tert-butyl ester (Compound C180)

Compound C180 was obtained in a similar manner as described in Example 11.78 as a yellow solid (143 mg, 88%). Exact mass calculated for $C_{27}H_{37}FN_4O_7S$ 580.2, found 581.4 ($MH^+$).

Example 11.88

Preparation of 2-Amino-1-{4-[6-(2-fluoro-4-methanesulfonyl-phenoxy)-5-methyl-pyrimidin-4-yloxy]-piperidin-1-yl}-3-methyl-butan-1-one (Compound C183)

Mixture of compound C180 (68 mg, 0.12 mmole) in 4M HCl in Dioxane (1.5 mL) and dioxane (2 mL) was stirred at room temperature for 40 minutes. Mixture was purified by HPLC to give Compound C183 as a white solid (50 mg, 86%). $^1$H NMR ($CD_3OD$, 400 MHz) δ 1.04 (d, 3H), 1.13 (d, 3H), 1.87-1.92 (m, 2H), 2.04-2.14 (m, 3H), 2.24 (d, $NH_2$), 2.82 (s, 3H), 3.20 (s, 3H), 3.52-3.65 (m, 2H), 3.81-3.83 (m, 2H), 4.36 (m, 1H), 5.49-5.51 (m, 1H), 7.55 (t, 1H), 7.86-7.90 (m, 2H), 8.18 (s, 1H). Exact mass calculated for $C_{22}H_{29}FN_4O_5S$ 480.2, found 481.3 ($MH^+$).

Example 11.89

Preparation of 4-[6-(3-Fluoro-biphenyl-4-yloxy)-5-methyl-pyrimidin-4-yloxy]-piperidine-1-carboxylic acid isopropyl ester (Compound C236)

Compound C236 was made in a similar manner as described in Example 11.70 as a white solid (51 mg, 55%). $^1$HNMR ($CDCl_3$, 400 MHz) δ 1.28 (d, 6H), 1.81-1.86 (m, 2H), 1.99-2.04 (m, 2H), 2.23 (s, 3H), 3.44-3.50 (m, 2H), 3.74-3.80 (m, 2H), 4.96 (sep, 1H), 5.34-5.38 (m, 1H), 7.27 (t, 1H), 7.36-7.47 (m, 5H), 7.57 (d, 2H), 8.28 (s, 1H). Exact mass calculated for $C_{26}H_{28}FN_3O_4$ 465.2, found 466.5.

Example 11.90

Preparation of 4-[6-(2-Fluoro-4-pyridin-3-yl-phenoxy)-5-methyl-pyrimidin-4-yloxy]-piperidine-1-carboxylic acid isopropyl ester (Compound C237)

Compound C237 was made in a similar manner as described in Example 11.70 as a yellow solid (11 mg, 12%). $^1$HNMR ($CDCl_3$, 400 MHz) δ 1.27 (d, 6H), 1.80-1.83 (m, 2H), 1.98-2.02 (m, 2H), 2.23 (s, 3H), 3.41-3.47 (m, 2H), 3.74-3.79 (m, 2H), 4.94 (sep, 1H), 5.34-5.38 (m, 1H), 7.43 (t, 1H), 7.48 (d, 2H), 7.90-7.94 (m, 1H), 8.23 (s, 1H), 8.43-8.46 (m, 1H), 8.83 (d, 1H), 9.12 (s, 1H). Exact mass calculated for $C_{25}H_{27}FN_4O_4$ 466.2, found 467.6.

Example 11.91

Preparation of 4-[6-(2-Fluoro-4-pyridin-4-yl-phenoxy)-5-methyl-pyrimidin-4-yloxy]-piperidine-1-carboxylic acid isopropyl ester (Compound C235)

Compound C235 was made in a similar manner as described in Example 11.70 as a yellow solid (13 mg, 14%). $^1$HNMR ($CDCl_3$, 400 MHz) δ 1.27 (d, 6H), 1.79-1.83 (m, 2H), 1.98-2.04 (m, 2H), 2.23 (s, 3H), 3.40-3.47 (m, 2H), 3.75-3.79 (m, 2H), 4.95 (sep, 1H), 5.34-5.38 (m, 1H), 7.48 (t, 1H), 7.58-7.62 (m, 2H), 8.01 (d, 2H), 8.23 (s, 1H), 8.90 (d, 2H). Exact mass calculated for $C_{25}H_{27}FN_4O_4$ 466.2, found 467.6.

Example 11.92

Preparation of 4-[6-(2-Fluoro-4-thiophen-3-yl-phenoxy)-5-methyl-pyrimidin-4-yloxy]-piperidine-1-carboxylic acid isopropyl ester (Compound C239)

Compound C239 was made in a similar manner as described in Example 11.70 as a white solid (29 mg, 31%). $^1$HNMR ($CDCl_3$, 400 MHz) δ 1.27 (d, 6H), 1.78-1.83 (m, 2H), 1.97-2.01 (m, 2H), 2.21 (s, 3H), 3.40-3.47 (m, 2H), 3.73-3.79 (m, 2H), 4.94 (sep, 1H), 5.34-5.36 (m, 1H), 7.22 (t, 1H), 7.34 (d, 1H), 7.39-7.45 (m, 4H), 8.24 (s, 1H). Exact mass calculated for $C_{24}H_{26}FN_3O_4S$ 471.2, found 472.4.

Example 11.93

Preparation of 4-[6-(2-Fluoro-4-pyrimidin-5-yl-phenoxy)-5-methyl-pyrimidin-4-yloxy]-piperidine-1-carboxylic acid isopropyl ester (Compound C238)

Compound C238 was made in a similar manner as described in Example 11.70 as a white solid (10 mg, 11%). Exact mass calculated for $C_{24}H_{26}FN_5O_4$ 467.2, found 468.6.

Example 11.94

Preparation of 4-{6-[2-Fluoro-4-(5-methoxy-pyridin-3-yl)-phenoxy]-5-methyl-pyrimidin-4-yloxy}-piperidine-1-carboxylic acid isopropyl ester (Compound C234)

Compound C234 was made in a similar manner as described in Example 11.70 as a white solid (TFA salt, 192 mg, 71%). $^1$HNMR ($CDCl_3$, 400 MHz) 1.26-1.28 (d, J=6.3 Hz, 6H), 1.77-1.83 (m, 2H), 1.98-2.06 (m, 2H), 2.23 (s, 3H), 3.40-3.46 (m, 2H), 3.76-3.85 (m, 2H), 4.04 (s, 3H), 4.92-4.98 (m, 1H), 5.33-5.38 (m, 1H), 7.37-7.45 (m, 3H), 7.77-7.78 (m, 1H), 8.23-8.24 (d, J=4.67, 1H), 8.45-8.46 (d, J=2.3 Hz, 1H), 8.61 (s, 1H). Exact mass calculated for $C_{26}H_{29}FN_4O_5$ 496.21, found 497.4.

Example 11.95

Preparation of 4-[6-(4-Ethynyl-2-fluoro-phenoxy)-5-methyl-pyrimidin-4-yloxy]-piperidine-1-carboxylic acid isopropyl ester (Compound C240)

Pd(II)(PhCN)$_2$Cl$_2$ (15 mg, 0.039 mmol) and CuI (9 mg, 0.047 mmol) were dissolved in anhydrous dioxane (3 mL), 10 wt % P(t-Bu)$_3$ in hexanes (0.200 mL, 13.6 mg, 0.067 mmol), NH(i-Pr)$_2$, (0.085 mL, 0.60 mmol), 4-[6-(4-bromo-2-fluoro-phenoxy)-5-methyl-pyrimidin-4-yloxy]-piperidine-1-carboxylic acid isopropyl ester (243 mg, 0.50 mmol), and TMS-acetylene (0.083 mL, 0.60 mmol), were added and the reaction mixture was sealed, purged with nitrogen, and stirred at room temperature for 12 h. The reaction mixture was diluted with EtOAc (15 mL), the mixture was filtered through a silica pad, the solvent was evaporated in vacuo at 23 C to give a dark oil which was dissolved in THF (3.5 mL) and MeOH (1.5 mL). 1.0 N NaOH (0.75 mL, 0.75 mmol) was added and after 5 min glacial AcOH (0.086 mL, 1.5 mmol) was added. After addition of silica (2.4 g) the solvent was evaporated in vacuo at 25 C to give a solid which was pulverized with mortar and pestle. This crude product was adsorbed onto silica and purified by flash chromatography using hexanes-EtOAc, 82:18, then hexanes-EtOAc, 75:25, v/v, to give the title Compound C240 as a resin (67 mg, 32% over 2 steps). $^1$H NMR (400 HMz, CDCl$_3$) δ 1.25 (d, J=6 Hz, 6H), 1.78 (m, 2H), 1.98 (m, 2H), 2.17 (s, 3H), 3.07 (s, 1H), 3.40 (m, 2H), 3.74 (m, 2H), 4.92 (m, 1H), 5.32 (m, 1H), 7.14 (m, 1H), 7.29 (m, 2H), 8.18 (s, 1H). LRMS calculated for $C_{22}H_{24}FN_3O_4$: 413.18. Found: 414.5 (M+H).

Example 12

Syntheses of Compounds of the Present Invention

Example 12.1

Preparation of 4-({Cyclopropyl-[6-(2-fluoro-4-methanesulfonyl-phenoxy)-5-methyl-pyrimidin-4-yl]-amino}-methyl)-piperidine-1-carboxylic acid tert-butyl ester (Compound D1)

A mixture of 4-{[(6-chloro-5-methyl-pyrimidin-4-yl)-cyclopropyl-amino]-methyl}-piperidine-1-carboxylic acid tert-butyl ester (200 mg, 0.5 mmole), potassium carbonate (208 mg, 1.5 mmole), and 2-fluoro-4-methanesulfonyl-phenol (95 mg, 0.5 mmole) in 2 mL DMF was heated under microwave irradiation at 160° C. for 4 hours. Mixture was purified by HPLC to give compound D1 as a yellow solid (93 mg, 35%). $^1$H NMR (CDCl$_3$, 400 MHz) δ 0.69-0.73 (m, 2H), 0.97-1.02 (m, 2H), 1.10-1.17 (m, 2H), 1.45 (s, 9H), 1.71 (d, J=12.4 Hz, 2H), 1.98-2.07 (m, 1H), 2.38 (s, 3H), 2.72 (t, J=12.4 Hz, 2H), 3.07-3.11 (m, 1H), 3.12 (s, 3H), 3.52 (d, J=7.3 Hz, 2H), 4.12 (d, J=12.9 Hz, 2H), 7.45 (t, J=8.3 Hz, 1H), 7.80-7.84 (m, 2H), 8.34 (s, 1H). Exact mass calculated for $C_{26}H_{35}FN_4O_5S$ 534.2, found 535.4 (MH$^+$).

Example 12.2

Preparation of 4-({Cyclopropyl-[6-(2-fluoro-4-methanesulfonyl-phenoxy)-5-methyl-pyrimidin-4-yl]-amino}-methyl)-piperidine-1-carboxylic acid isopropyl ester (Compound D2)

A mixture of cyclopropyl-[6-(2-fluoro-4-methanesulfonyl-phenoxy)-5-methyl-pyrimidin-4-yl]-piperidin-4-ylmethyl-amine (65 mg, 0.15 mmole) and triethylamine (23 mg, 0.225 mmole) in 2 mL THF was stirred at room temperature for 10 minutes. Into this mixture was added drop-wise isopropyl chloroformate (0.225 mmole). The mixture was quenched with water, extracted with ethyl acetate, and dried in vacuum to give Compound D2 as a yellow solid (65 mg, 83%). $^1$H NMR (CDCl$_3$, 400 MHz) δ 0.69-0.64 (m, 2H), 0.83-0.88 (m, 2H), 1.12-1.15 (m, 2H), 1.23 (d, J=6.3 Hz, 6H), 1.72 (d, J=13.1 Hz, 2H), 1.94-2.02 (m, 1H), 2.04 (s, 3H), 2.73 (t, J=12.4 Hz, 2H), 2.97-3.17 (m, 1H), 3.10 (s, 3H), 3.49-3.55 (m, 2H), 4.09-4.23 (m, 2H), 4.90 (sept, J=6.3 Hz, 1H), 7.45 (t, J=8.3 Hz, 1H), 7.76-7.80 (m, 2H), 8.12 (s, 1H). Exact mass calculated for $C_{25}H_{33}FN_4O_5S$ 520.2, found 521.5 (MH$^+$).

Example 13

Syntheses of Compounds of the Present Invention

Example 13.1

Preparation of 4-[6-(2-Fluoro-4-methanesulfonyl-phenylamino)-5-methyl-pyrimidin-4-ylsulfanyl]-piperidine-1-carboxylic acid isopropyl ester (Compound E1)

Step 1: Preparation of 4-(6-chloro-5-methyl-pyrimidin-4-ylsulfanyl)-piperidine-1-carboxylic acid tert-butyl ester A mixture of 4-mercapto-piperidine-1-carboxylic acid tert-butyl ester (1.5352 g, 7.06 mmol) and 4,6-dichloro-5-methyl-pyrimidine (1.1512 g, 7.06 mmol) in 15 mL of THF with sodium t-butoxide (1M in THF, 8.3 mL, 8.3 mmol) added dropwise. After 5 min, mixture was concentrated and residue was extracted with CH$_2$Cl$_2$ and H$_2$O. Organic phase was dried over MgSO$_4$, filtered and concentrated to give 4-(6-chloro-5-methyl-pyrimidin-4-ylsulfanyl)-piperidine-1-carboxylic acid tert-butyl ester as a yellowish solid (2.3469 g, 97%). Exact mass calculated for $C_{15}H_{22}ClN_3O_2S$ 343.11, found 344.1 (MH$^+$).

Step 2: Preparation of 4-chloro-5-methyl-6-(piperidin-4-ylsulfanyl)-pyrimidine

A mixture of 4-(6-chloro-5-methyl-pyrimidin-4-ylsulfanyl)-piperidine-1-carboxylic acid tert-butyl ester (2.3469 g, 6.82 mmol) and 40 mL of 4M HCl in dioxane was stirred at room temperature over night. Mixture was concentrated to give 4-chloro-5-methyl-6-(piperidin-4-ylsulfanyl)-pyrimidine as a yellowish solid (1.8985 g, 99%). Exact mass calculated for $C_{10}H_{14}ClN_3S$ 243.06, found 244.1 (MH$^+$).

Step 3: Preparation of 4-(6-chloro-5-methyl-pyrimidin-4-ylsulfanyl)-piperidine-1-carboxylic acid isopropyl ester A mixture of 4-chloro-5-methyl-6-(piperidin-4-ylsulfanyl)-pyrimidine (HCl salt, 1.8985 g, 6.77 mmol) and triethylamine (2.825 mL, 0.02 mol) in 50 mL of CH$_3$CN was stirred under room temperature. After 15 min, isopropyl chloroformate (1M in toluene, 8.13 mL, 8.13 mmol) were added slowly under 0° C. Mixture was stirred under room temperature. After 3 h, mixture was concentrated and residue was extracted with EtOAc and saturated NaHCO$_3$. Organic phase was dried over MgSO$_4$, filtered and concentrated to give 4-(6-chloro-5-methyl-pyrimidin-4-ylsulfanyl)-piperidine-1-carboxylic acid isopropyl ester as yellowish oil (1.9143 g, 85%). Exact mass calculated for $C_{14}H_{20}ClN_3O_2S$ 329.1, found 330.3 (MH$^+$).

Step 4: Preparation of 4-[6-(2-fluoro-4-methanesulfonyl-phenylamino)-5-methyl-pyrimidin-4-ylsulfanyl]-piperidine-1-carboxylic acid isopropyl ester (Compound E1)

A mixture of 4-(6-chloro-5-methyl-pyrimidin-4-ylsulfanyl)-piperidine-1-carboxylic acid isopropyl ester (1.2234 g, 3.7 mmol), 2-fluoro-4-methanesulfonyl-phenylamine (702 mg, 3.7 mmol), palladium acetate (84.3 mg, 0.37 mmol), 2-(di-t-butylphosphino)biphenyl (11 mg, 0.037 mmol), and sodium tert-butoxide (891.8 mg, 9.28 mmol) in 15 mL 1,4-dioxane was heated in microwave for 2 hours at 120° C. The mixture was purified by HPLC to give Compound E1 as a tanned solid (TFA salt, 601.1 mg, 27%). $^1$H NMR (MeOH-d$_4$, 400 MHz) δ 1.16-1.17 (d, J=6.32 Hz, 6H), 1.49-1.58 (m, 2H), 2.00-2.04 (m, 2H), 2.14 (s, 3H), 3.07 (s, 3H), 3.21-3.23 (m, 2H), 3.90-3.94 (m, 2H), 4.01-4.08 (m, 1H), 4.75-4.81 (m, 1H), 7.66-7.68 (d, J=8.08 Hz, 2H), 8.01-8.05 (m, 1H), 8.27 (s, 1H). Exact mass calculated for $C_{21}H_{27}FN_4O_4S_2$ 482.15, found 483.4 (MH$^+$).

Example 14

Protocol for RUP3 Dose Responses in Melanophores

Melanophores are maintained in culture as reported by Potenza, M. N. and Lerner, M. R., in Pigment Cell Research, Vol. 5, 372-378, 1992 and transfected with the RUP3 expression vector (pCMV) using electroporation. Following electroporation, the transfected cells are plated into 96 well plates for the assay. The cells are then allowed to grow for 48 hours in order to both recover from the electroporation procedure and attain maximal receptor expression levels.

On the assay day, the growth medium on the cells is replaced with serum-free buffer containing 10 nM melatonin. The melatonin acts via an endogenous Gi-coupled GPCR in the melanophores to lower intracellular cAMP levels. In response to lowered cAMP levels, the melanophores translocate their pigment to the center of the cell. The net effect of this is a significant decrease in the absorbance reading of the cell monolayer in the well, measured at 600-650 nM.

After a 1-hour incubation in melatonin, the cells become completely pigment-aggregated. At this point a baseline absorbance reading is collected. Serial dilutions of test compounds are then added to the plate and compounds that stimulate RUP3 produce increases in intracellular cAMP levels. In response to these increased cAMP levels, the melanophores translocate their pigment back into the cell periphery. After one hour, stimulated cells are fully pigment-dispersed. The cell monolayer in the dispersed state absorbs much more light in the 600-650 nm range. The measured increase in absorbance compared to the baseline reading allows one to quantitate the degree of receptor stimulation and plot a dose-response curve.

The compounds in the above examples were screened using the melanophore assay. Representative compounds and their corresponding EC$_{50}$ values are shown in the Table 8 below:

TABLE 8

| Compound | RUP3 (EC$_{50}$) (nM) |
|---|---|
| A11 | 86 |
| A14 | 242 |
| A24 | 185 |
| A27 | 76.5 |
| A32 | 43.5 |
| A39 | 16.9 |
| A90 | 52 |
| B4 | 300 |
| C168 | 28.3 |

Other compounds in the Examples showed EC$_{50}$ activities in the membrane cyclase assay less than about 10 μM.

Example 15

Food Intake Study

Male ZDF (Zucker diabetic fatty) rats weighing 350 g-400 g were dosed independently with two structurally divergent chemotypes exhibiting agonism to the RUP3 receptor. Rats were dosed daily via oral gavage with either vehicle (100% PEG 400), First Compound (30 mg/kg, 100 mg/kg), or Second Compound (10 mg/kg, 30 mg/kg) at a volume of 3 ml/kg. Body weight and food intake were monitored and recorded daily. The table shown below illustrates the body weight (g) and cumulative food intake (g) taken after both seven days and 14 days of dosing.

| Substance | Dose (mg/Kg) | Cumulative Food Intake (g) | | Body Weight (g) | |
|---|---|---|---|---|---|
| | | Week 1 | Week 2 | Week 1 | Week 2 |
| First Compound | Vehicle | 321 | 672 | 390 | 395 |
| | 30 mg/Kg | 271 | 557 | 383 | 383 |
| | 100 mg/Kg | 211 | 457 | 361 | 376 |
| Second Compound | Vehicle | 261 | 563 | 393 | 393 |
| | 10 mg/Kg | 217 | 459 | 388 | 390 |
| | 30 mg/Kg | 159 | 307 | 377 | 373 |

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

We claim:

1. A compound of Formula (I):

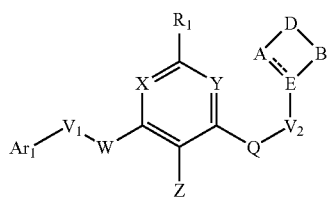

or a pharmaceutically acceptable salt, hydrate or solvate, or N-oxide thereof;

wherein:
A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;
D is S, S(O), S(O)$_2$, or N—R$_2$;
E is N or CR$_4$;
--- is a single bond when E is N or CR$_4$;
V$_1$ is a bond;
V$_2$ is a bond;
W is NR$_5$, O, S, S(O) or S(O)$_2$;
Q is NR$_6$, O, S, S(O) or S(O)$_2$;
X is N;
Y is N;
Z is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$-alkoxy, carboxamide, carboxy, cyano, $C_{3-7}$ cycloalkyl, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxycarbamimidoyl, hydroxylamino, nitro and tetrazolyl, wherein $C_{1-8}$ alkyl, $C_{3-7}$ cycloalkyl, and heterocyclic are each optionally substituted with 1, 2, 3 or 4 groups selected from the group consisting of $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro, and wherein said $C_{1-7}$ alkyl is optionally substituted with amino; or
Z is a group of Formula (A):

(A)

wherein:
R$_9$ is H, $C_{1-8}$ alkyl or $C_{3-7}$ cycloalkyl; and
R$_{10}$ is H, nitro or nitrile;
Ar$_1$ is phenyl, naphthyl, pyridyl, benzofuranyl, pyrazinyl, pyridazinyl, pyrimidinyl, triazinyl, quinoline, benzoxazole, benzothiazole, 1H-benzimidazole, isoquinoline, quinazoline, or quinoxaline, each optionally substituted with R$_{11}$, R$_{12}$, R$_{13}$, R$_{14}$, and R$_{15}$; wherein R$_{11}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbo-$C_{1-6}$-alkoxy, carboxamide, carboxy, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein $C_{1-5}$ acyl, $C_{1-6}$ acylsulfonamide, $C_{1-4}$ alkoxy, $C_{1-8}$ alkyl, $C_{1-4}$ alkylamino, $C_{1-4}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloallkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, wherein said $C_{1-7}$ alkyl and $C_{1-4}$ alkylcarboxamide are each optionally substituted with 1 to 5 substituents selected from the group consisting of $C_{1-4}$ alkoxy and hydroxy; or $R_{11}$ is a group of Formula (B):

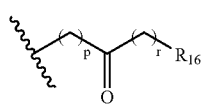

(B)

wherein:

"p" and "r" are each independently 0, 1, 2 or 3; and $R_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{12}$, $R_{13}$, $R_{14}$, and $R_{15}$ are each independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ lkylcarboxamide, $C_{2-6}$ alkynyl, $C_{1-4}$ alkylsulfonamide, $C_{1-4}$, alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent groups selected from the group consisting of $R_{12}$, $R_{13}$, $R_{14}$ and $R_{15}$ together with the atoms to which they are attached form a 5-, 6- or 7-membered cycloalkyl, cycloalkenyl or heterocyclic group fused with $Ar_1$, wherein the 5-, 6- or 7-membered group is optionally substituted with halogen;

$R_1$ is independently selected from the group consisting of H, $C_{1-5}$ acyloxy, $C_{2-6}$ alkenyl, $C_{1-4}$ alkoxy, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylureyl, $C_{1-4}$ alkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;

$R_2$ is selected from the group consisting of $C_{1-8}$ alkyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalklkoxy, $C_{1-4}$ haloalkyl, halogen, hydroxyl and nitro; or $R_2$ is a group of Formula (C):

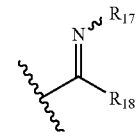

(C)

wherein:

$R_{17}$, is H, $C_{1-8}$ alkyl, $C_{3-7}$ cycloallkyl, aryl, heteroaryl or $OR_{19}$; and $R_{18}$ is F, Cl, Br, CN or $NR_{20}R_{21}$; where $R_{19}$ is H, $C_{1-8}$ alkyl or $C_{3-7}$ cycloalkyl, and $R_{20}$ and $R_{21}$ are each independently H, $C_{1-8}$ alkyl, $C_{3-7}$ cycloalkyl, aryl or heteroaryl; or $R_2$ is a group of Formula (D):

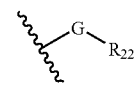

(D)

wherein:

G is:

—$CR_{23}R_{24}C(O)$—, —$C(O)$—, —$CR_{23}R_{24}C(O)NR_{25}$—, —$C(O)NR_{23}$—, —$C(O)O$—, —$C(S)$—, —$C(S)NR_{23}$—, —$C(S)O$—, —$CR_{23}R_{24}$—, —$S(O)_2$—, or a bond, wherein $R_{23}$, $R_{24}$ and $R_{25}$ are each independently H or $C_{1-8}$ alkyl; and $R_{22}$ is $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, CM alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloallkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$R_3$ is H, $C_{1-8}$ alkyl, $C_{1-4}$ alkoxy or hydroxyl; and $R_4$, $R_5$ and $R_6$ are each independently H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl.

2. A compound according to claim 1, or a pharmaceutically acceptable salt, hydrate or solvate thereof wherein:
D is N—$R_2$; and
E is $CR_4$.

3. A compound according to claim 2, or a pharmaceutically acceptable salt, hydrate or solvate thereof, wherein $R_2$ is selected from the group consisting of amino, aryl, carboxamide, carboxy, cyano, $C_{3-6}$-cycloalkyl, $C_{1-4}$ haloalkoxy, $C_{1-4}$ haloallkyl, halogen, heteroaryl and hydroxyl; and wherein aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (C):

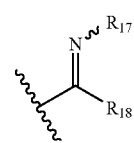

(C)

wherein:
$R_{17}$ is H, $C_{1-8}$ alkyl, $C_{3-7}$ cycloalkyl, aryl, heteroaryl or $OR_{19}$; and $R_{18}$ is F, Cl, Br, CN or $NR_{20}R_{21}$; where $R_{19}$ is H, $C_{1-8}$ alkyl or $C_{3-7}$ cycloalkyl, and $R_{20}$ and $R_{21}$ are each independently H, $C_{1-8}$ alkyl, $C_{3-7}$ cycloallkyl, aryl or heteroaryl; or $R_2$ is a group of Formula (D):

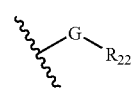

(D)

wherein:
G is:
—$CR_{23}R_{24}C(O)$—, —$C(O)$—, —$CR_{23}R_{24}C(O)NR_{25}$—, —$C(O)NR_{23}$—, —$C(O)O$—, —$C(S)$—, —$C(S)NR_{23}$—, —$C(S)O$—, —$CR_{23}R_{24}$—, or —$S(O)_2$;
wherein $R_{23}$, $R_{24}$ and $R_{25}$ are each independently H or $C_{1-8}$ alkyl; and $R_{22}$ is $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro.

4. The compound according to claim 2, or a pharmaceutically acceptable salt, hydrate or solvate thereof, wherein Q is O.

5. A compound according to claim 1, or a pharmaceutically acceptable salt, hydrate or solvate thereof, wherein E is $CR_4$ and $R_6$ is H.

6. A compound according to claim 1, or a pharmaceutically acceptable salt, hydrate or solvate thereof, wherein E is $CR_4$ and $R_6$ is $C_{3-7}$ cycloalkyl.

7. A compound according to claim 1, or a pharmaceutically acceptable salt, hydrate or solvate thereof, wherein E is N and $R_6$ is $C_{1-8}$ alkyl.

8. A compound according to claim 1, or a pharmaceutically acceptable salt, hydrate or solvate thereof, wherein E is N and $R_6$ is $C_{3-7}$ cycloalkyl.

9. A compound according to claim 1, or a pharmaceutically acceptable salt, hydrate or solvate thereof, wherein $R_2$ is selected from the group consisting of amino, aryl, carboxamide, carboxy, cyano, $C_{36}$-cycloalkyl, $C_{1-4}$ haloalkoxy, $C_{1-4}$ haloalkyl, halogen, heteroaryl and hydroxyl; and wherein aryl or heteroaryl optionally substituted with 1 to 5 substituents selected from the group consisting of $C_{1-5}$ acyl, $C_{1-4}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ allkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (C):

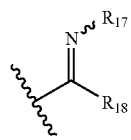

(C)

wherein:
$R_{17}$ is H, $C_{1-8}$ alkyl, $C_{3-7}$ cycloalkyl, aryl, heteroaryl or $OR_{19}$; and $R_{18}$ is F, Cl, Br, CN or $NR_{20}R_{21}$; where $R_{19}$ is H, $C_{1-8}$ alkyl or $C_{3-7}$ cycloalkyl, and $R_{20}$ and $R_{21}$ are each independently H, $C_{1-8}$ alkyl, $C_{3-7}$ cycloalkyl, aryl or heteroaryl; or $R_2$ is a group of Formula (D):

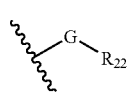

(D)

wherein:
G is:
—$CR_{23}R_{24}C(O)$—, —$C(O)$—, —$CR_{23}R_{24}C(O)NR_{25}$—, —$C(O)NR_{23}$—, —$C(O)O$—, —$C(S)$—, —$C(S)NR_{23}$—, —$C(S)O$—, —$CR_{23}R_{24}$—, or —$S(O)_2$;

wherein $R_{23}R_{24}$ and $R_{25}$ are each independently H or $C_{1-8}$ alkyl; and $R_{22}$ is $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloallkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ diallkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro.

10. The compound according to claim 1, or a pharmaceutically acceptable salt, hydrate or solvate thereof, wherein Q is O.

11. The compound according to claim 1, or a pharmaceutically acceptable salt, hydrate or solvate thereof, wherein W is NH.

12. The compound according to claim 1, or a pharmaceutically acceptable salt, hydrate or solvate thereof, wherein W is O.

13. The compound according to claim 1, or a pharmaceutically acceptable salt, hydrate or solvate thereof, wherein Q is $NR_6$.

14. The compound according to claim 1, or a pharmaceutically acceptable salt, hydrate or solvate thereof, wherein $R_6$ is $C_{1-8}$ alkyl.

15. The compound according to claim 1, or a pharmaceutically acceptable salt, hydrate or solvate thereof, wherein $R_6$ is $C_{3-7}$ cycloalkyl.

16. The compound according to claim 1, or a pharmaceutically acceptable salt, hydrate or solvate thereof, wherein $R_6$ is H.

17. The compound according to claim 1, or a pharmaceutically acceptable salt, hydrate or solvate thereof, wherein Q is S.

18. The compound according to claim 1, or a pharmaceutically acceptable salt, hydrate or solvate thereof, wherein both A and B are —$CH_2$—.

19. The compound according to claim 1, or a pharmaceutically acceptable salt, hydrate or solvate thereof, wherein A is —$CH_2CH_2$— and B is —$CH_2$—.

20. The compound according to claim 1, or a pharmaceutically acceptable salt, hydrate or solvate thereof, wherein both A and B are —$CH_2CH_2$—.

21. The compound according to claim 1, or a pharmaceutically acceptable salt, hydrate or solvate thereof, wherein D is $N-R_2$.

22. The compound according to claim 1, or a pharmaceutically acceptable salt, hydrate or solvate thereof, wherein $R_2$ is a group of Formula (D):

wherein:

G is $-CR_{23}R_{24}C(O)-$, $-C(O)-$, $-CR_{23}R_{24}C(O)NR_{23}-$, $-C(O)NR_{23}-$, $-C(O)O-$, $-C(S)-$, $-C(S)NR_{23}-$, $-C(S)O-$, $-CR_{23}R_{24}-$, $-S(O)_2-$, or a bond; wherein $R_{23}$ and $R_{24}$ are each independently H or $C_{1-8}$ alkyl; and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, intro, phenyl, phenoxy, and sulfonic acid, wherein said $C_{1-7}$ alkyl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{34}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro.

23. The compound according to claim 1, or a pharmaceutically acceptable salt, hydrate or solvate thereof, wherein $R_2$ is $-C(O)OR_{22}$ and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

24. The compound according to claim 1, or a pharmaceutically acceptable salt, hydrate or solvate thereof, wherein $R_2$ is $-C(O)OR_{22}$ and $R_{22}$ is $C_{1-8}$ alkyl, or $C_{3-7}$ cycloalkyl each optionally substituted with 1 to 5 substituents selected from the group consisting of $C_{1-4}$ alkoxy, $C_{1-7}$ alkyl, $C_{1-4}$ alkylsulfonyl, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid.

25. The compound according to claim 1, or a pharmaceutically acceptable salt, hydrate or solvate thereof, wherein $R_2$ is $-C(O)OR_{22}$ and $R_{22}$ is $C_{1-8}$ alkyl, or $C_{3-7}$ cycloalkyl.

26. The compound according to claim 1, or a pharmaceutically acceptable salt, hydrate or solvate thereof, wherein $R_2$ is $-C(O)R_{22}$ and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

27. The compound according to claim 1, or a pharmaceutically acceptable salt, hydrate or solvate thereof, wherein $R_2$ is $-CH_2R_{22}$, or $-R_{22}$ and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

28. The compound according to claim 1, or a pharmaceutically acceptable salt, hydrate or solvate thereof, wherein $R_2$ is $-S(O)_2R_{22}$ and $R_{22}$ is $C_{1-8}$ alkyl, $C_{3-7}$, cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-4}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

29. The compound according to claim 1, or a pharmaceutically acceptable salt, hydrate or solvate thereof, wherein $R_2$ is $-CR_{23}R_{24}C(O)R_{22}$ and wherein $R_{23}$ and $R_{24}$ are each independently H or $C_{1-8}$ alkyl; and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

30. The compound according to claim 1, or a pharmaceutically acceptable salt, hydrate or solvate thereof, wherein $R_2$ is $-CR_{23}R_{24}C(O)NR_{25}R_{22}$ and wherein $R_{23}$, $R_{24}$ and $R_{25}$ are each independently H or $C_{1-8}$ alkyl; and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{1-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

31. The compound according to claim 1, or a pharmaceutically acceptable salt, hydrate or solvate thereof, wherein $Ar_1$ is phenyl, naphthyl, pyridyl, benzofuranyl, pyrazinyl, pyridazinyl, pyrimidinyl, triazinyl, quinoline, benzoxazole, benzothiazole, 1H-benzimidazole, isoquinoline, quinazoline, or quinoxaline, each optionally substituted with $R_{11}$, $R_{12}$, $R_{13}$, $R_{14}$, and $R_{15}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carboxamide, carboxy, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, and halogen.

32. The compound according to claim 1, or a pharmaceutically acceptable salt, hydrate or solvate thereof, wherein $Ar_1$ is phenyl optionally substituted with $R_{11}$, $R_{12}$, $R_{13}$, $R_{14}$, and $R_{15}$;

wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carboxamide, carboxy, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, and halogen.

33. The compound according to claim 1, or a pharmaceutically acceptable salt, hydrate or solvate thereof, wherein $Ar_1$ is pyridyl optionally substituted with $R_{11}$, $R_{12}$, $R_{13}$, and $R_{14}$;

wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-4}$ alkylsulfonyl, $C_{1-4}$ alkylthio, amino, $C_{2-6}$ dialkylamino, halogen, heterocyclic, and sulfonamide, and wherein $C_{1-4}$ alkoxy, $C_{1-8}$ alkyl, $C_{1-4}$ alkylamino, alkylsulfonyl, $C_{1-4}$ alkylthio, $C_{2-6}$ dialkylamino, and heterocyclic are each optionally substituted with 1 to 5 substituents selected independently from the group consisting of $C_{1-6}$ acylsulfonamide, $C_{1-4}$ alkoxy, $C_{1-4}$ alkylsulfonyl, $C_{3-7}$ cycloalkyloxy, heteroaryl, hydroxyl, phenyl, and phosphonooxy; and $R_{12}$, $R_{13}$, $R_{14}$, and $R_{15}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, and halogen.

34. The compound according to claim 1, or a pharmaceutically acceptable salt, hydrate or solvate thereof, wherein Z is selected from the group consisting of $C_{1-5}$ acyl, $C_{1-8}$ alkyl, $C_{2-6}$ alkynyl, $C_{1-4}$ alkylsulfonamide, amino, carbamimidoyl, cyano, $C_{3-7}$ cycloalkyl, heterocyclic, and hydroxycarbamimidoyl, wherein $C_{1-8}$ alkyl, $C_{3-7}$ cycloalkyl, and heterocyclic are each optionally substituted with 1, 2, 3 or 4 groups selected from the group consisting of $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro, and wherein said $C_{1-7}$ alkyl is optionally substituted with amino.

35. The compound according to claim 1, or a pharmaceutically acceptable salt, hydrate or solvate thereof, wherein Z is selected from the group consisting of $C_{1-5}$ acyl, $C_{1-8}$ alkyl, $C_{2-6}$ alkynyl, $C_{1-4}$ alkylsulfonamide, amino, carbamimidoyl, cyano, $C_{3-7}$ cycloalkyl, heterocyclic, and hydroxycarbamimidoyl, wherein said heterocyclic is optionally substituted with a —$CH_2NH_2$ group.

36. The compound according to claim 1, or a pharmaceutically acceptable salt, hydrate or solvate thereof, wherein Z is selected from the group consisting of $C(O)CH_3$, $C(O)CH_2CH_3$, $CH_3$, $CH_2C_3$, $C\equiv CH$, $NHS(O)_2CH_3$, amino, carbamimidoyl, cyano, cyclopropyl, 4,5-dihydro-1H-imidazol-2-yl, 5-aminomethyl-4,5-dihydro-oxazol-2-yl, and hydroxycarbamimidoyl.

37. The compound according to claim 1, or a pharmaceutically acceptable salt, hydrate or solvate thereof, wherein:

A and B are each independently —$CH_2CH_2$— or —$CH_2$—;

D is N—$R_2$;

W and Q are each independently NH or O;

X and Y are each

Z is selected from the group consisting of nitro, $C_{1-5}$ acyl, $C_{1-8}$ alkyl, $C_{2-6}$ alkynyl, $C_{1-4}$ alkylsulfonamide, amino, carbamimidoyl, cyano, $C_{3-7}$ cycloalkyl, heterocyclic, and hydroxycarbamimidoyl, wherein said heterocyclic is optionally substituted with a —$CH_2NH2$ group;

$R_2$ is —$C(O)OR_{22}$, —$C(O)R_{22}$, —$CH_2R_{22}$, —$R_{22}$, —$S(O)OR_{22}$, —$CR_{23}R_{24}C(O)R_{22}$, or —$CR_{23}R_{24}C(O)NR_{25}R_{22}$, wherein $R_{22}$ is $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$- alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic; and $R_{23}$ and $R_{24}$ are each independently H or $C_{1-8}$ alkyl;

$Ar_1$ is phenyl, naphthyl, pyridyl, benzofuranyl, pyrazinyl, pyridazinyl, pyrimidinyl, triazinyl, quinoline, benzoxazole, benzothiazole, 1H-benzimidazole, isoquinoline, quinazoline, or quinoxaline, each optionally substituted with $R_{11}$, $R_{12}$, $R_{13}$, $R_{14}$, and $R_{15}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carboxamide, carboxy, $C_{2-6}$ dialkylamino, halogen, heterocyclic, heterocyclic-oxy, heterocyclic-carbonyl, heteroaryl, and sulfonamide, and wherein $C_{3-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-4}$ alkyl, $C_{1-4}$ alkylcarboxamide, $C_1A$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, and halogen.

38. The compound according to claim 1, or a pharmaceutically acceptable salt, hydrate or solvate thereof wherein:

A and B are each independently —$CH_2CH_2$— or —$CH_2$—;

D is N—$R_2$;

W and Q are each independently NH or O;

X and Y are each N;

Z is selected from the group consisting of nitro, $C_{1-5}$ acyl, $C_{1-8}$ alkyl, $C_{2-6}$ alkynyl, $C_{1-4}$ alkylsulfonamide, amino, carbamimidoyl, cyano, $C_{3-7}$ cycloalkyl, heterocyclic, and hydroxycarbamimidoyl, wherein said heterocyclic is optionally substituted with a —$CH_2NH_2$ group;

$R_2$ is —C(O)O$R_{22}$, —C(O)$R_{22}$, —$CH_2R_{22}$, —S(O)$_2R_{22}$, —$CR_{23}R_{24}C(O)R_{22}$, or —$CR_{23}R_{24}C(O)NR_{25}R_{22}$, wherein $R_{22}$ is $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic; and $R_{23}$ and $R_{24}$ are each independently H or $C_{1-8}$ alkyl;

$Ar_1$ is phenyl, naphthyl, pyridyl, benzofuranyl, pyrazinyl, pyridazinyl, pyrimidinyl. triazinyl, quinoline, benzoxazole, benzothiazole, 1H-benzimidazole, isoquinoline, quinazoline, or quinoxaline, each optionally substituted with $R_{11}$, $R_{12}$, $R_{13}$, $R_{14}$, and $R_{15}$; wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carboxamide, carboxy, $C_{2-6}$ dialkylamino, halogen, heterocyclic, heterocyclic-oxy, heterocyclic-carbonyl, heteroaryl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, and halogen.

39. The compound according to claim 1, or a pharmaceutically acceptable salt, hydrate or solvate thereof, wherein:

A and B are both —$CH_2CH_2$—;

D is N—$R_2$;

W and Q are each independently NH or O;

X and Y are both N;

Z is selected from the group consisting of nitro, $C(O)CH_3$, $C(O)CH_2CH_3$, $CH_3$, $CH_2CH_3$, C≡CH, $NHS(O)_2CH_3$, amino, carbamimidoyl, cyano, cyclopropyl, 4,5-dihydro-1H-imidazol-2-yl, 5-aminomethyl-4,5-dihydro-oxazol-2-yl, and hydroxycarbamimidoyl;

$R_2$ is —C(O)O$R_{22}$, wherein $R_{22}$ is $C_{1-8}$ alkyl, or $C_{3-7}$ cycloalkyl each optionally substituted with 1 to 5 substituents selected from the group consisting of $C_{1-4}$ alkoxy, $C_{1-8}$ alkyl, $C_{1-4}$ alkylsulfonyl, amino, carboxy, cyano, $C_{3-7}$ cycloalkyl, $C_{2-8}$ dialkylamino, $C_{1-4}$ haloalkoxy, $C_{1-4}$ haloalkyl, halogen, and hydroxyl;

$Ar_1$ is phenyl optionally substituted with $R_{11}$, $R_{12}$, $R_{13}$, $R_{14}$, and $R_{15}$;

wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-8}$ alkyl and halogen.

40. The compound according to claim 1, or a pharmaceutically acceptable salt, hydrate or solvate thereof, wherein:

A and B are both —CH$_2$CH$_2$—;
D is N—R$_2$;
W is NH;
Q is O;
X and Y are both N;
Z is nitro, cyano, C(O)CH$_3$, amino, CH$_3$, CH$_2$CH$_3$, or C≡CH;
R$_2$ is —C(O)OR$_{22}$, —C(O)R$_{22}$, —R$_{22}$, or —S(O)$_2$R$_{22}$ wherein R$_{22}$ is C$_{1-8}$ alkyl, C$_{3-7}$ cycloalkyl, phenyl, heteroaryl, or heterocyclic each optionally substituted with 1 to 5 substituents selected from the group consisting of C$_{1-5}$ acyl, C$_{2-6}$ alkenyl, C$_{1-4}$ alkoxy, C$_{1-7}$ alkyl, C$_{1-4}$ alkylsulfonyl, amino, carbo-C$_{1-6}$-alkoxy, carboxy, cyano, C$_{3-7}$ cycloalkyl, C$_{24}$ dialkylamino, C$_{1-4}$ haloalkoxy, C$_{1-4}$ haloalkyl, halogen, heteroaryl, heterocyclic, hydroxyl, phenyl, phenoxy, and sulfonic acid, wherein said C$_{1-7}$ alkyl, phenyl and phenoxy are each optionally substituted with 1 to 5 substituents selected from the group consisting of amino, C$_{1-4}$ haloalkoxy, and heterocyclic;
Ar$_1$ is phenyl, 3-pyridyl, or 2-pyridyl each optionally substituted with R$_{11}$, R$_{12}$, R$_{13}$, R$_{14}$, and R$_{15}$, wherein R$_{11}$ is selected from the group consisting of C$_{1-6}$ acylsulfonamide, C$_{1-4}$ alkoxy, C$_{1-8}$ alkyl, C$_{1-4}$ alkylamino, C$_{1-6}$ alkylcarboxamide, C$_{1-4}$ alkylsulfonamide, C$_{1-4}$ alkylsulfonyl, C$_{1-4}$ alkylthio, carboxamide, carboxy, C$_{2-6}$ dialkylamino, halogen, heterocyclic, heterocyclic-oxy, heterocyclic-carbonyl, heteroaryl, heteroarylcarbonyl, and sulfonamide, and wherein C$_{1-4}$ alkoxy, C$_{1-8}$ alkyl, C$_{1-4}$ alkylamino, C$_{1-6}$ alkylcarboxamide, C$_{1-4}$ alkylsulfonamide, C$_{1-4}$ alkylsulfonyl, C$_{1-4}$ alkylthio, carbamimidoyl, C$_{2-6}$ dialkylamino, heterocyclic, heterocyclic-carbonyl, and heteroaryl are each optionally substituted with 1 to 5 substituents selected independently from the group consisting of C$_{1-6}$ acylsulfonamide, C$_{1-4}$ alkoxy, C$_{1-7}$ alkyl, C$_{1-4}$ alkylcarboxamide, C$_{1-4}$ alkylsulfonyl, carboxy, C$_{2-6}$ dialkylamino, C$_{2-6}$ dialkylcarboxamide, heteroaryl, heterocyclic, hydroxyl, phenyl, and phosphonooxy wherein said C$_{1-7}$ alkyl and C$_{1-4}$ alkylcarboxamide are each optionally substituted with 1 to 5 substituents selected from the group consisting of C$_{1-4}$ alkoxy and hydroxy; and
R$_{12}$, R$_{13}$, R$_{14}$, and R$_{15}$ are each independently CH$_3$, or F.

41. The compound according to claim 1, or a pharmaceutically acceptable salt, hydrate or solvate thereof, wherein:
A and B are both —CH$_2$CH$_2$—;
D is N—R$_2$;
W and Q are both O;
X and Y are both N;
Z is selected from the group consisting of CH$_3$, CH$_2$CH$_3$, cyclopropyl, or C≡CH;
R$_2$ is —C(O)OR$_{22}$, —C(O)R$_{22}$, —R$_{22}$, —CH$_2$C(O)R$_{22}$, or —CH$_2$C(O)NHR$_{22}$ wherein R$_{22}$ is C$_{1-8}$ alkyl, C$_{2-6}$ alkynyl, C$_{3-7}$ cycloalkyl, phenyl, heteroaryl, or heterocyclic each optionally substituted with 1 to 5 substituents selected from the group consisting of C$_{1-4}$ alkoxy, C$_{1-7}$ alkyl, C$_{1-4}$ alkylsulfonyl, amino, carboxy, cyano, C$_{2-8}$ dialkylamino, C$_{1-4}$ haloalkoxy, C$_{1-4}$ haloalkyl, halogen, heteroaryl, hydroxyl, phenyl, and phenoxy, wherein said C$_{1-7}$ alkyl, is optionally substituted with 1 or 2 substituents selected from the group consisiing of C$_{1-4}$ haloalkoxy, and heterocyclic;
Ar$_1$ is phenyl, 2-pyridyl, or 3-pyridyl each optionally substituted with R$_{11}$, R$_{12}$, R$_{13}$, R$_{14}$, and R$_{15}$, wherein R$_{11}$ is selected from the group consisting of C$_{1-6}$ acylsulfonamide, C$_{1-4}$ alkoxy, C$_{1-8}$ alkyl, C$_{1-4}$ alkylamino, C$_{1-6}$ alkylcarboxamide, C$_{1-4}$ alkylsulfonyl, C$_{1-4}$ alkylthio, amino, carboxy, C$_{2-6}$ dialkylamino, halogen, heterocyclic, heterocyclic-oxy, heterocyclic-carbonyl, heteroaryl, and sulfonamide, and wherein C$_{1-4}$ alkoxy, C$_{1-8}$ alkyl, C$_{1-4}$ alkylamino, C$_{1-6}$ alkylcarboxamide, C$_{1-4}$ alkylsulfonyl, C$_{1-4}$ alkylthio, C$_{2-6}$ dialkylamino, and heteroaryl are each optionally substituted with 1 to 5 substituents selected independently from the group consisting of C$_{1-4}$ alkoxy, C$_{1-4}$ alkyl, C$_{1-4}$ alkylcarboxamide, heteroaryl, hydroxyl, and phosphonooxy wherein said C$_{1-7}$ alkyl and C$_{1-4}$ alkylcarboxamide are each optionally substituted with 1 to 5 substituents selected from the group consisting of C$_{1-4}$ alkoxy and hydroxy; and
R$_{12}$, R$_{13}$, R$_{14}$, and R$_{15}$ are each independently selected form the group consisting of C$_{1-8}$ alkyl, and halogen.

42. The compound according to any one of claims 37 to 41, or a pharmaceutically acceptable salt, hydrate or solvate thereof, wherein R$_2$ is selected from the group consisting of methoxycarbonyl, ethoxycarbonyl, iso-propoxycarbonyl, n-propoxycarbonyl, n-butoxycarbonyl, tert-butoxycarbonyl, iso-butoxycarbonyl, and n-pentyloxycarbonyl.

43. The compound according to any one of claims 37 to 41, or a pharmaceutically acceptable salt, hydrate or solvate thereof, wherein R$_{11}$ is selected from the group consisting of sulfamoyl, acetylsulfamoyl, propionylsulfamoyl, butyrylsulfamoyl, pentanoylsulfamoyl, methanesulfonyl, ethanesulfonyl, propane-1-sulfonyl, hydroxymethyl, 2-hydroxyethyl, 3-hydroxypropyl; 4-hydroxy-butyl, phosphonooxymethyl, 2-phosphonooxy-ethyl, 3-phosphonooxy-propyl, and 4-phosphonooxy-butyl.

44. The compound according to claim 1 wherein said compound is selected from the group consisting of:
4-[5-Cyano-6-(6-methylsulfanyl-pyridin-3-ylamino)-pyrimidin-4-yloxy]-piperidine-1-carboxylic acid tert-butyl ester;
4-[5-Cyano-6-(6-methanesulfonyl-pyridin-3-ylamino)-pyrimidin-4-yloxy]-piperidine-1-carboxylic acid tert-butyl ester;
[6-(1-Cyclopropylmethyl-piperidin-4-yloxy)-5-nitro-pyrimidin-4-yl]-(4-methanesulfonyl-phenyl)-amine;
4-[6-(4-Methanesulfonyl-phenylamino)-5-nitro-pyrimidin-4-yloxy]-piperidine-1-carboxylic acid isopropyl ester;
4-[6-(4-Methanesulfonyl-phenylamino)-5-nitro-pyrimidin-4-yloxy]-piperidine-1-carboxylic acid 2-isopropyl-5-methyl-cyclohexyl ester;
{4-[6-(4-Methanesulfonyl-phenylamino)-5-nitro-pyrimidin-4-yloxy]-piperidin-1-yl}-pyridin-3-yl-methanone;
(2-Chloro-pyridin-3-yl)-{4-[6-(4-methanesulfonyl-phenylamino)-5-nitro-pyrimidin-4-yloxy]-piperidin-1-yl}-methanone;
{4-[6-(4-Methanesulfonyl-phenylamino)-5-nitro-pyrimidin-4-yloxy]-piperidin-1-yl}-pyridin-2-yl-methanone;
(4-Methanesulfonyl-phenyl)-[6-(1-methanesulfonyl-piperidin-4-yloxy)-5-nitro-pyrimidin-4-yl]-amine;
(4-Methanesulfonyl-phenyl)-{5-nitro-6-[1-(propane-1-sulfonyl)-piperidin-4-yloxy]-pyrimidin-4-yl}-amine;
{6-[1-(Butane-i -sulfonyl)-piperidin-4-yloxy]-5-nitro-pyrimidin-4-yl}-(4-methanesulfonyl-phenyl)-amine;
(4-Methanesulfonyl-phenyl)-{5-nitro-6-[1-(thiophene-2-sulfonyl)-piperidin-4-yloxy]-pyrimidin-4-yl}-amine;
(4-Methanesulfonyl-phenyl)-{6-[1-(1-methyl-i H-imidazole-4-sulfonyl)-piperidin-4-yloxy]-5-nitro-pyrimidin-4-yl}-amine;
{6-[1-(2,4-Dimethyl-thiazole-5-sulfonyl)-piperidin-4-yloxy]-5-nitro-pyrimidin-4-yl}-(4-methanesulfonyl-phenyl)-amine;

4-[5-Cyano-6-(3-fluoro-4-methanesulfonyl-phenylamino)-pyrimidin-4-yloxy]-piperidine-1-carboxylic acid tert-butyl ester;

4-[6-(2-Fluoro-4-methanesulfonyl-phenylamino)-5-nitro-pyrimidin-4-yloxy]-piperidine-1-carboxylic acid tert-butyl ester;

4-[5-Cyano-6-(4-methanesulfonyl-phenylamino)-pyrimidin-4-yloxy]-piperidine-1-carboxylic acid tert-butyl ester;

4-{6-(6-Methanesulfonyl-pyridin-3-ylamino)-5-nitro-pyrimidin-4-yloxy]-piperidine-1-carboxylic acid tert-butyl ester;

4-[5-Acetyl-6-(6-methanesulfonyl-pyridin-3-ylamino)-pyrimidin-4-yloxy]-piperidine-1-carboxylic acid tert-butyl ester;

4-[5-Amino-6-(2-fluoro-4-methanesulfonyl-phenylamino)-pyrimidin-4-yloxy]-piperidine-1-carboxylic acid tert-butyl ester;

4-[5-Cyano-6-(4-methanesulfonyl-phenylamino)-pyrimidin-4-yloxy]-piperidine-1-carboxylic acid isopropyl ester;

4-[5-Cyano-6-(4-methanesulfonyl-phenylamino)-pyrimidin-4-yloxy]-piperidine-1-carboxylic acid ethyl ester;

4-[5-Cyano-6-(4-methanesulfonyl-phenylamino)-pyrimidin-4-yloxy]-piperidine-1-carboxylic acid isobutyl ester; 4-(4-Methanesulfonyl-phenylamino)-6-[1-(tetrahydro-furan-2-carbonyl)-piperidin-4-yloxy]-pyrimidine-5-carbonitrile;

4-[1-(3,3-Dimethyl-2-oxo-butyl)-piperidin-4-yloxy]-6-(4-methanesulfonyl-phenylamino)-pyrimidine-5-carbonitrile;

4-(4-Methanesulfonyl-phenylamino)-6-[1-(pyridine-3-carbonyl)-piperidin-4-yloxy]-pyrimidine-5-carbonitrile;

4-(4-Methanesulfonyl-phenylamino)-6-[1-(pyridine-2-carbonyl)-piperidin-4-yloxy]-pyrimidine-5-carbonitrile;

4-[6-(4-Methanesulfonyl-phenylamino)-5-nitro-pyrimidin-4-yloxy]-piperidine-1-carboxylic acid tert-butyl ester;

1-{4-[6-(4-Methanesulfonyl-phenylamino)-5-nitro-pyrimidin-4-yloxy]-piperidin-1-yl}-3,3-dimethyl-butan-1-one;

(4-Methanesulfonyl-phenyl)-[5-nitro-6-(1-pyridin-2-ylmethyl-piperidin-4-yloxy)-pyrimidin-4-yl]-amine;

(4-Methanesulfonyl-phenyl)-[5-nitro-6-(1-pyridin-3-ylmethyl-piperidin-4-yloxy)-pyrimidin-4-yl]-amine;

(4-Methanesulfonyl-phenyl)-[5-nitro-6-(3,4,5,6-tetrahydro-2H-[1,2']bipyridinyl-4-yloxy)-pyrimidin-4-yl]-amine;

4-[6-(4-Methanesulfonyl-phenylamino)-5-nitro-pyrimidin-4-yloxy]-piperidine-1-carboxylic acid ethyl ester;

1-{4-[6-(4-Methanesulfonyl-phenylamino)-5-nitro-pyrimidin-4-yloxy]-piperidin-1-yl}-3,3-dimethyl-butan-2-one;

3-[6-(4-Methanesulfonyl-phenylamino)-5-nitro-pyrimidin-4-yloxy]-pyrrolidine-1-carboxylic acid tert-butyl ester;

4-[6-(4-Methanesulfonyl-phenylamino)-5-nitro-pyrimidin-4-ylamino]-piperidine-1-carboxylic acid tert-butyl ester;

1-{4-[6-(4-Methanesulfonyl-phenylamino)-5-nitro-pyrimidin-4-ylamino]-piperidin-1-yl}-ethanone;

1-{4-[6-(4-Methanesulfonyl-phenylamino)-5-nitro-pyrimidin-4-ylamino]-piperidin-1-yl}-2,2-dimethyl-propan-1-one;

4-[5-Ethynyl-6-(2-fluoro-4-[1,2,4]triazol-1-yl-phenylamino)-pyrimidin-4-yloxy]-piperidine-1-carboxylic acid isopropyl ester;

{5-Ethynyl-6-[1-(3-isopropyl-[1,2,4]oxadiazol-5-yl)-piperidin-4-yloxy]-pyrimidin-4-yl}-(2-fluoro-4-methanesulfonyl-phenyl)-amine;

4-{6-[2,5-Difluoro-4-(2-methanesulfonyl-ethyl)-phenylamino]-5-methyl-pyrimidin-4-yloxy}-piperidine-1-carboxylic acid isopropyl ester;

4-{6-[6-(2-Fluoro-ethyl)-2-methyl-pyridin-3-ylamino]-5-methyl-pyrimidin-4-yloxy}-piperidine-1-carboxylic acid isopropyl ester;

4-{6-[2,5-Difluoro-4-(2-[1,2,4]triazol-1-yl-ethyl)-phenylamino]-5-methyl-pyrimidin-4-yloxy}-piperidine-1-carboxylic acid isopropyl ester;

4-{5-Ethynyl-6-[2-fluoro-4-(4-methoxy-pyridin-2-yl)-phenylamino]-pyrimidin-4-yloxy}-piperidine-1-carboxylic acid isopropyl ester;

4-{6-[2-Fluoro-4-(2-methanesulfonyl-ethyl)-phenylamino]-5-methyl-pyrimidin-4-yloxy}-piperidine-1-carboxylic acid isopropyl ester;

4-{6-[2,3-Difluoro-4-(2-methanesulfonyl-ethyl)-phenylamino]-5-methyl-pyrimidin-4-yloxy}-piperidine-1-carboxylic acid isopropyl ester;

4-[5-Acetyl-6-(6-methanesulfonyl-pyridin-3-ylamino)-pyrimidin-4-yloxy]-piperidine-1-carboxylic acid isobutyl ester;

1-[4-(1-Benzyl-azetidin-3-yloxy)-6-(6-methanesulfonyl-pyridin-3-ylamino)-pyrimidin-5-yl]-ethanone;

4-[5-Cyano-6-(6-propylamino-pyridin-3-ylamino)-pyrimidin-4-yloxyl]-piperidine-1-carboxylic acid isopropyl ester;

4-115-Cyano-6-(2-fluoro-4-isopropylamino-phenylamino)-pyrimidin-4-yloxy]-piperidine-1-carboxylic acid isopropyl ester;

4-[5-Cyano-6-(2-fluoro-4-propylamino-phenylamino)-pyrimidin-4-yloxy]-piperidine-1-carboxylic acid isopropyl ester;

4-[5-Cyano-6-(2-fluoro-4-propoxy-phenylamino)-pyrimidin-4-yloxy]-piperidine-1-carboxylic acid isopropyl ester;

4-[5-Cyano-6-(6-propyl-pyridin-3-ylamino)-pyrimidin-4-yloxy]-piperidine-1-carboxylic acid isopropyl ester;

4-{5-Cyano-6-[4-(2-dimethylamino-ethylsulfanyl)-2-fluoro-phenylamino]-pyrimidin-4-yloxy}-piperidine-1-carboxylic acid isopropyl ester;

4-{5-Cyano-6-[4-(2-dimethylamino-ethanesulfonyl)-2-fluoro-phenylamino]-3-oxy-pyrimidin-4-yloxy}-piperidine-1-carboxylic acid isopropyl ester;

4-{5-Cyano-6-[2-fluoro-4-(4-methyl-piperazin-1-yl)-phenylamino]-pyrimidin-4-yloxy}-piperidine-1-carboxylic acid isopropyl ester;

4-{5-Cyano-6-[2-fluoro-4-(3-methyl-butylamino)-phenylamino]-pyrimidin-4-yloxy}-piperidine-1-carboxylic acid isopropyl ester;

4-[5-Cyano-6-(2-fluoro-4-morpholin-4-yl-phenylamino)-pyrimidin-4-yloxy]-piperidine-1-carboxylic acid isopropyl ester;

4-{5-Cyano-6-[4-(2-dimethylamino-ethylamino)-2-fluoro-phenylamino]-pyrimidin-4-yloxy}-piperidine-1-carboxylic acid isopropyl ester;

4-[5-Cyano-6-(4-dimethylamino-2-fluoro-phenylamino)-pyrimidin-4-yloxy]-piperidine-1-carboxylic acid isopropyl ester;

4-{5-Cyano-6-[2-fluoro-4-(2-pyrrolidin-1-yl-ethylamino)-phenylamino]-pyrimidin-4-yloxy}-piperidine-1-carboxylic acid isopropyl ester;

4-[6-(2-Fluoro-4-methanesulfonyl-phenylamino)-5-methyl-pyrimidin-4-yloxy]-piperidine-1-carboxylic acid isopropyl ester;

4-{5-Cyano-6-[2-fluoro-4-(2-morpholin-4-yl-ethylamino)-phenylamino]-pyrimidin-4-yloxy}-piperidine-1-carboxylic acid isopropyl ester;

4-[6-(2-Fluoro-4-iodo-phenylamino)-5-methyl-pyrimidin-4-yloxy]-piperidine-1-carboxylic acid isopropyl ester;

4-[5-Cyano-6-(2-fluoro-4-methanesulfonyl-phenylamino)-pyrimidin-4-yloxy]-piperidine-1-carboxylic acid isopropyl ester;

4-[6-(2-Fluoro-4-morpholin-4-yl-phenylamino)-5-methyl-pyrimidin-4-yloxy]-piperidine-1-carboxylic acid isopropyl ester;

4-[6-(2,5-Difluoro-4-propoxy-phenylamino)-5-methyl-pyrimidin-4-yloxy]-piperidine-1-carboxylic acid isopropyl ester;

4-[6-(2-Fluoro-4-propylamino-phenylamino)-5-methyl-pyrimidin-4-yloxy]-piperidine-1-carboxylic acid isopropyl ester;

4-{6-[2-Fluoro-4-(2-methoxy-ethylamino)-phenylamino]-5-methyl-pyrimidin-4-yloxy}-piperidine-1-carboxylic acid isopropyl ester;

4-(6-{2-Fluoro-4-[(tetrahydro-furan-2-ylmethyl)-amino]-phenylamino}-5-methyl-pyrimidin-4-yloxy)-piperidine-1-carboxylic acid isopropyl ester;

4-{6-[2-Fluoro-4-(2-methanesulfonyl-ethylamino)-phenylamino]-5-methyl-pyrimidin-4-yloxy}-piperidine-1-carboxylic acid isopropyl ester;

4-(6-{2-Fluoro-4-[(2-methanesulfonyl-ethyl)-methyl-amino]-phenylamino}-5-methyl-pyrimidin-4-yloxy)-piperidine-1-carboxylic acid isopropyl ester;

4-[6-(4-Bromo-2,5-difluoro-phenylamino)-5-methyl-pyrimidin-4-yloxy]-piperidine-1-carboxylic acid isopropyl ester;

4-[6-(2,5-Difluoro-4-morpholin-4-yl-phenylamino)-5-methyl-pyrimidin-4-yloxy]-piperidine-1-carboxylic acid isopropyl ester;

4-[6-(6-Chloro-2-methyl-pyridin-3-ylamino)-5-methyl-pyrimidin-4-yloxy]-piperidine-1-carboxylic acid isopropyl ester;

4-[5-Methyl-6-(2-methyl-6-morpholin-4-yl-pyridin-3-ylamino)-pyrimidin-4-yloxy]-piperidine-1-carboxylic acid isopropyl ester;

4-[5-(4,5-Dihydro-1H-imidazol-2-yl)-6-(2-fluoro-4-methanesulfonyl-phenylamino)-pyrimidin-4-yloxy]-piperidine-1-carboxylic acid isopropyl ester;

(2-Fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine;

4-[6-(2-Fluoro-4-propoxy-phenylamino)-5-methyl-pyrimidin-4-yloxy]-piperidine-1-carboxylic acid isopropyl ester;

4-{6-[2-Fluoro-4-(2-methanesulfonyl-ethoxy)-phenylamino]-5-methyl-pyrimidin-4-yloxy}-piperidine-1-carboxylic acid isopropyl ester;

4-{6-[2-Fluoro-4-(2-methoxy-ethoxy)-phenylamino]-5-methyl-pyrimidin-4-yloxy}-piperidine-1-carboxylic acid isopropyl ester;

4-{6-[2-Fluoro-4-(2-isopropoxy-ethoxy)-phenylamino]-5-methyl-pyrimidin-4-yloxy}-piperidine-1-carboxylic acid isopropyl ester;

4-[6-(6-Chloro-4-methyl-pyridin-3-ylamino)-5-methyl-pyrimidin-4-yloxy]-piperidine-1-carboxylic acid isopropyl ester;

4-[6-(2-Fluoro-4-methanesulfonyl-phenylamino)-5-(N-hydroxycarbamimidoyl)-pyrimidin-4-yloxy]-piperidine-1-carboxylic acid isopropyl ester;

4-[5-Carbamimidoyl-6-(2-fluoro-4-methanesulfonyl-phenylamino)-pyrimidin-4-yloxy]-piperidine-1-carboxylic acid isopropyl ester;

4-{6-[2-Fluoro-4-(tetrahydro-furan-2-ylmethoxy)-phenylamino]-5-methyl-pyrimidin-4-yloxy}-piperidine-1-carboxylic acid isopropyl ester;

4-[5-Methyl-6-(4-methyl-6-morpholin-4-yl-pyridin-3-ylamino)-pyrimidin-4-yloxy]-piperidine-1-carboxylic acid isopropyl ester;

4-{6-[6-(2-Methoxy-ethoxy)-2-methyl-pyridin-3-ylamino]-5-methyl-pyrimidin-4-yloxy}-piperidine-1-carboxylic acid isopropyl ester;

4-{6-[6-(2-Methoxy-ethoxy)-4-methyl-pyridin-3-ylamino]-5-methyl-pyrimidin-4-yloxy}-piperidine-1-carboxylic acid isopropyl ester;

4-{6-[2,5-Difluoro-4-(2-methoxy-ethoxy)-phenylamino]-5-methyl-pyrimidin-4-yloxy}-piperidine-1-carboxylic acid isopropyl ester;

4-{6-[2-Fluoro-4-(2-isopropoxy-ethylsulfamoyl)-phenylamino]-5-methyl-pyrimidin-4-yloxy}-piperidine-1-carboxylic acid isopropyl ester;

4-[6-(4-Carbamoyl-2,5-difluoro-phenylamino)-5-methyl-pyrimidin-4-yloxy]-piperidine-1-carboxylic acid isopropyl ester;

4-{6-[(2-Fluoro-4-methanesulfonyl-phenyl)-(2-methoxy-ethyl)-amino]-5-methyl-pyrimidin-4-yloxy}-piperidine-1-carboxylic acid isopropyl ester;

4-{6-[4-(2-Ethoxy-ethoxy)-2-fluoro-phenylamino]-5-methyl-pyrimidin-4-yloxy}-piperidine-1-carboxylic acid isopropyl ester;

4-{6-[2-Fluoro-4-(tetrahydro-pyran-4-yloxy)-phenylamino]-5-methyl-pyrimidin-4-yloxy}-piperidine-1-carboxylic acid isopropyl ester;

4-{6-[2-Fluoro-4-(2-hydroxy-ethoxy)-phenylamino]-5-methyl-pyrimidin-4-yloxy}-piperidine-1-carboxylic acid isopropyl ester;

1-{4-[6-(2-Fluoro-4-methanesulfonyl-phenylamino)-5-methyl-pyrimidin-4-yloxy]-piperidin-1-yl}-butan-1-one;

1-{4-[6-(2-Fluoro-4-methanesulfonyl-phenylamino)-5-methyl-pyrimidin-4-yloxy]-piperidin-1-yl}-pentan-1-one;

1-{4-[6-(2-Fluoro-4-methanesulfonyl-phenylamino)-5-methyl-pyrimidin-4-yloxy]-piperidin-1-yl}-3-methyl-butan-1-one;

4-{6-[2-Fluoro-4-(pyridin-2-ylmethoxy)-phenylamino]-5-methyl-pyrimidin-4-yloxy}-piperidine-1-carboxylic acid isopropyl ester;

4-[6-(6-Chloro-4-fluoro-pyridin-3-ylamino)-5-cyano-pyrimidin-4-yloxy]-piperidine-1-carboxylic acid isopropyl ester;

4-[5-Amino-6-(2-fluoro-4-methanesulfonyl-phenylamino)-pyrimidin-4-yloxy]-piperidine-1-carboxylic acid isopropyl ester;

4-{6-[2-Fluoro-4-(5-isopropoxymethyl-[1,2,4]oxadiazol-3-yl)-phenoxy]-5-methyl-pyrimidin-4-yloxy}-piperidine-1-carboxylic acid isopropyl ester;

4-{6-[2-Fluoro-4-(5-methoxy-pyridin-2-yl)-phenoxy]-5-methyl-pyrimidin-4-yloxy}-piperidine-1-carboxylic acid isopropyl ester;

4-{6-[6-(2-Cyclopropoxy-ethylamino)-2-methyl-pyridin-3-yloxy]-5-methyl-pyrimidin-4-yloxy}-piperidine-1-carboxylic acid isopropyl ester;

4-{6-[2-Fluoro-4-(pyridine-2-carbonyl)-phenoxy]-5-methyl-pyrimidin-4-yloxy}-piperidine-1-carboxylic acid isopropyl ester;

4-[6-(2-Fluoro-4-methanesulfonyl-phenoxy)-5-methanesulfonylamino-pyrimidin-4-yloxy]-piperidine-1-carboxylic acid isopropyl ester;

4-[6-(4-Methoxy-6'-methyl-3,4,5,6-tetrahydro-2H-[1,2']bipyridinyl-5'-yloxy)-5-methyl-pyrimidin-4-yloxy]-piperidine-1-carboxylic acid isopropyl ester;

1-{4-[6-(2-Fluoro-4-methanesulfonyl-phenoxy)-5-methyl-pyrimidin-4-yloxy]-piperidin-1-yl}-2-(4-trifluoromethoxy-phenoxy)-propan-1-one;

1-{4-[6-(2-Fluoro-4-methanesulfonyl-phenoxy)-5-methyl-pyrimidin-4-yloxy]-piperidin-1-yl}-2-(4-trifluoromethoxy-phenoxy)-ethanone;

N-(4-Chloro-phenyl)-2-{4-[6-(2-fluoro-4-methanesulfonyl-phenoxy)-5-methyl-pyrimidin-4-yloxy]-piperidin-1-yl}-acetamide;

N-(3-Chloro-phenyl)-2-{4-[6-(2-fluoro-4-methanesulfonyl-phenoxy)-5-methyl-pyrimidin-4-yloxy]-piperidin-1-yl}-acetamide;

N-(3,5-Dichloro-phenyl)-2-{4-[6-(2-fluoro-4-methanesulfonyl-phenoxy)-5-methyl-pyrimidin-4-yloxy]-piperidin-1-yl}-acetamide;

2-{4-[6-(2-Fluoro-4-methanesulfonyl-phenoxy)-5-methyl-pyrimidin-4-yloxy]-piperidin-1-yl}-N-(4-trifluoromethyl-phenyl)-acetamide;

2-{4-[6-(2-Fluoro-4-methanesulfonyl-phenoxy)-5-methyl-pyrimidin-4-yloxy]-piperidin-1-yl}-N-phenyl-acetamide;

2-{4-[6-(2-Fluoro-4-methanesulfonyl-phenoxy)-5-methyl-pyrimidin-4-yloxy]-piperidin-1-yl}-N-(4-isopropyl-phenyl)-acetamide;

2-{4-[6-(2-Fluoro-4-methanesulfonyl-phenoxy)-5-methyl-pyrimidin-4-yloxy]-piperidin-1-yl}-N-(4-methoxy-phenyl)-acetamide;

2-{4-[6-(2-Fluoro-4-methanesulfonyl-phenoxy)-5-methyl-pyrimidin-4-yloxy]-piperidin-1-yl}-N-(3-trifluoromethyl-phenyl)-acetamide;

4-{6-[2-Fluoro-4-(3-methoxy-propane-1-sulfonyl)-phenoxy]-5-methyl-pyrimidin-4-yloxy}-piperidine-1-carboxylic acid isopropyl ester;

4-{6-[6-(2-Isopropoxy-ethyl)-2-methyl-pyridin-3-yloxy]-5-methyl-pyrimidin-4-yloxy}-piperidine-1-carboxylic acid isopropyl ester;

4-{5-Methyl-6-[2-methyl-6-(2-pyridin-2-yl-ethoxy)-pyridin-3-yloxy]-pyrimidin-4-yloxy}-piperidine-1-carboxylic acid isopropyl ester;

4-{6-[2-Fluoro-4-(thiophene-2-carbonyl)-phenoxy]-5-methyl-pyrimidin-4-yloxy}-piperidine-1-carboxylic acid isopropyl ester;

4-(6-{6-[(2-Isopropoxy-ethyl)-methyl-amino]-2-methyl-pyridin-3-yloxy}-5-methyl-pyrimidin-4-yloxy)-piperidine-1-carboxylic acid isopropyl ester;

4-{6-[6-(2-Isopropoxy-ethanesulfonyl)-2-methyl-pyridin-3-yloxy]-5-methyl-pyrimidin-4-yloxy}-piperidine-1-carboxylic acid isopropyl ester;

4-{6-[6-(2-Hyclroxy-ethanesulfonyl)-2-methyl-pyridin-3-yloxy]-5-methyl-pyrimidin-4-yloxy}-piperidine-1-carboxylic acid isopropyl ester;

4-[6-(6-Amino-2-methyl-pyridin-3-yloxy)-5-methyl-pyrimidin-4-yloxy]-piperidine-1-carboxylic acid isopropyl ester;

2-{4-[6-(2-Fluoro-4-niethanesulfonyl-phenoxy)-5-methyl-pyrimidin-4-yloxy]-piperidin-1-yl}-1-morpholin-4-yl-ethanone;

1-(3,4-Dichloro-phenyl)-2-{4-[6-(2-fluoro-4-methanesulfonyl-phenoxy)-5-methyl-pyrimidin-4-yloxy]-piperidin-1-yl}-ethanone;

1-(3-Chloro-phenyl)-2-{4-[6-(2-fluoro-4-methanesulfonyl-phenoxy)-5-methyl-pyrimidin-4-yloxy]-piperidin-1-yl}-ethanone;

2-{4-[6-(2-Fluoro-4-methanesulfonyl-phenoxy)-5-methyl-pyrimidin-4-yloxy]-piperidin-1-yl}-1-thiophen-3-yl-ethanone;

2-{4-[6-(2-Fluoro-4-methanesulfonyl-phenoxy)-5-methyl-pyrimidin-4-yloxy]-piperidin-1-yl}-1-phenyl-ethanone;

1-(2,4-Dimethoxy-phenyl)-2-{4-[6-(2-fluoro-4-methanesulfonyl-phenoxy)-5-methyl-pyrimidin-4-yloxy]-piperidin-1-yl}-ethanone;

1-{4-[6-(2-Fluoro-4-methanesulfonyl-phenoxy)-5-methyl-pyrimidin-4-yloxy]-piperidin-1-yl}-3-isopropoxy-propan-1-one;

1-{4-[6-(2-Fluoro-4-methanesulfonyl-phenoxy)-5-methyl-pyrimidin-4-yloxy]-piperidin-1-yl}-4-isopropoxy-butan-1-one;

1-{4-[6-(2-Fluoro-4-methanesulfonyl-phenoxy)-5-methyl-pyrimidin-4-yloxy]-piperidin-1-yl}-3-hydroxy-propan-1-one;

2-{4-[6-(2-Fluoro-4-methanesulfonyl-phenoxy)-5-methyl-pyrimidin-4-yloxy]-piperidin-1-yl}-1-(5-pyridin-2-yl-thiophen-2-yl)-ethanone;

3-{4-[6-(2-Fluoro-4-methanesulfonyl-phenoxy)-5-methyl-pyrimidin-4-yloxy]-piperidin-1-yl}-3-oxo-propane-1-sulfonic acid 2-{4-[6-(2-Fluoro-4-methanesulfonyl-phenoxy)-5-methyl-pyrimidin-4-yloxy]-piperidin-1-yl}-1-thiophen-2-yl-ethanone;

4-{4-[6-(2-Fluoro-4-methanesulfonyl-phenoxy)-5-methyl-pyrimidin-4-yloxy]-piperidin-1-yl}-cyclohexanecarboxylic acid;

1-(4-Diethylamino-phenyl)-2-{4-[6-(2-fluoro-4-methanesulfonyl-phenoxy)-5-methyl-pyrimidin-4-yloxy]-pipendin-1-yl}-ethanone;

2-{4-[6-(2-Fluoro-4-methanesulfonyl-phenoxy)-5-methyl-pyrimidin-4-yloxy]-piperidin-1-yl}-1-(2-methyl-4-phenyl-furan-3-yl)-ethanone;

1-{4-[6-(2-Fluoro-4-methanesulfonyl-phenoxy)-5-methyl-pyrimidin-4-yloxy]-piperidin-1-yl}-pentan-2-one;

1-{4-[6-(2-Fluoro-4-methanesulfonyl-phenoxy)-5-methyl-pyrimidin-4-yloxy]-piperidin-1-yl}-hexan-2-one;

1-{4-[6-(2-Fluoro-4-methanesulfonyl-phenoxy)-5-methyl-pyrimidin-4-yloxy]-piperidin-1-yl}-hexan-2-one;

1-{4-[6-(2-Fluoro-4-methanesulfonyl-phenoxy)-5-methyl-pyrimidin-4-yloxy]-piperidin-1-yl}-4-methyl-pentan-2-one;

1-{4-[6-(2-Fluoro-4-methanesulfonyl-phenoxy)-5-methyl-pyrimidin-4-yloxy]-piperidin-1-yl}-5-methyl-hexan-2-one;

1-{4-[6-(2-Fluoro-4-methanesulfonyl-phenoxy)-5-methyl-pyrimidin-4-yloxy]-piperidin-1-yl}-6-methyl-heptan-2-one;

5-{4-[6-(2-Fluoro-4-methanesulfonyl-phenoxy)-5-methyl-pyrimidin-4-yloxy]-piperidin-1-yl}-4-oxo-pentanoic acid;

5-{4-[6-(2-Fluoro-4-methanesulfonyl-phenoxy)-5-methyl-pyrimidin-4-yloxy]-piperidin-1-yl}-4-oxo-pentanenitrile;

1-{4-[6-(2-Fluoro-4-methanesulfonyl-phenoxy)-5-methyl-pyrimidin-4-yloxy]-piperidin-1-yl}-2-pyridin-2-yl-ethanone;

2-{4-[6-(2-Fluoro-4-methanesulfonyl-phenoxy)-5-methyl-pyrimidin-4-yloxy]-piperidin-1-yl}-1-pyridin-4-yl-ethanone;
2-{4-[6-(2-Fluoro-4-methanesulfonyl-phenoxy)-5-methyl-pyrimidin-4-yloxy]-piperidin-1-ylmethyl}-acrylic acid;
1-[1,4]Dioxan-2-yl-2-{4-[6-(2-fluoro-4-methanesulfonyl-phenoxy)-5-methyl-pyrimidin-4-yloxy]-piperidin-1-yl}-ethanone;
1-(2,3-Dihydro-[1,4]dioxin-2-yl)-2-{4-[6-(2-fluoro-4-methanesulfonyl-phenoxy)-5-methyl-pyrimidin-4-yloxy]-piperidin-1-yl}-ethanone;
2-{4-[6-(2-Fluoro-4-methanesulfonyl-phenoxy)-5-methyl-pyrimidin-4-yloxy]-piperidin-1-yl}-1-p-tolyl-ethanone;
2-{4-[6-(2-Fluoro-4-methanesulfonyl-phenoxy)-5-methyl-pyrimidin-4-yloxy]-piperidin-1-yl}-1-(4-methoxy-phenyl)-ethanone;
1-(2-Chloro-phenyl)-2-{4-[6-(2-fluoro-4-methanesulfonyl-phenoxy)-5-methyl-pyrimidin-4-yloxy]-piperidin-1-yl}-ethanone;
3-(2-{4-[6-(2-Fluoro-4-methanesulfonyl-phenoxy)-5-methyl-pyrimidin-4-yloxy]-piperidin-1-yl}-acetyl)-benzonitrile;
1-(2,4-Dimethyl-phenyl)-2-{4-[6-(2-fluoro-4-methanesulfonyl-phenoxy)-5-methyl-pyrimidin-4-yloxy]-piperidin-1-yl}-ethanone;
1-(4-Chloro-3-methyl-phenyl)-2-{4-[6-(2-fluoro-4-methanesulfonyl-phenoxy)-5-methyl-pyrimidin-4-yloxy]-piperidin-1-yl}-ethanone;
1-(4-Difluoromethoxy-phenyl)-2-{4-[6-(2-fluoro-4-methanesulfonyl-phenoxy)-5-methyl-pyrimidin-4-yloxy]-piperidin-1-yl}-ethanone;
1-(2,3-Dihydro-benzo[1,4]dioxin-6-yl)-2-{4-[6-(2-fluoro-4-methanesulfonyl-phenoxy)-5-methyl-pyrimidin-4-yloxy]-piperidin-1-yl}-ethanone;
2-{4-[6-(2-Fluoro-4-methanesulfonyl-phenoxy)-5-methyl-pyrimidin-4-yloxy]-piperidin-1-yl}-1-(5-phenyl-thiophen-2-yl)-ethanone;
2-{4-[6-(2-Fluoro-4-methanesulfonyl-phenoxy)-5-methyl-pyrimidin-4-yloxy]-piperidin-1-yl}-1-thiophen-2-yl-ethanone;
{4-[6-(2-Fluoro-4-methanesulfonyl-phenoxy)-5-methyl-pyrimidin-4-yloxy]-piperidin-1-yl}-acetic acid ethyl ester;
4-(2-Fluoro-4-methanesulfonyl-phenoxy)-6-[1-(4-methoxy-cyclohexyl)-piperidin-4-yloxy]-5-methyl-pyrimidine;
1-{4-[6-(2-Fluoro-4-methanesulfonyl-phenoxy)-5-methyl-pyrimidin-4-yloxy]-piperidin-1-yl}-hexan-1-one;
4-{6-[2-Fluoro-4-(2-isobutoxy-ethoxy)-phenoxy]-5-methyl-pyrimidin-4-yloxy}-piperidine-1-carboxylic acid isopropyl ester;
4-{6-[4-(2-Cyclopropoxy-ethoxy)-2-fluoro-phenoxy]-5-methyl-pyrimidin-4-yloxy}-piperidine-1-carboxylic acid isopropyl ester;
4-{6-[4-(2-Ethoxy-ethoxy)-2-fluoro-phenoxy]-5-methyl-pyrimidin-4-yloxy}-piperidine-1-carboxylic acid isopropyl ester;
4-{6-[2-Fluoro-4-(3-methoxy-propoxy)-phenoxy]-5-methyl-pyrimidin-4-yloxy}-piperidine-1-carboxylic acid isopropyl ester;
4-{6-[2-Fluoro-4-(2-pyridin-2-yl-ethoxy)-phenoxy]-5-methyl-pyrimidin-4-yloxy}-piperidine-1-carboxylic acid isopropyl ester;
4-{6-[2-Fluoro-4-(tetrahydro-pyran-4-yloxy)-phenoxy]-5-methyl-pyrimidin-4-yloxy}-piperidine-1-carboxylic acid isopropyl ester;
4-{6-[4-(2-tert-Butoxy-ethoxy)-2-fluoro-phenoxy]-5-methyl-pyrimidin-4-yloxy}-piperidine-1-carboxylic acid isopropyl ester;
4-[6-(2-Fluoro-4-sulfo-phenoxy)-5-methyl-pyrimidin-4-yloxy]-piperidine-1-carboxylic acid isopropyl ester;
4-[6-(2,5-Difluoro-4-trifluoromethoxy-phenoxy)-5-ethynyl-pyrimidin-4-yloxy]-piperidine-1-carboxylic acid isopropyl ester;
4-[6-(2,5-Difluoro-4-trifluoromethoxy-phenoxy)-5-prop-1-ynyl-pyrimidin-4-yloxyl]-piperidine-1-carboxylic acid isopropyl ester;
4-[5-Ethynyl-6-(2-fluoro-4-methoxy-phenoxy)-pyrimidin-4-yloxy]-piperidine-1-carboxylic acid isopropyl ester;
4-[5-Ethynyl-6-(6-methoxy-4-methyl-pyridin-3-yloxy)-pyrimidin-4-yloxy]-piperidine-1-carboxylic acid isopropyl ester;
4-{5-Ethynyl-6-[6-(2-isopropoxy-ethyl)-2-methyl-pyridin-3-yloxy]-pyrimidin-4-yloxy}-piperidine-1-carboxylic acid isopropyl ester;
4-[5-Ethynyl-6-(2-fluoro-4-[1,2,4]triazol-4-yl-phenoxy)-pyrimidin-4-yloxy]-piperidine-1-arboxylic acid isopropyl ester;
4-[5-Ethynyl-6-(2-fluoro-4-[1,2,4]triazol-1-yl-phenoxy)-pyrimidin-4-yloxy]-piperidine-1-arboxylic acid isopropyl ester;
1-{4-[5-Ethynyl-6-(2-fluoro-4-[1,2,4]triazol-1-yl-phenoxy)-pyrimidin-4-yloxy]-piperidin-1-yl}-3-pyridin-2-yl-propan-1-one;
5-Ethynyl-4-(2-fluoro-4-methanesulfonyl-phenoxy)-6-[1-(3-isopropyl-[1,2,4]oxadiazol-5-yl)-piperidin-4-yloxy]-pyrimidine;
4-[1-(3-Ethyl-[1,2,4]oxadiazol-5-yl)-piperidin-4-yloxy]-5-ethynyl-6-(2-fluoro-4-methanesulfonyl-phenoxy)-pyrimidine;
4-[1-(3-Ethyl-[1,2,4]oxadiazol-5-yl)-piperidin-4-yloxy]-6-(2-fluoro-4-methanesulfonyl-phenoxy)-5-methyl-pyrimidine;
4-(2-Fluoro-4-methanesulfonyl-phenoxy)-5-methyl-6-[1-(3-methyl-[1,2,4]oxadiazol-5-yl)-piperidin-4-yloxy]-pyrimidine;
4-[6-(2-Fluoro-4-methanesulfonylamino-phenoxy)-5-methyl-pyrimidin-4-yloxy]-piperidine-1-carboxylic acid isopropyl ester;
4-{6-[2,5-Difluoro-4-(2-methanesulfonyl-ethyl)-phenoxy]-5-methyl-pyrimidin-4-yloxy}-piperidine-1-carboxylic acid isopropyl ester;
4-{6-[4-Fluoro-6-(2-methanesulfonyl-ethyl)-pyridin-3-yloxy]-5-methyl-pyrimidin-4-yloxy}-piperidine-1-carboxylic acid isopropyl ester;
4-{5-Cyclopropyl-6-[2,5-difluoro-4-(2-hydroxy-ethyl)-phenoxy]-pyrimidin-4-yloxy}-piperidine-1-carboxylic acid isopropyl ester;
4-{6-[2,5-Difluoro-4-(2-morpholin-4-yl-ethyl)-phenoxy]-5-methyl-pyrimidin-4-yloxy}-piperidine-1-carboxylic acid isopropyl ester;
4-{6-[6-(2-Fluoro-ethyl)-2-methyl-pyridin-3-yloxy]-5-methyl-pyrimidin-4-yloxy}-piperidine-1-carboxylic acid isopropyl ester;
4-{6-[4-Fluoro-6-(2-morpholin-4-yl-ethyl)-pyridin-3-yloxy]-5-methyl-pyrimidin-4-yloxy}-piperidine-1-carboxylic acid isopropyl ester;

4-{5-Ethynyl-6-[4-fluoro-6-(2-methanesulfonyl-ethyl)-pyridin-3-yloxy]-pyrimidin-4-yloxy}-piperidine-1-carboxylic acid isopropyl ester;

4-{6-[2,5-Difluoro-4-(2-[1,2,4]triazol-1-yl-ethyl)-phenoxy]-5-methyl-pyrimidin-4-yloxy}-piperidine-1-carboxylic acid isopropyl ester;

4-{6-[2,3-Difluoro-4-(2-methanesulfonyl-ethyl)-phenoxy]-5-methyl-pyrimidin-4-yloxy}-piperidine-1-carboxylic acid isopropyl ester;

4-[6-(3-Fluoro-1-oxy-pyridin-4-yloxy)-5-methyl-pyrimidin-4-yloxy]-piperidine-1-carboxylic acid isopropyl ester;

4-[6-(5'-Methoxy-6-methyl-[2,2']bipyridinyl-5-yloxy)-5-methyl-pyrimidin-4-yloxy]-piperidine-1-carboxylic acid isopropyl ester;

4-{5-Ethynyl-6-[2-fluoro-4-(4-methoxy-pyridin-2-yl)-phenoxy]-pyrimidin-4-yloxy}-piperidine-1-carboxylic acid isopropyl ester;

4-{6-[2-Fluoro-4-(3-methoxy-pyridin-2-yl)-phenoxy]-5-methyl-pyrimidin-4-yloxy}-piperidine-1-carboxylic acid isopropyl ester;

4-[6-(2-Fluoro-4-morpholin-4-yl-phenoxy)-5-methyl-pyrimidin-4-yloxy]-piperidine-1-carboxylic acid isopropyl ester;

{4-[6-(2-Fluoro-4-methanesulfonyl-phenoxy)-5-methyl-pyrimidin-4-yloxy]-piperidin-1-yl}-[6-(2-pyrrolidin-1-yl-ethyl)-pyridin-3-yl]-methanone;

(6-Amino-pyridin-3-yl)-{4-[6-(2-fluoro-4-methanesulfonyl-phenoxy)-5-methyl-pyrimidin-4-yloxy]-piperidin-1-yl}-methanone;

4-[5-Ethyl-6-(2-fluoro-4-methanesulfonyl-phenoxy)-pyrimidin-4-yloxy]-piperidine-1-carboxylic acid isopropyl ester;

4-[6-(2-Fluoro-phenoxy)-5-methyl-pyrimidin-4-yloxy]-piperidine-1-carboxylic acid isopropyl ester;

4-{6-[6-(2-Isopropoxy-ethylamino)-2-methyl-pyridin-3-yloxy]-5-methyl-pyrimidin-4-yloxy}-piperidine-1-carboxylic acid isopropyl ester;

4-{6-[6-(2-Hydroxy-ethylsulfanyl)-2-methyl-pyridin-3-yloxy]-5-methyl-pyrimidin-4-yloxy}-piperidine-1-carboxylic acid isopropyl ester;

4-[5-Methyl-6-(2-methyl-6-pentyl-pyridin-3-yloxy)-pyrimidin-4-yloxy]-piperidine-1-carboxylic acid isopropyl ester;

2-{4-[6-(2-Fluoro-4-methanesulfonyl-phenoxy)-5-methyl-pyrimidin-4-yloxy]-piperidin-1-yl}-1-(3-fluoro-phenyl)-ethanone;

2-{4-[6-(2-Fluoro-4-methanesulfonyl-phenoxy)-5-methyl-pyrimidin-4-yloxy]-piperidin-1-yl}-1-(4-trifluoromethoxy-phenyl)-ethanone;

2-{4-[6-(2-Fluoro-4-methanesulfonyl-phenoxy)-5-methyl-pyrimidin-4-yloxy]-piperidin-1-yl}-1-pyridin-2-yl-ethanone;

4-{6-[6-(2-Methoxy-ethanesulfonyl)-2-methyl-pyridin-3-yloxy]-5-methyl-pyrimidin-4-yloxy}-piperidine-1-carboxylic acid isopropyl ester;

4-(2-Fluoro-4-methanesulfonyl-phenoxy)-6-[1-(3-isopropyl-[1,2,4]oxadiazol-5-yl)-piperidin-4-yloxy]-5-methyl-pyrimidine;

4-(6-{2-Fluoro-4-[(2-hydroxy-ethylcarbamoyl)-methyl]-phenoxy}-5-methyl-pyrimidin-4-yloxy)-piperidine-1-carboxylic acid isopropyl ester;

4-[6-(5-Iodo-pyridin-2-yloxy)-5-methyl-pyrimidin-4-yloxy]-piperidine-1-carboxylic acid isopropyl ester;

4-(6-{2-Fluoro-4-[N-(2-isopropoxy-ethyl)-carbamimidoyl]-phenoxy}-5-methyl-pyrimidin-4-yloxy)-piperidine-1-carboxylic acid isopropyl ester;

4-[6-(4-Carboxy-2-fluoro-phenoxy)-5-methyl-pyrimidin-4-yloxy]-piperidine-1-carboxylic acid isopropyl ester;

4-(4-Bromo-2-fluoro-phenoxy)-6-[1-(3-isopropyl-[1,2,4]oxadiazol-5-yl)-pipendin-4-yloxy]-5-methyl-pyrimidine;

4-[6-(5-Methanesulfonyl-pyridin-2-yloxy)-5-methyl-pyrimidin-4-yloxy]-piperidine-1-carboxylic acid isopropyl ester;

4-{6-[6-(2-Hydroxy-ethylamino)-2-methyl-pyridin-3-yloxy]-5-methyl-pyrimidin-4-yloxy}-piperidine-1-carboxylic acid isopropyl ester;

4-[5-Cyclopropyl-6-(2-fluoro-4-methanesulfonyl-phenoxy)-pyrimidin-4-yloxy]-piperidine-1-carboxylic acid isopropyl ester;

4-{6-[6-(2-Methanesulfonyl-ethylamino)-2-methyl-pyridin-3-yloxy]-5-methyl-pyrimidin-4-yloxy}-piperidine-1-carboxylic acid isopropyl ester;

4-{4-[6-(2-Fluoro-4-methanesulfonyl-phenoxy)-5-methyl-pyrimidin-4-yloxy]-piperidin-1-yl}-4-oxo-butyric acid;

2-{4-[6-(2-Fluoro-4-methanesulfonyl-phenoxy)-5-methyl-pyrimidin-4-yloxy]-piperidin-1-yl}-1-(3-trifluoromethyl-phenyl)-ethanone;

4-{6-[6-(2-Methoxy-ethylsulfanyl)-2-methyl-pyridin-3-yloxy]-5-methyl-pyrimidin-4-yloxy}-piperidine-1-carboxylic acid isopropyl ester;

1-(2,5-Dimethoxy-phenyl)-2-{4-[6-(2-fluoro-4-methanesulfonyl-phenoxy)-5-methyl-pyrimidin-4-yloxy]-piperidin-1-yl}-ethanone;

2-{4-{6-(2-Fluoro-4-methanesulfonyl-phenoxy)-5-methyl-pyrimidin-4-yloxy]-piperidin-1-yl}-1-pyridin-2-yl-ethanone;

4-[6-(6-Chloro-2-methyl-pyridin-3-yloxy)-5-methyl-pyrimidin-4-yloxy]-piperidine-1-carboxylic acid isopropyl ester;

2-{4-[6-(2-Fluoro-4-methanesulfonyl-phenoxy)-5-methyl-pyrimidin-.4-yloxy]-piperidin-1-yl}-1-(4-fluoro-phenyl)-ethanone;

2-{4-[6-(2-Fluoro-4-methanesulfonyl-phenoxy)-5-methyl-pyrimidin-4-yloxy]-piperidin-1-yl}-1-(4-trifluoromethyl-phenyl)-ethanone;

1-{4-[6-(2-Fluoro-4-methanesulfonyl-phenoxy)-5-methyl-pyrimidin-4-yloxy]-piperidin-1-yl}-3,3-dimethyl-butan-2-one;

2-{4-[6-(2-Fluoro-4-methanesulfonyl-phenoxy)-5-methyl-pyrimidin-4-yloxy]-piperidin-1-yl}-1-pyridin-3-yl-ethanone;

1-{4-[6-(2-Fluoro-4-methanesulfonyl-phenoxy)-5-methyl-pyrimidin-4-yloxy]-piperidin-1-yl}-butan-2-one;

4-(6-{2-Fluoro-4-[(2-isopropoxy-ethylcarbamoyl)-methyl]-phenoxy}-5-methyl-pyrimidin-4-yloxy)-piperidine-1-carboxylic acid isopropyl ester;

2-{4-[6-(2-Fluoro-4-methanesulfonyl-phenoxy)-5-methyl-pyrimidin-4-yloxy]-piperidin-1-yl}-1-(4-methanesulfonyl-phenyl)-ethanone;

1-(4-Chloro-phenyl)-2-{4-[6-(2-fluoro-4-methanesulfonyl-phenoxy)-5-methyl-pyrimidin-4-yloxy]-piperidin-1-yl}-ethanone;

4-(2-{4-[6-(2-Fluoro-4-methanesulfonyl-phenoxy)-5-methyl-pyrimidin-4-yloxy]-piperidin-1-yl}-acetyl)-benzonitrile;

1-(3,4-Difluoro-phenyl)-2-{4-[6-(2-fluoro-4-methanesulfonyl-phenoxy)-5-methyl-pyrimidin-4-yloxy]-piperidin-1-yl}-ethanone;

1-{4-[6-(2-Fluoro-4-methanesulfonyl-phenoxy)-5-methyl-pyrimidin-4-yloxy]-piperidin-1-yl}-butan-1-one;

1-{4-[6-(2-Fluoro-4-methanesulfonyl-phenoxy)-5-methyl-pyrimidin-4-yloxy]-piperidin-1-yl}-pentan-1-one;

4-[6-(2,4-Difluoro-phenoxy)-5-methyl-pyrimidin-4-yloxy]-piperidine-1-carboxylic acid isopropyl ester;

1-{4-[6-(2-Fluoro-4-methanesulfonyl-phenoxy)-5-methyl-pyrimidin-4-yloxy]-piperidin-1-yl}-3-methyl-butan-1-one;

1-{4-[6-(2-Fluoro-4-methanesulfonyl-phenoxy)-5-methyl-pyrimidin-4-yloxy]-piperidin-1-yl}-4-methyl-pentan-1-one;

1-{4-[6-(2-Fluoro-4-methanesulfonyl-phenoxy)-5-methyl-pyrimidin-4-yloxy]-piperidin-1-yl}-5-methyl-hexan-1-one;

4-{6-[2-Fluoro-4-(2-methoxy-ethylcarbamoyl)-phenoxy]-5-methyl-pyrimidin-4-yloxy}-piperidine-1-carboxylic acid isopropyl ester;

4-[6-(2-Fluoro-4-methanesulfonyl-phenoxy)-5-methyl-pyrimidin-4-yloxy]-piperidine-1-carboxylic acid isopropyl ester;

4-[6-(4-Bromo-2-fluoro-phenoxy)-5-methyl-pyrimidin-4-yloxy]-piperidine-1-carboxylic acid isopropyl ester;

1-{4-[6-(2-Fluoro-4-methanesulfonyl-phenoxy)-5-methyl-pyrimidin-4-yloxy]-piperidin-1-yl}-3-methoxy-propan-1-one;

4-[5-(5-Aminomethyl-4,5-dihydro-oxazol-2-yl)-6-(2-fluoro-4-methanesulfonyl-phenoxy)-pyrimidin-4-yloxy]-piperidine-1-carboxylic acid isopropyl ester;

4-{6-[6-(2-Methoxy-ethylamino)-2-methyl-pyridin-3-yloxy]-5-methyl-pyrimidin-4-yloxy}-piperidine-1-carboxylic acid isopropyl ester;

4-{6-[6-(3-Methanesulfonyl-pyrrolidin-1-yl)-2-methyl-pyridin-3-yloxy]-5-methyl-pyrimidin-4-yloxy}-piperidine-1-carboxylic acid isopropyl ester;

4-[6-(6-Benzylamino-2-methyl-pyridin-3-yloxy)-5-methyl-pyrimidin-4-yloxy]-piperidine-1-carboxylic acid isopropyl ester;

4-[6-(4-Carbamoyl-2-fluoro-phenoxy)-5-methyl-pyrimidin-4-yloxy]-piperidine-1-carboxylic acid isopropyl ester;

4-{6-[2-Fluoro-4-(2-isopropoxy-ethylamino)-phenoxy]-5-methyl-pyrimidin-4-yloxy}-piperidine-1-carboxylic acid isopropyl ester;

4-(6-{2-Fluoro-4-[(tetrahydro-furan-2-ylmethyl)-amino]-phenoxy}-5-methyl-pyrimidin-4-yloxy)-piperidine-1-carboxylic acid isopropyl ester;

4-(6-{6-[(2-Methanesulfonyl-ethyl)-methyl-amino]-2-methyl-pyridin-3-yloxy}-5-methyl-pyrimidin-4-yloxy)-piperidine-1-carboxylic acid isopropyl ester;

4-{6-[2-Fluoro-4-(4-isopropyl-piperazine-1-carbonyl)-phenoxy]-5-methyl-pyrimidin-4-yloxy}-piperidine-1-carboxylic acid isopropyl ester;

4-{6-[2-Fluoro-4-(2-morpholin-4-yl-ethyl)-phenoxy]-5-methyl-pyrimidin-4-yloxy}-piperidine-1-carboxylic acid isopropyl ester;

4-{6-[2-Fluoro-4-(2-methanesulfonyl-ethyl)-phenoxy]-5-methyl-pyrimidin-4-yloxy}-piperidine-1-carboxylic acid isopropyl ester;

4-{6-[2-Fluoro-4-(2-hydroxy-ethyl)-phenoxy]-5-methyl-pyrimidin-4-yloxy}-piperidine-1-carboxylic acid isopropyl ester;

4-[6-(4-Carboxymethyl-2-fluoro-phenoxy)-5-methyl-pyrimidin-4-yloxy]-piperidine-1-carboxylic acid isopropyl ester;

4-[6-(4-Dimethylcarbamoylmethyl-2-fluoro-phenoxy)-5-methyl-pyrimidin-4-yloxy]-piperidine-1-carboxylic acid isopropyl ester;

4-[6-(2-Fluoro-4-sulfamoyl-phenoxy)-5-methyl-pyrimidin-4-yloxy]-piperidine-1-carboxylic acid isopropyl ester;

4-[6-(2-Fluoro-4-propionylsulfamoyl-phenoxy)-5-methyl-pyrimidin-4-yloxy]-piperidine-1-carboxylic acid isopropyl ester;

4-[5-Ethynyl-6-(2-fluoro-4-methanesulfonyl-phenoxy)-pyrimidin-4-yloxyl]-piperidine-1-carboxylic acid isopropyl ester;

4-{6-[2-Fluoro-4-(2-phosphonooxy-ethyl)-phenoxy]-5-methyl-pyrimidin-4-yloxy}-piperidine-1-carboxylic acid isopropyl ester;

4-[5-Bromo-6-(2-fluoro-4-methanesulfonyl-phenoxy)-pyrimidin-4-yloxy]-piperidine-1-carboxylic acid isopropyl ester;

4-[6-(4-Carbamoylmethyl-2-fluoro-phenoxy)-5-methyl-pyrimidin-4-yloxy]-piperidine-1-carboxylic acid isopropyl ester;

4-[6-(2-Fluoro-3-sulfamoyl-phenoxy)-5-methyl-pyrimidin-4-yloxy]-piperidine-1-carboxylic acid isopropyl ester;

3-tert-Butoxy-1-{4-[6-(2-fluoro-4-methanesulfonyl-phenoxy)-5-methyl-pyrimidin-4-yloxy]-piperidin-1-yl}-propan-1-one;

2-Ethoxy-1-{4-[6-(2-fluoro-4-methanesulfonyl-phenoxy)-5-methyl-pyrimidin-4-yloxy]-piperidin-1-yl}-ethanone;

{4-[6-(2-Fluoro-4-methanesulfonyl-phenoxy)-5-methyl-pyrimidin-4-yloxy]-piperidin-1-yl}-(tetrahydro-furan-2-yl)-methanone;

(S)-1-{4-[6-(2-Fluoro-4-methanesulfonyl-phenoxy)-5-methyl-pyrimidin-4-yloxy]-piperidin-1-yl}-3-methyl-2-methylamino-butan-1-one;

4-{6-[2-Fluoro-4-(2-imidazol-1-yl-ethyl)-phenoxy]-5-methyl-pyrimidin-4-yloxy}-piperidine-1-carboxylic acid isopropyl ester;

4-{6-[2-Fluoro-4-(2-[1,2,3]triazol-1-yl-ethyl)-phenoxy]-5-methyl-pyrimidin-4-yloxy}-piperidine-1-carboxylic acid isopropyl ester;

(R)-1-{4-[6-(2-Fluoro-4-methanesulfonyl-phenoxy)-5-methyl-pyrimidin-4-yloxy]-piperidin-1-yl}-3-methyl-2-methylamino-butan-1-one;

(S)-1-{4-[6-(2-Fluoro-4-methanesulfonyl-phenoxy)-5-methyl-pyrimidin-4-yloxy]-piperidin-1-yl}-3-hydroxy-butan-1-one;

(R)-N-(1-{4-[6-(2-Fluoro-4-methanesulfonyl-phenoxy)-5-methyl-pyrimidin-4-yloxy]-piperidine-1-carbonyl}-2-methyl-propyl)-acetamide;

(S)-N-(1-{4-[6-(2-Fluoro-4-methanesulfonyl-phenoxy)-5-methyl-pyrimidin-4-yloxy]-piperidine-1-carbonyl}-2-methyl-propyl)-acetamide;

(R)-N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide;

(S)-N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide;

4-[6-(2-Fluoro-4-methanesulfonyl-phenoxy)-5-methyl-pyrimidin-4-yloxy]-piperidine-1-carboxylic acid (S)-tetrahydro-furan-3-yl ester;

4-[6-(2-Fluoro-4-methanesulfonyl-phenoxy)-5-methyl-pyrimidin-4-yloxy]-piperidine-1-carboxylic acid (R)-tetrahydro-furan-3-yl ester;

4-[6-(2-Amino-4-ethanesulfonyl-phenoxy)-5-methyl-pyrimidin-4-yloxy]-piperidine-1-carboxylic acid isopropyl ester;

4-[6-(4-Methanesulfonyl-phenoxy)-5-methyl-pyrimidin-4-yloxy]-piperidine-1-carboxylic acid isopropyl ester;
4-{6-[2-Fluoro-4-(6-methoxy-pyridin-3-yl)-phenoxy]-5-methyl-pyrimidin-4-yloxy}-piperidine-1-carboxylic acid isopropyl ester;
3-Amino-1-{4-[6-(2-fluoro-4-methanesulfonyl-phenoxy)-5-methyl-pyrimidin-4-yloxy]-piperidin-1-yl}-4-methyl-pentan-1-one;
2-Amino-1-{4-[6-(2-fluoro-4-methanesulfonyl-phenoxy)-5-methyl-pyrimidin-4-yloxy]-piperidin-1-yl}-3-methyl-butan-1-one;
4-{6-[2-Fluoro-4-(2-isopropoxy-ethoxy)-phenoxy]-5-methyl-pyrimidin-4-yloxy}-piperidine-1-carboxylic acid isopropyl ester;
4-[5-Methyl-6-(4-sulfo-phenoxy)-pyrimidin-4-yloxy]-piperidine-1-carboxylic acid isopropyl ester;
4-[6-(2-Fluoro-4-methanesulfonyl-phenylamino)-5-methyl-pyrimidin-4-ylsulfanyl]-piperidine-1-carboxylic acid isopropyl ester;
4-{6-[2-Fluoro-4-(5-methoxy-pyridin-3-yl)-phenoxy]-5-methyl-pyrimidin-4-yloxy}-piperidine-1-carboxylic acid isopropyl ester;
4-[6-(2-Fluoro-4-pyridin-4-yl-phenoxy)-5-methyl-pyrimidin-4-yloxy]-piperidine-1-carboxylic acid isopropyl ester;
4-[6-(3-Fluoro-biphenyl-4-yloxy)-5-methyl-pyrimidin-4-yloxy]-piperidine-1-carboxylic acid isopropyl ester;
4-[6-(2-Fluoro-4-pyridin-3-yl-phenoxy)-5-methyl-pyrimidin-4-yloxy]-piperidine-1-carboxylic acid isopropyl ester;
4-[6-(2-Fluoro-4-pyrimidin-5-yl-phenoxy)-5-methyl-pyrimidin-4-yloxy]-piperidine-1-carboxylic acid isopropyl ester;
4-[6-(2-Fluoro-4-thiophen-3-yl-phenoxy)-5-methyl-pyrimidin-4-yloxy]-piperidine-1-carboxylic acid isopropyl ester;
4-[6-(4-Ethynyl-2-fluoro-phenoxy)-5-methyl-pyrimidin-4-yloxy]-piperidine-1-carboxylic acid isopropyl ester;
(R)-4-{6-[2-Fluoro-4-(2-oxo-oxazolidin-4-yl)-phenoxy]-5-methyl-pyrimidin-4-yloxy}-piperidine-1-carboxylic acid isopropyl ester; and
(S)-4-{6-[2-Fluoro-4-(2-oxo-oxazolidin-4-yl)-phenoxy]-5-methyl-pyrimidin-4-yloxy}-piperidine-1-carboxylic acid isopropyl ester;
or a pharmaceutically acceptable salt, hydrate or solvate thereof.

45. A compound according to claim 1 wherein the compound is selected from:
[6-(1-Hexyl-piperidin-4-yloxy)-5-nitro-pyrimidin-4-yl]-(4-methanesulfonyl-phenyl)-amine;
{6-[1-(3,3-Dimethyl-butyl)-piperidin-4-yloxy]-5-nitro-pyrimidin-4-yl}-(4-methanesulfonyl-phenyl)-amine;
(4-Methanesulfonyl-phenyl)-{6-[1-(3-methyl-butyl)-piperidin-4-yloxy]-5-nitro-pyrimidin-4-yl}-amine;
{6-[1-(2-Ethoxy-ethyl)-piperidin-4-yloxy]-5-nitro-pyrimidin-4-yl}-(4-methanesulfonyl-phenyl)-amine;
4-(2-Fluoro-4-methanesulfonyl-phenoxy)-6-[1-(3-methoxy-propyl)-piperidin-4-yloxy]-5-methyl-pyrimidine;
1-{4-[6-(2-Fluoro-4-methanesulfonyl-phenoxy)-5-methyl-pyrimidin-4-yloxy]-piperidin-1-yl}-3-methoxy-propan-2-ol;
4-(2-Fluoro-4-methanesulfonyl-phenoxy)-5-methyl-6-[1-(3-methyl-butyl)-piperidin-4-yloxy]-pyrimidine;
4-(2-Fluoro-4-methanesulfonyl-phenoxy)-5-methyl-6-[1-(4-methyl-pentyl)-piperidin-4-yloxy]-pyrimidine;
4-(2-Fluoro-4-methanesulfonyl-phenoxy)-5-methyl-6-[1-(5-methyl-hexyl)-piperidin-4-yloxy]-pyrimidine;
4-(2-Fluoro-4-methanesulfonyl-phenoxy)-5-methyl-6-(1-pentyl-piperidin-4-yloxy)-pyrimidine;
4-(1-Butyl-piperidin-4-yloxy)-6-(2-fluoro-4-methanesulfonyl-phenoxy)-5-methyl-pyrimidine;
4-(2-Fluoro-4-methanesulfonyl-phenoxy)-6-(1-hexyl-piperidin-4-yloxy)-5-methyl-pyrimidine;
4-{4-[6-(2-Fluoro-4-methanesulfonyl-phenoxy)-5-methyl-pyrimidin-4-yloxy]-piperidin-1-yl}-butyric acid; and
4-(2-Fluoro-4-methanesulfonyl-phenoxy)-5-methyl-6-[1-(2-pyridin-3-yl-ethyl)-piperidin-4-yloxy]-pyrimidine;
or a pharmaceutically acceptable salt, hydrate or solvate thereof.

46. A compound selected from:
(4-Methanesulfonyl-phenyl)-[5-nitro-6-piperidin-4-yloxy)-pyrimidin-4-yl]-amine;
N-(4-Methanesulfonyl-phenyl)-5-nitro-N'-piperidin-4-yl-pyrimidine-4,6-diamine;
4-[6-(4-Cyano-2-fluoro-phenylamino)-5-ethynyl-pyrimidin-4-yloxy]-piperidine-1-carboxylic acid isopropyl ester;
4-{5-Ethynyl-6-[1-(3-isopropyl-[1,2,4]oxadiazol-5-yl)-piperidin-4-yloxy]-pyrimidin-4-ylamino}-3-fluoro-benzonitrile;
4-[6-(4-Cyano-2-fluoro-phenylamino)-5-methyl-pyrimidin-4-yloxy]-piperidine-1-carboxylic acid isopropyl ester;
4-[6-(4-Cyano-2,5-difluoro-phenylamino)-5-methyl-pyrimidin-4-yloxy]-piperidine-1-carboxylic acid isopropyl ester;
4-{6-[2,5-Difluoro-4-(N-hydroxycarbamimidoyl)-phenylamino]-5-methyl-pyrimidin-4-yloxy}-piperidine-1-carboxylic acid isopropyl ester;
4-[6-(4-Carbamimidoyl-2,5-difluoro-phenylamino)-5-methyl-pyrimidin-4-yloxy]-piperidine-1-carboxylic acid isopropyl ester;
4-[6-(4-Gyano-2-fluoro-phenoxy)-5-ethynyl-pyrimidin-4-yloxy]-piperidine-1-carboxylic acid isopropyl ester;
4-{5-Ethynyl-6-[1-(3-isopropyl-[1,2,4]oxadiazol-5-yl)-piperidin-4-yloxy]-pyrimidin-4-yloxy}-3-fluoro-benzonitrile;
4-(1-Formyl-piperidin-4-yloxy)-6-(4-methanesulfonyl-phenylamino)-pyrimidine-5-carbonitrile;
4-[6-(4-Cyano-2-fluoro-phenoxy)-5-methyl-pyrimidin-4-yloxy]-piperidine-1-carboxylic acid isopropyl ester;
(1-{4-[6-(2-Fluoro-4-methanesulfonyl-phenoxy)-5-methyl-pyrimidin-4-yloxy]-piperidine-1-carbonyl}-2-methyl-propyl)-carbamic acid tert-butyl ester;
4-(6-{2-Fluoro-4-[2-(3-hydroxy-piperidin-1-yl)-2-oxo-ethyl]-phenoxy}-5-methyl-pyrimidin-4-yloxy)-piperidine-1-carboxylic acid isopropyl ester;
4-{6-[2-Fluoro-4-(2-morpholin-4-yl-2-oxo-ethyl)-phenoxy]-5-methyl-pyrimidin-4-yloxy}-piperidine-1-carboxylic acid isopropyl ester;
C-{4-[6-(2-Fluoro-4-methanesulfonyl-phenoxy)-5-methyl-pyrimidin-4-yloxy]-piperidin-1-yl}-C-(4-fluoro-phenyl)-methyleneamine;
4-(6-{2-Fluoro-4-[2-(2-methanesulfonyl-pyrrolidin-1-yl)-2-oxo-ethyl]-phenoxy}-5-methyl-pyrimidin-4-yloxy)-piperidine-1-carboxylic acid isopropyl ester;
4-[6-(2-Fluoro-4-{[(tetrahydro-furan-2-ylmethyl)-carbamoyl]-methyl}-phenoxy)-5-methyl-pyrimidin-4-yloxy]-piperidine-1-carboxylic acid isopropyl ester;
4-(6-{2,5-Difluoro-4-[2-(3-methoxy-piperidin-1-yl)-ethyl]-phenoxy}-5-methyl-pyrimidin-4-yloxy)-piperidine-1-carboxylic acid isopropyl ester;

4-(6-{2,5-Difluoro-4-[2-(3-methoxy-piperidin-1-yl)-ethyl]-phenoxy}-5-ethynyl-pyrimidin-4-yloxy)-piperidine-1-carboxylic acid isopropyl ester;

4-(6-{2-Fluoro-4-[2-(3-methoxy-pyridin-2-yl)-ethyl]-phenoxy}-5-methyl-pyrimidin-4-yloxy)-piperidine-1-carboxylic acid isopropyl ester;

(R)-4-(6-{2-Fluoro-4-[2-(3-methoxy-piperidin-1-yl)-ethyl]-phenoxy}-5-methyl-pyrimidin-4-yloxy)-piperidine-1-carboxylic acid isopropyl ester;

(S)-4-(6-{2-Fluoro-4-[2-(3-methoxy-piperidin-1-yl)-ethyl]-phenoxy}-5-methyl-pyrimidin-4-yloxy)-piperidine-1-carboxylic acid isopropyl ester;

(R)-4-(5-Ethynyl-6-{2-fluoro-4-[2-(2-methoxy-piperidin-1-yl)-ethyl]-phenoxy}-pyrimidin-4-yloxy)-piperidine-1-carboxylic acid isopropyl ester;

4-{6-[2-Fluoro-4-(2-propionylsulfamoyl-ethyl)-phenoxy]-5-methyl-pyrimidin-4-yloxy}-piperidine-1-carboxylic acid isopropyl ester;

4-(5-Cyclopropyl-6-{2,5-difluoro-4-[2-(4-methoxy-piperidin-1-yl)-ethyl]-phenoxy}-pyrimidin-4-yloxy)-piperidine-1-carboxylic acid isopropyl ester;

4-(6-{2-Fluoro-4-[2-(4-methoxy-piperidin-1-yl)-ethyl]-phenoxy}-5-methyl-pyrimidin-4-yloxy)-piperidine-1-carboxylic acid isopropyl ester;

4-{6-[2-Fluoro-4-(2-propionylsulfamoyl-ethyl)-phenylamino]-5-methyl-pyrimidin-4-yloxy}-piperidine-1-carboxylic acid isopropyl ester;

4-{6-[2-Fluoro-4-(2-sulfamoyl-ethyl)-phenylamino]-5-methyl-pyrimidin-4-yloxy}-piperidine-1-carboxylic acid isopropyl ester;

4-{6-[2-Fluoro-4-(1-hydroxy-cyclopropylmethyl)-phenoxy]-5-methyl-pyrimidin-4-yloxy}-piperidine-1-carboxylic acid isopropyl ester;

4-{6-[2-Fluoro-4-(2-sulfamoyl-ethyl)-phenoxy]-5-methyl-pyrimidin-4-yloxy}-piperidine-1-carboxylic acid isopropyl ester;

4-{6-[2,5-Difluoro-4-(2-sulfamoyl-ethyl)-phenoxy]-5-ethynyl-pyrimidin-4-yloxy}-piperidine-1-carboxylic acid isopropyl ester;

4-{6-[2-Fluoro-4-(2-isopropoxy-ethylcarbamoyl)-phenoxy]-5-methyl-pyrimidin-4-yloxy}-piperidine-1-carboxylic acid isopropyl ester;

4-{6-[2-Fluoro-4-(methoxy-methyl-carbamoyl)-phenoxy]-5-methyl-pyrimidin-4-yloxy}-piperidine-1-carboxylic acid isopropyl ester;

4-[6-(2-Fluoro-4-hydroxycarbamoyl-phenoxy)-5-methyl-pyrimidin-4-yloxy]-piperidine-1-carboxylic acid isopropyl ester; and 4-{6-[2-Fluoro-4-(2-pyrrolidin-1-yl-ethylcarbamoyl)-phenoxy]-5-methyl-pyrimidin-4-yloxy}-piperidine-1-carboxylic acid isopropyl ester;

or a pharmaceutically acceptable salt, hydrate or solvate thereof.

47. The compound according to claim 1, or a pharmaceutically acceptable salt, hydrate or solvate thereof, wherein:

A and B are each independently —CH$_2$CH$_2$— or —CH$_2$—;

D is N—R$_2$;

W and Q are each independently NH or O;

X and Y are each N;

Z is selected from the group consisting of nitro, C$_{1-5}$ acyl, C$_{1-8}$ alkyl, C$_{2-6}$ alkynyl, C$_{1-4}$ alkylsulfonamide, amino, carbamimidoyl, cyano, C$_{3-7}$ cycloalkyl, heterocyclic, and hydroxycarbamimidoyl, wherein said heterocyclic is optionally substituted with a —CH$_2$NH$_2$ group;

R$_2$ is a group of Formula (D):

wherein:

G is —CR$_{23}$R$_{24}$C(O)—, —C(O)—, —CR$_{23}$R$_{24}$C(O)NR$_{23}$—, —C(O)NR$_{23}$—, —C(O)O—, —C(S)—, —C(S)NR$_{23}$—, —C(S)O—, —CR$_{23}$R$_{24}$—, —S(O)$_2$—, or a bond; wherein R$_{23}$ and R$_{24}$ are each independently H or C$_{1-8}$ alkyl; and R$_{22}$ is C$_{1-8}$ alkyl, C$_{3-7}$ cycloalkyl, phenyl, heteroaryl, or heterocyclic each optionally substituted with 1 to 5 substituents selected from the group consisting of C$_{1-5}$ acyl, C$_{1-5}$ acyloxy, C$_{2-6}$ alkenyl, C$_{1-4}$ alkoxy, C$_{17}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, earboxy, cyano, C$_{3-7}$ cycloalkyl, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalklkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heteroaryl, heterocyclic, hydroxyl, hydroxylamino, nitro, phenyl, phenoxy, and sulfonic acid, wherein said C$_{1-7}$ alkyl, phenyl and phenoxy are each optionally substituted with 1 to 5 substituents selected from the group consisting of C$_{1-5}$ acyl, C$_{1-5}$ acyloxy, C$_{1-4}$ alkoxy, C$_{1-8}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-7}$ cycloalkyl, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloallkylthio, halogen, heterocyclic, hydroxyl, hydroxylamino, and nitro;

Ar$_1$ is a phenyl, naphthyl, pyridyl, benzofuranyl, pyrazinyl, pyridazinyl, pyrimidinyl, triazinyl, quinoline, benzoxazole, benzothiazole, 1H-benzimidazole, isoquinoline, quinazoline, or quinoxaline, each optionally substituted with R$_{11}$, R$_{12}$, R$_{13}$, R$_{14}$, and R$_{15}$; wherein R$_{11}$ is selected from the group consisting of C$_{1-6}$ acylsulfonamide, C$_{1-4}$ alkoxy, C$_{1-8}$ alkyl, C$_{1-4}$ alkylamino, C$_{1-6}$ alkylcarboxamide, C$_{1-4}$ alkylsulfonamide, C$_{1-4}$ alkylsulfonyl, C$_{1-4}$ alkylthio, amino, carboxamide, carboxy, C$_{2-6}$ dialkylamino, halogen, heterocyclic, heterocyclic-oxy, heterocyclic-carbonyl, heteroaryl, and sulfonamide, and wherein C$_{1-6}$ acylsulfonamide, C$_{1-4}$ alkoxy, C$_{1-8}$ alkyl, C$_{1-4}$ alkylamino, C$_{1-4}$ alkylsulfonamide, alkylsulfonyl, C$_{1-4}$ alkylthio, carbamimidoyl, C$_{2-6}$ dialkylamino, heterocyclic, heterocyclic-carbonyl, and heteroaryl are each optionally substituted with 1 to 5 substituents selected independently from the group consisting of C$_{1-6}$ acylsulfonamide, C$_{1-4}$ alkoxy, C$_{1-7}$ alkyl, C$_{1-4}$ alkylcarboxamide, C$_{1-4}$ alkylsulfonyl, carboxy, C$_{3-7}$ cycloalkyloxy, C$_{2-6}$ dialkylamino, C$_{2-6}$ dialkylcarboxamide, heteroaryl, heterocyclic, hydroxyl, phenyl, and phosphonooxy wherein said C$_{1-7}$ alkyl and C$_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, and halogen.

48. The compound according to claim 1, or a pharmaceutically acceptable salt, hydrate or solvate thereof, wherein:

A and B are both —$CH_2CH_2$—;

D is N—$R_2$;

W is NH;

Q is O;

X and Y are both N;

Z is nitro, cyano, $C(O)CH_3$, amino, $CH_3$, $CH_2CH_3$, or C≡CH;

$R_2$ is a group of Formula (D):

$$\text{(D)} \quad \overset{\xi}{\underset{\xi}{\diagdown}}\!\!\!\diagup^{G}\!\!\diagdown_{R_{22}}$$

wherein:

G is —$CR_{23}R_{24}C(O)$—, —$C(O)$—, —$CR_{23}R_{24}C(O)NR_{23}$—, —$C(O)NR_{23}$—, —$C(O)O$—, —$C(S)$—, —$C(S)NR_{23}$—, —$C(S)O$—, —$CR_{23}R_{24}$—, —$S(O)_2$—, or a bond; wherein 1(23 and $R_{24}$ are each independently H or $C_{1-8}$ alkyl; and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{24}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-4}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$Ar_1$ is phenyl, 3-pyridyl, or 2-pyridyl each optionally substituted with $R_{11}$, $R_{12}$, $R_{13}$, $R_{14}$, and $R_{15}$, wherein $R_{11}$, is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carboxamide, carboxy, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-4}$ alcoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of CM alkoxy and hydroxy; and $R_{12}$, $R_{13}$, $R_{14}$, and $R_{15}$ are each independently $CH_3$, or F.

49. The compound according to claim 1, or a pharmaceutically acceptable salt, hydrate or solvate thereof, wherein:

A and B are both —$CH_2CH_2$—;

D is N—$R_2$;

W and Q are both O;

X and Y are both N;

Z is selected from the group consisting of $CH_3$, $CH_2CH_3$, cyclopropyl, or C≡CH;

$R_2$ is a group of Formula (D):

$$\text{(D)} \quad \overset{\xi}{\underset{\xi}{\diagdown}}\!\!\!\diagup^{G}\!\!\diagdown_{R_{22}}$$

wherein:

G is —$CR_{23}R_{24}C(O)$—, —$C(O)$—, —$CR_{23}$—, $R_{24}C(O)NR_{23}$—, —$C(O)NR_{23}$—, —$C(O)O$—, —$C(S)$—, —$C(S)NR_{23}$—, —$C(S)O$—, —$CR_{23}R_{24}$—, —$S(O)_2$—, or a bond; wherein $R_{23}$ and $R_{24}$ are each independently H or $C_{1-8}$ alkyl; and $R_{22}$ is $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-7}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$Ar_1$ is phenyl, 2-pyridyl, or 3-pyridyl each optionally substituted with $R_{11}$, $R_{12}$, $R_{13}$, $R_{14}$, and $R_{15}$, wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonyl, $C_{1-4}$ alkylthio, amino, carboxy, $C_{2-6}$ dialkylamino, halogen, heterocyclic, heterocyclic-oxy, heterocyclic-carbonyl, heteroaryl, and sulfonamide, and wherein $C_{1-4}$ alkoxy, $C_{1-8}$ alkyl, $C_{1-4}$ alkylamino, $C_{1-6}$ alkylcarboxamide, $C_{1-4}$ alkylsulfonyl, $C_{1-4}$ alkylthio, $C_{2-6}$ dialkylamino, and heteroaryl are each optionally substituted with 1 to 5 substituents selected independently from the group consisting of $C_{1-4}$ alkoxy, $C_{1-7}$ alkyl, $C_{1-4}$ alkylcarboxamide, heteroaryl, hydroxyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{12}$, $R_{13}$, $R_{14}$, and $R_{15}$ are each independently selected form the group consisting of $C_{1-8}$ alkyl, and halogen.

50. A pharmaceutical composition comprising at least one compound according to claim 1, or a pharmaceutically acceptable salt, hydrate or solvate thereof, and a pharmaceutically acceptable carrier.

51. A pharmaceutical composition comprising at least one compound according to any one of claims 3, 9, 37-41, 44-45, 46, and 47-49, or a pharmaceutically acceptable salt, hydrate or solvate thereof, and a pharmaceutically acceptable carrier.

52. A method of producing a pharmaceutical composition comprising admixing at least one compound of claim 1, or a pharmaceutically acceptable salt, hydrate or solvate thereof, and a pharmaceutically acceptable carrier.

53. A method of producing a pharmaceutical composition comprising admixing at least one compound according to any one of claims 3, 9, 37-41, 44-45, 46, and 47-49, or a pharmaceutically acceptable salt, hydrate or solvate thereof, and a pharmaceutically acceptable carrier.

54. A method for treatment of type II diabetes in an individual comprising administering to said individual in need of such treatment a therapeutically effective amount of a compound according to claim 1, or a phannaceutically acceptable salt, hydrate or solvate thereof.

55. A method for treatment of type II diabetes in an individual comprising administering to said individual in need of such treatment a therapeutically effective amount of a compound according to any one of claims 3, 9, 37-41, 44-45, 46, and 47-49, or a pharmaceutically acceptable salt, hydrate or solvate thereof.

56. A method of treating type II diabetes in an individual comprising administering to said individual in need thereof a therapeutically effective amount of a compound of Formula (I)

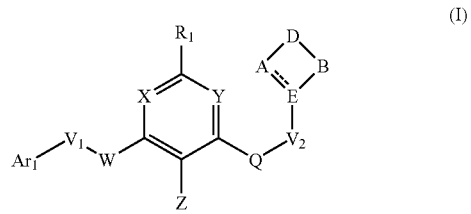

or a pharmaceutically acceptable salt, hydrate or solvate, or N-oxide thereof;

wherein:

A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloallkyl and halogen;

D is O, S, S(O), S(O)$_2$, $CR_2R_3$ or N—$R_2$;

E is N, C or $CR_4$;

--- is a single bond when E is N or $CR_4$, or a double bond when E is C;

$V_1$ is selected from the group consisting of $C_{1-3}$ alkylene, ethynylene and $C_{1-2}$ heteroalkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or $V_1$ is a bond;

$V_2$ is $C_{3-6}$ cycloalkylene or $C_{1-3}$ alkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or $V_2$ is a bond;

W is $NR_5$, O, S, S(O) or S(O)$_2$; or W is absent;

Q is $NR_6$, O, S, S(O) or S(O)$_2$;

X is N;

Y is N;

Z is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$-alkoxy, carboxamide, carboxy, cyano, $C_{3-7}$ cycloalkyl, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxycarbamimidoyl, hydroxylamino, nitro and tetrazolyl, wherein $C_{1-8}$ alkyl, $C_{3-7}$ cycloalkyl, and heterocyclic are each optionally substituted with 1, 2, 3 or 4 groups selected from the group consisting of $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro, and wherein said $C_{1-7}$ alkyl is optionally substituted with amino; or Z is a group of Formula (A):

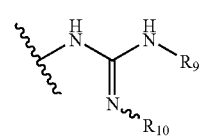

wherein:

$R_9$ is H, $C_{1-8}$ alkyl or $C_{3-7}$ cycloalkyl; and $R_{10}$ is H, nitro or nitrile;

$Ar_1$ is a phenyl, naphthyl, pyridyl, benzofuranyl, pyrazinyl, pyridazinyl, pyrimidinyl, triazinyl, quinoline, benzoxazole, benzothiazole, 1H-benzimidazole, isoquinoline, quinazoline, or quinoxaline, each optionally substituted with $R_{11}$, $R_{12}$, $R_{13}$, $R_{14}$, and $R_{15}$; wherein $R_{11}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$ alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein $C_{1-5}$ acyl, $C_{1-6}$ acylsulfonamide, $C_{1-4}$ alkoxy, $C_{1-8}$ alkyl, $C_{1-4}$ alkylamino, $C_{1-4}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloallkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, wherein said $C_{1-7}$ alkyl and $C_{1-4}$ alkylcarboxamide are each optionally substituted with 1 to 5 substituents selected from the group consisting of $C_{1-4}$ alkoxy and hydroxy; or $R_{11}$ is a group of Formula (B):

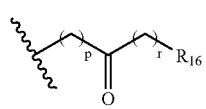

(B)

wherein:

"p" and "r" are each independently 0, 1, 2 or 3; and $R_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{12}$, $R_{13}$, $R_{14}$, and $R_{15}$ are each independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent groups selected from the group consisting of $R_{12}$, $R_{13}$, $R_{14}$ and $R_{15}$ together with the atoms to which they are attached form a 5-, 6- or 7-membered cycloalkyl, cycloalkenyl or heterocyclic group fused with $Ar_1$, wherein the 5-, 6- or 7-membered group is optionally substituted with halogen;

$R_1$ is selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;

$R_2$ is selected from the group consisting of $C_{1-8}$ alkyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (C):

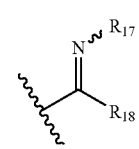

(C)

wherein:

$R_{17}$ is H, $C_{1-8}$ alkyl, $C_{3-7}$ cycloalkyl, aryl, heteroaryl or $OR_{19}$; and $R_{18}$ is F, Cl, Br, CN or $NR_{20}R_{21}$; where $R_{19}$ is H, $C_{1-4}$ alkyl or $C_{3-7}$ cycloalkyl, and $R_{20}$ and $R_{21}$ are each independently H, $C_{1-8}$ alkyl, $C_{3-7}$ cycloalkyl, aryl or heteroaryl; or $R_2$ is a group of Formula (D):

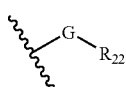

wherein:
G is:
i) —C(O)—, —C(O)$NR_{23}$—, —C(O)O—, —OC(O)$NR_{23}$—, —$NR_{23}$C(O)O—, —OC(O)—, —C(S)—, —C(S)$NR_{23}$—, —C(S)O—, —OC(S)—, —$CR_{23}R_{24}$—, —O—, —S—, —S(O)— or —S(O)$_2$— when D is $CR_2R_3$, or
ii) —$CR_{23}R_{24}$C(O)—, —C(O)—, —$CR_{23}R_{24}$C(O)$NR_{25}$—, —C(O)$NR_{23}$—, —C(O)O—, —C(S)—, —C(S)$NR_{23}$—, —C(S)O—, —$CR_{23}R_{24}$—, —S(O)$_7$—, or a bond when D is $NR_2$,
wherein $R_{23}$, $R_{24}$ and $R_{25}$ are each independently H or $C_{1-4}$ alkyl; and $R_{22}$ is H, $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloallkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$R_3$ is H, $C_{1-8}$ alkyl, $C_{1-4}$ alkoxy or hydroxyl; and $R_4$, $R_5$ and $R_6$ are each independently H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl.

57. A method of treating type II diabetes in an individual comprising contacting a RUP3 receptor with a compound according to claim 1.

* * * * *

UNITED STATES PATENT AND TRADEMARK OFFICE
CERTIFICATE OF CORRECTION

PATENT NO. : 7,470,699 B2  Page 1 of 5
APPLICATION NO. : 10/888747
DATED : December 30, 2008
INVENTOR(S) : Graeme Semple et al.

It is certified that error appears in the above-identified patent and that said Letters Patent is hereby corrected as shown below:

In Col. 67, replace the formula of compound A18

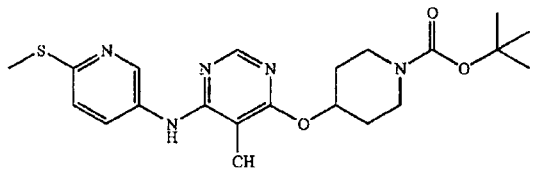

with the following formula of compound A18

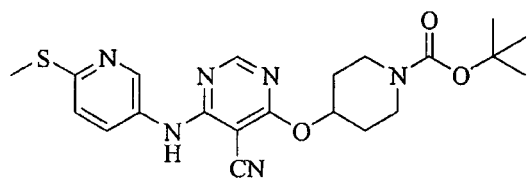

In Col. 151, replace the formula of compound C190

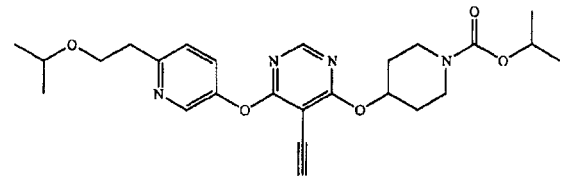

with the following formula of compound C190

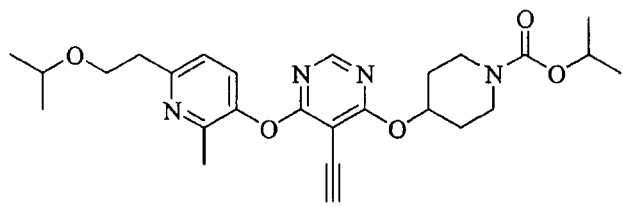

Signed and Sealed this

Thirty-first Day of August, 2010

David J. Kappos
*Director of the United States Patent and Trademark Office*

In Col. 155, replace the formula of compound C203

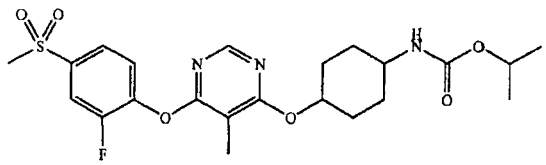

with the following formula of compound C203

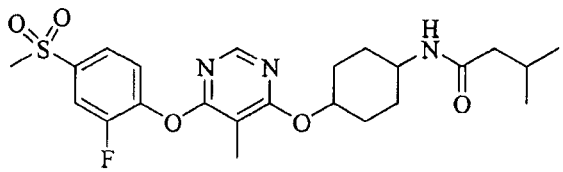

In the claims:

In Col. 293, Line 2, replace "$C_{3-7}$," with -- $C_{3-7}$ --

In Col. 293, Line 9, replace "$C_{4-7}$," with -- $C_{4-7}$ --

In Col. 293, Line 18, replace "$C_{1-7}$," with -- $C_{1-7}$ --

In Col. 293, Line 22 (approx.), replace "cycloallkyl," with -- cycloalkyl, --

In Col. 293, Lines 54-55 (approx.), replace "lkylcarboxamide," with -- alkylcarboxamide, --

In Col. 293, Line 55, replace "$C_{1-4}$," with -- $C_{1-4}$ --

In Col. 294, Line 35, replace "haloalklkoxy," with -- haloalkoxy, --

In Col. 294, Line 49 (approx.), replace "$R_{17}$," with -- $R_{17}$ --

In Col. 294, Line 49 (approx.), replace "cycloallkyl," with -- cycloalkyl, --

In Col. 295, Line 5, replace "CM" with -- $C_{1-4}$ --

In Col. 295, Line 14, replace "haloallkyl," with -- haloalkyl, --

In Col. 295, Line 44, replace "haloallkyl," with -- haloalkyl, --

In Col. 296, Line 15 (approx.), replace "cycloallkyl," with -- cycloalkyl, --

In Col. 297, Line 13, replace "$C_{36-}$" with -- $C_{3-6}$- --

In Col. 297, Line 16, replace "$C_{1-4}$" with -- $C_{1-5}$ --

In Col. 297, Line 19, replace "allkylthio," with -- alkylthio, --

In Col. 298, Line 1, replace "$R_{23}R_{24}$" with -- $R_{23}$, $R_{24}$ --

In Col. 298, Line 2, replace "$C_{3-7}$," with -- $C_{3-7}$ --

In Col. 298, Line 11, replace "cycloallkyl," with -- cycloalkyl, --

In Col. 298, Line 26, replace "diallkylamino," with -- dialkylamino, --

In Col. 299, Line 35 (approx.), replace "intro," with -- nitro, --

In Col. 299, Line 43 (approx.), replace "$C_{34}$" with -- $C_{3-7}$ --

In Col. 300, Line 35, replace "$C_{3-7}$," with -- $C_{3-7}$ --

In Col. 300, Line 38, replace "$C_{1-4}$," with -- $C_{1-7}$ --

In Col. 300, Line 67, replace "$C_{1-6}$" with -- $C_{2-6}$ --

In Col. 301, Line 2, replace "$C_{3-7}$," with -- $C_{3-7}$ --

In Col. 302, Line 45, replace "$CH_2C_3$," with -- $CH_2CH_3$, --

In Col. 302, Lines 61-62, replace "—$S(O)OR_{22}$," with -- —$S(O)2R_{22}$, --

In Col. 303, Line 20, replace "$C_{3-6}$" with -- $C_{1-6}$ --

In Col. 303, Line 21, replace "alkylsuIfonamide," with -- alkylsulfonamide, --

In Col. 303, Line 26, replace "$C_{1-4}$" with -- $C_{1-7}$ --

In Col. 303, Line 27, replace "$C_1A$" with -- $C_{1-4}$ --

In Col. 303, Line 39, replace "thereof" with -- thereof, --

In Col. 303, Line 66, replace "pyrimidinyl." with -- pyrimidinyl, --

In Col. 305, Line 14, replace "$C_{24}$" with -- $C_{2-8}$ --

In Col. 305, Line 61, replace "consisiing" with -- consisting --

In Col. 306, Line 8, replace "$C_{1-4}$" with -- $C_{1-7}$ --

In Col. 306, Line 58, replace "(Butane-i -sulfonyl)" with -- (Butane-1-sulfonyl) --

In Col. 306, Line 62, replace "-methyl-i H-" with -- -methyl-1H- --

In Col. 307, Line 10, replace "4-{6-" with -- 4-[6- --

In Col. 307, Lines 26-28, after "ester;" delete "4-(4-Methanesulfonylphenylamino)-6-[1-(tetrahydro-furan-2- carbonyl)-piperidin-4-yloxy]- pyrimidine-5-carbonitrile;" and insert -- 4-(4-Methanesulfonylphenylamino)- 6-[1-(tetrahydro-furan-2- carbonyl)-piperidin-4-yloxy]- pyrimidine-5-carbonitrile;" on Line 27 as a new paragraph.

In Col. 308, Line 23, replace "-l" with -- -1 --

In Col. 308, Line 31, replace "yloxyl]" with -- yloxy] --

In Col. 308, Line 33, replace "4-115-" with -- 4-[5- --

In Col. 311, Line 59, replace "-Hyclroxy-" with -- -Hydroxy- --

In Col. 311, Line 65, replace "-niethanesulfonyl-" with -- -methanesulfonyl- --

In Col. 312, Line 30 (approx.), after "acid" insert -- ; --

In Col. 312, Line 40 (approx.), replace "pipendin-" with -- piperidin- --

In Col. 312, Line 49 (approx.), replace "-hexan-" with -- -heptan- --

In Col. 314, Line 12 (approx.), replace "-prop-i" with -- -prop-1 --

In Col. 314, Line 13 (approx.), replace "-yloxyll-" with -- -yloxy]- --

In Col. 314, Line 26 (approx.), replace "-arboxylic" with -- -carboxylic --

In Col. 314, Line 29 (approx.), replace "-arboxylic" with -- -carboxylic --

In Col. 316, Line 4, replace "pipendin-" with -- piperidin- --

In Col. 316, Line 30 (approx.), replace "-{6-" with -- -[6- --

In Col. 316, Line 38 (approx.), replace "-pyrimidin-.4-" with -- -pyrimidin-4- --

In Col. 318, Line 8, replace "-yloxyl]-" with -- -yloxy]- --

In Col. 320, Line 15, replace "-piperidin-" with -- -(piperidin- --

In Col. 320, Line 38 (approx.), replace "-Gyano-" with -- -Cyano- --

In Col. 321, Line 21 (approx.), replace "eridine-l -" with -- eridine-1- --

In Col. 321, Line 48, replace "-yloxyl]-" with -- -yloxy]- --

In Col. 322, Line 19, replace "$C_{17}$" with -- $C_{1-7}$ --

In Col. 322, Line 24, replace "earboxy," with -- carboxy, --

CERTIFICATE OF CORRECTION (continued)
U.S. Pat. No. 7,470,699 B2

In Col. 322, Line 27, replace "haloalklkoxy," with -- haloalkoxy, --

In Col. 322, Lines 39-40, replace "diallkylcarboxamide," with -- dialkylcarboxamide, --

In Col. 322, Line 43, replace "haloallkylthio," with -- haloalkylthio, --

In Col. 322, Line 46, after "is" delete "a".

In Col. 323, Line 30, replace "1(23" with -- $R_{23}$ --

In Col. 323, Line 40, replace "$C_{24}$" with -- $C_{2-8}$ --

In Col. 323, Line 50, replace "$C_{1-4}$" with -- $C_{1-8}$ --

In Col. 323, Line 62, replace "$R_{11}$," with -- $R_{11}$ --

In Col. 324, Line 2, replace "alcoxy," with -- alkoxy, --

In Col. 324, Line 14, replace "CM" with -- $C_{1-4}$ --

In Col. 324, Lines 36-37, replace "—$CR_{23}$—, $R_{24}C(O)NR_{23}$—," with -- —$CR_{23}R_{24}C(O)NR_{23}$—, --

In Col. 324, Line 44, replace "$C_{1-7}$" with -- $C_{1-5}$ --

In Col. 325, Line 44, replace "phannaceutically" with -- pharmaceutically --

In Col. 325, Line 55, after "(I)" insert -- : --

In Col. 326, Line 7, replace "haloallkyl" with -- haloalkyl --

In Col. 326, Line 65, after "is" delete "a"

In Col. 327, Line 31, replace "haloallkyl," with -- haloalkyl, --

In Col. 328, Line 65, replace "$C_{1-4}$" with -- $C_{1-8}$ --

In Col. 329, Line 19, replace "—$S(O)_7$—," with -- —$S(O)_2$—, --

In Col. 329, Line 20, replace "$C_{1-4}$" with -- $C_{1-8}$ --

In Col. 330, Line 18, replace "haloallkylsulfinyl," with -- haloalkylsulfinyl, --

UNITED STATES PATENT AND TRADEMARK OFFICE
CERTIFICATE OF CORRECTION

| | | |
|---|---|---|
| PATENT NO. | : 7,470,699 B2 | Page 1 of 1 |
| APPLICATION NO. | : 10/888747 | |
| DATED | : December 30, 2008 | |
| INVENTOR(S) | : Jones et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 896 days.

Signed and Sealed this

Ninth Day of November, 2010

David J. Kappos
*Director of the United States Patent and Trademark Office*

SEQUENCE LISTING

<160> NUMBER OF SEQ ID NOS: 7

<210> SEQ ID NO 1
<211> LENGTH: 1191
<212> TYPE: DNA
<213> ORGANISM: Homo sapiens

<400> SEQUENCE: 1

```
atgtacccat acgacgtccc agactacgct ggaagcttgg aatcatcttt ctcatttgga    60
gtgatccttg ctgtcctggc ctccctcatc attgctacta acacactagt ggctgtggct   120
gtgctgctgt tgatccacaa gaatgatggt gtcagtctct gcttcacctt gaatctggct   180
gtggctgaca ccttgattgg tgtggccatc tctggcctac tcacagacca gctctccagc   240
ccttctcggc ccacacagaa gaccctgtgc agcctgcgga tggcatttgt cacttcctcc   300
gcagctgcct ctgtcctcac ggtcatgctg atcccttttg acaggtacct tgccatcaag   360
cagcccttcc gctacttgaa gatcatgagt gggttcgtgg ccggggcctg cattgccggg   420
ctgtggttag tgtcttacct cattggcttc ctcccactcg gaatccccat gttccagcag   480
actgcctaca aagggcagtg cagcttcttt gctgtatttc accctcactt cgtgctgacc   540
ctctcctgcg ttggcttctt cccagccatg ctcctctttg tcttcttcta ctgcgacatg   600
ctcaagattg cctccatgca cagccagcag attcgaaaga tggaacatgc aggagccatg   660
gctggaggtt atcgatcccc acggactccc agcgacttca agctctccg tactgtgtct   720
gttctcattg ggagctttgc tctatcctgg accccttcc ttatcactgg cattgtgcag   780
gtggcctgcc aggagtgtca cctctaccta gtgctggaac ggtacctgtg ctgctcggc   840
gtgggcaact ccctgctcaa cccactcatc tatgcctatt ggcagaagga ggtgcgactg   900
cagctctacc acatggccct aggagtgaag aaggtgctca cctcattcct cctctttctc   960
tcggccagga attgtggccc agagaggccc agggaaagtt cctgtcacat cgtcactatc  1020
tccagctcag agtttgatgg cgaattcgga tccaagggca attctgcaga tatccagcac  1080
agtggcggcc gctcgagtct agagggcccg cggttcgaag gtaagcctat ccctaaccct  1140
ctcctcggtc tcgattctac gcgtaccggt catcatcacc atcaccattg a            1191

<210> SEQ ID NO 2
<211> LENGTH: 396
<212> TYPE: PRT
<213> ORGANISM: Homo sapiens

<400> SEQUENCE: 2

Met Tyr Pro Tyr Asp Val Pro Asp Tyr Ala Gly Ser Leu Glu Ser Ser
1               5                   10                  15

Phe Ser Phe Gly Val Ile Leu Ala Val Leu Ala Ser Leu Ile Ile Ala
                20                  25                  30

Thr Asn Thr Leu Val Ala Val Ala Val Leu Leu Leu Ile His Lys Asn
            35                  40                  45

Asp Gly Val Ser Leu Cys Phe Thr Leu Asn Leu Ala Val Ala Asp Thr
        50                  55                  60

Leu Ile Gly Val Ala Ile Ser Gly Leu Leu Thr Asp Gln Leu Ser Ser
65                  70                  75                  80

Pro Ser Arg Pro Thr Gln Lys Thr Leu Cys Ser Leu Arg Met Ala Phe
                85                  90                  95

Val Thr Ser Ser Ala Ala Ala Ser Val Leu Thr Val Met Leu Ile Thr
                100                 105                 110

Phe Asp Arg Tyr Leu Ala Ile Lys Gln Pro Phe Arg Tyr Leu Lys Ile
            115                 120                 125

Met Ser Gly Phe Val Ala Gly Ala Cys Ile Ala Gly Leu Trp Leu Val
        130                 135                 140

Ser Tyr Leu Ile Gly Phe Leu Pro Leu Gly Ile Pro Met Phe Gln Gln
145                 150                 155                 160

Thr Ala Tyr Lys Gly Gln Cys Ser Phe Phe Ala Val Phe His Pro His
```

-continued

```
                165                 170                 175
Phe Val Leu Thr Leu Ser Cys Val Gly Phe Phe Pro Ala Met Leu Leu
            180                 185                 190

Phe Val Phe Phe Tyr Cys Asp Met Leu Lys Ile Ala Ser Met His Ser
            195                 200                 205

Gln Gln Ile Arg Lys Met Glu His Ala Gly Ala Met Ala Gly Gly Tyr
            210                 215                 220

Arg Ser Pro Arg Thr Pro Ser Asp Phe Lys Ala Leu Arg Thr Val Ser
225                 230                 235                 240

Val Leu Ile Gly Ser Phe Ala Leu Ser Trp Thr Pro Phe Leu Ile Thr
                245                 250                 255

Gly Ile Val Gln Val Ala Cys Gln Glu Cys His Leu Tyr Leu Val Leu
                260                 265                 270

Glu Arg Tyr Leu Trp Leu Leu Gly Val Gly Asn Ser Leu Leu Asn Pro
                275                 280                 285

Leu Ile Tyr Ala Tyr Trp Gln Lys Glu Val Arg Leu Gln Leu Tyr His
                290                 295                 300

Met Ala Leu Gly Val Lys Lys Val Leu Thr Ser Phe Leu Leu Phe Leu
305                 310                 315                 320

Ser Ala Arg Asn Cys Gly Pro Glu Arg Pro Arg Glu Ser Ser Cys His
                325                 330                 335

Ile Val Thr Ile Ser Ser Ser Glu Phe Asp Gly Glu Phe Gly Ser Lys
                340                 345                 350

Gly Asn Ser Ala Asp Ile Gln His Ser Gly Gly Arg Ser Ser Leu Glu
                355                 360                 365

Gly Pro Arg Phe Glu Gly Lys Pro Ile Pro Asn Pro Leu Leu Gly Leu
                370                 375                 380

Asp Ser Thr Arg Thr Gly His His His His His
385                 390                 395

<210> SEQ ID NO 3
<211> LENGTH: 24
<212> TYPE: DNA
<213> ORGANISM: Artificial
<220> FEATURE:
<223> OTHER INFORMATION: Homo sapiens Primer

<400> SEQUENCE: 3
cattgccggg ctgtggttag tgtc                                      24

<210> SEQ ID NO 4
<211> LENGTH: 24
<212> TYPE: DNA
<213> ORGANISM: Artificial
<220> FEATURE:
<223> OTHER INFORMATION: Homo sapiens Primer

<400> SEQUENCE: 4
ggcatagatg agtgggttga gcag                                      24

<210> SEQ ID NO 5
<211> LENGTH: 22
<212> TYPE: DNA
<213> ORGANISM: Artificial
<220> FEATURE:
<223> OTHER INFORMATION: Rat Primer

<400> SEQUENCE: 5
catgggccct gcaccttctt tg                                        22
```

```
<210> SEQ ID NO 6
<211> LENGTH: 24
<212> TYPE: DNA
<213> ORGANISM: Artificial
<220> FEATURE:
<223> OTHER INFORMATION: Rat Primer

<400> SEQUENCE: 6
gctccggatg gctgatgata gtga                                              24

<210> SEQ ID NO 7
<211> LENGTH: 23
<212> TYPE: PRT
<213> ORGANISM: Artificial
<220> FEATURE:
<223> OTHER INFORMATION: Chemically synthesized peptide

<400> SEQUENCE: 7

Arg Gly Pro Glu Arg Thr Arg Glu Ser Ala Tyr His Ile Val Thr Ile
1               5                   10                  15

Ser His Pro Glu Leu Asp Gly
            20
```